US011434242B2

(12) United States Patent
Kiss et al.

(10) Patent No.: US 11,434,242 B2
(45) Date of Patent: Sep. 6, 2022

(54) DOPAMINE-B-HYDROXYLASE INHIBITORS

(71) Applicant: BIAL-PORTELA & Cª, S.A., S. Mamede Do Coronado (PT)

(72) Inventors: Laszlo Erno Kiss, São Mamede Do Coronado (PT); Alexander Beliaev, São Mamede Do Coronado (PT); Tino Rossi, São Mamede Do Coronado (PT); Pedro Nuno Leal Palma, São Mamede Do Coronado (PT); Patrício Manuel Vieira Araujo Soares Da Silva, São Mamede Do Coronado (PT); Rui Pinto, São Mamede Do Coronado (PT); Francisco Cardona, São Mamede Do Coronado (PT)

(73) Assignee: BIAL—PORTELA & CA, S.A., Coronado (PT)

( * ) Notice: Subject to any disclaimer, the term of this patent is extended or adjusted under 35 U.S.C. 154(b) by 10 days.

(21) Appl. No.: 16/769,045

(22) PCT Filed: Nov. 30, 2018

(86) PCT No.: PCT/PT2018/050043
§ 371 (c)(1),
(2) Date: Jun. 2, 2020

(87) PCT Pub. No.: WO2019/112457
PCT Pub. Date: Jun. 13, 2019

(65) Prior Publication Data
US 2021/0171528 A1    Jun. 10, 2021

(30) Foreign Application Priority Data

Dec. 4, 2017   (GB) ...................................... 1720189
Mar. 20, 2018  (GB) ...................................... 1804439

(51) Int. Cl.
C07D 487/04   (2006.01)
C07D 519/00   (2006.01)
A61P 19/10    (2006.01)
A61P 9/04     (2006.01)
A61P 9/12     (2006.01)

(52) U.S. Cl.
CPC .............. C07D 487/04 (2013.01); A61P 9/04 (2018.01); A61P 9/12 (2018.01); A61P 19/10 (2018.01); C07D 519/00 (2013.01); C07B 2200/05 (2013.01)

(58) Field of Classification Search
CPC .................................................. C07D 487/04
See application file for complete search history.

(56) References Cited

U.S. PATENT DOCUMENTS 3,644,414 A    2/1972  Helsley
3,647,790 A    3/1972  Potoski et al.
4,628,059 A    12/1986 Finkelstein et al.
2019/0337950 A1 11/2019 Soares Da Silva et al.
2020/0181148 A1  6/2020 Soares Da Silva et al.
2022/0017523 A1  1/2022 Soares Da Silva et al.

FOREIGN PATENT DOCUMENTS

DE    2017255 A1      10/1970
EP    0015171 A1       9/1980
WO    1995/29165 A2   11/1995
WO    2002/092019 A2  11/2002
WO    2004/033447 A1   4/2004
WO    2008/085008 A1   7/2008
WO    2008/136695 A1  11/2008
WO    2009/015248 A1   1/2009
WO    2014/127350 A1   8/2014
WO    2018/056854 A1   3/2018
WO    2018/056855 A1   3/2018
WO    2019/112457 A1   6/2019

OTHER PUBLICATIONS

U.S. Appl. No. 16/335,521, filed Mar. 21, 2019, 2019-0337950, Allowed.
U.S. Appl. No. 16/335,529, filed Mar. 21, 2019, 2020-0181148, Published.
Beliaev et al., Dopamine beta-Monooxygenase: Mechanism, Substrates and Inhibitors. Current Enzyme Inhibition. 2009;5:27-43.
Goldstein et al., Inhibition of Dopamine-beta-Hydroxylase by Disulfiram. Life Sciences. 1964;3:763-767.
Hidaka, Fusaric (5-butylpicolinic) acid, an inhibitor of dopamine beta-hydroxylase, affects serotonin and noradrenaline. Nature. May 7, 1971;231(5297):54-5.
Johnson et al., In vivo inhibition of dopamine beta-hydroxylase by 1-phenyl-3-(2-thiazolyl)-2-thiourea (U-14,624). J Pharmacol Exp Ther. Jan. 1970;171(1):80-7.

(Continued)

Primary Examiner — Susanna Moore
(74) Attorney, Agent, or Firm — McCarter & English, LLP; Steven G. Davis; Wei Song

(57) ABSTRACT

This invention relates to: (a) compounds of formula Ia (with R1, R4 to R6, n and A as defined herein) and pharmaceutically acceptable salts or solvates thereof that are useful as dopamine-β-hydroxylase inhibitors; (b) pharmaceutical compositions (comprising such compounds, salts or solvates; (c) the use of such compounds, salts or solvates in therapy; (d) therapeutic methods of treatment using such compounds, salts or solvates; and (e) processes and intermediates useful for the synthesis of such compounds.

14 Claims, No Drawings

(56) References Cited

OTHER PUBLICATIONS

Koczka et al., Adatok AZ 1,2,4-Triazol-Szarmazekok Antimikrobas Hatasahoz. (Antimicrobial Activity of 1,2,4-Triazole Derivatives.) Sejtosztodas Farmakologiaja. 1979;8(1):79-100.

Lippmann et al., Dopamine-beta-hydroxylase inhibition by dimethyldithiocarbamate and related compounds. Biochem Pharmacol. Oct. 1969;18(10):2507-16.

Stanley et al., Catecholamine modulatory effects of nepicastat (RS-25560-197), a novel, potent and selective inhibitor of dopamine-beta-hydroxylase Br J Pharmacol. Aug. 1997;121(8):1803-9.

International Search Report and Written Opinion for Application No. PCT/PT2018/050043, dated Feb. 15, 2019, 10 Pages.

International Search Report for Application No. PCT/PT2017/050022, dated Nov. 24, 2017, 4 pages.

International Search Report for Application No. PCT/PT2017/050023, dated Dec. 15, 2017, 3 pages.

International Search Report and Written Opinion for Application No. PCT/PT2020/050022, dated Jul. 28, 2020, 8 pages.

DOPAMINE-B-HYDROXYLASE INHIBITORS

CROSS-REFERENCE TO RELATED APPLICATIONS

This application is a U.S. national stage filing, under 35 U.S.C. § 371(c), of International Application No. PCT/PT2018/050043, filed on Nov. 30, 2018, which claims priority to United Kingdom Patent Application No. 1720189.8, filed on Dec. 4, 2017, and United Kingdom Patent Application No. 1804439.6, filed on Mar. 20, 2018. The entire contents of each of the aforementioned applications are incorporated herein by reference.

FIELD OF THE INVENTION

This invention relates to: (a) compounds and pharmaceutically acceptable salts or solvates thereof that are useful as dopamine-β-hydroxylase inhibitors; (b) pharmaceutical compositions comprising such compounds, salts or solvates; (c) the use of such compounds, salts or solvates in therapy; and (d) therapeutic methods of treatment using such compounds, salts or solvates.

BACKGROUND OF THE INVENTION

The enzyme dopamine-μ-hydroxylase (DβH), also known as dopamine β-monooxygenase, is expressed both in the periphery and the central nervous system (CNS). DβH catalyses the specific hydroxylation of dopamine (DA) to produce norepinephrine, also known as noradrenaline (NA). As such, inhibitors of DβH can inhibit the biosynthesis of NA, limiting its concentration and increasing DA levels.

In recent years, interest in the development of inhibitors of DβH has centred on the hypothesis that inhibition of this enzyme may provide significant clinical improvements in patients suffering from cardiovascular disorders such as hypertension or chronic heart failure. The rationale for the use of DβH inhibitors is based on their capacity to inhibit the biosynthesis of NA, which is achieved via enzymatic hydroxylation of DA. Reduction of the biosynthesis of NA via inhibition of DβH can directly dampen sympathetic nerve function, the activation of which is the principal clinical manifestation of congestive heart failure (Parmley, W. W., Clin. Cardiol., 18: 440-445, 1995). Congestive heart failure patients have elevated concentrations of plasma noradrenaline (Levine, T. B. et al., Am. J. Cardiol., 49:1659-1666, 1982), increased central sympathetic outflow (Leimbach, W. N. et al., Circulation, 73: 913-919, 1986) and augmented cardiorenal noradrenaline spillover (Hasking, G. J. et al., Circulation, 73:615-621, 1966). Prolonged and excessive exposure of the myocardium to noradrenaline may lead to down-regulation of cardiac $\beta_1$-adrenoceptors, remodelling of the left ventricle, arrhythmias and necrosis, all of which can diminish the functional integrity of the heart. Congestive heart failure patients who have high plasma concentrations of noradrenaline also have the most unfavourable long-term prognosis (Cohn, J. N. et al., N. Engl. J. Med., 311:819-823, 1984). Of greater significance is the observation that plasma noradrenaline concentrations are already elevated in asymptomatic patients with no overt heart failure and can predict ensuing mortality and morbidity (Benedict, C. R. et al., Circulation, 94:690-697, 1996). An activated sympathetic drive is not therefore merely a clinical marker of congestive heart failure, but may contribute to progressive worsening of the disease.

DβH inhibitors may also display activity the CNS, if they cross the blood-brain barrier (BBB).

Several inhibitors of DβH have been thus far reported in the literature. Early first and second generation examples such as disulfiram (Goldstein, M. et al., Life Sci., 3:763, 1964) and diethyldithiocarbamate (Lippmann, W. et al., Biochem. Pharmacol., 18: 2507, 1969) or fusaric acid (Hidaka, H. Nature, 231, 1971) and aromatic or alkyl thioureas (Johnson, G. A. et al, J. Pharmacol. Exp. Ther., 171: 80, 1970) were found to be of low potency, exhibited poor selectivity for DβH and caused toxic side effects. The third generation of DβH inhibitors, however, were found to have much greater potency, such as, for example, nepicastat (RS-25560-197, $IC_{50}$ 9 nM) (Stanley, W. C., et al., Br. J. Pharmacol., 121: 1803-1809, 1997), which was developed to early clinical trials. Although it was initially developed for peripheral indications (hypertension and congestive heart failure), an important discovery was that nepicastat was found to cross the BBB, and was thereby able to cause central as well as peripheral effects.

Nepicastat and its analogues are disclosed in WO95/29165. Furthermore, WO 2004/033447 and WO 2008/136695 disclose DβH inhibitors having high potency and significantly reduced brain access, giving rise to potent and peripherally selective DβH inhibitors. However, these compounds are also difficult to synthesise requiring many steps in the synthetic route making them expensive to manufacture. In particular, potent compounds disclosed in WO 2008/136695 are sparingly soluble and display improved levels of exposure when administered with high-fat meals. A review of the mechanism, substrates and inhibitors of DβH, is given by Beliaev, A., et al. in Current Enzyme Inhibition, 5, 27-43, 2009.

WO2018/056854 and WO2018/056855 disclose DβH inhibitors which are useful for the treatment of conditions ameliorated by inhibition of DβH within the CNS. Compared with the compounds of formula Ia of the present invention, the compounds of WO2018/056854 and WO2018/056855 have different substituents at position $R_6$. In addition, the sub-headings to Step 3 of Example 80 of WO2018/056854 and Step 3 of Example 3 of WO2018/056855 incorrectly disclose the chemical name (S)-1-benzyl-6-(3,5-difluorophenyl)-6,7-dihydro-2H-pyrrolo[1,2-c]imidazole-3(5H)-thione instead of the actual compound name (S)-1-butyl-6-(3,5-difluorophenyl)-6,7-dihydro-2H-pyrrolo[1,2-c]imidazole-3(5H)-thione (emphasis added).

Therefore, there remains an unfulfilled clinical requirement for a potent, non-toxic and peripherally selective inhibitor of DβH, which could be used for treatment of certain cardiovascular disorders. A DβH inhibitor with similar or even greater potency than nepicastat, but devoid of CNS effects (i.e. unable to efficiently cross the BBB), yet exhibiting a long residence time in the periphery so as to provide a long duration of DβH inhibition would provide a significant improvement over all DβH inhibitor compounds thus far described in the prior art. Additionally, such compounds would preferably be orally bioavailable, highly soluble and easier and cheaper to synthesise.

SUMMARY OF THE INVENTION

The present invention provides a compound of formula Ia, or a pharmaceutically acceptable salt or solvate thereof:

(Ia)

wherein:
$R_1$ is hydrogen, $C_1$-$C_6$ alkyl, partially or fully deuterated $C_1$-$C_6$ alkyl or $C_3$-$C_6$ cycloalkyl;
$R_4$ is hydrogen or $C_1$-$C_3$ alkyl;
$R_5$ is hydrogen;
or $R_4$ and $R_5$ combine, together with the carbon atoms to which they are attached, to form a cyclopropyl ring;
$R_6$ is —COOH, —CHO, or —$(CH_2)_m$—X,
  wherein:
   m is 1, 2 or 3 and one —$CH_2$— moiety within —$(CH_2)_m$ may optionally be replaced by X is hydroxy, $C_1$-$C_3$ alkoxy, cyano, —N=CH(NHCN)(NH$_2$), —NH—C(pyrrolidin-1-yl)=NCN, 5- or 6-membered heteroaryl optionally substituted with one methyl group, phenyl, —$SO_2$—$R_7$, —$NR_8R_9$, —$CO_2R_{10}$, —$CH(CO_2R_{10})_2$, —$CONR_{11}R_{12}$ or —$NR_{13}COR_{14}$;
wherein:
$R_7$ is $C_1$-$C_3$ alkyl;
$R_8$ is hydrogen or $C_1$-$C_3$ alkyl;
$R_9$ is hydrogen,
  $C_1$-$C_4$ alkyl optionally substituted with up to three fluoro substituents or with one substituent selected from the group consisting of hydroxy, methylsulfonyl, $C_3$-$C_6$ cycloalkyl, phenyl, 5- or 6-membered heterocyclyl and 5- or 6-membered heteroaryl optionally substituted with one methyl substituent,
  $C_3$-$C_6$ cycloalkyl,
  5- or 6-membered heteroaryl, or
  5- or 6-membered heterocyclyl optionally substituted with one or two oxo substituents;
or $R_8$ and $R_9$ combine together with the N atom to which they are attached to form a
  5- or 6-membered N-heterocyclyl group optionally substituted with one substituent selected from methyl, trifluoromethyl, hydroxy, hydroxymethyl, methoxymethyl, methylsulfonyl, amido, (N,N-dimethyl)acetamide and pyridyl or with one or two substituents selected from fluoro and oxo, or a
  9- or 10-membered heterospirocyclyl group;
$R_{10}$ is hydrogen or $C_1$-$C_3$ alkyl;
$R_{11}$ is hydrogen or $C_1$-$C_3$ alkyl;
$R_{12}$ is hydrogen,
  $C_1$-$C_4$ alkyl optionally substituted with up to three fluoro substituents or with one substituent selected from the group consisting of cyano, hydroxy, methylsulfonyl, $C_1$-$C_2$ alkoxy, dimethylamino, $C_3$-$C_6$ cycloalkyl, phenyl, 5- or 6-membered heteroaryl optionally substituted with one methyl substituent and 5- or 6-membered heterocyclyl optionally substituted with one t-Boc group or with one or two fluoro substituents,
  $C_3$-$C_6$ cycloalkyl optionally substituted with one substituent selected from the group consisting of cyano, hydroxy, hydroxymethyl and oxo,
  cyano,
  methylsulfonyl,
  $CH_2COO(C_1$-$C_3$ alkyl),
  5- or 6-membered heteroaryl optionally substituted with one methyl substituent,
  4-, 5- or 6-membered heterocyclyl optionally substituted with one or two substituents selected from oxo and methyl,
  $CH_2CH(NH_2)(COOH)$, or
  $CH(CH_3)CONH_2$;
or $R_{11}$ and $R_{12}$ combine together with the N atom to which they are attached to form a
  5- or 6-membered N-heterocyclyl group optionally substituted with one substituent selected from monofluoromethyl, trifluoromethyl, hydroxy, hydroxymethyl, methoxymethyl, methylsulfonyl, cyano, amido, (N,N-dimethyl)acetamide and pyridyl, or with one or two substituents selected from fluoro, methyl and oxo, or optionally fused to a cyclopropyl ring which may be substituted with one or two methyl substituents, or a
  9- or 10-membered heterospirocyclyl group;
$R_{13}$ is hydrogen or $C_1$-$C_3$ alkyl;
$R_{14}$ is $C_1$-$C_4$ alkyl optionally substituted with up to three fluoro substituents or with one substituent selected from the group consisting of hydroxy, methylsulfonyl, $C_3$-$C_6$ cycloalkyl and phenyl,
  $C_3$-$C_6$ cycloalkyl,
  5- or 6-membered heteroaryl, or
  5- or 6-membered heterocyclyl optionally substituted with one or two oxo substituents;
A is $C_5$-$C_7$ cycloalkyl, furanyl, thiophenyl, methylthiophenyl or wherein:
$X_1$ is hydrogen, halo or methyl;
$X_1'$ is hydrogen or halo;
$X_2$ is hydrogen, halo or methyl;
$X_2'$ is hydrogen or halo;
$X_3$ is hydrogen or fluoro;
n is 0 or 1, and when n is 0 a single bond joins the carbon atoms to which the $CH_2$ moiety would be attached when n is 1.

This invention is also directed to a compound of formula Ia, as defined above, or a pharmaceutically acceptable salt or solvate thereof, for use in therapy.

This invention is also directed to a compound of formula Ia, as defined above, or a pharmaceutically acceptable salt or solvate thereof, for use in the treatment of conditions ameliorated by inhibition of DβH outside the CNS.

This invention is also directed to a compound of formula Ia, as defined above, or a pharmaceutically acceptable salt or solvate thereof, in the manufacture of a medicament for treatment of conditions ameliorated by inhibition of DβH outside the CNS.

This invention is also directed to a method for treating or preventing conditions ameliorated by inhibition of DβH outside the CNS comprising administering a therapeutically effective amount of a compound of formula Ia, as defined above, or a pharmaceutically acceptable salt or solvate thereof, to a patient in need thereof.

This invention is also directed to a pharmaceutical composition comprising (i) a therapeutically effective amount of a compound of formula Ia, as defined above, or a pharmaceutically acceptable salt or solvate thereof; and (ii) a pharmaceutically acceptable excipient.

This invention is also directed to a compound of formula Ia, as defined above, or a pharmaceutically acceptable salt or solvate thereof, with the proviso that the compound (S)-1-benzyl-6-(3,5-difluorophenyl)-6,7-dihydro-2H-pyrrolo[1,2-c]imidazole-3(5H)-thione is excluded.

Certain compounds of formula Ia may exist as tautomers. Where tautomers exist, each tautomeric form, and mixtures thereof, are contemplated as included in the present invention. Any reference in this specification to one specific tautomer of a compound of formula Ia is understood to encompass every tautomeric form as well as any mixtures thereof, in any ratio. The same applies to tautomers of more specific embodiments of compounds of formula Ia described herein, such as, but not limited to, tautomers of compounds of formula Ib, Ic, Id, Ie, If, Ig, Ih, Ii and Ij described below, and tautomers of the specific examples described in the experimental section below.

DETAILED DESCRIPTION OF THE EMBODIMENTS

A. Definitions

"$C_1$-$C_6$ alkyl" means a monovalent unsubstituted saturated straight-chain or branched-chain hydrocarbon radical having from 1 to 6 carbon atoms. "$C_1$-$C_2$ alkyl", "$C_1$-$C_3$ alkyl", "$C_1$-$C_4$ alkyl" and "$C_1$-$C_5$ alkyl" have analogous meanings.

"partially or fully deuterated $C_1$-$C_6$ alkyl" means a $C_1$-$C_6$ alkyl wherein some or all of the hydrogen atoms have been replaced by deuterium.

"$C_3$-$C_6$ cycloalkyl" means a monovalent unsubstituted saturated cyclic hydrocarbon radical having from 3 to 6 carbon atoms. "$C_5$-$C_7$ cycloalkyl" has analogous meaning.

"$C_1$-$C_3$ alkoxy" means a monovalent unsubstituted saturated straight-chain or branched-chain hydrocarbon having from 1 to 3 carbon atoms connected to the rest of the compound of formula Ia via a single oxygen atom. "$C_1$-$C_2$ alkoxy" has analogous meaning.

"5- or 6-membered heteroaryl" means a monocyclic aromatic group with a total of 5 atoms in the ring wherein from 1 to 4 of those atoms are each independently selected from N, O and S; or a monocyclic aromatic group with a total of 6 atoms in the ring wherein from 1 to 3 of those atoms are N. 5-membered heteroaryl groups include pyrrolyl (also called azolyl), furanyl, thienyl (also called thiophenyl), pyrazolyl (also called 1H-pyrazolyl and 1,2-diazolyl), imidazolyl, oxazolyl (also called 1,3-oxazolyl), isoxazolyl (also called 1,2-oxazolyl), thiazolyl (also called 1,3-thiazolyl), isothiazolyl (also called 1,2-thiazolyl), triazolyl, oxadiazolyl, thiadiazolyl, tetrazolyl, oxatriazolyl and thiatriazolyl. 6-membered heteroaryl groups include pyridinyl, pyrimidyl, pyrazinyl, pyridazinyl and triazinyl.

"4-, 5- or 6-membered heterocyclyl" means a saturated monocyclic group with a total of 4 atoms in the ring wherein 1 of those atoms is selected from N, O and S; or a saturated monocyclic group with a total of 5 atoms in the ring wherein 1 or 2 of those atoms are each independently selected from N, O and S; or a saturated monocyclic group with a total of 6 atoms in the ring wherein 1 or 2 of those atoms are each independently selected from N, O and S. 4-membered heterocyclyl groups include azetidine, oxetane and thietane. 5-membered heterocyclyl groups include pyrrolidinyl, tetrahydrofuranyl, tetrahydrothienyl (also called terahydrothiophenyl), imidazolidinyl, pyrazolidinyl, dioxolanyl, dithiolanyl, oxazolidinyl, isoxazolidinyl, thiazolidinyl and isothiazolidinyl. 6-membered heterocyclyl groups include piperidinyl, tetrahydropyranyl, tetrahydrothiopyranyl, piperazinyl, dioxanyl, dithianyl, morpholinyl and thiomorpholinyl.

"5- or 6-membered N-heterocyclyl" means a saturated monocyclic group with a total of 5 atoms in the ring wherein 1 of those atoms is N and another one of those atoms is optionally selected from N, O and S; or a saturated monocyclic group with a total of 6 atoms in the ring wherein 1 of those atoms is N and another one of those atoms is optionally independently selected from N, O and S. 5-membered N-heterocyclyl groups include pyrrolidinyl, imidazolidinyl, pyrazolidinyl, oxazolidinyl, isoxazolidinyl, thiazolidinyl and isothiazolidinyl. 6-membered N-heterocyclyl groups include piperidinyl, piperazinyl, morpholinyl and thiomorpholinyl.

"9- or 10-membered heterospirocyclyl" means a saturated spirocyclic group with a total of 9 atoms in the two rings wherein from 1 to 4 of those atoms are each independently selected from N, O and S; or a saturated spirocyclic group with a total of 10 atoms in the two rings wherein from 1 to 5 of those atoms are each independently selected from N, O and S. 9-membered heterospirocyclyl groups include 2-oxa-7-azaspiro[4.4]nonanyl. 10-membered heterospirocyclyl groups include 2-oxa-8-azaspiro[4.5]decanyl and 1,4-dioxa-8-azaspiro[4.5]decanyl.

"oxo" means an oxo radical, and may be depicted as =O.

"halo" means a fluorine (which may be depicted as —F), chlorine (which may be depicted as —Cl), bromine (which may be depicted as —Br) or iodine (which may be depicted as —I) radical.

"amido" means —$CONH_2$.

"t-Boc" means tert-butyloxycarbonyl.

"pharmaceutically acceptable salt" means a salt such as those described in standard texts on salt formation, see for example: P. Stahl, et al., Handbook of Pharmaceutical Salts: Properties, Selection and Use (VCHA/Wiley-VCH, 2002), or S. M. Berge, et al., "Pharmaceutical Salts" (1977) *Journal of Pharmaceutical Sciences*, 66, 1-19.

"pharmaceutically acceptable solvate" means a molecular complex comprising the compound of the invention and one or more pharmaceutically acceptable solvent molecules, for example, water or ethanol. The term "hydrate" maybe employed when said solvent is water. Pharmaceutically acceptable solvates include hydrates and other solvates wherein the solvent of crystallization may be isotopically substituted, e.g. $D_2O$, $d_6$-acetone, $d_6$-DMSO.

"pharmaceutically acceptable excipient" means any ingredient other than the compound(s) of the invention, or other known pharmacologically active components. The choice of excipient will to a large extent depend on factors such as the particular mode of administration, the effect of the excipient on solubility and stability, and the nature of the dosage form.

"therapy", "treatment" and "treating" include both preventative and curative treatment of a condition, disease or disorder. It also includes slowing, interrupting, controlling or stopping the progression of a condition, disease or disorder. It also includes preventing, curing, slowing, interrupting, controlling or stopping the symptoms of a condition, disease or disorder.

Other variations to the disclosed embodiments can be understood and effected by those skilled in the art in practicing the claimed invention, from a study of the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

B. Compounds

The invention provides a compound of formula Ia, as defined above, or a pharmaceutically acceptable salt or solvate thereof:

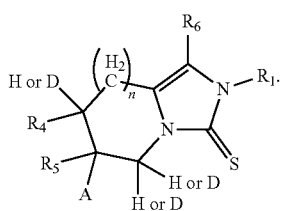
(Ia)

The invention also provides a compound of formula Ia, as defined above, or a pharmaceutically acceptable salt or solvate thereof, with the proviso that the compound (S)-1-benzyl-6-(3,5-difluorophenyl)-6,7-dihydro-2H-pyrrolo[1,2-c]imidazole-3(5H)-thione is excluded.

B0. Core Structures

In some embodiments of formula Ia, n is 0 and a single bond joins the carbon atoms to which the $CH_2$ moiety would be attached when n is 1 to form a structure of formula Ib

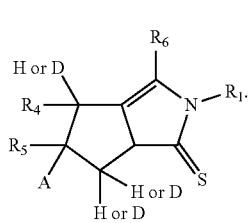
(Ib)

In some embodiments of formula Ia, $R_4$ and $R_5$ combine, together with the carbon atom to which they are attached, to form a structure of formula Ic:

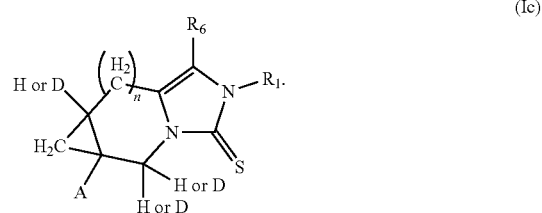
(Ic)

In some embodiments more than 50%, preferably more than 90%, more preferably more than 95% and even more preferably more than 99% of substituents $R_5$ and A of compounds of formula Ia have the stereochemical configuration of formula Id

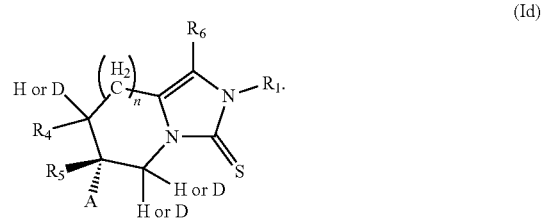
(Id)

In some embodiments more than 50%, preferably more than 90%, more preferably more than 95% and even more preferably more than 99% of substituents $R_5$ and A of compounds of formula Ia have the stereochemical configuration of formula Ie

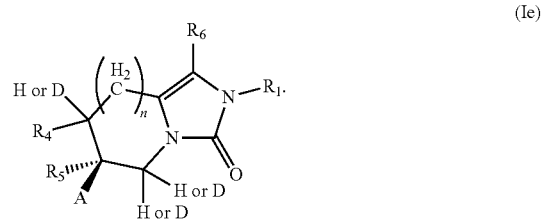
(Ie)

Preferred embodiments of formula Ia include compounds of formula If.

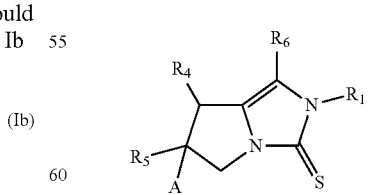
(If)

In some particularly preferred embodiments of formula If more than 50%, preferably more than 90%, more preferably more than 95% and even more preferably more than 99% of substituents $R_5$ and A of compounds of formula If have the stereochemical configuration of formula Ig

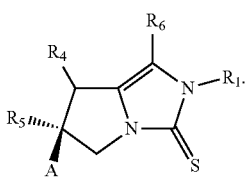

(Ig)

In other more particularly preferred embodiments of formula If more than 50%, preferably more than 90%, more preferably more than 95% and even more preferably more than 99% of substituents $R_5$ and A of compounds of formula If have the stereochemical configuration of formula Ih

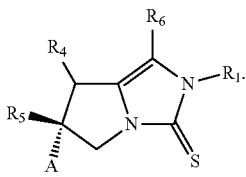

(Ih)

More preferred embodiments of formula Ia include compounds of formula Ii.

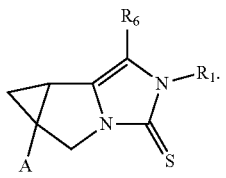

(Ii)

In some particularly preferred embodiments of formula Ii more than 50%, preferably more than 90%, more preferably more than 95% and even more preferably more than 99% have the stereochemical configuration of formula Ij.

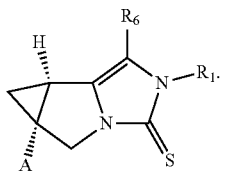

(Ij)

B1. Substituent $R_1$ $R_1$ is selected from the group consisting of hydrogen, $C_1$-$C_6$ alkyl, partially or fully deuterated $C_1$-$C_6$ alkyl or $C_3$-$C_6$ cycloalkyl.

$R_1$ is preferably selected from the group consisting of hydrogen, $C_1$-$C_6$ alkyl and partially or fully deuterated $C_1$-$C_6$ alkyl.

In some embodiments $R_1$ is hydrogen.
In some embodiments $R_1$ is $C_1$-$C_6$ alkyl.
In some embodiments $R_1$ is partially deuterated $C_1$-$C_6$ alkyl.
In some embodiments $R_1$ is fully deuterated $C_1$-$C_6$ alkyl.
In some embodiments $R_1$ is $C_3$-$C_6$ cycloalkyl.

$R_1$ is preferably selected from the group consisting of hydrogen, methyl, d3-methyl, propyl and cyclopropyl.

$R_1$ is more preferably selected from the group consisting of hydrogen, methyl and d3-methyl.

In some embodiments $R_1$ is preferably hydrogen.
In some embodiments $R_1$ is preferably methyl.
In some embodiments $R_1$ is preferably d3-methyl.

$R_1$ is most preferably hydrogen or methyl.

B2. Substituent $R_4$ (when not Combined with $R_5$)

$R_4$ is selected from the group consisting of hydrogen and $C_1$-$C_3$ alkyl.

In some embodiments $R_4$ is hydrogen.
In some embodiments $R_4$ is $C_1$-$C_3$ alkyl.

$R_4$ is preferably selected from the group consisting of hydrogen and methyl.

In some embodiments $R_4$ is preferably hydrogen.
In some embodiments $R_4$ is preferably methyl.

$R_4$ is most preferably hydrogen.

B3. Substituent $R_5$ (when not Combined with $R_4$)

$R_5$ is hydrogen.

B4. Substituent $R_6$ $R_6$ is selected from the group consisting of —COOH, —CHO, or —(CH$_2$)$_m$—X, wherein:
m is 1, 2 or 3 and one —CH$_2$— moiety within —(CH$_2$)$_m$ may optionally be replaced by

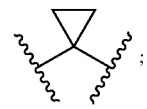 [SMILES: *C1(*)CC1]

;

X is hydroxy, $C_1$-$C_3$ alkoxy, cyano, —N═CH(NHCN)(NH$_2$), —NH—C(pyrrolidin-1-yl)═NCN, 5- or 6-membered heteroaryl optionally substituted with one methyl group, phenyl, —SO$_2$—R$_7$, —NR$_8$R$_9$, —CO$_2$R$_{10}$, —CH(CO$_2$R$_{10}$)$_2$, —CONR$_{11}$R$_{12}$ or —NR$_{13}$COR$_{14}$;

wherein:
$R_7$ is $C_1$-$C_3$ alkyl;
$R_8$ is hydrogen or $C_1$-$C_3$ alkyl;
$R_9$ is hydrogen,
  $C_1$-$C_4$ alkyl optionally substituted with up to three fluoro substituents or with one substituent selected from the group consisting of hydroxy, methylsulfonyl, $C_3$-$C_6$ cycloalkyl, phenyl, 5- or 6-membered heterocyclyl and 5- or 6-membered heteroaryl optionally substituted with one methyl substituent,
  $C_3$-$C_6$ cycloalkyl,
  5- or 6-membered heteroaryl, or
  5- or 6-membered heterocyclyl optionally substituted with one or two oxo substituents;
or $R_8$ and $R_9$ combine together with the N atom to which they are attached to form a
  5- or 6-membered N-heterocyclyl group optionally substituted with one substituent selected from methyl, trifluoromethyl, hydroxy, hydroxymethyl, methoxymethyl, methylsulfonyl, amido, (N,N-dimethyl)acetamide and pyridyl or with one or two substituents selected from fluoro and oxo, or a 9- or 10-membered heterospirocyclyl group;

$R_{10}$ is hydrogen or $C_1$-$C_3$ alkyl;

$R_{11}$ is hydrogen or $C_1$-$C_3$ alkyl;

$R_{12}$ is hydrogen, $C_1$-$C_4$ alkyl optionally substituted with up to three fluoro substituents or with one substituent selected from the group consisting of cyano, hydroxy, methylsulfonyl, $C_1$-$C_2$ alkoxy, dimethylamino, $C_3$-$C_6$ cycloalkyl, phenyl, 5- or 6-membered heteroaryl optionally substituted with one methyl substituent and 5- or 6-membered heterocyclyl optionally substituted with one t-Boc group or with one or two fluoro substituents, $C_3$-$C_6$ cycloalkyl optionally substituted with one substituent selected from the group consisting of cyano, hydroxy, hydroxymethyl and oxo, cyano, methylsulfonyl, $CH_2COO(C_1$-$C_3$ alkyl), 5- or 6-membered heteroaryl optionally substituted with one methyl substituent, 4-, 5- or 6-membered heterocyclyl optionally substituted with one or two substituents selected from oxo and methyl, $CH_2CH(NH_2)(COOH)$, or $CH(CH_3)CONH_2$;

or $R_{11}$ and $R_{12}$ combine together with the N atom to which they are attached to form a 5- or 6-membered N-heterocyclyl group optionally substituted with one substituent selected from monofluoromethyl trifluoromethyl, hydroxy, hydroxymethyl, methoxymethyl, methylsulfonyl, cyano, amido, (N,N-dimethyl)acetamide and pyridyl, or with one or two substituents selected from fluoro, methyl and oxo, or optionally fused to a cyclopropyl ring which may be substituted with one or two methyl substituents, or a 9- or 10-membered heterospirocyclyl group;

$R_{13}$ is hydrogen or $C_1$-$C_3$ alkyl;

$R_{14}$ is $C_1$-$C_4$ alkyl optionally substituted with up to three fluoro substituents or with one substituent selected from the group consisting of hydroxy, methylsulfonyl, $C_3$-$C_6$ cycloalkyl and phenyl, $C_3$-$C_6$ cycloalkyl, 5- or 6-membered heteroaryl, or 5- or 6-membered heterocyclyl optionally substituted with one or two oxo substituents.

In one embodiment $R_6$ is as defined above with the proviso that $R_9$ may not be 5- or 6-membered heterocyclyl.

In another embodiment $R_6$ is —COOH, —CHO, or —$(CH_2)_m$—X, wherein:

m is 1, 2 or 3 and one —$CH_2$— moiety within —$(CH_2)_m$ may optionally be replaced by

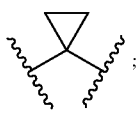 [SMILES: *C1(*)CC1];

X is hydroxy, $C_1$-$C_3$ alkoxy, cyano, —N=CH(NHCN)(NH_2), —NH—C(pyrrolidin-1-yl)=NCN, 5- or 6-membered heteroaryl optionally substituted with one methyl group, phenyl, —$SO_2$—$R_7$, —$NR_8R_9$, —$CO_2R_{10}$, —$CH(CO_2R_{10})_2$, —$CONR_{11}R_{12}$ or —$NR_{13}COR^{14}$;

wherein:

$R_7$ is $C_1$-$C_3$ alkyl;

$R_8$ is hydrogen or $C_1$-$C_3$ alkyl;

$R_9$ is hydrogen, $C_1$-$C_4$ alkyl optionally substituted with up to three fluoro substituents or with one substituent selected from the group consisting of hydroxy, methylsulfonyl, $C_3$-$C_6$ cycloalkyl and phenyl, $C_3$-$C_6$ cycloalkyl, 5- or 6-membered heteroaryl, or 5- or 6-membered heterocyclyl optionally substituted with one or two oxo substituents;

or $R_8$ and $R_9$ combine together with the N atom to which they are attached to form a 5- or 6-membered N-heterocyclyl group optionally substituted with one substituent selected from methyl, trifluoromethyl, hydroxy, hydroxymethyl, methoxymethyl, methylsulfonyl, amido, (N,N-dimethyl)acetamide and pyridyl or with one or two substituents selected from fluoro and oxo, or a 9- or 10-membered heterospirocyclyl group;

$R_{10}$ is hydrogen or $C_1$-$C_3$ alkyl;

$R_{11}$ is hydrogen or $C_1$-$C_3$ alkyl;

$R_{12}$ is hydrogen, $C_1$-$C_4$ alkyl optionally substituted with up to three fluoro substituents or with one substituent selected from the group consisting of cyano, hydroxy, methylsulfonyl, $C_1$-$C_2$ alkoxy, dimethylamino, $C_3$-$C_6$ cycloalkyl, phenyl, 5- or 6-membered heteroaryl and 5- or 6-membered heterocyclyl optionally substituted with one t-Boc group or with one or two fluoro substituents, $C_3$-$C_6$ cycloalkyl optionally substituted with one substituent selected from the group consisting of cyano, hydroxy, hydroxymethyl and oxo, cyano, methylsulfonyl, $CH_2COO(C_1$-$C_3$ alkyl), 5- or 6-membered heteroaryl, 5- or 6-membered heterocyclyl optionally substituted with one or two oxo substituents, $CH_2CH(NH_2)(COOH)$, or $CH(CH_3)CONH_2$;

or $R_{11}$ and $R_{12}$ combine together with the N atom to which they are attached to form a 5- or 6-membered N-heterocyclyl group optionally substituted with one substituent selected from methyl, trifluoromethyl, hydroxy, hydroxymethyl, methoxymethyl, methylsulfonyl, amido, (N,N-dimethyl)acetamide and pyridyl, or with one or two substituents selected from fluoro and oxo, or a 9- or 10-membered heterospirocyclyl group;

$R_{13}$ is hydrogen or $C_1$-$C_3$ alkyl;

$R_{14}$ is $C_1$-$C_4$ alkyl optionally substituted with up to three fluoro substituents or with one substituent selected from the group consisting of hydroxy, methylsulfonyl, $C_3$-$C_6$ cycloalkyl and phenyl, $C_3$-$C_6$ cycloalkyl, 5- or 6-membered heteroaryl, or 5- or 6-membered heterocyclyl optionally substituted with one or two oxo substituents.

In some embodiments $R_6$ is —COOH.
In some embodiments $R_6$ is —CHO.
In some embodiments $R_6$ is —$(CH_2)_m$—X wherein m and X are as defined above.
$R_6$ is preferably —$(CH_2)_m$—X wherein m and X are as defined above.
In some preferred embodiments $R_6$ is —$CH_2$—X wherein X is as defined above.
In some preferred embodiments $R_6$ is —$CH_2CH_2$—X wherein X is as defined above.
In some preferred embodiments $R_6$ is —$CH_2CH_2CH_2$—X wherein X is as defined above.
In some preferred embodiments $R_6$ is —$(CH_2)_m$—X wherein m is 1, 2 or 3 and one —$CH_2$— moiety within —$(CH_2)_m$ is replaced by

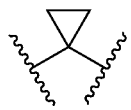

and X is as defined above.
In some preferred embodiments $R_6$ is —$(CH_2)_m$—X wherein m is 1, 2 or 3 and one —$CH_2$— moiety within —$(CH_2)_m$— may optionally be replaced by

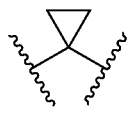

and X is hydroxy.
In some preferred embodiments $R_6$ is —$(CH_2)_m$—X wherein m is 1, 2 or 3 and one —$CH_2$— moiety within —$(CH_2)_m$ may optionally be replaced by

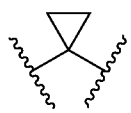

and X is $C_1$-$C_3$ alkoxy.
In some preferred embodiments $R_6$ is —$(CH_2)_m$—X wherein m is 1, 2 or 3 and one —$CH_2$— moiety within —$(CH_2)_m$ may optionally be replaced by

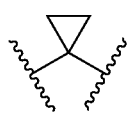

and X is cyano.
In some preferred embodiments $R_6$ is —$(CH_2)_m$—X wherein m is 1, 2 or 3 and one —$CH_2$— moiety within —$(CH_2)_m$ may optionally be replaced by

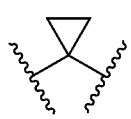

and X is —N=CH(NHCN)($NH_2$) or —NH—C(pyrrolidin-1-yl)=NCN.
In some preferred embodiments $R_6$ is —$(CH_2)_m$—X wherein m is 1, 2 or 3 and one —$CH_2$— moiety within —$(CH_2)_m$ may optionally be replaced by

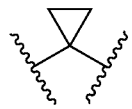

and X is 5- or 6-membered heteroaryl optionally substituted with one methyl group.
In some preferred embodiments $R_6$ is —$(CH_2)_m$—X wherein m is 1, 2 or 3 and one —$CH_2$— moiety within —$(CH_2)_m$ may optionally be replaced by

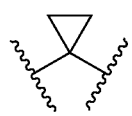

and X is phenyl.
In some preferred embodiments $R_6$ is —$(CH_2)_m$—X wherein m is 1, 2 or 3 and one —$CH_2$— moiety within —$(CH_2)_m$ may optionally be replaced by

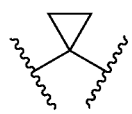

and X is —$SO_2$—$R_7$ wherein $R_7$ is as defined above.
In some preferred embodiments $R_6$ is —$(CH_2)_m$—X wherein m is 1, 2 or 3 and one —$CH_2$— moiety within —$(CH_2)_m$ may optionally be replaced by

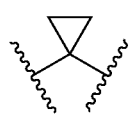

and X is —$NR_8R_9$ wherein $R_8$ and $R_9$ are as defined above.
In some preferred embodiments $R_6$ is —$(CH_2)_m$—X wherein m is 1, 2 or 3 and one —$CH_2$— moiety within —$(CH_2)_m$— may optionally be replaced by

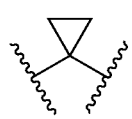 [SMILES: *C1(*)CC1]

and X is —$CO_2R_{10}$ wherein $R_{10}$ is as defined above.
In some preferred embodiments $R_6$ is —$(CH_2)_m$—X wherein m is 1, 2 or 3 and one —$CH_2$— moiety within —$(CH_2)_m$ may optionally be replaced by

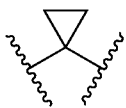

and X is —CH(CO$_2$R$_{10}$)$_2$ wherein R$_{10}$ is as defined above.

In some preferred embodiments R$_6$ is —(CH$_2$)$_m$—X wherein m is 1, 2 or 3 and one —CH$_2$— moiety within —(CH$_2$)$_m$ may optionally be replaced by

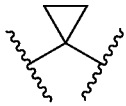

and X is —CONR$_{11}$R$_{12}$ wherein R$_{11}$ and R$_{12}$ are as defined above.

In some preferred embodiments R$_6$ is —(CH$_2$)$_m$—X wherein m is 1, 2 or 3 and one —CH$_2$— moiety within (CH$_2$)$_m$ may optionally be replaced by

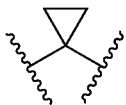

and X is-NR$_{13}$COR$_{14}$ wherein R$_{13}$ and R$_{14}$ are as defined above.

R$_6$ is preferably —(CH$_2$)$_m$—X wherein m is 1, 2 or 3 and one —CH$_2$— moiety within —(CH$_2$)$_m$ may optionally be replaced by

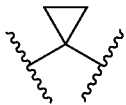

and X is hydroxy, ethoxy, cyano, —N═C(NHCN)(NH$_2$), —NH—C(pyrrolidin-1-yl)═NCN, 1-methylimidazol-2-yl, 3-methyl-1,2,4-oxadiazol-5-yl, tetrazol-5-yl, pyridin-2-yl, pyridin-3-yl, pyridin-4-yl, phenyl, —SO$_2$—R$_7$, —NR$_8$R$_9$, —COOR$_{10}$, —CH(COOR$_{10}$)$_2$, —CONR$_{11}$R$_{12}$ or —NR$_3$COR$_{14}$;

wherein:

R$_7$ is methyl;

R$_8$ is hydrogen or methyl;

R$_9$ is hydrogen, methyl, cyclopropylmethyl, benzyl, 2-hydroxyethyl, 2,2,2-trifluoroethyl, 2-methylsulfonylethyl, 1-cyclohexylethyl, isopropyl, butyl, cyclopropyl, cyclobutyl, cyclopentyl, tetrahydrofuran-3-yl, (tetrahydrofuran-2-yl)methyl, (1,1-dioxido)tetrahydrothiopyran-4-yl, (tetrahydro-2H-pyran-4-yl)methyl, pyridin-2-yl, pyridin-3-yl, tetrahydropyran-3-yl, cyclohexyl, (pyridin-2-yl)methyl or (1-methylpyrazol-4-yl)methyl;

or R$_8$ and R$_9$ combine together with the N atom to which they are attached to form a pyrrolidinyl, piperidinyl, 4-methylsulfonyl-piperidinyl, 4,4-difluoro-piperidinyl or morpholinyl group;

R$_{10}$ is hydrogen, methyl or ethyl;

R$_{11}$ is hydrogen or methyl;

R$_{12}$ is hydrogen, methyl, cyanomethyl, cyclopropylmethyl, benzyl, (pyridin-2-yl)methyl, (pyridin-3-yl)methyl, (N-t-Boc-pyrrolidin-2-yl)methyl, 2-hydroxyethyl, 2-methoxyethyl, 2,2,2-trifluoroethyl, 2-methylsulfonylethyl, 1-cyclohexylethyl, 2-(pyridin-2-yl)ethyl, 2-(1H-pyrazol-1-yl)ethyl, 2-(4,4-difluoropiperidin-1-yl)ethyl, propyl, isopropyl, 3-(N,N-dimethylamino)propyl, 3-(morpholin-1-yl)propyl, butyl, cyclopropyl, 1-cyanocyclopropyl, cyclobutyl, cyclopentyl, 2-hydroxycyclopentyl, 2-hydroxymethylcyclopentyl, 2-oxocyclopentyl, cyclohexyl, 2-hydroxycyclohexyl, 4-hydroxycyclohexyl, cyano, methylsulfonyl, CH$_2$COOEt, tetrahydrofuran-3-yl, 2-oxotetrahydrofuran-3-yl, tetrahydropyran-3-yl, tetrahydropyran-4-yl, (1,1-dioxido)tetrahydrothiopyran-4-yl, 1,3,4-thiadiazol-2-yl, pyridin-2-yl, pyridin-3-yl, CH$_2$CH(NH$_2$)(COOH), CH(CH$_3$)CONH$_2$, oxazol-2-yl, (pyrazine-2-yl)methyl, oxetan-3-yl, (tetrahydrofuran-2-yl)methyl, (1-methylpyrazol-4-yl)methyl, thiazol-2-yl, 2-oxopyrrolidin-3-yl, 2-cyanocyclopentyl, isoxazol-4-yl, 3-methyl-1,2,4-oxadiazol-5-yl, (tetrahydropyran-4-yl)methyl, 2-oxopiperidin-3-yl, 1-methylpyrazol-4-yl, isothiazol-4-yl, 1-methyl-2-oxopiperidin-5-yl, 1-methyl-2-oxopyrrolidin-3-yl, 1-methyl-5-oxopyrrolidin-3-yl or 1-methyl-2-oxopyrrolidin-4-yl;

or R$_{11}$ and R$_{12}$ combine together with the N atom to which they are attached to form a pyrrolidinyl, 2-hydroxymethyl-pyrrolidinyl, 2-methoxymethyl-pyrrolidinyl, 2-trifluoromethyl-pyrrolidinyl, 3-(fluoromethyl)pyrrolidinyl, 3-methylsulfonyl-pyrrolidinyl, N,N-dimethylpyrrolidinyl-3-carboxamide, isoxazolidin-2-yl, piperidinyl, 3-hydroxy-piperidinyl, 4-hydroxypiperidinyl, 4-methyl-piperidinyl, 4-hydroxymethylpiperidinyl, 4-amido-piperidinyl, 4-methylsulfonylpiperidinyl, 4,4-difluoro-piperidinyl, N,N-dimethylpiperidinyl-4-carboxamide, N4-methylpiperazinyl, N4-(N,N-dimethyl)acetamide-piperazinyl, N4-(pyridine-2-yl)piperazinyl, morpholinyl, thiomorpholinyl, 1-oxidothiomorpholinyl, 1,1-dioxidothiomorpholinyl, 2-oxa-7-azaspiro[4.4]nonanyl, 2-oxa-8-azaspiro[4.5]decanyl, 1,4-dioxa-8-azaspiro[4.5]decanyl group, 6,6-dimethyl-3-azabicyclo[3.1.0]hexanyl, piperazinyl, 3-oxopiperazinyl, 4-methyl-3-oxopiperazinyl, 2-cyanopyrrolidinyl, 3-cyanopyrrolidinyl, 3-fluoromethylpyrrolidinyl or 3-(N,N-dimethylacetamide)pyrrolidinyl;

R$_{13}$ is hydrogen or methyl; and

R$_{14}$ is cyclopropyl, cyclopentyl, pyrrolidin-1-yl, tetrahydropyran-4-yl or pyridin-3-yl.

R$_6$ is preferably —(CH$_2$)$_m$—X wherein m is 1, 2 or 3 and one —CH$_2$— moiety within —(CH$_2$)$_m$— may optionally be replaced by

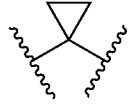

and X is hydroxy, ethoxy, cyano, —N═C(NHCN)(NH$_2$), 1-methylimidazol-2-yl, 3-methyl-1,2,4-oxadiazol-5-yl, tetrazol-5-yl, pyridin-2-yl, pyridin-3-yl, pyridin-4-yl, phenyl, —SO$_2$—R$_7$, —NR$_8$R$_9$, —COOR$_{10}$, —CH(COOR$_{10}$)$_2$, —CONR$_{11}$R$_{12}$ or —NR$_3$COR$_{14}$;

wherein:

R$_7$ is methyl;

R$_8$ is hydrogen or methyl;

R$_9$ is hydrogen, methyl, cyclopropylmethyl, benzyl, 2-hydroxyethyl, 2,2,2-trifluoroethyl, 2-methylsulfonylethyl, 1-cyclohexylethyl, isopropyl, butyl, cyclopropyl, cyclobutyl, cyclopentyl, tetrahydrofuran-3-yl, (1,1-dioxido)tetrahydrothiopyran-4-yl, pyridin-2-yl, pyridin-3-yl, tetrahydropyran-3-yl, cyclohexyl, (pyridin-2-yl)methyl or (1-methylpyrazol-4-yl)methyl;

or R$_8$ and R$_9$ combine together with the N atom to which they are attached to form a pyrrolidinyl, piperidinyl, 4-methylsulfonyl-piperidinyl, 4,4-difluoro-piperidinyl or morpholinyl group;

R$_{10}$ is hydrogen, methyl or ethyl;

R$_{11}$ is hydrogen or methyl;

R$_{12}$ is hydrogen, methyl, cyanomethyl, cyclopropylmethyl, benzyl, (pyridin-2-yl)methyl, (pyridin-3-yl)methyl, (N-t-Boc-pyrrolidin-2-yl)methyl, 2-hydroxyethyl, 2-methoxyethyl, 2,2,2-trifluoroethyl, 2-methylsulfonylethyl, 1-cyclohexylethyl, 2-(pyridin-2-yl)ethyl, 2-(1H-pyrazol-1-yl)ethyl, 2-(4,4-difluoropiperidin-1-yl)ethyl, propyl, isopropyl, 3-(N,N-dimethylamino)propyl, 3-(morpholin-1-yl)propyl, butyl, cyclopropyl, 1-cyanocyclopropyl, cyclobutyl, cyclopentyl, 2-hydroxycyclopentyl, 2-hydroxymethylcyclopentyl, 2-oxocyclopentyl, cyclohexyl, 2-hydroxycyclohexyl, 4-hydroxycyclohexyl, cyano, methylsulfonyl, CH$_2$COOEt, tetrahydrofuran-3-yl, 2-oxotetrahydrofuran-3-yl, tetrahydropyran-3-yl, tetrahydropyran-4-yl, (1,1-dioxido)tetrahydrothiopyran-4-yl, 1,3,4-thiadiazol-2-yl, pyridin-2-yl, pyridin-3-yl, CH$_2$CH(NH$_2$)(COOH), CH(CH$_3$)CONH$_2$, oxazol-2-yl, (pyrazine-2-yl)methyl, oxetan-3-yl, (tetrahydrofuran-2-yl)methyl, (1-methylpyrazol-4-yl)methyl, thiazol-2-yl, 2-oxopyrrolidin-3-yl, 2-cyanocyclopentyl, isoxazol-4-yl, 3-methyl-1,2,4-oxadiazol-5-yl, (tetrahydropyran-4-yl)methyl, 2-oxopiperidin-3-yl, 1-methylpyrazol-4-yl, isothiazol-4-yl, 1-methyl-2-oxopiperidin-5-yl, 1-methyl-2-oxopyrrolidin-3-yl or 1-methyl-2-oxopyrrolidin-4-yl;

or R$_{11}$ and R$_{12}$ combine together with the N atom to which they are attached to form a pyrrolidinyl, 2-hydroxymethyl-pyrrolidinyl, 2-methoxymethyl-pyrrolidinyl, 2-trifluoromethyl-pyrrolidinyl, 3-methylsulfonyl-pyrrolidinyl, piperidinyl, 3-hydroxy-piperidinyl, 4-hydroxy-piperidinyl, 4-methyl-piperidinyl, 4-hydroxymethyl-piperidinyl, 4-amido-piperidinyl, 4-methylsulfonyl-piperidinyl, 4,4-difluoro-piperidinyl, N4-methyl-piperazinyl, N4-(N,N-dimethyl)acetamide-piperazinyl, N4-(pyridine-2-yl)piperazinyl, morpholinyl, thiomorpholinyl, 1-oxidothiomorpholinyl, 1,1-dioxidothiomorpholinyl, 2-oxa-7-azaspiro[4.4]nonanyl, 2-oxa-8-azaspiro[4.5]decanyl, 1,4-dioxa-8-azaspiro[4.5]decanyl group, 6,6-dimethyl-3-azabicyclo[3.1.0]hexanyl, piperazinyl, 3-oxopiperazinyl, 4-methyl-3-oxopiperazinyl, 2-cyanopyrrolidinyl, 3-cyanopyrrolidinyl, 3-fluoromethylpyrrolidinyl or 3-(N,N-dimethylacetamide)pyrrolidinyl;

R$_{13}$ is hydrogen or methyl; and

R$_{14}$ is cyclopropyl, cyclopentyl, pyrrolidin-1-yl, tetrahydropyran-4-yl or pyridin-3-yl.

R$_6$ is preferably —(CH$_2$)$_m$—X wherein m is 1, 2 or 3 and one —CH$_2$— moiety within —(CH$_2$)$_m$ may optionally be replaced by

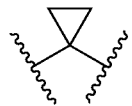

and X is hydroxy, ethoxy, cyano, —N=C(NHCN)(NH$_2$), 1-methylimidazol-2-yl, 3-methyl-1,2,4-oxadiazol-5-yl, tetrazol-5-yl, pyridin-2-yl, pyridin-3-yl, pyridin-4-yl, phenyl, —SO$_2$—R$_7$, —NR$_8$R$_9$, —COOR$_{10}$, —CH(COOR$_{10}$)$_2$, —CONR$_{11}$R$_{12}$ or —NR$_{13}$COR$_{14}$;

wherein:

R$_7$ is methyl;

R$_8$ is hydrogen or methyl;

R$_9$ is hydrogen, methyl, cyclopropylmethyl, benzyl, 2-hydroxyethyl, 2,2,2-trifluoroethyl, 2-methylsulfonylethyl, 1-cyclohexylethyl, isopropyl, butyl, cyclopropyl, cyclobutyl, cyclopentyl, tetrahydrofuran-3-yl, (1,1-dioxido)tetrahydrothiopyran-4-yl, pyridin-2-yl or pyridin-3-yl;

or R$_8$ and R$_9$ combine together with the N atom to which they are attached to form a pyrrolidinyl, piperidinyl, 4-methylsulfonyl-piperidinyl, 4,4-difluoro-piperidinyl or morpholinyl group;

R$_{10}$ is hydrogen, methyl or ethyl;

R$_{11}$ is hydrogen or methyl;

R$_{12}$ is hydrogen, methyl, cyanomethyl, cyclopropylmethyl, benzyl, (pyridin-2-yl)methyl, (pyridin-3-yl)methyl, (N-t-Boc-pyrrolidin-2-yl)methyl, 2-hydroxyethyl, 2-methoxyethyl, 2,2,2-trifluoroethyl, 2-methylsulfonylethyl, 1-cyclohexylethyl, 2-(pyridin-2-yl)ethyl, 2-(1H-pyrazol-1-yl)ethyl, 2-(4,4-difluoropiperidin-1-yl)ethyl, propyl, isopropyl, 3-(N,N-dimethylamino)propyl, 3-(morpholin-1-yl)propyl, butyl, cyclopropyl, 1-cyanocyclopropyl, cyclobutyl, cyclopentyl, 2-hydroxycyclopentyl, 2-hydroxymethylcyclopentyl, 2-oxocyclopentyl, cyclohexyl, 2-hydroxycyclohexyl, 4-hydroxycyclohexyl, cyano, methylsulfonyl, CH$_2$COOEt, tetrahydrofuran-3-yl, 2-oxotetrahydrofuran-3-yl, tetrahydropyran-3-yl, tetrahydropyran-4-yl, (1,1-dioxido)tetrahydrothiopyran-4-yl, 1,3,4-thiadiazol-2-yl, pyridin-2-yl, pyridin-3-yl, CH$_2$CH(NH$_2$)(COOH) or CH(CH$_3$)CONH$_2$;

or R$_{11}$ and R$_{12}$ combine together with the N atom to which they are attached to form a pyrrolidinyl, 2-hydroxymethyl-pyrrolidinyl, 2-methoxymethyl-pyrrolidinyl, 2-trifluoromethyl-pyrrolidinyl, 3-methylsulfonyl-pyrrolidinyl, piperidinyl, 3-hydroxy-piperidinyl, 4-hydroxy-piperidinyl, 4-methyl-piperidinyl, 4-hydroxymethyl-piperidinyl, 4-amido-piperidinyl, 4-methylsulfonyl-piperidinyl, 4,4-difluoro-piperidinyl, N4-methyl-piperazinyl, N4-(N,N-dimethyl)acetamide-piperazinyl, N4-(pyridine-2-yl)piperazinyl, morpholinyl, thiomorpholinyl, 1-oxidothiomorpholinyl, 1,1-dioxidothiomorpholinyl, 2-oxa-7-azaspiro[4.4]nonanyl, 2-oxa-8-azaspiro[4.5]decanyl or 1,4-dioxa-8-azaspiro[4.5]decanyl group;

R$_{13}$ is hydrogen or methyl; and

R$_{14}$ is cyclopropyl, cyclopentyl, pyrrolidin-1-yl, tetrahydropyran-4-yl or pyridin-3-yl.

R$_6$ is preferably —(CH$_2$)$_m$—X wherein m is 1 or 2 and X is —NR$_8$R$_9$, or —CONR$_{11}$R$_{12}$;

wherein:

R$_8$ is hydrogen or methyl;

R$_9$ is 5- or 6-membered heterocyclyl optionally substituted with one or two oxo substituents;

or $R_8$ and $R_9$ combine together with the N atom to which they are attached to form a 5- or 6-membered N-heterocyclyl group optionally substituted with one substituent selected from methyl, trifluoromethyl, hydroxy, hydroxymethyl, methoxymethyl, methylsulfonyl, amido, (N,N-dimethyl)acetamide and pyridyl or with one or two substituents selected from fluoro and oxo;

Rn is hydrogen or methyl;

$R_{12}$ is 4-, 5- or 6-membered heterocyclyl optionally substituted with one or two substituents selected from oxo and methyl;

or $R_{11}$ and $R_{12}$ combine together with the N atom to which they are attached to form a 5- or 6-membered N-heterocyclyl group optionally substituted with one substituent selected from monofluoromethyl, trifluoromethyl, hydroxy, hydroxymethyl, methoxymethyl, methylsulfonyl, cyano, amido, (N,N-dimethyl)acetamide and pyridyl, or with one or two substituents selected from fluoro, methyl and oxo.

$R_6$ is most preferably —$(CH_2)_m$—X wherein m is 2 or 3 and X is —$NR_8R_9$;

wherein:

$R_8$ is hydrogen; and $R_9$ is 5- or 6-membered heterocyclyl;

or $R_8$ and $R_9$ combine together with the N atom to which they are attached to form a 5- or 6-membered N-heterocyclyl group.

B5. Substituent A

A is selected from the group consisting of $C_5$-$C_7$ cycloalkyl, furanyl, thiophenyl, methylthiophenyl and

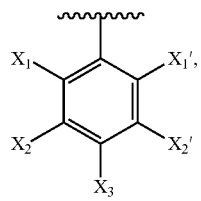

wherein:

$X_1$ is hydrogen, halo or methyl;

$X_1'$ is hydrogen or halo;

$X_2$ is hydrogen, halo or methyl;

$X_2'$ is hydrogen or halo; and $X_3$ is hydrogen or fluoro.

Preferably A is

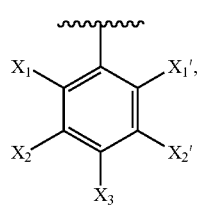

wherein $X_1$, $X_1'$, $X_2$, $X_2'$ and $X_3$ are as defined above.

More preferably A is

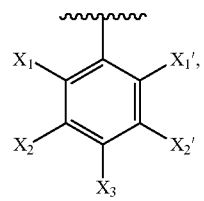

wherein:

$X_1$ is hydrogen, fluoro or chloro;

$X_1'$ is hydrogen, fluoro or chloro;

$X_2$ is hydrogen, fluoro, chloro or bromo;

$X_2'$ is hydrogen, fluoro, chloro or bromo; and $X_3$ is hydrogen or fluoro.

In one preferred embodiment not all of $X_1$, $X_1'$, $X_2$, $X_2'$ and $X_3$ are hydrogen.

Preferably A is selected from the group consisting of

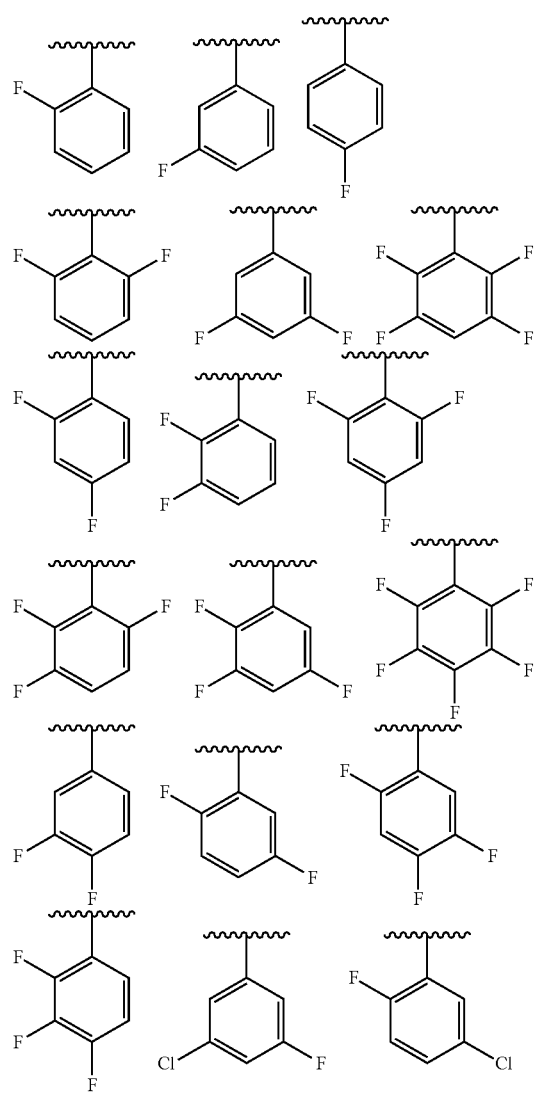

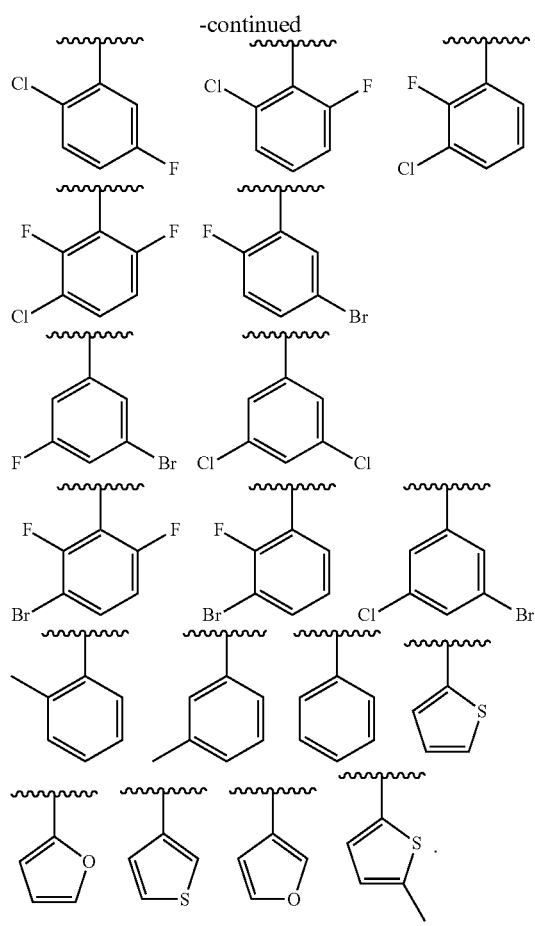
More preferably A is selected from the group consisting of
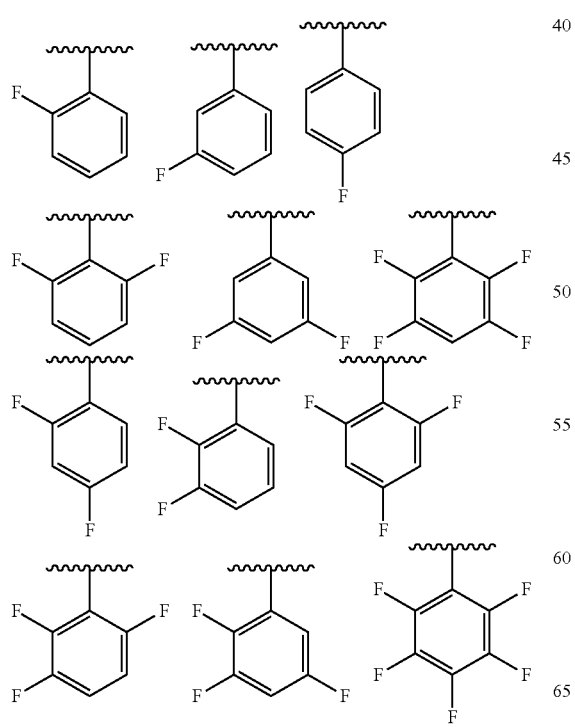
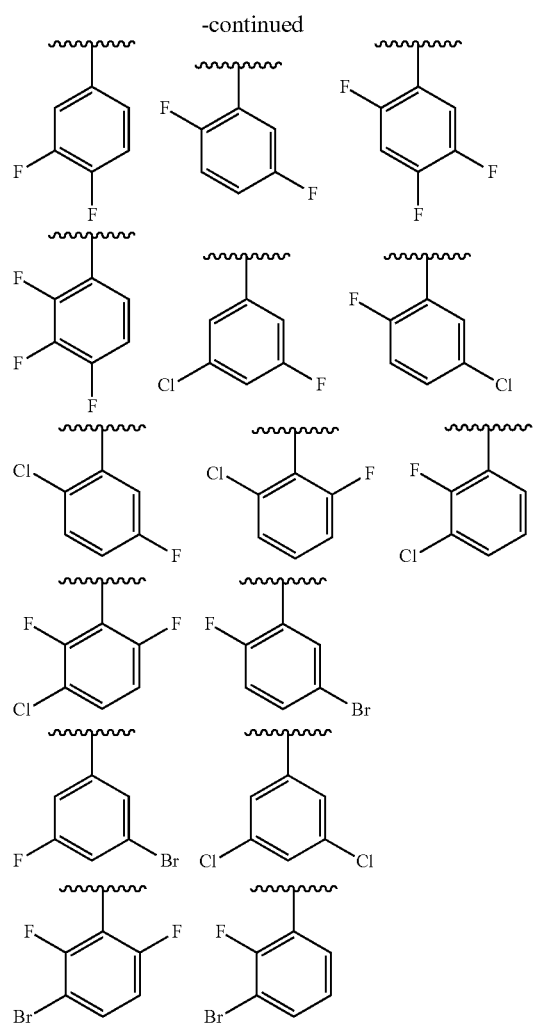
Even more preferably A is selected from the group consisting of
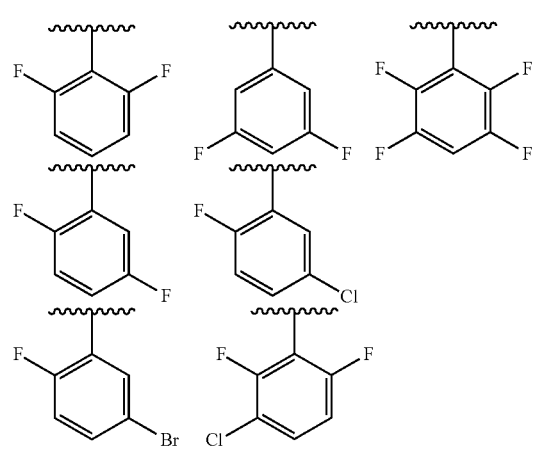

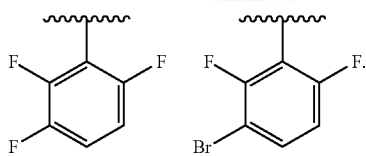

Most preferably A is selected from the group consisting of

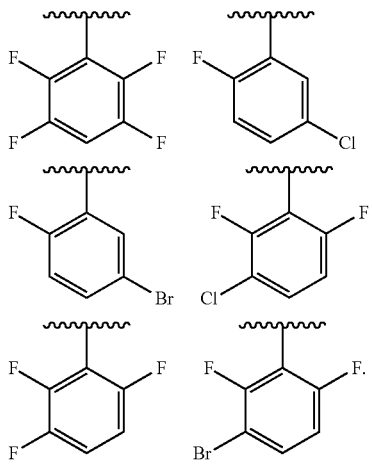

B6. Specific Embodiments of Compounds of Formula I

Various embodiments of substituents $R_1$, $R_4$, $R_5$, $R_6$, A, X, $X_1$, $X_1'$, $X_2$, $X_2'$ and $X_3$ have been discussed in B1 to B5 above. These "substituent" embodiments can be combined with any of the "core structure" embodiments, discussed in B0 above, to form further embodiments of compounds of formula Ia. All embodiments of compounds of formula Ia formed by combining the "substituent" embodiments and "core structure" embodiments, discussed above, are within the scope of Applicants' invention, and some preferred further embodiments of the compounds of formula Ia are provided below.

In some embodiments of formula Ia structures of formula If, Ii, and Ij are highly preferred

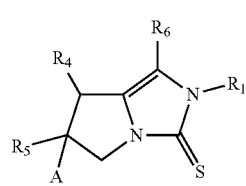 (If)

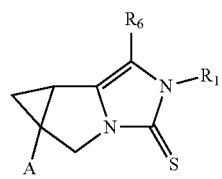 (Ii)

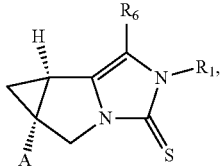 (Ij)

wherein:
$R_1$ is selected from the group consisting of hydrogen, $C_1$-$C_6$ alkyl and partially or fully deuterated $C_1$-$C_6$ alkyl;
$R_4$ (if present) is selected from the group consisting of hydrogen and methyl;
$R_5$ (if present) is hydrogen;
$R_6$ is selected from the group consisting of —COOH, —CHO,
or —(CH$_2$)$_m$—X wherein m is 1, 2 or 3 and one —CH$_2$— moiety within —(CH$_2$)$_m$— may optionally be replaced by

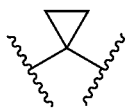 [SMILES: *C1(*)CC1]

and X is hydroxy, ethoxy, cyano, —N═C(NHCN)(NH$_2$), —NH—C(pyrrolidin-1-yl)═NCN, 1-methylimidazol-2-yl, 3-methyl-1,2,4-oxadiazol-5-yl, tetrazol-5-yl, pyridin-2-yl, pyridin-3-yl, pyridin-4-yl, phenyl,
—SO$_2$—R$_7$, —NR$_8$R$_9$, —COOR$_{10}$, —CH(COOR$_{10}$)$_2$, —CONR$_{11}$R$_{12}$ or —NR$_3$COR$_{14}$;
wherein:
$R_7$ is methyl;
$R_8$ is hydrogen or methyl;
$R_9$ is hydrogen, methyl, cyclopropylmethyl, benzyl, 2-hydroxyethyl, 2,2,2-trifluoroethyl, 2-methylsulfonylethyl, 1-cyclohexylethyl, isopropyl, butyl, cyclopropyl, cyclobutyl, cyclopentyl, tetrahydrofuran-3-yl, (tetrahydrofuran-2-yl)methyl, (1,1-dioxido) tetrahydrothiopyran-4-yl, (tetrahydro-2H-pyran-4-yl)methyl, pyridin-2-yl, pyridin-3-yl, tetrahydropyran-3-yl, cyclohexyl, (pyridine-2-yl) methyl or (1-methylpyrazol-4-yl)methyl;
or $R_8$ and $R_9$ combine together with the N atom to which they are attached to form a pyrrolidinyl, piperidinyl, 4-methylsulfonyl-piperidinyl, 4,4-difluoro-piperidinyl or morpholinyl group;
$R_{10}$ is hydrogen, methyl or ethyl;
$R_{11}$ is hydrogen or methyl;
$R_{12}$ is hydrogen, methyl, cyanomethyl, cyclopropylmethyl, benzyl, (pyridin-2-yl)methyl, (pyridin-3-yl) methyl, (N-t-Boc-pyrrolidin-2-yl)methyl, 2-hydroxyethyl, 2-methoxyethyl, 2,2,2-trifluoroethyl, 2-methylsulfonylethyl, 1-cyclohexylethyl, 2-(pyridin-2-yl)ethyl, 2-(1H-pyrazol-1-yl)ethyl, 2-(4,4-difluoropiperidin-1-yl)ethyl, propyl, isopropyl, 3-(N,N-dimethylamino)propyl, 3-(morpholin-1-yl)propyl, butyl, cyclopropyl, 1-cyanocyclopropyl, cyclobutyl, cyclopentyl, 2-hydroxycyclopentyl, 2-hydroxymethylcyclopentyl, 2-oxocyclopentyl, cyclohexyl, 2-hydroxycyclohexyl, 4-hydroxycyclohexyl, cyano, methylsulfonyl, CH$_2$COOEt, tetrahydrofuran-3-yl, 2-oxotetrahydrofuran-3-yl, tetrahydropyran-3-yl, tetrahydropyran-4-yl, (1,1-dioxido)tetrahydrothiopyran-4-yl, 1,3,4-thiadiazol-2-yl, pyridin-2-yl, pyridin-3-yl, CH₂CH(NH₂)(COOH), CH(CH₃)CONH₂, oxazol-2-yl, (pyrazine-2-yl)methyl, oxetan-3-yl, (tetrahydrofuran-2-yl)methyl, (1-methylpyrazol-4-yl)methyl, thiazol-2-yl, 2-oxopyrrolidin-3-yl, 2-cyanocyclopentyl, isoxazol-4-yl, 3-methyl-1,2,4-oxadiazol-5-yl, (tetrahydropyran-4-yl)methyl, 2-oxopiperidin-3-yl, 1-methylpyrazol-4-yl, isothiazol-4-yl, 1-methyl-2-oxopiperidin-5-yl, 1-methyl-2-oxopyrrolidin-3-yl, 1-methyl-5-oxopyrrolidin-3-yl or 1-methyl-2-oxopyrrolidin-4-yl;

or $R_{11}$ and $R_{12}$ combine together with the N atom to which they are attached to form a pyrrolidinyl, 2-hydroxymethyl-pyrrolidinyl, 2-methoxymethyl-pyrrolidinyl, 2-trifluoromethyl-pyrrolidinyl, 3-(fluoromethyl)pyrrolidinyl, 3-methylsulfonyl-pyrrolidinyl, N,N-dimethylpyrrolidinyl-3-carboxamide, isoxazolidin-2-yl, piperidinyl, 3-hydroxy-piperidinyl, 4-hydroxy-piperidinyl, 4-methyl-piperidinyl, 4-hydroxymethyl-piperidinyl, 4-amido-piperidinyl, 4-methylsulfonyl-piperidinyl, 4,4-difluoro-piperidinyl, N,N-dimethylpiperidinyl-4-carboxamide, N4-methyl-piperazinyl, N4-(N,N-dimethyl)acetamide-piperazinyl, N4-(pyridine-2-yl)piperazinyl, morpholinyl, thiomorpholinyl, 1-oxidothiomorpholinyl, 1,1-dioxidothiomorpholinyl, 2-oxa-7-azaspiro[4.4]nonanyl, 2-oxa-8-azaspiro[4.5]decanyl, 1,4-dioxa-8-azaspiro[4.5]decanyl group, 6,6-dimethyl-3-azabicyclo[3.1.0]hexanyl, piperazinyl, 3-oxopiperazinyl, 4-methyl-3-oxopiperazinyl, 2-cyanopyrrolidinyl, 3-cyanopyrrolidinyl, 3-fluoromethylpyrrolidinyl or 3-(N,N-dimethylacetamide)pyrrolidinyl;

$R_{13}$ is hydrogen or methyl; and $R_{14}$ is cyclopropyl, cyclopentyl, pyrrolidin-1-yl, tetrahydropyran-4-yl or pyridin-3-yl; and A is

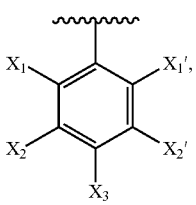

wherein:
$X_1$ is hydrogen, halo or methyl;
$X_1'$ is hydrogen or halo;
$X_2$ is hydrogen, halo or methyl;
$X_2'$ is hydrogen or halo; and
$X_3$ is hydrogen or fluoro.

In some embodiments of formula Ia structures of formula If, Ii, and Ij are highly preferred

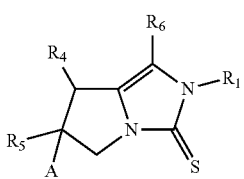 (If)

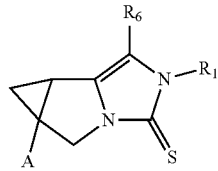 (Ii)

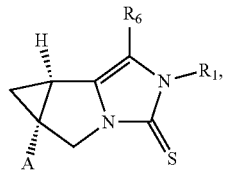 (Ij)

wherein:
$R_1$ is selected from the group consisting of hydrogen, $C_1$-$C_6$ alkyl and partially or fully deuterated $C_1$-$C_6$ alkyl;

$R_4$ (if present) is selected from the group consisting of hydrogen and methyl;

$R_5$ (if present) is hydrogen;

$R_6$ is selected from the group consisting of —COOH, —CHO, or —(CH₂)$_m$—X wherein m is 1, 2 or 3 and one —CH₂— moiety within —(CH₂)$_m$ may optionally be replaced by

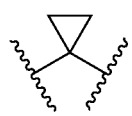

and X is hydroxy, ethoxy, cyano, —N=C(NHCN)(NH₂), —NH—C(pyrrolidin-1-yl)=NCN, 1-methylimidazol-2-yl, 3-methyl-1,2,4-oxadiazol-5-yl, tetrazol-5-yl, pyridin-2-yl, pyridin-3-yl, pyridin-4-yl, phenyl, —SO₂—$R_7$, —N$R_8R_9$, —COO$R_{10}$, —CH(COO$R_{10}$)₂, —CON$R_{11}R_{12}$ or —N$R_{13}$CO$R_{14}$;

wherein:
$R_7$ is methyl;
$R_8$ is hydrogen or methyl;
$R_9$ is hydrogen, methyl, cyclopropylmethyl, benzyl, 2-hydroxyethyl, 2,2,2-trifluoroethyl, 2-methylsulfonylethyl, 1-cyclohexylethyl, isopropyl, butyl, cyclopropyl, cyclobutyl, cyclopentyl, tetrahydrofuran-3-yl, (1,1-dioxido)tetrahydrothiopyran-4-yl, pyridin-2-yl, pyridin-3-yl, tetrahydropyran-3-yl, cyclohexyl, (pyridine-2-yl)methyl or (1-methylpyrazol-4-yl)methyl;

or $R_8$ and $R_9$ combine together with the N atom to which they are attached to form a pyrrolidinyl, piperidinyl, 4-methylsulfonyl-piperidinyl, 4,4-difluoro-piperidinyl or morpholinyl group;

$R_{10}$ is hydrogen, methyl or ethyl;
$R_{11}$ is hydrogen or methyl;
$R_{12}$ is hydrogen, methyl, cyanomethyl, cyclopropylmethyl, benzyl, (pyridin-2-yl)methyl, (pyridin-3-yl)methyl, (N-t-Boc-pyrrolidin-2-yl)methyl, 2-hydroxyethyl, 2-methoxyethyl, 2,2,2-trifluoroethyl, 2-methylsulfonylethyl, 1-cyclohexylethyl, 2-(pyridin-2-yl)ethyl, 2-(1H-pyrazol-1-yl)ethyl, 2-(4,4-difluoropiperidin-1-yl)ethyl, propyl, isopropyl, 3-(N,N-dimethylamino)propyl, 3-(morpholin-1-yl)propyl, butyl, cyclopropyl, 1-cyanocyclopropyl, cyclobutyl, cyclopentyl, 2-hydroxycyclopentyl, 2-hydroxymethylcyclopentyl, 2-oxocyclopentyl, cyclohexyl, 2-hydroxycyclohexyl, 4-hydroxycyclohexyl, cyano, methylsulfonyl, $CH_2COOEt$, tetrahydrofuran-3-yl, 2-oxotetrahydrofuran-3-yl, tetrahydropyran-3-yl, tetrahydropyran-4-yl, (1,1-dioxido)tetrahydrothiopyran-4-yl, 1,3,4-thiadiazol-2-yl, pyridin-2-yl, pyridin-3-yl, $CH_2CH(NH_2)(COOH)$, $CH(CH_3)CONH_2$, oxazol-2-yl, (pyrazine-2-yl)methyl, oxetan-3-yl, (tetrahydrofuran-2-yl)methyl, (1-methylpyrazol-4-yl)methyl, thiazol-2-yl, 2-oxopyrrolidin-3-yl, 2-cyanocyclopentyl, isoxazol-4-yl, 3-methyl-1,2,4-oxadiazol-5-yl, (tetrahydropyran-4-yl)methyl, 2-oxopiperidin-3-yl, 1-methylpyrazol-4-yl, isothiazol-4-yl, 1-methyl-2-oxopiperidin-5-yl, 1-methyl-2-oxopyrrolidin-3-yl or 1-methyl-2-oxopyrrolidin-4-yl;

- or $R_1$ and $R_{12}$ combine together with the N atom to which they are attached to form a pyrrolidinyl, 2-hydroxymethyl-pyrrolidinyl, 2-methoxymethyl-pyrrolidinyl, 2-trifluoromethyl-pyrrolidinyl, 3-methylsulfonyl-pyrrolidinyl, piperidinyl, 3-hydroxy-piperidinyl, 4-hydroxy-piperidinyl, 4-methyl-piperidinyl, 4-hydroxymethyl-piperidinyl, 4-amido-piperidinyl, 4-methylsulfonyl-piperidinyl, 4,4-difluoro-piperidinyl, N4-methyl-piperazinyl, N4-(N,N-dimethyl)acetamide-piperazinyl, N4-(pyridine-2-yl)piperazinyl, morpholinyl, thiomorpholinyl, 1-oxidothiomorpholinyl, 1,1-dioxidothiomorpholinyl, 2-oxa-7-azaspiro[4.4]nonanyl, 2-oxa-8-azaspiro[4.5]decanyl, 1,4-dioxa-8-azaspiro[4.5]decanyl group, 6,6-dimethyl-3-azabicyclo[3.1.0]hexanyl, piperazinyl, 3-oxopiperazinyl, 4-methyl-3-oxopiperazinyl, 2-cyanopyrrolidinyl, 3-cyanopyrrolidinyl, 3-fluoromethylpyrrolidinyl or 3-(N,N-dimethylacetamide)pyrrolidinyl;
- $R_{13}$ is hydrogen or methyl; and
- $R_{14}$ is cyclopropyl, cyclopentyl, pyrrolidin-1-yl, tetrahydropyran-4-yl or pyridin-3-yl; and A is

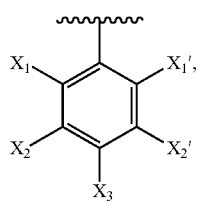

wherein:
- $X_1$ is hydrogen, halo or methyl;
- $X_1'$ is hydrogen or halo;
- $X_2$ is hydrogen, halo or methyl;
- $X_2'$ is hydrogen or halo; and
- $X_3$ is hydrogen or fluoro.

In some embodiments of formula Ia structures of formula If, Ii, and Ij are highly preferred

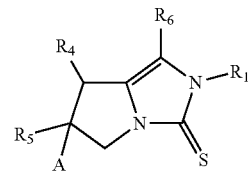

(If)

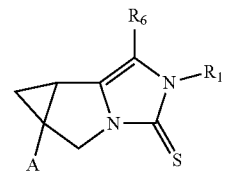

(Ii)

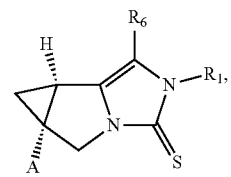

(Ij)

wherein:
- $R_1$ is selected from the group consisting of hydrogen, $C_1$-$C_6$ alkyl and partially or fully deuterated $C_1$-$C_6$ alkyl.
- $R_4$ (if present) is selected from the group consisting of hydrogen and methyl.
- $R_5$ (if present) is hydrogen.
- $R_6$ is selected from the group consisting of —COOH, —CHO,
- or —$(CH_2)_m$—X wherein m is 1, 2 or 3 and one —$CH_2$— moiety within —$(CH_2)_m$ may optionally be replaced by

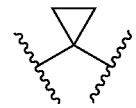

and X is hydroxy, ethoxy, cyano, —N=C(NHCN)(NH_2), —NH—C(pyrrolidin-1-yl)=NCN, 1-methylimidazol-2-yl, 3-methyl-1,2,4-oxadiazol-5-yl, tetrazol-5-yl, pyridin-2-yl, pyridin-3-yl, pyridin-4-yl, phenyl, —$SO_2$—$R_7$, —$NR_8R_9$, —$COOR_{10}$, —$CH(COOR_{10})_2$, —$CONR_{11}R_{12}$ or —$NR_{13}COR_{14}$;
wherein:
- $R_7$ is methyl;
- $R_8$ is hydrogen or methyl;
- $R_9$ is hydrogen, methyl, cyclopropylmethyl, benzyl, 2-hydroxyethyl, 2,2,2-trifluoroethyl, 2-methylsulfonylethyl, 1-cyclohexylethyl, isopropyl, butyl, cyclopropyl, cyclobutyl, cyclopentyl, tetrahydrofuran-3-yl, (1,1-dioxido)tetrahydrothiopyran-4-yl, pyridin-2-yl or pyridin-3-yl;
- or $R_8$ and $R_9$ combine together with the N atom to which they are attached to form a pyrrolidinyl, piperidinyl, 4-methylsulfonyl-piperidinyl, 4,4-difluoro-piperidinyl or morpholinyl group;
- $R_{10}$ is hydrogen, methyl or ethyl;
- $R_{11}$ is hydrogen or methyl;
- $R_{12}$ is hydrogen, methyl, cyanomethyl, cyclopropylmethyl, benzyl, (pyridin-2-yl)methyl, (pyridin-3-yl)

methyl, (N-t-Boc-pyrrolidin-2-yl)methyl, 2-hydroxyethyl, 2-methoxyethyl, 2,2,2-trifluoroethyl, 2-methylsulfonylethyl, 1-cyclohexylethyl, 2-(pyridin-2-yl)ethyl, 2-(1H-pyrazol-1-yl)ethyl, 2-(4,4-difluoropiperidin-1-yl)ethyl, propyl, isopropyl, 3-(N,N-dimethylamino)propyl, 3-(morpholin-1-yl)propyl, butyl, cyclopropyl, 1-cyanocyclopropyl, cyclobutyl, cyclopentyl, 2-hydroxycyclopentyl, 2-hydroxymethylcyclopentyl, 2-oxocyclopentyl, cyclohexyl, 2-hydroxycyclohexyl, 4-hydroxycyclohexyl, cyano, methylsulfonyl, $CH_2COOEt$, tetrahydrofuran-3-yl, 2-oxotetrahydrofuran-3-yl, tetrahydropyran-3-yl, tetrahydropyran-4-yl, (1,1-dioxido)tetrahydrothiopyran-4-yl, 1,3,4-thiadiazol-2-yl, pyridin-2-yl, pyridin-3-yl, $CH_2CH(NH_2)(COOH)$ or $CH(CH_3)CONH_2$;

or $R_{11}$ and $R_{12}$ combine together with the N atom to which they are attached to form a pyrrolidinyl, 2-hydroxymethyl-pyrrolidinyl, 2-methoxymethyl-pyrrolidinyl, 2-trifluoromethyl-pyrrolidinyl, 3-methylsulfonyl-pyrrolidinyl, piperidinyl, 3-hydroxy-piperidinyl, 4-hydroxy-piperidinyl, 4-methyl-piperidinyl, 4-hydroxymethyl-piperidinyl, 4-amido-piperidinyl, 4-methylsulfonyl-piperidinyl, 4,4-difluoro-piperidinyl, N4-methyl-piperazinyl, N4-(N,N-dimethyl)acetamide-piperazinyl, N4-(pyridine-2-yl)piperazinyl, morpholinyl, thiomorpholinyl, 1-oxidothiomorpholinyl, 1,1-dioxidothiomorpholinyl, 2-oxa-7-azaspiro[4.4]nonanyl, 2-oxa-8-azaspiro[4.5]decanyl or 1,4-dioxa-8-azaspiro[4.5]decanyl group;

$R_{13}$ is hydrogen or methyl; and $R_{14}$ is cyclopropyl, cyclopentyl, pyrrolidin-1-yl, tetrahydropyran-4-yl or pyridin-3-yl A is

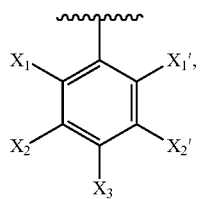

wherein:

$X_1$ is hydrogen, halo or methyl;

$X_1'$ is hydrogen or halo;

$X_2$ is hydrogen, halo or methyl;

$X_2'$ is hydrogen or halo; and $X_3$ is hydrogen or fluoro.

In other embodiments of formula Ia structures of formula If, Ii, and Ij are highly preferred

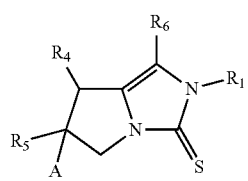
(If)

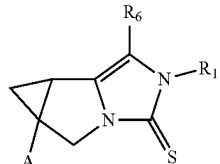
(Ii)

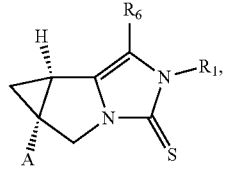
(Ij)

wherein:

$R_1$ is selected from the group consisting of hydrogen and methyl;

$R_4$ (if present) is hydrogen;

$R_5$ (if present) is hydrogen;

$R_6$ is $-(CH_2)_m-X$ wherein m is 1 or 2 and X is $-NR_8R_9$, or $-CONR_{11}R_{12}$;

wherein:

$R_8$ is hydrogen or methyl;

$R_9$ is 5- or 6-membered heterocyclyl optionally substituted with one or two oxo substituents;

or $R_8$ and $R_9$ combine together with the N atom to which they are attached to form a 5- or 6-membered N-heterocyclyl group optionally substituted with one substituent selected from methyl, trifluoromethyl, hydroxy, hydroxymethyl, methoxymethyl, methylsulfonyl, amido, (N,N-dimethyl)acetamide and pyridyl or with one or two substituents selected from fluoro and oxo;

$R_{11}$ is hydrogen or methyl;

$R_{12}$ is 4-, 5- or 6-membered heterocyclyl optionally substituted with one or two substituents selected from oxo and methyl;

or $R_{11}$ and $R_{12}$ combine together with the N atom to which they are attached to form a 5- or 6-membered N-heterocyclyl group optionally substituted with one substituent selected from monofluoromethyl, trifluoromethyl, hydroxy, hydroxymethyl, methoxymethyl, methylsulfonyl, cyano, amido, (N,N-dimethyl)acetamide and pyridyl, or with one or two substituents selected from fluoro, methyl and oxo; and A is selected from the group consisting of

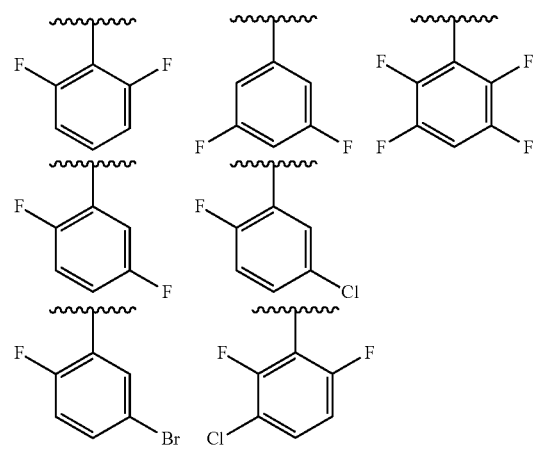

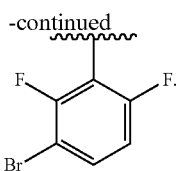

In other embodiments of formula Ia structures of formula If are highly preferred

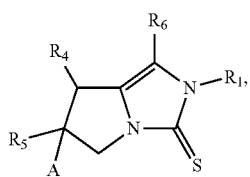

wherein:
R$_1$ is selected from the group consisting of hydrogen and methyl;
R$_4$ is hydrogen;
R$_5$ is hydrogen;
R$_6$ is —(CH$_2$)$_m$—X wherein m is 2 or 3 and X is —NR$_8$R$_9$;
wherein:
R$_8$ is hydrogen; and
R$_9$ is 5- or 6-membered heterocyclyl;
or R$_8$ and R$_9$ combine together with the N atom to which they are attached to form a 5- or 6-membered N-heterocyclyl group; and
A is selected from the group consisting of

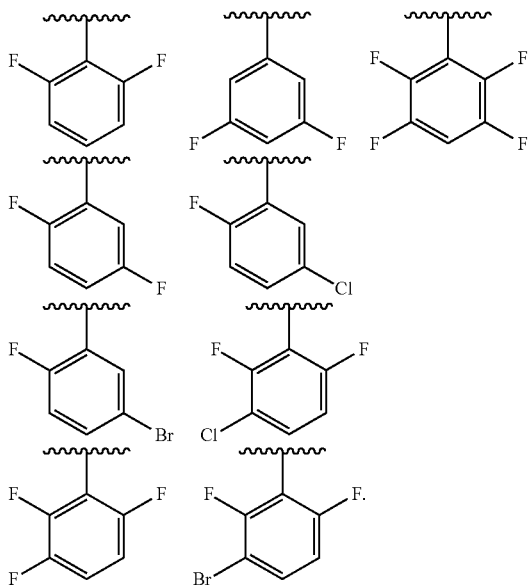

Especially preferred embodiments of compounds of formula Ia are described in Examples 1 to 478 below. Where these examples describe the preparation of a compound of formula Ia in the form of a pharmaceutically acceptable salt or solvate, it will be appreciated that the present invention also relates to said compound in the form of the corresponding free acid or free base. Similarly, where these examples describe the preparation of a compound of formula Ia in the form of a free acid or free base, it will be appreciated that the present invention also relates to said compound in the form of a pharmaceutically acceptable salt or solvate thereof.

The non-salt, non-solvated forms of Examples 1 to 478 are listed below. The invention also relates to the pharmaceutically acceptable salts or solvates of each of these individual compounds. Should any of these compounds exist as tautomers, each tautomeric form, and mixtures thereof, are contemplated as included in the present invention.

Example 1: (S)-ethyl 2-(6-(3,5-difluorophenyl)-3-thioxo-3,5,6,7-tetrahydro-2H-pyrrolo[1,2-c]imidazol-1-yl)acetate Example 2: (S)-ethyl 2-(6-(2,5-difluorophenyl)-3-thioxo-3,5,6,7-tetrahydro-2H-pyrrolo[1,2-c]imidazol-1-yl)acetate Example 3: (S)-2-(6-(2,5-difluorophenyl)-3-thioxo-3,5,6,7-tetrahydro-2H-pyrrolo[1,2-c]imidazol-1-yl)acetic acid Example 4: Methyl 2-((5aS,6aR)-5a-(2,5-difluorophenyl)-3-thioxo-2,3,5,5a,6,6a-hexahydrocyclopropa[3,4]pyrrolo[1,2-c]imidazol-1-yl)acetate Example 5: methyl 2-((5aS,6aR)-5a-(3,5-difluorophenyl)-3-thioxo-2,3,5,5a,6,6a-hexahydrocyclopropa[3,4]pyrrolo[1,2-c]imidazol-1-yl)acetate Example 6: 2-((5aS,6aR)-5a-(2,5-difluorophenyl)-3-thioxo-2,3,5,5a,6,6a-hexahydrocyclopropa[3,4]pyrrolo[1,2-c]imidazol-1-yl)acetic acid Example 7: 2-((5aS,6aR)-5a-(3,5-difluorophenyl)-3-thioxo-2,3,5,5a,6,6a-hexahydrocyclopropa[3,4]pyrrolo[1,2-c]imidazol-1-yl)acetic acid.

Example 8: (5aS,6aR)-5a-(3,5-difluorophenyl)-1-(2-hydroxyethyl)-5,5a,6,6a-tetrahydrocyclopropa[3,4]pyrrolo[1,2-c]imidazole-3(2H)-thione Example 9: (S)-2-(6-(3,5-difluorophenyl)-3-thioxo-3,5,6,7-tetrahydro-2H-pyrrolo[1,2-c]imidazol-1-yl)-1-morpholinoethanone Example 10: (S)-2-(6-(2,3,5,6-tetrafluorophenyl)-3-thioxo-3,5,6,7-tetrahydro-2H-pyrrolo[1,2-c]imidazol-1-yl)acetic acid Example 11: (S)-2-(6-(3,5-difluorophenyl)-3-thioxo-3,5,6,7-tetrahydro-2H-pyrrolo[1,2-c]imidazol-1-yl)acetic acid Example 12: (S)-2-(6-(3-bromo-2,6-difluorophenyl)-3-thioxo-2,5,6,7-tetrahydro-3H-pyrrolo[1,2-c]imidazol-1-yl)acetic acid Example 13: (R)-2-(6-(3-bromo-2,6-difluorophenyl)-3-thioxo-2,5,6,7-tetrahydro-3H-pyrrolo[1,2-c]imidazol-1-yl)acetic acid Example 14: (R)-2-(6-(2,5-difluorophenyl)-3-thioxo-2,5,6,7-tetrahydro-3H-pyrrolo[1,2-c]imidazol-1-yl)acetic acid Example 15: (R)-2-(6-(2,3,5,6-tetrafluorophenyl)-3-thioxo-2,5,6,7-tetrahydro-3H-pyrrolo[1,2-c]imidazol-1-yl)acetic acid Example 16: (S)-2-(6-(5-bromo-2-fluorophenyl)-3-thioxo-2,5,6,7-tetrahydro-3H-pyrrolo[1,2-c]imidazol-1-yl)acetic acid Example 17: (R)-2-(6-(5-chloro-2-fluorophenyl)-3-thioxo-2,5,6,7-tetrahydro-3H-pyrrolo[1,2-c]imidazol-1-yl)acetic acid Example 18: (R)-2-(6-(2,6-difluorophenyl)-3-thioxo-2,5,6,7-tetrahydro-3H-pyrrolo[1,2-c]imidazol-1-yl)acetic acid Example 19: (S)—N-cyano-2-(6-(2,3,5,6-tetrafluorophenyl)-3-thioxo-3,5,6,7-tetrahydro-2H-pyrrolo[1,2-c]imidazol-1-yl)acetamide Example 20: (S)-2-(6-(3-bromo-2,6-difluorophenyl)-3-thioxo-2,5,6,7-tetrahydro-3H-pyrrolo[1,2-c]imidazol-1-yl)-N-(methylsulfonyl)acetamide Example 21: (S)-2-(6-(5-bromo-2-fluorophenyl)-3-thioxo-2,5,6,7-tetrahydro-3H-pyrrolo[1,2-c]imidazol-1-yl)-N-(methylsulfonyl)acetamide Example 22: 2-((R)-6-(3-bromo-2,6-difluorophenyl)-3-thioxo-2,5,6,7-tetrahydro-3H-pyrrolo[1,2-c]imidazol-1-yl)-N-(2-oxotetrahydrofuran-3-yl)acetamide Example 23: (R)—N-(methylsulfonyl)-2-(6-(2,3,5,6-tetrafluorophenyl)-3-thioxo-3,5,6,7-tetrahydro-2H-pyrrolo[1,2-c]imidazol-1-yl)acetamide Example 24: (R)-2-(6-(2,5-difluorophenyl)-3-thioxo-2,5,6,7-tetrahydro-3H-pyrrolo[1,2-c]imidazol-1-yl)-N-(methylsulfonyl)acetamide Example 25: Ethyl (R)-(2-(6-(2,3,5,6-tetrafluorophenyl)-3-thioxo-2,5,6,7-tetrahydro-3H-pyrrolo[1,2-c]imidazol-1-yl)acetyl)glycinate Example 26: (S)-2-(2-((R)-6-(2,3,5,6-tetrafluorophenyl)-3-thioxo-2,5,6,7-tetrahydro-3H-pyrrolo[1,2-c]imidazol-1-yl)acetamido)propanamide Example 27: (R)—N-(cyanomethyl)-2-(6-(2,3,5,6-tetrafluorophenyl)-3-thioxo-2,5,6,7-tetrahydro-3H-pyrrolo[1,2-c]imidazole-1-yl)acetamide Example 28: N-((1r,4R)-4-hydroxycyclohexyl)-2-((R)-6-(2,3,5,6-tetrafluorophenyl)-3-thioxo-2,5,6,7-tetrahydro-3H-pyrrolo[1,2-c]imidazol-1-yl)acetamide Example 29: N-(2-hydroxycyclohexyl)-2-((R)-6-(2,3,5,6-tetrafluorophenyl)-3-thioxo-2,5,6,7-tetrahydro-3H-pyrrolo[1,2-c]imidazol-1-yl)acetamide Example 30: (R)—N,N-dimethyl-2-(6-(2,3,5,6-tetrafluorophenyl)-3-thioxo-2,5,6,7-tetrahydro-3H-pyrrolo[1,2-c]imidazol-1-yl)acetamide Example 31: (S)-2-amino-3-(2-((R)-6-(2,3,5,6-tetrafluorophenyl)-3-thioxo-3,5,6,7-tetrahydro-2H-pyrrolo[1,2-c]imidazol-1-yl)acetamido)propanoic acid Example 32: ((R)—N-cyclopentyl-2-(6-(2,3,5,6-tetrafluorophenyl)-3-thioxo-3,5,6,7-tetrahydro-2H-pyrrolo[1,2-c]imidazol-1-yl)acetamide Example 33: 2-((5aS,6aR)-5a-(3,5-difluorophenyl)-3-thioxo-2,3,5,5a,6,6a-hexahydrocyclopropa[3,4]pyrrolo[1,2-c]imidazol-1-yl)acetamide Example 34: 2-((S)-6-(3-bromo-2,6-difluorophenyl)-3-thioxo-3,5,6,7-tetrahydro-2H-pyrrolo[1,2-c]imidazol-1-yl)-N-(2-oxocyclopentyl)acetamide Example 35: (5aS,6aR)-1-(2-aminoethyl)-5a-(3,5-difluorophenyl)-5,5a,6,6a-tetrahydrocyclopropa[3,4]pyrrolo[1,2-c]imidazole-3(2H)-thione Example 36: 2-((5aS,6aR)-5a-(2,5-difluorophenyl)-3-thioxo-2,3,5,5a,6,6a-hexahydrocyclopropa[3,4]pyrrolo[1,2-c]imidazol-1-yl)acetonitrile Example 37: N-benzyl-2-((5aS,6aR)-5a-(2,5-difluorophenyl)-3-thioxo-2,3,5,5a,6,6a-hexahydrocyclopropa[3,4]pyrrolo[1,2-c]imidazol-1-yl)-N-methylacetamide Example 38: N-butyl-2-((5aS,6aR)-5a-(2,5-difluorophenyl)-3-thioxo-2,3,5,5a,6,6a-hexahydrocyclopropa[3,4]pyrrolo[1,2-c]imidazol-1-yl)-N-methylacetamide Example 39: (5aS,6aR)-1-(2-(butyl(methyl)amino)ethyl)-5a-(2,5-difluorophenyl)-5,5a,6,6a-tetrahydrocyclopropa[3,4]pyrrolo[1,2-c]imidazole-3(2H)-thione Example 40: (5aS,6aR)-1-(2-(benzyl(methyl)amino)ethyl)-5a-(2,5-difluorophenyl)-5,5a,6,6a-tetrahydrocyclopropa[3,4]pyrrolo[1,2-c]imidazole-3(2H)-thione Example 41: (5aS,6aR)-1-((1H-tetrazol-5-yl)methyl)-5a-(2,5-difluorophenyl)-5,5a,6,6a-tetrahydrocyclopropa[3,4]pyrrolo[1,2-c]imidazole-3(2H)-thione Example 42: (5aS,6aR)-5a-(2,5-difluorophenyl)-1-(2-hydroxyethyl)-5,5a,6,6a-tetrahydrocyclopropa[3,4]pyrrolo[1,2-c]imidazole-3(2H)-thione Example 43: (S)-6-(3,5-difluorophenyl)-3-thioxo-3,5,6,7-tetrahydro-2H-pyrrolo[1,2-c]imidazole-1-carboxylic acid Example 44: ethyl 2-(5a-(thiophen-2-yl)-3-thioxo-2,3,5,5a,6,6a-hexahydrocyclopropa[3,4]pyrrolo[1,2-c]imidazol-1-yl)acetate Example 45: (S)-6-(3,5-difluorophenyl)-3-thioxo-3,5,6,7-tetrahydro-2H-pyrrolo[1,2-c]imidazole-1-carbaldehyde Example 46: (S)-1-(hydroxymethyl)-6-(2,3,5,6-tetrafluorophenyl)-6,7-dihydro-2H-pyrrolo[1,2-c]imidazole-3(5H)-thione Example 47: (S)-1-(methylsulfonylmethyl)-6-(2,3,5,6-tetrafluorophenyl)-6,7-dihydro-2H-pyrrolo[1,2-c]imidazole-3(5H)-thione Example 48: (5aS,6aR)-5a-(2,5-difluorophenyl)-1-phenethyl-5,5a,6,6a-tetrahydrocyclopropa[3,4]pyrrolo[1,2-c]imidazole-3(2H)-thione Example 49: (5aS,6aR)-5a-(2,5-difluorophenyl)-1-(3-phenylpropyl)-5,5a,6,6a-tetrahydrocyclopropa[3,4]pyrrolo[1,2-c]imidazole-3(2H)-thione Example 50: (5aS,6aR)-5a-(3,5-difluorophenyl)-1-(hydroxymethyl)-5,5a,6,6a-tetrahydrocyclopropa[3,4]pyrrolo[1,2-c]imidazole-3(2H)-thione Example 51: 2-((5aS,6aR)-5a-(3-bromo-2,6-difluorophenyl)-3-thioxo-2,3,5,5a,6,6a-hexahydrocyclopropa[3,4]pyrrolo[1,2-c]imidazol-1-yl)acetic acid Example 52: 2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)acetic acid Example 53: 2-((5aS,6aR)-5a-(3-chloro-5-fluorophenyl)-3-thioxo-2,3,5,5a,6,6a-hexahydrocyclopropa[3,4]pyrrolo[1,2-c]imidazol-1-yl)acetic acid Example 54: ethyl 2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)acetate Example 55: ethyl 2-((5aS,6aR)-5a-(3-chloro-5-fluorophenyl)-3-thioxo-2,3,5,5a,6,6a-hexahydrocyclopropa[3,4]pyrrolo[1,2-c]imidazol-1-yl)acetate Example 56: (2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)acetamide Example 57: 2-((5aS,6aR)-5a-(3-bromo-2,6-difluorophenyl)-3-thioxo-2,3,5,5a,6,6a-hexahydrocyclopropa[3,4]pyrrolo[1,2-c]imidazol-1-yl)acetamide Example 58: 2-((5aS,6aR)-5a-(3-chloro-5-fluorophenyl)-3-thioxo-2,3,5,5a,6,6a-hexahydrocyclopropa[3,4]pyrrolo[1,2-c]imidazol-1-yl)acetamide Example 59: ethyl (S)-2-(6-(3-bromo-2,6-difluorophenyl)-3-thioxo-2,5,6,7-tetrahydro-3H-pyrrolo[1,2-c]imidazol-1-yl)acetate Example 60: ethyl (R)-2-(6-(3-bromo-2,6-difluorophenyl)-3-thioxo-2,5,6,7-tetrahydro-3H-pyrrolo[1,2-c]imidazol-1-yl)acetate Example 61: ethyl (R)-2-(6-(2,5-difluorophenyl)-3-thioxo-2,5,6,7-tetrahydro-3H-pyrrolo[1,2-c]imidazol-1-yl)acetate Example 62: ethyl (S)-2-(6-(5-bromo-2-fluorophenyl)-3-thioxo-2,5,6,7-tetrahydro-3H-pyrrolo[1,2-c]imidazol-1-yl)acetate Example 63: ethyl (R)-2-(6-(2,3,5,6-tetrafluorophenyl)-3-thioxo-2,5,6,7-tetrahydro-3H-pyrrolo[1,2-c]imidazol-1-yl)acetate Example 64: ethyl (R)-2-(6-(5-chloro-2-fluorophenyl)-3-thioxo-2,5,6,7-tetrahydro-3H-pyrrolo[1,2-c]imidazol-1-yl)acetate Example 65: ethyl (R)-2-(6-(2,6-difluorophenyl)-3-thioxo-2,5,6,7-tetrahydro-3H-pyrrolo[1,2-c]imidazol-1-yl)acetate Example 66: 2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)-1-morpholinoethan-1-one
Example 67: 2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)-N-isopropylacetamide
Example 68: 2-((5aS,6aR)-5a-(3-chloro-5-fluorophenyl)-3-thioxo-2,3,5,5a,6,6a-hexahydrocyclopropa[3,4]pyrrolo[1,2-c]imidazol-1-yl)-N-methylacetamide
Example 69: 2-((5aS,6aR)-5a-(3-chloro-5-fluorophenyl)-3-thioxo-2,3,5,5a,6,6a-hexahydrocyclopropa[3,4]pyrrolo[1,2-c]imidazol-1-yl)-N,N-dimethylacetamide
Example 70: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-1-(pyrrolidin-1-yl)ethan-1-one
Example 71: (R)—N-(3-(dimethylamino)propyl)-2-(6-(2,3,5,6-tetrafluorophenyl)-3-thioxo-2,5,6,7-tetrahydro-3H-pyrrolo[1,2-c]imidazol-1-yl)acetamide
Example 72: (R)—N-(2-hydroxyethyl)-2-(6-(2,3,5,6-tetrafluorophenyl)-3-thioxo-2,5,6,7-tetrahydro-3H-pyrrolo[1,2-c]imidazol-1-yl)acetamide
Example 73: (R)—N-(2-methoxyethyl)-2-(6-(2,3,5,6-tetrafluorophenyl)-3-thioxo-2,5,6,7-tetrahydro-3H-pyrrolo[1,2-c]imidazol-1-yl)acetamide
Example 74: (S)-2-(6-(5-bromo-2-fluorophenyl)-3-thioxo-2,5,6,7-tetrahydro-3H-pyrrolo[1,2-c]imidazol-1-yl)-N-cyclopentylacetamide
Example 75: 2-((R)-6-(5-chloro-2-fluorophenyl)-3-thioxo-2,5,6,7-tetrahydro-3H-pyrrolo[1,2-c]imidazol-1-yl)-N—((R)-tetrahydrofuran-3-yl)acetamide
Example 76: (R)—N-cyclopentyl-2-(6-(2,6-difluorophenyl)-3-thioxo-2,5,6,7-tetrahydro-3H-pyrrolo[1,2-c]imidazol-1-yl)acetamide
Example 77: 2-((R)-6-(2,6-difluorophenyl)-3-thioxo-2,5,6,7-tetrahydro-3H-pyrrolo[1,2-c]imidazol-1-yl)-N—((R)-tetrahydrofuran-3-yl)acetamide
Example 78: (R)—N-cyclopropyl-2-(6-(2,3,5,6-tetrafluorophenyl)-3-thioxo-2,5,6,7-tetrahydro-3H-pyrrolo[1,2-c]imidazol-1-yl)acetamide
Example 79: (R)—N-(cyclopropylmethyl)-2-(6-(2,3,5,6-tetrafluorophenyl)-3-thioxo-2,5,6,7-tetrahydro-3H-pyrrolo[1,2-c]imidazol-1-yl)acetamide
Example 80: (R)—N-cyclobutyl-2-(6-(2,3,5,6-tetrafluorophenyl)-3-thioxo-2,5,6,7-tetrahydro-3H-pyrrolo[1,2-c]imidazol-1-yl)acetamide
Example 81: (R)-1-(4-methylpiperazin-1-yl)-2-(6-(2,3,5,6-tetrafluorophenyl)-3-thioxo-2,5,6,7-tetrahydro-3H-pyrrolo[1,2-c]imidazol-1-yl)ethan-1-one
Example 82: (R)-1-(4-hydroxypiperidin-1-yl)-2-(6-(2,3,5,6-tetrafluorophenyl)-3-thioxo-2,5,6,7-tetrahydro-3H-pyrrolo[1,2-c]imidazol-1-yl)ethan-1-one
Example 83: (R)-1-(4-(hydroxymethyl)piperidin-1-yl)-2-(6-(2,3,5,6-tetrafluorophenyl)-3-thioxo-2,5,6,7-tetrahydro-3H-pyrrolo[1,2-c]imidazol-1-yl)ethan-1-one
Example 84: (S)-2-(6-(3-chloro-2,6-difluorophenyl)-3-thioxo-2,5,6,7-tetrahydro-3H-pyrrolo[1,2-c]imidazol-1-yl)-N-cyclopentylacetamide
Example 85: (R)—N,N-dimethyl-2-(4-(2-(6-(2,3,5,6-tetrafluorophenyl)-3-thioxo-2,5,6,7-tetrahydro-3H-pyrrolo[1,2-c]imidazol-1-yl)acetyl)piperazin-1-yl)acetamide
Example 86: (R)-1-(2-(6-(2,3,5,6-tetrafluorophenyl)-3-thioxo-2,5,6,7-tetrahydro-3H-pyrrolo[1,2-c]imidazol-1-yl)acetyl)piperidine-4-carboxamide
Example 87: (R)-1-(1,4-dioxa-8-azaspiro[4.5]decan-8-yl)-2-(6-(2,3,5,6-tetrafluorophenyl)-3-thioxo-2,5,6,7-tetrahydro-3H-pyrrolo[1,2-c]imidazol-1-yl)ethan-1-one
Example 88: (S)-2-(6-(3-chloro-2,6-difluorophenyl)-3-thioxo-2,5,6,7-tetrahydro-3H-pyrrolo[1,2-c]imidazol-1-yl)-N-isopropylacetamide
Example 89: (S)-2-(6-(3-chloro-2,6-difluorophenyl)-3-thioxo-2,5,6,7-tetrahydro-3H-pyrrolo[1,2-c]imidazol-1-yl)-N-(3-morpholinopropyl)acetamide
Example 90: 2-((S)-6-(3-bromo-2,6-difluorophenyl)-3-thioxo-2,5,6,7-tetrahydro-3H-pyrrolo[1,2-c]imidazol-1-yl)-N—((R)-tetrahydrofuran-3-yl)acetamide
Example 91: (S)-2-(6-(3-bromo-2,6-difluorophenyl)-3-thioxo-2,5,6,7-tetrahydro-3H-pyrrolo[1,2-c]imidazol-1-yl)-1-(4-methylpiperazin-1-yl)ethan-1-one
Example 92: (S)-2-(6-(3-bromo-2,6-difluorophenyl)-3-thioxo-2,5,6,7-tetrahydro-3H-pyrrolo[1,2-c]imidazol-1-yl)-N-butyl-N-methylacetamide
Example 93: (S)-2-(6-(3-bromo-2,6-difluorophenyl)-3-thioxo-2,5,6,7-tetrahydro-3H-pyrrolo[1,2-c]imidazol-1-yl)-N-(2-hydroxyethyl)acetamide
Example 94: (S)-2-(6-(3-bromo-2,6-difluorophenyl)-3-thioxo-2,5,6,7-tetrahydro-3H-pyrrolo[1,2-c]imidazol-1-yl)-N-cyclopropylacetamide
Example 95: (S)-2-(6-(3-bromo-2,6-difluorophenyl)-3-thioxo-2,5,6,7-tetrahydro-3H-pyrrolo[1,2-c]imidazol-1-yl)-N-(cyclopropylmethyl)acetamide
Example 96: (S)-2-(6-(3-bromo-2,6-difluorophenyl)-3-thioxo-2,5,6,7-tetrahydro-3H-pyrrolo[1,2-c]imidazol-1-yl)acetamide
Example 97: (S)-2-(6-(3-bromo-2,6-difluorophenyl)-3-thioxo-2,5,6,7-tetrahydro-3H-pyrrolo[1,2-c]imidazol-1-yl)-N-propylacetamide
Example 98: 1-((S)-2-(hydroxymethyl)pyrrolidin-1-yl)-2-((R)-6-(2,3,5,6-tetrafluorophenyl)-3-thioxo-2,5,6,7-tetrahydro-3H-pyrrolo[1,2-c]imidazol-1-yl)ethan-1-one
Example 99: (S)—N-cyclobutyl-2-(6-(2,3,5,6-tetrafluorophenyl)-3-thioxo-2,5,6,7-tetrahydro-3H-pyrrolo[1,2-c]imidazol-1-yl)acetamide
Example 100: 2-((S)-6-(3-bromo-2,6-difluorophenyl)-3-thioxo-2,5,6,7-tetrahydro-3H-pyrrolo[1,2-c]imidazol-1-yl)-1-((S)-2-(hydroxymethyl)pyrrolidin-1-yl)ethan-1-one
Example 101: (S)-2-(6-(3-bromo-2,6-difluorophenyl)-3-thioxo-2,5,6,7-tetrahydro-3H-pyrrolo[1,2-c]imidazol-1-yl)-1-(pyrrolidin-1-yl)ethan-1-one
Example 102: (S)-2-(6-(3-bromo-2,6-difluorophenyl)-3-thioxo-2,5,6,7-tetrahydro-3H-pyrrolo[1,2-c]imidazol-1-yl)-N-cyclobutylacetamide
Example 103: (S)-2-(6-(3-bromo-2,6-difluorophenyl)-3-thioxo-2,5,6,7-tetrahydro-3H-pyrrolo[1,2-c]imidazol-1-yl)-N-(2-methoxyethyl)acetamide
Example 104: (R)-1-(pyrrolidin-1-yl)-2-(6-(2,3,5,6-tetrafluorophenyl)-3-thioxo-2,5,6,7-tetrahydro-3H-pyrrolo[1,2-c]imidazol-1-yl)ethan-1-one
Example 105: (S)-1-(pyrrolidin-1-yl)-2-(6-(2,3,5,6-tetrafluorophenyl)-3-thioxo-2,5,6,7-tetrahydro-3H-pyrrolo[1,2-c]imidazol-1-yl)ethan-1-one
Example 106: (S)-2-(6-(3-chloro-2,6-difluorophenyl)-3-thioxo-2,5,6,7-tetrahydro-3H-pyrrolo[1,2-c]imidazol-1-yl)-N-(2-(pyridin-2-yl)ethyl)acetamide
Example 107: (S)-2-(6-(3-chloro-2,6-difluorophenyl)-3-thioxo-2,5,6,7-tetrahydro-3H-pyrrolo[1,2-c]imidazol-1-yl)-N-(2-methoxyethyl)acetamide
Example 108: (S)-2-(6-(3-chloro-2,6-difluorophenyl)-3-thioxo-2,5,6,7-tetrahydro-3H-pyrrolo[1,2-c]imidazol-1-yl)acetamide
Example 109: (S)-2-(6-(3-chloro-2,6-difluorophenyl)-3-thioxo-2,5,6,7-tetrahydro-3H-pyrrolo[1,2-c]imidazol-1-yl)-N-(pyridin-3-ylmethyl)acetamide Example 110: (S)-2-(6-(3-chloro-2,6-difluorophenyl)-3-thioxo-2,5,6,7-tetrahydro-3H-pyrrolo[1,2-c]imidazol-1-yl)-1-(pyrrolidin-1-yl)ethan-1-one Example 111: (S)-2-(6-(3-chloro-2,6-difluorophenyl)-3-thioxo-2,5,6,7-tetrahydro-3H-pyrrolo[1,2-c]imidazol-1-yl)-1-(4,4-difluoropiperidin-1-yl)ethan-1-one Example 112: (S)-2-(6-(3-chloro-2,6-difluorophenyl)-3-thioxo-2,5,6,7-tetrahydro-3H-pyrrolo[1,2-c]imidazol-1-yl)-N-(1,1-dioxidotetrahydro-2H-thiopyran-4-yl)acetamide Example 113: (S)-2-(6-(3-chloro-2,6-difluorophenyl)-3-thioxo-2,5,6,7-tetrahydro-3H-pyrrolo[1,2-c]imidazol-1-yl)-N-(2,2,2-trifluoroethyl)acetamide Example 114: (S)-2-(6-(3-chloro-2,6-difluorophenyl)-3-thioxo-2,5,6,7-tetrahydro-3H-pyrrolo[1,2-c]imidazol-1-yl)-N-(2-(methylsulfonyl)ethyl)acetamide Example 115: (S)-2-(6-(3-chloro-2,6-difluorophenyl)-3-thioxo-2,5,6,7-tetrahydro-3H-pyrrolo[1,2-c]imidazol-1-yl)-N-(2-(4,4-difluoropiperidin-1-yl)ethyl)acetamide Example 116: 2-((R)-6-(3-bromo-2,6-difluorophenyl)-3-thioxo-2,5,6,7-tetrahydro-3H-pyrrolo[1,2-c]imidazol-1-yl)-N—((R)-tetrahydrofuran-3-yl)acetamide Example 117: (R)-2-(6-(3-bromo-2,6-difluorophenyl)-3-thioxo-2,5,6,7-tetrahydro-3H-pyrrolo[1,2-c]imidazol-1-yl)-1-(4,4-difluoropiperidin-1-yl)ethan-1-one Example 118: (R)-2-(6-(3-bromo-2,6-difluorophenyl)-3-thioxo-2,5,6,7-tetrahydro-3H-pyrrolo[1,2-c]imidazol-1-yl)-N-(2-(methylsulfonyl)ethyl)acetamide Example 119: (R)-2-(6-(3-bromo-2,6-difluorophenyl)-3-thioxo-2,5,6,7-tetrahydro-3H-pyrrolo[1,2-c]imidazol-1-yl)-N-(2-hydroxyethyl)acetamide Example 120: 2-((R)-6-(3-bromo-2,6-difluorophenyl)-3-thioxo-2,5,6,7-tetrahydro-3H-pyrrolo[1,2-c]imidazol-1-yl)-N-(2-(hydroxymethyl)cyclopentyl)acetamide Example 121: 2-((R)-6-(3-bromo-2,6-difluorophenyl)-3-thioxo-2,5,6,7-tetrahydro-3H-pyrrolo[1,2-c]imidazol-1-yl)-1-(3-hydroxypiperidin-1-yl)ethan-1-one Example 122: tert-butyl (R)-2-((2-((S)-6-(3-bromo-2,6-difluorophenyl)-3-thioxo-2,5,6,7-tetrahydro-3H-pyrrolo[1,2-c]imidazol-1-yl)acetamido)methyl)pyrrolidine-1-carboxylate Example 123: (S)-2-(6-(3-bromo-2,6-difluorophenyl)-3-thioxo-2,5,6,7-tetrahydro-3H-pyrrolo[1,2-c]imidazol-1-yl)-1-(4-(methylsulfonyl)piperidin-1-yl)ethan-1-one Example 124: (S)-2-(6-(3-bromo-2,6-difluorophenyl)-3-thioxo-2,5,6,7-tetrahydro-3H-pyrrolo[1,2-c]imidazol-1-yl)-N-(pyridin-3-ylmethyl)acetamide Example 125: (R)-2-(6-(3-bromo-2,6-difluorophenyl)-3-thioxo-2,5,6,7-tetrahydro-3H-pyrrolo[1,2-c]imidazol-1-yl)-1-(1,1-dioxidothiomorpholino)ethan-1-one Example 126: (R)-2-(6-(3-bromo-2,6-difluorophenyl)-3-thioxo-2,5,6,7-tetrahydro-3H-pyrrolo[1,2-c]imidazol-1-yl)-1-(4-(methylsulfonyl)piperidin-1-yl)ethan-1-one Example 127: 2-((R)-6-(3-bromo-2,6-difluorophenyl)-3-thioxo-2,5,6,7-tetrahydro-3H-pyrrolo[1,2-c]imidazol-1-yl)-N—((R)-1-cyclohexylethyl)acetamide Example 128: (R)-2-(6-(3-bromo-2,6-difluorophenyl)-3-thioxo-2,5,6,7-tetrahydro-3H-pyrrolo[1,2-c]imidazol-1-yl)-N-methyl-N-(tetrahydro-2H-pyran-4-yl)acetamide Example 129: (R)—N-(1,1-dioxidotetrahydro-2H-thiopyran-4-yl)-2-(6-(2,3,5,6-tetrafluorophenyl)-3-thioxo-2,5,6,7-tetrahydro-3H-pyrrolo[1,2-c]imidazol-1-yl)acetamide Example 130: (R)-2-(6-(3-bromo-2,6-difluorophenyl)-3-thioxo-2,5,6,7-tetrahydro-3H-pyrrolo[1,2-c]imidazol-1-yl)-N-(1,1-dioxidotetrahydro-2H-thiopyran-4-yl)acetamide Example 131: (R)-2-(6-(3-bromo-2,6-difluorophenyl)-3-thioxo-2,5,6,7-tetrahydro-3H-pyrrolo[1,2-c]imidazol-1-yl)-N-(2-hydroxyethyl)-N-methylacetamide Example 132: (R)-2-(6-(3-bromo-2,6-difluorophenyl)-3-thioxo-2,5,6,7-tetrahydro-3H-pyrrolo[1,2-c]imidazol-1-yl)-N-cyclohexyl-N-methylacetamide Example 133: (R)-2-(6-(3-bromo-2,6-difluorophenyl)-3-thioxo-2,5,6,7-tetrahydro-3H-pyrrolo[1,2-c]imidazol-1-yl)-N-isopropylacetamide Example 134: (S)-2-(6-(3-chloro-2,6-difluorophenyl)-3-thioxo-2,5,6,7-tetrahydro-3H-pyrrolo[1,2-c]imidazol-1-yl)-N-methyl-N-(pyridin-3-ylmethyl)acetamide Example 135: 2-((R)-6-(3-bromo-2,6-difluorophenyl)-3-thioxo-2,5,6,7-tetrahydro-3H-pyrrolo[1,2-c]imidazol-1-yl)-1-(3-(methylsulfonyl)pyrrolidin-1-yl)ethan-1-one Example 136: (S)-2-(6-(3-bromo-2,6-difluorophenyl)-3-thioxo-2,5,6,7-tetrahydro-3H-pyrrolo[1,2-c]imidazol-1-yl)-1-(1,1-dioxidothiomorpholino)ethan-1-one Example 137: (S)-2-(6-(3-bromo-2,6-difluorophenyl)-3-thioxo-2,5,6,7-tetrahydro-3H-pyrrolo[1,2-c]imidazol-1-yl)-1-thiomorpholinoethan-1-one Example 138: 2-((S)-6-(3-bromo-2,6-difluorophenyl)-3-thioxo-2,5,6,7-tetrahydro-3H-pyrrolo[1,2-c]imidazol-1-yl)-1-(2-oxa-7-azaspiro[4.4]nonan-7-yl)ethan-1-one Example 139: (R)-2-(6-(3-bromo-2,6-difluorophenyl)-3-thioxo-2,5,6,7-tetrahydro-3H-pyrrolo[1,2-c]imidazol-1-yl)-N-(pyridin-2-ylmethyl)acetamide Example 140: (S)-2-(6-(3-bromo-2,6-difluorophenyl)-3-thioxo-2,5,6,7-tetrahydro-3H-pyrrolo[1,2-c]imidazol-1-yl)-1-morpholinoethan-1-one Example 141: (R)-2-(6-(3-bromo-2,6-difluorophenyl)-3-thioxo-2,5,6,7-tetrahydro-3H-pyrrolo[1,2-c]imidazol-1-yl)-1-morpholinoethan-1-one Example 142: N-(2-(1H-pyrazol-1-yl)ethyl)-2-((5aS,6aR)-5a-(3-chloro-2,6-difluorophenyl)-3-thioxo-2,3,5,5a,6,6a-hexahydrocyclopropa[3,4]pyrrolo[1,2-c]imidazol-1-yl)acetamide Example 143: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-(cyclopropylmethyl)acetamide Example 144: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-(cyanomethyl)acetamide Example 145: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-(2-(pyridin-2-yl)ethyl)acetamide Example 146: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-(3-(dimethylamino)propyl)acetamide Example 147: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-1-(4-(pyridin-2-yl)piperazin-1-yl)ethan-1-one Example 148: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-(tetrahydrofuran-3-yl)acetamide Example 149: 2-((5aS,6aR)-5a-(3-chloro-2,6-difluorophenyl)-3-thioxo-2,3,5,5a,6,6a-hexahydrocyclopropa[3,4]pyrrolo[1,2-c]imidazol-1-yl)-1-(4,4-difluoropiperidin-1-yl)ethan-1-one Example 150: 2-((5aS,6aR)-5a-(3-chloro-2,6-difluorophenyl)-3-thioxo-2,3,5,5a,6,6a-hexahydrocyclopropa[3,4]pyrrolo[1,2-c]imidazol-1-yl)-N-(2,2,2-trifluoroethyl)acetamide Example 151: 2-((5aS,6aR)-5a-(3-chloro-2,6-difluorophenyl)-3-thioxo-2,3,5,5a,6,6a-hexahydrocyclopropa[3,4]pyrrolo[1,2-c]imidazol-1-yl)-N-(pyridin-3-ylmethyl)acetamide Example 152: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-(2,2,2-trifluoroethyl)acetamide Example 153: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-cyclobutylacetamide Example 154: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-cyclopropylacetamide Example 155: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-cyclopentyl-N-methylacetamide Example 156: N-benzyl-2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)acetamide Example 157: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-1-morpholinoethan-1-one Example 158: 2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)-1-(piperidin-1-yl)ethan-1-one Example 159: (R)-2-(6-(3-bromo-2,6-difluorophenyl)-3-thioxo-2,5,6,7-tetrahydro-3H-pyrrolo[1,2-c]imidazol-1-yl)-N-(cyanomethyl)acetamide Example 160: 2-((R)-6-(3-bromo-2,6-difluorophenyl)-3-thioxo-2,5,6,7-tetrahydro-3H-pyrrolo[1,2-c]imidazol-1-yl)-N-((1R,2R)-2-hydroxycyclohexyl)acetamide Example 161: 2-((R)-6-(3-bromo-2,6-difluorophenyl)-3-thioxo-2,5,6,7-tetrahydro-3H-pyrrolo[1,2-c]imidazol-1-yl)-N-((1S,2S)-2-hydroxycyclopentyl)acetamide Example 162: (S)—N-(2-(1H-pyrazol-1-yl)ethyl)-2-(6-(3-chloro-2,6-difluorophenyl)-3-thioxo-2,5,6,7-tetrahydro-3H-pyrrolo[1,2-c]imidazol-1-yl)acetamide Example 163: (S)-2-(6-(3-chloro-2,6-difluorophenyl)-3-thioxo-2,5,6,7-tetrahydro-3H-pyrrolo[1,2-c]imidazol-1-yl)-N-(1,1-dioxidotetrahydro-2H-thiopyran-4-yl)-N-methylacetamide Example 164: 2-((S)-6-(3-bromo-2,6-difluorophenyl)-3-thioxo-2,5,6,7-tetrahydro-3H-pyrrolo[1,2-c]imidazol-1-yl)-1-(3-(methylsulfonyl)pyrrolidin-1-yl)ethan-1-one Example 165: (S)-2-(6-(3-bromo-2,6-difluorophenyl)-3-thioxo-2,5,6,7-tetrahydro-3H-pyrrolo[1,2-c]imidazol-1-yl)-1-(2-oxa-8-azaspiro[4.5]decan-8-yl)ethan-1-one Example 166: (S)-2-(6-(3-bromo-2,6-difluorophenyl)-3-thioxo-2,5,6,7-tetrahydro-3H-pyrrolo[1,2-c]imidazol-1-yl)-1-(1-oxidothiomorpholino)ethan-1-one Example 167: 2-((S)-6-(3-bromo-2,6-difluorophenyl)-3-thioxo-2,5,6,7-tetrahydro-3H-pyrrolo[1,2-c]imidazol-1-yl)-N-methyl-N-(tetrahydrofuran-3-yl)acetamide Example 168: (S)-2-(6-(3-chloro-2,6-difluorophenyl)-3-thioxo-2,5,6,7-tetrahydro-3H-pyrrolo[1,2-c]imidazol-1-yl)-N-(1,3,4-thiadiazol-2-yl)acetamide Example 169: (S)-2-(6-(3-chloro-2,6-difluorophenyl)-3-thioxo-2,5,6,7-tetrahydro-3H-pyrrolo[1,2-c]imidazol-1-yl)-N-(pyridin-2-yl)acetamide Example 170: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-(pyridin-2-yl)acetamide Example 171: 2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)-N-(pyridin-3-yl)acetamide Example 172: (R)-1-(2-hydroxyethyl)-6-(2,3,5,6-tetrafluorophenyl)-2,5,6,7-tetrahydro-3H-pyrrolo[1,2-c]imidazole-3-thione Example 173: (R)-6-(3-bromo-2,6-difluorophenyl)-1-(2-hydroxyethyl)-2,5,6,7-tetrahydro-3H-pyrrolo[1,2-c]imidazole-3-thione Example 174: (5aS,6aR)-5a-(5-chloro-2-fluorophenyl)-1-(2-morpholinoethyl)-5,5a,6,6a-tetrahydrocyclopropa[3,4]pyrrolo[1,2-c]imidazole-3(2H)-thione Example 175: (5aS,6aR)-5a-(5-chloro-2-fluorophenyl)-1-(2-(isopropylamino)ethyl)-5,5a,6,6a-tetrahydrocyclopropa[3,4]pyrrolo[1,2-c]imidazole-3(2H)-thione Example 176: (R)-6-(3-bromo-2,6-difluorophenyl)-1-(2-(((R)-tetrahydrofuran-3-yl)amino)ethyl)-2,5,6,7-tetrahydro-3H-pyrrolo[1,2-c]imidazole-3-thione Example 177: (R)-6-(3-bromo-2,6-difluorophenyl)-1-(2-(4,4-difluoropiperidin-1-yl)ethyl)-2,5,6,7-tetrahydro-3H-pyrrolo[1,2-c]imidazole-3-thione Example 178: (R)-6-(3-bromo-2,6-difluorophenyl)-1-(2-((1,1-dioxidotetrahydro-2H-thiopyran-4-yl)amino)ethyl)-2,5,6,7-tetrahydro-3H-pyrrolo[1,2-c]imidazole-3-thione Example 179: (R)-6-(3-bromo-2,6-difluorophenyl)-1-(2-(4-(methylsulfonyl)piperidin-1-yl)ethyl)-2,5,6,7-tetrahydro-3H-pyrrolo[1,2-c]imidazole-3-thione Example 180: (5aS,6aR)-5a-(5-bromo-2-fluorophenyl)-1-(2-((2,2,2-trifluoroethyl)amino)ethyl)-5,5a,6,6a-tetrahydrocyclopropa[3,4]pyrrolo[1,2-c]imidazole-3(2H)-thione Example 181: (S)-6-(3-bromo-2,6-difluorophenyl)-1-(2-(cyclobutylamino)ethyl)-2,5,6,7-tetrahydro-3H-pyrrolo[1,2-c]imidazole-3-thione Example 182: (R)-6-(3-bromo-2,6-difluorophenyl)-1-(2-((2-(methylsulfonyl)ethyl)amino)ethyl)-2,5,6,7-tetrahydro-3H-pyrrolo[1,2-c]imidazole-3-thione Example 183: (R)-6-(3-bromo-2,6-difluorophenyl)-1-(2-((2-hydroxyethyl)(methyl)amino)ethyl)-2,5,6,7-tetrahydro-3H-pyrrolo[1,2-c]imidazole-3-thione Example 184: (R)-6-(3-bromo-2,6-difluorophenyl)-1-(2-(((R)-1-cyclohexylethyl)amino)ethyl)-2,5,6,7-tetrahydro-3H-pyrrolo[1,2-c]imidazole-3-thione Example 185: (5aS,6aR)-5a-(5-bromo-2-fluorophenyl)-1-(2-(pyrrolidin-1-yl)ethyl)-5,5a,6,6a-tetrahydrocyclopropa[3,4]pyrrolo[1,2-c]imidazole-3(2H)-thione Example 186: (5aS,6aR)-5a-(5-bromo-2-fluorophenyl)-1-(2-((cyclopropylmethyl)amino)ethyl)-5,5a,6,6a-tetrahydrocyclopropa[3,4]pyrrolo[1,2-c]imidazole-3(2H)-thione Example 187: (5aS,6aR)-5a-(5-bromo-2-fluorophenyl)-1-(2-(cyclopropylamino)ethyl)-5,5a,6,6a-tetrahydrocyclopropa[3,4]pyrrolo[1,2-c]imidazole-3(2H)-thione Example 188: (5aS,6aR)-5a-(5-bromo-2-fluorophenyl)-1-(2-(cyclobutylamino)ethyl)-5,5a,6,6a-tetrahydrocyclopropa[3,4]pyrrolo[1,2-c]imidazole-3(2H)-thione Example 189: (5aS,6aR)-1-(2-(benzylamino)ethyl)-5a-(5-chloro-2-fluorophenyl)-5,5a,6,6a-tetrahydrocyclopropa[3,4]pyrrolo[1,2-c]imidazole-3(2H)-thione Example 190: (5aS,6aR)-5a-(5-bromo-2-fluorophenyl)-1-(2-(cyclopentyl(methyl)amino)ethyl)-5,5a,6,6a-tetrahydrocyclopropa[3,4]pyrrolo[1,2-c]imidazole-3(2H)-thione Example 191: (5aS,6aR)-5a-(5-bromo-2-fluorophenyl)-1-(2-morpholinoethyl)-5,5a,6,6a-tetrahydrocyclopropa[3,4]pyrrolo[1,2-c]imidazole-3(2H)-thione Example 192: (5aS,6aR)-5a-(5-bromo-2-fluorophenyl)-1-(2-(pyridin-2-ylamino)ethyl)-5,5a,6,6a-tetrahydrocyclopropa[3,4]pyrrolo[1,2-c]imidazole-3(2H)-thione Example 193: (S)-6-(3-chloro-2,6-difluorophenyl)-1-(2-(methylamino)ethyl)-2,5,6,7-tetrahydro-3H-pyrrolo[1,2-c]imidazole-3-thione Example 194: (5aS,6aR)-5a-(5-chloro-2-fluorophenyl)-1-(2-(piperidin-1-yl)ethyl)-5,5a,6,6a-tetrahydrocyclopropa[3,4]pyrrolo[1,2-c]imidazole-3(2H)-thione Example 195: (S)-6-(3-bromo-2,6-difluorophenyl)-1-(2-morpholinoethyl)-2,5,6,7-tetrahydro-3H-pyrrolo[1,2-c]imidazole-3-thione Example 196: (S)-6-(3-chloro-2,6-difluorophenyl)-1-(2-morpholinoethyl)-2,5,6,7-tetrahydro-3H-pyrrolo[1,2-c]imidazole-3-thione Example 197: (5aS,6aR)-5a-(5-chloro-2-fluorophenyl)-1-(2-(pyridin-3-ylamino)ethyl)-5,5a,6,6a-tetrahydrocyclopropa[3,4]pyrrolo[1,2-c]imidazole-3(2H)-thione Example 198: (R)-1-(2-(pyrrolidin-1-yl)ethyl)-6-(2,3,5,6-tetrafluorophenyl)-2,5,6,7-tetrahydro-3H-pyrrolo[1,2-c]imidazole-3-thione Example 199: (R)-1-(2-morpholinoethyl)-6-(2,3,5,6-tetrafluorophenyl)-2,5,6,7-tetrahydro-3H-pyrrolo[1,2-c]imidazole-3-thione Example 200: (R)-diethyl 2-((6-(2,3,5,6-tetrafluorophenyl)-3-thioxo-3,5,6,7-tetrahydro-2H-pyrrolo[1,2-c]imidazol-1-yl)methyl)malonate Example 201: (R)-2-((6-(2,3,5,6-tetrafluorophenyl)-3-thioxo-2,5,6,7-tetrahydro-3H-pyrrolo[1,2-c]imidazol-1-yl)methyl)malonic acid Example 202: (R)-3-(6-(2,3,5,6-tetrafluorophenyl)-3-thioxo-2,5,6,7-tetrahydro-3H-pyrrolo[1,2-c]imidazol-1-yl)propanoic acid Example 203: (R)—N-(cyclopropylmethyl)-3-(6-(2,3,5,6-tetrafluorophenyl)-3-thioxo-2,5,6,7-tetrahydro-3H-pyrrolo[1,2-c]imidazol-1-yl)propanamide Example 204: (R)-1-(pyrrolidin-1-yl)-3-(6-(2,3,5,6-tetrafluorophenyl)-3-thioxo-2,5,6,7-tetrahydro-3H-pyrrolo[1,2-c]imidazol-1-yl)propan-1-one Example 205: (R)-1-morpholino-3-(6-(2,3,5,6-tetrafluorophenyl)-3-thioxo-2,5,6,7-tetrahydro-3H-pyrrolo[1,2-c]imidazol-1-yl)propan-1-one Example 206: (R)-1-(4,4-difluoropiperidin-1-yl)-3-(6-(2,3,5,6-tetrafluorophenyl)-3-thioxo-2,5,6,7-tetrahydro-3H-pyrrolo[1,2-c]imidazol-1-yl)propan-1-one Example 207: (R)-1-(piperidin-1-yl)-3-(6-(2,3,5,6-tetrafluorophenyl)-3-thioxo-2,5,6,7-tetrahydro-3H-pyrrolo[1,2-c]imidazol-1-yl)propan-1-one Example 208: (R)-1-(4-methylpiperidin-1-yl)-3-(6-(2,3,5,6-tetrafluorophenyl)-3-thioxo-2,5,6,7-tetrahydro-3H-pyrrolo[1,2-c]imidazol-1-yl)propan-1-one Example 209: (R)-1-(morpholinomethyl)-6-(2,3,5,6-tetrafluorophenyl)-6,7-dihydro-2H-pyrrolo[1,2-c]imidazole-3(5H)-thione Example 210: (R)-1-(pyrrolidin-1-ylmethyl)-6-(2,3,5,6-tetrafluorophenyl)-2,5,6,7-tetrahydro-3H-pyrrolo[1,2-c]imidazole-3-thione Example 211: (R)-1-(((2-hydroxyethyl)(methyl)amino)methyl)-6-(2,3,5,6-tetrafluorophenyl)-2,5,6,7-tetrahydro-3H-pyrrolo[1,2-c]imidazole-3-thione Example 212: (R)-1-(2-(pyridin-3-yl)ethyl)-6-(2,3,5,6-tetrafluorophenyl)-6,7-dihydro-2H-pyrrolo[1,2-c]imidazole-3(5H)-thione Example 213: (R)-1-(2-(pyridin-2-yl)ethyl)-6-(2,3,5,6-tetrafluorophenyl)-2,5,6,7-tetrahydro-3H-pyrrolo[1,2-c]imidazole-3-thione Example 214: (R)-6-(3-bromo-2,6-difluorophenyl)-1-(2-(pyridin-3-yl)ethyl)-2,5,6,7-tetrahydro-3H-pyrrolo[1,2-c]imidazole-3-thione Example 215: (S)-6-(3-chloro-2,6-difluorophenyl)-1-(2-(pyridin-3-yl)ethyl)-2,5,6,7-tetrahydro-3H-pyrrolo[1,2-c]imidazole-3-thione Example 216: (R)-1-(3-ethoxypropyl)-6-(2,3,5,6-tetrafluorophenyl)-2,5,6,7-tetrahydro-3H-pyrrolo[1,2-c]imidazole-3-thione Example 217: (R)-1-(2-(1-methyl-1H-imidazol-2-yl)ethyl)-6-(2,3,5,6-tetrafluorophenyl)-2,5,6,7-tetrahydro-3H-pyrrolo[1,2-c]imidazole-3-thione Example 218: (R)-1-(2-(pyridin-4-yl)ethyl)-6-(2,3,5,6-tetrafluorophenyl)-2,5,6,7-tetrahydro-3H-pyrrolo[1,2-c]imidazole-3-thione Example 219: (R)-1-(3-(pyrrolidin-1-yl)propyl)-6-(2,3,5,6-tetrafluorophenyl)-2,5,6,7-tetrahydro-3H-pyrrolo[1,2-c]imidazole-3-thione Example 220: (S)—N-((6-(3-chloro-2,6-difluorophenyl)-3-thioxo-3,5,6,7-tetrahydro-2H-pyrrolo[1,2-c]imidazol-1-yl)methyl)cyclopropanecarboxamide Example 221: (S)—N-((6-(3-chloro-2,6-difluorophenyl)-3-thioxo-3,5,6,7-tetrahydro-2H-pyrrolo[1,2-c]imidazol-1-yl)methyl)cyclopropanecarboxamide Example 222: (S)—N-((6-(3-chloro-2,6-difluorophenyl)-3-thioxo-2,5,6,7-tetrahydro-3H-pyrrolo[1,2-c]imidazol-1-yl)methyl)tetrahydro-2H-pyran-4-carboxamide Example 223: (S)—N-((6-(3-chloro-2,6-difluorophenyl)-3-thioxo-2,5,6,7-tetrahydro-3H-pyrrolo[1,2-c]imidazol-1-yl)methyl)nicotinamide Example 224: 2-{[(6S)-6-(3-bromo-2,6-difluorophenyl)-3-thioxo-2,5,6,7-tetrahydro-3H-pyrrolo[1,2-c]imidazol-1-yl]methyl}-1-cyanoguanidine Example 225: (S,Z)—N-((6-(3-bromo-2,6-difluorophenyl)-3-thioxo-2,5,6,7-tetrahydro-3H-pyrrolo[1,2-c]imidazol-1-yl)methyl)-N'-cyanopyrrolidine-1-carboximidamide Example 226: (S)—N-(2-(6-(3-chloro-2,6-difluorophenyl)-3-thioxo-2,5,6,7-tetrahydro-3H-pyrrolo[1,2-c]imidazol-1-yl)ethyl)-N-methylnicotinamide Example 227: (S)—N-(2-(6-(3-chloro-2,6-difluorophenyl)-3-thioxo-2,5,6,7-tetrahydro-3H-pyrrolo[1,2-c]imidazol-1-yl)ethyl)-N-methylpyrrolidine-1-carboxamide Example 228: (S)-6-(3-chloro-2,6-difluorophenyl)-1-((3-methyl-1,2,4-oxadiazol-5-yl)methyl)-6,7-dihydro-2H-pyrrolo[1,2-c]imidazole-3(5H)-thione Example 229: (R)-2-(2-methyl-6-(2,3,5,6-tetrafluorophenyl)-3-thioxo-3,5,6,7-tetrahydro-2H-pyrrolo[1,2-c]imidazol-1-yl)acetic acid Example 230: (S)-2-(6-(5-chloro-2-fluorophenyl)-2-methyl-3-thioxo-2,5,6,7-tetrahydro-3H-pyrrolo[1,2-c]imidazol-1-yl)acetic acid Example 231: 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)acetic acid Example 232: 2-((S)-6-(3-bromo-2,6-difluorophenyl)-2-methyl-3-thioxo-2,5,6,7-tetrahydro-3H-pyrrolo[1,2-c]imidazol-1-yl)-N—((R)-tetrahydrofuran-3-yl)acetamide Example 233: (S)-2-(6-(3-bromo-2,6-difluorophenyl)-2-methyl-3-thioxo-2,5,6,7-tetrahydro-3H-pyrrolo[1,2-c]imidazol-1-yl)-1-morpholinoethan-1-one Example 234: 1-((S)-6-(3-bromo-2,6-difluorophenyl)-2-methyl-3-thioxo-2,5,6,7-tetrahydro-3H-pyrrolo[1,2-c]imidazol-1-yl)-N—((R)-tetrahydrofuran-3-yl)cyclopropane-1-carboxamide Example 235: (S)-2-(6-(3-bromo-2,6-difluorophenyl)-2-methyl-3-thioxo-2,5,6,7-tetrahydro-3H-pyrrolo[1,2-c]imidazol-1-yl)-1-(1,1-dioxidothiomorpholino)ethan-1-one Example 236: (S)-2-(6-(3-chloro-2,6-difluorophenyl)-2-methyl-3-thioxo-2,5,6,7-tetrahydro-3H-pyrrolo[1,2-c]imidazol-1-yl)-N-isopropylacetamide Example 237: (R)-2-(2-methyl-3-thioxo-6-(2,3,6-trifluorophenyl)-2,5,6,7-tetrahydro-3H-pyrrolo[1,2-c]imidazol-1-yl)-1-morpholinoethan-1-one
Example 238: (S)-1-(6-(3-bromo-2,6-difluorophenyl)-2-methyl-3-thioxo-2,5,6,7-tetrahydro-3H-pyrrolo[1,2-c]imidazol-1-yl)-N-(2-(methylsulfonyl)ethyl)cyclopropane-1-carboxamide
Example 239: (R)—N-(1,1-dioxidotetrahydro-2H-thiopyran-4-yl)-2-(2-methyl-3-thioxo-6-(2,3,6-trifluorophenyl)-2,5,6,7-tetrahydro-3H-pyrrolo[1,2-c]imidazol-1-yl)acetamide
Example 240: (S)-2-(6-(3-bromo-2,6-difluorophenyl)-2-methyl-3-thioxo-2,5,6,7-tetrahydro-3H-pyrrolo[1,2-c]imidazol-1-yl)acetamide
Example 241: 2-((S)-6-(3-bromo-2,6-difluorophenyl)-2-methyl-3-thioxo-2,5,6,7-tetrahydro-3H-pyrrolo[1,2-c]imidazol-1-yl)-1-((S)-2-(hydroxymethyl)pyrrolidin-1-yl)ethan-1-one
Example 242: (R)-2-(2-methyl-6-(2,3,5,6-tetrafluorophenyl)-3-thioxo-2,5,6,7-tetrahydro-3H-pyrrolo[1,2-c]imidazol-1-yl)-1-morpholinoethan-1-one
Example 243: 2-((R)-2-methyl-6-(2,3,5,6-tetrafluorophenyl)-3-thioxo-2,5,6,7-tetrahydro-3H-pyrrolo[1,2-c]imidazol-1-yl)-N—((R)-tetrahydrofuran-3-yl)acetamide
Example 244: 2-((R)-2-methyl-3-thioxo-6-(2,3,6-trifluorophenyl)-2,5,6,7-tetrahydro-3H-pyrrolo[1,2-c]imidazol-1-yl)-N-((R)-tetrahydrofuran-3-yl)acetamide
Example 245: (R)-2-(6-(5-chloro-2-fluorophenyl)-2-methyl-3-thioxo-2,5,6,7-tetrahydro-3H-pyrrolo[1,2-c]imidazol-1-yl)-N-cyclopentylacetamide
Example 246: 2-((R)-6-(5-chloro-2-fluorophenyl)-2-methyl-3-thioxo-2,5,6,7-tetrahydro-3H-pyrrolo[1,2-c]imidazol-1-yl)-N—((R)-tetrahydrofuran-3-yl)acetamide
Example 247: 1-((S)-2-(methoxymethyl)pyrrolidin-1-yl)-2-((R)-2-methyl-3-thioxo-6-(2,3,6-trifluorophenyl)-2,5,6,7-tetrahydro-3H-pyrrolo[1,2-c]imidazol-1-yl)ethan-1-one
Example 248: 2-((R)-2-methyl-3-thioxo-6-(2,3,6-trifluorophenyl)-2,5,6,7-tetrahydro-3H-pyrrolo[1,2-c]imidazol-1-yl)-1-((S)-2-(trifluoromethyl)pyrrolidin-1-yl)ethan-1-one
Example 249: (S)-2-(6-(3-chloro-2,6-difluorophenyl)-2-methyl-3-thioxo-2,5,6,7-tetrahydro-3H-pyrrolo[1,2-c]imidazol-1-yl)acetamide
Example 250: 2-((S)-6-(3-chloro-2,6-difluorophenyl)-2-methyl-3-thioxo-2,5,6,7-tetrahydro-3H-pyrrolo[1,2-c]imidazol-1-yl)-N—((R)-tetrahydrofuran-3-yl)acetamide
Example 251: 2-((S)-6-(5-chloro-2-fluorophenyl)-2-methyl-3-thioxo-2,5,6,7-tetrahydro-3H-pyrrolo[1,2-c]imidazol-1-yl)-N—((R)-tetrahydrofuran-3-yl)acetamide
Example 252: 2-((S)-6-(3-bromo-2,6-difluorophenyl)-2-methyl-3-thioxo-2,5,6,7-tetrahydro-3H-pyrrolo[1,2-c]imidazol-1-yl)-N-methyl-N-(tetrahydrofuran-3-yl)acetamide
Example 253: (S)-2-(6-(3-bromo-2,6-difluorophenyl)-2-methyl-3-thioxo-2,5,6,7-tetrahydro-3H-pyrrolo[1,2-c]imidazol-1-yl)-N-(cyanomethyl)acetamide
Example 254: (R)—N-(1-cyanocyclopropyl)-2-(2-methyl-3-thioxo-6-(2,3,6-trifluorophenyl)-2,5,6,7-tetrahydro-3H-pyrrolo[1,2-c]imidazol-1-yl)acetamide
Example 255: 2-((R)-2-methyl-3-thioxo-6-(2,3,6-trifluorophenyl)-2,5,6,7-tetrahydro-3H-pyrrolo[1,2-c]imidazol-1-yl)-N—((R)-tetrahydro-2H-pyran-3-yl)acetamide
Example 256: (S)-6-(3-bromo-2,6-difluorophenyl)-2-methyl-1-(2-(((R)-tetrahydrofuran-3-yl)amino)ethyl)-2,5,6,7-tetrahydro-3H-pyrrolo[1,2-c]imidazole-3-thione
Example 257: (R)-2-methyl-1-(2-morpholinoethyl)-6-(2,3,5,6-tetrafluorophenyl)-2,5,6,7-tetrahydro-3H-pyrrolo[1,2-c]imidazole-3-thione
Example 258: (S)-2-amino-3-(2-((R)-6-(2,3,5,6-tetrafluorophenyl)-3-thioxo-2,5,6,7-tetrahydro-3H-pyrrolo[1,2-c]imidazol-1-yl)acetamido)propanoic acid
Example 259: (R)-2-methyl-1-(2-(pyridin-3-yl)ethyl)-6-(2,3,5,6-tetrafluorophenyl)-6,7-dihydro-2H-pyrrolo[1,2-c]imidazole-3(5H)-thione
Example 260: (R)-3-(2-methyl-6-(2,3,5,6-tetrafluorophenyl)-3-thioxo-2,5,6,7-tetrahydro-3H-pyrrolo[1,2-c]imidazol-1-yl)propanoic acid
Example 261: (R)-3-(2-methyl-6-(2,3,5,6-tetrafluorophenyl)-3-thioxo-2,5,6,7-tetrahydro-3H-pyrrolo[1,2-c]imidazol-1-yl)-1-(pyrrolidin-1-yl)propan-1-one
Example 262: (S)-3-(6-(3-chloro-2,6-difluorophenyl)-2-methyl-3-thioxo-2,5,6,7-tetrahydro-3H-pyrrolo[1,2-c]imidazol-1-yl)propanamide
Example 263: (R)-3-(6-(2,6-difluorophenyl)-2-methyl-3-thioxo-2,5,6,7-tetrahydro-3H-pyrrolo[1,2-c]imidazol-1-yl)propanamide
Example 264: (R)-3-(6-(2,6-difluorophenyl)-2-methyl-3-thioxo-2,5,6,7-tetrahydro-3H-pyrrolo[1,2-c]imidazol-1-yl)-1-(pyrrolidin-1-yl)propan-1-one
Example 265: 3-((R)-2-methyl-3-thioxo-6-(2,3,6-trifluorophenyl)-2,5,6,7-tetrahydro-3H-pyrrolo[1,2-c]imidazol-1-yl)-N—((R)-tetrahydrofuran-3-yl)propanamide
Example 266: (R)-3-(2-methyl-3-thioxo-6-(2,3,6-trifluorophenyl)-2,5,6,7-tetrahydro-3H-pyrrolo[1,2-c]imidazol-1-yl)-1-morpholinopropan-1-one
Example 267: 1-((S)-2-(hydroxymethyl)pyrrolidin-1-yl)-3-((R)-2-methyl-3-thioxo-6-(2,3,6-trifluorophenyl)-2,5,6,7-tetrahydro-3H-pyrrolo[1,2-c]imidazol-1-yl)propan-1-one
Example 268: (S)-3-(6-(3-chloro-2,6-difluorophenyl)-2-methyl-3-thioxo-2,5,6,7-tetrahydro-3H-pyrrolo[1,2-c]imidazol-1-yl)-N-(pyridin-2-yl)propanamide
Example 269: (R)-3-(6-(2,6-difluorophenyl)-2-methyl-3-thioxo-2,5,6,7-tetrahydro-3H-pyrrolo[1,2-c]imidazol-1-yl)-N-(pyridin-2-yl)propanamide
Example 270: (R)—N-(cyanomethyl)-3-(2-methyl-3-thioxo-6-(2,3,6-trifluorophenyl)-2,5,6,7-tetrahydro-3H-pyrrolo[1,2-c]imidazol-1-yl)propanamide
Example 271: 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-N-cyclopentylacetamide
Example 272: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-cyclopentylacetamide
Example 273: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-cyclopentylacetamide
Example 274: 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-N—((R)-tetrahydrofuran-3-yl)acetamide
Example 275: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)acetic acid
Example 276: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)acetic acid
Example 277: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N—(R)-tetrahydro-2H-pyran-3-yl)acetamide
Example 278: 2-((R)-2-methyl-6-(2,3,5,6-tetrafluorophenyl)-3-thioxo-2,5,6,7-tetrahydro-3H-pyrrolo[1,2-c]imidazol-1-yl)-N—((R)-tetrahydro-2H-pyran-3-yl)acetamide Example 279: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N—((R)-tetrahydrofuran-3-yl)acetamide Example 280: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)acetamide Example 281: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N—((R)-tetrahydrofuran-3-yl)acetamide Example 282: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)acetamide Example 283: 1-((S)-2-(methoxymethyl)pyrrolidin-1-yl)-2-((R)-2-methyl-6-(2,3,5,6-tetrafluorophenyl)-3-thioxo-2,5,6,7-tetrahydro-3H-pyrrolo[1,2-c]imidazol-1-yl)ethan-1-one Example 284: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-isopropylacetamide Example 285: (S)-2-(6-(3-chloro-2,6-difluorophenyl)-2-methyl-3-thioxo-2,5,6,7-tetrahydro-3H-pyrrolo[1,2-c]imidazol-1-yl)-N-(1,3,4-thiadiazol-2-yl)acetamide Example 286: (R)-2-(2-methyl-3-thioxo-6-(2,3,6-trifluorophenyl)-2,5,6,7-tetrahydro-3H-pyrrolo[1,2-c]imidazol-1-yl)-N-(oxazol-2-yl)acetamide Example 287: (S)-2-(6-(3-chloro-2,6-difluorophenyl)-2-methyl-3-thioxo-2,5,6,7-tetrahydro-3H-pyrrolo[1,2-c]imidazol-1-yl)-N-(pyridin-4-yl)acetamide Example 288: 3-((R)-2-methyl-3-thioxo-6-(2,3,6-trifluorophenyl)-2,5,6,7-tetrahydro-3H-pyrrolo[1,2-c]imidazol-1-yl)-N—((R)-tetrahydro-2H-pyran-3-yl)propanamide Example 289: 2-((R)-2-methyl-3-thioxo-6-(2,3,6-trifluorophenyl)-2,5,6,7-tetrahydro-3H-pyrrolo[1,2-c]imidazol-1-yl)-N—((S)-tetrahydrofuran-3-yl)acetamide Example 290: (S)-2-(6-(3-chloro-2,6-difluorophenyl)-2-methyl-3-thioxo-2,5,6,7-tetrahydro-3H-pyrrolo[1,2-c]imidazol-1-yl)-N-(pyridin-3-ylmethyl)acetamide Example 291: (S)—N-(benzo[d][1,3]dioxol-5-ylmethyl)-2-(6-(3-chloro-2,6-difluorophenyl)-2-methyl-3-thioxo-2,5,6,7-tetrahydro-3H-pyrrolo[1,2-c]imidazol-1-yl)acetamide Example 292: 1-((R)-3-fluoropyrrolidin-1-yl)-2-((R)-2-methyl-3-thioxo-6-(2,3,6-trifluorophenyl)-2,5,6,7-tetrahydro-3H-pyrrolo[1,2-c]imidazol-1-yl)ethan-1-one Example 293: (R)—N-(2-hydroxyethyl)-N-methyl-2-(2-methyl-3-thioxo-6-(2,3,6-trifluorophenyl)-2,5,6,7-tetrahydro-3H-pyrrolo[1,2-c]imidazol-1-yl)acetamide Example 294: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-cyclohexylacetamide Example 295: 2-((R)-2-methyl-3-thioxo-6-(2,3,5,6-tetrafluorophenyl)-2,5,6,7-tetrahydro-3H-pyrrolo[1,2-c]imidazol-1-yl)-N—((S)-tetrahydrofuran-3-yl)acetamide Example 296: 1-((S)-2-(fluoromethyl)pyrrolidin-1-yl)-2-((R)-2-methyl-3-thioxo-6-(2,3,6-trifluorophenyl)-2,5,6,7-tetrahydro-3H-pyrrolo[1,2-c]imidazol-1-yl)ethan-1-one Example 297: (R)-2-(2-methyl-6-(2,3,5,6-tetrafluorophenyl)-3-thioxo-2,5,6,7-tetrahydro-3H-pyrrolo[1,2-c]imidazol-1-yl)-N-(tetrahydro-2H-pyran-4-yl)acetamide Example 298: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-(2,2,2-trifluoroethyl)acetamide Example 299: (R)-2-(2-methyl-6-(2,3,6-trifluorophenyl)-3-thioxo-2,5,6,7-tetrahydro-3H-pyrrolo[1,2-c]imidazol-1-yl)-N-(tetrahydro-2H-pyran-4-yl)acetamide Example 300: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-(2,2,2-trifluoroethyl)acetamide Example 301: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N—((R)-tetrahydro-2H-pyran-3-yl)acetamide Example 302: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-cyclohexylacetamide Example 303: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-isopropylacetamide Example 304: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-(cyanomethyl)acetamide Example 305: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-(cyanomethyl)acetamide Example 306: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N—((S)-tetrahydrofuran-3-yl)acetamide Example 307: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N—((R)-tetrahydrofuran-3-yl)acetamide Example 308: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N—((S)-tetrahydrofuran-3-yl)acetamide Example 309: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(pyrrolidin-1-yl)ethan-1-one Example 310: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(pyrrolidin-1-yl)ethan-1-one Example 311: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(piperidin-1-yl)ethan-1-one Example 312: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(piperidin-1-yl)ethan-1-one Example 313: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-(tetrahydro-2H-pyran-4-yl)acetamide Example 314: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-(tetrahydro-2H-pyran-4-yl)acetamide Example 315: (R)-2-(2-methyl-6-(2,3,5,6-tetrafluorophenyl)-3-thioxo-2,5,6,7-tetrahydro-3H-pyrrolo[1,2-c]imidazol-1-yl)-N-(2,2,2-trifluoroethyl)acetamide Example 316: (R)-2-(2-methyl-3-thioxo-6-(2,3,5,6-tetrafluorophenyl)-2,5,6,7-tetrahydro-3H-pyrrolo[1,2-c]imidazol-1-yl)-N-(oxazol-2-yl)acetamide Example 317: (S)-2-(6-(3-chloro-2,6-difluorophenyl)-2-methyl-3-thioxo-2,5,6,7-tetrahydro-3H-pyrrolo[1,2-c]imidazol-1-yl)-N-(oxazol-2-yl)acetamide
Example 318: (R)-3-(2-methyl-3-thioxo-6-(2,3,5,6-tetrafluorophenyl)-2,5,6,7-tetrahydro-3H-pyrrolo[1,2-c]imidazol-1-yl)-1-morpholinopropan-1-one
Example 319: 1-(6,6-dimethyl-3-azabicyclo[3.1.0]hexan-3-yl)-3-((R)-2-methyl-6-(2,3,5,6-tetrafluorophenyl)-3-thioxo-2,5,6,7-tetrahydro-3H-pyrrolo[1,2-c]imidazol-1-yl)propan-1-one
Example 320: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(piperazin-1-yl)ethan-1-one
Example 321: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(piperazin-1-yl)ethan-1-one
Example 322: (5aS,6aR)-5a-(5-chloro-2-fluorophenyl)-1-(2-(cyclopentylamino)ethyl)-2-methyl-5,5a,6,6a-tetrahydrocyclopropa[3,4]pyrrolo[1,2-c]imidazole-3(2H)-thione
Example 323: (R)-4-(2-(2-methyl-6-(2,3,5,6-tetrafluorophenyl)-3-thioxo-2,5,6,7-tetrahydro-3H-pyrrolo[1,2-c]imidazol-1-yl)acetyl)piperazin-2-one
Example 324: (R)-1-methyl-4-(2-(2-methyl-6-(2,3,5,6-tetrafluorophenyl)-3-thioxo-2,5,6,7-tetrahydro-3H-pyrrolo[1,2-c]imidazol-1-yl)acetyl)piperazin-2-one
Example 325: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-((1r,4R)-4-hydroxycyclohexyl)acetamide
Example 326: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(4-methylpiperazin-1-yl)ethan-1-one
Example 327: 2-((S)-6-(3-chloro-2,6-difluorophenyl)-2-methyl-3-thioxo-2,5,6,7-tetrahydro-3H-pyrrolo[1,2-c]imidazol-1-yl)-N—((R)-tetrahydro-2H-pyran-3-yl)acetamide
Example 328: (S)-2-(6-(3-chloro-2,6-difluorophenyl)-2-methyl-3-thioxo-2,5,6,7-tetrahydro-3H-pyrrolo[1,2-c]imidazol-1-yl)-N-(pyrazin-2-ylmethyl)acetamide
Example 329: (S)-2-(6-(3-chloro-2,6-difluorophenyl)-2-methyl-3-thioxo-2,5,6,7-tetrahydro-3H-pyrrolo[1,2-c]imidazol-1-yl)-1-morpholinoethan-1-one
Example 330: (5aS,6aR)-5a-(5-bromo-2-fluorophenyl)-1-(2-(cyclopentylamino)ethyl)-2-methyl-5,5a,6,6a-tetrahydrocyclopropa[3,4]pyrrolo[1,2-c]imidazole-3(2H)-thione
Example 331: (5aS,6aR)-5a-(5-bromo-2-fluorophenyl)-2-methyl-1-(2-(((R)-tetrahydro-2H-pyran-3-yl)amino)ethyl)-5,5a,6,6a-tetrahydrocyclopropa[3,4]pyrrolo[1,2-c]imidazole-3(2H)-thione
Example 332: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-(pyridin-2-ylmethyl)acetamide
Example 333: (S)-2-(6-(3-chloro-2,6-difluorophenyl)-2-methyl-3-thioxo-2,5,6,7-tetrahydro-3H-pyrrolo[1,2-c]imidazol-1-yl)-N-(oxetan-3-yl)acetamide
Example 334: (5aS,6aR)-5a-(5-bromo-2-fluorophenyl)-2-methyl-1-(2-((2,2,2-trifluoroethyl)amino)ethyl)-5,5a,6,6a-tetrahydrocyclopropa[3,4]pyrrolo[1,2-c]imidazole-3(2H)-thione
Example 335: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-(pyrazin-2-ylmethyl)acetamide
Example 336: 2-((S)-6-(3-chloro-2,6-difluorophenyl)-2-methyl-3-thioxo-2,5,6,7-tetrahydro-3H-pyrrolo[1,2-c]imidazol-1-yl)-N—(((S)-tetrahydrofuran-2-yl)methyl)acetamide
Example 337: 2-((S)-6-(3-chloro-2,6-difluorophenyl)-2-methyl-3-thioxo-2,5,6,7-tetrahydro-3H-pyrrolo[1,2-c]imidazol-1-yl)-N—(((R)-tetrahydrofuran-2-yl)methyl)acetamide
Example 338: (S)-2-(6-(3-chloro-2,6-difluorophenyl)-2-methyl-3-thioxo-2,5,6,7-tetrahydro-3H-pyrrolo[1,2-c]imidazol-1-yl)-N-((1-methyl-1H-pyrazol-4-yl)methyl)acetamide
Example 339: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-((1-methyl-1H-pyrazol-4-yl)methyl)acetamide
Example 340: (R)-2-(2-methyl-6-(2,3,5,6-tetrafluorophenyl)-3-thioxo-2,5,6,7-tetrahydro-3H-pyrrolo[1,2-c]imidazol-1-yl)-N-(thiazol-2-yl)acetamide
Example 341: (5aS,6aR)-5a-(5-bromo-2-fluorophenyl)-1-(2-(cyclohexylamino)ethyl)-2-methyl-5,5a,6,6a-tetrahydrocyclopropa[3,4]pyrrolo[1,2-c]imidazole-3(2H)-thione
Example 342: 2-((S)-6-(3-bromo-2,6-difluorophenyl)-2-methyl-3-thioxo-2,5,6,7-tetrahydro-3H-pyrrolo[1,2-c]imidazol-1-yl)-N—((R)-2-oxopyrrolidin-3-yl)acetamide
Example 343: (5aS,6aR)-5a-(5-chloro-2-fluorophenyl)-2-methyl-1-(2-((pyridin-2-ylmethyl)amino)ethyl)-5,5a,6,6a-tetrahydrocyclopropa[3,4]pyrrolo[1,2-c]imidazole-3(2H)-thione
Example 344: 2-((R)-2-methyl-3-thioxo-6-(2,3,6-trifluorophenyl)-2,5,6,7-tetrahydro-3H-pyrrolo[1,2-c]imidazol-1-yl)-1-((R)-2-(trifluoromethyl)pyrrolidin-1-yl)ethan-1-one
Example 345: N-(2-cyanocyclopentyl)-2-((R)-2-methyl-3-thioxo-6-(2,3,6-trifluorophenyl)-2,5,6,7-tetrahydro-3H-pyrrolo[1,2-c]imidazol-1-yl)acetamide
Example 346: (5aS,6aR)-5a-(5-chloro-2-fluorophenyl)-2-methyl-1-(2-(((1-methyl-1H-pyrazol-4-yl)methyl)amino)ethyl)-5,5a,6,6a-tetrahydrocyclopropa[3,4]pyrrolo[1,2-c]imidazole-3(2H)-thione
Example 347: (R)—N-(isoxazol-4-yl)-2-(2-methyl-3-thioxo-6-(2,3,6-trifluorophenyl)-2,5,6,7-tetrahydro-3H-pyrrolo[1,2-c]imidazol-1-yl)acetamide
Example 348: (S)-1-(2-((R)-2-methyl-3-thioxo-6-(2,3,6-trifluorophenyl)-2,5,6,7-tetrahydro-3H-pyrrolo[1,2-c]imidazol-1-yl)acetyl)pyrrolidine-3-carbonitrile
Example 349: (S)-2-(6-(3-chloro-2,6-difluorophenyl)-2-methyl-3-thioxo-2,5,6,7-tetrahydro-3H-pyrrolo[1,2-c]imidazol-1-yl)-N-(5-methyl-1,3,4-oxadiazol-2-yl)acetamide
Example 350: (S)-2-(6-(3-chloro-2,6-difluorophenyl)-2-methyl-3-thioxo-2,5,6,7-tetrahydro-3H-pyrrolo[1,2-c]imidazol-1-yl)-N-(1-methyl-1H-pyrazol-4-yl)acetamide
Example 351: (R)—N-(isothiazol-4-yl)-2-(2-methyl-3-thioxo-6-(2,3,6-trifluorophenyl)-2,5,6,7-tetrahydro-3H-pyrrolo[1,2-c]imidazol-1-yl)acetamide
Example 352: (S)-2-(6-(3-chloro-2,6-difluorophenyl)-2-methyl-3-thioxo-2,5,6,7-tetrahydro-3H-pyrrolo[1,2-c]imidazol-1-yl)-N-((tetrahydro-2H-pyran-4-yl)methyl)acetamide
Example 353: 1-(3-(fluoromethyl)pyrrolidin-1-yl)-2-((R)-2-methyl-3-thioxo-6-(2,3,6-trifluorophenyl)-2,5,6,7-tetrahydro-3H-pyrrolo[1,2-c]imidazol-1-yl)ethan-1-one
Example 354: 2-((R)-2-methyl-3-thioxo-6-(2,3,6-trifluorophenyl)-2,5,6,7-tetrahydro-3H-pyrrolo[1,2-c]imidazol-1-yl)-N—((R)-2-oxopiperidin-3-yl)acetamide Example 355: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-((1r,4R)-4-hydroxycyclohexyl)acetamide Example 356: (S)-2-(6-(3-chloro-2,6-difluorophenyl)-2-methyl-3-thioxo-2,5,6,7-tetrahydro-3H-pyrrolo[1,2-c]imidazol-1-yl)-N-cyclohexylacetamide Example 357: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-cyclopropylacetamide Example 358: N,N-dimethyl-1-(2-((R)-2-methyl-3-thioxo-6-(2,3,6-trifluorophenyl)-2,5,6,7-tetrahydro-3H-pyrrolo[1,2-c]imidazol-1-yl)acetyl)pyrrolidine-3-carboxamide Example 359: (5aS,6aR)-5a-(5-bromo-2-fluorophenyl)-2-methyl-1-(2-(((R)-tetrahydrofuran-3-yl)amino)ethyl)-5,5a,6,6a-tetrahydrocyclopropa[3,4]pyrrolo[1,2-c]imidazole-3(2H)-thione Example 360: 2-((R)-6-(2,3,5,6-tetrafluorophenyl)-3-thioxo-2,5,6,7-tetrahydro-3H-pyrrolo[1,2-c]imidazol-1-yl)-N—((R)-tetrahydrofuran-3-yl)acetamide Example 361: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)acetic acid Example 362: 2-((S)-6-(3-chloro-2,6-difluorophenyl)-3-thioxo-2,5,6,7-tetrahydro-3H-pyrrolo[1,2-c]imidazol-1-yl)-N—((R)-tetrahydrofuran-3-yl)acetamide Example 363: (S)-2-(6-(3-chloro-2,6-difluorophenyl)-3-thioxo-2,5,6,7-tetrahydro-3H-pyrrolo[1,2-c]imidazol-1-yl)-1-morpholinoethan-1-one Example 364: N-methyl-N-(tetrahydrofuran-3-yl)-2-((R)-3-thioxo-6-(2,3,6-trifluorophenyl)-2,5,6,7-tetrahydro-3H-pyrrolo[1,2-c]imidazol-1-yl)acetamide Example 365: N—((R)-tetrahydro-2H-pyran-3-yl)-2-((R)-3-thioxo-6-(2,3,6-trifluorophenyl)-2,5,6,7-tetrahydro-3H-pyrrolo[1,2-c]imidazol-1-yl)acetamide Example 366: (R)-2-(6-(2,3,6-trifluorophenyl)-3-thioxo-2,5,6,7-tetrahydro-3H-pyrrolo[1,2-c]imidazol-1-yl)-1-morpholinoethan-1-one Example 367: (S)-2-(6-(3-chloro-2,6-difluorophenyl)-2-methyl-3-thioxo-2,5,6,7-tetrahydro-3H-pyrrolo[1,2-c]imidazol-1-yl)-N-(tetrahydro-2H-pyran-4-yl)acetamide Example 368: 2-((R)-6-(2,3,6-trifluorophenyl)-3-thioxo-2,5,6,7-tetrahydro-3H-pyrrolo[1,2-c]imidazol-1-yl)-N—((R)-tetrahydrofuran-3-yl)acetamide Example 369: 2-((R)-6-(2,3,5,6-tetrafluorophenyl)-3-thioxo-2,5,6,7-tetrahydro-3H-pyrrolo[1,2-c]imidazol-1-yl)-N—((S)-tetrahydrofuran-3-yl)acetamide Example 370: 2-((R)-6-(2,3,6-trifluorophenyl)-3-thioxo-2,5,6,7-tetrahydro-3H-pyrrolo[1,2-c]imidazol-1-yl)-N—((S)-tetrahydrofuran-3-yl)acetamide Example 371: 2-((R)-2-methyl-3-thioxo-6-(2,3,6-trifluorophenyl)-2,5,6,7-tetrahydro-3H-pyrrolo[1,2-c]imidazol-1-yl)-N-(1-methyl-6-oxopiperidin-3-yl)acetamide Example 372: (R)—N-methyl-2-(2-methyl-3-thioxo-6-(2,3,6-trifluorophenyl)-2,5,6,7-tetrahydro-3H-pyrrolo[1,2-c]imidazol-1-yl)-N-(tetrahydro-2H-pyran-4-yl)acetamide Example 373: (S)-2-(6-(3-chloro-2,6-difluorophenyl)-2-methyl-3-thioxo-2,5,6,7-tetrahydro-3H-pyrrolo[1,2-c]imidazol-1-yl)-N-methyl-N-(tetrahydro-2H-pyran-4-yl)acetamide Example 374: N-methyl-2-((R)-2-methyl-3-thioxo-6-(2,3,6-trifluorophenyl)-2,5,6,7-tetrahydro-3H-pyrrolo[1,2-c]imidazol-1-yl)-N-(tetrahydrofuran-3-yl)acetamide Example 375: N-methyl-2-((R)-2-methyl-6-(2,3,5,6-tetrafluorophenyl)-3-thioxo-2,5,6,7-tetrahydro-3H-pyrrolo[1,2-c]imidazol-1-yl)-N-(tetrahydrofuran-3-yl)acetamide Example 376: (R)—N-(tetrahydro-2H-pyran-4-yl)-2-(3-thioxo-6-(2,3,6-trifluorophenyl)-2,5,6,7-tetrahydro-3H-pyrrolo[1,2-c]imidazol-1-yl)acetamide Example 377: (R)—N-(tetrahydro-2H-pyran-4-yl)-2-(3-thioxo-6-(2,3,5,6-tetrafluorophenyl)-2,5,6,7-tetrahydro-3H-pyrrolo[1,2-c]imidazol-1-yl)acetamide Example 378: (R)—N-methyl-2-(6-(2,3,5,6-tetrafluorophenyl)-3-thioxo-2,5,6,7-tetrahydro-3H-pyrrolo[1,2-c]imidazol-1-yl)-N-(tetrahydro-2H-pyran-4-yl)acetamide Example 379: (R)—N-methyl-2-(6-(2,3,6-trifluorophenyl)-3-thioxo-2,5,6,7-tetrahydro-3H-pyrrolo[1,2-c]imidazol-1-yl)-N-(tetrahydro-2H-pyran-4-yl)acetamide Example 380: (S)-2-(6-(3-chloro-2,6-difluorophenyl)-3-thioxo-2,5,6,7-tetrahydro-3H-pyrrolo[1,2-c]imidazol-1-yl)-N-methyl-N-(tetrahydro-2H-pyran-4-yl)acetamide Example 381: 2-((5aS,6aR)-5a-(3-chloro-2,6-difluorophenyl)-3-thioxo-2,3,5,5a,6,6a-hexahydrocyclopropa[3,4]pyrrolo[1,2-c]imidazol-1-yl)-N-methyl-N-(tetrahydro-2H-pyran-4-yl)acetamide Example 382: 2-((S)-6-(3-bromo-2,6-difluorophenyl)-2-methyl-3-thioxo-2,5,6,7-tetrahydro-3H-pyrrolo[1,2-c]imidazol-1-yl)-N—((R)-tetrahydro-2H-pyran-3-yl)acetamide Example 383: 2-((S)-6-(3-chloro-2,6-difluorophenyl)-2-methyl-3-thioxo-2,5,6,7-tetrahydro-3H-pyrrolo[1,2-c]imidazol-1-yl)-N-methyl-N-(tetrahydrofuran-3-yl)acetamide Example 384: 2-((S)-6-(3-chloro-2,6-difluorophenyl)-3-thioxo-2,5,6,7-tetrahydro-3H-pyrrolo[1,2-c]imidazol-1-yl)-N-methyl-N-(tetrahydrofuran-3-yl)acetamide Example 385: 2-((S)-6-(3-chloro-2,6-difluorophenyl)-2-methyl-3-thioxo-2,5,6,7-tetrahydro-3H-pyrrolo[1,2-c]imidazol-1-yl)-N—((S)-tetrahydrofuran-3-yl)acetamide Example 386: N—((R)-tetrahydro-2H-pyran-3-yl)-2-((R)-3-thioxo-6-(2,3,5,6-tetrafluorophenyl)-2,5,6,7-tetrahydro-3H-pyrrolo[1,2-c]imidazol-1-yl)acetamide Example 387: 2-((R)-2-methyl-6-(2,3,5,6-tetrafluorophenyl)-3-thioxo-2,5,6,7-tetrahydro-3H-pyrrolo[1,2-c]imidazol-1-yl)-N—(((S)-tetrahydrofuran-2-yl)methyl)acetamide Example 388: N-(1-methyl-2-oxopyrrolidin-3-yl)-2-((R)-2-methyl-3-thioxo-6-(2,3,6-trifluorophenyl)-2,5,6,7-tetrahydro-3H-pyrrolo[1,2-c]imidazol-1-yl)acetamide Example 389: 2-((R)-2-methyl-3-thioxo-6-(2,3,6-trifluorophenyl)-2,5,6,7-tetrahydro-3H-pyrrolo[1,2-c]imidazol-1-yl)-N—((S)-1-methyl-5-oxopyrrolidin-3-yl)acetamide Example 390: (R)-1-(2-((R)-2-methyl-3-thioxo-6-(2,3,6-trifluorophenyl)-2,5,6,7-tetrahydro-3H-pyrrolo[1,2-c]imidazol-1-yl)acetyl)pyrrolidine-3-carbonitrile Example 391: 2-((R)-2-methyl-6-(2,3,5,6-tetrafluorophenyl)-3-thioxo-2,5,6,7-tetrahydro-3H-pyrrolo[1,2-c]imidazol-1-yl)-N—(((R)-tetrahydrofuran-2-yl)methyl)acetamide Example 392: 2-((5aS,6aR)-5a-(3-chloro-2,6-difluorophenyl)-3-thioxo-2,3,5,5a,6,6a-hexahydrocyclopropa[3,4]pyrrolo[1,2-c]imidazol-1-yl)-N—((R)-tetrahydrofuran-3-yl)acetamide Example 393: (R)—N-(oxetan-3-yl)-2-(6-(2,3,5,6-tetrafluorophenyl)-3-thioxo-2,5,6,7-tetrahydro-3H-pyrrolo[1,2-c]imidazol-1-yl)acetamide Example 394: (R)-2-(2-methyl-6-(2,3,5,6-tetrafluorophenyl)-3-thioxo-2,5,6,7-tetrahydro-3H-pyrrolo[1,2-c]imidazol-1-yl)-N-(oxetan-3-yl)acetamide Example 395: 2-((R)-6-(2,3,5,6-tetrafluorophenyl)-3-thioxo-2,5,6,7-tetrahydro-3H-pyrrolo[1,2-c]imidazol-1-yl)-N—(((S)-tetrahydrofuran-2-yl)methyl)acetamide Example 396: 2-((5aS,6aR)-5a-(3-chloro-2,6-difluorophenyl)-3-thioxo-2,3,5,5a,6,6a-hexahydrocyclopropa[3,4]pyrrolo[1,2-c]imidazol-1-yl)-N-methyl-N-(tetrahydrofuran-3-yl)acetamide Example 397: (R)-2-(2-methyl-6-(2,3,5,6-tetrafluorophenyl)-3-thioxo-2,5,6,7-tetrahydro-3H-pyrrolo[1,2-c]imidazol-1-yl)-N-((tetrahydro-2H-pyran-4-yl)methyl)acetamide Example 398: (R)—N-methyl-2-(2-methyl-6-(2,3,5,6-tetrafluorophenyl)-3-thioxo-2,5,6,7-tetrahydro-3H-pyrrolo[1,2-c]imidazol-1-yl)-N-(oxetan-3-yl)acetamide Example 399: 2-((S)-6-(3-chloro-2,6-difluorophenyl)-2-methyl-3-thioxo-2,5,6,7-tetrahydro-3H-pyrrolo[1,2-c]imidazol-1-yl)-N-methyl-N—((R)-tetrahydrofuran-3-yl)acetamide Example 400: 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-N-(oxetan-3-yl)acetamide Example 401: 2-((S)-6-(3-chloro-2,6-difluorophenyl)-3-thioxo-2,5,6,7-tetrahydro-3H-pyrrolo[1,2-c]imidazol-1-yl)-N—((R)-tetrahydro-2H-pyran-3-yl)acetamide Example 402: 2-((S)-6-(3-bromo-2,6-difluorophenyl)-3-thioxo-2,5,6,7-tetrahydro-3H-pyrrolo[1,2-c]imidazol-1-yl)-N—((R)-tetrahydro-2H-pyran-3-yl)acetamide Example 403: 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-N-methyl-N-(oxetan-3-yl)acetamide Example 404: 2-((S)-6-(3-chloro-2,6-difluorophenyl)-3-thioxo-2,5,6,7-tetrahydro-3H-pyrrolo[1,2-c]imidazol-1-yl)-N—((S)-tetrahydrofuran-3-yl)acetamide Example 405: (S)-2-(6-(3-bromo-2,6-difluorophenyl)-2-methyl-3-thioxo-2,5,6,7-tetrahydro-3H-pyrrolo[1,2-c]imidazol-1-yl)-N-methyl-N-(tetrahydro-2H-pyran-4-yl)acetamide Example 406: (S)-2-(6-(3-bromo-2,6-difluorophenyl)-2-methyl-3-thioxo-2,5,6,7-tetrahydro-3H-pyrrolo[1,2-c]imidazol-1-yl)-N-(tetrahydro-2H-pyran-4-yl)acetamide Example 407: (S)-2-(6-(3-chloro-2,6-difluorophenyl)-3-thioxo-2,5,6,7-tetrahydro-3H-pyrrolo[1,2-c]imidazol-1-yl)acetic acid Example 408: (S)-2-(6-(3-bromo-2,6-difluorophenyl)-3-thioxo-2,5,6,7-tetrahydro-3H-pyrrolo[1,2-c]imidazol-1-yl)-N-methyl-N-(oxetan-3-yl)acetamide Example 409: (S)-2-(2-methyl-3-thioxo-6-(2,3,6-trifluorophenyl)-2,5,6,7-tetrahydro-3H-pyrrolo[1,2-c]imidazol-1-yl)acetic acid Example 410: (S)-2-(6-(3-bromo-2,6-difluorophenyl)-3-thioxo-2,5,6,7-tetrahydro-3H-pyrrolo[1,2-c]imidazol-1-yl)-N-(tetrahydro-2H-pyran-4-yl)acetamide Example 411: (S)-2-(2-methyl-3-thioxo-6-(2,3,6-trifluorophenyl)-2,5,6,7-tetrahydro-3H-pyrrolo[1,2-c]imidazol-1-yl)-1-morpholinoethan-1-one Example 412: 2-((S)-2-methyl-3-thioxo-6-(2,3,6-trifluorophenyl)-2,5,6,7-tetrahydro-3H-pyrrolo[1,2-c]imidazol-1-yl)-N—((R)-tetrahydrofuran-3-yl)acetamide Example 413: (S)-2-(6-(3-bromo-2,6-difluorophenyl)-2-methyl-3-thioxo-2,5,6,7-tetrahydro-3H-pyrrolo[1,2-c]imidazol-1-yl)-N-(oxetan-3-yl)acetamide Example 414: (R)-2-(2-methyl-3-thioxo-6-(2,3,6-trifluorophenyl)-2,5,6,7-tetrahydro-3H-pyrrolo[1,2-c]imidazol-1-yl)-N-(oxetan-3-yl)acetamide Example 415: 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-N—((R)-tetrahydro-2H-pyran-3-yl)acetamide Example 416: (S)-2-(2-methyl-3-thioxo-6-(2,3,6-trifluorophenyl)-2,5,6,7-tetrahydro-3H-pyrrolo[1,2-c]imidazol-1-yl)-N-(tetrahydro-2H-pyran-4-yl)acetamide Example 417: 2-((S)-2-methyl-3-thioxo-6-(2,3,6-trifluorophenyl)-2,5,6,7-tetrahydro-3H-pyrrolo[1,2-c]imidazol-1-yl)-N—((S)-tetrahydrofuran-3-yl)acetamide Example 418: 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-N—((S)-tetrahydrofuran-3-yl)acetamide Example 419: (S)-2-(6-(3,5-difluorophenyl)-2-methyl-3-thioxo-2,5,6,7-tetrahydro-3H-pyrrolo[1,2-c]imidazol-1-yl)-1-morpholinoethan-1-one Example 420: (R)—N-methyl-N-(oxetan-3-yl)-2-(3-thioxo-6-(2,3,6-trifluorophenyl)-2,5,6,7-tetrahydro-3H-pyrrolo[1,2-c]imidazol-1-yl)acetamide Example 421: 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-1-morpholinoethan-1-one Example 422: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-morpholinoethan-1-one Example 423: 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-N-(tetrahydro-2H-pyran-4-yl)acetamide Example 424: (S)-2-(6-(3-chloro-2,6-difluorophenyl)-2-methyl-3-thioxo-2,5,6,7-tetrahydro-3H-pyrrolo[1,2-c]imidazol-1-yl)acetic acid Example 425: 2-((S)-6-(3,5-difluorophenyl)-2-methyl-3-thioxo-2,5,6,7-tetrahydro-3H-pyrrolo[1,2-c]imidazol-1-yl)-N—((R)-tetrahydrofuran-3-yl)acetamide Example 426: 2-((S)-6-(3,5-difluorophenyl)-2-methyl-3-thioxo-2,5,6,7-tetrahydro-3H-pyrrolo[1,2-c]imidazol-1-yl)-N—((S)-tetrahydrofuran-3-yl)acetamide Example 427 (S)-2-(2-methyl-3-thioxo-6-(2,3,6-trifluorophenyl)-2,5,6,7-tetrahydro-3H-pyrrolo[1,2-c]imidazol-1-yl)-N-((tetrahydro-2H-pyran-4-yl)methyl)acetamide Example 428: (S)-2-(6-(3,5-difluorophenyl)-2-methyl-3-thioxo-2,5,6,7-tetrahydro-3H-pyrrolo[1,2-c]imidazol-1-yl)-N-((tetrahydro-2H-pyran-4-yl)methyl)acetamide Example 429: (S)-2-(6-(3-chloro-2,6-difluorophenyl)-2-methyl-3-thioxo-2,5,6,7-tetrahydro-3H-pyrrolo[1,2-c]imidazol-1-yl)-N-methyl-N-(oxetan-3-yl)acetamide Example 430: (S)-2-(6-(3-chloro-2,6-difluorophenyl)-2-methyl-3-thioxo-2,5,6,7-tetrahydro-3H-pyrrolo[1,2-c]imidazol-1-yl)-N-methyl-N-((1-methyl-1H-pyrazol-4-yl)methyl)acetamide Example 431: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-methyl-N-(oxetan-3-yl)acetamide Example 432: (S)-2-(2-methyl-3-thioxo-6-(2,3,6-trifluorophenyl)-2,5,6,7-tetrahydro-3H-pyrrolo[1,2-c]imidazol-1-yl)-N-(oxetan-3-yl)acetamide Example 433: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-(oxetan-3-yl)acetamide Example 434: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-methyl-N-(tetrahydro-2H-pyran-4-yl)acetamide Example 435: (S)—N-methyl-2-(2-methyl-3-thioxo-6-(2,3,6-trifluorophenyl)-2,5,6,7-tetrahydro-3H-pyrrolo[1,2-c]imidazol-1-yl)-N-(oxetan-3-yl)acetamide Example 436: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-morpholinoethan-1-one Example 437: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-(oxetan-3-yl)acetamide Example 438: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-methyl-N-(oxetan-3-yl)acetamide Example 439: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-methyl-N-(tetrahydro-2H-pyran-4-yl)acetamide Example 440: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-methyl-N-(tetrahydrofuran-3-yl)acetamide Example 441: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-methyl-N-(tetrahydrofuran-3-yl)acetamide Example 442: 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-N-methyl-N-(tetrahydrofuran-3-yl)acetamide Example 443: 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-N-methyl-N-(tetrahydro-2H-pyran-4-yl)acetamide Example 444: (S)-2-(6-(3-chloro-2,6-difluorophenyl)-2-methyl-3-thioxo-2,5,6,7-tetrahydro-3H-pyrrolo[1,2-c]imidazol-1-yl)-1-(isoxazolidin-2-yl)ethan-1-one Example 445: (R)-2-(6-(2,6-difluorophenyl)-2-methyl-3-thioxo-2,5,6,7-tetrahydro-3H-pyrrolo[1,2-c]imidazol-1-yl)-1-morpholinoethan-1-one Example 446: 2-((R)-6-(2,6-difluorophenyl)-2-methyl-3-thioxo-2,5,6,7-tetrahydro-3H-pyrrolo[1,2-c]imidazol-1-yl)-N—((R)-tetrahydrofuran-3-yl)acetamide Example 447 (R)-2-(6-(2,6-difluorophenyl)-2-methyl-3-thioxo-2,5,6,7-tetrahydro-3H-pyrrolo[1,2-c]imidazol-1-yl)-N-(tetrahydro-2H-pyran-4-yl)acetamide Example 448: (R)-2-(6-(2,6-difluorophenyl)-2-methyl-3-thioxo-2,5,6,7-tetrahydro-3H-pyrrolo[1,2-c]imidazol-1-yl)-N-methyl-N-(oxetan-3-yl)acetamide Example 449: 2-((S)-6-(3-bromo-2,6-difluorophenyl)-2-methyl-3-thioxo-2,5,6,7-tetrahydro-3H-pyrrolo[1,2-c]imidazol-1-yl)-N—((S)-1-methyl-5-oxopyrrolidin-3-yl)acetamide Example 450: (S)-1-(2-((S)-6-(3-bromo-2,6-difluorophenyl)-2-methyl-3-thioxo-2,5,6,7-tetrahydro-3H-pyrrolo[1,2-c]imidazol-1-yl)acetyl)pyrrolidine-3-carbonitrile Example 451: 2-((S)-6-(3-bromo-2,6-difluorophenyl)-2-methyl-3-thioxo-2,5,6,7-tetrahydro-3H-pyrrolo[1,2-c]imidazol-1-yl)-N-methyl-N—((R)-tetrahydrofuran-3-yl)acetamide Example 452: (S)-1-(2-(6-(3-bromo-2,6-difluorophenyl)-2-methyl-3-thioxo-2,5,6,7-tetrahydro-3H-pyrrolo[1,2-c]imidazol-1-yl)acetyl)-N,N-dimethylpiperidine-4-carboxamide Example 453: 1-(2-((S)-6-(3-bromo-2,6-difluorophenyl)-2-methyl-3-thioxo-2,5,6,7-tetrahydro-3H-pyrrolo[1,2-c]imidazol-1-yl)acetyl)-N,N-dimethylpyrrolidine-3-carboxamide Example 454: (S)-2-(6-(3-bromo-2,6-difluorophenyl)-2-methyl-3-thioxo-2,5,6,7-tetrahydro-3H-pyrrolo[1,2-c]imidazol-1-yl)-N-methyl-N-(oxetan-3-yl)acetamide Example 455: N-methyl-2-((R)-2-methyl-3-thioxo-6-(2,3,6-trifluorophenyl)-2,5,6,7-tetrahydro-3H-pyrrolo[1,2-c]imidazol-1-yl)-N—((R)-tetrahydrofuran-3-yl)acetamide Example 456: (S)-6-(3-bromo-2,6-difluorophenyl)-1-(2-hydroxyethyl)-2-methyl-2,5,6,7-tetrahydro-3H-pyrrolo[1,2-c]imidazole-3-thione Example 457:2-((S)-6-(3-bromo-2,6-difluorophenyl)-2-methyl-3-thioxo-2,5,6,7-tetrahydro-3H-pyrrolo[1,2-c]imidazol-1-yl)-N-(1-methyl-6-oxopiperidin-3-yl)acetamide Example 458:2-((S)-6-(3-bromo-2,6-difluorophenyl)-2-methyl-3-thioxo-2,5,6,7-tetrahydro-3H-pyrrolo[1,2-c]imidazol-1-yl)-1-(3-(fluoromethyl)pyrrolidin-1-yl)ethan-1-one Example 459:2-((S)-6-(3-bromo-2,6-difluorophenyl)-2-methyl-3-thioxo-2,5,6,7-tetrahydro-3H-pyrrolo[1,2-c]imidazol-1-yl)-N—((S)-tetrahydrofuran-3-yl)acetamide Example 460: (S)-2-(6-(3-chloro-2,6-difluorophenyl)-2-(methyl-d)-3-thioxo-2,5,6,7-tetrahydro-3H-pyrrolo[1,2-c]imidazol-1-yl)-1-morpholinoethan-1-one Example 461:2-((5aS,6aR)-5a-(5-bromo-2-fluorophenyl)-2-(methyl-d)-3-thioxo-2,3,5,5a,6,6a-hexahydrocyclopropa[3,4]pyrrolo[1,2-c]imidazol-1-yl)-N—((S)-tetrahydrofuran-3-yl)acetamide Example 462:2-((5aS,6aR)-5a-(5-bromo-2-fluorophenyl)-2-(methyl-d)-3-thioxo-2,3,5,5a,6,6a-hexahydrocyclopropa[3,4]pyrrolo[1,2-c]imidazol-1-yl)acetic acid Example 463:2-((5aS,6aR)-5a-(5-bromo-2-fluorophenyl)-2-(methyl-d)-3-thioxo-2,3,5,5a,6,6a-hexahydrocyclopropa[3,4]pyrrolo[1,2-c]imidazol-1-yl)-N-(tetrahydro-2H-pyran-4-yl)acetamide Example 464:2-((5aS,6aR)-5a-(5-bromo-2-fluorophenyl)-2-(methyl-d)-3-thioxo-2,3,5,5a,6,6a-hexahydrocyclopropa[3,4]pyrrolo[1,2-c]imidazol-1-yl)-N—((R)-tetrahydro-2H-pyran-3-yl)acetamide Example 465:2-((5aS,6aR)-5a-(5-bromo-2-fluorophenyl)-2-(methyl-d)-3-thioxo-2,3,5,5a,6,6a-hexahydrocyclopropa[3,4]pyrrolo[1,2-c]imidazol-1-yl)-N—((R)-tetrahydrofuran-3-yl)acetamide Example 466:2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-methyl-N—((R)-tetrahydrofuran-3-yl)acetamide Example 467:2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-N-methyl-N—((R)-tetrahydrofuran-3-yl)acetamide Example 468: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-methyl-N—((R)-tetrahydrofuran-3-yl)acetamide Example 469: (S)-2-(6-(3-chloro-2,6-difluorophenyl)-2-(methyl-d)-3-thioxo-2,5,6,7-tetrahydro-3H-pyrrolo[1,2-c]imidazol-1-yl)-N-(tetrahydro-2H-pyran-4-yl)acetamide Example 470: R)-6-(2,3,6-trifluorophenyl)-1-(2-(((R)-tetrahydrofuran-3-yl)amino)ethyl)-2,5,6,7-tetrahydro-3H-pyrrolo[1,2-c]imidazole-3-thione Example 471: (R)-1-(3-(pyrrolidin-1-yl)propyl)-6-(2,3,5,6-tetrafluorophenyl)-2,5,6,7-tetrahydro-3H-pyrrolo[1,2-c]imidazole-3-thione Example 472: (R)-1-(3-(isopropylamino)propyl)-6-(2,3,6-trifluorophenyl)-2,5,6,7-tetrahydro-3H-pyrrolo[1,2-c]imidazole-3-thione Example 473: (R)-1-(2-(((tetrahydro-2H-pyran-4-yl)methyl)amino)ethyl)-6-(2,3,6-trifluorophenyl)-2,5,6,7-tetrahydro-3H-pyrrolo[1,2-c]imidazole-3-thione Example 474: (R)-2-methyl-1-(2-(pyrrolidin-1-yl)ethyl)-6-(2,3,6-trifluorophenyl)-2,5,6,7-tetrahydro-3H-pyrrolo[1,2-c]imidazole-3-thione Example 475: (R)-1-(2-((((S)-tetrahydrofuran-2-yl)methyl)amino)ethyl)-6-(2,3,6-trifluorophenyl)-2,5,6,7-tetrahydro-3H-pyrrolo[1,2-c]imidazole-3-thione Example 476: (R)-1-(2-(tert-butylamino)ethyl)-2-methyl-6-(2,3,6-trifluorophenyl)-2,5,6,7-tetrahydro-3H-pyrrolo[1,2-c]imidazole-3-thione Example 477: (R)-2-methyl-1-(2-(((tetrahydro-2H-pyran-4-yl)methyl)amino)ethyl)-6-(2,3,6-trifluorophenyl)-2,5,6,7-tetrahydro-3H-pyrrolo[1,2-c]imidazole-3-thione Example 478: (R)-1-(3-(pyrrolidin-1-yl)propyl)-6-(2,3,6-trifluorophenyl)-2,5,6,7-tetrahydro-3H-pyrrolo[1,2-c]imidazole-3-thione

C. Compositions

The compounds of the invention intended for pharmaceutical use may be administered alone or in combination with one or more other compounds of the invention or in combination with one or more other drugs (or as any combination thereof). Generally, they will be administered as a formulation in association with one or more pharmaceutically acceptable excipients. Accordingly, the present invention is also directed to a pharmaceutical composition comprising (i) a therapeutically effective amount of a compound of formula Ia, as defined above, or a pharmaceutically acceptable salt or solvate thereof; and (ii) a pharmaceutically acceptable excipient.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

D. Methods of Use

This invention is also directed to compounds of formula Ia, as defined above, or a pharmaceutically acceptable salt or solvate thereof, for use in therapy, in particular for the treatment of conditions ameliorated by inhibition of DβH outside the CNS.

This invention is also directed to the use of compounds of formula Ia, as defined above, or a pharmaceutically acceptable salt or solvate thereof, in the manufacture of a medicament for treatment of conditions ameliorated by inhibition of DβH outside the CNS.

This invention is also directed to a method for treating conditions ameliorated by inhibition of dopamine-beta-hydroxylase outside the CNS comprising administering a therapeutically effective amount of a compound of formula Ia, as defined in claim 1, or a pharmaceutically acceptable salt or solvate thereof, to a patient in need thereof.

Conditions ameliorated by inhibition of DβH outside the CNS can include, but are not limited to: cardiovascular disorders such as Angina, Hypertension, Chronic or Congestive Heart Failure, Pulmonary Hypertension (PH) and Pulmonary Arterial Hypertension (PAH).

Reference is made to the "Guidelines for the diagnosis and treatment of pulmonary hypertension" (European Heart Journal (2009) 30, 2493-2537) for details on the definition, classification and pathology and pathobiological features of PH.

Typically, pulmonary hypertension is a group of diseases characterized by a progressive increase of pulmonary vascular resistance leading to right ventricular failure and premature death. It may be defined by a mean pulmonary artery pressure equal or greater than 25 mmHg at rest.

PH has been clinically classified by the WHO into 5 groups, according to the cause of the disease, and symptoms may differ, depending on the 'group' that caused the disease. However, 'common' symptoms are as follows:

Difficulty in breathing or shortness of breath (main symptom)
Fatigue
Dizziness
Swelling in the ankles or legs (edema)
Bluish lips and skin (cyanosis)
Chest pain
Racing pulse and palpitations A clinical classification of pulmonary hypertension (PH) has been undertaken and reported by McLaughlin et al in "ACCF/AHA 2009 Expert Consensus Document on Pulmonary Hypertension", J Am Coll Cardiol 53, 1573-1619, 2009. PH was classified as follows:

1. Pulmonary arterial hypertension (PAH)
   1.1. Idiopathic (IPAH)
   1.2. Familial (FPAH)
   1.3. Associated with (APAH):
      1.3.1. Connective tissue disorder
      1.3.2. Congenital systemic-to-pulmonary shunts
      1.3.3. Portal hypertension
      1.3.4. HIV infection
      1.3.5. Drugs and toxins
      1.3.6. Other (thyroid disorders, glycogen storage disease, Gaucher's disease, hereditary hemorrhagic telangiectasia, hemoglobinopathies, chronic myeloproliferative disorders, splenectomy)
   1.4. Associated with significant venous or capillary involvement
      1.4.1. Pulmonary veno-occlusive disease (PVOD)
      1.4.2. Pulmonary capillary hemangiomatosis (PCH)
   1.5. Persistent pulmonary hypertension of the newborn
2. Pulmonary hypertension with left heart disease
   2.1. Left-sided atrial or ventricular heart disease
   2.2. Left-sided valvular heart disease
3. Pulmonary hypertension associated with lung diseases and/or hypoxemia
   3.1. Chronic obstructive pulmonary disease
   3.2. Interstitial lung disease
   3.3. Sleep disordered breathing
   3.4. Alveolar hypoventilation disorders
   3.5. Chronic exposure to high altitude
   3.6. Developmental abnormalities
4. Pulmonary hypertension due to chronic thrombotic and/or embolic disease (CTEPH)
   4.1. Thromboembolic obstruction of proximal pulmonary arteries
   4.2. Thromboembolic obstruction of distal pulmonary arteries
   4.3. Nonthrombotic pulmonary embolism (tumor, parasites, foreign material)
5. Miscellaneous
Sarcoidosis, histiocytosis X, lymphangiomatosis, compression of pulmonary vessels (adenopathy, tumor, fibrosing mediastinitis)

The WHO has also provided the following functional assessment classification:
Functional Symptomatic profile
Class
I Patients with pulmonary hypertension but without resulting limitation of physical activity. Ordinary physical activity does not cause dyspnoea or fatigue, chest pain, or near syncope II Patients with pulmonary hypertension resulting in slight limitation of physical activity. They are comfortable at rest. Ordinary physical activity causes undue dyspnoea or fatigue, chest pain, or near syncope III Patients with pulmonary hypertension resulting in marked limitation of physical activity. They are comfortable at rest. Less than ordinary activity causes undue dyspnoea or fatigue, chest pain, or near syncope IV Patients with pulmonary hypertension with inability to carry out any physical activity without symptoms. These patients manifest signs of right heart failure. Dyspnoea and/or fatigue may even be present at rest. Discomfort is increased by any physical activity.

E. General Synthetic Methodology

The methods used for the synthesis of the compounds of the invention are illustrated by the schemes below. The starting materials and reagents used in preparing these compounds are available from commercial suppliers or can be prepared by methods obvious to those skilled in the art. To make the schemes easier to read, the option to incorporate deuterium at certain positions is not shown. Specifically, deuterated products can be produced using specifically deuterated starting materials, including, but not limited to, those used in Examples 1-478.

The starting material for compounds of formula If, when $R_1$=H can generally be synthesised by the method outlined in Scheme 1 as either enriched enantiomers or racemates:

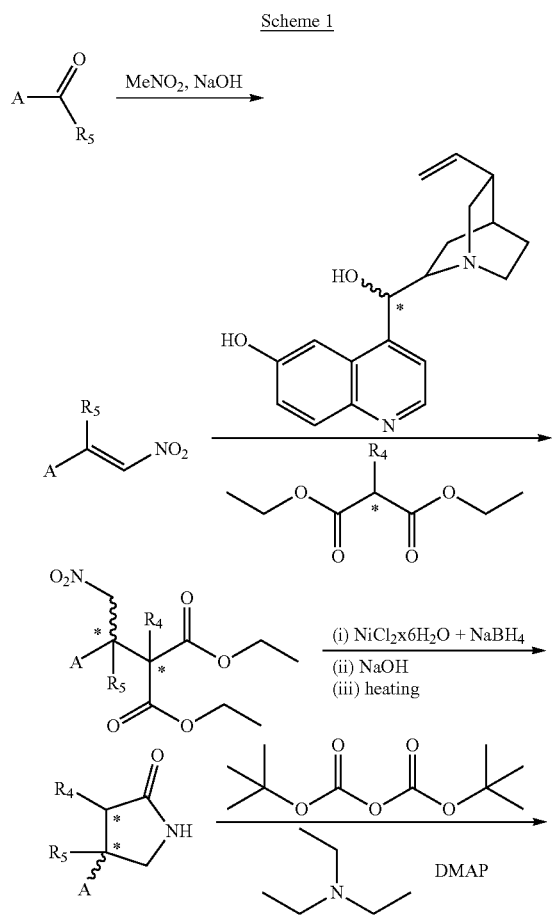

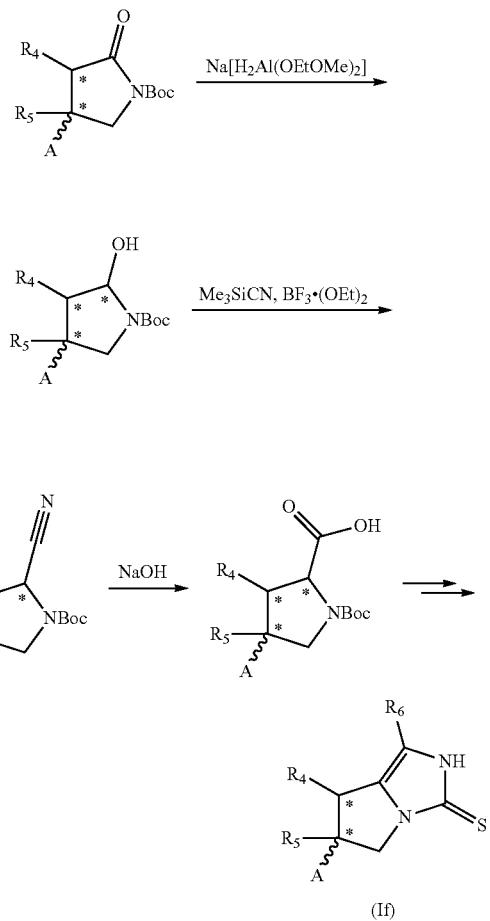

The starting material for compounds of formula Ii, when $R_1$=H can generally be synthesised by the method outlined in Scheme 2 as either enriched enantiomers or racemates:

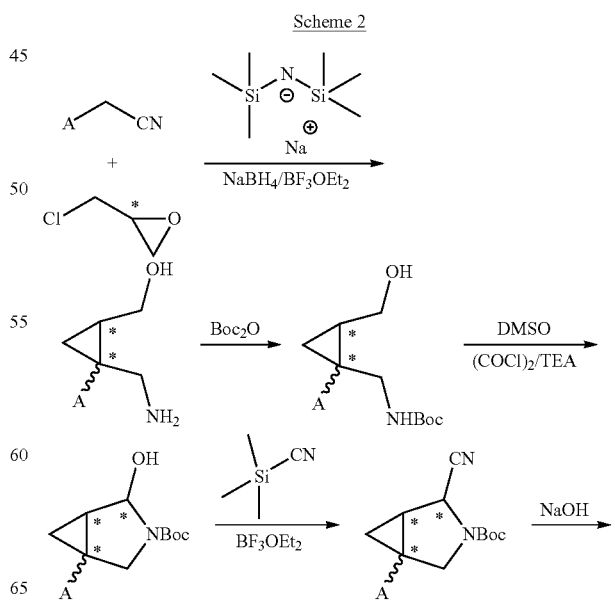

59
-continued
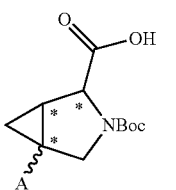
Compounds of formula If or Ii, with various identities for $R_6$, can generally be synthesised by the methods outlined in Schemes 3-15 as either enriched enantiomers or racemates:
Scheme 3
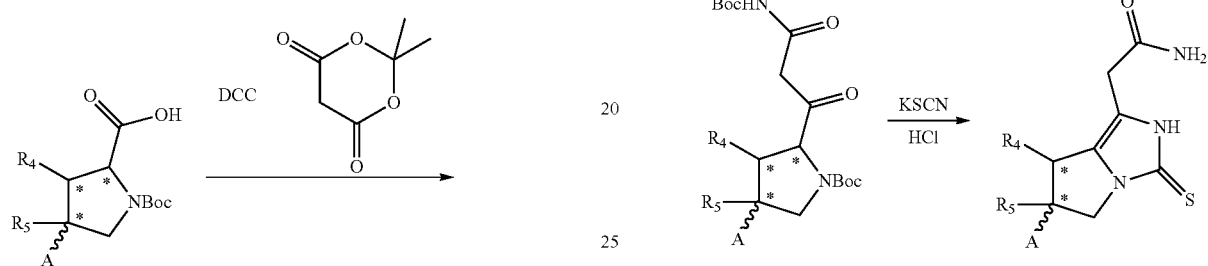
60
-continued
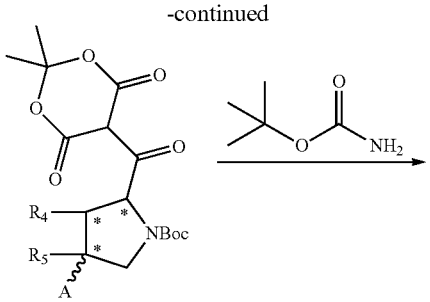
Scheme 4
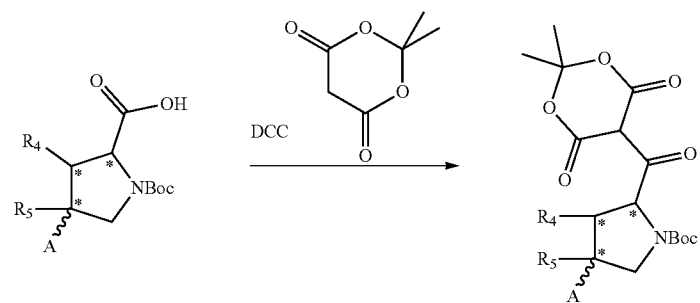
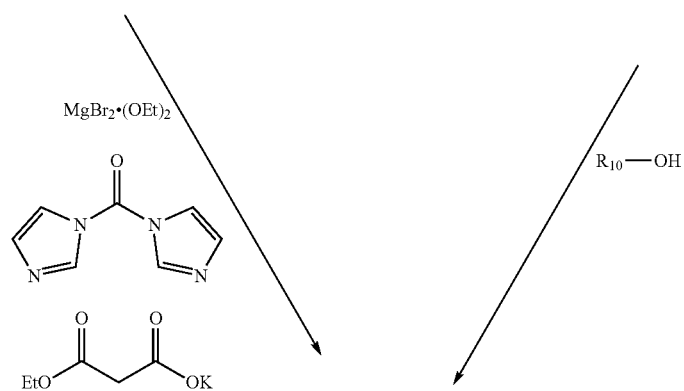

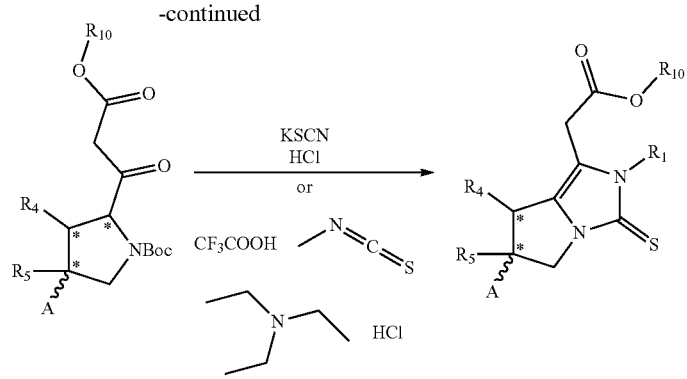
Scheme 5
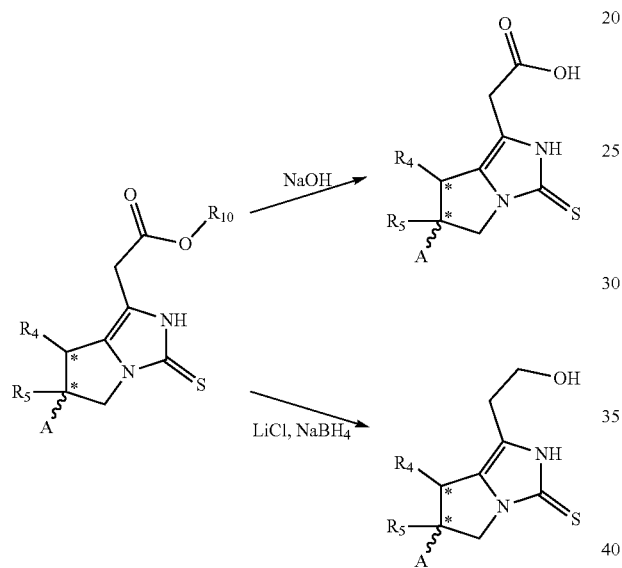
Scheme 6
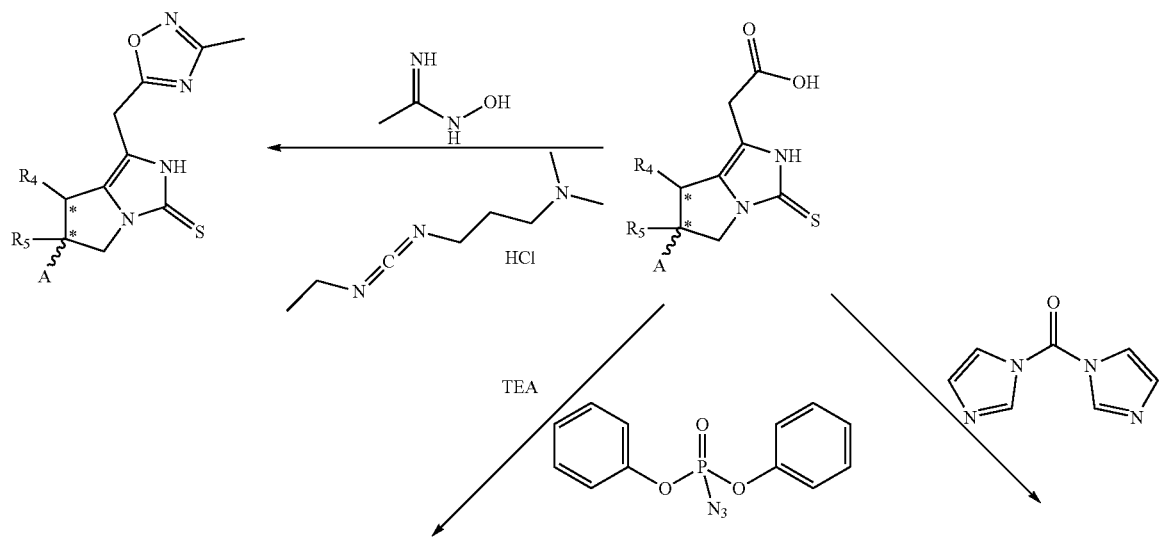

63 64
-continued
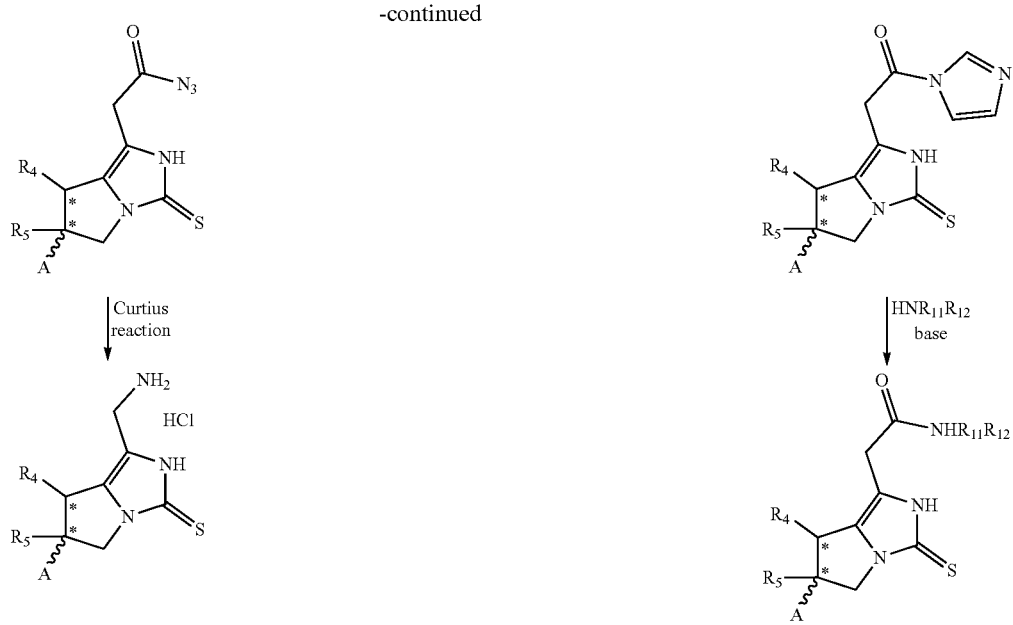
Scheme 7
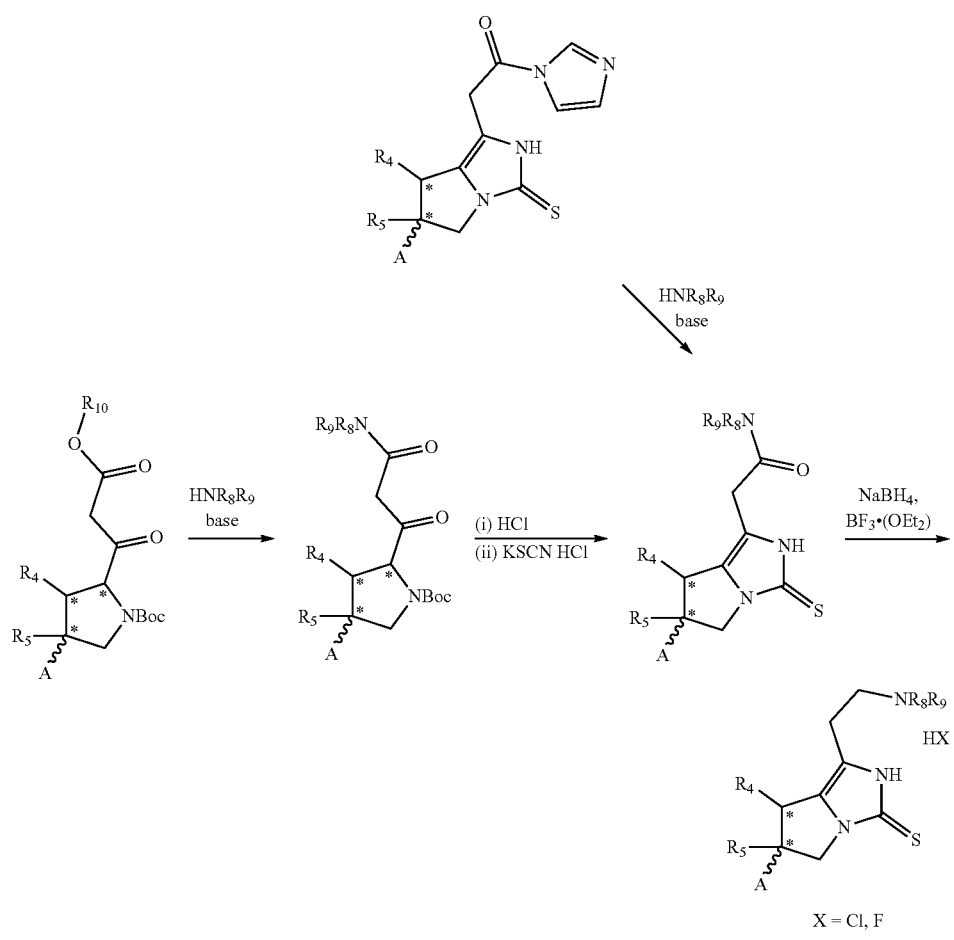
X = Cl, F

Scheme 8
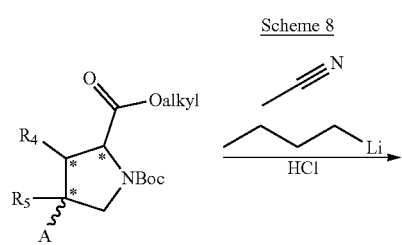
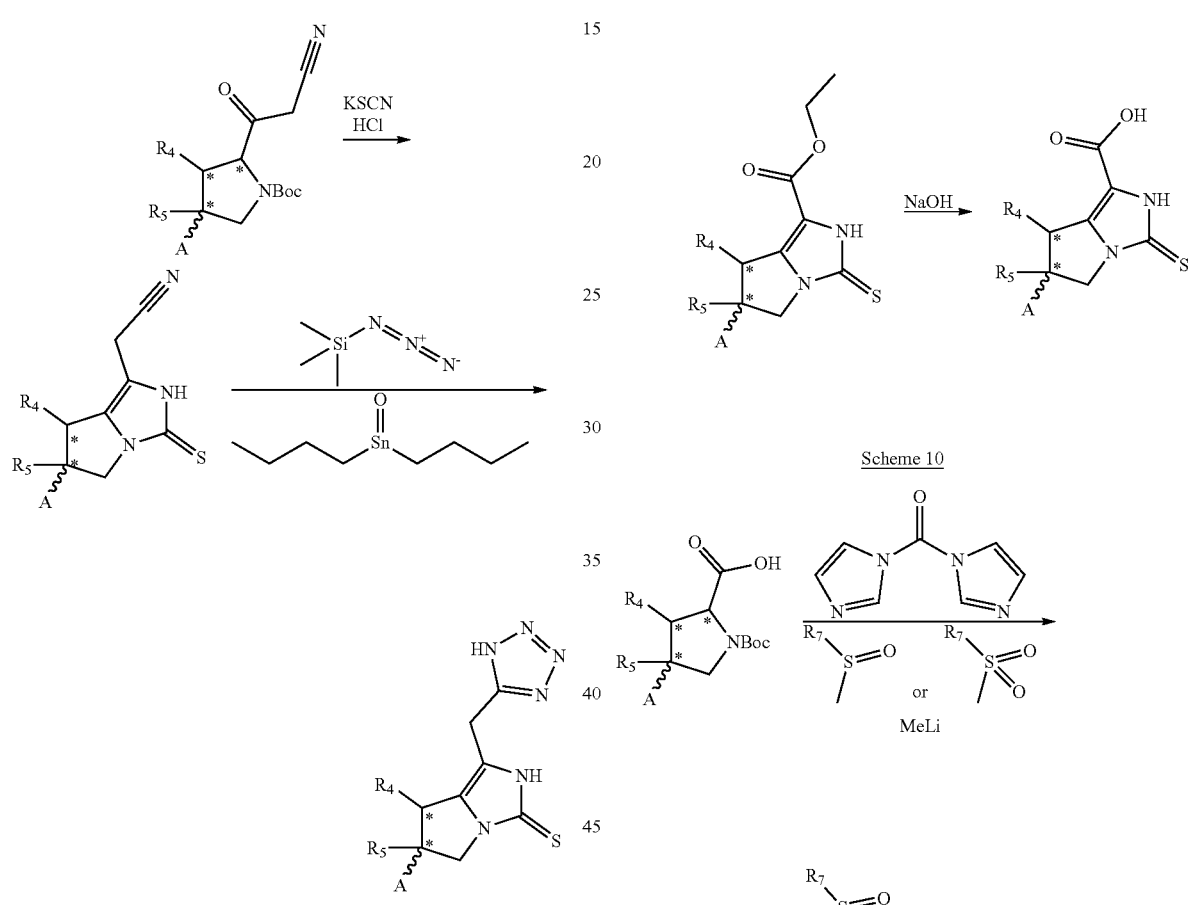
Scheme 9
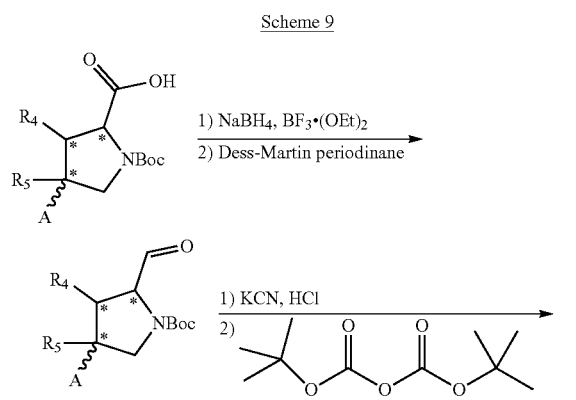
Scheme 10
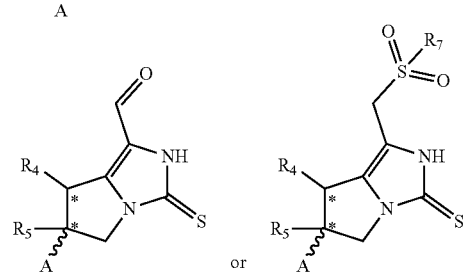

Scheme 11
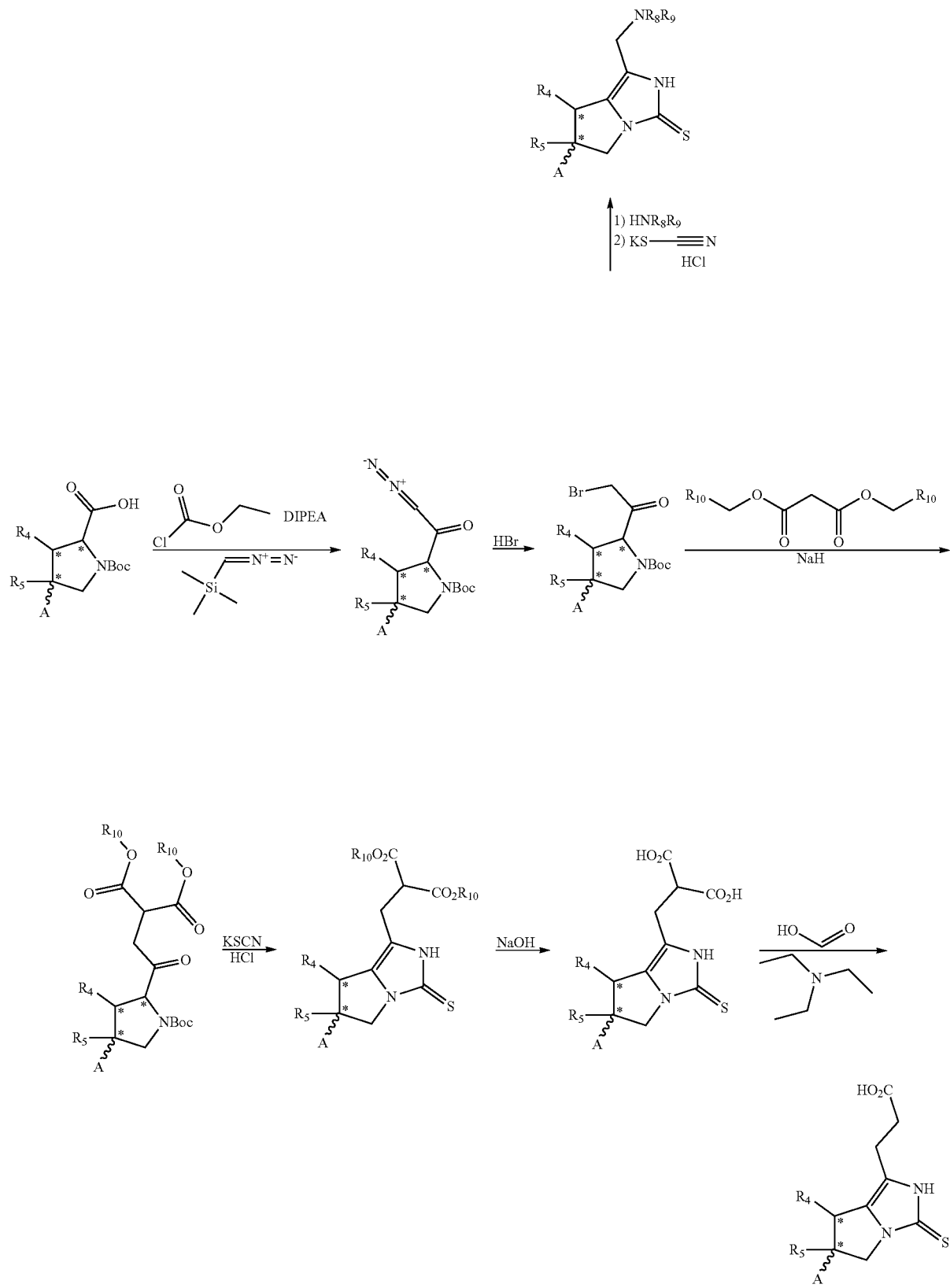

Scheme 12
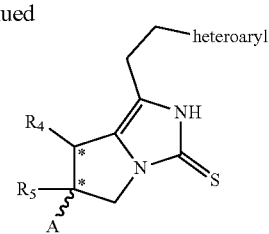
Scheme 13
Scheme 14

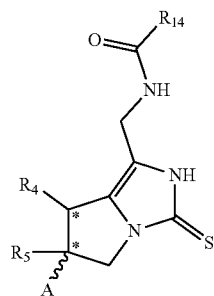
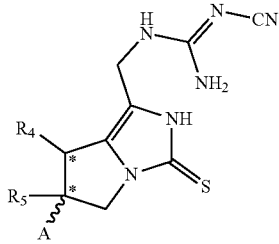

Scheme 15

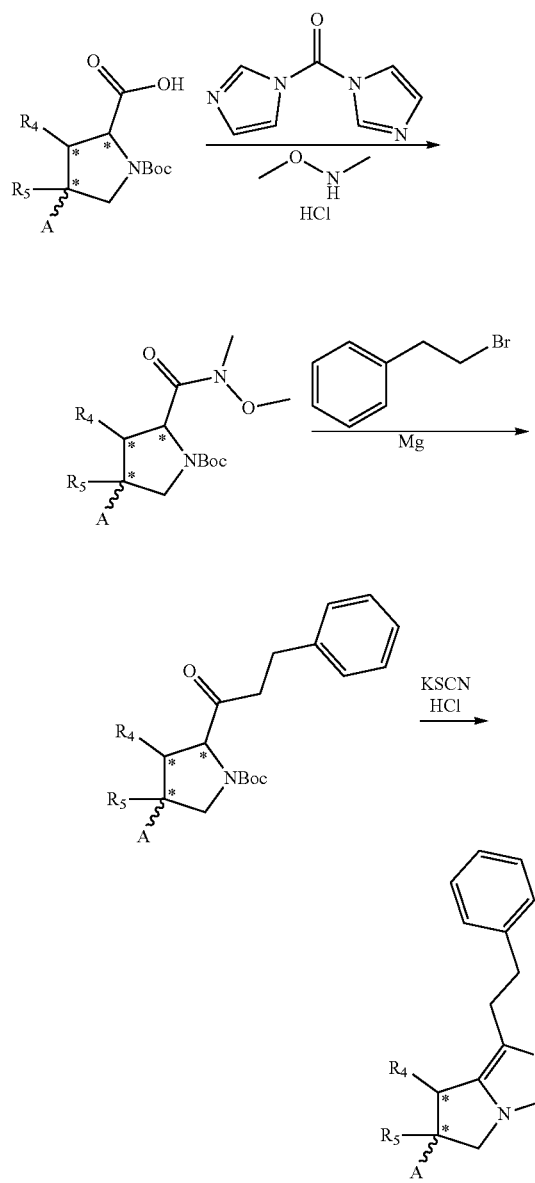

Scheme 16

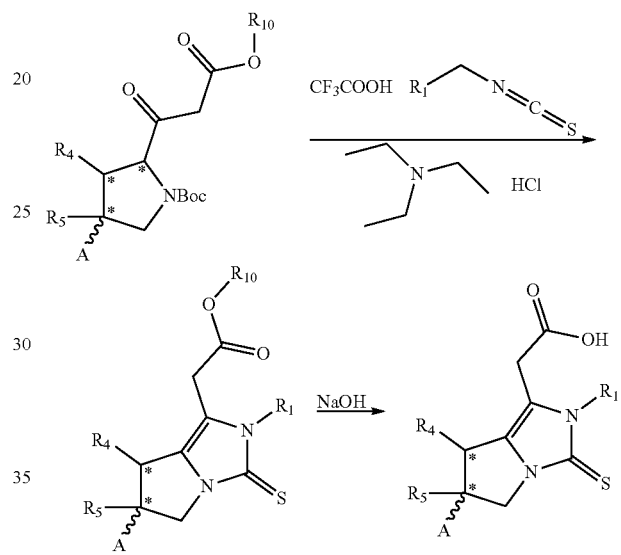

Compounds wherein $R_1$ is $C_1$-$C_6$ alkyl, partially or fully deuterated $C_1$-$C_6$ alkyl or $C_3$-$C_6$ cycloalkyl can be synthesised using an alkyl isothiocyanate as shown in Scheme 16 below:

F. Examples

All compounds and intermediates were characterised by NMR. The spectra were recorded on a Bruker Avance III 600 MHz spectrometer with solvent used as internal standard. $^{13}C$ spectra were recorded at 150 MHz and $^1H$ spectra were recorded at 600 MHz. Data are reported in the following order: approximate chemical shift (ppm), number of protons, multiplicity (br, broad; d, doublet; m, multiplet; s, singlet; t, triplet) and coupling constant (Hz).

Room temperature in the following protocols means the temperature ranging from 20° C. to 25° C.

Example 1: (S)-ethyl 2-(6-(3,5-difluorophenyl)-3-thioxo-3,5,6,7-tetrahydro-2H-pyrrolo[1,2-c]imidazol-1-yl)acetate Step 1: (E)-1,3-difluoro-5-(2-nitrovinyl)benzene

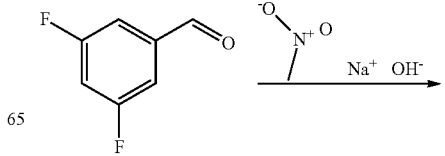

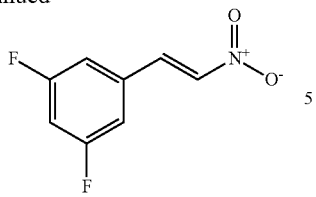
5

To a solution of methanol (72 mL), water (36 mL), and 2.5 M sodium hydroxide (32.4 mL, 81 mmol) was added a solution of 3,5-difluorobenzaldehyde (10 g, 70.4 mmol) and nitromethane (4.36 mL, 81 mmol) in methanol (12.00 mL) dropwise over 30 min at 5° C., while the internal temperature was maintained between 5 and 10° C. with external cooling. The reaction was then agitated in the cold for an additional 0.5, and then a solution of cc. HCl (11.73 mL, 141 mmol) in water (36 mL) was added in one portion at 0-10° C. with stirring. The resulting crystals were collected, washed with water and dried to give the product as a light yellow powder. (Yield: 7.0 g, 54%).

Step 2: (S)-diethyl 2-(1-(3,5-difluorophenyl)-2-nitroethyl)malonate

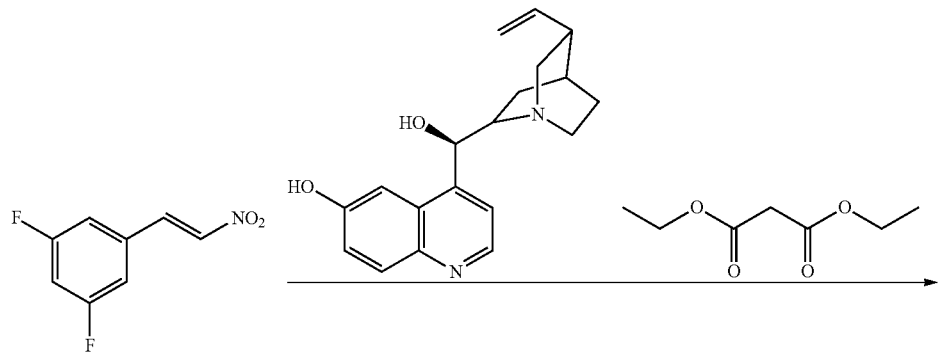

To a stirred solution of (E)-1,3-difluoro-5-(2-nitrovinyl) benzene (7.4 g, 40.0 mmol) in dry tetrahydrofuran (75 mL) was added 4-((1R)-hydroxy((4S,8R)-8-vinylquinuclidin-2-yl)methyl)quinolin-6-ol (0.620 g, 1.999 mmol) at room temperature with stirring followed by addition of diethyl malonate (9.15 mL, 60.0 mmol). The mixture was cooled to −15 to −17° C. under inert atmosphere and stirred for 20 h in the cold. Thereupon, the mixture was evaporated to dryness under vacuum and the residue was taken up in dichloromethane (100 mL), washed with 1 M HCl, brine, dried over MgSO$_4$ and filtered on a silica pad. The filtrate was concentrated to 20 mL, and the residue was crystallized on dilution with petroleum ether (ca. 50 mL). The mixture was further diluted with petroleum ether (120 mL), and aged at 5-10° C. The resulting solid was collected, washed with petroleum ether, and dried to give the product as an off-white powder. (Yield: 11.46 g, 83%).

Step 3: (4)-ethyl 4-(3,5-difluorophenyl)-2-oxopyrrolidine-3-carboxylate

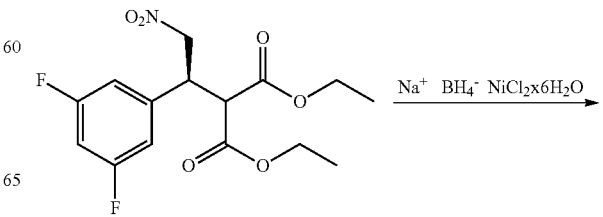

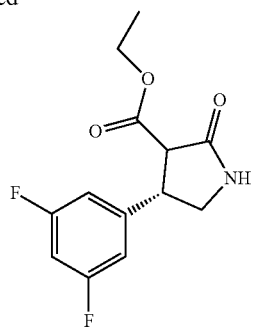

To a suspension of (S)-diethyl 2-(1-(3,5-difluorophenyl)-2-nitroethyl)malonate (11 g, 31.9 mmol) in methanol (170 mL) was added nickel(II) chloride hexahydrate (7.57 g, 31.9 mmol) followed by addition of sodium borohydride (9.64 g, 255 mmol) in portions with ice cooling. The mixture was stirred for 6 h at room temperature, then quenched with ammonium chloride solution (300 mL), diluted with dichloromethane (150 mL), acidified with 6 M HCl to pH=2, and stirred for 16 h. Thereupon, the mixture was extracted with dichloromethane, the organic phase was dried over MgSO$_4$ and evaporated to dryness to give the product as a light yellow crystalline. (Yield: 8.31 g, 97%).

Step 4: (4S)-4-(3,5-difluorophenyl)-2-oxopyrrolidine-3-carboxylic Acid

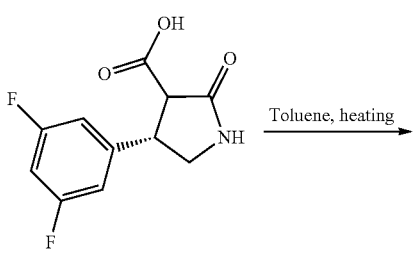

To a stirred solution of (4S)-ethyl 4-(3,5-difluorophenyl)-2-oxopyrrolidine-3-carboxylate (8.3 g, 30.8 mmol) in ethanol (130 mL) was added 1 M sodium hydroxide (37.0 mL, 37.0 mmol). The resulting suspension was stirred for 1 h, the organics were then removed under vacuum, and the residue was dissolved in water (300 mL). The product was crystallized on acidification with 6 M HCl. The resulting crystals were collected, washed with cold water and dried under vacuum at 50° C. to give the product as a beige powder Yield: 6.0 g, 81%.

Step 5: (S)-4-(3,5-difluorophenyl)pyrrolidin-2-one

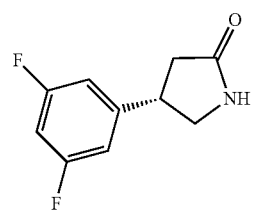

A solution of (4S)-4-(3,5-difluorophenyl)-2-oxopyrrolidine-3-carboxylic acid (6.0 g, 24.88 mmol) in toluene (350 mL) was stirred under reflux for 3 h, whereupon the mixture was evaporated to 30 mL, and then diluted with petroleum ether. The resulting crystals were collected, washed with petroleum ether and dried under vacuum to give an off-white powder. Yield: 4.83 g, 98%.

Step 6: (S)-tert-butyl 4-(3,5-difluorophenyl)-2-oxopyrrolidine-1-carboxylate

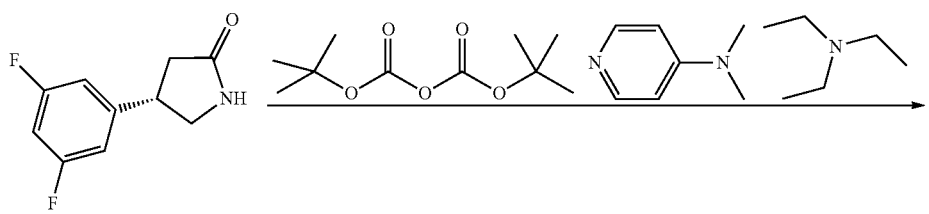

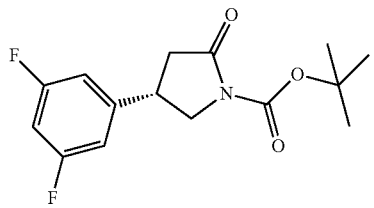

To a stirred solution of (S)-4-(3,5-difluorophenyl)pyrrolidin-2-one (4.8 g, 24.34 mmol) in dry dichloromethane (15 mL) was added at room temperature di-tert-butyl dicarbonate (7.80 g, 36.5 mmol) followed by addition of N,N-dimethylpyridin-4-amine (2.97 g, 24.34 mmol) and triethyl amine (3.32 ml, 23.84 mmol). The mixture was then stirred at room temperature for 3 h, and then concentrated under vacuum. Chromatography (petroleum ether-ethyl acetate; 4:1) gave an oil which was crystallized from petroleum ether (60 mL). The product was isolated as a white powder. Yield: 6.24 g, 88%.

Step 7: (4S)-tert-butyl 4-(3,5-difluorophenyl)-2-hydroxypyrrolidine-1-carboxylate

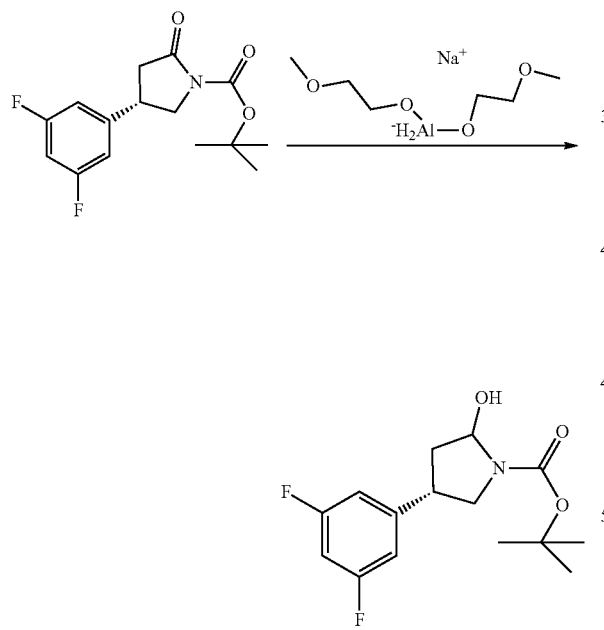

To a stirred solution of (S)-tert-butyl 4-(3,5-difluorophenyl)-2-oxopyrrolidine-1-carboxylate (2.5 g, 8.41 mmol) in dry diethyl ether (37 mL) was added dropwise 65% RED-Al (bis(2-methoxyethoxy)aluminum(III) sodium hydride) (1.51 ml, 5.05 mmol) in toluene at 0-5° C. under nitrogen and the mixture was stirred for 1 h in the cold. Thereupon, the mixture was quenched with sodium bicarbonate solution and stirred for 30 min. The organic phase was dried over MgSO$_4$, and evaporated to dryness to give the product as a yellowish oil. (Yield: 2.56 g, 92%).

Step 8: (4S)-tert-butyl 2-cyano-4-(3,5-difluorophenyl)pyrrolidine-1-carboxylate

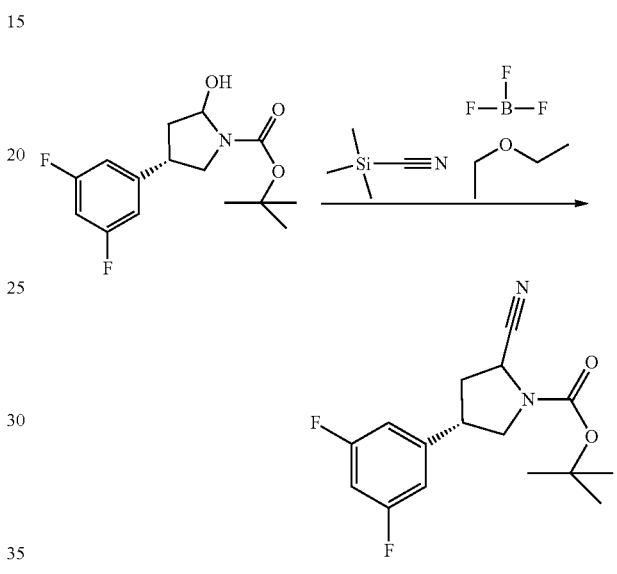

To a stirred solution of (4S)-tert-butyl 4-(3,5-difluorophenyl)-2-hydroxypyrrolidine-1-carboxylate (3.5 g, 11.69 mmol) in dry dichloromethane (75 mL) was added trimethylsilanecarbonitrile (3.14 ml, 23.39 mmol) followed by addition of boron trifluoride etherate (3.26 ml, 25.7 mmol) at −70° C. The mixture was stirred for 4 h in the cold, thereupon quenched with sodium bicarbonate solution, and then allowed to warm up with stirring to room temperature. The organic phase was dried over MgSO$_4$, filtered and evaporated to dryness under vacuum. Chromatography (petroleum ether-ethyl acetate; 9:1) afforded the compound as a colourless oil. (Yield: 2.43 g, 67%).

Step 9: (4S)-1-(tert-butoxycarbonyl)-4-(3,5-difluorophenyl)pyrrolidine-2-carboxylic acid

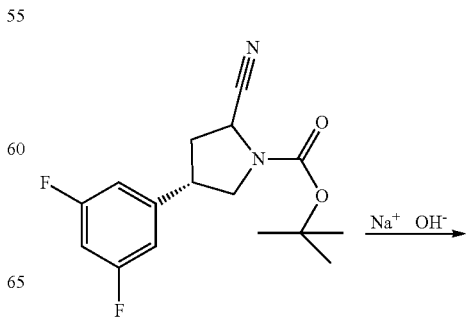

-continued

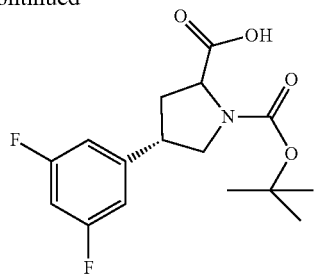

To a stirred solution of (4S)-tert-butyl 2-cyano-4-(3,5-difluorophenyl)pyrrolidine-1-carboxylate (2.25 g, 7.30 mmol) in ethanol (25 mL) was added 3 M sodium hydroxide (12.16 mL, 36.5 mmol) and the solution was gently refluxed (oil bath at 80° C.) for 3 h. Thereupon, ethanol was removed under vacuum and the residue was diluted with water (30 mL), and then acidified with 2 M HCl to pH=2 at 10-15° C. The mixture was extracted with dichloromethane (50 mL), the insoluble materials in both phases was filtered off, whereupon the organic phase was washed with brine, dried over MgSO$_4$ and evaporated to dryness to give 0.90 g of yellowish foam. (Yield: 37%).

Step 10: (4S)-tert-butyl 4-(3,5-difluorophenyl)-2-(2,2-dimethyl-4,6-dioxo-1,3-dioxane-5-carbonyl)pyrrolidine-1-carboxylate

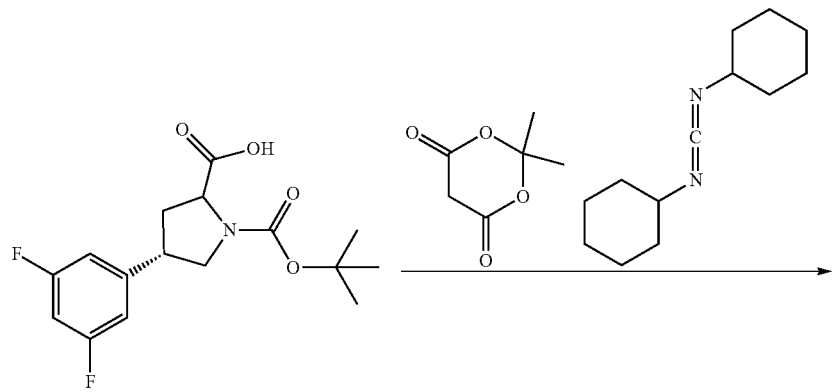

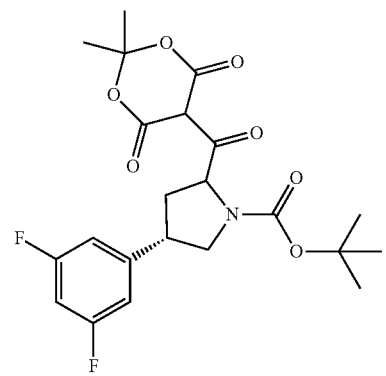

To a solution of (4S)-1-(tert-butoxycarbonyl)-4-(3,5-difluorophenyl)pyrrolidine-2-carboxylic acid (0.35 g, 1.069 mmol), 2,2-dimethyl-1,3-dioxane-4,6-dione (0.154 g, 1.069 mmol) and N,N-dimethylpyridin-4-amine (0.131 g, 1.069 mmol) was added dicyclohexylmethanediimine (0.221 g, 1.069 mmol) dropwise at 0-5° C. and the mixture was stirred in the cold for 2 h. The mixture was then filtered through a celite, plug, the filtrate was washed with 1 M HCl, brine, dried over MgSO$_4$, and then evaporated to dryness to give the product as oil. (Yield: 0.42 g, 87

Step 11: (4S)-tert-butyl 4-(3,5-difluorophenyl)-2-(3-ethoxy-3-oxopropanoyl)pyrrolidine-1-carboxylate

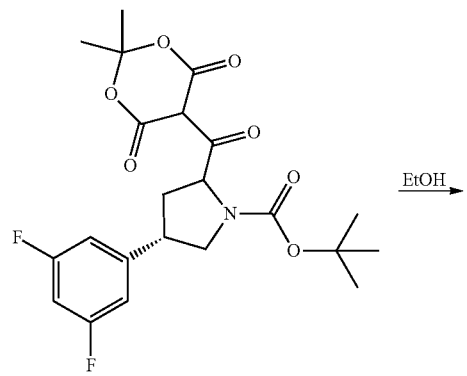

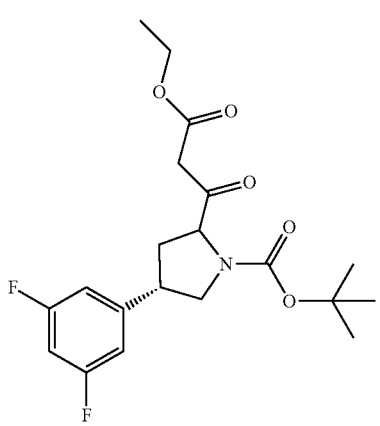

A solution of (4S)-tert-butyl 4-(3,5-difluorophenyl)-2-(2,2-dimethyl-4,6-dioxo-1,3-dioxane-5-carbonyl)pyrrolidine-1-carboxylate (0.41 g, 0.904 mmol) in abs. ethanol (5 mL) was stirred under reflux for 3 h. The solvent was then removed under vacuum and the residue was subjected to chromatography (petroleum ether-ethyl acetate; 9:1). The product was isolated as a colourless oil. (Yield: 0.124 g, 34%).

Step 12: ((S)-ethyl 2-(6-(3,5-difluorophenyl)-3-thioxo-3,5,6,7-tetrahydro-2H-pyrrolo[1,2-c]imidazol-1-yl)acetate

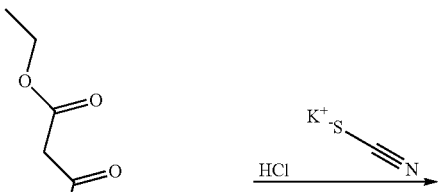

A solution (4S)-tert-butyl 4-(3,5-difluorophenyl-2-(3-ethoxy-3-oxopropanoyl)pyrroline-1-carboxylate (0.11 g, 0.277 mmol) in 2 M HCl (1.107 mL, 2.214 mmol) in diethyl ether was stirred at room temperature for 5 h. and then the solvent was removed under vacuum. The residue was dissolved in a mixture of ethanol (1.5 mL) and water (1.5 mL), treated with potassium thiocyanate (0.030 g, 0.304 mmol) followed by addition of 6N HCl (0.023 mL, 0.138 mmol) and then the mixture was stirred at 90° C. for 3 h. Thereupon, ethanol was removed under vacuum, and the residue was extracted with a mixture of ethyl acetate-petroleum ether (2:1). The organic phase was dried over MgSO$_4$, evaporated to dryness and the residue was subjected to chromatography (petroleum ether-EtOAc; 1:1, then 1:2). The product was isolated as a light yellow powder. (Yield: 0.038 g, 40%).

$^1$H NMR (DMSO$_{d6}$): 1.78 (1H, s), 7.13 (3H, m), 4.17 (1H, dd, J=11.1, 7.8 Hz), 4.09 (2H, q, J=7.0 Hz), 4.09 (1H, m), 3.70 (1H, dd, J=11.2, 7.8 Hz), 3.52 (2H, m, J=3.1 Hz), 3.20 (1H, dd, J=15.4, 7.9 Hz), 2.84 (1H, dd, J=15.4, 8.4 Hz), 1.19 (3H, t, J=7.1 Hz).

$^{13}$C NMR (DMSO$_{d6}$): 169.2, 163.3, 163.2, 161.7, 161.6, 155.6, 145.8, 145.8, 145.7, 129.9, 113, 110.7, 110.7, 110.6, 110.6, 102.7, 102.5, 102.3, 60.7, 50.3, 46.4, 30.4, 29.8, 14.1.

Example 2: (S)-ethyl 2-(6-(2,5-difluorophenyl)-3-thioxo-3,5,6,7-tetrahydro-2H-pyrrolo[1,2-c]imidazol-1-yl)acetate and Example 3: (S)-2-(6-(2,5-difluorophenyl)-3-thioxo-3,5,6,7-tetrahydro-2H-pyrrolo[1,2-c]imidazol-1-yl)acetic Acid Step 1: Tert-Butyl (4S)-4-(2,5-difluorophenyl)-2-(3-ethoxy-3-oxopropanoyl)pyrrolidine-1-carboxylate

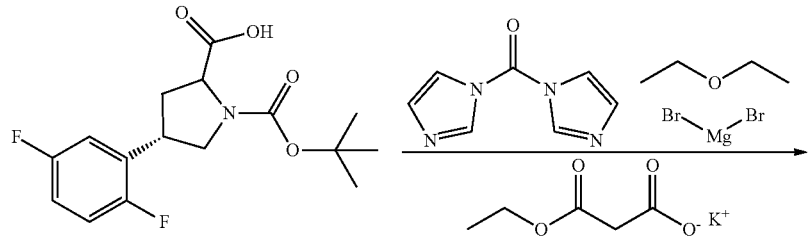

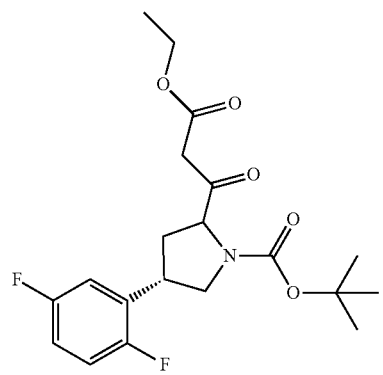

A mixture of potassium 3-ethoxy-3-oxopropanoate (0.741 g, 4.35 mmol) and magnesium bromide diethyletherate (0.749 g, 2.90 mmol) in dry tetrahydrofuran (10 ml) was stirred under inert atmosphere at 50° C. for 6 h. In parallel, di(1H-imidazol-1-yl)methanone (0.706 g, 4.35 mmol) was added portionwise to a solution of (4S)-1-(tert-butoxycarbonyl)-4-(2,5-difluorophenyl)pyrrolidine-2-carboxylic acid (prepared analogous manner to Example 1 step 9) (0.95 g, 2.90 mmol) in dry tetrahydrofuran (8.00 mL) at 0-5° C. and the mixture was stirred for 2 h at room temperature. The solution was then added to the first suspension dropwise and the mixture was stirred for 16 h at ambient temperature. Thereupon, the mixture was quenched with aq. NaHSO₄ solution and then extracted with a mixture of ethyl acetate-petroleum ether (2:1). The organic phase was washed with sodium bicarbonate, dried over MgSO₄ and evaporated to dryness. Chromatography in a mixture of petroleumether-ethyl acetate (9:1) afforded (4S)-tert-butyl 4-(2,5-difluorophenyl)-2-(3-ethoxy-3-oxopropanoyl)pyrrolidine-1-carboxylate. (Yield: 0.56 g, 48.6%).

Step 2: (S)-ethyl 2-(6-(2,5-difluorophenyl)-3-thioxo-3,5,6,7-tetrahydro-2H-pyrrolo[1,2-c]imidazol-1-yl)acetate and (S)-2-(6-(2,5-difluorophenyl)-3-thioxo-3,5,6,7-tetrahydro-2H-pyrrolo[1,2-c]imidazol-1-yl)acetic Acid

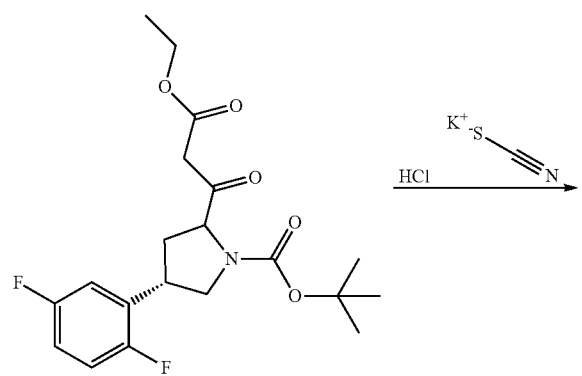

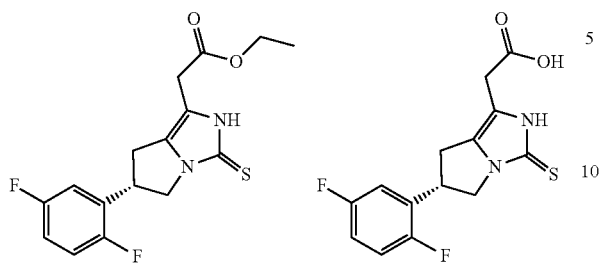

A solution of (4S)-tert-butyl 4-(2,5-difluorophenyl)-2-(3-ethoxy-3-oxopropanoyl)pyrrolidine-1-carboxylate (0.56 g, 1.409 mmol) in 2 M HCl (5.64 mL, 11.27 mmol) in diethyl ether was stirred at room temperature for 16 h, whereupon the solvent was removed under vacuum, and the residue was dissolved in a mixture of ethanol (6 mL) and water (6 mL). The reaction mixture was treated with potassium thiocyanate (0.151 g, 1.550 mmol) followed by addition of 6 M HCl (0.117 mL, 0.705 mmol) and then stirred for 2 h Thereupon, ethanol was removed under vacuum, were upon the resulting solid was collected and washed with water. The precipitate was dissolved in ethyl acetate, dried over MgSO$_4$, filtered through a silica pad, and then evaporated to dryness. Crystallization from petroleum ether afforded (S)-ethyl 2-(6-(2,5-difluorophenyl)-3-thioxo-3,5,6,7-tetrahydro-2H-pyrrolo[1,2-c]imidazol-1-yl)acetate as an off-white powder. (Yield: 0.19 g, 39%).

$^1$H NMR (DMSO$_{d6}$): 11.79 (1H, br s), 7.27 (2H, m), 7.18 (1H, m), 4.23 (1H, quin, J=7.7 Hz), 4.15 (1H, dd, J=11.2, 8.0 Hz), 4.09 (2H, q, J=7.1 Hz), 3.75 (1H, dd, J=11.2, 7.5 Hz), 3.52 (2H, m), 3.22 (1H, dd, J=15.5, 8.0 Hz), 2.87 (1H, br dd, J=15.6, 7.8 Hz), 1.19 (3H, t, J=7.0 Hz).

$^{13}$C NMR (DMSO$_{d6}$): 169.2, 159, 157.5, 157.1, 155.6, 155.5, 130.1, 130, 130, 129.9, 129.8, 117.2, 117.1, 117, 116.9, 115.5, 115.4, 115.3, 115.3, 115.2, 115.2, 115.1, 115, 113, 60.7, 49.4, 40.3, 29.8, 29.6, 14.1.

The aqueous mother liqueur of the above procedure was extracted with dichloromethane. The organic phase was extracted with aq. NaOH, then the aqueous phase was acidified and extracted with dichloromethane, The organic phase was dried over MgSO$_4$, evaporated to dryness to give 67 mg (15% yield) of (S)-2-(6-(2,5-difluorophenyl)-3-thioxo-3,5,6,7-tetrahydro-2H-pyrrolo[1,2-c]imidazol-1-yl) acetic acid as an off-white powder.

$^1$H NMR (DMSO$_{d6}$): 12.58 (1H, br s), 11.75 (1H, s), 7.28 (2H, m), 7.18 (1H, m), 4.22 (1H, quin, J=7.8 Hz), 4.14 (1H, dd, J=11.2, 7.9 Hz), 3.73 (1H, dd, J=11.3, 7.3 Hz), 3.43 (2H, m), 3.21 (1H, dd, J=15.5, 8.0 Hz), 2.87 (1H, dd, J=15.4, 7.8 Hz).

$^{13}$C NMR (DMSO$_{d6}$): 170.8, 159.1, 157.5, 157.1, 155.5, 155.5, 130.1, 130, 130, 129.9, 129.5, 117.1, 117.1, 117, 116.9, 115.5, 115.4, 115.3, 115.3, 115.2, 115.1, 115.1, 113.8, 49.4, 40.3, 30, 29.5.

Example 4: Methyl 2-((5aS,6aR)-5a-(2,5-difluorophenyl)-3-thioxo-2,3,5,5a,6,6a-hexahydrocyclopropa[3,4]pyrrolo[1,2-c]imidazol-1-yl)acetate Step 1: ((1R,2S)-2-(aminomethyl)-2-(2,5-difluorophenyl)cyclopropyl)methanol

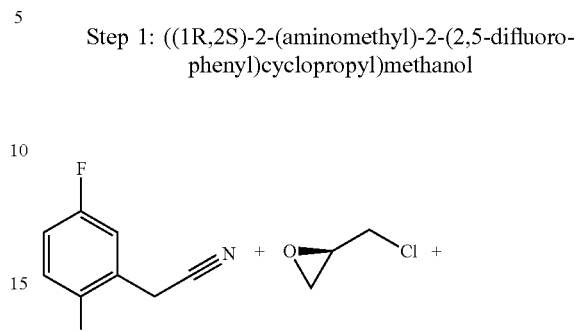

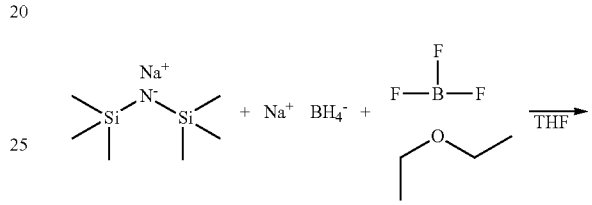

To a stirred solution of 2-(2,5-difluorophenyl)acetonitrile (10.0 g, 65.3 mmol) in dry terahydrofuran (100 mL), was added (R)-2-(chloromethyl)oxirane (6.13 mL, 78.0 mmol) at room temperature, under nitrogen. The reaction was then cooled to 15° C. and 2 M sodium bis(trimethylsilyl)amide in terahydrofuran (57.1 mL, 114.0 mmol) was added, dropwise at 15° C. over a period of 2 h. Thereupon, the thus obtained red mixture was allowed to warm up to room temperature and stirred for 3 h. The reaction was diluted with dry terahydrofuran (100 mL), cooled to 0° C., and then sodium borohydride (9.88 g, 261 mmol) was added followed by dropwise addition of boron trifluoride etherate (33.10 ml, 261 mmol). The mixture was allowed to warm up to room temperature and stirred overnight. The resulting pale yellow suspension was cooled to 0° C. and carefully quenched with 2 M HCl (196 mL, 392 mmol). The terahydrofuran was then evaporated off and the aqueous phase was washed with diethyl ether. The pH of the aqueous phase was set to pH=10 by adding 3 M sodium hydroxide and then extracted with dichloromethane. The organic phase was dried over MgSO$_4$, filtered and evaporated to dryness under vacuum to leave a yellow oil. (Yield: 12.91 g, 74%).

Step 2: tert-butyl (((S,2R)-1-(2,5-difluorophenyl)-2-(hydroxymethyl)cyclopropyl)methyl)carbamate

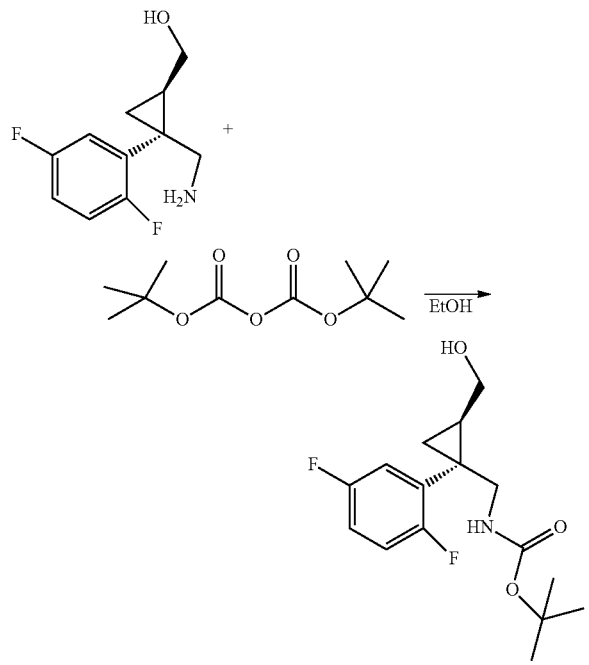

To an ice-cold solution of ((1R,2S)-2-(aminomethyl)-2-(2,5-difluorophenyl)cyclopropyl)methanol (12.91 g, 60.5 mmol) in ethanol (207 mL) was added di-tert-butyl dicarbonate (13.21 g, 60.5 mmol). The solution was stirred at room temperature for 3 h and then the solvent was evaporated off under vacuum. The resulting yellow oil was purified by chromatography (petroleum ether-ethyl acetate). The product was isolated as a white powder. (Yield: 14.28 g, 64%).

Step 3: tert-butyl (S,5R)-1-(2,5-difluorophenyl)-4-hydroxy-3-azabicyclo[3.1.0]hexane-3-carboxylate

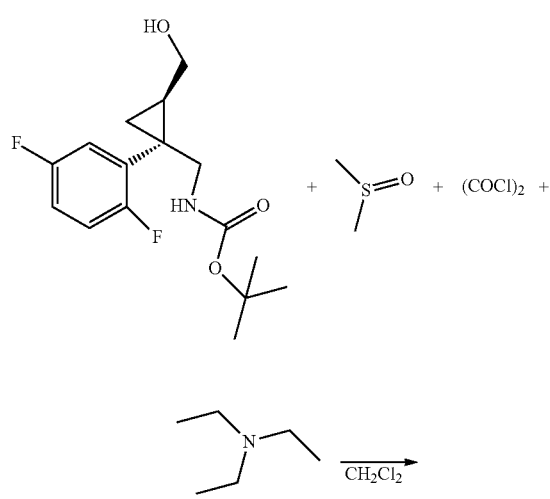

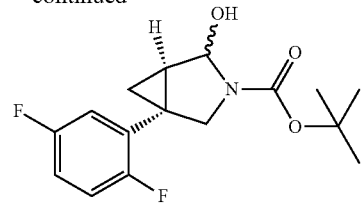

To a stirred solution of oxalyl dichloride (4.39 mL, 50.10 mmol) in dry dichloromethane (120 mL), was added dropwise a solution of dimethylsulfoxide (4.12 mL, 100.0 mmol) in dry dichloromethane (22 mL) at −78° C. The reaction mixture was stirred in the cold for 15 min, and then a solution of tert-butyl tert-butyl (((1S,2R)-1-(2,5-difluorophenyl)-2-(hydroxymethyl)cyclopropyl)methyl)carbamate (14.28 g, 45.60 mmol) in dry dichloromethane (44 mL) was added dropwise. The mixture was stirred at −78° C. for 1 h and then triethylamine (31.8 mL, 228.0 mmol) was added. The reaction was allowed to warm up gradually to room temperature and stirred at room temperature for 2 h. Thereupon, the mixture was washed three times with water, dried over MgSO$_4$, filtered and evaporated to dryness to give a yellow oil. (Yield: 14.5 g, ≈100%).

Step 4: tert-butyl (S,5R)-4-cyano-1-(2,5-difluorophenyl)-3-azabicyclo[3.1.0]hexane-3-carboxylate

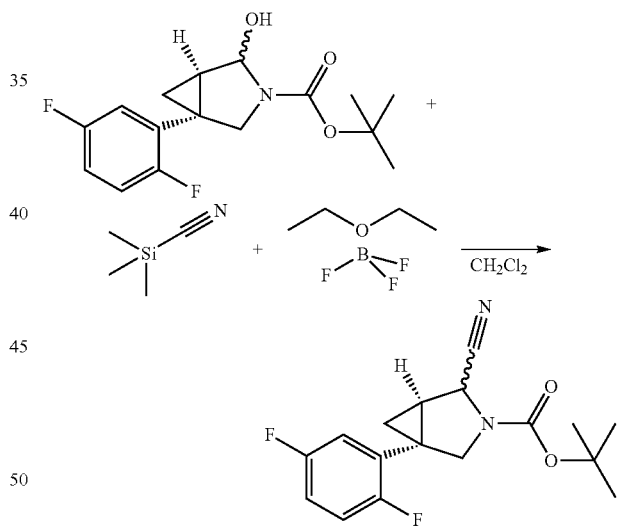

To a stirred solution of tert-butyl (1S,5R)-1-(2,5-difluorophenyl)-4-hydroxy-3-azabicyclo[3.1.0]hexane-3-carboxylate (14.2 g, 45.60 mmol) in dry dichloromethane (230 mL) was added trimethylsilanecarbonitrile (16.33 ml, 122.0 mmol) at room temperature under nitrogen. The solution was then cooled to −78° C. and boron trifluoride etherate (16.83 mL, 134.0 mmol) was added dropwise. The reaction mixture was stirred in the cold for 4 h., and then saturated solution of sodium bicarbonate was added and allowed to warm up to room temperature. The organic phase was separated and aqueous phase was extracted with dichloromethane. The combined organic phases were dried over MgSO$_4$, filtered and evaporated to dryness to leave a yellow oil. (Yield: 14.9 g, 92%).

Step 5: (1R,5S)-3-(tert-butoxycarbonyl)-5-(2,5-difluorophenyl)-3-azabicyclo[3.1.0]hexane-2-carboxylic Acid

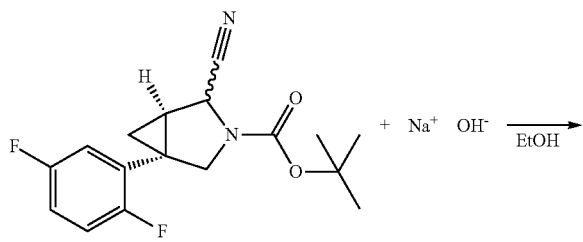

To a stirred solution of tert-butyl (1S,5R)-4-cyano-1-(2,5-difluorophenyl)-3-azabicyclo[3.1.0]hexane-3-carboxylate (14.61 g, 45.6 mmol) in ethanol (145 mL), was added a solution of 3 M sodium hydroxide (76 mL, 228.0 mmol) at room temperature. The solution was heated at 80° C. for 4 h. and then was cooled to room temperature. Thereupon, ethanol was evaporated off and the aqueous phase was acidified with 2 M HCl solution and then extracted with a mixture of dichloromethane-isopropanol (7:3). The organic phase was dried over MgSO$_4$, filtered and evaporated to dryness to leave a yellow oil, which solidified on standing. (Yield: 17.0 g, 93%).

Step 6: (1S,5R)-tert-butyl 1-(2,5-difluorophenyl)-4-(2,2-dimethyl-4,6-dioxo-1,3-dioxane-5-carbonyl)-3-azabicyclo[3.1.0]hexane-3-carboxylate

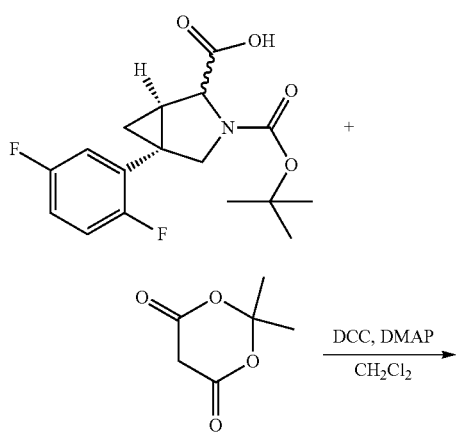

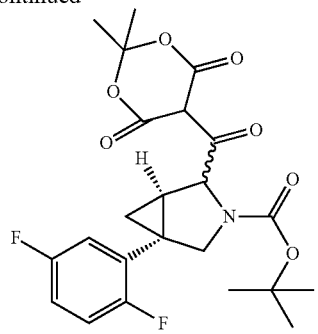

To a stirred solution of (1R,5S)-3-(tert-butoxycarbonyl)-5-(2,5-difluorophenyl)-3-azabicyclo[3.1.0]hexane-2-carboxylic acid (2.5 g, 7.37 mmol) in dichloromethane (50 mL) was added 2,2-dimethyl-1,3-dioxane-4,6-dione (1.062 g, 7.37 mmol) at room temperature followed by addition of N,N-dimethylpyridin-4-amine (0.900 g, 7.37 mmol). The thus obtained solution was cooled to 0° C. and a solution of N,N-dicyclohexylcarbodiimide (1.520 g, 7.37 mmol) in dichloromethane was added dropwise. The mixture was stirred in the cold for 2 h, and then filtered through a celite plug. The filtrate was washed with 1 M HCl and brine, dried over MgSO$_4$, filtered and evaporated to dryness to give a yellow semisolid. Yield: 3.45 g, 100%.

Step 7 (1S,5R)-tert-butyl 1-(2,5-difluorophenyl)-4-(3-methoxy-3-oxopropanoyl)-3-azabicyclo[3.1.0]hexane-3-carboxylate A solution of (1S,5R)-tert-butyl 1-(2,5-difluorophenyl)-4-(2,2-dimethyl-4,6-dioxo-1,3-dioxane-5-carbonyl)-3-azabicyclo[3.1.0]hexane-3-carboxylate (3.43 g, 7.37 mmol) in dry methanol (40 mL), was heated at reflux for 3.5 h under inert atmosphere. The solution was then cooled to room temperature and the solvent was evaporated off. The resulting yellow oil was purified by chromatography (petroleum ether-ethyl acetate; 9/1, 4/1, 2/1, then 1/1). The product was isolated as a colourless oil. (Yield: 1.84 g, 53%).

Step 8: methyl 3-((1R,5S)-5-(2,5-difluorophenyl)-3-azabicyclo[3.1.0]hexan-2-yl)-3-oxopropanoate Hydrochloride

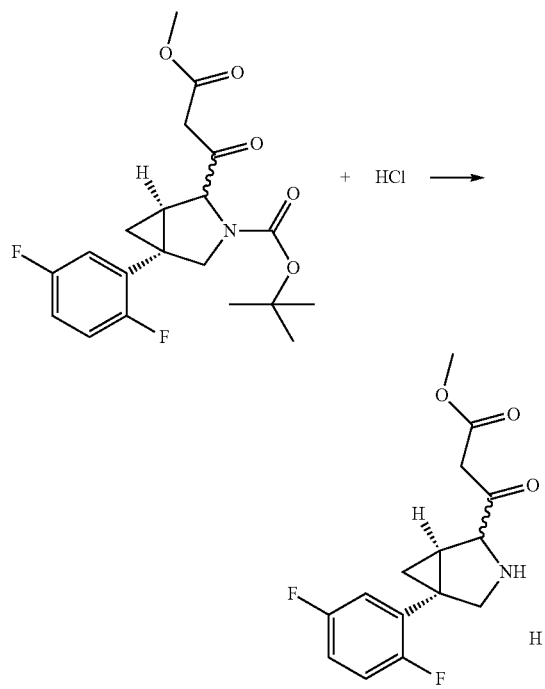

(1S,5R)-tert-butyl 1-(2,5-difluorophenyl)-4-(3-methoxy-3-oxopropanoyl)-3-azabicyclo[3.1.0]hexane-3-carboxylate (1.79 g, 4.53 mmol) was stirred in 2 M ethereal HCl solution (18.11 mL, 36.2 mmol) for 8 h. Thereupon, the reaction mixture was evaporated to dryness to leave the product as a white foam. (Yield: 1.14 g, 76%).

Step 9: Methyl 2-((5aS,6aR)-5a-(2,5-difluorophenyl)-3-thioxo-2,3,5,5a,6,6a-hexahydrocyclopropa[3,4]pyrrolo[1,2-c]imidazol-1-yl)acetate

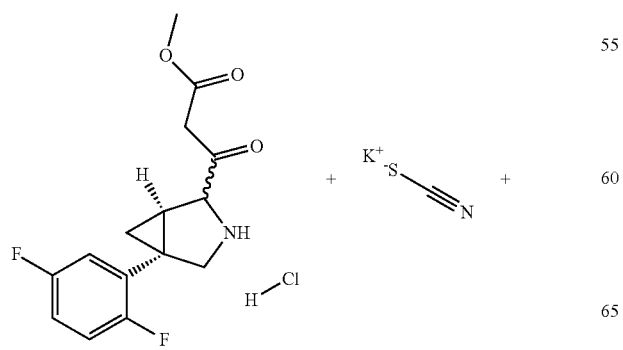

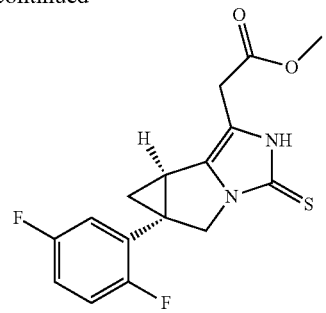

To a stirred solution of methyl 3-((1R,5S)-5-(2,5-difluorophenyl)-3-azabicyclo[3.1.0]hexan-2-yl)-3-oxopropanoate hydrochloride (1.14 g, 3.44 mmol) in a mixture of ethanol (14 mL) and water (14 mL) was added potassium thiocyanate (0.367 g, 3.78 mmol) followed by addition of cc. HCl (0.14 mL, 1.718 mmol). The solution was heated at reflux for 5 h, then cooled to room temperature and evaporated to dryness. The resulting oil was extracted from the aqueous phase with dichloromethane. The organic phase was dried over MgSO$_4$, filtered and evaporated to dryness. The thus obtained yellow oil was separated by chromatography (dichloromethane-methanol; 98:2, then 95:5), then chromatographed again (petroleum ether-ethyl acetate; 1:1, then 1:2). The product was isolated as a yellow solid. (Yield: 90 mg, 7%).

$^1$H NMR (DMSO$_{d6}$): 11.73 (1H, s), 7.29 (1H, m), 7.26 (1H, m), 7.21 (1H, m), 4.10 (1H, br d, J=12.3 Hz), 3.82 (1H, d, J=12.0 Hz), 3.66 (3H, s), 3.59 (2H, m), 2.87 (1H, dd, J=8.2, 4.3 Hz), 1.67 (1H, dd, J=8.2, 5.4 Hz), 1.14 (1H, br t, J=4.7 Hz).

$^{13}$C NMR (DMSO$_{d6}$): 169.7, 158.8, 158.6, 157.2, 157, 156.3, 132.3, 128.6, 128.5, 128.4, 117.2, 117.1, 117, 117, 116.8, 116.8, 116, 115.9, 115.8, 115.7, 112.2, 52, 51.6, 51.5, 32.5, 29.6, 22.2, 20.7.

Example 5: Methyl 2-((5aS,6aR)-5a-(3,5-difluorophenyl)-3-thioxo-2,3,5,5a,6,6a-hexahydrocyclopropa[3,4]pyrrolo[1,2-c]imidazol-1-yl)acetate

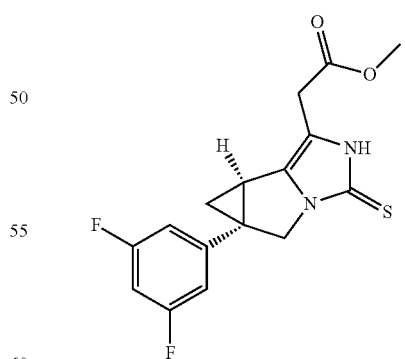

(1R,5S)-3-(tert-butoxycarbonyl)-5-(3,5-difluorophenyl)-3-azabicyclo[3.1.0]hexane-2-carboxylic acid was converted to methyl 2-((5aS,6aR)-5a-(3,5-difluorophenyl)-3-thioxo-2,3,5,5a,6,6a-hexahydrocyclopropa[3,4]pyrrolo[1,2-c]imidazol-1-yl)acetate by a similar procedure as described for Example 4 and the product was isolated as a yellow solid.

$^1$H NMR (DMSO$_{d6}$): 1.72 (1H, s), 7.11 (3H, m), 4.20 (1H, d, J=12.0 Hz), 4.06 (1H, d, J=12.2 Hz), 3.65 (3H, s), 3.57 (2H, m), 2.97 (1H, dd, J=8.2, 4.4 Hz), 1.70 (1H, dd, J=8.2, 5.3 Hz), 1.16 (1H, t, J=4.8 Hz).

$^{13}$C NMR (DMSO$_{d6}$): 169.7, 163.4, 163.3, 161.8, 161.7, 156.5, 144.8, 144.7, 144.7, 132.3, 112, 110, 110, 109.9, 109.8, 102.3, 102.1, 102, 52, 50.7, 36.2, 29.6, 25.2, 22.9.

Example 6: 2-((5aS,6aR)-5a-(2,5-difluorophenyl)-3-thioxo-2,3,5,5a,6,6a-hexahydrocyclopropa[3,4]pyrrolo[1,2-c]imidazol-1-yl)acetic Acid

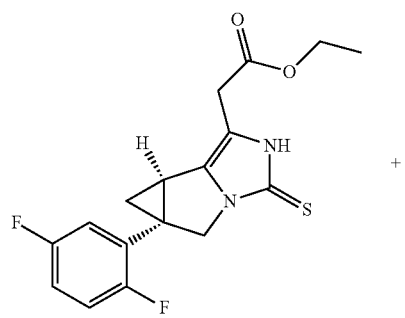

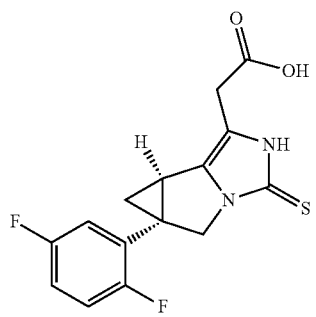

To a stirred solution of ethyl 2-((5aS,6aR)-5a-(2,5-difluorophenyl)-3-thioxo-2,3,5,5a,6,6a-hexahydrocyclopropa[3,4]pyrrolo[1,2-c]imidazol-1-yl)acetate (prepared analogous manner to Example 4) (275 mg, 0.785 mmol) in ethanol (3 mL) was added 1M sodium hydroxide (0.942 ml, 0.942 mmol) at room temperature and the solution was stirred for 2 h. Thereupon, a second crop of 1 M sodium hydroxide was added (0.942 ml, 0.942 mmol) and the reaction was allowed to stir for additional 1 h. Ethanol was then removed under vacuum and the aqueous phase was extracted dichloromethane. The aqueous phase was acidified to pH=1 by adding aqueous HCL solution and then extracted with dichloromethane. The organic phase was evaporated to dryness to give the product as a yellow foam. (Yield: 0.206 g, 76%).

$^1$H NMR (DMSO$_{d6}$): 12.57 (1H, br s), 11.70 (1H, s), 7.29 (1H, td, J=9.4, 4.6 Hz), 7.25 (1H, ddd, J=9.1, 5.9, 3.2 Hz), 7.21 (1H, m), 4.09 (1H, d, J=11.9 Hz), 3.81 (1H, d, J=12.0 Hz), 3.47 (2H, m), 2.87 (1H, dd, J=8.4, 4.3 Hz), 1.66 (1H, dd, J=8.4, 5.3 Hz), 1.13 (1H, t, J=4.8 Hz).

$^{13}$C NMR (DMSO$_{d6}$): 170.7, 158.8, 158.6, 157.2, 157, 157, 156.1, 132.1, 128.6, 128.6, 128.5, 128.5, 117.2, 117.1, 117, 117, 116.9, 116.8, 116.8, 115.9, 115.9, 115.8, 115.7, 113, 51.6, 51.5, 32.5, 29.9, 22.3, 20.7.

Example 7: 2-((5aS,6aR)-5a-(3,5-difluorophenyl)-3-thioxo-2,3,5,5a,6,6a-hexahydrocyclopropa[3,4]pyrrolo[1,2-c]imidazol-1-yl)acetic Acid

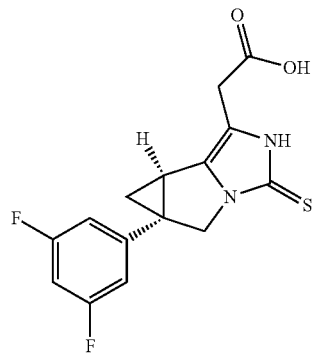 [SMILES: O=C(O)Cc1[nH]c(=S)n2c1[C@@H]1C[C@]1(c1cc(F)cc(F)c1)C2]

Compound was prepared by a similar procedure as described for Example 6 and the product was isolated as a yellow solid.

$^1$H NMR (DMSO$_{d6}$): 12.60 (1H, br s), 11.69 (1H, s), 7.10 (3H, m), 4.20 (1H, d, J=12.2 Hz), 4.05 (1H, d, J=12.2 Hz), 3.45 (2H, m), 2.98 (1H, dd, J=8.3, 4.3 Hz), 1.70 (1H, dd, J=8.3, 5.4 Hz), 1.16 (1H, t, J=4.8 Hz).

$^{13}$C NMR (DMSO$_{d6}$): 170.7, 163.4, 163.3, 161.8, 161.7, 156.3, 144.9, 144.8, 144.7, 132, 112.8, 110, 110, 109.8, 109.8, 102.3, 102.1, 101.9, 50.7, 36.2, 29.9, 25.3, 22.9.

Example 8: (5aS,6aR)-5a-(3,5-difluorophenyl)-1-(2-hydroxyethyl)-5,5a,6,6a-tetrahydrocyclopropa[3,4]pyrrolo[1,2-c]imidazole-3(2H)-thione

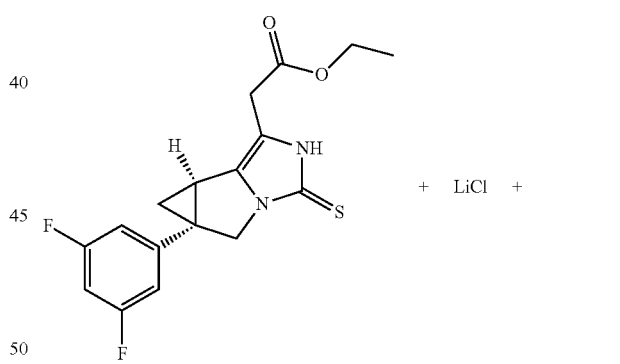

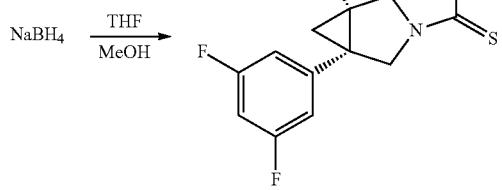

To a stirred solution of ethyl 2-((5aS,6aR)-5a-(3,5-difluorophenyl)-3-thioxo-2,3,5,5a,6,6a-hexahydrocyclopropa[3,4]pyrrolo[1,2-c]imidazol-1-yl)acetate (300 mg, 0.856 mmol) (analogous to Example 5) in a mixture of abs. methanol (2.3 mL) and dry tetrahydrofuran (2.3 mL) was added lithium chloride (0.061 ml, 3.00 mmol). The reaction mixture was then cooled to 0° C. and sodium borohydride (113 mg, 3.00 mmol) was added portionwise. The thus obtained white suspension was allowed to warm up to room temperature and stirred for 24 h. Thereupon, water was added and the mixture was extracted with dichloromethane. The organic phase was dried over MgSO$_4$, filtered and evaporated to dryness to leave a yellow oil. Chromatography (petroleum ether-ethyl acetate; 1:1, 1:4, then 5% methanol in dichloromethane) followed by trituration with heptane afforded the product as a light yellow solid. (Yield: 0.065 g, 23%).

$^1$H NMR (DMSO$_{d6}$): 1.64 (1H, s), 7.10 (3H, m), 4.74 (1H, t, J=5.4 Hz), 4.17 (1H, d, J=12.0 Hz), 4.02 (1H, d, J=12.0 Hz), 3.59 (2H, m), 2.98 (1H, dd, J=8.2, 4.3 Hz), 2.53 (2H, td, J=6.8, 2.9 Hz), 1.65 (1H, dd, J=8.1, 5.2 Hz), 1.16 (1H, t, J=4.8 Hz).

$^{13}$C NMR (DMSO$_{d6}$): 163.4, 163.3, 161.8, 161.7, 155.9, 145.1, 145.1, 145, 130.9, 116.8, 109.9, 109.9, 109.8, 109.8, 102.2, 102, 101.9, 59.4, 50.5, 36, 28, 25.6, 22.9.

Example 9: (S)-2-(6-(3,5-difluorophenyl)-3-thioxo-3,5,6,7-tetrahydro-2H-pyrrolo[1,2-c]imidazol-1-yl)-1-morpholinoethanone Step 1: (4S)-tert-butyl 4-(3,5-difluorophenyl)-2-(3-morpholino-3-oxopropanoyl)pyrrolidine-1-carboxylate

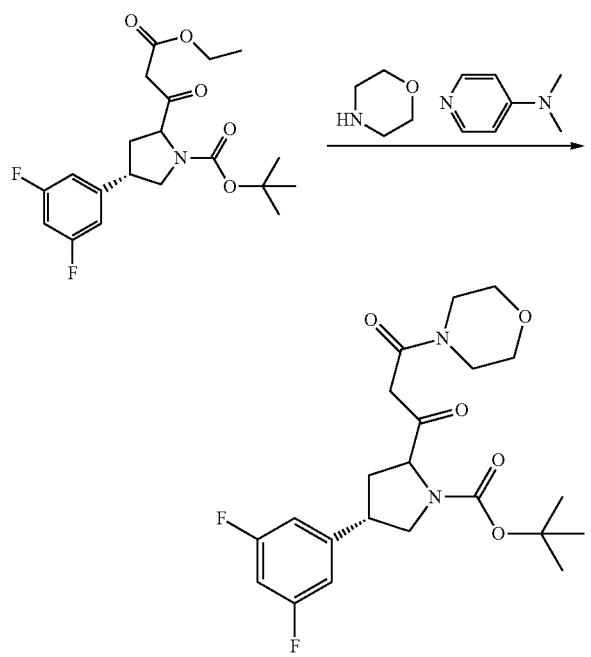

A mixture of (4S)-tert-butyl 4-(3,5-difluorophenyl)-2-(3-ethoxy-3-oxopropanoyl)pyrrolidine-1-carboxylate (prepared according to protocol of Example 2 Step 1) (0.74 g, 1.862 mmol), morpholine (0.324 ml, 3.72 mmol) and N,N-dimethylpyridin-4-amine (0.068 g, 0.559 mmol) in toluene (3 mL) was stirred at 100° C. for 20 h. The reaction was then diluted with a mixture of ethyl acetate-petroleum ether (1:1) and washed with 1 M HCl. The organic phase was dried over MgSO$_4$, stripped down to dryness and purified by chromatography in a mixture of ethyl acetate-petroleum ether (1:1) to give (4S)-tert-butyl 4-(3,5-difluorophenyl)-2-(3-morpholino-3-oxopropanoyl)pyrrolidine-1-carboxylate. Yield: 0.634 g, 78%.

Step 2: (1-((4S)-4-(3,5-difluorophenyl)pyrrolidin-2-yl)-3-morpholinopropane-1,3-dione hydrochloride

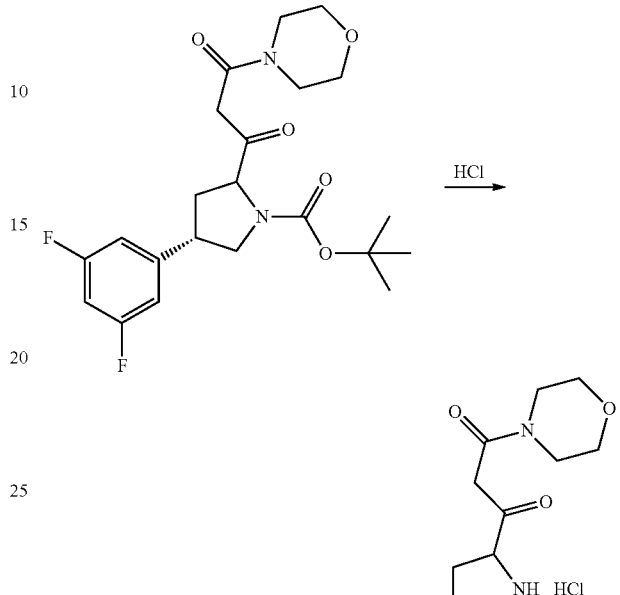

A solution of (4S)-tert-butyl 4-(2,5-difluorophenyl)-2-(3-morpholino-3-oxopropanoyl)pyrrolidine-1-carboxylate (0.66 g, 1.505 mmol) in 4 M HCl (7.53 mL, 30.1 mmol) in dioxane was stirred for 4 h at room temperature. Thereupon, the reaction mixture was diluted with diethyl ether, the resulting solid was collected, washed with diethyl ether and petroleum ether, respectively and then dried in vacuum at 50° C. to give 1-((4S)-4-(3,5-difluorophenyl)pyrrolidin-2-yl)-3-morpholinopropane-1,3-dione hydrochloride as a white powder. Yield: 0.52 g, 92%.

Step 3: (S)-2-(6-(3,5-difluorophenyl)-3-thioxo-2,5,6,7-tetrahydro-3H-pyrrolo[1,2-c]imidazol-1-yl)-1-morpholinoethan-1-one

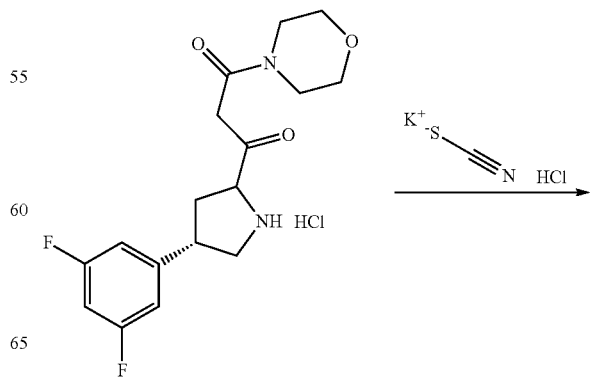

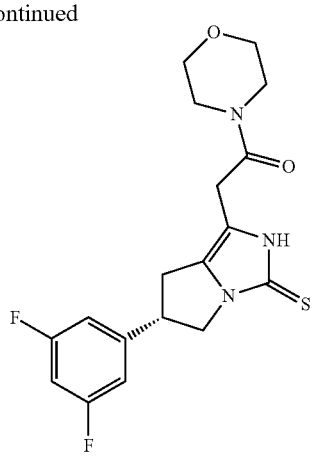

A solution of 1-((4S)-4-(3,5-difluorophenyl)pyrrolidin-2-yl)-3-morpholinopropane-1,3-dione hydrochloride (0.52 g, 1.387 mmol), potassium thiocyanate (0.148 g, 1.526 mmol) and 6 M HCl (0.12 ml, 0.69 mmol) in a mixture of ethanol (7 mL) and water (7.00 mL) was stirred under reflux for 1 h. Ethanol was evaporated under vacuum. The aqueous phase was extracted with ethyl acetate, the organic phase was diluted with petroleum ether without drying until crystallization occurred. The resultant solid was collected and recrystallized from a mixture of DCM-petroleum ether to give (S)-2-(6-(3,5-difluorophenyl)-3-thioxo-3,5,6,7-tetrahydro-2H-pyrrolo[1,2-c]imidazol-1-yl)-1-morpholinoethanone as a white powder. (Yield: 0.051 g, 9%.)

$^1$H NMR (DMSO$_{d6}$): 1.66 (1H, s), 7.12 (3H, br d, J=8.2 Hz), 4.16 (1H, dd, J=11.1, 7.8 Hz), 4.07 (1H, quin, J=7.8 Hz), 3.69 (1H, dd, J=11.1, 7.8 Hz), 3.56 (4H, m), 3.52 (2H, s), 3.46 (4H, m), 3.15 (1H, br dd, J=15.2, 7.8 Hz), 2.80 (1H, br dd, J=15.3, 8.2 Hz).

$^{13}$C NMR (DMSO$_{d6}$): 166.9, 163.3, 163.2, 161.7, 161.6, 155.4, 145.9, 145.8, 145.8, 129.4, 114.4, 110.7, 110.7, 110.6, 110.6, 102.6, 102.5, 102.3, 66, 50.2, 46.4, 45.7, 41.7, 30.5, 28.8.

Example 10: (S)-2-(6-(2,3,5,6-tetrafluorophenyl)-3-thioxo-3,5,6,7-tetrahydro-2H-pyrrolo[1,2-c]imidazol-1-yl)acetic Acid

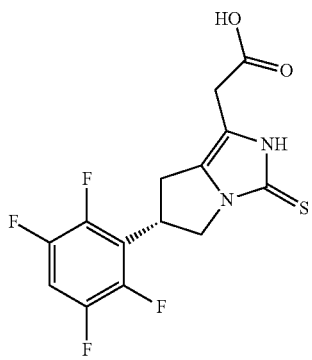 [SMILES: O=C(O)Cc1[nH]c(=S)n2c1C[C@@H](c1c(F)c(F)cc(F)c1F)C2]

Compound was prepared analogous manner to Example 3 from (4S)-1-(tert-butoxycarbonyl)-4-(2,3,5,6-tetrafluorophenyl)pyrrolidine-2-carboxylic acid and isolated as an off-white powder.

$^1$H NMR (DMSO$_{d6}$): 12.58 (1H, m), 11.79 (1H, s), 7.85 (1H, m), 4.50 (1H, quin, J=8.5 Hz), 4.18 (1H, dd, J=11.6, 9.2 Hz), 3.78 (1H, dd, J=11.7, 7.8 Hz), 3.41 (2H, s), 3.30 (1H, br dd, J=15.9, 9.3 Hz), 2.91 (1H, dd, J=15.9, 8.0 Hz).

$^{13}$C NMR (DMSO$_{d6}$): 170.7, 155.3, 146.4, 145.3, 144.7, 143.7, 129.4, 120.5, 120.4, 120.3, 113.5, 105.9, 105.7, 105.6, 48.5, 35.7, 30, 29.1.

Example 11: (S)-2-(6-(3,5-difluorophenyl)-3-thioxo-3,5,6,7-tetrahydro-2H-pyrrolo[1,2-c]imidazol-1-yl)acetic Acid

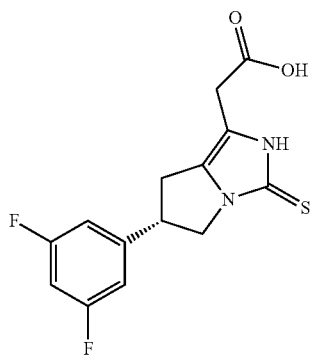 [SMILES: O=C(O)Cc1[nH]c(=S)n2c1C[C@@H](c1cc(F)cc(F)c1)C2]

Compound was prepared analogous manner to Example 3 from (4S)-tert-butyl 4-(3,5-difluorophenyl)-2-(3-ethoxy-3-oxopropanoyl)pyrrolidine-1-carboxylate and isolated as an off-white powder.

$^1$H NMR (DMSO$_{d6}$): 12.58 (1H, br s), 11.74 (1H, br s), 7.13 (3H, m), 4.16 (1H, dd, J=11.2, 7.9 Hz), 4.08 (1H, quin, J=8.0 Hz), 3.70 (1H, dd, J=11.2, 7.8 Hz), 3.42 (2H, m), 3.20 (1H, dd, J=15.4, 7.8 Hz), 2.85 (1H, dd, J=15.4, 8.4 Hz).

$^{13}$C NMR (DMSO$_{d6}$): 170.7, 163.3, 163.2, 161.7, 161.6, 155.5, 145.9, 145.8, 145.7, 129.7, 113.6, 110.8, 110.7, 110.6, 110.6, 102.7, 102.5, 102.3, 50.3, 46.4, 30.4, 29.9.

Example 12: (S)-2-(6-(3-bromo-2,6-difluorophenyl)-3-thioxo-2,5,6,7-tetrahydro-3H-pyrrolo[1,2-c]imidazol-1-yl)acetic Acid

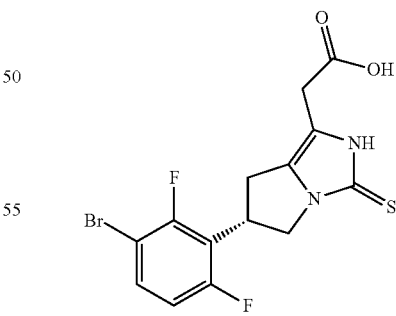

Compound was prepared analogous manner to Example 3 from (4S)-tert-butyl 4-(3-bromo-2,6-difluorophenyl)-2-(3-ethoxy-3-oxopropanoyl)pyrrolidine-1-carboxylate and isolated as a yellowish solid.

$^1$H NMR (DMSO$_{d6}$): 12.56 (2H, m), 11.78 (1H, s), 7.72 (1H, ddd, J=5.8, 8.1, 8.8 Hz), 7.16 (1H, dt, J=1.4, 9.4 Hz), 4.46 (1H, quin, J=8.6 Hz), 4.16 (1H, dd, J=11.5, 9.3 Hz), 3.73 (1H, dd, J=11.6, 7.9 Hz), 3.41 (2H, s), 3.26 (1H, dd, J=15.8, 9.3 Hz), 2.86 (1H, dd, J=15.8, 8.1 Hz).

$^{13}$C NMR (DMSO$_{d6}$): 170.7, 160.8, 160.8, 159.2, 159.1, 157.6, 157.5, 155.9, 155.9, 155.3, 132.5, 132.4, 129.6, 118.8, 118.7, 118.5, 113.8, 113.8, 113.7, 113.6, 113.4, 104.1, 104.1, 103.9, 103.9, 48.7, 35.6, 29.9, 29.2.

Example 13: (R)-2-(6-(3-bromo-2,6-difluorophenyl)-3-thioxo-2,5,6,7-tetrahydro-3H-pyrrolo[1,2-c]imidazol-1-yl)acetic Acid

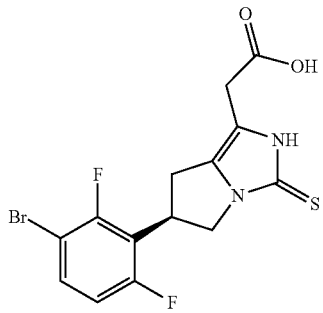 [SMILES: O=C(O)Cc1[nH]c(=S)n2c1C[C@H](c1c(F)ccc(Br)c1F)C2]

Compound was prepared analogous manner to Example 3 from (4R)-tert-butyl 4-(3-bromo-2,6-difluorophenyl)-2-(3-ethoxy-3-oxopropanoyl)pyrrolidine-1-carboxylate and isolated as a yellowish solid.

$^1$H NMR (DMSO$_{d6}$): 12.56 (1H, br s), 11.78 (1H, s), 7.72 (1H, ddd, J=5.8, 8.1, 8.8 Hz), 7.17 (1H, dt, J=1.4, 9.6 Hz), 4.46 (1H, quin, J=8.6 Hz), 4.16 (1H, dd, J=11.4, 9.3 Hz), 3.73 (1H, dd, J=11.7, 8.0 Hz), 3.41 (2H, m), 3.26 (1H, dd, J=15.8, 9.4 Hz), 2.86 (1H, dd, J=15.8, 8.2 Hz).

$^{13}$C NMR (DMSO$_{d6}$): 170.7, 160.8, 160.8, 159.2, 159.1, 157.6, 157.5, 155.9, 155.9, 155.3, 132.5, 132.4, 129.6, 118.8, 118.7, 118.5, 113.8, 113.8, 113.7, 113.6, 113.3, 104.1, 104.1, 103.9, 103.9, 48.7, 35.6, 29.9, 29.2.

Example 14: (R)-2-(6-(2,5-difluorophenyl)-3-thioxo-2,5,6,7-tetrahydro-3H-pyrrolo[1,2-c]imidazol-1-yl)acetic Acid

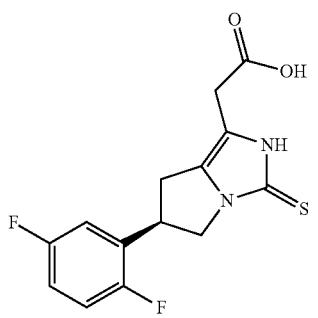 [SMILES: O=C(O)Cc1[nH]c(=S)n2c1C[C@H](c1cc(F)ccc1F)C2]

Compound was prepared analogous manner to Example 3 from (4R)-tert-butyl 4-(2,5-difluorophenyl)-2-(3-ethoxy-3-oxopropanoyl)pyrrolidine-1-carboxylate and isolated as a pale yellow solid.

$^1$H NMR (DMSO$_{d6}$): 12.60 (1H, s br), 11.78 (1H, s), 7.32-7.26 (2H, m), 7.18 (1H, m), 4.22 (1H, quin, J=7.8 Hz), 4.14 (1H, dd, J=11.3, 7.9 Hz), 3.73 (1H, dd, J=11.3, 7.5 Hz), 3.40 (2H, m), 3.21 (1H, dd, J=15.5, 8.0 Hz), 2.86 (1H, dd, J=15.5, 7.8 Hz).

$^{13}$C NMR (DMSO$_{d6}$): 170.8, 159.1, 159.1, 157.5, 157.5, 157.1, 157.1, 155.5, 155.5, 155.5, 130.1, 130.1, 130, 130, 129.5, 117.2, 117.1, 117, 116.9, 115.5, 115.4, 115.3, 115.3, 115.2, 115.1, 115.1, 113.8, 49.4, 40.3, 30, 29.5.

Example 15: (R)-2-(6-(2,3,5,6-tetrafluorophenyl)-3-thioxo-2,5,6,7-tetrahydro-3H-pyrrolo[1,2-c]imidazol-1-yl)acetic Acid

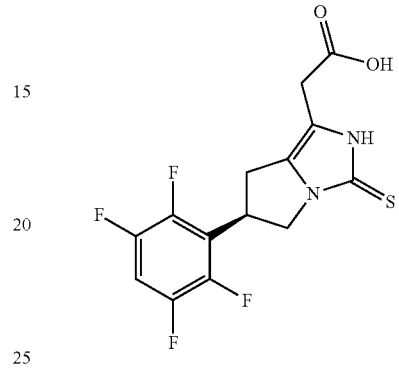

Compound was prepared analogous manner to Example 3 from (4R)-tert-butyl 4-(2,3,5,6-tetrafluorophenyl)-2-(3-ethoxy-3-oxopropanoyl)pyrrolidine-1-carboxylate and isolated as a light cream powder.

$^1$H NMR (DMSO$_{d6}$): 12.58 (1H, br s), 11.80 (1H, s), 7.86 (1H, m), 4.50 (1H, quin, J=8.5 Hz), 4.18 (1H, dd, J=11.6, 9.2 Hz), 3.78 (1H, dd, J=11.7, 7.8 Hz), 3.41 (2H, s), 3.30 (1H, dd, J=15.9, 9.3 Hz), 2.91 (1H, dd, J=15.8, 8.1 Hz).

$^{13}$C NMR (DMSO$_{d6}$): 170.7, 155.3, 146.4, 146.4, 146.4, 146.3, 146.3, 146.3, 146.2, 145.4, 145.3, 145.3, 145.3, 145.3, 145.2, 145.2, 145.2, 144.8, 144.8, 144.7, 144.6, 144.6, 143.7, 143.7, 143.7, 143.7, 143.6, 143.6, 129.4, 120.5, 120.3, 120.2, 113.4, 105.9, 105.7, 105.6, 48.5, 35.7, 29.9, 29.1.

Example 16: (S)-2-(6-(5-bromo-2-fluorophenyl)-3-thioxo-2,5,6,7-tetrahydro-3H-pyrrolo[1,2-c]imidazol-1-yl)acetic Acid

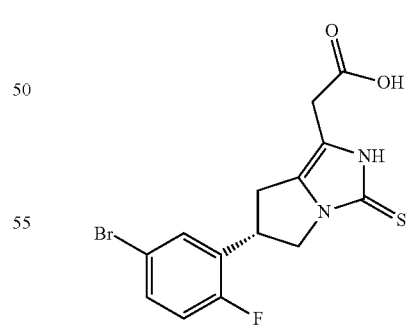

Compound was prepared analogous manner to Example 3 from (4S)-tert-butyl 4-(5-bromo-2-fluorophenyl)-2-(3-ethoxy-3-oxopropanoyl)pyrrolidine-1-carboxylate and isolated as a yellow solid.

$^1$H NMR (DMSO$_{d6}$): 12.58 (1H, br s), 11.76 (1H, br s), 7.59 (1H, dd, J=6.6, 2.5 Hz), 7.53 (1H, ddd, J=8.8, 4.5, 2.6 Hz), 7.23 (1H, dd, J=10.3, 8.8 Hz), 4.22 (1H, quin, J=7.9

Hz), 4.14 (1H, dd, J=11.2, 8.1 Hz), 3.74 (1H, dd, J=11.2, 7.5 Hz), 3.43 (2H, m), 3.21 (1H, dd, J=15.5, 8.1 Hz), 2.88 (1H, dd, J=15.4, 7.9 Hz).

$^{13}$C NMR (DMSO$_{d6}$): 170.7, 160.3, 158.7, 155.5, 131.9, 131.8, 131.4, 131.4, 130.7, 130.6, 129.5, 118, 117.9, 116.5, 116.5, 113.7, 49.3, 40.4, 29.9, 29.4.

Example 17: (R)-2-(6-(5-chloro-2-fluorophenyl)-3-thioxo-2,5,6,7-tetrahydro-3H-pyrrolo[1,2-c]imidazol-1-yl)acetic Acid

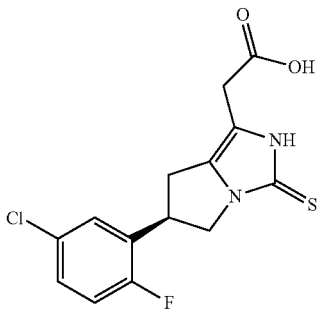 [SMILES: O=C(O)Cc1[nH]c(=S)n2c1C[C@H](c1cc(Cl)ccc1F)C2]

Compound was prepared analogous manner to Example 3 from (4R)-tert-butyl 4-(5-chloro-2-fluorophenyl)-2-(3-ethoxy-3-oxopropanoyl)pyrrolidine-1-carboxylate and isolated as a pale yellow solid.

$^1$H NMR (DMSO$_{d6}$): 12.54 (1H, m), 11.75 (1H, s), 7.47 (1H, dd, J=6.5, 2.6 Hz), 7.40 (1H, ddd, J=8.7, 4.3, 2.8 Hz), 7.29 (1H, dd, J=9.9, 8.9 Hz), 4.22 (1H, quin, J=7.8 Hz), 4.14 (1H, dd, J=11.2, 8.0 Hz), 3.74 (1H, dd, J=11.3, 7.5 Hz), 3.42 (2H, m), 3.22 (1H, dd, J=15.5, 8.1 Hz), 2.88 (1H, dd, J=15.6, 7.8 Hz).

$^{13}$C NMR (DMSO$_{d6}$): 170.7, 159.8, 158.2, 155.5, 130.3, 130.2, 129.5, 128.9, 128.9, 128.6, 128.5, 128.5, 117.6, 117.4, 113.7, 49.3, 40.4, 29.9, 29.4.

Example 18: (R)-2-(6-(2,6-difluorophenyl)-3-thioxo-2,5,6,7-tetrahydro-3H-pyrrolo[1,2-c]imidazol-1-yl)acetic Acid

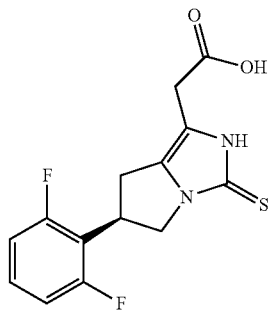 [SMILES: O=C(O)Cc1[nH]c(=S)n2c1C[C@H](c1c(F)cccc1F)C2]

Compound was prepared analogous manner to Example 3 from (4R)-tert-butyl 4-(2,6-difluorophenyl)-2-(3-ethoxy-3-oxopropanoyl)pyrrolidine-1-carboxylate and isolated as a pale pink solid.

$^1$H NMR (DMSO$_{d6}$): 12.55 (1H, br s), 11.76 (1H, s), 7.41 (1H, m), 7.13 (2H, m), 4.43 (1H, quin, J=8.8 Hz), 4.15 (1H, dd, J=10.6, 9.9 Hz), 3.72 (1H, dd, J=11.3, 8.4 Hz), 3.41 (2H, m), 3.24 (1H, dd, J=15.7, 9.2 Hz), 2.86 (1H, dd, J=15.7, 8.7 Hz).

$^{13}$C NMR (DMSO$_{d6}$): 170.7, 161.6, 161.6, 160, 159.9, 155.3, 129.8, 129.7, 129.7, 116.5, 116.4, 113.3, 112.3, 112.2, 112.1, 112.1, 48.7, 35.3, 29.9, 29.3.

Example 19: (S)—N-cyano-2-(6-(2,3,5,6-tetrafluorophenyl)-3-thioxo-3,5,6,7-tetrahydro-2H-pyrrolo[1,2-c]imidazol-1-yl)acetamide

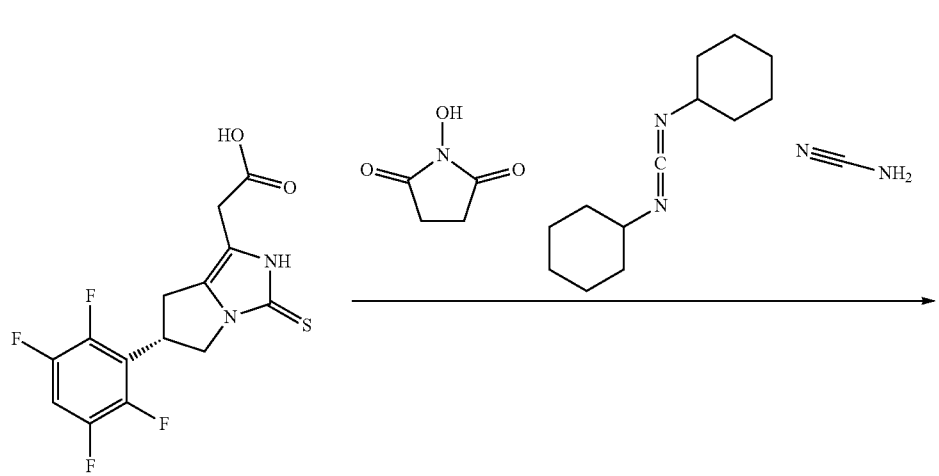

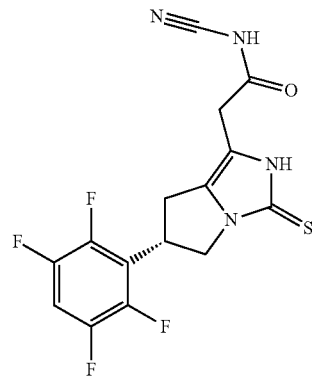

To a stirred suspension of (S)-2-(6-(2,3,5,6-tetrafluorophenyl)-3-thioxo-3,5,6,7-tetrahydro-2H-pyrrolo[1,2-c]imidazol-1-yl)acetic acid (Example 10) (0.035 g, 0.1 mmol) in acetonitrile (1 ml) was added 1-hydroxypyrrolidine-2,5-dione (0.012 g, 0.100 mmol) followed by addition of N,N'-methanediylidenedicyclohexanamine (0.021 g, 0.100 mmol). The reaction was stirred at room temperature for 1 h. The mixture was diluted with N,N-dimethylformamide (1 mL), whereupon cyanamide (4.20 mg, 0.100 mmol) was added followed by addition of N-ethyl-N-isopropylpropan-2-amine (0.017 ml, 0.100 mmol) and the mixture was stirred for 16 h at room temperature. Thereupon, the insoluble materials were filtered off, the filtrate was diluted with brine, acidified, and then extracted with dichloromethane. The organic phase was dried over MgSO$_4$ and then concentrated under reduced pressure. The product was crystallized on trituration with petroleum ether as a beige powder. (Yield: 0.015 g, 40%.)

$^1$H NMR (DMSO$_{d6}$): 11.94 (1H, br), 11.79 (1H, s), 7.86 (1H, m), 4.50 (1H, quin, J=8.6 Hz), 4.19 (1H, dd, J=11.4, 9.4 Hz), 3.79 (1H, dd, J=11.7, 7.9 Hz), 3.56 (2H, br s), 3.30 (1H, br dd, J=16.0, 9.2 Hz), 2.92 (1H, dd, J=16.0, 8.1 Hz).

$^{13}$C NMR (DMSO$_{d6}$): 169.8, 155.8, 146.4, 146.4, 146.4, 146.4, 146.3, 146.3, 146.3, 146.2, 145.4, 145.4, 145.3, 145.3, 145.3, 145.3, 145.2, 145.2, 144.8, 144.8, 144.7, 144.7, 144.6, 144.6, 143.8, 143.7, 143.7, 143.7, 143.7, 143.7, 143.6, 143.6, 143.6, 130.4, 120.3, 120.2, 120.1, 111.7, 108.3, 105.9, 105.8, 105.6, 48.5, 35.8, 30.8, 29.1.

Example 20: (S)-2-(6-(3-bromo-2,6-difluorophenyl)-3-thioxo-2,5,6,7-tetrahydro-3H-pyrrolo[1,2-c]imidazol-1-yl)-N-(methylsulfonyl)acetamide

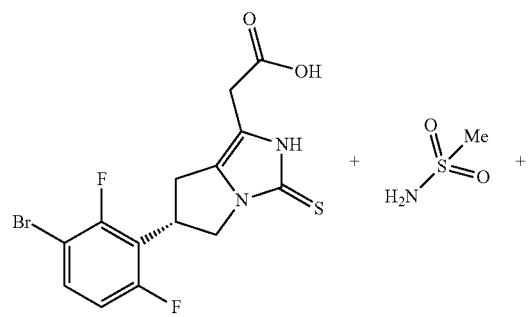

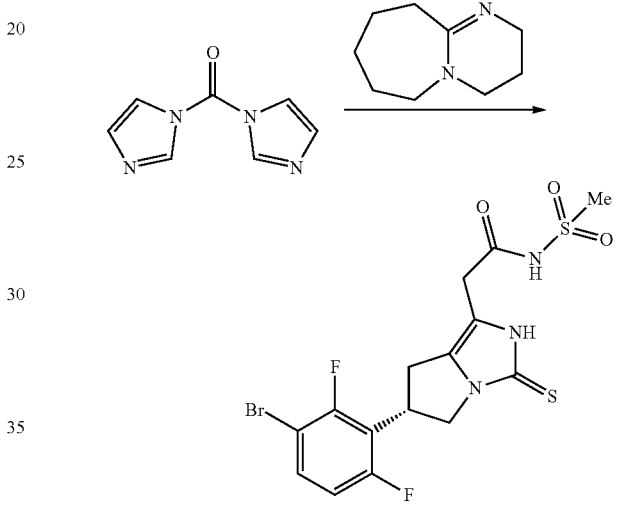

To a stirred suspension of (S)-2-(6-(3-bromo-2,6-difluorophenyl)-3-thioxo-3,5,6,7-tetrahydro-2H-pyrrolo[1,2-c]imidazol-1-yl)acetic acid (Example 12) (100 mg, 0.257 mmol)) in dry dichloromethane (3 mL) was added portionwise di(1H-imidazol-1-yl)methanone (45.8 mg, 0.283 mmol) at room temperature to give a clear solution. The mixture was stirred for 30 min, and then methanesulfonamide (26.9 mg, 0.283 mmol) was added followed by addition of 2,3,4,6,7,8,9,10-octahydropyrimido[1,2-a]azepine (0.039 mL, 0.257 mmol) and the mixture was stirred at room temperature for 16 h. The mixture was poured onto 1 N HCl and extracted with ethyl acetate. The organic phase was washed with water and dried over MgSO$_4$. The solvent was concentrated in vacuum, and then purified by chromatography in a mixture of dichloromethane-methanol (9:1). Recrystallization from a mixture of diethyl ether-isopropanol afforded (S)-2-(6-(3-bromo-2,6-difluorophenyl)-3-thioxo-3,5,6,7-tetrahydro-2H-pyrrolo[1,2-c]imidazol-1-yl)-N-(methylsulfonyl)acetamide as a brown solid. Yield: 30 mg, 22%.

$^1$H NMR (DMSO$_{d6}$): 11.67 (1H, s), 7.72 (1H, ddd, J=5.8, 8.1, 8.8 Hz), 7.17 (1H, dt, J=1.4, 9.4 Hz), 4.43 (1H, quin, J=8.7 Hz), 4.14 (1H, dd, J=11.4, 9.3 Hz), 3.72 (1H, dd, J=11.6, 8.1 Hz), 3.25 (2H, s), 3.25 (1H, dd, J=9.5, 15.6 Hz), 2.95 (3H, s), 2.86 (1H, dd, J=15.9, 8.4 Hz).

$^{13}$C NMR (DMSO$_{d6}$): 171, 160.9, 160.8, 159.2, 159.2, 157.6, 157.5, 155.9, 155.9, 154.8, 132.5, 132.4, 129.2, 118.8, 118.7, 118.5, 114.6, 113.8, 113.8, 113.7, 113.6, 104.1, 103.9, 48.5, 40.5, 35.7, 33.5, 29.5.

Example 21: (S)-2-(6-(5-bromo-2-fluorophenyl)-3-thioxo-2,5,6,7-tetrahydro-3H-pyrrolo[1,2-c]imidazol-1-yl)-N-(methylsulfonyl)acetamide

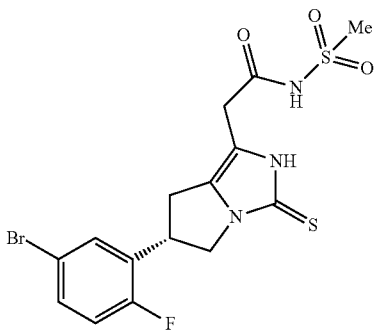 [SMILES: CS(=O)(=O)NC(=O)Cc1[nH]c(=S)n2c1C[C@@H](c1cc(Br)ccc1F)C2]

Compound was prepare analogous manner to Example 20 from (S)-2-(6-(5-bromo-2-fluorophenyl)-3-thioxo-2,5,6,7-tetrahydro-3H-pyrrolo[1,2-c]imidazol-1-yl)acetic acid and isolated as a yellow solid.

$^1$H NMR (DMSO$_{d6}$): 1.90 (1H, br), 11.72 (1H, s), 7.60 (1H, dd, J=6.6, 2.2 Hz), 7.53 (1H, ddd, J=8.6, 4.4, 2.5 Hz), 7.23 (1H, dd, J=10.1, 9.0 Hz), 4.21 (1H, quin, J=7.9 Hz), 4.13 (1H, dd, J=11.1, 8.3 Hz), 3.73 (1H, dd, J=11.2, 7.7 Hz), 3.40 (2H, m), 3.21 (1H, br dd, J=15.4, 8.1 Hz), 3.12 (3H, s), 2.88 (1H, br dd, J=15.4, 8.1 Hz).

$^{13}$C NMR (DMSO$_{d6}$): 169.5, 160.3, 158.7, 155.4, 131.9, 131.8, 131.4, 131.4, 130.7, 130.6, 129.7, 118, 117.9, 116.5, 113.5, 49.2, 40.8, 40.4, 32.4, 29.6.

Example 22: 2-((R)-6-(3-bromo-2,6-difluorophenyl)-3-thioxo-2,5,6,7-tetrahydro-3H-pyrrolo[1,2-c]imidazol-1-yl)-N-(2-oxotetrahydrofuran-3-yl)acetamide

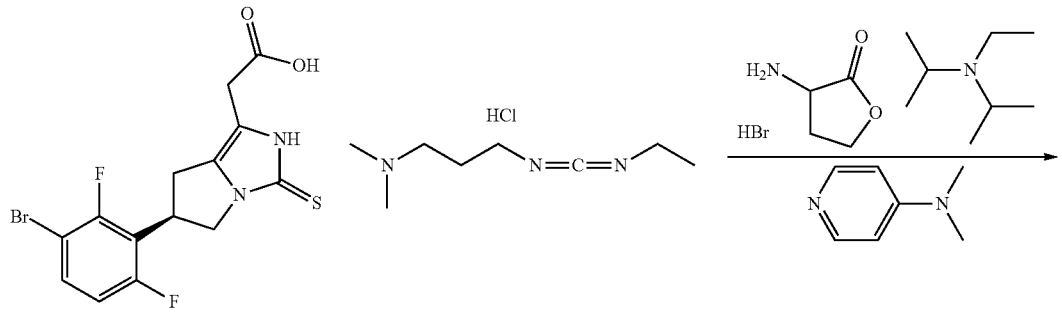

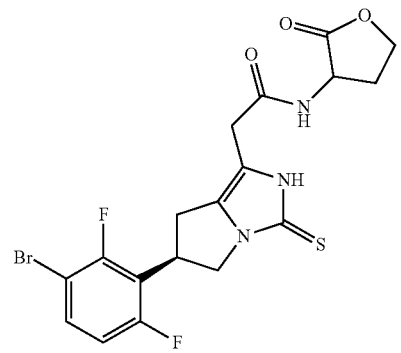

A mixture of (R)-2-(6-(3-bromo-2,6-difluorophenyl)-3-thioxo-3,5,6,7-tetrahydro-2H-pyrrolo[1,2-c]imidazol-1-yl)acetic acid (Example 13) (70 mg, 0.180 mmol), 3-aminodihydrofuran-2(3H)-one hydrobromide (32.7 mg, 0.180 mmol), 3-(((ethylimino)methylene)amino)-N,N-dimethylpropan-1-amine hydrochloride (34.5 mg, 0.180 mmol), N,N-dimethylpyridin-4-amine (24.17 mg, 0.198 mmol), N-ethyl-N-isopropylpropan-2-amine (0.041 mL, 0.234 mmol) in dry N,N dimethyl formamide (3 mL) was stirred for 3 h at room temperature. Thereupon, solvent was removed under reduced pressure and the residue was diluted with ethyl acetate. The mixture was washed with saturated aq. NaHCO₃ solution and brine, respectively. The organic phase was dried over MgSO₄ and then evaporated. Chromatography in a mixture of dichloromethane methanol (9:1) afforded the titled product as a yellow solid. Yield: 50 mg, 53%.

¹H NMR (DMSO$_{d6}$): 11.80 (1H, s), 8.49 (1H, dd, J=7.8, 4.5 Hz), 7.73 (1H, ddd, J=5.8, 8.1, 8.8 Hz), 7.17 (1H, dt, J=1.4, 9.6 Hz), 4.57 (1H, dtd, J=10.6, 8.7, 8.7, 2.4 Hz), 4.44 (1H, d quin, J=8.7, 3.9 Hz), 4.34 (1H, dt, J=1.3, 9.0 Hz), 4.20 (1H, ddd, J=10.5, 8.7, 6.6 Hz), 4.15 (1H, dd, J=9.5, 11.3 Hz), 3.73 (1H, dd, J=11.5, 8.1 Hz), 3.31 (2H, t, J=5.9 Hz), 3.23 (1H, td, J=15.6, 9.4 Hz), 2.87 (1H, ddd, J=15.7, 10.7, 9.1 Hz), 2.39 (1H, m), 2.15 (1H, m).

¹³C NMR (DMSO$_{d6}$): 175.2, 167.8, 160.8, 160.8, 159.2, 159.2, 157.6, 157.5, 155.9, 155.9, 155.2, 132.5, 132.4, 129.5, 129.5, 118.7, 118.6, 118.6, 118.5, 118.4, 118.4, 113.8, 113.8, 113.7, 113.6, 113.6, 113.6, 104.1, 104.1, 103.9, 103.9, 65.3, 48.6, 48.5, 48.1, 35.7, 35.7, 31.2, 29.3, 28.2, 28.2.

Example 23: (R)—N-(methylsulfonyl)-2-(6-(2,3,5,6-tetrafluorophenyl)-3-thioxo-3,5,6,7-tetrahydro-2H-pyrrolo[1,2-c]imidazol-1-yl)acetamide

Step 1: (R)-1-(H-imidazol-1-yl)-2-(6-(2,3,5,6-tetrafluorophenyl)-3-thioxo-2,5,6,7-tetrahydro-3H-pyrrolo[1,2-c]imidazol-1-yl)ethan-1-one

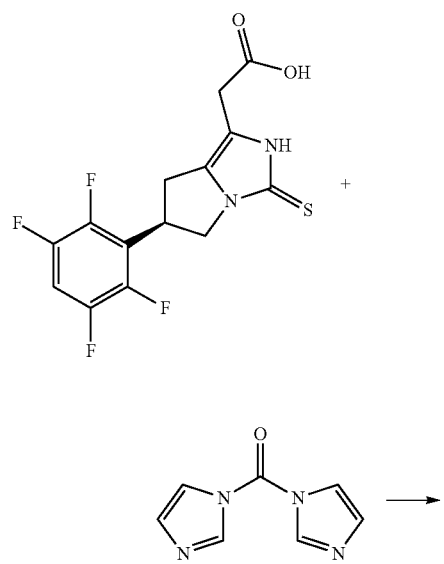

+

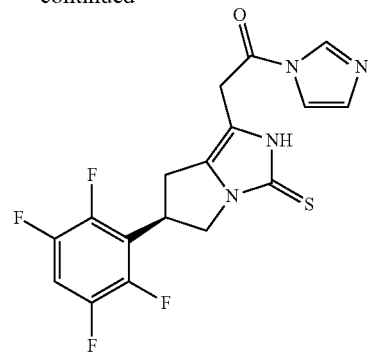

→

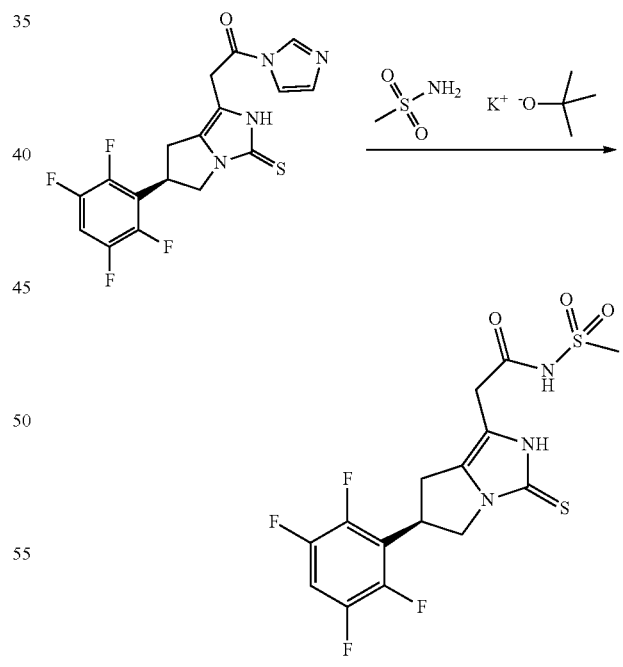

To a stirred suspension of (R)-2-(6-(2,3,5,6-tetrafluorophenyl)-3-thioxo-3,5,6,7-tetrahydro-2H-pyrrolo[1,2-c]imidazol-1-yl)acetic acid (Example 15) (1.8 g, 5.20 mmol) in dry dichloromethane (35 mL) was added di(1H-imidazol-1-yl)methanone (1.011 g, 6.24 mmol) portionwise at room temperature. The mixture was stirred for additional 30 min, the resulting solid was collected, washed with petroleum ether and dried on air to give (R)-1-(1H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone as a beige powder. Yield: 1.70 g, 83%.

Step 2: (R)—N-(methylsulfonyl)-2-(6-(2,3,5,6-tetrafluorophenyl)-3-thioxo-2,5,6,7-tetrahydro-3H-pyrrolo[1,2-c]imidazol-1-yl)acetamide To a stirred suspension of methanesulfonamide (0.132 g, 1.388 mmol) and potassium tert-butoxide (0.142 g, 1.261 mmol) was added dry N,N-dimethyl formamide (1. mL) at room temperature. Thereupon, (R)-1-(H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone (0.5 g, 1.261 mmol) was added, and the stirring was continued for 30 min.

The reaction mixture was evaporated to dryness and the residue was partitioned between ethyl acetate (50 mL) and 1M HCl (25 mL). The organic phase was dried over $MgSO_4$, and then evaporated to dryness. The solid residue was slurried in ethyl acetate. The obtained solid was filtered, washed with ethyl acetate and diethyl ether, respectively, and then dried to, ether, dried to give (R)—N-(methylsulfonyl)-2-(6-(2,3,5,6-tetrafluorophenyl)-3-thioxo-3,5,6,7-tetrahydro-2H-pyrrolo[1,2-c]imidazol-1-yl)acetamide as a light brown powder. Yield: 0.28 g, 52%.

$^1$H NMR (DMSO$_{d6}$): 1.93 (1H, br s), 11.83 (1H, s), 7.86 (1H, m), 4.50 (1H, quin, J=8.5 Hz), 4.19 (1H, dd, J=11.5, 9.3 Hz), 3.79 (1H, dd, J=11.6, 7.8 Hz), 3.49 (2H, m), 3.29 (1H, dd, J=15.9, 9.3 Hz), 3.24 (3H, m), 2.92 (1H, dd, J=8.2, 16.0 Hz).

$^{13}$C NMR (DMSO$_{d6}$): 168.3, 155.6, 146.4, 146.4, 146.3, 146.3, 146.3, 146.2, 145.3, 145.3, 145.3, 145.3, 145.2, 145.2, 145.2, 144.8, 144.8, 144.8, 144.7, 144.7, 144.6, 144.6, 143.7, 143.7, 143.7, 143.6, 143.6, 143.6, 130, 120.4, 120.3, 120.2, 112.2, 105.9, 105.7, 105.6, 48.5, 41.1, 35.7, 31.5, 29.1.

Example 24: (R)-2-(6-(2,5-difluorophenyl)-3-thioxo-2,5,6,7-tetrahydro-3H-pyrrolo[1,2-c]imidazol-1-yl)-N-(methylsulfonyl)acetamide

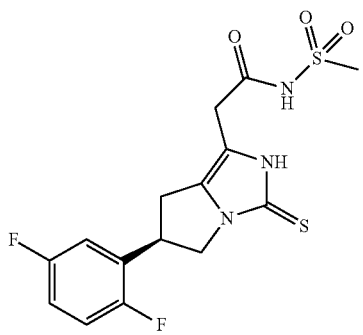 [SMILES: CS(=O)(=O)NC(=O)Cc1[nH]c(=S)n2c1C[C@H](c1cc(F)ccc1F)C2]

Compound was prepared analogous manner to Example 23 from (R)-2-(6-(2,5-difluorophenyl)-3-thioxo-2,5,6,7-tetrahydro-3H-pyrrolo[1,2-c]imidazol-1-yl)acetic acid (Example 14) and isolated as a yellow solid.

$^1$H NMR (DMSO$_{d6}$): 1.93 (1H, br s), 11.78 (1H, s), 7.28 (2H, m), 7.18 (1H, m), 4.23 (1H, quin, J=7.8 Hz), 4.14 (1H, dd, J=11.2, 8.0 Hz), 3.74 (1H, dd, J=11.2, 7.6 Hz), 3.50 (2H, s), 3.25 (3H, s), 3.22 (1H, dd, J=15.6, 8.1 Hz), 2.87 (1H, br dd, J=15.6, 7.9 Hz).

$^{13}$C NMR (DMSO$_{d6}$): 168.3, 159, 157.4, 157.1, 155.7, 155.5, 130.2, 130, 129.9, 129.9, 129.8, 117.1, 117.1, 117, 116.9, 115.5, 115.4, 115.3, 115.3, 115.3, 115.1, 115.1, 112.4, 49.3, 41.1, 40.2, 40, 31.5, 29.6.

Example 25: Ethyl (R)-(2-(6-(2,3,5,6-tetrafluorophenyl)-3-thioxo-2,5,6,7-tetrahydro-3H-pyrrolo[1,2-c]imidazol-1-yl)acetyl)glycinate

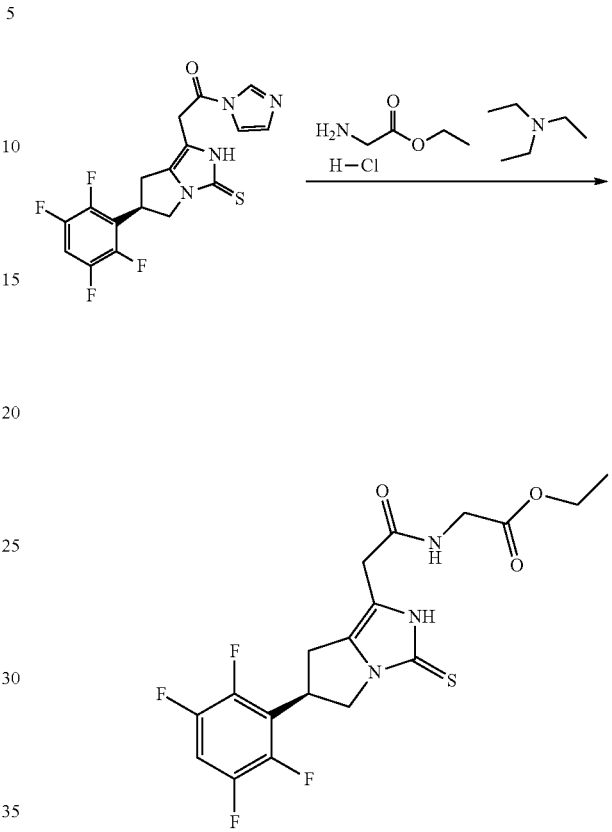

To a stirred mixture of aminoacetic acid ethyl ester hydrochloride (0.070 g, 0.505 mmol) and triethylamine (0.07 mL, 0.505 mmol) in a mixture of dry tetrahydrofuran (2 mL) and dry N,N-dimethyl formamide (0.2 mL) was added (R)-1-(1H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone (Example 23 step 1) (0.1 g, 0.252 mmol). The reaction mixture was stirred for 30 min, and then diluted with ethyl acetate. The organic phase was washed with sodium bicarbonate solution and 1N HCl, respectively. After drying over $MgSO_4$ the solvent was removed under vacuum. Crystallization from diethyl ether afforded the titled compound as a light beige powder. Yield: 0.053 g, 49%.

$^1$H NMR (DMSO$_{d6}$): 1.77 (1H, s), 8.38 (1H, t, J=5.9 Hz), 7.85 (1H, m), 4.48 (1H, quin, J=8.6 Hz), 4.17 (1H, dd, J=11.5, 9.2 Hz), 4.07 (2H, q, J=7.0 Hz), 3.82 (2H, d, J=5.9 Hz), 3.78 (1H, dd, J=11.6, 7.9 Hz), 3.32 (2H, m), 3.26 (1H, dd, J=15.9, 9.3 Hz), 2.90 (1H, dd, J=15.8, 8.2 Hz), 1.16 (3H, t, J=7.1 Hz).

$^{13}$C NMR (DMSO$_{d6}$): 169.7, 168.2, 155.3, 146.4, 146.4, 146.4, 146.3, 146.3, 146.3, 146.2, 145.3, 145.3, 145.3, 145.2, 145.2, 144.8, 144.8, 144.7, 144.7, 144.6, 144.6, 143.7, 143.7, 143.7, 143.7, 143.7, 143.6, 143.6, 129.2, 120.3, 120.2, 120.1, 113.9, 105.9, 105.7, 105.6, 60.4, 48.4, 40.9, 35.8, 31.1, 29.2, 14.

Example 26: (S)-2-(2-((R)-6-(2,3,5,6-tetrafluorophenyl)-3-thioxo-2,5,6,7-tetrahydro-3H-pyrrolo[1,2-c]imidazol-1-yl)acetamido)propanamide

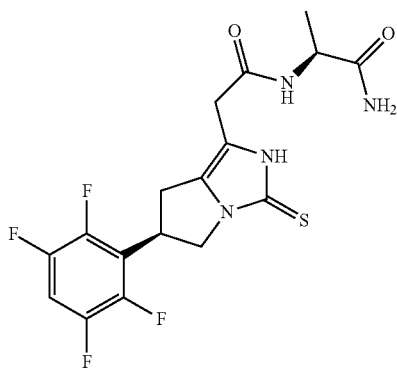 [SMILES: C[C@H](NC(=O)Cc1[nH]c(=S)n2c1C[C@H](c1c(F)c(F)cc(F)c1F)C2)C(N)=O]

Compound was prepared analogous manner to Example 25 from (R)-1-(H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone (Example 23 step 1) and isolated as a beige powder.

$^1$H NMR (DMSO$_{d6}$): 1.75 (1H, s), 8.14 (1H, d, J=7.5 Hz), 7.85 (1H, m), 7.34 (1H, br s), 7.02 (1H, br s), 4.48 (1H, quin, J=8.6 Hz), 4.17 (2H, m), 3.77 (1H, dd, J=11.6, 7.9 Hz), 3.30 (2H, s), 3.26 (1H, dd, J=15.9, 9.3 Hz), 2.88 (1H, dd, J=8.2, 15.9 Hz), 1.19 (3H, d, J=7.2 Hz).

$^{13}$C NMR (DMSO$_{d6}$): 174.1, 167.3, 155.2, 146.4, 146.4, 146.4, 146.4, 146.3, 146.3, 146.3, 146.3, 146.2, 145.3, 145.3, 145.3, 145.3, 145.3, 145.2, 145.2, 145.2, 144.8, 144.7, 144.7, 144.7, 144.7, 144.6, 144.6, 143.7, 143.7, 143.7, 143.7, 143.6, 143.6, 143.6, 143.6, 143.6, 129, 120.4, 120.3, 120.2, 114.4, 105.9, 105.7, 105.6, 48.4, 48.2, 35.8, 31.3, 29.2, 18.3.

Example 27: (R)—N-(cyanomethyl)-2-(6-(2,3,5,6-tetrafluorophenyl)-3-thioxo-2,5,6,7-tetrahydro-3H-pyrrolo[1,2-c]imidazol-1-yl)acetamide

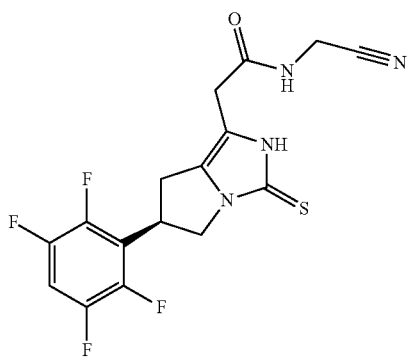 [SMILES: N#CCNC(=O)Cc1[nH]c(=S)n2c1C[C@H](c1c(F)c(F)cc(F)c1F)C2]

Compound was prepared analogous manner to Example 25 from (R)-1-(1H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone (Example 23 step 1) and isolated as a beige powder.

$^1$H NMR (DMSO$_{d6}$): 1.82 (1H, s), 8.66 (1H, br t, J=5.4 Hz), 7.86 (1H, m), 4.49 (1H, quin, J=8.6 Hz), 4.18 (1H, dd, J=11.4, 9.3 Hz), 4.14 (2H, d, J=5.6 Hz), 3.79 (1H, dd, J=11.6, 7.9 Hz), 3.35 (2H, m), 3.26 (1H, br dd, J=15.8, 9.2 Hz), 2.90 (1H, m).

$^{13}$C NMR (DMSO$_{d6}$): 168.5, 155.5, 146.4, 146.4, 146.3, 146.3, 146.3, 146.2, 145.4, 145.3, 145.3, 145.2, 145.2, 144.8, 144.8, 144.7, 144.7, 144.6, 144.6, 143.7, 143.7, 143.7, 143.6, 143.6, 143.6, 129.5, 120.3, 120.2, 120.1, 117.6, 113.4, 105.9, 105.7, 105.6, 48.4, 35.8, 30.9, 29.1, 27.2.

Example 28: N-((1r,4R)-4-hydroxycyclohexyl)-2-((R)-6-(2,3,5,6-tetrafluorophenyl)-3-thioxo-2,5,6,7-tetrahydro-3H-pyrrolo[1,2-c]imidazol-1-yl)acetamide

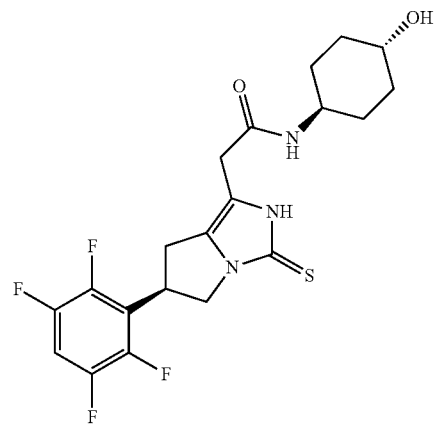 [SMILES: O=C(Cc1[nH]c(=S)n2c1C[C@H](c1c(F)c(F)cc(F)c1F)C2)N[C@H]1CC[C@H](O)CC1]

Compound was prepared analogous manner to Example 25 from (R)-1-(1H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone (Example 23 step 1) and isolated as a brown powder.

$^1$H NMR (DMSO$_{d6}$): 1.74 (1H, s), 7.85 (1H, m), 7.82 (1H, d, J=7.7 Hz), 4.48 (1H, quin, J=8.4 Hz), 4.17 (1H, dd, J=9.4, 11.6 Hz), 3.77 (1H, dd, J=7.8, 11.6 Hz), 3.43 (1H, m), 3.34 (1H, m), 3.24 (1H, br dd, J=15.9, 9.3 Hz), 3.20 (2H, s), 2.87 (1H, dd, J=7.8, 15.8 Hz), 1.77 (2H, m), 1.73 (2H, br m), 1.16 (4H, m).

$^{13}$C NMR (DMSO$_{d6}$): 166.7, 155.1, 146.4, 146.3, 146.3, 146.3, 146.3, 146.2, 145.3, 145.3, 145.3, 145.2, 145.2, 145.2, 144.8, 144.8, 144.7, 144.7, 144.7, 144.7, 144.6, 143.7, 143.7, 143.6, 143.6, 143.6, 143.6, 143.5, 143.5, 128.7, 120.5, 120.4, 120.3, 114.5, 105.8, 105.7, 105.5, 68.1, 48.4, 47.4, 35.7, 33.9, 31.5, 30.2, 29.3.

Example 29: N-(2-hydroxycyclohexyl)-2-((R)-6-(2,3,5,6-tetrafluorophenyl)-3-thioxo-2,5,6,7-tetrahydro-3H-pyrrolo[1,2-c]imidazol-1-yl)acetamide

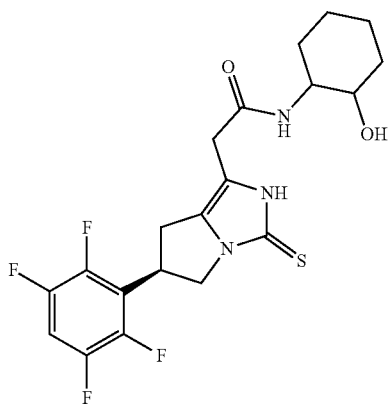 [SMILES: O=C(Cc1[nH]c(=S)n2c1C[C@H](c1c(F)c(F)cc(F)c1F)C2)NC1CCCCC1O]

Compound was prepared analogous manner to Example 25 from (R)-1-(H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone (Example 23 step 1) and isolated as a brown powder.

$^1$H NMR (DMSO$_{d6}$): 1.73 (1H, m), 7.84 (2H, m), 4.47 (1H, m), 4.17 (1H, m), 3.77 (1H, m), 3.36 (1H, m), 3.32-3.16 (4H, m), 2.89 (1H, m), 2.07-1.0 (8H, several multiplets).

$^{13}$C NMR (DMSO$_{d6}$): 167.2, 167.2, 155.1, 146.4, 146.3, 146.2, 145.3, 145.2, 145.2, 145.2, 144.8, 144.8, 144.7, 144.6, 143.7, 143.7, 143.7, 143.6, 143.6, 143.6, 128.8, 120.5, 120.4, 120.3, 120.3, 120.2, 114.7, 105.9, 105.7, 105.5, 71.1, 54.5, 48.4, 35.7, 33.9, 31.8, 31.7, 30.9, 29.3, 29.2, 24.1, 23.8.

Example 30: (R)—N,N-dimethyl-2-(6-(2,3,5,6-tetrafluorophenyl)-3-thioxo-2,5,6,7-tetrahydro-3H-pyrrolo[1,2-c]imidazol-1-yl)acetamide

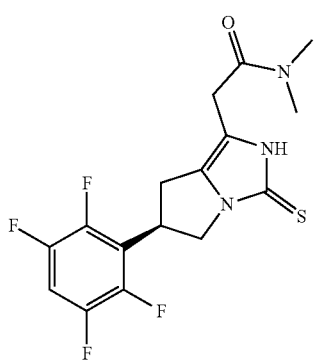 [SMILES: CN(C)C(=O)Cc1[nH]c(=S)n2c1C[C@H](c1c(F)c(F)cc(F)c1F)C2]

Compound was prepared analogous manner to Example 25 from (R)-1-(H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone (Example 23 step 1) and isolated as a light khaki powder.

$^1$H NMR (DMSO$_{d6}$): 1.70 (1H, s), 7.84 (1H, m), 4.49 (1H, quin, J=8.5 Hz), 4.18 (1H, dd, J=11.6, 9.2 Hz), 3.77 (1H, dd, J=11.7, 7.8 Hz), 3.48 (2H, s), 3.23 (1H, dd, J=15.8, 9.4 Hz), 2.98 (3H, s), 2.86 (1H, dd, J=15.8, 8.1 Hz), 2.82 (3H, s).

$^{13}$C NMR (DMSO$_{d6}$): 167.9, 155.1, 146.4, 146.4, 146.4, 146.3, 146.3, 146.3, 146.3, 146.2, 145.4, 145.3, 145.3, 145.3, 145.3, 145.3, 145.2, 145.2, 145.2, 144.8, 144.8, 144.8, 144.7, 144.7, 144.7, 144.6, 143.7, 143.7, 143.7, 143.7, 143.6, 143.6, 143.6, 129, 120.5, 120.4, 120.3, 114.4, 105.9, 105.7, 105.6, 48.5, 37, 35.8, 35.1, 29.2, 29.1.

Example 31: (S)-2-amino-3-(2-((R)-6-(2,3,5,6-tetrafluorophenyl)-3-thioxo-3,5,6,7-tetrahydro-2H-pyrrolo[1,2-c]imidazol-1-yl)acetamido)propanoic acid

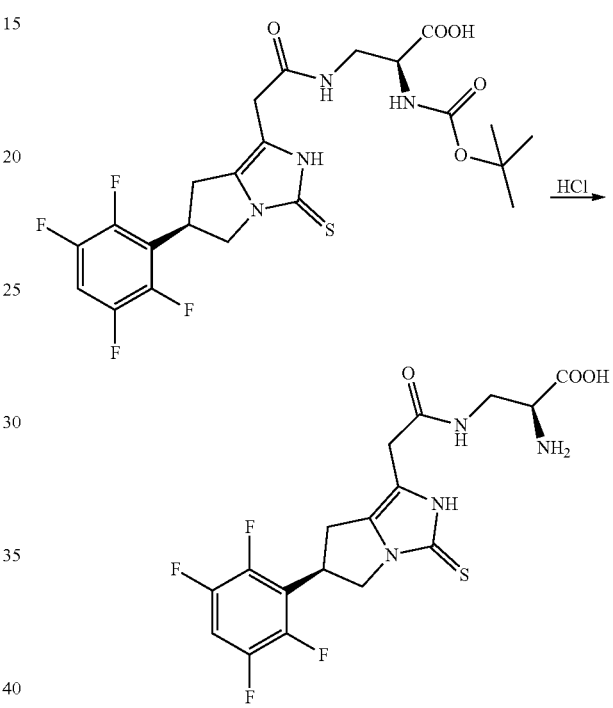

To a solution of (S)-2-((tert-butoxycarbonyl)amino)-3-(2-((R)-6-(2,3,5,6-tetrafluorophenyl)-3-thioxo-3,5,6,7-tetrahydro-2H-pyrrolo[1,2-c]imidazol-1-yl)acetamido)propanoic acid (prepared analogous manner to Example 25 from (R)-1-(H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone (Example 23 step 1)) (0.3 g, 0.563 mmol) in tetrahydrofuran (4 mL) was added cc. HCl (1.17 ml, 14.08 mmol) at room temperature and the solution was stirred for 4 h. Thereupon, the solvent was removed under vacuum, the residue was taken up in water (ca. 10 mL) and then the resultant dark insoluble material was filtered off. The filtrate was neutralized to pH 7 by addition of 5 M NaOH, and then aged in ice for 30 min. The precipitate was collected, washed with minimum volume of water and dried in vacuum at 50° C. The crude product was re-slurried in acetone, and then dried to give (S)-2-amino-3-(2-((R)-6-(2,3,5,6-tetrafluorophenyl)-3-thioxo-3,5,6,7-tetrahydro-2H-pyrrolo[1,2-c]imidazol-1-yl)acetamido)propanoic acid as a beige powder. Yield: 0.11 g, 45%.

$^1$H NMR (DMSO$_{d6}$): 10.4-6.5 (4H, br), 8.31 (1H, br s), 7.84 (1H, m), 4.48 (1H, quin, J=8.6 Hz), 4.17 (1H, br dd, J=11.1, 9.5 Hz), 3.77 (1H, br dd, J=11.7, 8.0 Hz), 3.54 (1H, m), 3.35 (1H, m), 3.32 (1H, m), 3.31 (2H, m), 3.29 (1H, m), 2.91 (1H, br dd, J=15.7, 8.2 Hz).

$^{13}$C NMR (DMSO$_{d6}$): 168.8, 168.5, 155.2, 146.4, 146.4, 146.3, 146.3, 146.2, 146.2, 145.4, 145.3, 145.3, 145.3, 145.3, 145.2, 145.2, 144.8, 144.8, 144.7, 144.7, 144.7, 144.6, 143.7, 143.7, 143.7, 143.7, 143.6, 143.6, 129.2, 120.3, 120.2, 120.1, 114.3, 105.9, 105.7, 105.6, 54.1, 48.4, 40.3, 35.8, 31.5, 29.1.

Example 32: ((R)—N-cyclopentyl-2-(6-(2,3,5,6-tetrafluorophenyl)-3-thioxo-3,5,6,7-tetrahydro-2H-pyrrolo[1,2-c]imidazol-1-yl)acetamide

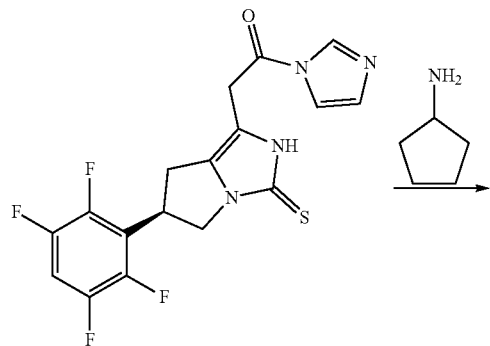

To a stirred solution of aminocyclopentane (0.05 mL, 0.505 mmol) in dry tetrahydrofuran (2 mL) was added (R)-1-(H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone (Example 23 step 1) (0.1 g, 0.252 mmol). The reaction was stirred 30 min. at room temperature. Thereupon, the mixture was diluted with ethyl acetate (ca. 10 mL), washed with a solution of sodium bicarbonate, 1 M HCl, respectively. The organic phase was dried over MgSO$_4$, filtered and evaporated to dryness. Crystallization from a mixture of diethyl ether-petroleum ether afforded (R)—N-cyclopentyl-2-(6-(2,3,5,6-tetrafluorophenyl)-3-thioxo-3,5,6,7-tetrahydro-2H-pyrrolo[1,2-c]imidazol-1-yl)acetamide as a beige powder. Yield: 0.064 g, 61%.

$^1$H NMR (DMSO$_{d6}$): 1.74 (1H, br s), 7.93 (1H, br d, J=7.0 Hz), 7.85 (1H, m), 4.48 (1H, quin, J=8.5 Hz), 4.17 (1H, dd, J=11.4, 9.3 Hz), 3.96 (1H, sxt, J=6.8 Hz), 3.77 (1H, dd, J=11.7, 7.8 Hz), 3.25 (1H, br dd, J=15.8, 9.2 Hz), 3.21 (2H, s), 2.87 (1H, dd, J=15.8, 7.9 Hz), 1.77 (2H, m), 1.61 (2H, m), 1.48 (2H, m), 1.35 (2H, dq, J=12.7, 6.6 Hz).

$^{13}$C NMR (DMSO$_{d6}$): 166.9, 155.1, 146.4, 146.3, 146.3, 145.3, 145.3, 145.3, 145.3, 145.2, 145.2, 145.2, 144.8, 144.8, 144.7, 144.7, 144.6, 144.6, 143.7, 143.7, 143.6, 143.6, 143.6, 143.6, 143.6, 128.8, 120.5, 120.4, 120.3, 114.6, 105.9, 105.7, 105.5, 50.5, 48.4, 35.7, 32.2, 32.2, 31.5, 29.3, 23.4.

Example 33: 2-((5aS,6aR)-5a-(3,5-difluorophenyl)-3-thioxo-2,3,5,5a,6,6a-hexahydrocyclopropa[3,4]pyrrolo[1,2-c]imidazol-1-yl)acetamide Step 1: tert-butyl (1S,5R)-4-(3-((tert-butoxycarbonyl)amino)-3-oxopropanoyl)-1-(3,5-difluorophenyl)-3-azabicyclo[3.1.0]hexane-3-carboxylate

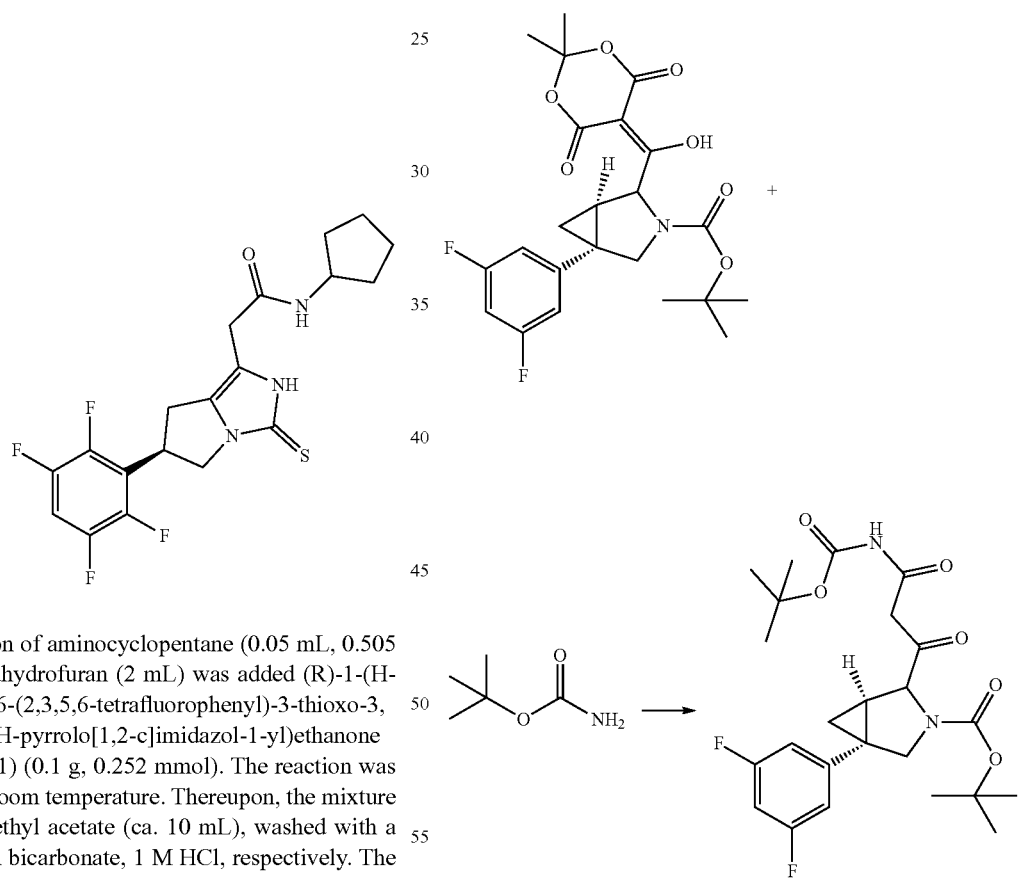

A solution of tert-butyl (1S,5R)-1-(3,5-difluorophenyl)-4-((2,2-dimethyl-4,6-dioxo-1,3-dioxan-5-ylidene)(hydroxy)methyl)-3-azabicyclo[3.1.0]hexane-3-carboxylate (1.0 g, 2.148 mmol) (Example 1 Step 10) and tert-butyl carbamate (0.252 g, 2.148 mmol) in acetonitrile (20 mL) was stirred under reflux for 3 h. The mixture was then evaporated to dryness and chromatographed twice (dichloromethane-methanol, and then petroleum ether-ethyl acetate). The product was isolated as a light yellow oil. (Yield: 0.33 g, 27%).

Step 2: 3-((1R,5S)-5-(3,5-difluorophenyl)-3-azabicyclo[3.1.0]hexan-2-yl)-3-oxopropanamide hydrochloride

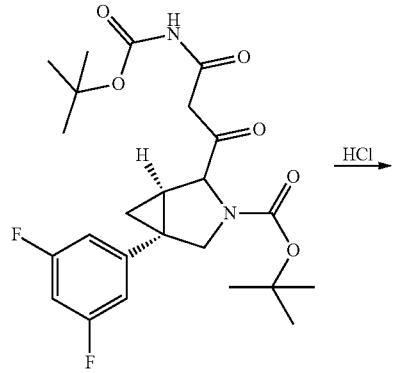

A solution of tert-butyl (1S,5R)-4-(3-((tert-butoxycarbonyl)amino)-3-oxopropanoyl)-1-(3,5-difluorophenyl)-3-azabicyclo[3.1.0]hexane-3-carboxylate (0.33 g, 0.687 mmol) in 4 M HCl (1.37 mL, 5.49 mmol) in dioxane was stirred at room temperature for 4 h. The resulting precipitate was filtered off, washed with diethyl ether and dried under vacuum to give the product as a white solid. (Yield: 0.125 g, 52%).

Step 3: 2-((5aS,6aR)-5a-(3,5-difluorophenyl)-3-thioxo-2,3,5,5a,6,6a-hexahydrocyclopropa[3,4]pyrrolo[1,2-c]imidazol-1-yl)acetamide)

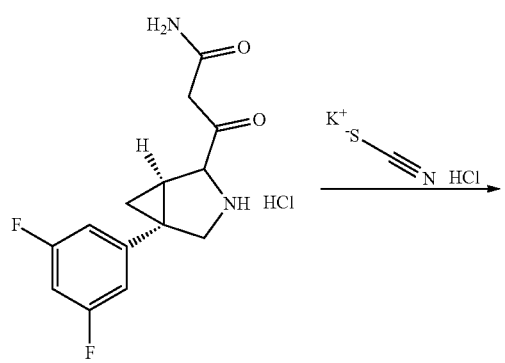

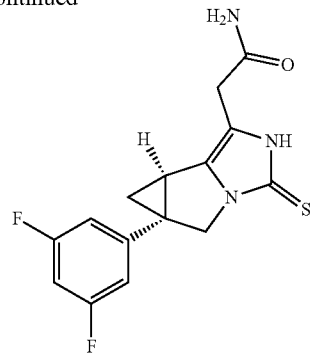

A solution of 3-((1R,5S)-5-(3,5-difluorophenyl)-3-azabicyclo[3.1.0]hexan-2-yl)-3-oxopropanamide hydrochloride (0.117 g, 0.369 mmol), potassium thiocyanate (0.0395 g, 0.406 mmol) and 6 M HCl (0.015 mL, 0.185 mmol) in a mixture of ethanol (1.5 mL) and water (1.5 mL) was stirred under reflux for 2 h. Thereupon, the mixture was cooled to room temperature and ethanol was evaporated. The residue was partitioned between water and dichloromethane and then the organic phase was dried over MgSO$_4$, filtered and evaporated. Chromatography in a mixture of dichloromethane-methanol afforded the titled product as a light yellow solid.

Yield: 0.031 g, 25%.

$^1$H NMR (DMSO$_{d6}$): 1.63 (1H, s), 7.36 (1H, br s), 7.10 (3H, m), 7.05 (1H, br s), 4.18 (1H, d, J=12.2 Hz), 4.03 (1H, d, J=12.2 Hz), 3.25 (2H, m), 2.93 (1H, dd, J=8.4, 4.3 Hz), 1.67 (1H, dd, J=8.2, 5.3 Hz), 1.20 (1H, t, J=4.8 Hz).

$^{13}$C NMR (DMSO$_{d6}$): 169.9, 163.4, 163.3, 161.8, 161.7, 156.1, 145, 144.9, 144.9, 131.9, 113.7, 110, 110, 109.9, 109.8, 102.3, 102.1, 101.9, 50.8, 36.1, 31.2, 25.1, 23.

Example 34: 2-((S)-6-(3-bromo-2,6-difluorophenyl)-3-thioxo-3,5,6,7-tetrahydro-2H-pyrrolo[1,2-c]imidazol-1-yl)-N-(2-oxocyclopentyl)acetamide

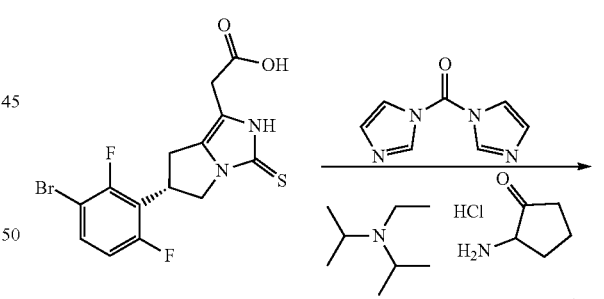

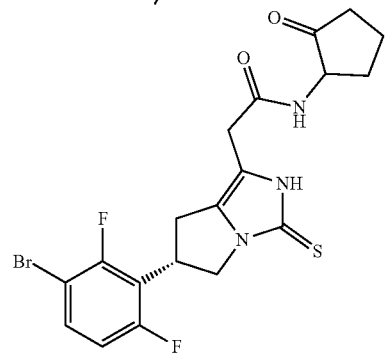

To a stirred suspension of (S)-2-(6-(3-bromo-2,6-difluorophenyl)-3-thioxo-3,5,6,7-tetrahydro-2H-pyrrolo[1,2-c]imidazol-1-yl)acetic acid (Example 12) (100 mg, 0.257 mmol) in dry tetrahydrofuran (2 mL) was added di(1H-imidazol-1-yl)methanone (50 mg, 0.308 mmol) and the mixture was stirred for 1 h. Thereupon, 2-aminocyclopentanone hydrochloride (77 mg, 0.565 mmol) and the reaction mixture was stirred for additional 1 h. The mixture was then diluted with ethyl acetate (5 mL), washed with 1 M HCl solution. The organic phase was dried (MgSO$_4$), filtered and stripped down to dryness under vacuum. The crude product was purified by chromatography in a mixture of dichloromethane-methanol (9:1). The thus obtained oil was crystalized by trituration in n-heptane (light brown powder). Yield: 68 mg, 56%.

$^1$H NMR (DMSO$_{d6}$): 11.78 (1H, s), 8.18, 8.17 (1H, 2 d, J=3.4 Hz), 7.73 (1H, m), 7.17 (1H, m), 4.43 (1H, m), 4.15 (1H, dd, J=9.5, 11.3 Hz), 4.03 (1H, m), 3.73 (1H, dd, J=11.5, 8.1 Hz), 3.28 (2H, t, J=5.1 Hz), 3.22 (1H, m), 2.86 (1H, m), 2.24 (1H, 2 m), 2.18-2.04 (2H, m), 1.91 (1H, m), 1.81-1.66 (2H, m).

$^{13}$C NMR (DMSO$_{d6}$): 214.8, 214.8, 167.5, 160.8, 160.8, 159.2, 159.1, 157.6, 157.5, 155.9, 155.9, 155.1, 132.5, 132.4, 129.3, 129.2, 118.7, 118.7, 118.6, 118.5, 118.5, 118.4, 113.9, 113.9, 113.8, 113.8, 113.6, 113.6, 104.1, 104, 103.9, 103.9, 56.3, 48.5, 35.7, 35.6, 35.5, 31.2, 29.3, 28.7, 28.7, 17.9.

Example 35: (5aS,6aR)-1-(2-aminoethyl)-5a-(3,5-difluorophenyl)-5,5a,6,6a-tetrahydrocyclopropa[3,4]pyrrolo[1,2-c]imidazole-3(2H)-thione Hydrochloride

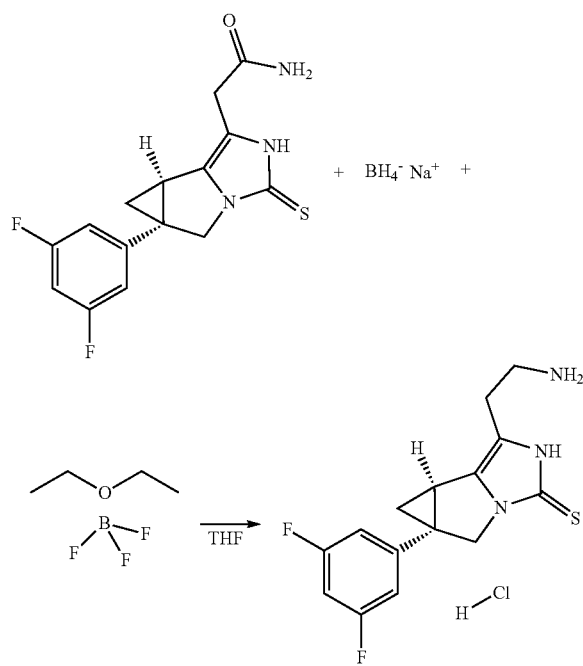

To a stirred solution of 2-((5aS,6aR)-5a-(3,5-difluorophenyl)-3-thioxo-2,3,5,5a,6,6a-hexahydrocyclopropa[3,4]pyrrolo[1,2-c]imidazol-1-yl)acetamide (Example 33) (52 mg, 0.162 mmol) in dry tetrahydrofuran (1 mL), was added sodium borohydride (0.032 g, 0.809 mmol) at room temperature, and then the mixture was cooled to 0° C. A solution of boron trifluoride diethyl etherate (0.103 ml, 0.809 mmol) in dry tetrahydrofuran (0.5 ml) was added dropwise to the above mixture, whereupon the reaction was allowed to warm up to room temperature and stirred for 2 h. Thereupon, the reaction was cooled again to 0° C. and quenched with 1 M HCl (~0.3 mL), followed by addition of 2 M HCl (~0.2 mL, to pH=1). The mixture was then allowed to warm up to room temperature and heated at reflux for 30 min. Thereupon, the mixture was cooled to room temperature, diluted with water, and then tetrahydrofuran was evaporated off. The aqueous phase was extracted with dichloromethane, whereupon, the organic phase was dried over MgSO$_4$, filtered and evaporated to dryness to give the product as a yellow solid. Yield: 0.037 g, 60%).

$^1$H NMR (DMSO$_{d6}$): 11.78 (1H, s), 7.77 (3H, br s), 7.13 (1H, tt, J=2.3, 9.3 Hz), 7.11 (2H, m), 4.19 (1H, d, J=12.2 Hz), 4.00 (1H, d, J=12.2 Hz), 3.05 (2H, m), 2.97 (1H, dd, J=8.2, 4.4 Hz), 2.71 (2H, m), 1.69 (1H, dd, J=8.3, 5.2 Hz), 1.24 (1H, t, J=4.8 Hz).

$^{13}$C NMR (DMSO$_{d6}$): 163.4, 163.3, 161.8, 161.7, 156.8, 144.9, 144.8, 144.8, 132.1, 114.1, 110.2, 110.1, 110, 110, 102.4, 102.2, 102, 50.8, 37.5, 36.3, 24.9, 22.5, 22.4.

Example 36: 2-((5aS,6aR)-5a-(2,5-difluorophenyl)-3-thioxo-2,3,5,5a,6,6a-hexahydrocyclopropa[3,4]pyrrolo[1,2-c]imidazol-1-yl)acetonitrile Step 1: (1S,5R)-tert-butyl 4-(2-cyanoacetyl)-1-(2,5-difluorophenyl)-3-azabicyclo[3.1.0]hexane-3-carboxylate

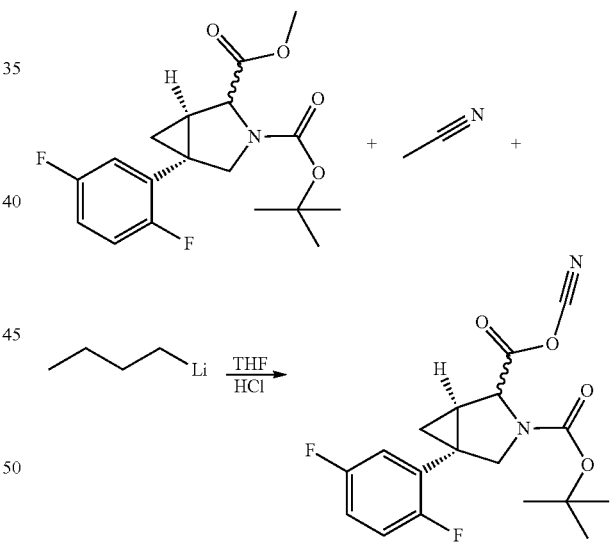

To a cooled mixture (−78° C.) of acetonitrile (0.357 ml, 6.79 mmol) and dry tetrahydrofuran (10 mL) was added 1.6 N n-butyllithium (6.19 ml, 9.90 mmol) dropwise. The mixture was stirred in the cold for 30 min., and then a solution of (1R,5S)-3-tert-butyl 2-methyl 5-(2,5-difluorophenyl)-3-azabicyclo[3.1.0]hexane-2,3-dicarboxylate (2 g, 5.66 mmol) (Example 4, step 1) in anhydrous tetrahydrofuran (5 mL) was added, dropwise. The reaction mixture was stirred in the cold for 3 h, and then quenched by addition of 1 M HCl (9.90 ml, 9.90 mmol). Thereupon, the mixture was and allowed to warm up to room temperature and the pH of the mixture was adjusted to 3 by addition of 1 M HCl. The mixture was then partitioned between diethyl ether and brine, the organic phase was separated, dried over MgSO₄, filtered and evaporated to dryness. The resulting yellow oil was purified by chromatography (petroleum ether-ethyl acetate; 9:1, 4:1, then 2:1). (Yield: 1.31 g, 57%).

Step 2: 3-((1R,5S)-5-(2,5-difluorophenyl)-3-azabicyclo[3.1.0]hexan-2-yl)-3-oxopropanenitrile hydrochloride

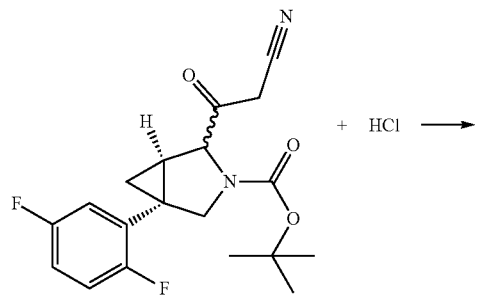

A mixture of (1S,5R)-tert-butyl 4-(2-cyanoacetyl)-1-(2,5-difluorophenyl)-3-azabicyclo[3.1.0]hexane-3-carboxylate (1.3 g, 3.59 mmol) and a solution of 4 M HCl in dioxane (17.94 mL, 71.7 mmol) was stirred at room temperature for 4 h. Diethyl ether was then added and the mixture was stirred for 15 min. The resulting yellow solid was filtered off and dried under vacuum. (Yield: 0.96 g, 81%).

Step 3: 2-((5aS,6aR)-5a-(2,5-difluorophenyl)-3-thioxo-2,3,5,5a,6,6a-hexahydrocyclopropa[3,4]pyrrolo[1,2-c]imidazol-1-yl)acetonitrile

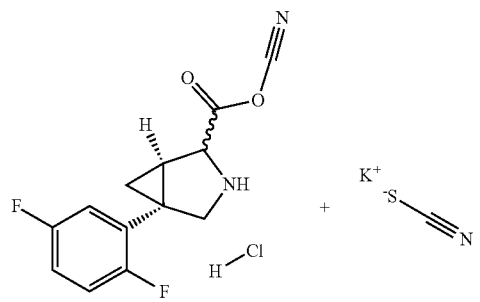

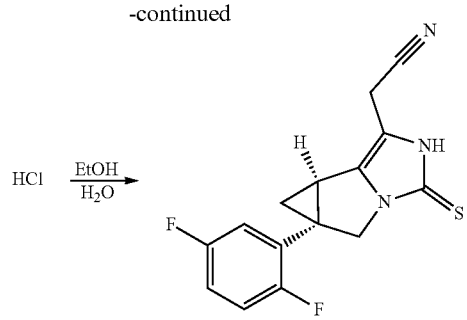

To a solution of 3-((1R,5S)-5-(2,5-difluorophenyl)-3-azabicyclo[3.1.0]hexan-2-yl)-3-oxopropanenitrile hydrochloride (950 mg, 3.18 mmol) in a mixture of ethanol (13 mL) and water (13 mL) was added potassium thiocyanate (340 mg, 3.50 mmol) followed by addition of cc HCl (0.131 ml, 1.590 mmol). The solution was heated at reflux for 1 h. and then cooled to room temperature. Thereupon, ethanol was evaporated off, and the aqueous phase was extracted with dichloromethane. The organic phase was separated and evaporated to dryness. Chromatography (dichloromethane-methanol (98:2, then 95:5) afforded the product as a yellow foam. (Yield: 0.35 g, 32%).

$^1$H NMR (DMSO$_{d6}$): 12.06 (1H, s), 7.29 (2H, m), 7.22 (1H, m), 4.10 (1H, d, J=12.0 Hz), 3.91 (2H, m), 3.82 (1H, d, J=12.0 Hz), 2.90 (1H, dd, J=8.4, 4.3 Hz), 1.72 (1H, dd, J=8.4, 5.5 Hz), 1.23 (1H, t, J=4.8 Hz).

$^{13}$C NMR (DMSO$_{d6}$): 158.8, 158.6, 157.4, 157.2, 157, 132.5, 128.3, 128.3, 128.2, 128.2, 117.2, 117.1, 117.1, 117, 117, 117, 116.1, 116, 115.9, 115.9, 108.8, 51.6, 51.6, 32.7, 21.9, 20.5, 13.4.

Example 37: N-benzyl-2-((5aS,6aR)-5a-(2,5-difluorophenyl)-3-thioxo-2,3,5,5a,6,6a-hexahydrocyclopropa[3,4]pyrrolo[1,2-c]imidazol-1-yl)-N-methylacetamide Step 1: (1S,5R)-tert-butyl 1-(2,5-difluorophenyl)-4-(3-ethoxy-3-oxopropanoyl)-3-azabicyclo[3.1.0]hexane-3-carboxylate

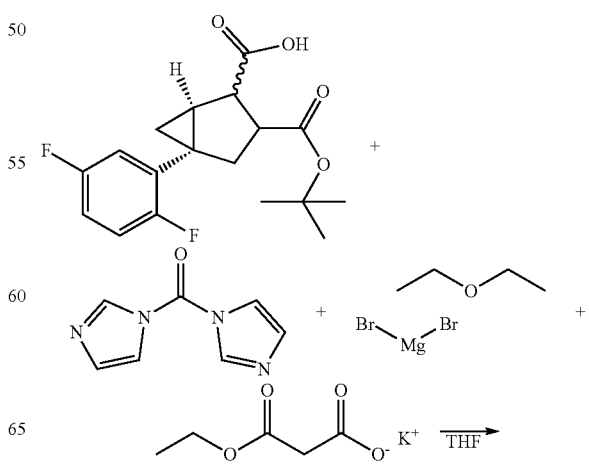

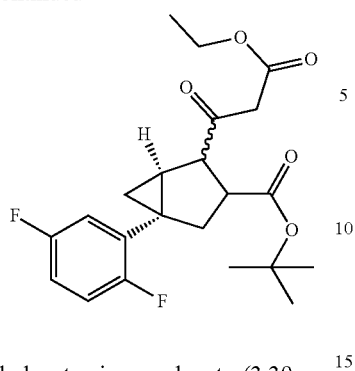

To a stirred mixture of ethyl potassium malonate (3.39 g, 19.89 mmol) in dry tetrahydrofuran (43 mL) was added magnesium bromide diethyl etherate (3.42 g, 13.26 mmol), at room temperature under inert atmosphere, and then the thus obtained white suspension was heated at 50° C. for 3 h (1$^{st}$ mixture).

In parallel, 1,1'-carbonyldiimidazole (3.66 g, 22.54 mmol) was added, in portions to a light yellow solution of (1R, 5S)-3-(tert-butoxycarbonyl)-5-(2,5-difluorophenyl)-3-azabicyclo[3.1.0]hexane-2-carboxylic acid (Example 4 step 1) (4.5 g, 13.26 mmol) in dry tetrahydrofuran (35 mL) at 0° C., under nitrogen. The thus obtained yellow solution was allowed to warm up to room temperature, stirred for 2 h, and then added to the 1$^{st}$ suspension at room temperature dropwise. Thereupon, the reaction was stirred at room temperature for 24 h, and the mixture was quenched with sodium hydrogen sulfate. The aqueous phase was extracted with a mixture of ethyl acetate-petroleum ether (2:1). The combined organic phases were washed with saturated solution of sodium bicarbonate, dried over MgSO$_4$, filtered and evaporated to dryness. Chromatography (ethyl acetate-petroleum ether; 9:1, then 4:1) gave the product as a light oil. (Yield: 3.52 g, 61%).

Step 2: (1S,5R)-tert-butyl 4-(3-(benzyl(methyl) amino)-3-oxopropanoyl)-1-(2,5-difluorophenyl)-3-azabicyclo[3.1.0]hexane-3-carboxylate

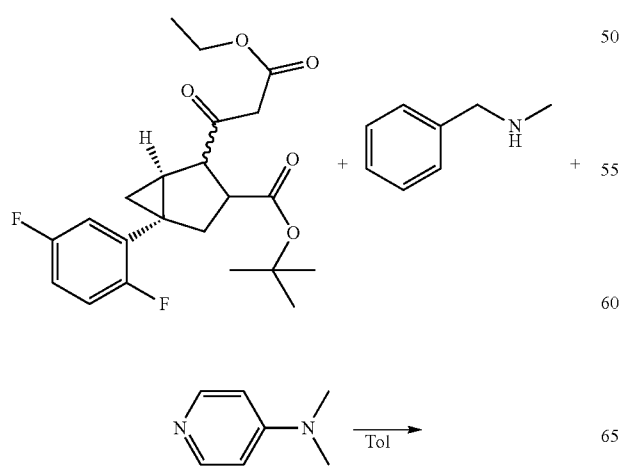

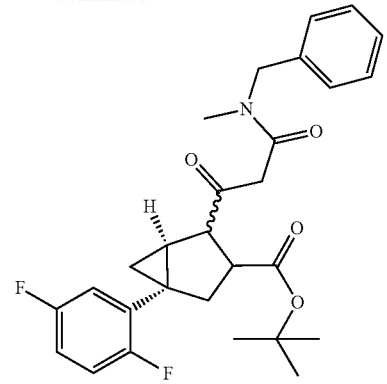

To a stirred solution of (1S,5R)-tert-butyl 1-(2,5-difluorophenyl)-4-(3-ethoxy-3-oxopropanoyl)-3-azabicyclo[3.1.0] hexane-3-carboxylate (1 g, 2.442 mmol) in toluene (4 mL) was added N-methylbenzylamine (0.63 ml, 4.88 mmol) followed by addition of N,N-dimethylpyridin-4-amine (0.090 g, 0.733 mmol) at room temperature. The solution was heated at 100° C. for 20 h, whereupon cooled to room temperature, diluted with a mixture of ethyl acetate-petroleum ether (1:1) and washed with 1M HCl. The organic phase was dried over MgSO$_4$, filtered and evaporated to dryness. The thus obtained yellow oil was purified by chromatography (petroleum ether-ethyl acetate; 4:1, then 2:1) to leave the product as a yellow oil. (Yield: 0.88 g, 67%).

Step 3: N-benzyl-3-((1R,5S)-5-(2,5-difluorophenyl)-3-azabicyclo[3.1.0]hexan-2-yl)-N-methyl-3-oxopropanamide Hydrochloride

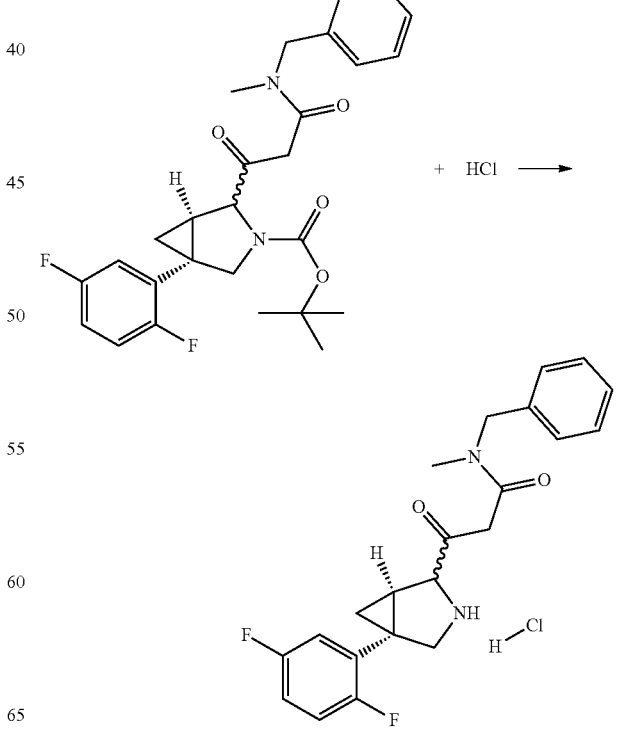

A mixture of (1S,5R)-tert-butyl 4-(3-(benzyl(methyl)amino)-3-oxopropanoyl)-1-(2,5-difluorophenyl)-3-azabicyclo[3.1.0]hexane-3-carboxylate (870 mg, 1.796 mmol) and 4 M HCl in dioxane (6.7 mL, 26.9 mmol) was stirred at room temperature for 2 h. Diethyl ether was then added and the suspension was stirred for 15 min. The resulting off-white precipitate was filtered and dried under vacuum. (Yield: 0.57 g, 67%).

Step 4: N-benzyl-2-((5aS,6aR)-5a-(2,5-difluorophenyl)-3-thioxo-2,3,5,5a,6,6a-hexahydrocyclopropa[3,4]pyrrolo[1,2-c]imidazol-1-yl)-N-methylacetamide

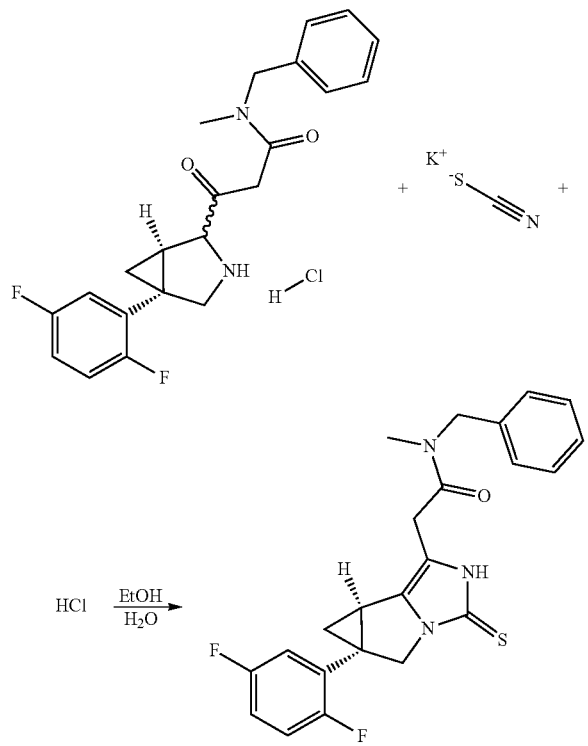

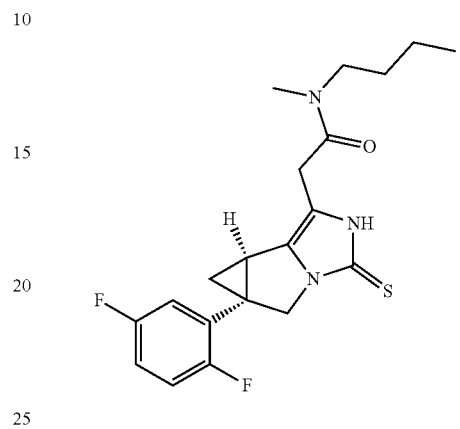

To a stirred solution of N-benzyl-3-((1R,5S)-5-(2,5-difluorophenyl)-3-azabicyclo[3.1.0]hexan-2-yl)-N-methyl-3-oxopropanamide hydrochloride (556 mg, 1.321 mmol) in a mixture of ethanol (5.4 mL) and water (5.4 mL) was added potassium thiocyanate (0.141 mg, 1.453 mmol) followed by addition of cc. HCl (0.054 mL, 0.661 mmol). The solution was heated at reflux for 1 h, and then cooled to room temperature. Thereupon, ethanol was evaporated off and the aqueous phase was extracted with dichloromethane. The organic phase was then dried over MgSO$_4$, filtered and evaporated to dryness to give the product as a light yellow semi-solid. (Yield: 0.17 g, 29%).

$^1$H NMR (DMSO$_{d6}$): 11.70 (0.65H, s), 1.68 (0.35H, s), 7.38 (0.7H, t, J=7.8 Hz), 7.34-7.17 (7.3H, m), 4.64 (0.7H, s), 4.53 (1.3H, m), 4.09, 4.08 (1H, 2 d, J=12 Hz), 3.81, 3.79 (1H, 2 d, J=12 Hz), 3.69-3.58 (2H, m), 2.98 (1.95H, s), 2.81 (1.05H, s), 2.76 (0.35H, dd, J=8.4, 4.3 Hz), 2.72 (0.65H, dd, J=8.3, 4.2 Hz), 1.63 (1H, m), 1.11 (0.65H, t, J=4.8 Hz), 1.09 (0.35H, t, J=4.8 Hz).

$^{13}$C NMR (DMSO$_{d6}$): 168.3, 158.8, 158.6, 157.2, 157, 155.9, 137.5, 137.1, 131.8, 131.7, 128.7, 128.7, 128.6, 128.5, 128.5, 128.4, 127.7, 127.3, 127.1, 126.8, 117.2, 117.1, 117, 117, 117, 116.9, 116.8, 116.8, 116.8, 115.9, 115.9, 115.8, 115.7, 113.9, 52.6, 51.5, 50.2, 35, 33.

Example 38: N-butyl-2-((5aS,6aR)-5a-(2,5-difluorophenyl)-3-thioxo-2,3,5,5a,6,6a-hexahydrocyclopropa[3,4]pyrrolo[1,2-c]imidazol-1-yl)-N-methylacetamide Compound was prepare analogous manner to Example 37 from (1R,5S)-3-(tert-butoxycarbonyl)-5-(2,5-difluorophenyl)-3-azabicyclo[3.1.0]hexane-2-carboxylic acid and isolated as a light yellow foam.

$^1$H NMR (DMSO$_{d6}$): 11.62 (1H, 2 s), 7.29 (1H, td, J=9.4, 4.6 Hz), 7.25 (1H, ddd, J=9.1, 5.9, 3.2 Hz), 7.20 (1H, m), 4.08 (1H, d, J=11.9 Hz), 3.81 (1H, d, J=12.2 Hz), 3.53 (2H, m), 3.29 (2H, m), 2.99 (1.65H, s), 2.82 (1.35H, s), 2.79, 2.78 (1H, 2 dd, J=8.3, 4.1 Hz), 1.65 (1H, dd, J=8.4, 5.3 Hz), 1.52 (0.9H, m), 1.43 (1.1H, m), 1.30 (0.9H, m), 1.24 (1.1H, m), 1.11 (1H, m), 0.92 (1.35H, t, J=7.4 Hz), 0.87 (1.65H, t, J=7.3 Hz).

$^{13}$C NMR (DMSO$_{d6}$): 167.7, 167.6, 158.8, 158.6, 157.2, 157, 155.8, 131.7, 131.6, 128.7, 128.6, 128.6, 128.5, 117.2, 117.1, 117, 117, 116.8, 115.9, 115.9, 115.8, 115.7, 114.1, 114, 51.5, 49.1, 46.8, 35.1, 33.2, 32.4, 30, 29.5, 28.9, 28.9, 22.3, 22.2, 20.9, 20.8, 19.5, 19.4, 1.

Example 39: (5aS,6aR)-1-(2-(butyl(methyl)amino)ethyl)-5a-(2,5-difluorophenyl)-5,5a,6,6a-tetrahydrocyclopropa[3,4]pyrrolo[1,2-c]imidazole-3(2H)-thione Hydrochloride

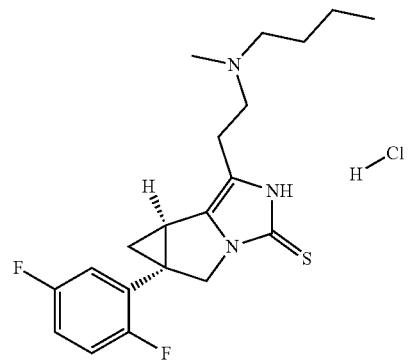 [SMILES: CCCCN(C)CCc1[nH]c(=S)n2c1[C@@H]1C[C@]1(c1cc(F)ccc1F)C2 ; Cl]

Compound was prepared analogous manner to Example 35 from N-butyl-2-((5aS,6aR)-5a-(2,5-difluorophenyl)-3-thioxo-2,3,5,5a,6,6a-hexahydrocyclopropa[3,4]pyrrolo[1,2-c]imidazol-1-yl)-N-methylacetamide (Example 37) and isolated as a light yellow solid.

¹H NMR (DMSO$_{d6}$): 11.81 (1H, br s), 9.25 (1H, br s), 7.30 (1H, m), 7.27 (1H, m), 7.22 (1H, m), 4.08 (1H, br d, J=12.2 Hz), 3.81 (1H, d, J=12.0 Hz), 3.17 (2H, br m), 2.95 (2H, m), 2.93 (1H, dd, J=8.2, 4.2 Hz), 2.81 (2H, br m), 2.69 (3H, br s), 1.67 (1H, br dd, J=8.2, 5.3 Hz), 1.57 (2H, br m), 1.31 (2H, dq, J=14.9, 7.4 Hz), 1.18 (1H, br t, J=4.7 Hz), 0.91 (3H, t, J=7.3 Hz).

¹³C NMR (DMSO$_{d6}$): 158.8, 158.7, 157.2, 157.1, 156.5, 131.6, 128.6, 128.5, 128.5, 128.4, 117.2, 117.2, 117.1, 117, 117, 116.8, 116, 116, 115.9, 115.8, 55.1, 53.5, 51.5, 39.8, 32.6, 26, 22.2, 20.5, 19.8, 19.5, 13.6.

Example 40: (5aS,6aR)-1-(2-(benzyl(methyl)amino)ethyl)-5a-(2,5-difluorophenyl)-5,5a,6,6a-tetrahydrocyclopropa[3,4]pyrrolo[1,2-c]imidazole-3(2H)-thione

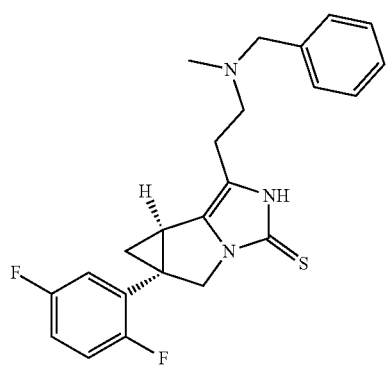 [SMILES: CN(CCc1[nH]c(=S)n2c1[C@@H]1C[C@]1(c1cc(F)ccc1F)C2)Cc1ccccc1]

Compound was prepared analogous manner to Example 35 from N-benzyl-2-((5aS,6aR)-5a-(2,5-difluorophenyl)-3-thioxo-2,3,5,5a,6,6a-hexahydrocyclopropa[3,4]pyrrolo[1,2-c]imidazol-1-yl)-N-methylacetamide (Example 37) and isolated as a white foam.

¹H NMR (CDCl₃): 10.33 (1H, br s), 7.37 (2H, t, J=7.3 Hz), 7.33 (2H, t, J=8.5 Hz), 7.29 (1H, t, J=7.3 Hz), 7.05 (1H, td, J=9.1, 4.5 Hz), 7.00-6.93 (2H, m), 4.25 (1H, d, J=12.2 Hz), 4.03 (1H, d, J=12.3 Hz), 3.57 (2H, m), 2.67 (4H, m), 2.51 (1H, dd, J=8.2, 4.1 Hz), 2.28 (3H, s), 1.58 (1H, dd, J=8.2, 5.5 Hz), 1.12 (1H, m).

¹³C NMR (CDCl₃): 159.3, 158.9, 157.6, 157.2, 155.8, 137.5, 130.3, 129.4, 128.6, 128.1, 128.1, 128, 128, 127.5, 119.3, 117.1, 117, 116.9, 116.8, 116.7, 116.6, 116.5, 116.5, 116, 115.9, 115.8, 115.8, 62.8, 55.8, 52.1, 52.1, 41.5, 32.7, 22.3, 21.2, 20.9.

Example 41: (5aS,6aR)-1-((1H-tetrazol-5-yl)methyl)-5a-(2,5-difluorophenyl)-5,5a,6,6a-tetrahydrocyclopropa[3,4]pyrrolo[1,2-c]imidazole-3(2H)-thione

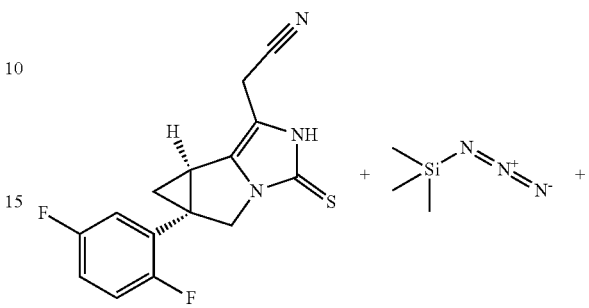

To a stirred solution of 2-((5aS,6aR)-5a-(2,5-difluorophenyl)-3-thioxo-2,3,5,5a,6,6a-hexahydrocyclopropa[3,4]pyrrolo[1,2-c]imidazol-1-yl)acetonitrile (Example 36) (50 mg, 0.165 mmol) in dry toluene (1 mL) was added dibutyltin oxide (41.0 mg, 0.165 mmol) followed by addition of azidotrimethylsilane (0.044 mL, 0.330 mmol). The reaction mixture was heated at 100° C. for 24 h. The mixture was then cooled to room temperature, partitioned between diethyl ether and 1 M sodium hydroxide (1.6 mL) and the aqueous phase was washed with diethyl ether. The ethereal phase was discarded and the aqueous phase was acidified with 2 M HCl to pH=1. The resulting solid was collected by filtration, washed with water and dried under vacuum. (Yield: 25 mg, 37%).

¹H NMR (DMSO$_{d6}$): 11.85 (1H, s), 7.29 (1H, td, J=9.4, 4.5 Hz), 7.25 (1H, ddd, J=9.0, 5.9, 3.2 Hz), 7.21 (1H, m), 4.18 (2H, m), 4.10 (1H, br d, J=12.0 Hz), 3.80 (1H, br d, J=5.7 Hz), 2.69 (1H, dd, J=8.3, 4.2 Hz), 1.63 (1H, dd, J=8.4, 5.3 Hz), 1.20 (1H, t, J=4.8 Hz).

¹³C NMR (DMSO$_{d6}$): 158.8, 158.6, 157.2, 157, 156.8, 153.1, 132.4, 128.5, 117.2, 116.9, 115.9, 51.6, 32.6, 22, 20.5, 19.3.

Example 42: (5aS,6aR)-5a-(2,5-difluorophenyl)-1-(2-hydroxyethyl)-5,5a,6,6a-tetrahydrocyclopropa[3,4]pyrrolo[1,2-c]imidazole-3(2H)-thione

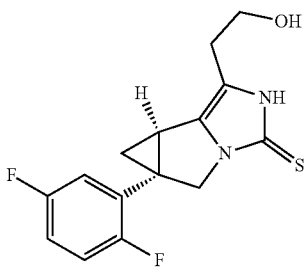 [SMILES: OCCc1[nH]c(=S)n2c1[C@@H]1C[C@]1(c1cc(F)ccc1F)C2]

Compound was prepared analogous manner to Example 8 from ethyl 2-((5aS,6aR)-5a-(2,5-difluorophenyl)-3-thioxo-2,3,5,5a,6,6a-hexahydrocyclopropa[3,4]pyrrolo[1,2-c]imidazol-1-yl)acetate and isolated as a yellow solid.

$^1$H NMR (DMSO$_{d6}$): 11.65 (1H, br s), 7.28 (2H, m), 7.20 (1H, m), 4.75 (1H, t, J=5.3 Hz), 4.06 (1H, br d, J=12.0 Hz), 3.79 (1H, d, J=12.0 Hz), 3.60 (2H, m), 2.88 (1H, dd, J=8.2, 4.1 Hz), 2.55 (2H, m), 1.61 (1H, dd, J=8.1, 5.4 Hz), 1.14 (1H, t, J=4.7 Hz).

$^{13}$C NMR (DMSO$_{d6}$): 158.8, 158.6, 157.2, 157, 155.7, 130.9, 128.9, 128.8, 128.7, 128.7, 117.2, 117.1, 117, 117, 116.9, 116.9, 116.8, 116.7, 116.7, 115.9, 115.8, 115.7, 115.6, 59.4, 51.4, 51.4, 32.4, 28, 22.5, 20.6.

Example 43: (S)-6-(3,5-difluorophenyl)-3-thioxo-3,5,6,7-tetrahydro-2H-pyrrolo[1,2-c]imidazole-1-carboxylic Acid Step 1: (4S)-tert-butyl 4-(3,5-difluorophenyl)-2-(hydroxymethyl)pyrrolidine-1-carboxylate

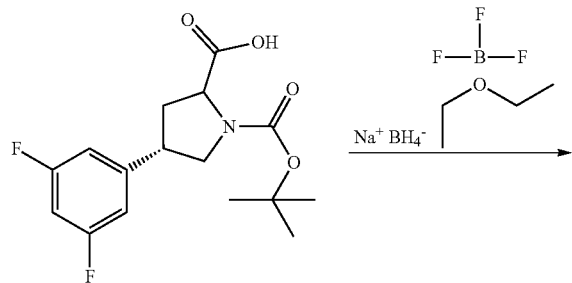

To a stirred solution of (4S)-1-(tert-butoxycarbonyl)-4-(3,5-difluorophenyl)pyrrolidine-2-carboxylic acid (Example 44, step 9) (1.4 g, 4.28 mmol) in isopropyl acetate (7 mL) was added sodium borohydride (0.259 g, 6.84 mmol) at 0-5° C. followed by addition of boron trifluoride etharate (1.084 mL, 8.55 mmol. The mixture was stirred for 2 h in the cold, then quenched with 0.5 M sodium hydroxide (30.8 mL, 15.4 mmol), and allowed to stir at room temperature for 30 min. The organic phase was separated, dried over MgSO$_4$, evaporated to dryness to leave a yellowish oil. Yield: 1.37 g, 97%).

Step 2: (4S)-tert-butyl 4-(3,5-difluorophenyl)-2-formylpyrrolidine-1-carboxylate

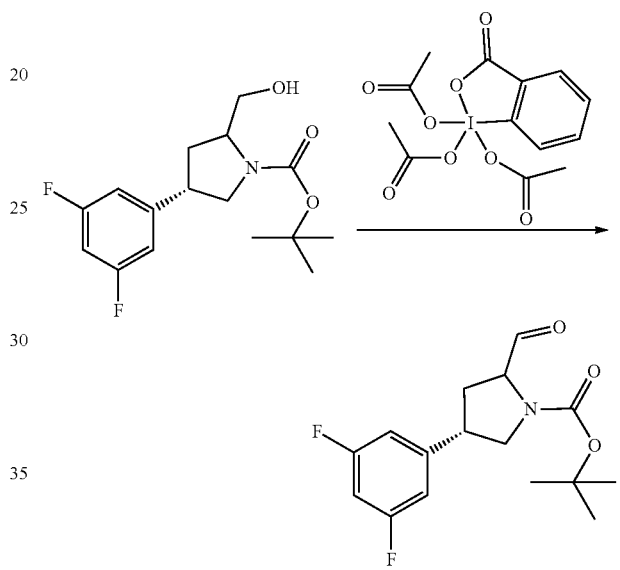

To a stirred solution of (4S)-tert-butyl 4-(3,5-difluorophenyl)-2-(hydroxymethyl)pyrrolidine-1-carboxylate (0.46 g, 1.468 mmol) in dry dichloromethane (14 mL) was added Dess-Martin periodinane (3-oxo-1-benzo[d][1,2]iodaoxole-1,1,1(3H)-triyl triacetate) (0.623 g, 1.468 mmol) in one portion to give a clear solution. Thereupon, the mixture was stirred at room temperature for 3 h, concentrated to approximately one third and subjected to chromatography (petroleum ether-ethyl acetate 9:1, then 4:1). The product was isolated as yellowish oil. (Yield: 1.21 g, 94%).

Step 3: ((4S)-tert-butyl 2-(cyano(hydroxy)methyl)-4-(3,5-difluorophenyl)pyrrolidine-1-carboxylate

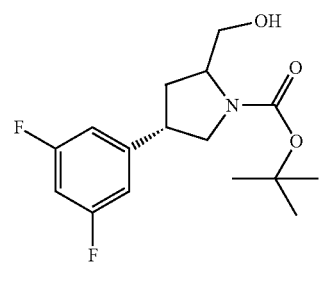

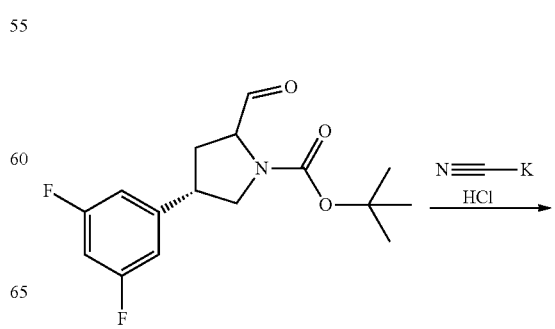

-continued

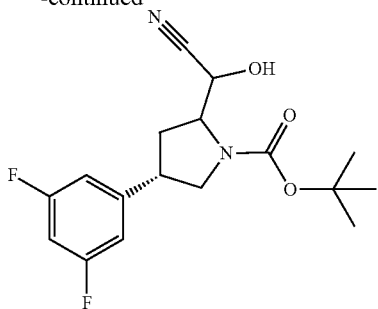

To a stirred solution of (4S)-tert-butyl 4-(3,5-difluorophenyl)-2-formylpyrrolidine-1-carboxylate (1.2 g, 3.85 mmol) in a mixture of tetrahydrofuran (10 mL) and water (5 mL) was added potassium cyanide (0.301 g, 4.63 mmol) followed by addition of cc HCl (0.319 ml, 3.85 mmol). The mixture was stirred for 8 h, then extracted with dichloromethane. The organic phase was washed with brine, dried over MgSO₄ and evaporated to dryness to give (4S)-tert-butyl 2-(cyano(hydroxy)methyl)-4-(3,5-difluorophenyl)pyrrolidine-1-carboxylate as a yellowish oil. (Yield: 1.44 g, 99%).

Step 4: (4S)-tert-butyl 4-(3,5-difluorophenyl)-2-(2-ethoxy-1-hydroxy-2-oxoethyl)pyrrolidine-1-carboxylate

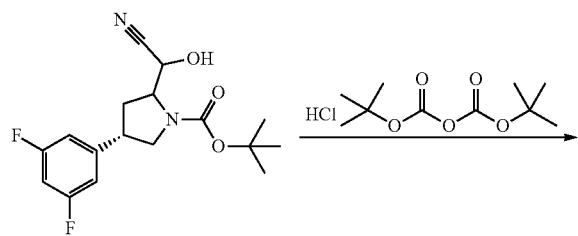

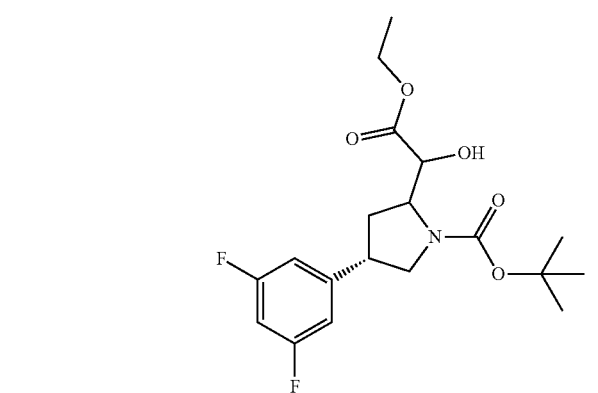

A mixture of (4S)-tert-butyl 2-(cyano(hydroxy)methyl)-4-(3,5-difluorophenyl)pyrrolidine-1-carboxylate (1.43 g, 3.80 mmol) and 2 M HCl (28.5 ml, 57.1 mmol) was stirred under reflux for 16 h. After cooling to room temperature the mixture was filtered through a celite plug to remove insoluble coloured stuff and then the filtrate was evaporated to dryness under vacuum. The residue was azeotroped twice with dry ethanol and the residue was taken up in abs. ethanol (20 mL). The thus obtained solution was treated with 4 M HCl (9.51 ml, 38.0 mmol) in dioxane and stirred under reflux for 2 h. The mixture was evaporated to dryness, and then azeotroped with abs. ethanol. The resulting semisolid was taken up in abs. ethanol (30 mL), neutralized by addition of triethylamine to pH=6-7, then a second crop of triethylamine (0.530 ml, 3.80 mmol) was added followed by addition of di-tert-butyl dicarbonate (0.830 g, 3.80 mmol). The reaction was allowed to stir at room temperature for 2 h, and then evaporated to dryness at 40° C. The residue was partitioned between dichloromethane and water, the organic phase was dried over MgSO₄ and concentrated under reduced pressure. Chromatography (petroleum ether-ethyl acetate; 9:1, then 4:1) gave the product as a yellow oil. (Yield: 1.16 g, 79%).

Step 5: (4S)-tert-butyl 4-(3,5-difluorophenyl)-2-(2-ethoxy-2-oxoacetyl)pyrrolidine-1-carboxylate

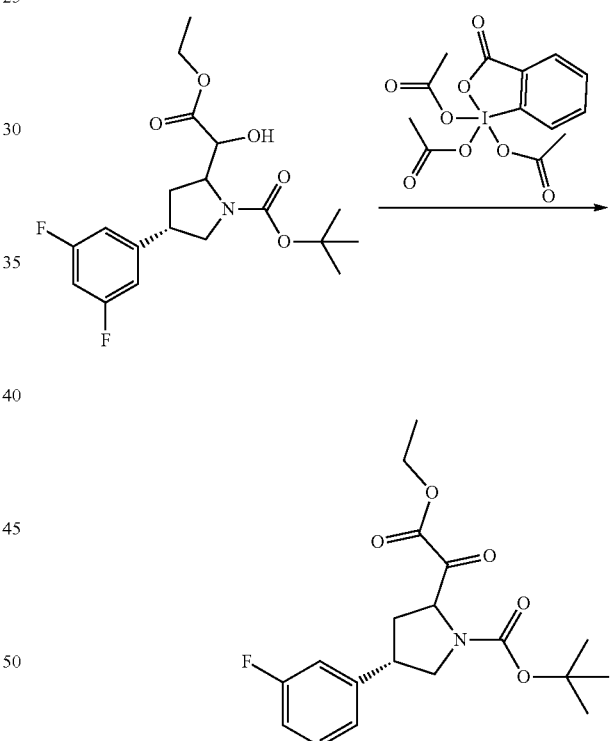

To a stirred solution of (4S)-tert-butyl 4-(3,5-difluorophenyl)-2-(2-ethoxy-1-hydroxy-2-oxoethyl)pyrrolidine-1-carboxylate (1.15 g, 2.98 mmol) in dry dichloromethane (25 mL) was added Dess-Martin periodinane (3-oxo-1λ⁵-benzo[d][1,2]iodaoxole-1,1,1(3H)-triyl triacetate) (1.266 g, 2.98 mmol) at room temperature in one portion and the mixture was stirred for 2 h. The reaction mixture was concentrated under vacuum, whereupon the reside was purified by chromatography (petroleum ether-ethyl acetate; 4:1). The product was isolated as a yellowish oil. (1.08 g, 94% yield).

Step 6: ethyl 2-((4S)-4-(3,5-difluorophenyl)pyrrolidin-2-yl)-2-oxoacetate Hydrochloride

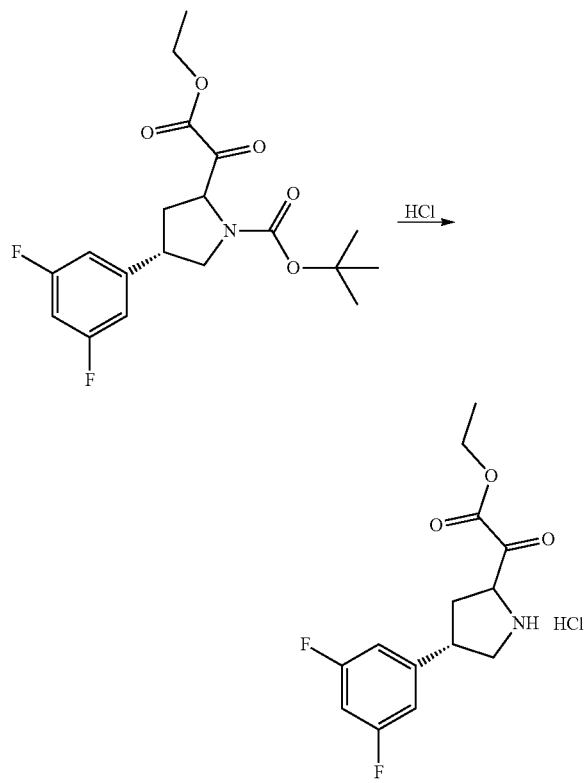

To a stirred solution of (4S)-tert-butyl 4-(3,5-difluorophenyl)-2-(2-ethoxy-2-oxoacetyl)pyrrolidine-1-carboxylate (0.4 g, 1.043 mmol) in 4 M HCl (5.22 mL, 20.87 mmol) in dioxane was stirred at room temperature for 4 h. The reaction mixture was diluted with a mixture of diethyl ether (20 mL) and petroleum ether (5 mL) and stirred for 30 min, Thereupon, the resulting precipitate was collected, washed with diethyl ether, petroleum ether and dried under vacuum at 50° C. to give ethyl 2-((4S)-4-(3,5-difluorophenyl)pyrrolidin-2-yl)-2-oxoacetate hydrochloride as a white powder. (Yield: 0.34 g, 92%).

Step 7: (S)-ethyl 6-(3,5-difluorophenyl)-3-thioxo-3,5,6,7-tetrahydro-2H-pyrrolo[1,2-c]imidazole-1-carboxylate

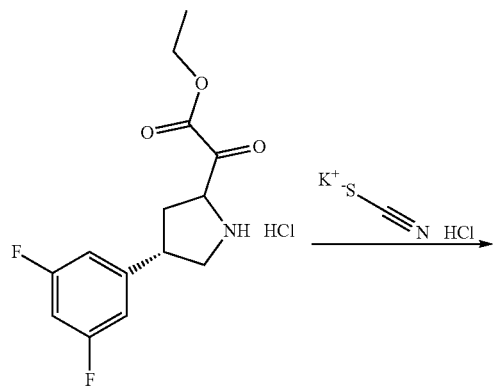

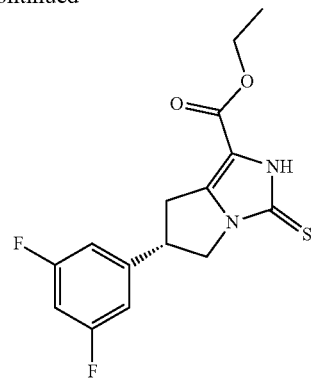

A solution of ethyl 2-((4S)-4-(3,5-difluorophenyl)pyrrolidin-2-yl)-2-oxoacetate hydrochloride (0.33 g, 1.032 mmol), 6 M HCl (0.086 ml, 0.516 mmol) and potassium thiocyanate (0.110 g, 1.135 mmol) in a mixture of ethanol (5 mL) and water (5 mL) was stirred under reflux for 30 min. The reaction was then cooled to room temperature, and the resulting solid was collected, washed with a mixture of ethanol and water (1:1), and dried under vacuum at 50° C. to give (S)-ethyl 6-(3,5-difluorophenyl)-3-thioxo-3,5,6,7-tetrahydro-2H-pyrrolo[1,2-c]imidazole-1-carboxylate as a white solid. (Yield: 0.28 g, 84%).

Step 8: (S)-6-(3,5-difluorophenyl)-3-thioxo-3,5,6,7-tetrahydro-2H-pyrrolo[1,2-c]imidazole-1-carboxylic Acid

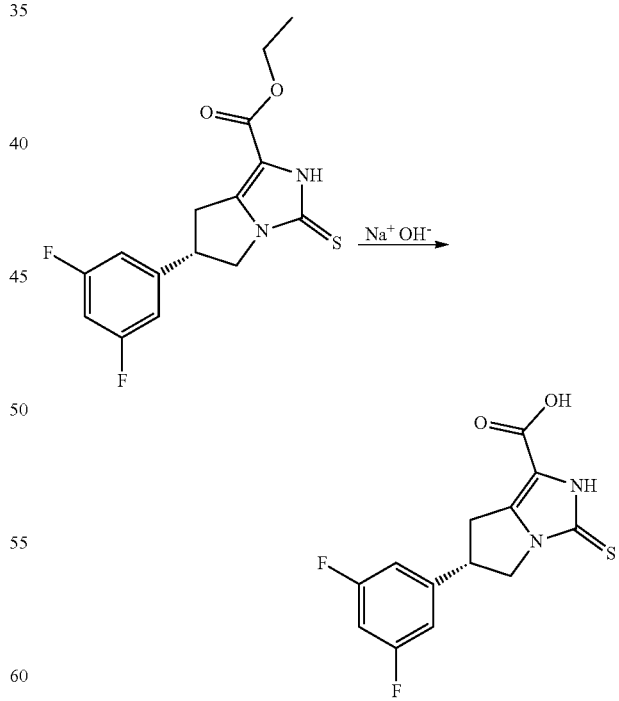

To a stirred solution of (S)-ethyl 6-(3,5-difluorophenyl)-3-thioxo-3,5,6,7-tetrahydro-2H-pyrrolo[1,2-c]imidazole-1-carboxylate (0.08 g, 0.247 mmol) in methanol (2 ml) was added 5 M sodium hydroxide (0.148 ml, 0.740 mmol) at room temperature and the solution was stirred for 24 h. The mixture was then diluted with water (2 mL) and a second crop of 5 M sodium hydroxide (0.148 ml, 0.740 mmol) was added and the mixture was stirred for 48 h, Methanol was removed under vacuum, the residue was diluted with water (ca. 5 mL), and then acidified to pH=2 by adding 6 M HCl. The precipitate was collected, washed with water and dried under vacuum at 50° C. to give (S)-6-(3,5-difluorophenyl)-3-thioxo-3,5,6,7-tetrahydro-2H-pyrrolo[1,2-c]imidazole-1-carboxylic acid as white powder. (Yield: 0.052 g, 71%).

$^1$H NMR (DMSO$_{d6}$): 12.95 (1H, br s), 12.49 (1H, s), 7.16 (3H, m), 4.28 (1H, dd, J=11.1, 8.3 Hz), 4.20 (1H, quin, J=8.6 Hz), 3.76 (1H, dd, J=11.0, 8.8 Hz), 3.47 (1H, dd, J=16.7, 8.1 Hz), 3.10 (1H, dd, J=16.7, 9.3 Hz).

$^{13}$C NMR (DMSO$_{d6}$): 163.3, 163.2, 161.7, 161.6, 159.5, 158.9, 145, 145, 144.9, 140.4, 112.6, 110.9, 110.9, 110.8, 110.8, 102.8, 102.6, 102.4, 50.8, 45.7, 32.3.

Example 44: Ethyl 2-(5a-(thiophen-2-yl)-3-thioxo-2,3,5,5a,6,6a-hexahydrocyclopropa[3,4]pyrrolo[1,2-c]imidazol-1-yl)acetate

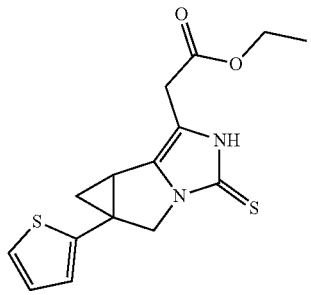 [SMILES: CCOC(=O)Cc1[nH]c(=S)n2c1C1CC1(c1cccs1)C2]

Compound was prepared analogous manner to Example 4 from 3-(tert-butoxycarbonyl)-5-(thiophen-2-yl)-3-azabicyclo[3.1.0]hexane-2-carboxylic acid and isolated as an orange foam.

$^1$H NMR (DMSO$_{d6}$): 11.74 (1H, s), 7.44 (1H, dd, J=5.1, 1.3 Hz), 7.11 (1H, dd, J=3.6, 1.2 Hz), 7.00 (1H, dd, J=5.1, 3.6 Hz), 4.16 (1H, d, J=12.0 Hz), 4.10 (2H, q, J=7.2 Hz), 4.00 (1H, d, J=12.0 Hz), 3.55 (2H, m), 2.68 (1H, dd, J=8.4, 4.0 Hz), 1.83 (1H, dd, J=8.4, 5.6 Hz), 1.24 (1H, dd, J=5.4, 4.5 Hz), 1.20 (3H, t, J=7.1 Hz).

$^{13}$C NMR (DMSO$_{d6}$): 169.2, 156.4, 143.6, 132.2, 127.5, 125.1, 124.7, 112.3, 60.7, 52.2, 32.7, 29.7, 24.9, 24.3, 14.1.

Example 45: (S)-6-(3,5-difluorophenyl)-3-thioxo-3,5,6,7-tetrahydro-2H-pyrrolo[1,2-c]imidazole-1-carbaldehyde Step 1: (4S)-tert-butyl 4-(3,5-difluorophenyl)-2-(2-(methylsulfinyl)acetyl)pyrrolidine-1-carboxylate

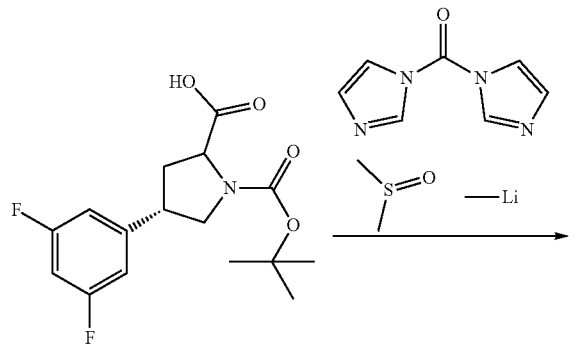

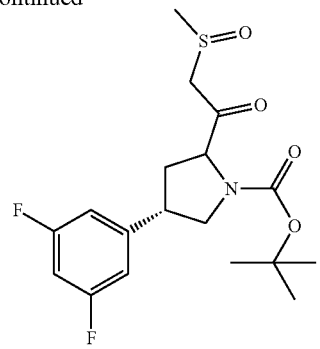

To a solution of dimethyl sulfoxide (0.543 mL, 7.64 mmol) in dry tetrahydrofuran (5 mL) was added 1.6 M methyllithium (4.77 mL, 7.64 mmol) in diethyl ether with external ice-water bath cooling. The mixture was allowed to warm up to room temperature and stirred for 40 min. Thereupon, a solution of (4S)-1-(tert-butoxycarbonyl)-4-(3,5-difluorophenyl)pyrrolidine-2-carboxylic acid (Example 1 step 9) (0.5 g, 1.528 mmol) and di(1H-imidazol-1-yl)methanone (0.248 g, 1.528 mmol) in dry tetrahydrofuran (5 mL) was added dropwise with external ice-water bath cooling and the mixture was allowed to warm up to room temperature and stir under nitrogen for 30 min. The mixture was then cooled 0° C. and neutralized by adding 2 M HCl (3.82 ml, 7.64 mmol) to pH=4-5. Followed by addition of brine. The mixture was extracted with a mixture of ethyl acetate-petroleum ether (2:1) and the organic phase was dried over MgSO$_4$ and evaporated to dryness to give the product as a yellowish oil. (Yield: 0.44 g, 74%).

Step 2: 1-((4S)-4-(3,5-difluorophenyl)pyrrolidin-2-yl)-2-(methylsulfinyl)ethanone Hydrochloride

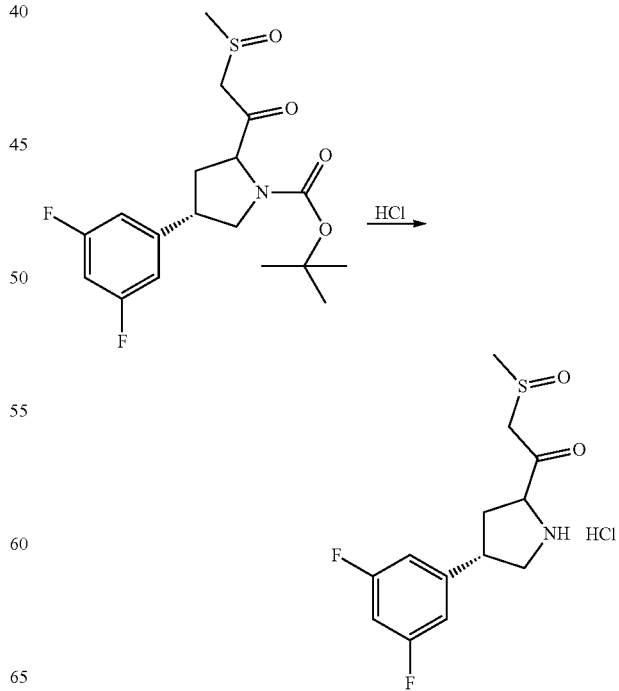

A stirred mixture of (4S)-tert-butyl 4-(3,5-difluorophenyl)-2-(2-(methylsulfinyl)acetyl)pyrrolidine-1-carboxylate (0.43 g, 1.110 mmol) and 4 M HCl (5.55 mL, 22.20 mmol) in dioxane was stirred at room temperature for 2 h. The mixture was then diluted with a mixture of diethyl ether-petroleum ether, aged for 30 min, the supernatant liquid was decanted from the separated oil which solidified on standing under high vacuum to give 1-((4S)-4-(3,5-difluorophenyl)pyrrolidin-2-yl)-2-(methylsulfinyl)ethanone hydrochloride. (Yield: 0.32 g, 89%).

Step 3: (S)-6-(3,5-difluorophenyl)-3-thioxo-3,5,6,7-tetrahydro-2H-pyrrolo[1,2-c]imidazole-1-carbaldehyde

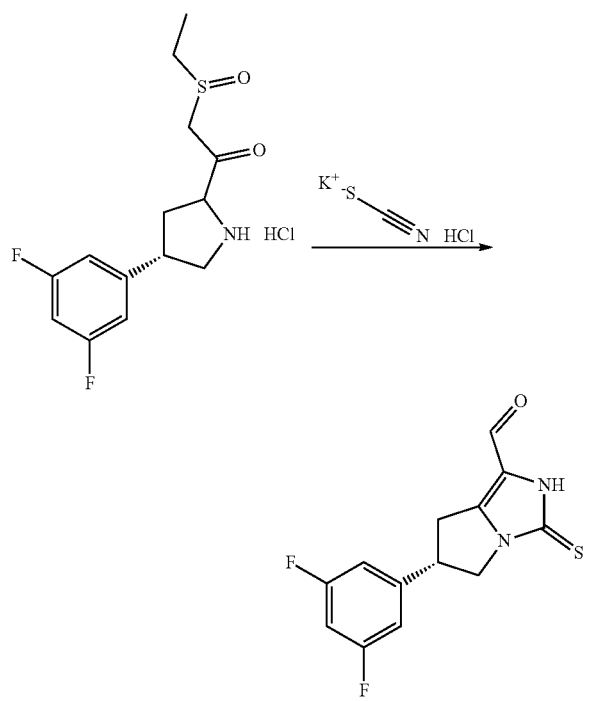

A solution of 1-((4S)-4-(3,5-difluorophenyl)pyrrolidin-2-yl)-2-(methylsulfinyl)ethanone hydrochloride (0.31 g, 0.957 mmol), 6 M HCl (0.080 ml, 0.479 mmol) and potassium thiocyanate (0.099 g, 1.019 mmol) in a mixture of ethanol (4 mL) and water (4 mL) was stirred under reflux for 30 min. Thereupon, the reaction was cooled to room temperature, diluted with water, the resultant solid was filtered off and the mother liqueur was extracted with dichloromethane. The organic phase was dried over $MgSO_4$, and evaporated to dryness. The residue was combined with the first precipitate and then recrystallised from ethyl acetate to give (S)-6-(3,5-difluorophenyl)-3-thioxo-3,5,6,7-tetrahydro-2H-pyrrolo[1,2-c]imidazole-1-carbaldehyde as a beige powder. (Yield: 0.035 g, 13%).

$^1$H NMR (DMSO$_{d6}$): 12.76 (1H, br s), 9.36 (1H, s), 7.18 (3H, m), 4.31 (1H, dd, J=8.4, 10.8 Hz), 4.26 (1H, q, J=8.4 Hz), 3.81 (1H, dd, J=10.8, 8.1 Hz), 3.63 (1H, dd, J=16.8, 8.0 Hz), 3.25 (1H, dd, J=16.8, 8.9 Hz).

$^{13}$C NMR (DMSO$_{d6}$): 175.9, 163.4, 163.3, 161.7, 161.6, 160.8, 145.8, 144.9, 144.8, 144.8, 121.2, 111, 111, 110.9, 110.8, 102.9, 102.8, 102.6, 51, 45.7, 31.4.

Example 46: (S)-1-(hydroxymethyl)-6-(2,3,5,6-tetrafluorophenyl)-6,7-dihydro-2H-pyrrolo[1,2-c]imidazole-3(5H)-thione

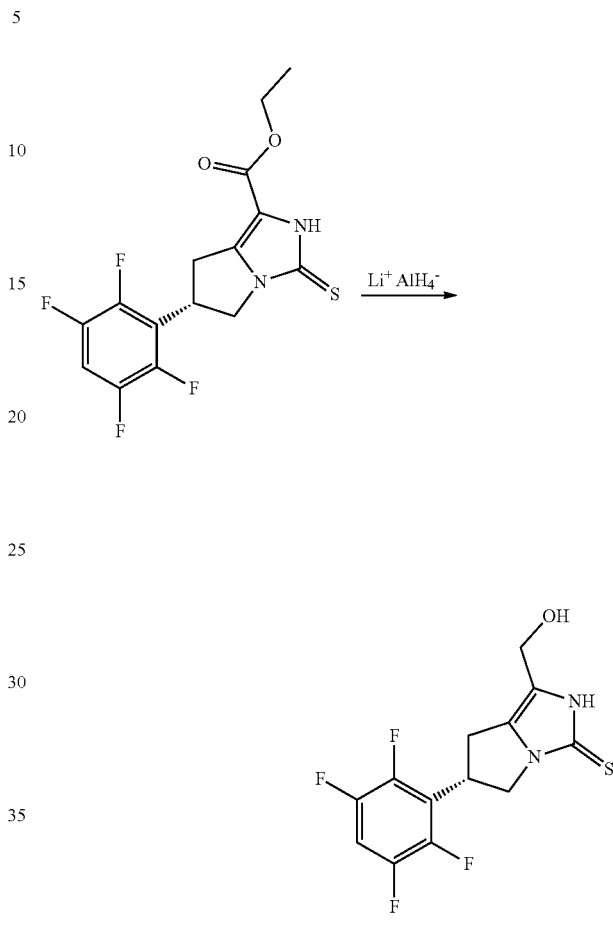

To a stirred solution of (S)-ethyl 6-(2,3,5,6-tetrafluorophenyl)-3-thioxo-3,5,6,7-tetrahydro-2H-pyrrolo[1,2-c]imidazole-1-carboxylate (analogous to Example 43, step 7) (0.08 g, 0.222 mmol) in dry diethyl ether (2 mL) and dry tetrahydrofuran (1 mL) was added dropwise 2.4 M suspension of lithium aluminumhydride (0.102 ml, 0.244 mmol) in tetrahydrofuran with external ice-water bath cooling. The reaction was stirred in the cold for 30 min, then quenched with 2 M HCl to pH=1-2. Thereupon, the mixture was diluted with dichloromethane (ca. 5 mL), the insoluble material was collected, washed with water and dichloromethane, respectively. The wet filter cake was dissolved in a mixture of ethanol and dichloromethane with heating, and then filtered. The filtrate was evaporated to dryness to give (S)-1-(hydroxymethyl)-6-(2,3,5,6-tetrafluorophenyl)-6,7-dihydro-2H-pyrrolo[1,2-c]imidazole-3(5H)-thione as an off-white solid. (Yield: 0.026 g, 36%).

$^1$H NMR (DMSO$_{d6}$): 11.85 (1H, br s), 7.86 (1H, m), 5.07 (1H, br t, J=5.1 Hz), 4.50 (1H, quin, J=8.5 Hz), 4.21 (2H, br d, J=4.7 Hz), 4.18 (1H, br dd, J=11.4, 9.4 Hz), 3.78 (1H, dd, J=11.6, 7.6 Hz), 3.33 (1H, m), 2.96 (1H, br dd, J=15.8, 8.0 Hz).

$^{13}$C NMR (DMSO$_{d6}$): 155.6, 146.4, 146.3, 146.3, 145.3, 145.2, 144.7, 143.7, 143.6, 128.8, 120.5, 120.4, 120.4, 120.3, 105.9, 105.7, 105.6, 53.1, 48.4, 35.7, 29.

Example 47: (S)-1-(methylsulfonylmethyl)-6-(2,3,5,6-tetrafluorophenyl)-6,7-dihydro-2H-pyrrolo[1,2-c]imidazole-3(5H)-thione

Step 1: (4S)-tert-butyl 2-(2-(methylsulfonyl)acetyl)-4-(2,3,5,6-tetrafluorophenyl)pyrrolidine-1-carboxylate

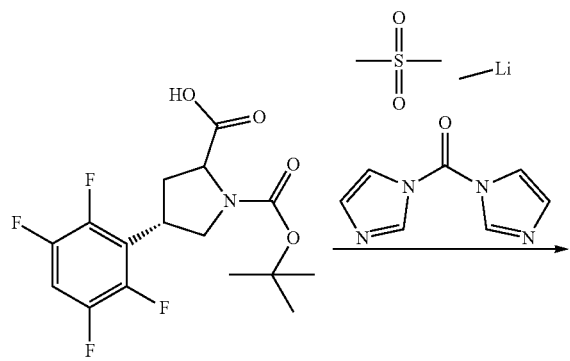

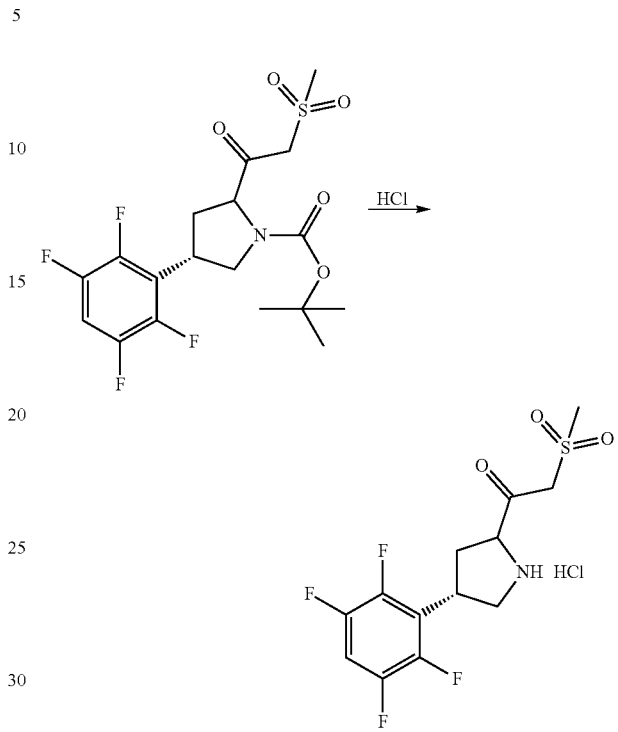

To a solution of (4S)-1-(tert-butoxycarbonyl)-4-(2,3,5,6-tetrafluorophenyl)pyrrolidine-2-carboxylic acid (0.5 g, 1.376 mmol) (analogous to Example 44, step 9) in dry tetrahydrofuran (5 mL) was added di(1H-imidazol-1-yl)methanone (0.223 g, 1.376 mmol) at room temperature and the mixture was stirred for 30 min. Thereupon, a solution of 1.6 M methyllithium (4.30 ml, 6.88 mmol) in diethyl ether was added to a solution of dimethyl sulfone (0.648 g, 6.88 mmol) in dry tetrahydrofuran (5 mL) at room temperature and the mixture was stirred for 15 min before addition of the previously prepared imidazolide solution with stirring and ice-water bath cooling. The mixture was stirred for 30 min in the cold, then quenched with 2 M HCl (3.44 ml, 6.88 mmol) and extracted with diethyl ether (ca. 15 mL). The organic phase was dried over MgSO₄) concentrated under reduced pressure and chromatographed (ethyl acetate-petroleum ether; 4:1, then 2:1) to give (4S)-tert-butyl 2-(2-(methylsulfonyl)acetyl)-4-(2,3,5,6-tetrafluorophenyl)pyrrolidine-1-carboxylate as a colourless oil. (Yield: 0.45 g, 74%).

Step 2: 2-(methylsulfonyl)-1-((4S)-4-(2,3,5,6-tetrafluorophenyl)pyrrolidin-2-yl)ethanone Hydrochloride To a stirred solution of (4S)-tert-butyl 2-(2-(methylsulfonyl)acetyl)-4-(2,3,5,6-tetrafluorophenyl)pyrrolidine-1-carboxylate (0.41 g, 0.933 mmol) in 4 M HCl (4.67 mL, 18.66 mmol) in dioxane was stirred at room temperature for 3 h. The mixture was then diluted with a mixture of diethyl ether (20 mL) and petroleum ether (5 mL), and aged for 30 min. The thus obtained precipitate was collected, washed with diethyl ether and petroleum ether, and then dried under vacuum at 50° C. to give 2-(methylsulfonyl)-1-((4S)-4-(2,3,5,6-tetrafluorophenyl)pyrrolidin-2-yl)ethanone hydrochloride as a white powder. (Yield: 0.28 g, 80%).

Step 3: (S)-1-((methylsulfonyl)methyl)-6-(2,3,5,6-tetrafluorophenyl)-6,7-dihydro-2H-pyrrolo[1,2-c]imidazole-3(5H)-thione

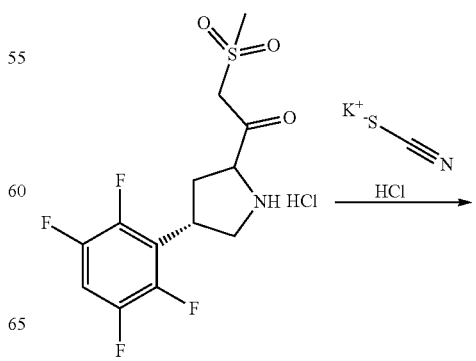

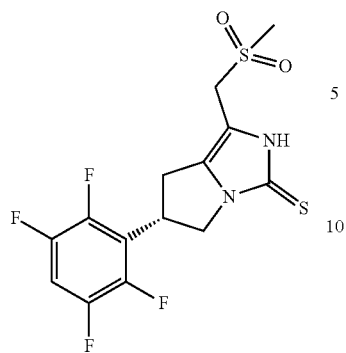

A solution of 2-(methylsulfonyl)-1-((4S)-4-(2,3,5,6-tetrafluorophenyl)pyrrolidin-2-yl)ethanone hydrochloride (0.27 g, 0.719 mmol), 6 M HCl (0.060 ml, 0.359 mmol) and potassium thiocyanate (0.077 g, 0.790 mmol) in a mixture of ethanol (4 mL) and water (4 mL) was stirred under reflux for 30 min. The mixture was then cooled to room temperature, the resulting solid was collected, washed with water and dried under vacuum at 50° C. to give (S)-1-(methylsulfonylmethyl)-6-(2,3,5,6-tetrafluorophenyl)-6,7-dihydro-2H-pyrrolo[1,2-c]imidazole-3(5H)-thione as a white powder. (Yield: 0.21 g, 77%).

$^1$H NMR (DMSO$_{d6}$): 12.08 (1H, s), 7.86 (1H, m), 4.57 (1H, quin, J=8.4 Hz), 4.30 (2H, m), 4.23 (1H, dd, J=11.6, 9.2 Hz), 3.83 (1H, dd, J=11.7, 7.5 Hz), 3.38 (1H, dd, J=16.3, 9.4 Hz), 2.99 (1H, dd, J=7.7, 16.4 Hz), 2.97 (3H, s).

$^{13}$C NMR (DMSO$_{d6}$): 156.6, 146.4, 146.3, 146.3, 145.2, 144.8, 144.7, 144.6, 143.6, 132.9, 120.5, 120.4, 120.3, 108, 105.9, 105.8, 105.6, 50.1, 49, 39.6, 35.6, 29.5.

Example 48: (5aS,6aR)-5a-(2,5-difluorophenyl)-1-phenethyl-5,5a,6,6a-tetrahydrocyclopropa[3,4]pyrrolo[1,2-c]imidazole-3(2H)-thione

Step 1 (1S,5R)-tert-butyl 1-(2,5-difluorophenyl)-4-(methoxy(methyl)carbamoyl)-3-azabicyclo[3.1.0]hexane-3-carboxylate

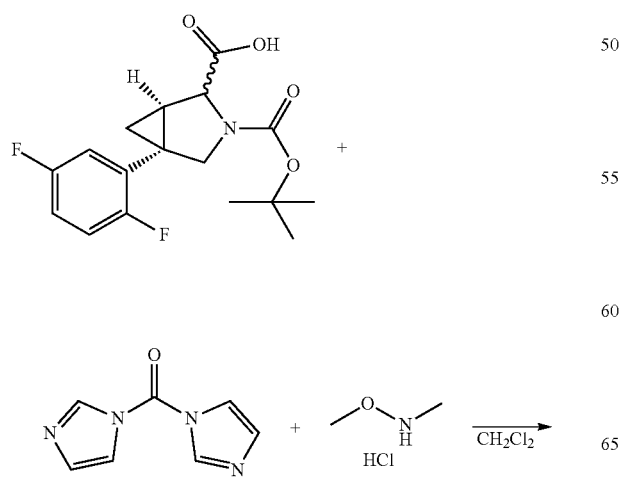

To a stirred solution of (1R,5S)-3-(tert-butoxycarbonyl)-5-(2,5-difluorophenyl)-3-azabicyclo[3.1.0]hexane-2-carboxylic acid (3 g, 8.84 mmol) (analogous to Example 44, step 9) in dry dichloromethane (30 mL) was added 1,1'-carbonyldiimidazole (1.720 g, 10.61 mmol) in portions at room temperature under nitrogen and the mixture was stirred for 1 h. Thereupon, N,O-dimethylhydroxylamine hydrochloride (1.035 g, 10.61 mmol) was added in one portion and the resulting suspension was stirred overnight. The mixture was then washed with water, the organic phase was dried over MgSO$_4$, filtered and evaporated to dryness. The thus obtained light yellow oil was purified by chromatography (petroleum ether-ethyl acetate; 4:1, then 2:1). The product was isolated as a light yellow foam. (Yield: 2.21 g, 59%).

Step 2 (1S,5R)-tert-butyl 1-(2,5-difluorophenyl)-4-(3-phenylpropanoyl)-3-azabicyclo[3.1.0]hexane-3-carboxylate

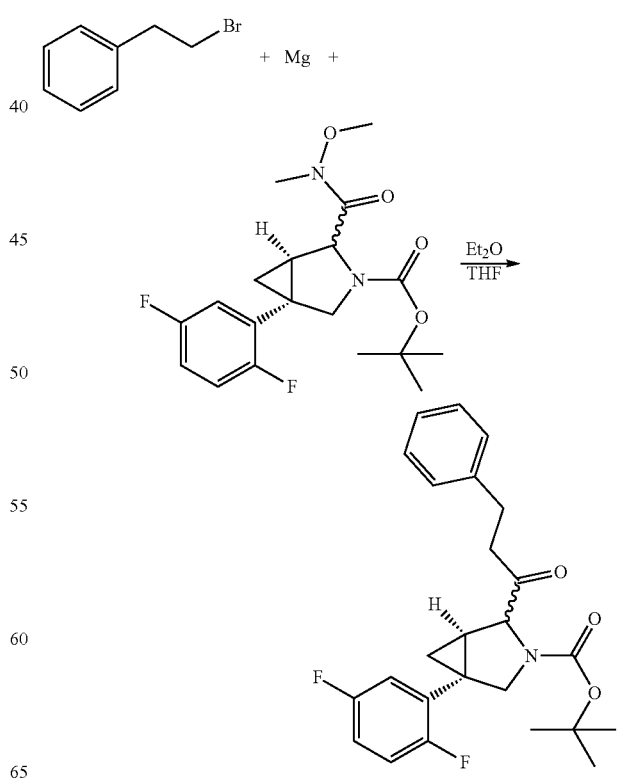

To a stirred ice-cooled mixture of phenethylmagnesium bromide in dry diethyl ether (8 mL) (prepared from (2-Bromoethyl)benzene (0.446 ml, 3.27 mmol) and magnesium turnings (0.165 g, 6.80 mmol)) was added a solution of (1S,5R)-tert-butyl 1-(2,5-difluorophenyl)-4-(methoxy(methyl)carbamoyl)-3-azabicyclo[3.1.0]hexane-3-carboxylate (1 g, 2.62 mmol) in dry tetrahydrofuran (5 mL) dropwise below 10° C. The reaction mixture was stirred at room temperature for 24 h. The mixture was then cooled to 0° C. and 2 M HCl was added carefully.

The phases were separated and organic phase was dried over MgSO₄, filtered and evaporated to dryness. The resulting light yellow oil purified by chromatography (petroleum ether-ethyl acetate; 9:1, 4:1, then 2:1). (Yield: 0.34 g, 30%).

Step 3 1-((1R,5S)-5-(2,5-difluorophenyl)-3-azabicyclo[3.1.0]hexan-2-yl)-3-phenylpropan-1-one Hydrochloride Step 4 (5aS,6aR)-5a-(2,5-difluorophenyl)-1-phenethyl-5,5a,6,6a-tetrahydrocyclopropa[3,4]pyrrolo[1,2-c]imidazole-3(2H)-thione

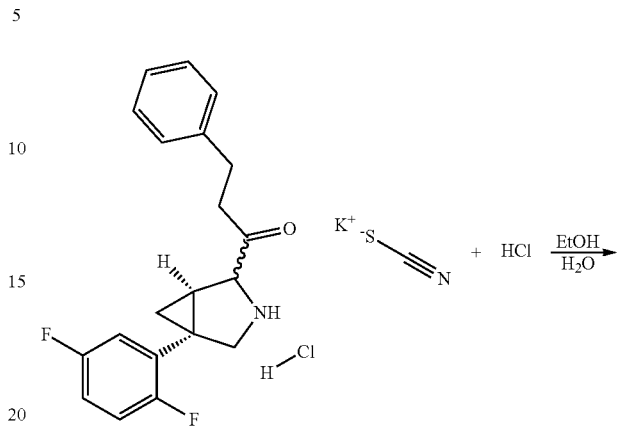

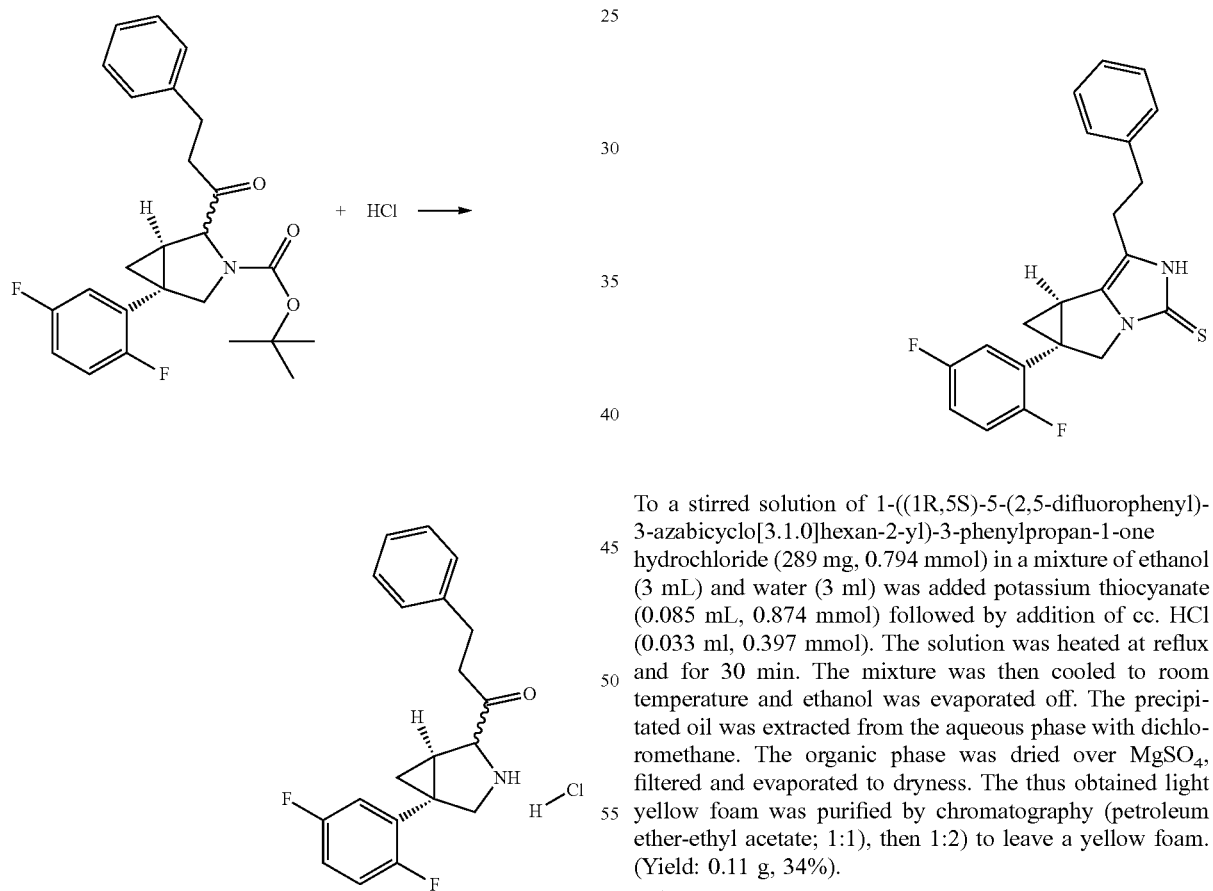

A solution of (1S,5R)-tert-butyl 1-(2,5-difluorophenyl)-4-(3-phenylpropanoyl)-3-azabicyclo[3.1.0]hexane-3-carboxylate (340 mg, 0.795 mmol) in 4 M HCl in dioxane (1.59 mL, 6.36 mmol) was stirred at room temperature for 2 h. The solvent was evaporated off and the thus obtained oil was used without purification. (Yield: 0.289 g, 100%).

To a stirred solution of 1-((1R,5S)-5-(2,5-difluorophenyl)-3-azabicyclo[3.1.0]hexan-2-yl)-3-phenylpropan-1-one hydrochloride (289 mg, 0.794 mmol) in a mixture of ethanol (3 mL) and water (3 ml) was added potassium thiocyanate (0.085 mL, 0.874 mmol) followed by addition of cc. HCl (0.033 ml, 0.397 mmol). The solution was heated at reflux and for 30 min. The mixture was then cooled to room temperature and ethanol was evaporated off. The precipitated oil was extracted from the aqueous phase with dichloromethane. The organic phase was dried over MgSO₄, filtered and evaporated to dryness. The thus obtained light yellow foam was purified by chromatography (petroleum ether-ethyl acetate; 1:1), then 1:2) to leave a yellow foam. (Yield: 0.11 g, 34%).

$^1$H NMR (DMSO$_{d6}$): 11.78 (1H, s), 7.29 (3H, m), 7.20 (5H, m), 4.03 (1H, d, J=12.2 Hz), 3.76 (1H, d, J=12.2 Hz), 2.88 (2H, m), 2.70 (3H, m), 1.53 (1H, dd, J=8.2, 5.3 Hz), 0.96 (1H, t, J=4.8 Hz).

$^{13}$C NMR (DMSO$_{d6}$): 158.8, 158.8, 158.6, 158.6, 157.2, 157, 157, 155.7, 140.8, 130.5, 128.8, 128.7, 128.6, 128.6, 128.5, 128.4, 128.3, 128.3, 128.2, 128.2, 126, 118.7, 117.2, 117.1, 117, 117, 116.8, 116.8, 116.7, 116.7, 115.9, 115.8, 115.7, 115.7, 51.3, 51.3, 33.9, 32.4, 25.9, 22.4, 20.5.

Example 49: (5aS,6aR)-5a-(2,5-difluorophenyl)-1-(3-phenylpropyl)-5,5a,6,6a-tetrahydrocyclopropa[3,4]pyrrolo[1,2-c]imidazole-3(2H)-thione

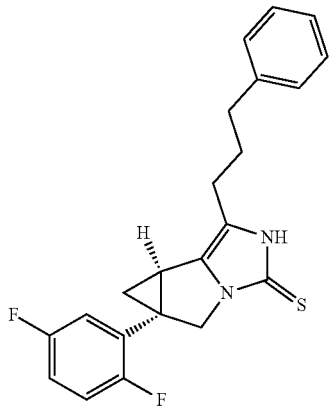 [SMILES: Fc1ccc(F)c([C@]23C[C@H]2c2c(CCCc4ccccc4)[nH]c(=S)n2C3)c1]

Compound was prepared analogous manner to Example 48 from (1S,5R)-tert-butyl 1-(2,5-difluorophenyl)-4-(methoxy(methyl)carbamoyl)-3-azabicyclo[3.1.0]hexane-3-carboxylate and (3-phenylpropyl)magnesium bromide. The product was isolated as a yellow foam.

$^1$H NMR (DMSO$_{d6}$): 11.71 (1H, s), 7.28 (3H, br t, J=6.9 Hz), 7.24-7.14 (4H, m), 4.07 (1H, br d, J=11.9 Hz), 3.79 (1H, d, J=12.0 Hz), 2.85 (1H, dd, J=8.1, 4.2 Hz), 2.61 (2H, br t, J=7.6 Hz), 2.42 (2H, m), 1.91 (2H, m), 1.64 (1H, dd, J=8.1, 5.4 Hz), 1.17 (1H, br t, J=4.7 Hz).

$^{13}$C NMR (DMSO$_{d6}$): 158.8, 158.7, 158.7, 157.2, 157.1, 157.1, 155.8, 141.5, 130.2, 128.8, 128.8, 128.7, 128.7, 128.4, 128.3, 125.8, 119.1, 117.2, 117.1, 117, 116.9, 116.9, 116.8, 116.7, 115.9, 115.8, 115.7, 115.6, 51.3, 51.3, 34.4, 32.5, 29.2, 23.6, 22.5, 20.6.

Example 50: (5aS,6aR)-5a-(3,5-difluorophenyl)-1-(hydroxymethyl)-5,5a,6,6a-tetrahydrocyclopropa[3,4]pyrrolo[1,2-c]imidazole-3(2H)-thione

Step 1 (1S,5R)-tert-butyl 4-(cyano(hydroxy)methyl)-1-(3,5-difluorophenyl)-3-azabicyclo[3.1.0]hexane-3-carboxylate

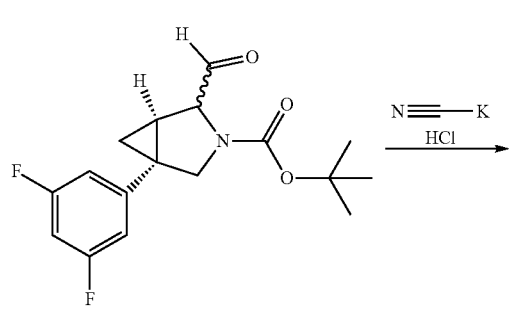

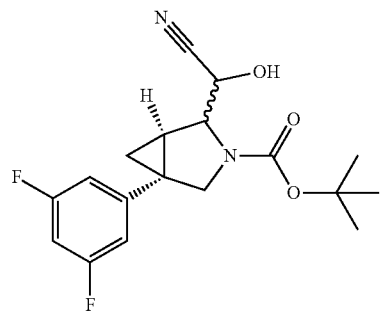

To a stirred solution of (1S,5R)-tert-butyl 1-(3,5-difluorophenyl)-4-formyl-3-azabicyclo[3.1.0]hexane-3-carboxylate (0.500 g, 1.546 mmol) (analogous to Example 39 step 8) in a mixture of tetrahydrofuran (3.4 mL) and water (1.72 mL) was added potassium cyanide (0.121 g, 1.856 mmol) followed by the addition of cc. HCl (0.127 mL, 1.546 mmol). The reaction was stirred at room temperature overnight. The mixture was then extracted with dichloromethane, washed with brine, dried over MgSO$_4$, filtered and concentrated under reduced pressure to give the product as a yellow oil. (Yield: 0.554 g, 87%).

Step 2 (1S,5R)-tert-butyl 1-(3,5-difluorophenyl)-4-(2-ethoxy-1-hydroxy-2-oxoethyl)-3-azabicyclo[3.1.0]hexane-3-carboxylate

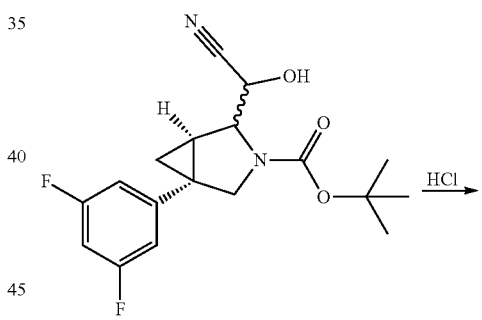

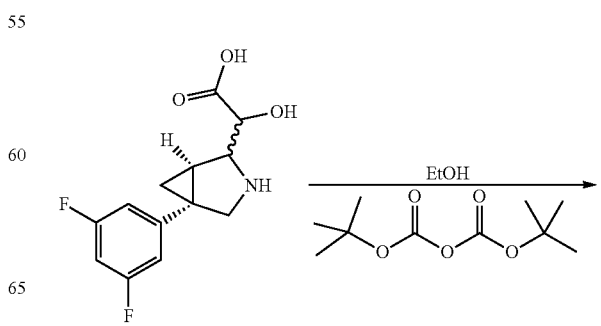

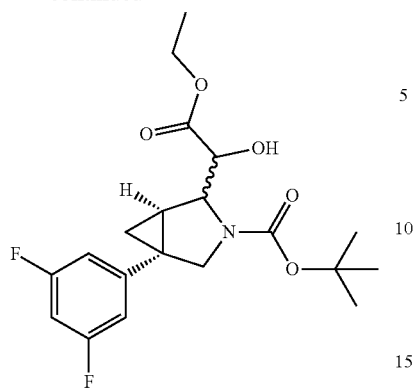

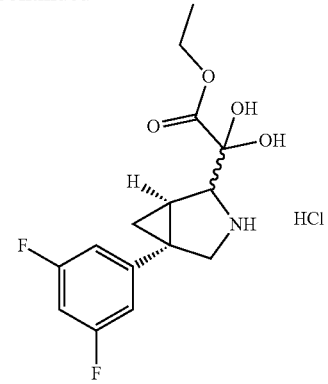

A solution of (1S)-tert-butyl 4-(cyano(hydroxy)methyl)-1-(3,5-difluorophenyl)-3-azabicyclo[3.1.0]hexane-3-carboxylate (0,554 g, 1,581 mmol) in 2 M HCl (11.86 mL, 23.72 mmol) was refluxed for 20 h. The mixture was then cooled to room temperature and precipitated brown solid was removed by filtration. The filtrate was evaporated to dryness, and then azeotroped twice with ethanol. The thus obtained residue was dissolved in ethanol (9 mL), and then treated with 4 M HCl in dioxane (3.95 mL, 15.81 mmol). The reaction mixture was refluxed for 2 h, whereupon cooled to room temperature and evaporated twice with ethanol. The resulting residue was dissolved in ethanol (11 mL), neutralized to pH=6-7 by addition of triethylamine (0.22 mL, 1,581 mmol) followed by addition of di-tert-butyl dicarbonate (0,345 g, 1,581 mmol). The reaction was stirred at room temperature overnight. Thereupon, the mixture was concentrated under reduced pressure (water bath <40° C.). The residue was quenched with water and extracted with dichloromethane. The organic phase was dried over MgSO$_4$, filtrated and concentrated. The crude material was purified by chromatography (8% ethyl acetate in petroleum Ether). The product was isolated as a pale yellow oil. (Yield: 0.21 g, 33%).

Step 3 Ethyl 2-((1R,5S)-5-(3,5-difluorophenyl)-3-azabicyclo[3.1.0]hexan-2-yl)-2,2-dihydroxyacetate Hydrochloride To a stirred solution of (1S)-tert-butyl 1-(3,5-difluorophenyl)-4-(2-ethoxy-1-hydroxy-2-oxoethyl)-3-azabicyclo [3.1.0]hexane-3-carboxylate (0,210 g, 0,528 mmol) in dichloromethane (5.3 mL) was added Dess-Martin periodinane (3-oxo-1l-benzo[d][1,2]iodaoxole-1,1,1(3H)-triyl triacetate) (0,224 g, 0,528 mmol) at room temperature. The reaction was stirred at room temperature for 4 h. The solvent was then removed under reduced pressure to give a light pink pastel. Chromatography (dichloromethane-methanol-aq. Ammonia) gave the product as a pale yellow oil. (Yield: 142 g, 68%).

Step 4 ethyl 2-((1R,5S)-5-(3,5-difluorophenyl)-3-azabicyclo[3.1.0]hexan-2-yl)-2,2-dihydroxyacetate hydrochloride

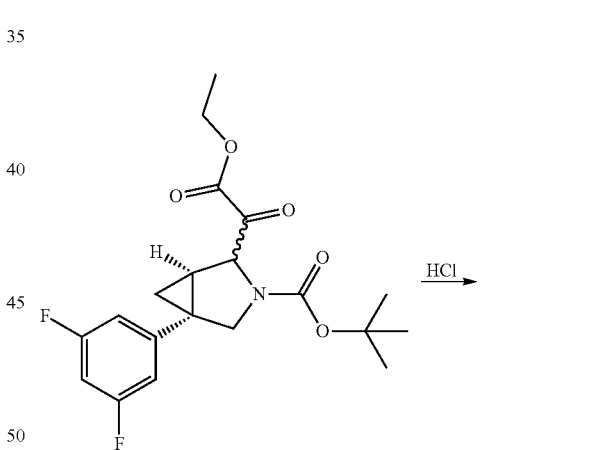

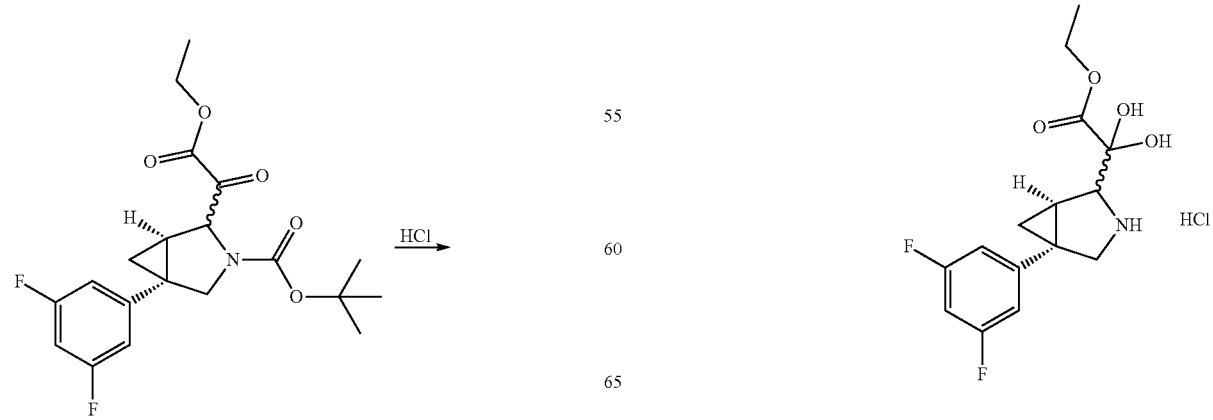

A solution of (1S)-tert-butyl 1-(3,5-difluorophenyl)-4-(2-ethoxy-2-oxoacetyl)-3-azabicyclo[3.1.0]hexane-3-carboxylate (0,142 g, 0,359 mmol) in 4 M HCl in dioxane (1,796 mL, 7.18 mmol) was stirred at room temperature for 2.5 h. The mixture was then diluted with a mixture of diethyl Ether (4 mL) and petroleum ether (1 mL), stirred for 30 min, whereupon the volatiles were evaporated off to give the product as a brown oil. (Yield: 0.126 g, 100%).

Step 5 (5aS,6aR)-ethyl 5a-(3,5-difluorophenyl)-3-thioxo-2,3,5,5a,6,6a-hexahydrocyclopropa[3,4]pyrrolo[1,2-c]imidazole-1-carboxylate

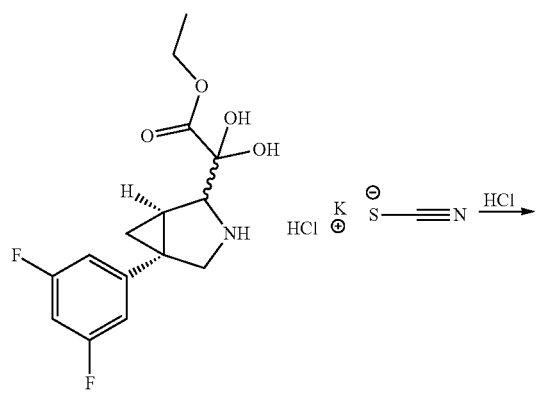

To a stirred solution of ethyl 2-((5S)-5-(3,5-difluorophenyl)-3-azabicyclo[3.1.0]hexan-2-yl)-2,2-dihydroxyacetate hydrochloride (0,126 g, 0,360 mmol) in a mixture of ethanol (1.5 mL) and water (1.5 mL) was added cc. HCl (0.03 mL, 0,180 mmol) and potassium thiocyanate (0,039 g, 0,396 mmol) at room temperature. The reaction mixture was refluxed for 30 min, and then cooled to room temperature. The stirring was continued overnight, and then the resultant off-white precipitate was filtered off, washed with cold water and dried under vacuum. (Yield: 0.79 mg, 65%).

Step 6 (5aS,6aR)-5a-(3,5-difluorophenyl)-1-(hydroxymethyl)-5,5a,6,6a-tetrahydrocyclopropa[3,4]pyrrolo[1,2-c]imidazole-3(2H)-thione

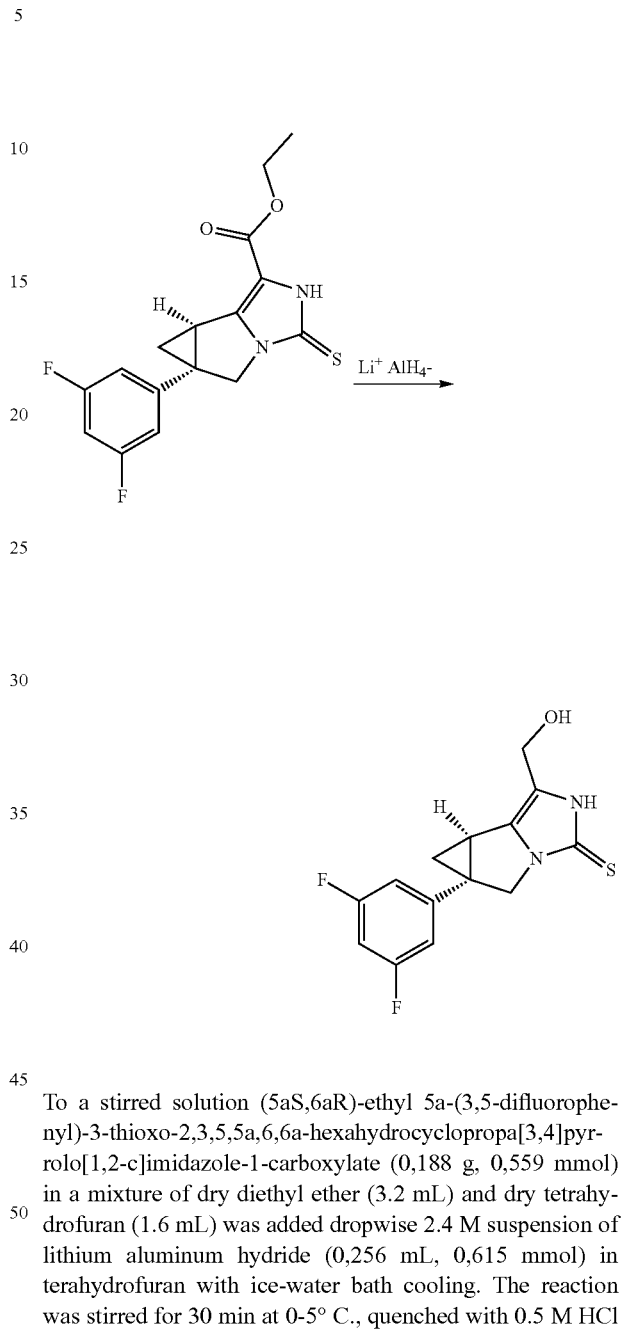

To a stirred solution (5aS,6aR)-ethyl 5a-(3,5-difluorophenyl)-3-thioxo-2,3,5,5a,6,6a-hexahydrocyclopropa[3,4]pyrrolo[1,2-c]imidazole-1-carboxylate (0,188 g, 0,559 mmol) in a mixture of dry diethyl ether (3.2 mL) and dry tetrahydrofuran (1.6 mL) was added dropwise 2.4 M suspension of lithium aluminum hydride (0,256 mL, 0,615 mmol) in terahydrofuran with ice-water bath cooling. The reaction was stirred for 30 min at 0-5° C., quenched with 0.5 M HCl to pH=1-2 (ca. 5 mL), and then diluted with diethyl ether (ca. 10 mL). The resulting solid was collected, washed with water and dried under vacuum at 50° C. to give a light yellow powder. (Yield: 0.038 g, 22%).

$^1$H NMR (DMSO$_{d6}$): 1.75 (1H, br s), 7.11 (3H, m), 5.10 (1H, br s), 4.25 (2H, m), 4.20 (1H, d, J=12.2 Hz), 4.03 (1H, d, J=12.0 Hz), 3.02 (1H, dd, J=8.3, 4.3 Hz), 1.69 (1H, dd, J=8.4, 5.3 Hz), 1.17 (1H, t, J=4.8 Hz).

$^{13}$C NMR (DMSO$_{d6}$): 163.4, 163.3, 161.8, 161.7, 156.7, 144.9, 144.8, 144.8, 131.4, 119.8, 110, 110, 109.9, 109.8, 102.3, 102.1, 101.9, 53.1, 50.7, 36.3, 25.4, 22.9.

Example 51: 2-((5aS,6aR)-5a-(3-bromo-2,6-difluorophenyl)-3-thioxo-2,3,5,5a,6,6a-hexahydrocyclopropa[3,4]pyrrolo[1,2-c]imidazol-1-yl)acetic Acid

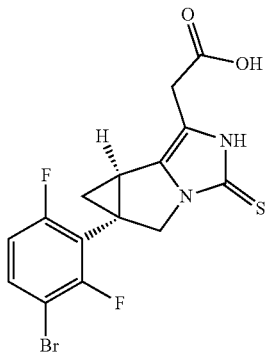 [SMILES: O=C(O)Cc1[nH]c(=S)n2c1[C@@H]1C[C@]1(c1c(F)ccc(Br)c1F)C2]

Compound was prepared analogous manner to Example 2 from (1R,5S)-3-(tert-butoxycarbonyl)-5-(3-bromo-2,6-difluorophenyl)-3-azabicyclo[3.1.0]hexane-2-carboxylic acid. The product was isolated as a yellow solid.

$^1$H NMR (DMSO$_{d6}$): 12.63 (1H, br s), 11.72 (1H, br s), 7.75 (1H, td, J=8.5, 5.8 Hz), 7.16 (1H, td, J=9.2, 1.0 Hz), 4.04 (1H, d, J=12.2 Hz), 3.74 (1H, br d, J=12.0 Hz), 3.49 (2H, m), 2.77 (1H, dd, J=8.4, 4.3 Hz), 1.67 (1H, dd, J=8.4, 5.4 Hz), 1.24 (1H, t, J=5.0 Hz).

$^{13}$C NMR (DMSO$_{d6}$): 170.8, 161.9, 161.9, 160.2, 160.2, 158.8, 158.8, 158.8, 157.2, 157.1, 133.1, 133, 131.9, 117.1, 117, 116.9, 113.5, 113.5, 113.4, 113.3, 103.7, 103.7, 103.6, 103.6, 51.5, 29.9, 26.5, 21.8, 21.2.

Example 52: 2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)acetic Acid

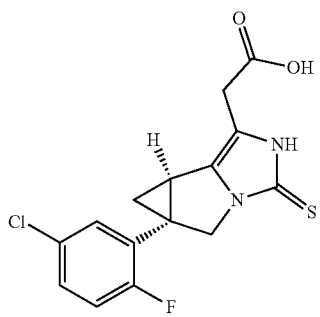 [SMILES: O=C(O)Cc1[nH]c(=S)n2c1[C@@H]1C[C@]1(c1cc(Cl)ccc1F)C2]

Compound was prepared analogous manner to Example 2 from (1R,5S)-3-(tert-butoxycarbonyl)-5-(5-chloro-2-fluorophenyl)-3-azabicyclo[3.1.0]hexane-2-carboxylic acid. The product was isolated as a light yellow solid.

$^1$H NMR (DMSO$_{d6}$): 12.60 (1H, br s), 11.70 (1H, s), 7.45 (1H, dd, J=6.5, 2.5 Hz), 7.42 (1H, ddd, J=8.6, 4.3, 2.8 Hz), 7.30 (1H, t, J=9.4 Hz), 4.09 (1H, br d, J=12.0 Hz), 3.80 (1H, d, J=12.0 Hz), 3.47 (2H, m), 2.88 (1H, dd, J=8.2, 4.1 Hz), 1.67 (1H, dd, J=8.2, 5.4 Hz), 1.12 (1H, t, J=4.8 Hz).

$^{13}$C NMR (DMSO$_{d6}$): 170.8, 161.3, 159.6, 156.1, 132.1, 130.1, 130.1, 129.4, 129.3, 128.9, 128.8, 128.3, 128.3, 117.6, 117.4, 113, 51.6, 32.4, 29.9, 22.2, 20.6.

Example 53: 2-((5aS,6aR)-5a-(3-chloro-5-fluorophenyl)-3-thioxo-2,3,5,5a,6,6a-hexahydrocyclopropa[3,4]pyrrolo[1,2-c]imidazol-1-yl)acetic Acid

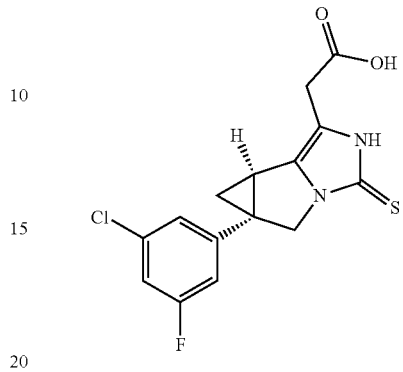

Compound was prepared analogous manner to Example 2 from (1R,5S)-3-(tert-butoxycarbonyl)-5-(3-chloro-5-fluorophenyl)-3-azabicyclo[3.1.0]hexane-2-carboxylic acid. The product was isolated as a light yellow solid.

$^1$H NMR (DMSO$_{d6}$): 12.60 (1H, br s), 11.68 (1H, s), 7.31 (1H, dt, J=8.7, 2.0 Hz), 7.27 (1H, t, J=1.5 Hz), 7.22 (1H, dt, J=9.9, 1.9 Hz), 4.21 (1H, d, J=12.0 Hz), 4.03 (1H, d, J=12.2 Hz), 3.45 (2H, m), 3.00 (1H, dd, J=8.4, 4.3 Hz), 1.69 (1H, dd, J=8.2, 5.3 Hz), 1.14 (1H, t, J=4.8 Hz).

$^{13}$C NMR (DMSO$_{d6}$): 170.7, 163.1, 161.5, 156.3, 144.8, 144.7, 134.2, 134.1, 132, 123, 122.9, 114.3, 114.2, 112.9, 112.8, 112.8, 50.8, 36.1, 36.1, 29.9, 25.1, 22.6.

Example 54: Ethyl 2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)acetate

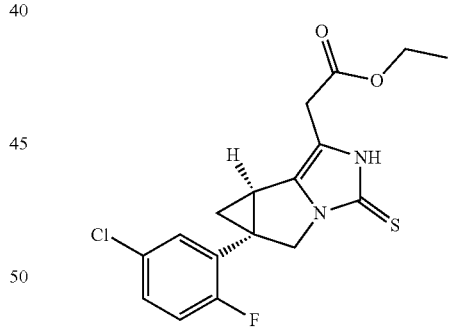

Compound was prepared analogous manner to Example 2 from (1R,5S)-3-(tert-butoxycarbonyl)-5-(5-chloro-2-fluorophenyl)-3-azabicyclo[3.1.0]hexane-2-carboxylic acid. The product was isolated as an off-white foam.

$^1$H NMR (DMSO$_{d6}$): 1.73 (1H, s), 7.46 (1H, dd, J=6.5, 2.6 Hz), 7.43 (1H, ddd, J=8.6, 4.3, 2.8 Hz), 7.30 (1H, t, J=9.4 Hz), 4.11 (2H, q, J=7.1 Hz), 4.09 (1H, d, J=12.2 Hz), 3.81 (1H, d, J=12.2 Hz), 3.57 (2H, m), 2.87 (1H, dd, J=8.3, 4.2 Hz), 1.68 (1H, dd, J=8.4, 5.4 Hz), 1.21 (3H, t, J=7.1 Hz), 1.13 (1H, t, J=4.8 Hz).

$^{13}$C NMR (DMSO$_{d6}$): 169.2, 161.3, 159.6, 156.2, 132.3, 130.2, 130.1, 129.4, 129.3, 128.8, 128.7, 128.3, 128.3, 117.6, 117.4, 112.3, 60.7, 51.6, 51.6, 32.4, 29.8, 22.1, 20.6, 14.1.

Example 55: Ethyl 2-((5aS,6aR)-5a-(3-chloro-5-fluorophenyl)-3-thioxo-2,3,5,5a,6,6a-hexahydrocyclopropa[3,4]pyrrolo[1,2-c]imidazol-1-yl)acetate

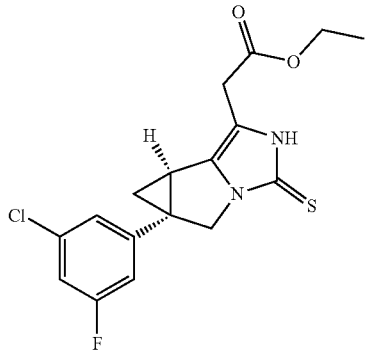 [SMILES: CCOC(=O)Cc1[nH]c(=S)n2c1[C@@H]1C[C@]1(c1cc(F)cc(Cl)c1)C2]

Compound was prepared analogous manner to Example 2 from (1R,5S)-3-(tert-butoxycarbonyl)-5-(3-chloro-5-fluorophenyl)-3-azabicyclo[3.1.0]hexane-2-carboxylic acid. The product was isolated as a white solid.

$^1$H NMR (DMSO$_{d6}$): 1.72 (1H, s), 7.32 (1H, dt, J=8.7, 2.0 Hz), 7.28 (1H, t, J=1.5 Hz), 7.23 (1H, dt, J=9.9, 2.0 Hz), 4.21 (1H, d, J=12.2 Hz), 4.11 (2H, q, J=7.0 Hz), 4.04 (1H, d, J=12.2 Hz), 3.54 (2H, m), 2.99 (1H, dd, J=8.4, 4.4 Hz), 1.70 (1H, dd, J=8.4, 5.3 Hz), 1.21 (3H, t, J=7.0 Hz), 1.15 (1H, t, J=4.8 Hz).

$^{13}$C NMR (DMSO$_{d6}$): 169.2, 163.1, 161.5, 156.4, 144.7, 144.7, 134.2, 134.1, 132.3, 123, 123, 114.4, 114.2, 112.9, 112.8, 112.1, 60.7, 50.9, 36.1, 36.1, 29.8, 25, 22.7, 14.1.

Example 56: (2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)acetamide

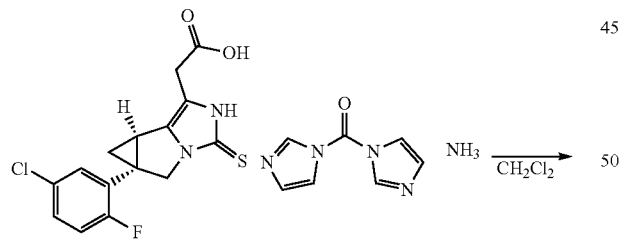

To a stirred solution of 2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)acetic acid (Example 52) (630 mg, 1.860 mmol) in anhydrous dichloromethane (11 mL) was added 1,1'-Carbonyldiimidazole (362 mg, 2.232 mmol) and the reaction was stirred for 30 min. at room temperature. Thereupon, ammonia (0.53 mL, 3.72 mL) 7 M in methanol was added and the mixture was stirred for 3 h at room temperature. The solvent was then evaporated and the obtained brown oil was separated by column chromatography (dichloromethane-methanol). Trituration in a mixture of dichloromethane-diethyl ether-petroleum ether afforded the titled product as a dark yellow solid.

$^1$H NMR (DMSO$_{d6}$): 11.64 (1H, s), 7.46 (1H, dd, J=6.6, 2.6 Hz), 7.43 (1H, ddd, J=8.7, 4.3, 2.7 Hz), 7.37 (1H, br s), 7.30 (1H, t, J=9.5 Hz), 7.03 (1H, m), 4.07 (1H, d, J=12.0 Hz), 3.79 (1H, d, J=12.0 Hz), 3.27 (2H, m), 2.85 (1H, dd, J=8.4, 4.3 Hz), 1.64 (1H, dd, J=8.4, 5.3 Hz), 1.17 (1H, t, J=4.8 Hz).

$^{13}$C NMR (DMSO$_{d6}$): 169.9, 161.2, 159.6, 155.9, 131.8, 130.1, 130.1, 129.3, 129.3, 129, 128.9, 128.3, 128.3, 117.6, 117.4, 114, 51.6, 32.3, 31.2, 22.1, 20.7.

Example 57: 2-((5aS,6aR)-5a-(3-bromo-2,6-difluorophenyl)-3-thioxo-2,3,5,5a,6,6a-hexahydrocyclopropa[3,4]pyrrolo[1,2-c]imidazol-1-yl)acetamide

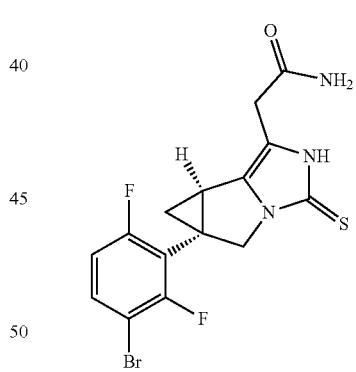

Compound was prepared analogous manner to Example 56 from 2-((5aS,6aR)-5a-(3-bromo-2,6-difluorophenyl)-3-thioxo-2,3,5,5a,6,6a-hexahydrocyclopropa[3,4]pyrrolo[1,2-c]imidazol-1-yl)acetic acid (Example 51). The product was isolated as a yellow solid.

$^1$H NMR (DMSO$_{d6}$): 1.67 (1H, m), 7.74 (1H, td, J=8.4, 5.9 Hz), 7.39 (1H, br s), 7.15 (1H, td, J=9.2, 1.2 Hz), 7.04 (1H, br s), 4.02 (1H, d, J=12.2 Hz), 3.72 (1H, d, J=12.2 Hz), 3.29 (2H, m), 2.74 (1H, dd, J=8.4, 4.4 Hz), 1.64 (1H, dd, J=8.2, 5.4 Hz), 1.28 (1H, br t, J=4.9 Hz).

$^{13}$C NMR (DMSO$_{d6}$): 169.9, 161.9, 161.9, 160.2, 160.2, 158.8, 158.8, 157.2, 157.1, 155.8, 133, 133, 131.5, 117.2, 117.1, 117, 114.4, 113.5, 113.5, 113.4, 113.3, 103.7, 103.7, 103.6, 103.6, 51.4, 31.2, 26.4, 21.7, 21.3.

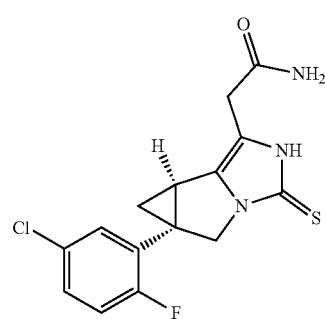

Example 58: 2-((5aS,6aR)-5a-(3-chloro-5-fluorophenyl)-3-thioxo-2,3,5,5a,6,6a-hexahydrocyclopropa[3,4]pyrrolo[1,2-c]imidazol-1-yl)acetamide

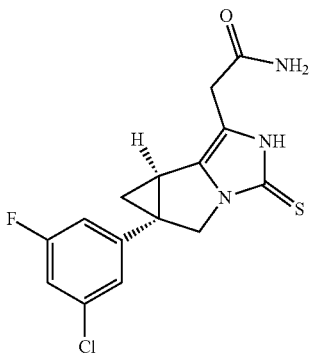 [SMILES: NC(=O)Cc1[nH]c(=S)n2c1[C@@H]1C[C@]1(c1cc(F)cc(Cl)c1)C2]

Compound was prepared analogous manner to Example 56 from 2-((5aS,6aR)-5a-(3-chloro-5-fluorophenyl)-3-thioxo-2,3,5,5a,6,6a-hexahydrocyclopropa[3,4]pyrrolo[1,2-c]imidazol-1-yl)acetic acid (Example 53). The product was isolated as a beige solid.

$^1$H NMR (DMSO$_{d6}$): 1.62 (1H, s), 7.35 (1H, br s), 7.31 (1H, dt, J=8.7, 2.1 Hz), 7.28 (1H, t, J=1.6 Hz), 7.23 (1H, dt, J=10.0, 1.9 Hz), 7.05 (1H, br s), 4.19 (1H, d, J=12.0 Hz), 4.01 (1H, d, J=12.0 Hz), 3.25 (2H, m), 2.95 (1H, dd, J=8.4, 4.3 Hz), 1.67 (1H, dd, J=8.4, 5.3 Hz), 1.19 (1H, t, J=4.8 Hz).

$^{13}$C NMR (DMSO$_{d6}$): 169.9, 163.1, 161.5, 156.1, 144.9, 144.9, 134.2, 134.1, 131.9, 123, 123, 114.3, 114.1, 113.7, 112.9, 112.8, 50.9, 36.1, 36.1, 31.2, 24.9, 22.8

Example 59: ethyl (S)-2-(6-(3-bromo-2,6-difluorophenyl)-3-thioxo-2,5,6,7-tetrahydro-3H-pyrrolo[1,2-c]imidazol-1-yl)acetate

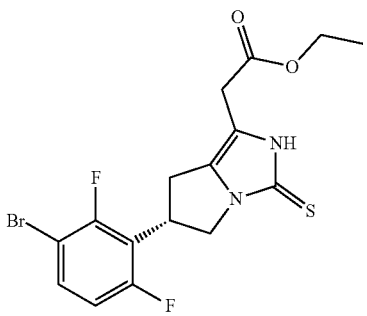 [SMILES: CCOC(=O)Cc1[nH]c(=S)n2c1C[C@@H](c1c(F)ccc(Br)c1F)C2]

Compound was prepared analogous manner to Example 2 from (4S)-1-(tert-butoxycarbonyl)-4-(3-bromo-2,6-difluorophenyl)pyrrolidine-2-carboxylic acid and isolated as a yellow solid.

$^1$H NMR (DMSO$_{d6}$): 11.81 (1H, s), 7.72 (1H, ddd, J=5.8, 8.1, 8.8 Hz), 7.16 (1H, dt, J=1.4, 9.4 Hz), 4.47 (1H, quin, J=8.5 Hz), 4.17 (1H, dd, J=11.2, 9.5 Hz), 4.09 (2H, q, J=7.1 Hz), 3.73 (1H, dd, J=11.6, 7.8 Hz), 3.50 (2H, s), 3.27 (1H, dd, J=15.8, 9.4 Hz), 2.86 (1H, dd, J=15.8, 7.9 Hz), 1.19 (3H, t, J=7.1 Hz).

$^{13}$C NMR (DMSO$_{d6}$): 169.1, 160.8, 160.8, 159.2, 159.1, 157.6, 157.5, 155.9, 155.9, 155.4, 132.5, 132.4, 129.9, 118.9, 118.7, 118.6, 113.8, 113.8, 113.6, 113.6, 112.6, 104.1, 104.1, 103.9, 103.9, 60.7, 48.7, 35.6, 29.8, 29.3, 14.1.

Example 60: Ethyl (R)-2-(6-(3-bromo-2,6-difluorophenyl)-3-thioxo-2,5,6,7-tetrahydro-3H-pyrrolo[1,2-c]imidazol-1-yl)acetate

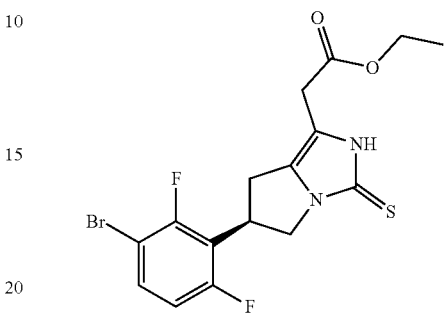

Compound was prepared analogous manner to Example 2 from (4R)-1-(tert-butoxycarbonyl)-4-(3-bromo-2,6-difluorophenyl)pyrrolidine-2-carboxylic acid and isolated as a yellow solid.

$^1$H NMR (DMSO$_{d6}$): 11.81 (1H, s), 7.72 (1H, ddd, J=5.8, 8.1, 8.8 Hz), 7.16 (1H, dt, J=1.4, 9.6 Hz), 4.47 (1H, quin, J=8.5 Hz), 4.17 (1H, dd, J=11.4, 9.2 Hz), 4.09 (2H, q, J=7.0 Hz), 3.73 (1H, dd, J=11.6, 7.8 Hz), 3.50 (2H, s), 3.27 (1H, dd, J=16.0, 9.4 Hz), 2.86 (1H, dd, J=15.9, 8.0 Hz), 1.19 (3H, t, J=7.1 Hz).

$^{13}$C NMR (DMSO$_{d6}$): 169.1, 160.8, 160.7, 159.2, 159.1, 157.5, 157.5, 155.9, 155.9, 155.4, 132.5, 132.4, 129.9, 118.9, 118.7, 118.6, 113.8, 113.8, 113.6, 113.6, 112.6, 104.1, 104.1, 103.9, 103.9, 60.7, 48.7, 35.6, 29.8, 29.2, 14.1.

Example 61: Ethyl (R)-2-(6-(2,5-difluorophenyl)-3-thioxo-2,5,6,7-tetrahydro-3H-pyrrolo[1,2-c]imidazol-1-yl)acetate

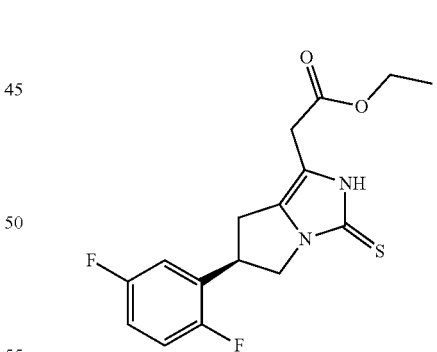

Compound was prepared analogous manner to Example 2 from (4R)-1-(tert-butoxycarbonyl)-4-(2,5-difluorophenyl)pyrrolidine-2-carboxylic acid and isolated as a white solid.

$^1$H NMR (DMSO$_{d6}$): 1.82 (1H, s), 7.29 (1H, dt, J=4.7, 9.5 Hz), 7.26 (1H, m), 7.19 (1H, m), 4.22 (1H, quin, J=7.8 Hz), 4.14 (1H, dd, J=11.3, 7.9 Hz), 4.09 (2H, q, J=7.0 Hz), 3.74 (1H, dd, J=11.3, 7.5 Hz), 3.53 (2H, m), 3.22 (1H, dd, J=15.5, 8.0 Hz), 2.86 (1H, dd, J=15.5, 7.8 Hz), 1.19 (3H, t, J=7.1 Hz).

$^{13}$C NMR (DMSO$_{d6}$): 169.2, 159.1, 159, 157.5, 157.5, 157.1, 157.1, 155.6, 155.5, 155.5, 130.1, 130, 130, 129.9, 129.8, 117.2, 117.1, 117, 116.9, 115.5, 115.4, 115.3, 115.3, 115.2, 115.2, 115.1, 115, 113.1, 60.7, 49.4, 40.3, 29.8, 29.6, 14.1.

Example 62: Ethyl (S)-2-(6-(5-bromo-2-fluorophenyl)-3-thioxo-2,5,6,7-tetrahydro-3H-pyrrolo[1,2-c]imidazol-1-yl)acetate

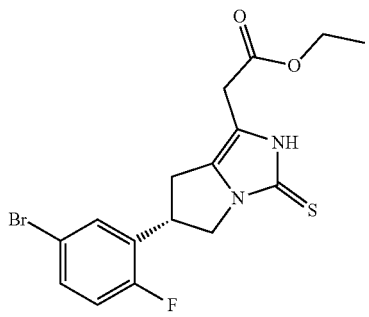 [SMILES: CCOC(=O)Cc1[nH]c(=S)n2c1C[C@@H](c1cc(Br)ccc1F)C2]

Compound was prepared analogous manner to Example 2 from (4S)-1-(tert-butoxycarbonyl)-4-(5-bromo-2-fluorophenyl)pyrrolidine-2-carboxylic acid and isolated as an orange solid.

$^1$H NMR (DMSO$_{d6}$): 11.80 (1H, s), 7.58 (1H, dd, J=6.6, 2.5 Hz), 7.53 (1H, ddd, J=8.7, 4.5, 2.6 Hz), 7.23 (1H, dd, J=10.1, 8.8 Hz), 4.22 (1H, quin, J=7.9 Hz), 4.14 (1H, dd, J=11.2, 8.1 Hz), 4.09 (2H, q, J=7.2 Hz), 3.75 (1H, dd, J=11.3, 7.5 Hz), 3.52 (2H, m), 3.22 (1H, dd, J=15.6, 8.2 Hz), 2.87 (1H, dd, J=15.6, 7.9 Hz), 1.19 (3H, t, J=7.1 Hz).

$^{13}$C NMR (DMSO$_{d6}$): 169.2, 160.3, 158.7, 155.6, 131.9, 131.8, 131.4, 131.3, 130.7, 130.6, 129.7, 118, 117.9, 116.5, 116.5, 113, 60.7, 49.3, 40.4, 29.8, 29.5, 14.1.

Example 63: Ethyl (R)-2-(6-(2,3,5,6-tetrafluorophenyl)-3-thioxo-2,5,6,7-tetrahydro-3H-pyrrolo[1,2-c]imidazol-1-yl)acetate

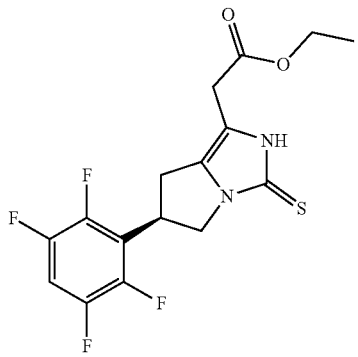 [SMILES: CCOC(=O)Cc1[nH]c(=S)n2c1C[C@H](c1c(F)c(F)cc(F)c1F)C2]

Compound was prepared analogous manner to Example 2 from (4R)-1-(tert-butoxycarbonyl)-4-(2,3,5,6-tetrafluorophenyl)pyrrolidine-2-carboxylic acid and isolated as a light cream powder.

$^1$H NMR (DMSO$_{d6}$): 11.83 (1H, s), 7.86 (1H, m), 4.51 (1H, quin, J=8.5 Hz), 4.19 (1H, dd, J=11.6, 9.1 Hz), 4.09 (2H, q, J=7.2 Hz), 3.79 (1H, dd, J=11.7, 7.6 Hz), 3.51 (2H, s), 3.30 (1H, dd, J=16.0, 9.4 Hz), 2.91 (1H, dd, J=15.9, 7.8 Hz), 1.19 (3H, t, J=7.1 Hz).

$^{13}$C NMR (DMSO$_{d6}$): 169.1, 155.5, 146.4, 146.3, 146.2, 145.3, 145.2, 144.7, 144.6, 143.7, 143.6, 129.6, 120.5, 120.4, 120.3, 112.7, 105.9, 105.7, 105.6, 60.6, 48.6, 35.7, 29.8, 29.1, 14.

Example 64: Ethyl (R)-2-(6-(5-chloro-2-fluorophenyl)-3-thioxo-2,5,6,7-tetrahydro-3H-pyrrolo[1,2-c]imidazol-1-yl)acetate

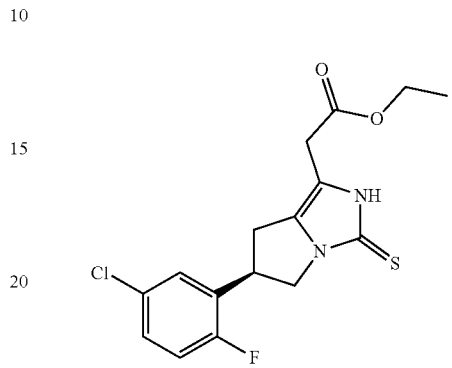

Compound was prepared analogous manner to Example 2 from (4R)-1-(tert-butoxycarbonyl)-4-(5-chloro-2-fluorophenyl)pyrrolidine-2-carboxylic acid and isolated as a pale yellow solid.

$^1$H NMR (DMSO$_{d6}$): 11.78 (1H, s), 7.45 (1H, dd, J=6.5, 2.6 Hz), 7.40 (1H, ddd, J=8.8, 4.4, 2.7 Hz), 7.29 (1H, dd, J=10.1, 8.9 Hz), 4.22 (1H, quin, J=7.8 Hz), 4.15 (1H, dd, J=11.3, 8.1 Hz), 4.10 (2H, q, J=7.2 Hz), 3.75 (1H, dd, J=11.3, 7.5 Hz), 3.52 (2H, m), 3.22 (1H, dd, J=15.5, 8.1 Hz), 2.88 (1H, dd, J=15.6, 7.8 Hz), 1.19 (3H, t, J=7.0 Hz).

$^{13}$C NMR (DMSO$_{d6}$): 169.1, 159.8, 158.1, 155.6, 130.3, 130.2, 129.7, 128.9, 128.8, 128.5, 128.5, 128.4, 128.4, 117.6, 117.4, 113, 60.7, 49.3, 40.3, 29.8, 29.5, 14.

Example 65: Ethyl (R)-2-(6-(2,6-difluorophenyl)-3-thioxo-2,5,6,7-tetrahydro-3H-pyrrolo[1,2-c]imidazol-1-yl)acetate

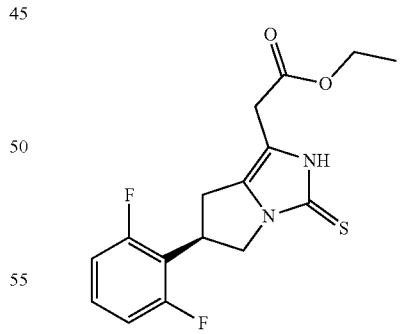

Compound was prepared analogous manner to Example 2 from (4R)-1-(tert-butoxycarbonyl)-4-(2,6-difluorophenyl)pyrrolidine-2-carboxylic acid and isolated as an orange solid.

$^1$H NMR (DMSO$_{d6}$): 1.80 (1H, s), 7.41 (1H, tt, J=8.4, 6.6 Hz), 7.13 (2H, m), 4.43 (1H, quin, J=8.7 Hz), 4.16 (1H, dd, J=9.2, 11.3 Hz), 4.09 (2H, q, J=7.0 Hz), 3.73 (1H, dd, J=11.4, 8.2 Hz), 3.50 (2H, s), 3.25 (1H, dd, J=15.7, 9.2 Hz), 2.86 (1H, dd, J=15.7, 8.5 Hz), 1.19 (3H, t, J=7.1 Hz).

¹³C NMR (DMSO_{d6}): 169.1, 161.6, 161.5, 160, 159.9, 155.4, 130, 129.8, 129.8, 129.7, 116.6, 116.5, 116.4, 112.6, 112.2, 112.2, 112.1, 112.1, 60.6, 48.7, 35.2, 29.8, 29.3, 14.

Example 66: 2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)-1-morpholinoethan-1-one

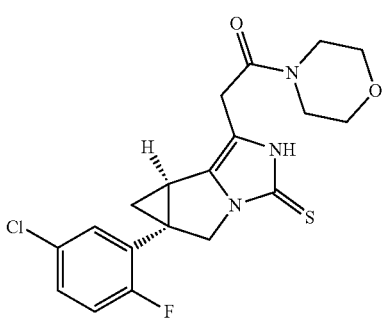 [SMILES: O=C(Cc1[nH]c(=S)n2c1[C@@H]1C[C@]1(c1cc(Cl)ccc1F)C2)N1CCOCC1]

Compound was prepared analogous manner to Example 37 from (1R,5S)-3-(tert-butoxycarbonyl)-5-(5-chloro-2-fluorophenyl)-3-azabicyclo[3.1.0]hexane-2-carboxylic acid and isolated as a greenish solid.

¹H NMR (DMSO_{d6}): 11.64 (1H, s), 7.45 (1H, dd, J=2.7, 6.5 Hz), 7.43 (1H, ddd, J=8.6, 4.4, 2.7 Hz), 7.30 (1H, dd, J=9.9, 8.7 Hz), 4.08 (1H, d, J=12.0 Hz), 3.79 (1H, d, J=12.2 Hz), 3.57 (6H, m), 3.49 (2H, m), 3.46 (2H, m), 2.78 (1H, dd, J=8.4, 4.3 Hz), 1.69 (1H, dd, J=8.3, 5.4 Hz), 1.11 (1H, t, J=4.8 Hz).

¹³C NMR (DMSO_{d6}): 166.9, 161.3, 159.6, 156, 131.8, 130.2, 130.2, 129.4, 129.3, 128.8, 128.7, 128.3, 128.3, 117.6, 117.4, 113.7, 66, 54.9, 51.6, 45.7, 41.8, 32.4, 29, 22.1, 20.7.

Example 67: 2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)-N-isopropylacetamide

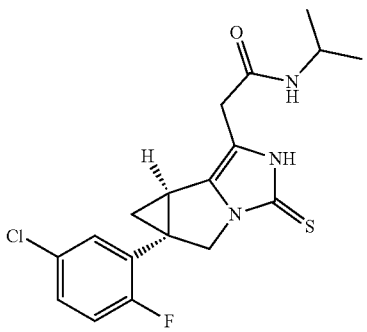 [SMILES: CC(C)NC(=O)Cc1[nH]c(=S)n2c1[C@@H]1C[C@]1(c1cc(Cl)ccc1F)C2]

Compound was prepared analogous manner to Example 37 from (1R,5S)-3-(tert-butoxycarbonyl)-5-(5-chloro-2-fluorophenyl)-3-azabicyclo[3.1.0]hexane-2-carboxylic acid and isolated as a light yellow solid.

¹H NMR (DMSO_{d6}): 1.69 (1H, s), 7.88 (1H, d, J=7.6 Hz), 7.45 (1H, dd, J=2.6, 6.5 Hz), 7.43 (1H, ddd, J=8.5, 4.3, 2.8 Hz), 7.30 (1H, dd, J=9.8, 8.8 Hz), 4.07 (1H, d, J=12.0 Hz), 3.83 (1H, oct, J=7.3 Hz), 3.79 (1H, d, J=12.2 Hz), 3.25 (2H, m), 2.80 (1H, dd, J=8.4, 4.3 Hz), 1.66 (1H, dd, J=8.4, 5.3 Hz), 1.13 (1H, t, J=4.8 Hz), 1.06 (6H, d, J=6.6 Hz).

¹³C NMR (DMSO_{d6}): 166.7, 161.2, 159.6, 155.8, 131.6, 130.2, 130.1, 129.3, 129.3, 128.9, 128.8, 128.3, 128.3, 117.6, 117.4, 114.1, 51.5, 51.5, 40.7, 32.3, 31.5, 22.4, 22.3, 22, 20.8.

Example 68: 2-((5aS,6aR)-5a-(3-chloro-5-fluorophenyl)-3-thioxo-2,3,5,5a,6,6a-hexahydrocyclopropa[3,4]pyrrolo[1,2-c]imidazol-1-yl)-N-methylacetamide

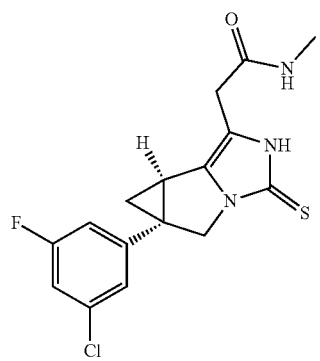 [SMILES: CNC(=O)Cc1[nH]c(=S)n2c1[C@@H]1C[C@]1(c1cc(F)cc(Cl)c1)C2]

Compound was prepared analogous manner to Example 37 from (1R,5S)-3-(tert-butoxycarbonyl)-5-(3-chloro-5-fluorophenyl)-3-azabicyclo[3.1.0]hexane-2-carboxylic acid and isolated as a light yellow solid.

¹H NMR (DMSO_{d6}): 1.62 (1H, s), 7.78 (1H, q, J=4.5 Hz), 7.31 (1H, dt, J=8.7, 1.9 Hz), 7.28 (1H, t, J=1.5 Hz), 7.23 (1H, dt, J=10.0, 1.8 Hz), 4.19 (1H, d, J=12.2 Hz), 4.02 (1H, d, J=12.0 Hz), 3.27 (2H, m), 2.93 (1H, dd, J=8.3, 4.3 Hz), 2.60 (3H, d, J=4.5 Hz), 1.67 (1H, dd, J=8.4, 5.3 Hz), 1.20 (1H, t, J=4.8 Hz).

¹³C NMR (DMSO_{d6}): 168.2, 163.1, 161.4, 156.2, 144.9, 144.8, 134.2, 134.1, 132, 123, 123, 114.3, 114.1, 113.4, 112.9, 112.8, 50.9, 36, 36, 31.3, 24.9, 22.8.

Example 69: 2-((5aS,6aR)-5a-(3-chloro-5-fluorophenyl)-3-thioxo-2,3,5,5a,6,6a-hexahydrocyclopropa[3,4]pyrrolo[1,2-c]imidazol-1-yl)-N,N-dimethylacetamide

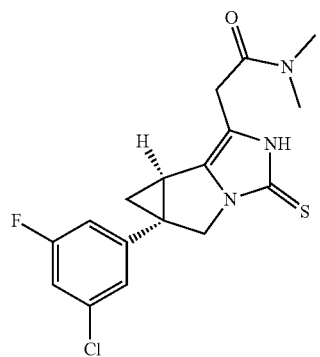 [SMILES: CN(C)C(=O)Cc1[nH]c(=S)n2c1[C@@H]1C[C@]1(c1cc(F)cc(Cl)c1)C2]

Compound was prepared analogous manner to Example 37 from (1R,5S)-3-(tert-butoxycarbonyl)-5-(3-chloro-5-fluorophenyl)-3-azabicyclo[3.1.0]hexane-2-carboxylic acid and isolated as a yellow solid.

¹H NMR (DMSO$_{d6}$): 11.58 (1H, s), 7.31 (1H, dt, J=8.7, 2.1 Hz), 7.27 (1H, t, J=1.6 Hz), 7.22 (1H, dt, J=10.0, 2.0 Hz), 4.20 (1H, d, J=12.0 Hz), 4.03 (1H, d, J=12.0 Hz), 3.52 (2 H, s), 3.02 (3H, s), 2.90 (1H, dd, J=8.4, 4.4 Hz), 2.85 (3H, s), 1.68 (1H, dd, J=8.3, 5.2 Hz), 1.13 (1H, t, J=4.8 Hz).

¹³C NMR (DMSO$_{d6}$): 167.9, 163.1, 161.5, 156.1, 144.8, 144.8, 134.2, 134.1, 131.6, 122.9, 122.9, 114.3, 114.1, 113.8, 112.9, 112.7, 50.8, 37, 36, 36, 35.1, 29.2, 25.1, 22.8.

Example 70: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-1-(pyrrolidin-1-yl)ethan-1-one

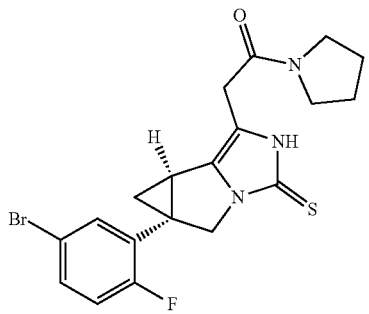 [SMILES: O=C(Cc1[nH]c(=S)n2c1[C@@H]1C[C@]1(c1cc(Br)ccc1F)C2)N1CCCC1]

Compound was prepared analogous manner to Example 37 from (1R,5S)-3-(tert-butoxycarbonyl)-5-(5-bromo-2-fluorophenyl)-3-azabicyclo[3.1.0]hexane-2-carboxylic acid and isolated as a light yellow solid.

¹H NMR (DMSO$_{d6}$): 11.61 (1H, s), 7.59-7.53 (2H, m), 7.24 (1H, dd, J=10.1, 8.7 Hz), 4.07 (1H, d, J=12.0 Hz), 3.79 (1H, d, J=12.0 Hz), 3.48 (2H, m), 3.46 (2H, t, 6.9 Hz), 3.31 (2H, t, J=6.9 Hz), 2.79 (1H, dd, J=8.4, 4.3 Hz), 1.90 (2H, quin, J=6.9 Hz), 1.78 (2H, quin, J=6.9 Hz), 1.67 (1H, dd, J=8.4, 5.3 Hz), 1.10 (1H, t br, J=4.8 Hz).

¹³C NMR (DMSO$_{d6}$): 166.2, 161.8, 160.1, 155.9, 133, 133, 132.3, 132.2, 131.7, 129.3, 129.2, 118, 117.8, 116.2, 116.2, 113.8, 51.6, 51.6, 46.1, 45.6, 32.2, 30.5, 25.6, 24, 22.1, 20.7.

Example 71: (R)—N-(3-(dimethylamino)propyl)-2-(6-(2,3,5,6-tetrafluorophenyl)-3-thioxo-2,5,6,7-tetrahydro-3H-pyrrolo[1,2-c]imidazol-1-yl)acetamide Hydrochloride

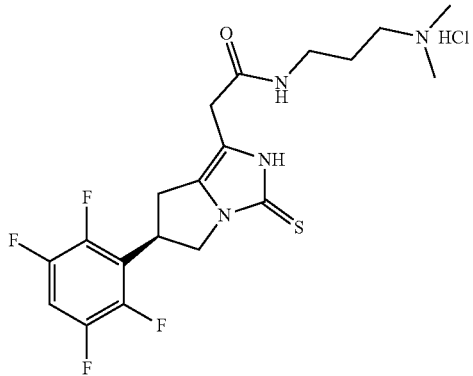

Compound was prepared analogous manner to Example 32 from (R)-1-(H-imidazol-1-yl)-2-(6-(2,3,5,6-tetrafluorophenyl)-3-thioxo-2H-pyrrolo[1,2-c]imidazol-1-yl)ethanone and isolated as a yellowish powder.

¹H NMR (DMSO$_{d6}$): 1.78 (1H, m), 10.33 (1H, br s), 8.22 (1H, br t, J=5.5 Hz), 7.85 (1H, m), 4.50 (1H, quin, J=8.5 Hz), 4.19 (1H, br t, J=10.3 Hz), 3.80 (1H, m), 3.29 (3H, m), 3.11 (2H, q, J=6.4 Hz), 3.01 (2H, m), 2.91 (1H, br dd, J=15.7, 8.2 Hz), 2.71 (6H, d, J=4.5 Hz), 1.79 (2H, m).

¹³C NMR (DMSO$_{d6}$): 168.1, 146.4, 146.4, 146.3, 145.4, 145.4, 145.3, 145.3, 145.2, 144.8, 144.8, 144.8, 144.7, 144.7, 144.7, 144.7, 144.6, 143.8, 143.7, 143.7, 143.7, 143.6, 143.6, 129.5, 120.3, 120.2, 119.2, 114.7, 105.9, 105.8, 105.6, 54.4, 48.5, 42, 42, 35.9, 35.8, 31.5, 29.2, 24.1.

Example 72: (R)—N-(2-hydroxyethyl)-2-(6-(2,3,5,6-tetrafluorophenyl)-3-thioxo-2,5,6,7-tetrahydro-3H-pyrrolo[1,2-c]imidazol-1-yl)acetamide

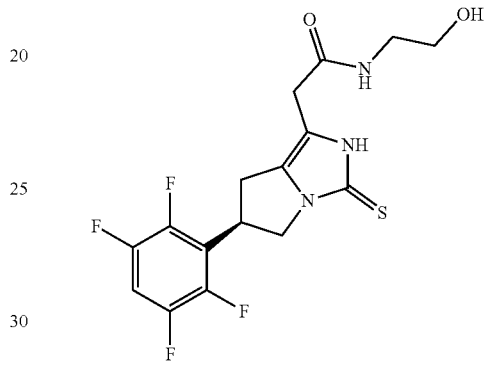

Compound was prepared analogous manner to Example 32 from (R)-1-(H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone and isolated as a light cream powder.

¹H NMR (DMSO$_{d6}$): 10.98 (1H, m), 7.98 (1H, br t, J=5.2 Hz), 7.84 (1H, m), 4.68 (1H, br s), 4.48 (1H, quin, J=8.5 Hz), 4.17 (1H, br dd, J=11.2, 9.5 Hz), 3.77 (1H, dd, J=11.5, 8.0 Hz), 3.39 (2H, br t, J=5.9 Hz), 3.25 (3H, m), 3.11 (2H, q, J=5.9 Hz), 2.89 (1H, br dd, J=15.8, 8.1 Hz).

¹³C NMR (DMSO$_{d6}$): 167.7, 155.2, 146.4, 146.3, 146.3, 145.4, 145.3, 145.3, 145.3, 145.2, 145.2, 145.2, 144.8, 144.7, 144.7, 144.7, 144.6, 144.6, 143.7, 143.7, 143.7, 143.7, 143.6, 143.6, 143.6, 143.6, 143.6, 128.9, 120.4, 120.3, 120.2, 114.4, 105.9, 105.7, 105.6, 59.7, 48.4, 41.7, 35.8, 31.5, 29.1.

Example 73: (R)—N-(2-methoxyethyl)-2-(6-(2,3,5,6-tetrafluorophenyl)-3-thioxo-2,5,6,7-tetrahydro-3H-pyrrolo[1,2-c]imidazol-1-yl)acetamide

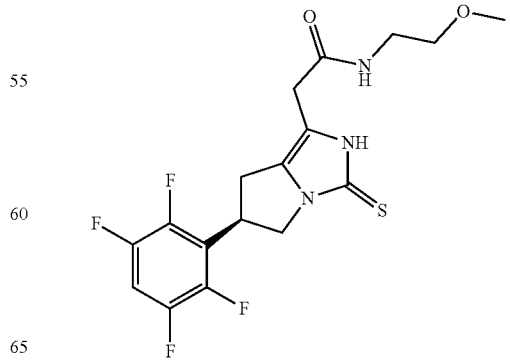

Compound was prepared analogous manner to Example 32 from (R)-1-(1H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone and isolated as a light beige powder.

¹H NMR (DMSO$_{d6}$): 1.74 (1H, br s), 8.04 (1H, br t, J=5.1 Hz), 7.85 (1H, m), 4.48 (1H, quin, J=8.5 Hz), 4.17 (1H, dd, J=9.5, 11.3 Hz), 3.77 (1H, dd, J=11.5, 8.0 Hz), 3.33 (2H, t, J=5.4 Hz), 3.29-3.16 (8H, m), 2.88 (1H, br dd, J=15.9, 8.1 Hz).

¹³C NMR (DMSO$_{d6}$): 167.7, 155.2, 146.4, 146.4, 146.4, 146.3, 146.3, 146.3, 146.2, 145.3, 145.3, 145.3, 145.3, 145.3, 145.3, 145.2, 145.2, 145.2, 144.8, 144.8, 144.7, 144.6, 144.6, 143.7, 143.7, 143.7, 143.6, 143.6, 143.6, 128.9, 120.4, 120.3, 120.2, 114.3, 105.9, 105.7, 105.6, 70.5, 57.8, 48.4, 38.6, 35.7, 31.4, 29.2.

Example 74: (S)-2-(6-(5-bromo-2-fluorophenyl)-3-thioxo-2,5,6,7-tetrahydro-3H-pyrrolo[1,2-c]imidazol-1-yl)-N-cyclopentylacetamide

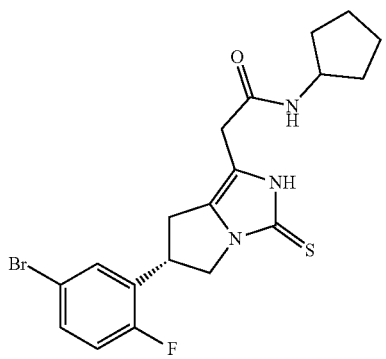 [SMILES: O=C(Cc1[nH]c(=S)n2c1C[C@@H](c1cc(Br)ccc1F)C2)NC1CCCC1]

Compound was prepared analogous manner to Example 32 from (S)-1-(1H-imidazol-1-yl)-2-(6-(5-bromo-2-fluorophenyl)-3-thioxo-3,5,6,7-tetrahydro-2H-pyrrolo[1,2-c]imidazol-1-yl)ethanone and isolated as a pale brown solid.

¹H NMR (DMSO$_{d6}$): 11.71 (1H, s), 7.93 (1H, br d, J=7.0 Hz), 7.57 (1H, dd, J=6.7, 2.4 Hz), 7.53 (1H, ddd, J=8.7, 4.5, 2.5 Hz), 7.23 (1H, dd, J=10.3, 8.8 Hz), 4.20 (1H, quin, J=7.8 Hz), 4.12 (1H, dd, J=11.2, 8.1 Hz), 3.97 (1H, sxt, J=6.9 Hz), 3.73 (1H, dd, J=11.3, 7.5 Hz), 3.21 (2H, s), 3.17 (1H, br dd, J=15.5, 8.1 Hz), 2.83 (1H, dd, J=15.5, 7.8 Hz), 1.77 (2H, m), 1.61 (2H, m), 1.48 (2H, m), 1.35 (2H, m).

¹³C NMR (DMSO$_{d6}$): 167, 160.3, 158.7, 155.2, 131.9, 131.8, 131.4, 131.3, 130.8, 130.7, 128.8, 118, 117.9, 116.5, 116.5, 114.8, 50.5, 49.2, 40.3, 32.2, 31.5, 29.7, 23.4.

Example 75: 2-((R)-6-(5-chloro-2-fluorophenyl)-3-thioxo-2,5,6,7-tetrahydro-3H-pyrrolo[1,2-c]imidazol-1-yl)-N—((R)-tetrahydrofuran-3-yl)acetamide

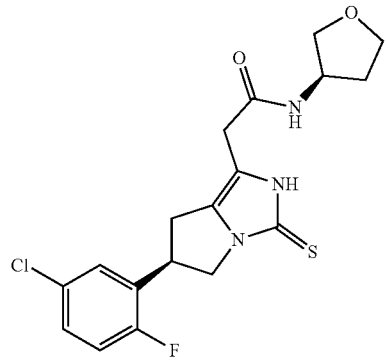 [SMILES: O=C(Cc1[nH]c(=S)n2c1C[C@H](c1cc(Cl)ccc1F)C2)N[C@@H]1CCOC1]

Compound was prepared analogous manner to Example 32 from (R)-1-(H-imidazol-1-yl)-2-(6-(5-chloro-2-fluorophenyl)-3-thioxo-3,5,6,7-tetrahydro-2H-pyrrolo[1,2-c]imidazol-1-yl)ethanone and isolated as a green solid.

¹H NMR (DMSO$_{d6}$): 11.72 (1H, s), 8.22 (1H, br d, J=6.5 Hz), 7.45 (1H, dd, J=6.5, 2.6 Hz), 7.40 (1H, ddd, J=8.7, 4.3, 2.8 Hz), 7.29 (1H, dd, J=10.1, 8.9 Hz), 4.21 (2H, m), 4.13 (1H, dd, J=11.3, 8.1 Hz), 3.77 (1H, m), 3.72 (2H, m), 3.66 (1H, td, J=8.2, 5.6 Hz), 3.46 (1H, dd, J=8.9, 3.7 Hz), 3.25 (2H, s), 3.18 (1H, dd, J=15.4, 8.1 Hz), 2.84 (1H, dd, J=15.4, 7.8 Hz), 2.07 (1H, dq, J=12.7, 7.6 Hz), 1.71 (1H, m).

¹³C NMR (DMSO$_{d6}$): 167.6, 159.8, 158.2, 155.3, 130.4, 130.3, 129, 128.9, 128.8, 128.5, 128.5, 128.5, 128.4, 117.6, 117.4, 114.6, 72.4, 66.3, 49.8, 49.2, 40.3, 32, 31.3, 29.6.

Example 76: (R)—N-cyclopentyl-2-(6-(2,6-difluorophenyl)-3-thioxo-2,5,6,7-tetrahydro-3H-pyrrolo[1,2-c]imidazol-1-yl)acetamide

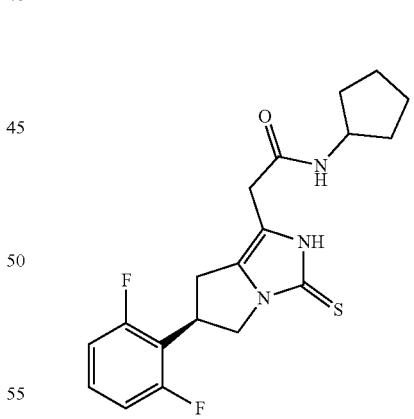

Compound was prepared analogous manner to Example 32 from (R)-1-(H-imidazol-1-yl)-2-(6-(2,6-difluorophenyl)-3-thioxo-3,5,6,7-tetrahydro-2H-pyrrolo[1,2-c]imidazol-1-yl)ethanone and isolated as a pale grey solid.

¹H NMR (DMSO$_{d6}$): 1.72 (1H, s), 7.92 (1H, br d, J=7.2 Hz), 7.40 (1H, m), 7.13 (2H, m), 4.41 (1H, quin, J=8.8 Hz), 4.14 (1H, dd, J=9.3, 11.3 Hz), 3.96 (1H, sxt, J=6.8 Hz), 3.71 (1H, dd, J=11.4, 8.4 Hz), 3.20 (2H, s), 3.18 (1H, dd, J=9.2, 15.6 Hz), 2.84 (1H, dd, J=15.6, 8.6 Hz), 1.77 (2H, m), 1.61 (2H, m), 1.48 (2H, m), 1.35 (2H, m).

¹³C NMR (DMSO$_{d6}$): 167, 161.6, 161.6, 160, 159.9, 155.1, 129.8, 129.7, 129.7, 129, 116.6, 116.4, 116.3, 114.5, 112.2, 112.2, 112.1, 112.1, 50.5, 48.6, 35.3, 32.2, 32.2, 31.5, 29.4, 23.4.

Example 77: 2-((R)-6-(2,6-difluorophenyl)-3-thioxo-2,5,6,7-tetrahydro-3H-pyrrolo[1,2-c]imidazol-1-yl)-N—((R)-tetrahydrofuran-3-yl)acetamide

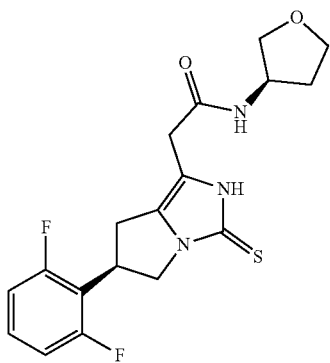 [SMILES: O=C(Cc1[nH]c(=S)n2c1C[C@H](c1c(F)cccc1F)C2)N[C@@H]1CCOC1]

Compound was prepared analogous manner to Example from (R)-1-(1H-imidazol-1-yl)-2-(6-(2,6-difluorophenyl)-3-thioxo-3,5,6,7-tetrahydro-2H-pyrrolo[1,2-c]imidazol-1-yl)ethanone and isolated as a pale grey solid.

¹H NMR (DMSO$_{d6}$): 1.73 (1H, s), 8.21 (1H, br d, J=6.5 Hz), 7.40 (1H, m), 7.13 (2H, t, J=8.1 Hz), 4.41 (1H, quin, J=8.8 Hz), 4.21 (1H, m), 4.14 (1H, dd, J=10.8, 9.8 Hz), 3.76 (1H, m), 3.71 (2H, m), 3.65 (1H, td, J=8.2, 5.6 Hz), 3.45 (1H, dd, J=8.9, 3.7 Hz), 3.24 (2H, s), 3.19 (1H, dd, J=15.6, 9.2 Hz), 2.84 (1H, dd, J=15.7, 8.7 Hz), 2.06 (1H, dq, J=12.7, 7.6 Hz), 1.71 (1H, m).

¹³C NMR (DMSO$_{d6}$): 167.5, 161.6, 161.6, 160, 159.9, 155.1, 129.8, 129.7, 129.7, 129.2, 116.5, 116.4, 116.3, 114.2, 112.2, 112.2, 112.1, 112.1, 72.4, 66.3, 49.8, 48.6, 35.3, 32, 31.3, 29.4.

Example 78: (R)—N-cyclopropyl-2-(6-(2,3,5,6-tetrafluorophenyl)-3-thioxo-2,5,6,7-tetrahydro-3H-pyrrolo[1,2-c]imidazol-1-yl)acetamide

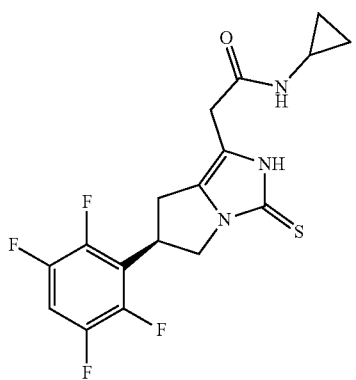 [SMILES: O=C(Cc1[nH]c(=S)n2c1C[C@H](c1c(F)c(F)cc(F)c1F)C2)NC1CC1]

Compound was prepared analogous manner to Example 32 from (R)-1-(H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone and isolated as a beige powder.

¹H NMR (DMSO$_{d6}$): 1.74 (1H, s), 8.04 (1H, br d, J=3.7 Hz), 7.85 (1H, m), 4.48 (1H, quin, J=8.6 Hz), 4.17 (1H, dd, J=11.5, 9.3 Hz), 3.77 (1H, dd, J=11.7, 7.9 Hz), 3.25 (1H, dd, J=15.8, 9.4 Hz), 3.19 (2H, m), 2.88 (1H, dd, J=15.9, 8.2 Hz), 2.59 (1H, tq, J=7.4, 3.8 Hz), 0.60 (2H, m), 0.38 (2H, m).

¹³C NMR (DMSO$_{d6}$): 168.7, 155.2, 146.4, 146.4, 146.4, 146.3, 146.3, 146.2, 145.3, 145.3, 145.3, 145.3, 145.3, 145.2, 145.2, 145.2, 144.8, 144.8, 144.7, 144.7, 144.7, 144.6, 144.6, 143.7, 143.7, 143.7, 143.7, 143.6, 143.6, 143.6, 128.9, 120.4, 120.3, 120.2, 114.3, 105.9, 105.7, 105.5, 48.4, 35.7, 31.3, 29.2, 22.4, 5.6, 5.6.

Example 79: (R)—N-(cyclopropylmethyl)-2-(6-(2,3,5,6-tetrafluorophenyl)-3-thioxo-2,5,6,7-tetrahydro-3H-pyrrolo[1,2-c]imidazol-1-yl)acetamide

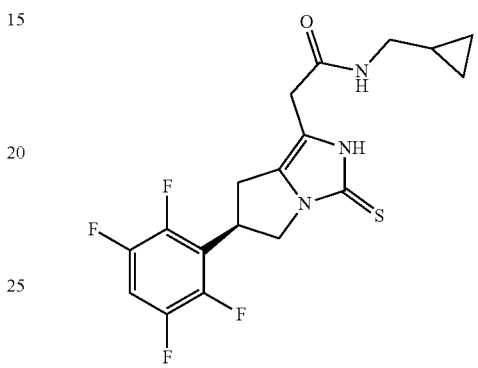

Compound was prepared analogous manner to Example 32 from (R)-1-(H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone and isolated as a cream powder.

¹H NMR (DMSO$_{d6}$): 1.76 (1H, s), 8.05 (1H, br t, J=5.4 Hz), 7.85 (1H, m), 4.48 (1H, quin, J=8.6 Hz), 4.17 (1H, dd, J=11.6, 9.1 Hz), 3.77 (1H, dd, J=11.6, 7.9 Hz), 3.25 (1H, dd, J=9.3, 11.7 Hz), 3.24 (2H, s), 2.92 (2H, t, J=6.2 Hz), 2.89 (1H, dd, J=16.1, 8.3 Hz), 0.87 (1H, m), 0.38 (2H, m), 0.13 (2H, m).

¹³C NMR (DMSO$_{d6}$): 167.4, 155.2, 146.4, 146.4, 146.4, 146.4, 146.4, 146.3, 146.3, 146.3, 146.2, 145.3, 145.3, 145.3, 145.3, 145.2, 145.2, 144.8, 144.8, 144.8, 144.7, 144.7, 144.7, 144.7, 144.6, 143.7, 143.7, 143.7, 143.6, 143.6, 143.6, 143.6, 128.9, 120.4, 120.3, 120.2, 114.4, 105.9, 105.7, 105.6, 48.4, 43.1, 35.8, 31.5, 29.2, 10.7, 3.2.

Example 80: (R)—N-cyclobutyl-2-(6-(2,3,5,6-tetrafluorophenyl)-3-thioxo-2,5,6,7-tetrahydro-3H-pyrrolo[1,2-c]imidazol-1-yl)acetamide

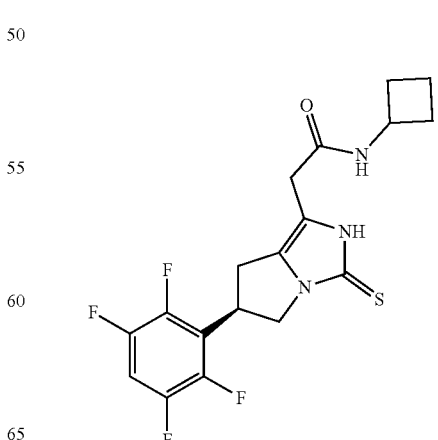

Compound was prepared analogous manner to Example 32 from (R)-1-(H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone and isolated as a beige powder.

¹H NMR (DMSO$_{d6}$): 1.74 (1H, s), 8.20 (1H, br d, J=7.6 Hz), 7.85 (1H, m), 4.48 (1H, quin, J=8.5 Hz), 4.16 (2H, m), 3.77 (1H, dd, J=11.6, 7.9 Hz), 3.24 (1H, br dd, J=15.8, 9.2 Hz), 3.20 (2H, s), 2.87 (1H, br dd, J=15.8, 8.1 Hz), 2.12 (2H, m), 1.86 (2H, m), 1.60 (2H, m).

¹³C NMR (DMSO$_{d6}$): 166.5, 155.2, 146.4, 146.4, 146.3, 146.3, 146.3, 146.2, 145.3, 145.3, 145.2, 145.2, 145.2, 145.2, 144.8, 144.7, 144.7, 144.7, 144.6, 144.6, 143.7, 143.7, 143.7, 143.6, 143.6, 143.6, 128.9, 120.4, 120.3, 120.2, 114.3, 105.9, 105.7, 105.5, 48.4, 44, 35.7, 31.4, 30.2, 30.2, 29.2, 14.6.

Example 81: (R)-1-(4-methylpiperazin-1-yl)-2-(6-(2,3,5,6-tetrafluorophenyl)-3-thioxo-2,5,6,7-tetrahydro-3H-pyrrolo[1,2-c]imidazol-1-yl)ethan-1-one

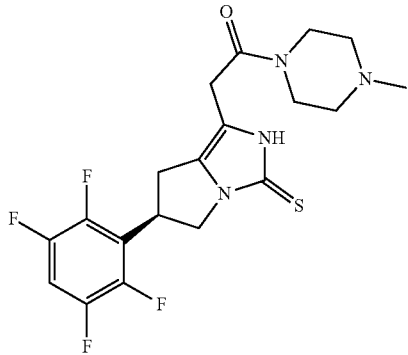 [SMILES: CN1CCN(C(=O)Cc2[nH]c(=S)n3c2C[C@H](c2c(F)c(F)cc(F)c2F)C3)CC1]

Compound was prepared analogous manner to Example 32 from (R)-1-(H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone and isolated as a cream powder.

¹H NMR (DMSO$_{d6}$): 1.70 (1H, br s), 7.85 (1H, m), 4.49 (1H, quin, J=8.5 Hz), 4.18 (1H, dd, J=11.4, 9.3 Hz), 3.78 (1H, dd, J=11.7, 7.7 Hz), 3.50 (2H, m), 3.48-3.38 (4H, m), 3.24 (1H, br dd, J=15.8, 9.4 Hz), 2.85 (1H, dd, J=15.8, 7.9 Hz), 2.26 (4H, m), 2.17 (3H, s).

¹³C NMR (DMSO$_{d6}$): 166.5, 155.2, 146.4, 146.4, 146.3, 146.3, 146.3, 146.2, 145.3, 145.2, 144.8, 144.8, 144.7, 144.7, 144.7, 144.6, 144.6, 143.7, 143.7, 143.6, 143.6, 143.6, 143.6, 143.6, 143.5, 129, 120.5, 120.4, 120.3, 114.2, 105.8, 105.7, 105.5, 54.6, 54.2, 48.5, 45.6, 45.1, 41.2, 35.8, 29.2, 29.1.

Example 82: (R)-1-(4-hydroxypiperidin-1-yl)-2-(6-(2,3,5,6-tetrafluorophenyl)-3-thioxo-2,5,6,7-tetrahydro-3H-pyrrolo[1,2-c]imidazol-1-yl)ethan-1-one

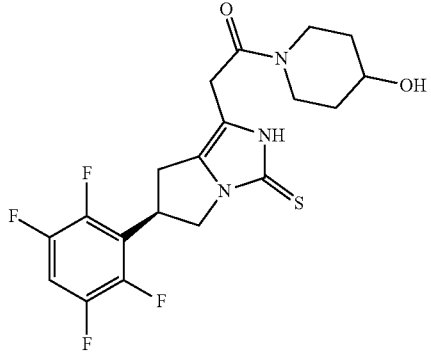 [SMILES: O=C(Cc1[nH]c(=S)n2c1C[C@H](c1c(F)c(F)cc(F)c1F)C2)N1CCC(O)CC1]

Compound was prepared analogous manner to Example 32 from (R)-1-(H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone and isolated as a cream powder.

¹H NMR (DMSO$_{d6}$): 1.70 (1H, br s), 7.85 (1H, m), 4.75 (1H, s br), 4.48 (1H, quin, J=8.5 Hz), 4.18 (1H, m), 3.86 (1H, m), 3.77 (1H, dd, J=11.6, 7.9 Hz), 3.67 (2H, m), 3.49 (2H, m), 3.24 (1H, br dd, J=15.8, 9.2 Hz), 3.16 (1H, m), 3.01 (1H, m), 2.86 (1H, dd, J=15.8, 7.9 Hz), 1.69 (2H, m), 1.32 (1H, br d, J=9.1 Hz), 1.24 (1H, m).

¹³C NMR (DMSO$_{d6}$): 66.2, 155.2, 146.4, 146.4, 146.4, 146.3, 146.3, 146.2, 145.3, 145.3, 145.3, 145.3, 145.2, 145.2, 145.2, 144.8, 144.8, 144.7, 144.7, 144.6, 144.6, 143.7, 143.7, 143.7, 143.6, 143.6, 143.6, 143.6, 129, 120.5, 120.4, 120.2, 114.4, 105.9, 105.7, 105.5, 65.4, 65.4, 48.4, 42.8, 39, 35.8, 34.5, 34.4, 33.8, 29.2, 29.1, 29.1.

Example 83: (R)-1-(4-(hydroxymethyl)piperidin-1-yl)-2-(6-(2,3,5,6-tetrafluorophenyl)-3-thioxo-2,5,6,7-tetrahydro-3H-pyrrolo[1,2-c]imidazol-1-yl)ethan-1-one

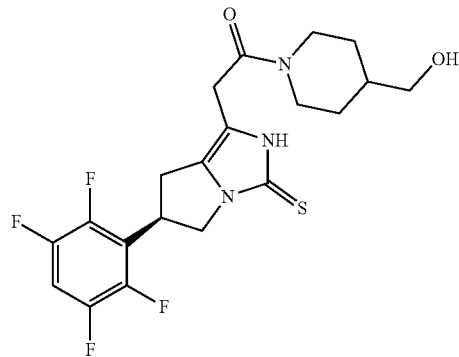 [SMILES: O=C(Cc1[nH]c(=S)n2c1C[C@H](c1c(F)c(F)cc(F)c1F)C2)N1CCC(CO)CC1]

Compound was prepared analogous manner to Example 32 from (R)-1-(H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone and isolated as a beige powder.

¹H NMR (DMSO$_{d6}$): 1.71 (1H, br d, J=5.1 Hz), 7.85 (1H, m), 4.48 (1H, m), 4.48 (1H, br), 4.34 (1H, br d, J=11.6 Hz), 4.17 (1H, m), 3.84 (1H, br d, J=12.5 Hz), 3.77 (1H, m), 3.48 (2H, m), 3.23 (3H, m), 2.98 (1H, m), 2.86 (1H, m), 2.52 (1H, m), 1.74-1.51 (3H, m), 0.98 (2H, m).

¹³C NMR (DMSO$_{d6}$): 166.1, 166.1, 155.2, 155.1, 146.4, 146.4, 146.4, 146.4, 146.4, 146.3, 146.3, 146.3, 146.2, 145.4, 145.4, 145.3, 145.3, 145.3, 145.3, 145.2, 145.2, 145.2, 145.2, 144.8, 144.7, 144.7, 144.7, 144.6, 144.6, 143.7, 143.7, 143.7, 143.7, 143.6, 143.6, 143.6, 143.5, 128.9, 120.4, 120.3, 120.2, 114.5, 114.4, 105.9, 105.7, 105.5, 65.5, 65.5, 48.5, 45.3, 45.3, 41.3, 38.3, 38.3, 35.8, 35.7, 29.2, 29.2, 29, 28.3, 28.3.

Example 84: (S)-2-(6-(3-chloro-2,6-difluorophenyl)-3-thioxo-2,5,6,7-tetrahydro-3H-pyrrolo[1,2-c]imidazol-1-yl)-N-cyclopentylacetamide

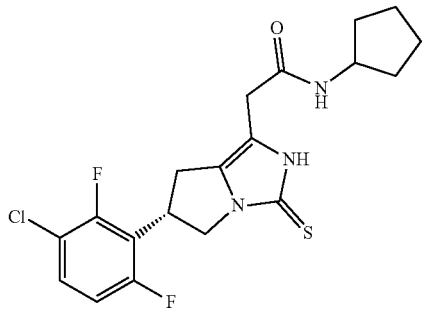 [SMILES: O=C(Cc1[nH]c(=S)n2c1C[C@@H](c1c(F)ccc(Cl)c1F)C2)NC1CCCC1]

Compound was prepared analogous manner to Example 32 from (S)-1-(1H-imidazol-1-yl)-2-(6-(3-chloro-2,6-difluorophenyl)-3-thioxo-3,5,6,7-tetrahydro-2H-pyrrolo[1,2-c]imidazol-1-yl)ethanone and isolated as a white solid.

$^1$H NMR (DMSO$_{d6}$): 1.55 (1H, br s), 7.93 (1H, br d, J=7.2 Hz), 7.61 (1H, m), 7.22 (1H, m), 4.44 (1H, quin, J=8.6 Hz), 4.15 (1H, dd, J=9.6, 10.5 Hz), 3.96 (1H, sxt, J=6.8 Hz), 3.73 (1H, dd, J=11.5, 8.0 Hz), 3.21 (1H, m), 3.20 (2H, s), 2.83 (1H, br dd, J=15.8, 8.1 Hz), 1.76 (2H, m), 1.61 (2H, m), 1.48 (2H, m), 1.35 (2H, m).

$^{13}$C NMR (DMSO$_{d6}$): 166.9, 160.1, 158.5, 158.5, 156.6, 156.5, 155.1, 154.9, 154.9, 129.7, 129.6, 128.9, 118.8, 118.7, 118.6, 116, 115.9, 114.5, 113.2, 113.2, 113.1, 113.1, 50.5, 48.5, 35.6, 32.2, 32.2, 31.5, 29.3, 23.4.

Example 85: (R)—N,N-dimethyl-2-(4-(2-(6-(2,3,5,6-tetrafluorophenyl)-3-thioxo-2,5,6,7-tetrahydro-3H-pyrrolo[1,2-c]imidazol-1-yl)acetyl)piperazin-1-yl) acetamide

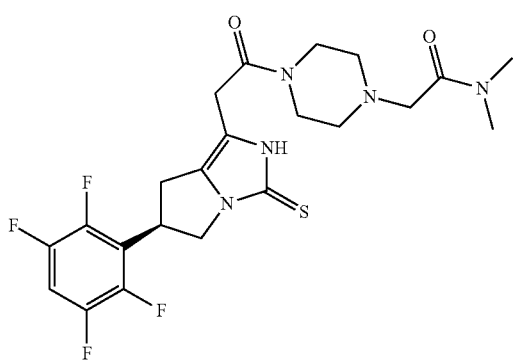 [SMILES: CN(C)C(=O)CN1CCN(C(=O)Cc2[nH]c(=S)n3c2C[C@H](c2c(F)c(F)cc(F)c2F)C3)CC1]

Compound was prepared analogous manner to Example 32 from (R)-1-(H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone and isolated as a light beige powder.

$^1$H NMR (DMSO$_{d6}$): 1.71 (1H, m), 7.85 (1H, m), 4.50 (1H, quin, J=8.5 Hz), 4.18 (1H, dd, J=11.2, 9.5 Hz), 3.77 (1H, dd, J=11.6, 7.8 Hz), 3.50 (2H, s), 3.44 (4H, m), 3.24 (1H, br dd, J=15.8, 9.5 Hz), 3.16 (2H, s), 2.99 (3H, s), 2.86 (1H, dd, J=7.8, 15.7 Hz), 2.80 (3H, s), 2.41 (4H, m).

$^{13}$C NMR (DMSO$_{d6}$): 168.7, 166.4, 155.2, 146.4, 146.4, 146.4, 146.4, 146.3, 146.3, 146.2, 146.2, 145.3, 145.3, 145.3, 145.3, 145.2, 145.2, 145.2, 145.2, 144.8, 144.8, 144.7, 144.7, 144.6, 144.6, 143.7, 143.7, 143.7, 143.7, 143.6, 143.6, 143.6, 143.6, 129, 120.5, 120.4, 120.3, 114.2, 105.8, 105.7, 105.5, 59.5, 52.5, 52.1, 48.5, 45.2, 41.3, 36.6, 35.8, 34.9, 29.2, 29.

Example 86: (R)-1-(2-(6-(2,3,5,6-tetrafluorophenyl)-3-thioxo-2,5,6,7-tetrahydro-3H-pyrrolo[1,2-c]imidazol-1-yl)acetyl)piperidine-4-carboxamide

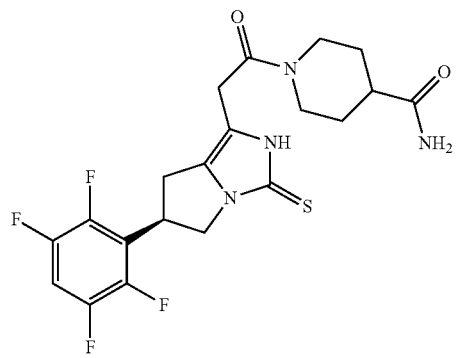 [SMILES: NC(=O)C1CCN(C(=O)Cc2[nH]c(=S)n3c2C[C@H](c2c(F)c(F)cc(F)c2F)C3)CC1]

Compound was prepared analogous manner to Example 32 from (R)-1-(H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone and isolated as a beige powder.

$^1$H NMR (DMSO$_{d6}$): 1.70 (1H, br d, J=4.5 Hz), 7.85 (1H, quin, J=8.7 Hz), 7.28 (1H, br s), 6.80 (1H, br s), 4.49 (1H, quin, J=8.4 Hz), 4.30 (1H, br d, J=13.1 Hz), 4.18 (1H, dd, J=9.7, 11.3 Hz), 3.86 (1H, br d, J=11.9 Hz), 3.77 (1H, dd, J=11.7, 7.8 Hz), 3.50 (2H, m), 3.24 (1H, ddd, J=15.7, 9.1, 6.5 Hz), 3.02 (1H, m), 2.87 (1H, dd, J=7.9, 15.7 Hz), 2.60 (1H, m), 2.32 (1H, tt, J=11.4, 3.8 Hz), 1.69 (2H, m), 1.47 (1H, m), 1.35 (1H, m).

$^{13}$C NMR (DMSO$_{d6}$): 175.9, 175.9, 166.3, 166.2, 155.2, 146.4, 146.4, 146.4, 146.3, 146.3, 146.3, 146.2, 145.3, 145.3, 145.3, 145.3, 145.2, 145.2, 145.2, 145.2, 144.8, 144.8, 144.7, 144.7, 144.6, 144.6, 143.7, 143.7, 143.7, 143.7, 143.7, 143.6, 143.6, 143.6, 143.6, 143.6, 143.6, 129, 120.4, 120.3, 120.2, 114.4, 105.9, 105.7, 105.5, 48.4, 44.8, 41.2, 41, 35.8, 29.1, 29.1, 29, 28.7, 28.1.

Example 87: (R)-1-(1,4-dioxa-8-azaspiro[4.5]decan-8-yl)-2-(6-(2,3,5,6-tetrafluorophenyl)-3-thioxo-2,5,6,7-tetrahydro-3H-pyrrolo[1,2-c]imidazol-1-yl)ethan-1-one

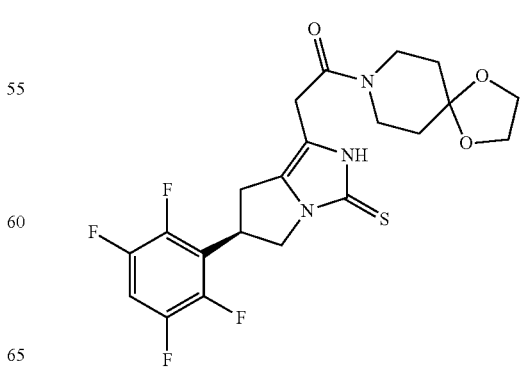

Compound was prepared analogous manner to Example 32 from (R)-1-(H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone and isolated as a white powder.

¹H NMR (DMSO$_{d6}$): 1.68 (1H, m), 7.85 (1H, m), 4.49 (1H, quin, J=8.5 Hz), 4.17 (1H, dd, J=11.4, 9.2 Hz), 3.90 (4H, s), 3.78 (1H, dd, J=11.7, 7.7 Hz), 3.53 (2H, s), 3.49 (4H, m), 3.24 (1H, dd, J=15.8, 9.4 Hz), 2.85 (1H, dd, J=15.8, 7.9 Hz), 1.63 (2H, m), 1.55 (2H, br s).

¹³C NMR (DMSO$_{d6}$): 166.4, 155.2, 146.4, 146.4, 146.4, 146.3, 146.3, 146.2, 145.3, 145.3, 145.3, 145.2, 145.2, 144.8, 144.8, 144.7, 144.7, 144.6, 144.6, 143.7, 143.7, 143.7, 143.6, 143.6, 143.6, 143.6, 143.6, 129.1, 120.5, 120.4, 120.3, 114.3, 106.3, 105.8, 105.7, 105.5, 63.8, 48.4, 43.4, 35.8, 34.9, 34.3, 29.2, 29.

Example 88: (S)-2-(6-(3-chloro-2,6-difluorophenyl)-3-thioxo-2,5,6,7-tetrahydro-3H-pyrrolo[1,2-c]imidazol-1-yl)-N-isopropylacetamide

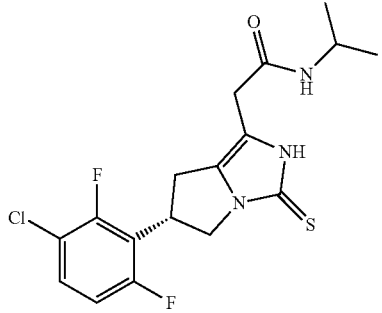 [SMILES: CC(C)NC(=O)Cc1[nH]c(=S)n2c1C[C@@H](c1c(F)ccc(Cl)c1F)C2]

Compound was prepared analogous manner to Example 32 from (S)-1-(1H-imidazol-1-yl)-2-(6-(3-chloro-2,6-difluorophenyl)-3-thioxo-3,5,6,7-tetrahydro-2H-pyrrolo[1,2-c]imidazol-1-yl)ethanone and isolated as a white solid.

¹H NMR (DMSO$_{d6}$): 1.75 (1H, br s), 7.86 (1H, br d, J=7.5 Hz), 7.61 (1H, m), 7.22 (1H, m), 4.44 (1H, quin, J=8.6 Hz), 4.14 (1H, dd, J=11.4, 9.3 Hz), 3.80 (1H, m), 3.72 (1H, dd, J=11.6, 8.1 Hz), 3.21 (1H, dd, J=9.2, 15.8 Hz), 3.19 (2H, s), 2.84 (1H, dd, J=15.8, 8.3 Hz), 1.03 (6H, d, J=6.6 Hz).

¹³C NMR (DMSO$_{d6}$): 166.5, 160.1, 160.1, 158.5, 158.5, 156.6, 156.5, 155.1, 154.9, 154.9, 129.7, 129.6, 128.9, 118.8, 118.7, 118.6, 116.1, 116, 115.9, 115.9, 114.5, 113.2, 113.2, 113.1, 113.1, 48.5, 40.6, 35.6, 31.5, 29.3, 22.3.

Example 89: (S)-2-(6-(3-chloro-2,6-difluorophenyl)-3-thioxo-2,5,6,7-tetrahydro-3H-pyrrolo[1,2-c]imidazol-1-yl)-N-(3-morpholinopropyl)acetamide

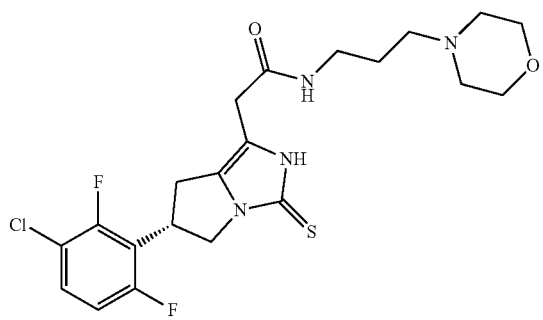 [SMILES: O=C(Cc1[nH]c(=S)n2c1C[C@@H](c1c(F)ccc(Cl)c1F)C2)NCCCN1CCOCC1]

Compound was prepared analogous manner to Example 32 from (S)-1-(1H-imidazol-1-yl)-2-(6-(3-chloro-2,6-difluorophenyl)-3-thioxo-3,5,6,7-tetrahydro-2H-pyrrolo[1,2-c]imidazol-1-yl)ethanone and isolated as a white solid.

¹H NMR (DMSO$_{d6}$): 11.75 (1H, s), 7.93 (1H, br t, J=5.5 Hz), 7.62 (1H, m), 7.22 (1H, m), 4.44 (1H, quin, J=8.7 Hz), 4.15 (1H, dd, J=11.2, 9.4 Hz), 3.73 (1H, dd, J=11.5, 8.1 Hz), 3.53 (4H, br t, J=4.5 Hz), 3.22 (2H, s), 3.21 (1H, m), 3.06 (2H, m), 2.84 (1H, dd, J=15.8, 8.4 Hz), 2.29 (4H, br s), 2.24 (2H, br t, J=7.2 Hz), 1.53 (2H, quin, J=7.1 Hz).

¹³C NMR (DMSO$_{d6}$): 167.5, 160.2, 160.1, 158.5, 158.5, 156.6, 156.5, 155.2, 154.9, 154.9, 129.7, 129.7, 129, 118.7, 118.6, 118.5, 116.1, 116.1, 116, 115.9, 114.3, 113.3, 113.2, 113.1, 113.1, 66.2, 55.8, 53.3, 48.5, 37.1, 35.6, 31.5, 29.3, 25.9.

Example 90: 2-((S)-6-(3-bromo-2,6-difluorophenyl)-3-thioxo-2,5,6,7-tetrahydro-3H-pyrrolo[1,2-c]imidazol-1-yl)-N—((R)-tetrahydrofuran-3-yl)acetamide

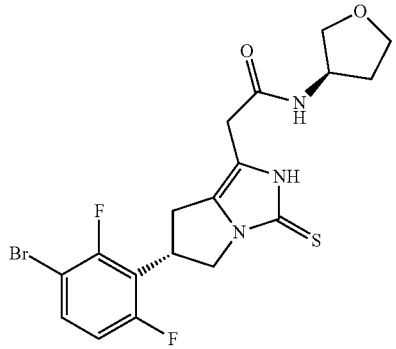 [SMILES: O=C(Cc1[nH]c(=S)n2c1C[C@@H](c1c(F)ccc(Br)c1F)C2)N[C@@H]1CCOC1]

Compound was prepared analogous manner to Example 32 from (S)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a light cream powder.

¹H NMR (DMSO$_{d6}$): 1.75 (1H, s), 8.22 (1H, d, J=6.6 Hz), 7.72 (1H, td, J=8.4, 5.7 Hz), 7.16 (1H, m), 4.44 (1H, quin, J=8.6 Hz), 4.20 (1H, m), 4.14 (1H, dd, J=11.4, 9.2 Hz), 3.76 (1H, m), 3.72 (2H, m), 3.65 (1H, td, J=8.2, 5.6 Hz), 3.45 (1H, dd, J=8.9, 3.6 Hz), 3.24 (2H, s), 3.21 (1H, dd, J=9.3, 15.7 Hz), 2.83 (1H, dd, J=15.6, 8.1 Hz), 2.06 (1H, m), 1.71 (1H, m).

¹³C NMR (DMSO$_{d6}$): 167.5, 160.8, 160.8, 159.2, 159.1, 157.5, 157.5, 155.9, 155.9, 155.1, 132.5, 132.4, 129.1, 118.8, 118.7, 118.5, 114.2, 113.8, 113.8, 113.6, 113.6, 104.1, 104, 103.9, 103.9, 72.4, 66.3, 49.8, 48.6, 35.6, 32, 31.3, 29.3.

Example 91: (S)-2-(6-(3-bromo-2,6-difluorophenyl)-3-thioxo-2,5,6,7-tetrahydro-3H-pyrrolo[1,2-c]imidazol-1-yl)-1-(4-methylpiperazin-1-yl)ethan-1-one

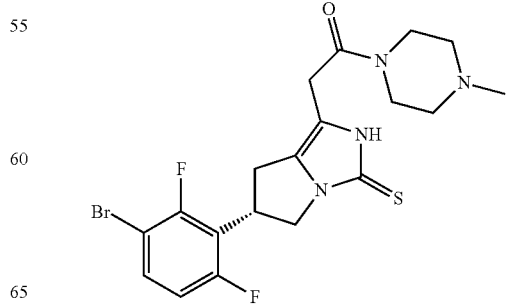

Compound was prepared analogous manner to Example 32 from (S)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a light cream solid.

$^1$H NMR (DMSO$_{d6}$): 1.70 (1H, s), 7.72 (1H, m), 7.16 (1H, m), 4.45 (1H, quin, J=8.5 Hz), 4.15 (1H, dd, J=11.4, 9.4 Hz), 3.72 (1H, dd, J=11.7, 7.8 Hz), 3.49 (2H, m), 3.43 (4H, m), 3.20 (1H, dd, J=15.8, 9.3 Hz), 2.81 (1H, dd, J=15.8, 8.0 Hz), 2.26 (4H, m), 2.17 (3H, s).

$^{13}$C NMR (DMSO$_{d6}$): 166.5, 160.8, 160.7, 159.1, 159.1, 157.5, 157.5, 155.9, 155.8, 155.2, 132.5, 132.4, 129.2, 118.9, 118.7, 118.6, 114.1, 113.8, 113.8, 113.6, 113.6, 104.1, 104, 103.9, 103.9, 54.6, 54.2, 48.6, 45.6, 45.1, 41.2, 35.7, 29.3, 29.1.

Example 92: (S)-2-(6-(3-bromo-2,6-difluorophenyl)-3-thioxo-2,5,6,7-tetrahydro-3H-pyrrolo[1,2-c]imidazol-1-yl)-N-butyl-N-methylacetamide

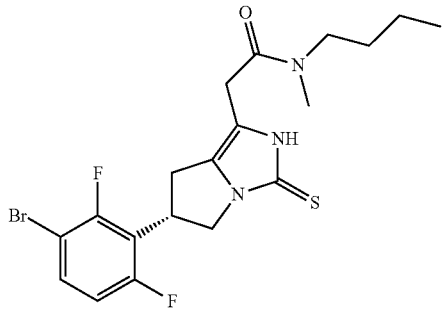 [SMILES: CCCCN(C)C(=O)Cc1[nH]c(=S)n2c1C[C@@H](c1c(F)ccc(Br)c1F)C2]

Compound was prepared analogous manner to Example 32 from (S)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a light beige solid.

$^1$H NMR (DMSO$_{d6}$): 1.71 (1H, br s), 7.72 (1H, m), 7.17 (1H, m), 4.44 (1H, m), 4.15 (1H, dd, J=9.4, 11.3 Hz), 3.72 (1H, dd, J=11.5, 7.8 Hz), 3.47 (2H, m), 3.24 (3H, m), 2.95 (1.6H, s), 2.82 (1H, m), 2.79 (1.4H, s), 1.49 (1H, quin, J=7.6 Hz), 1.40 (1H, m), 1.31-1.15 (2H, m), 0.90, 0.85 (3H, 2 t, J=7.2 Hz).

$^{13}$C NMR (DMSO$_{d6}$): 167.6, 167.5, 160.8, 160.7, 159.1, 159.1, 157.5, 157.5, 155.9, 155.8, 155, 132.5, 132.4, 129.2, 129.1, 118.8, 118.8, 118.7, 118.7, 118.6, 118.6, 114.4, 114.3, 113.8, 113.8, 113.6, 113.6, 104.1, 104, 103.9, 103.9, 49.1, 48.6, 46.7, 35.7, 35, 33.1, 30, 29.4, 29.3, 29.3, 28.9, 28.8, 19.5, 19.3, 13.7.

Example 93: (S)-2-(6-(3-bromo-2,6-difluorophenyl)-3-thioxo-2,5,6,7-tetrahydro-3H-pyrrolo[1,2-c]imidazol-1-yl)-N-(2-hydroxyethyl)acetamide

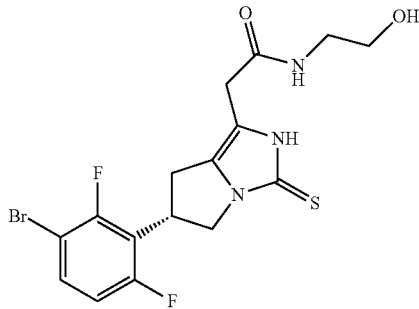 [SMILES: O=C(Cc1[nH]c(=S)n2c1C[C@@H](c1c(F)ccc(Br)c1F)C2)NCCO]

Compound was prepared analogous manner to Example 32 from (S)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a light beige powder.

$^1$H NMR (DMSO$_{d6}$): 11.73 (1H, s), 7.96 (1H, br t, J=5.5 Hz), 7.72 (1H, m), 7.17 (1H, m), 4.67 (1H, br s), 4.44 (1H, quin, J=8.7 Hz), 4.14 (1H, dd, J=9.5, 11.4 Hz), 3.72 (1H, dd, J=11.5, 8.1 Hz), 3.39 (2H, br t, J=5.7 Hz), 3.24 (2H, m), 3.21 (1H, dd, J=15.7, 9.5 Hz), 3.11 (2H, q, J=6.0 Hz), 2.84 (1H, dd, J=15.8, 8.4 Hz).

$^{13}$C NMR (DMSO$_{d6}$): 167.7, 160.8, 160.8, 159.2, 159.1, 157.6, 157.5, 155.9, 155.9, 155.1, 132.5, 132.4, 129.1, 118.7, 118.6, 118.4, 114.3, 113.8, 113.8, 113.6, 113.6, 104.1, 104, 103.9, 103.9, 59.7, 48.5, 41.7, 35.7, 31.5, 29.2.

Example 94: (S)-2-(6-(3-bromo-2,6-difluorophenyl)-3-thioxo-2,5,6,7-tetrahydro-3H-pyrrolo[1,2-c]imidazol-1-yl)-N-cyclopropylacetamide

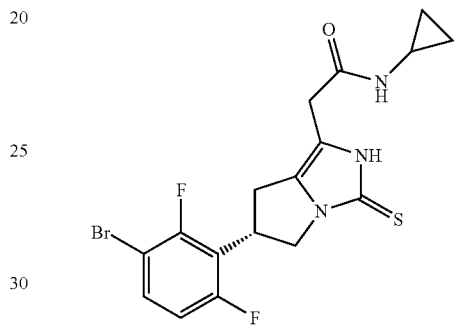

Compound was prepared analogous manner to Example 32 from (S)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a brown powder.

$^1$H NMR (DMSO$_{d6}$): 11.73 (1H, s), 8.03 (1H, br d, J=3.5 Hz), 7.72 (1H, td, J=8.4, 5.9 Hz), 7.16 (1H, t, J=9.5 Hz), 4.44 (1H, quin, J=8.7 Hz), 4.14 (1H, dd, J=9.6, 11.2 Hz), 3.72 (1H, dd, J=11.4, 8.1 Hz), 3.21 (1H, dd, J=9.7, 15.9 Hz), 3.18 (2H, s), 2.83 (1H, dd, J=15.6, 8.3 Hz), 2.59 (1H, m), 0.59 (2H, m), 0.38 (2H, m).

$^{13}$C NMR (DMSO$_{d6}$): 168.7, 160.8, 160.8, 159.2, 159.1, 157.6, 157.5, 155.9, 155.9, 155.1, 132.5, 132.4, 129.1, 118.7, 118.6, 118.5, 114.2, 113.8, 113.8, 113.6, 113.6, 104.1, 104, 103.9, 103.9, 48.5, 35.6, 31.3, 29.3, 22.4, 5.6, 5.6.

Example 95: (S)-2-(6-(3-bromo-2,6-difluorophenyl)-3-thioxo-2,5,6,7-tetrahydro-3H-pyrrolo[1,2-c]imidazol-1-yl)-N-(cyclopropylmethyl)acetamide

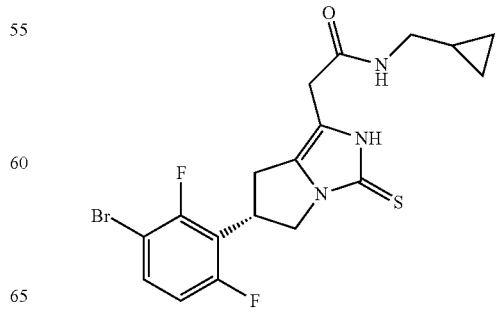

Compound was prepared analogous manner to Example 32 from (S)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a light cream powder.

$^1$H NMR (DMSO$_{d6}$): 1.75 (1H, s), 8.04 (1H, t, J=5.5 Hz), 7.72 (1H, ddd, J=8.9, 8.1, 5.8 Hz), 7.16 (1H, m), 4.44 (1H, quin, J=8.7 Hz), 4.15 (1H, dd, J=11.4, 9.3 Hz), 3.72 (1H, dd, J=11.6, 8.1 Hz), 3.24 (2H, s), 3.22 (1H, dd, J=9.5, 15.7 Hz), 2.92 (2H, t, J=6.2 Hz), 2.84 (1H, dd, J=15.7, 8.2 Hz), 0.87 (1H, m), 0.37 (2H, m), 0.13 (2H, m).

$^{13}$C NMR (DMSO$_{d6}$): 167.4, 160.8, 160.8, 159.2, 159.1, 157.6, 157.5, 155.9, 155.9, 155.1, 132.5, 132.4, 129.1, 118.7, 118.6, 118.5, 114.3, 113.8, 113.8, 113.6, 113.6, 104.1, 104, 103.9, 103.9, 48.5, 43.1, 35.6, 31.5, 29.3, 10.7, 3.2.

Example 96: (S)-2-(6-(3-bromo-2,6-difluorophenyl)-3-thioxo-2,5,6,7-tetrahydro-3H-pyrrolo[1,2-c]imidazol-1-yl)acetamide

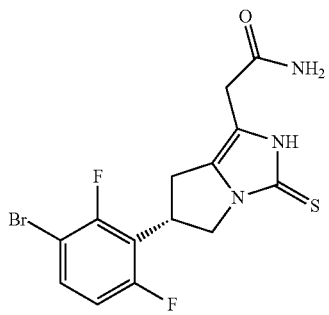 [SMILES: NC(=O)Cc1[nH]c(=S)n2c1C[C@@H](c1c(F)ccc(Br)c1F)C2]

Compound was prepared analogous manner to Example 32 from (S)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a light beige powder.

$^1$H NMR (DMSO$_{d6}$): 11.73 (1H, s), 7.72 (1H, td, J=8.4, 5.7 Hz), 7.37 (1H, br s), 7.17 (1H, m), 7.02 (1H, br s), 4.45 (1H, quin, J=8.8 Hz), 4.14 (1H, dd, J=9.5, 11.2 Hz), 3.73 (1H, dd, J=11.5, 8.1 Hz), 3.23 (1H, dd, J=9.3, 16.0 Hz), 3.21 (2H, d, J=4.8 Hz), 2.85 (1H, dd, J=15.7, 8.4 Hz).

$^{13}$C NMR (DMSO$_{d6}$): 169.8, 160.8, 160.8, 159.2, 159.1, 157.6, 157.5, 155.9, 155.9, 155.1, 132.5, 132.4, 129.2, 118.7, 118.5, 118.4, 114.3, 113.8, 113.8, 113.6, 113.6, 104.1, 104, 103.9, 103.9, 48.5, 35.7, 31.2, 29.2.

Example 97: (S)-2-(6-(3-bromo-2,6-difluorophenyl)-3-thioxo-2,5,6,7-tetrahydro-3H-pyrrolo[1,2-c]imidazol-1-yl)-N-propylacetamide

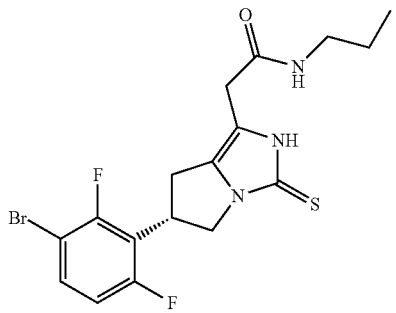 [SMILES: CCCNC(=O)Cc1[nH]c(=S)n2c1C[C@@H](c1c(F)ccc(Br)c1F)C2]

Compound was prepared analogous manner to Example 32 from (S)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a light cream powder.

$^1$H NMR (DMSO$_{d6}$): 1.74 (1H, s), 7.91 (1H, br t, J=5.5 Hz), 7.72 (1H, ddd, J=8.8, 8.1, 5.8 Hz), 7.16 (1H, m), 4.44 (1H, quin, J=8.7 Hz), 4.14 (1H, dd, J=11.4, 9.3 Hz), 3.72 (1H, dd, J=11.5, 8.0 Hz), 3.23 (2H, s), 3.20 (1H, dd, J=9.0, 15.8 Hz), 2.99 (2H, m), 2.83 (1H, dd, J=15.8, 8.3 Hz), 1.39 (2H, sxt, J=7.2 Hz), 0.82 (3H, t, J=7.4 Hz).

$^{13}$C NMR (DMSO$_{d6}$): 167.4, 160.8, 160.8, 159.2, 159.1, 157.6, 157.5, 155.9, 155.9, 155.1, 132.5, 132.4, 129.2, 129.1, 118.7, 118.6, 118.5, 114.3, 113.8, 113.8, 113.6, 113.6, 104.1, 104, 103.9, 103.9, 48.5, 40.5, 35.7, 31.5, 29.3, 22.3, 11.4.

Example 98: 1-((S)-2-(hydroxymethyl)pyrrolidin-1-yl)-2-((R)-6-(2,3,5,6-tetrafluorophenyl)-3-thioxo-2,5,6,7-tetrahydro-3H-pyrrolo[1,2-c]imidazol-1-yl)ethan-1-one

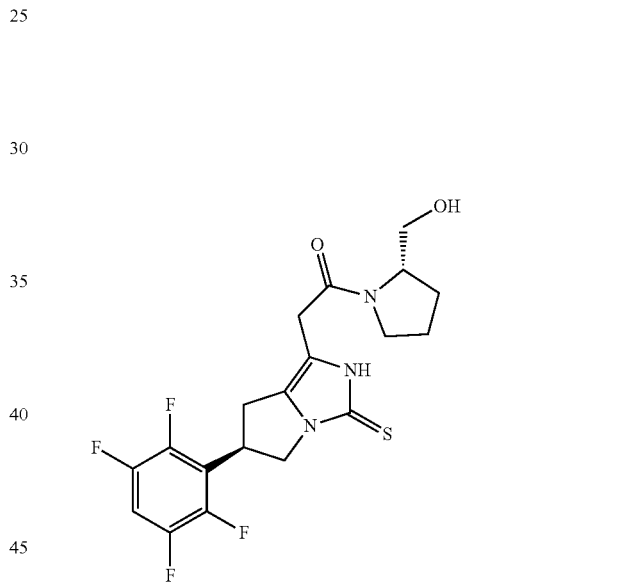

Compound was prepared analogous manner to Example 32 from (R)-1-(H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone and isolated as a light beige powder.

$^1$H NMR (DMSO$_{d6}$): 1.72 (1H, br s), 7.85 (1H, m), 5.18-4.57 (1H, 2 br s), 4.48 (1H, quin, J=8.5 Hz), 4.18 (1H, br t, J=10.3 Hz), 4.0-3.86 (1H, 2 m), 3.78 (1H, br dd, J=11.5, 7.8 Hz), 3.67-3.18 (7H, multiplets), 2.87 (1H, br dd, J=15.7, 7.9 Hz), 2.01-1.68 (4H, m).

$^{13}$C NMR (DMSO$_{d6}$): 166.8, 166.7, 155.1, 155, 146.4, 146.4, 146.4, 146.3, 146.3, 146.3, 146.2, 145.3, 145.3, 145.2, 145.2, 144.8, 144.8, 144.7, 144.7, 144.6, 143.7, 143.7, 143.7, 143.6, 143.6, 143.6, 143.6, 129, 129, 120.5, 120.4, 120.3, 114.6, 114.1, 105.8, 105.7, 105.5, 62.6, 60.9, 58.8, 58.8, 48.4, 47, 45.5, 35.8, 35.7, 30.7, 30, 29.2, 27.8, 26.7, 23.4, 21.4.

Example 99: (S)—N-cyclobutyl-2-(6-(2,3,5,6-tetrafluorophenyl)-3-thioxo-2,5,6,7-tetrahydro-3H-pyrrolo[1,2-c]imidazol-1-yl)acetamide

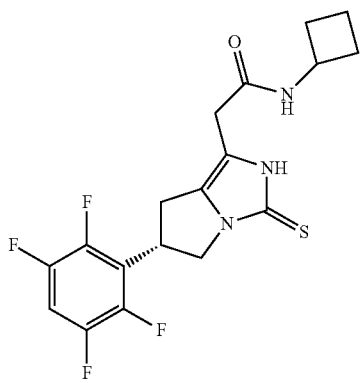 [SMILES: O=C(Cc1[nH]c(=S)n2c1C[C@@H](c1c(F)c(F)cc(F)c1F)C2)NC1CCC1]

Compound was prepared analogous manner to Example 32 from (S)-1-(1H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone and isolated as a beige powder.

$^{1}$H NMR (DMSO$_{d6}$): 11.74 (1H, s), 8.20 (1H, br d, J=7.6 Hz), 7.85 (1H, m), 4.48 (1H, quin, J=8.6 Hz), 4.16 (2H, m), 3.77 (1H, dd, J=11.7, 7.8 Hz), 3.24 (1H, dd, J=15.8, 9.4 Hz), 3.20 (2H, s), 2.87 (1H, dd, J=15.8, 8.1 Hz), 2.12 (2H, m), 1.86 (2H, m), 1.60 (2H, m).

$^{13}$C NMR (DMSO$_{d6}$): 166.5, 155.2, 146.4, 146.3, 146.3, 146.2, 145.3, 145.3, 145.3, 145.2, 145.2, 144.8, 144.8, 144.7, 144.7, 144.7, 144.6, 144.6, 143.7, 143.7, 143.7, 143.6, 143.6, 143.6, 143.6, 128.9, 120.3, 114.3, 105.9, 105.7, 105.6, 48.4, 44, 35.7, 31.4, 30.2, 30.2, 29.2, 14.6.

Example 100: 2-((S)-6-(3-bromo-2,6-difluorophenyl)-3-thioxo-2,5,6,7-tetrahydro-3H-pyrrolo[1,2-c]imidazol-1-yl)-1-((S)-2-(hydroxymethyl)pyrrolidin-1-yl)ethan-1-one

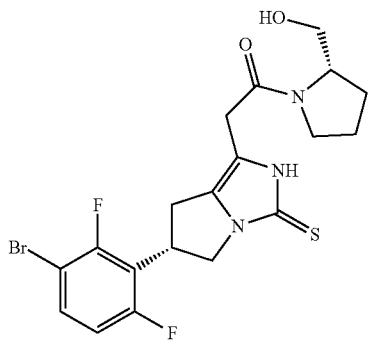 [SMILES: O=C(Cc1[nH]c(=S)n2c1C[C@@H](c1c(F)ccc(Br)c1F)C2)N1CCC[C@H]1CO]

Compound was prepared analogous manner to Example 32 from (S)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a brown solid.

$^{1}$H NMR (DMSO$_{d6}$): 1.70 (1H, s), 7.16 (1H, m), 4.97 (0.35H, br s), 4.71 (0.65H, br s), 4.45 (1H, m), 4.15 (1H, dd, J=9.0, 11.2 Hz), 3.95 (0.35H, m), 3.91 (0.65H, m), 3.72 (1H, dd, J=11.6, 7.9 Hz), 3.57 (0.35H, m), 3.52-3.36 (3.65H, m), 3.31-3.14 (3H, m), 2.83 (1H, m), 1.84 (4H, m).

$^{13}$C NMR (DMSO$_{d6}$): 166.8, 160.8, 160.7, 159.2, 159.1, 157.5, 157.5, 155.9, 155.9, 155, 155, 132.5, 132.4, 129.3, 129.1, 118.9, 118.8, 118.7, 118.7, 114.5, 114, 113.8, 113.8, 113.6, 113.6, 104.1, 104, 103.9, 103.9, 62.7, 60.9, 58.8, 58.8, 48.6, 48.6, 47, 45.5, 35.6, 30.7, 30.1, 29.4, 29.3, 27.8, 26.7, 23.4, 21.4.

Example 101: (S)-2-(6-(3-bromo-2,6-difluorophenyl)-3-thioxo-2,5,6,7-tetrahydro-3H-pyrrolo[1,2-c]imidazol-1-yl)-1-(pyrrolidin-1-yl)ethan-1-one

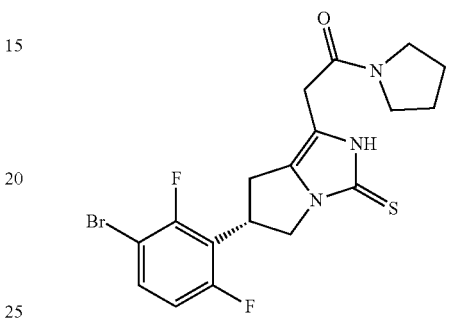

Compound was prepared analogous manner to Example 32 from (S)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a light brown powder.

$^{1}$H NMR (DMSO$_{d6}$): 1.71 (1H, s), 7.72 (1H, m), 7.17 (1H, m), 4.45 (1H, quin, J=8.6 Hz), 4.15 (1H, dd, J=11.4, 9.3 Hz), 3.72 (1H, dd, J=11.7, 7.8 Hz), 3.42 (2H, m), 3.41 (2H, s), 3.27 (2H, t, J=6.9 Hz), 3.21 (1H, dd, J=15.7, 9.4 Hz), 2.81 (1H, dd, J=15.7, 8.1 Hz), 1.87 (2H, m), 1.76 (2H, m).

$^{13}$C NMR (DMSO$_{d6}$): 166.1, 160.8, 160.8, 159.2, 159.1, 157.5, 157.5, 155.9, 155.9, 155.1, 132.5, 132.4, 129.2, 118.9, 118.8, 118.6, 114.1, 113.8, 113.8, 113.6, 113.6, 104.1, 104, 103.9, 103.9, 48.6, 46.2, 45.5, 35.6, 30.5, 29.3, 25.6, 24.

Example 102: (S)-2-(6-(3-bromo-2,6-difluorophenyl)-3-thioxo-2,5,6,7-tetrahydro-3H-pyrrolo[1,2-c]imidazol-1-yl)-N-cyclobutylacetamide

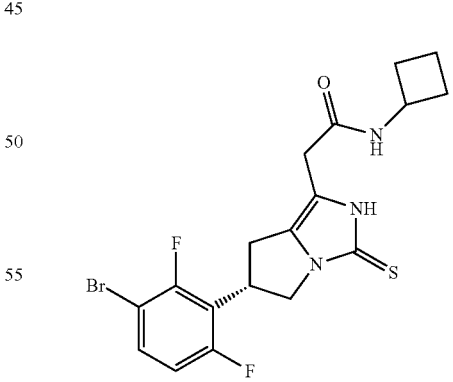

Compound was prepared analogous manner to Example 32 from (S)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a light beige powder.

$^{1}$H NMR (DMSO$_{d6}$): 1.73 (1H, s), 8.20 (1H, br d, J=7.6 Hz), 7.72 (1H, m), 7.17 (1H, m), 4.44 (1H, quin, J=8.7 Hz), 4.15 (2H, m), 3.72 (1H, dd, J=11.6, 7.9 Hz), 3.20 (1H, dd, J=9.3, 15.5 Hz), 3.19 (2H, s), 2.82 (1H, dd, J=15.6, 8.3 Hz), 2.12 (2H, m), 1.86 (2H, m), 1.60 (2H, m).

$^{13}$C NMR (DMSO$_{d6}$): 166.5, 160.8, 160.8, 159.2, 159.1, 157.6, 157.5, 155.9, 155.9, 155.1, 132.5, 132.4, 129.1, 118.8, 118.6, 118.5, 114.2, 113.8, 113.8, 113.6, 113.6, 104.1, 104, 103.9, 103.9, 48.6, 44, 35.6, 31.4, 30.2, 30.2, 29.3, 14.7.

Example 103: (S)-2-(6-(3-bromo-2,6-difluorophenyl)-3-thioxo-2,5,6,7-tetrahydro-3H-pyrrolo[1,2-c]imidazol-1-yl)-N-(2-methoxyethyl)acetamide

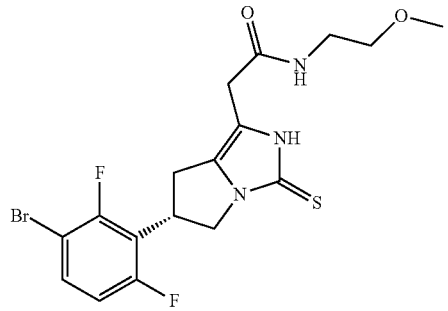

Compound was prepared analogous manner to Example 32 from (S)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a beige powder.

$^{1}$H NMR (DMSO$_{d6}$): 1.74 (1H, s), 8.04 (1H, br t, J=5.4 Hz), 7.72 (1H, m), 7.16 (1H, m), 4.44 (1H, quin, J=8.7 Hz), 4.14 (1H, dd, J=m), 3.72 (1H, dd, J=11.5, 8.0 Hz), 3.32 (2H, t, J=5.6 Hz), 3.24 (2H, m), 3.22-3.17 (3H, m), 3.20 (3H, s), 2.83 (1H, dd, J=15.8, 8.3 Hz).

$^{13}$C NMR (DMSO$_{d6}$): 167.7, 160.8, 160.8, 159.2, 159.1, 157.6, 157.5, 155.9, 155.9, 155.1, 132.5, 132.4, 129.1, 118.7, 118.6, 118.5, 114.3, 113.8, 113.8, 113.6, 104.1, 104, 103.9, 103.9, 70.5, 57.8, 48.5, 38.6, 35.6, 31.5, 29.3.

Example 104: (R)-1-(pyrrolidin-1-yl)-2-(6-(2,3,5,6-tetrafluorophenyl)-3-thioxo-2,5,6,7-tetrahydro-3H-pyrrolo[1,2-c]imidazol-1-yl)ethan-1-one

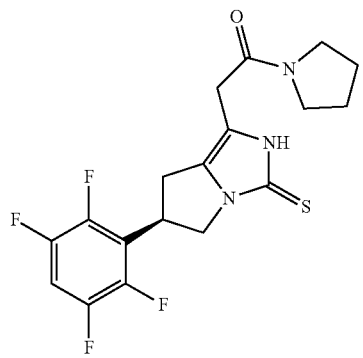 [SMILES: O=C(Cc1[nH]c(=S)n2c1C[C@H](c1c(F)c(F)cc(F)c1F)C2)N1CCCC1]

Compound was prepared analogous manner to Example 32 from (R)-1-(1H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone and isolated as a light beige powder.

$^{1}$H NMR (DMSO$_{d6}$): 1.71 (1H, br s), 7.85 (1H, m), 4.49 (1H, quin, J=8.5 Hz), 4.18 (1H, dd, J=11.6, 9.1 Hz), 3.78 (1H, dd, J=11.7, 7.7 Hz), 3.42 (4H, m), 3.27 (2H, t, J=7 Hz), 3.25 (1H, dd, J=9.3, 15.8 Hz), 2.87 (1H, dd, J=15.8, 7.9 Hz), 1.88 (2H, m), 1.76 (2H, m).

$^{13}$C NMR (DMSO$_{d6}$): 166.1, 155.1, 146.4, 146.4, 146.3, 146.3, 146.3, 146.3, 146.3, 146.2, 145.3, 145.3, 145.3, 145.2, 145.2, 145.2, 144.8, 144.8, 144.7, 144.7, 144.7, 144.6, 144.6, 143.7, 143.7, 143.6, 143.6, 143.6, 143.6, 129, 120.5, 120.4, 120.3, 114.2, 105.8, 105.7, 105.5, 48.5, 46.1, 45.5, 35.7, 30.4, 29.2, 25.6, 24.

Example 105: (S)-1-(pyrrolidin-1-yl)-2-(6-(2,3,5,6-tetrafluorophenyl)-3-thioxo-2,5,6,7-tetrahydro-3H-pyrrolo[1,2-c]imidazol-1-yl)ethan-1-one

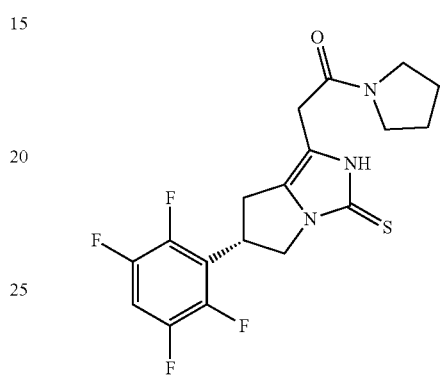

Compound was prepared analogous manner to Example 32 from (S)-1-(1H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone and isolated as a light beige powder.

$^{1}$H NMR (DMSO$_{d6}$): 1.72 (1H, br s), 7.85 (1H, m), 4.49 (1H, quin, J=8.5 Hz), 4.18 (1H, dd, J=11.5, 9.2 Hz), 3.77 (1H, dd, J=11.6, 7.8 Hz), 3.42 (4H, m), 3.27 (2H, t, J=7 Hz), 3.25 (1H, dd, J=9.3, 15.8 Hz), 2.87 (1H, dd, J=15.8, 7.9 Hz), 1.87 (2H, m), 1.76 (2H, m).

$^{13}$C NMR (DMSO$_{d6}$): 166.1, 155.1, 146.4, 146.4, 146.3, 146.3, 146.3, 146.3, 146.2, 145.3, 145.3, 145.3, 145.3, 145.2, 145.2, 145.2, 144.8, 144.8, 144.7, 144.7, 144.6, 144.6, 144.6, 143.7, 143.7, 143.6, 143.6, 143.6, 143.6, 129, 120.5, 120.4, 120.3, 114.2, 105.8, 105.7, 105.5, 48.5, 46.1, 45.5, 35.7, 30.4, 29.2, 25.6, 24.

Example 106: (S)-2-(6-(3-chloro-2,6-difluorophenyl)-3-thioxo-2,5,6,7-tetrahydro-3H-pyrrolo[1,2-c]imidazol-1-yl)-N-(2-(pyridin-2-yl)ethyl)acetamide hydrochloride

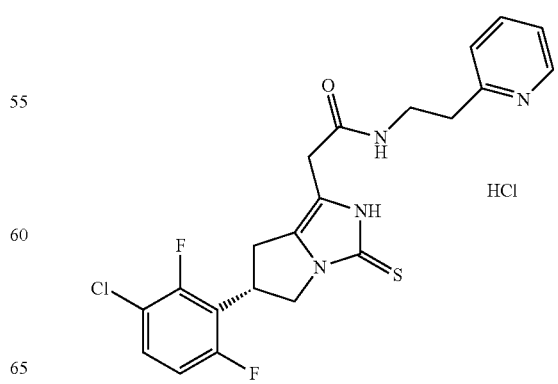

Compound was prepared analogous manner to Example 32 from (S)-1-(1H-imidazol-1-yl)-2-(6-(3-chloro-2,6-difluorophenyl)-3-thioxo-3,5,6,7-tetrahydro-2H-pyrrolo[1,2-c]imidazol-1-yl)ethanone and isolated as an off-white solid.

¹H NMR (DMSO$_{d6}$): 11.72 (1H, br s), 8.70 (1H, br d, J=5.1 Hz), 8.25 (1H, br s), 8.12 (1H, br t, J=5.6 Hz), 7.71 (2H, m), 7.62 (1H, m), 7.23 (1H, m), 4.41 (1H, quin, J=8.7 Hz), 4.14 (1H, dd, J=9.4, 11.4 Hz), 3.73 (1H, dd, J=11.4, 8.2 Hz), 3.47 (2H, m), 3.21 (2H, m), 3.15 (1H, dd, J=15.8, 9.2 Hz), 3.07 (2H, t, J=6.6 Hz), 2.79 (1H, dd, J=15.8, 8.4 Hz).

¹³C NMR (DMSO$_{d6}$): 168, 160.2, 160.1, 158.6, 158.5, 156.6, 156.6, 155.9, 155.8, 155.2, 155.2, 155, 154.9, 143.7, 143.2, 129.8, 129.7, 129.4, 126.3, 123.9, 118.7, 118.5, 118.4, 116.1, 116, 114.1, 114, 113.3, 113.1, 48.5, 38.1, 35.6, 34.3, 31.5, 29.2.

Example 107: (S)-2-(6-(3-chloro-2,6-difluorophenyl)-3-thioxo-2,5,6,7-tetrahydro-3H-pyrrolo[1,2-c]imidazol-1-yl)-N-(2-methoxyethyl)acetamide

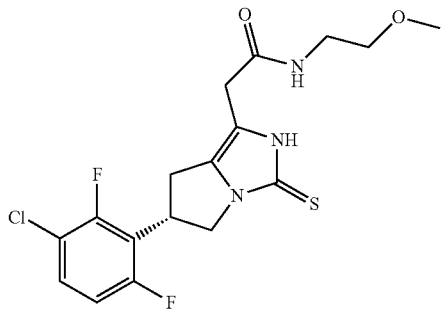 [SMILES: COCCNC(=O)Cc1[nH]c(=S)n2c1C[C@@H](c1c(F)ccc(Cl)c1F)C2]

Compound was prepared analogous manner to Example 32 from (S)-1-(1H-imidazol-1-yl)-2-(6-(3-chloro-2,6-difluorophenyl)-3-thioxo-3,5,6,7-tetrahydro-2H-pyrrolo[1,2-c]imidazol-1-yl)ethanone and isolated as an off-white solid.

¹H NMR (DMSO$_{d6}$): 1.74 (1H, s), 8.04 (1H, br t, J=5.6 Hz), 7.61 (1H, m), 7.22 (1H, m), 4.44 (1H, quin, J=8.7 Hz), 4.15 (1H, dd, J=11.4, 9.2 Hz), 3.73 (1H, dd, J=11.6, 8.1 Hz), 3.32 (2H, t, J=5.5 Hz), 3.26-3.15 (5H, m), 3.20 (3H, s), 2.84 (1H, dd, J=15.8, 8.2 Hz).

¹³C NMR (DMSO$_{d6}$): 167.7, 155.1, 129.7, 129.6, 129.1, 118.7, 118.6, 118.5, 116.1, 116, 115.9, 115.9, 114.2, 113.2, 113.2, 113.1, 113.1, 70.5, 57.8, 48.5, 38.6, 35.6, 31.5, 29.2.

Example 108: (S)-2-(6-(3-chloro-2,6-difluorophenyl)-3-thioxo-2,5,6,7-tetrahydro-3H-pyrrolo[1,2-c]imidazol-1-yl)acetamide

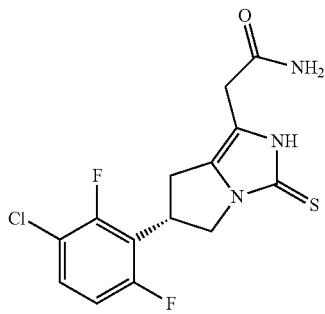 [SMILES: NC(=O)Cc1[nH]c(=S)n2c1C[C@@H](c1c(F)ccc(Cl)c1F)C2]

Compound was prepared analogous manner to Example 32 from (S)-1-(1H-imidazol-1-yl)-2-(6-(3-chloro-2,6-difluorophenyl)-3-thioxo-3,5,6,7-tetrahydro-2H-pyrrolo[1,2-c]imidazol-1-yl)ethanone and isolated as an off-white solid.

¹H NMR (DMSO$_{d6}$): 11.73 (1H, br s), 7.62 (1H, m), 7.37 (1H, br s), 7.22 (1H, m), 7.01 (1H, br s), 4.45 (1H, quin, J=8.7 Hz), 4.14 (1H, dd, J=9.4, 11.2 Hz), 3.74 (1H, dd, J=11.5, 8.1 Hz), 3.23 (1H, dd, J=9.3, 15.7 Hz), 3.21 (2H, m), 2.86 (1H, dd, J=15.7, 8.5 Hz).

¹³C NMR (DMSO$_{d6}$): 169.8, 160.2, 160.1, 158.5, 158.5, 156.6, 156.5, 155.1, 155, 154.9, 129.7, 129.6, 129.2, 118.7, 118.6, 118.4, 116.1, 116, 115.9, 115.9, 114.4, 113.2, 113.2, 113.1, 113.1, 48.5, 35.6, 31.2, 29.2.

Example 109: (S)-2-(6-(3-chloro-2,6-difluorophenyl)-3-thioxo-2,5,6,7-tetrahydro-3H-pyrrolo[1,2-c]imidazol-1-yl)-N-(pyridin-3-ylmethyl)acetamide Hydrochloride

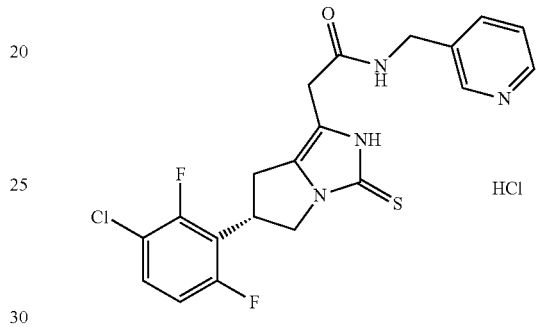

Compound was prepared analogous manner to Example 32 from (S)-1-(1H-imidazol-1-yl)-2-(6-(3-chloro-2,6-difluorophenyl)-3-thioxo-3,5,6,7-tetrahydro-2H-pyrrolo[1,2-c]imidazol-1-yl)ethanone and isolated as an off-white solid.

¹H NMR (DMSO$_{d6}$): 11.81 (1H, s), 8.51 (1H, t, J=5.9 Hz), 8.48 (1H, dd, J=0.6, 2.4 Hz), 8.41 (1H, dd, J=4.7, 1.6 Hz), 7.65 (1H, m), 7.62 (1H, m), 7.31 (1H, ddd, J=0.8, 4.8, 7.8 Hz), 7.22 (1H, m), 4.42 (1H, quin, J=8.7 Hz), 4.29 (2H, m), 4.14 (1H, dd, J=9.4, 11.3 Hz), 3.73 (1H, dd, J=11.5, 8.1 Hz), 3.32 (2H, m), 3.14 (1H, dd, J=15.7, 9.2 Hz), 2.76 (1H, dd, J=15.8, 8.4 Hz).

¹³C NMR (DMSO$_{d6}$): 167.9, 160.2, 160.1, 158.5, 158.5, 156.6, 156.5, 155.3, 154.9, 154.9, 148.8, 148.1, 135.2, 134.7, 129.7, 129.7, 129.3, 123.3, 118.6, 118.5, 118.4, 116.1, 116, 115.9, 115.9, 114, 113.3, 113.2, 113.1, 113.1, 48.5, 39.8, 35.6, 31.4, 29.2.

Example 110: (S)-2-(6-(3-chloro-2,6-difluorophenyl)-3-thioxo-2,5,6,7-tetrahydro-3H-pyrrolo[1,2-c]imidazol-1-yl)-1-(pyrrolidin-1-yl)ethan-1-one

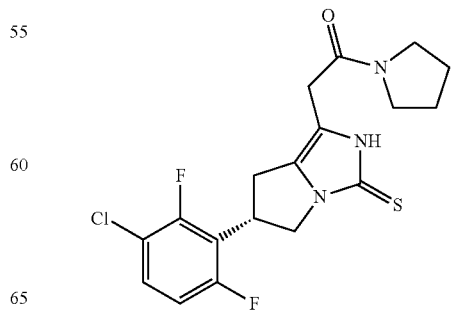

Compound was prepared analogous manner to Example 32 from (S)-1-(1H-imidazol-1-yl)-2-(6-(3-chloro-2,6-difluorophenyl)-3-thioxo-3,5,6,7-tetrahydro-2H-pyrrolo[1,2-c]imidazol-1-yl)ethanone and isolated as an off-white solid.

$^1$H NMR (DMSO$_{d6}$): 1.71 (1H, br s), 7.61 (1H, m), 7.21 (1H, m), 4.44 (1H, quin, J=8.5 Hz), 4.16 (1H, dd, J=11.2, 9.5 Hz), 3.73 (1H, dd, J=11.6, 7.9 Hz), 3.42 (2H, m), 3.41 (2 H, s), 3.27 (2H, t, J=6.9 Hz), 3.22 (1H, dd, J=15.8, 9.3 Hz), 2.82 (1H, dd, J=15.8, 8.1 Hz), 1.87 (2H, m), 1.76 (2H, m).

$^{13}$C NMR (DMSO$_{d6}$): 166.1, 160.1, 160.1, 158.5, 158.5, 156.6, 156.5, 155.1, 154.9, 154.9, 129.7, 129.6, 129.2, 118.9, 118.8, 118.6, 116.1, 116, 115.9, 115.9, 114.1, 113.2, 113.2, 113.1, 113.1, 48.6, 46.1, 45.5, 35.6, 30.4, 29.3, 25.6, 24.

Example 111: (S)-2-(6-(3-chloro-2,6-difluorophenyl)-3-thioxo-2,5,6,7-tetrahydro-3H-pyrrolo[1,2-c]imidazol-1-yl)-1-(4,4-difluoropiperidin-1-yl)ethan-1-one

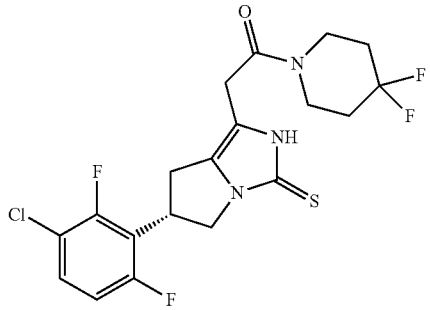 [SMILES: O=C(Cc1[nH]c(=S)n2c1C[C@@H](c1c(F)ccc(Cl)c1F)C2)N1CCC(F)(F)CC1]

Compound was prepared analogous manner to Example 32 from (S)-1-(1H-imidazol-1-yl)-2-(6-(3-chloro-2,6-difluorophenyl)-3-thioxo-3,5,6,7-tetrahydro-2H-pyrrolo[1,2-c]imidazol-1-yl)ethanone and isolated as an off-white solid.

$^1$H NMR (DMSO$_{d6}$): 1.68 (1H, s), 7.61 (1H, m), 7.21 (1H, m), 4.45 (1H, quin, J=8.6 Hz), 4.16 (1H, dd, J=11.5, 9.2 Hz), 3.74 (1H, dd, J=11.7, 7.8 Hz), 3.57 (2H, s), 3.56 (4H, m), 3.23 (1H, dd, J=15.8, 9.3 Hz), 2.83 (1H, dd, J=15.7, 8.1 Hz), 2.02 (2H, m), 1.91 (2H, m).

$^{13}$C NMR (DMSO$_{d6}$): 166.8, 160.1, 160.1, 158.5, 158.5, 156.6, 156.5, 155.2, 154.9, 154.9, 129.7, 129.6, 129.4, 124.3, 122.7, 121.1, 118.9, 118.7, 118.6, 116.1, 116, 115.9, 115.9, 114, 113.2, 113.2, 113.1, 113.1, 48.6, 42.1, 42.1, 42.1, 38.5, 38.4, 38.4, 35.6, 33.9, 33.8, 33.6, 33.3, 33.2, 33, 29.2, 28.9.

Example 112: (S)-2-(6-(3-chloro-2,6-difluorophenyl)-3-thioxo-2,5,6,7-tetrahydro-3H-pyrrolo[1,2-c]imidazol-1-yl)-N-(1,1-dioxidotetrahydro-2H-thiopyran-4-yl)acetamide

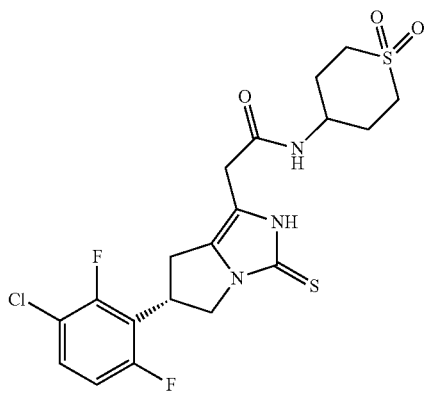 [SMILES: O=C(Cc1[nH]c(=S)n2c1C[C@@H](c1c(F)ccc(Cl)c1F)C2)NC1CCS(=O)(=O)CC1]

Compound was prepared analogous manner to Example 32 from (S)-1-(1H-imidazol-1-yl)-2-(6-(3-chloro-2,6-difluorophenyl)-3-thioxo-3,5,6,7-tetrahydro-2H-pyrrolo[1,2-c]imidazol-1-yl)ethanone and isolated as an off-white solid.

$^1$H NMR (DMSO$_{d6}$): 1.77 (1H, s), 8.09 (1H, d, J=7.6 Hz), 7.61 (1H, m), 7.22 (1H, m), 4.44 (1H, quin, J=8.6 Hz), 4.15 (1H, dd, J=11.4, 9.2 Hz), 3.93 (1H, m), 3.73 (1H, dd, J=11.7, 8.0 Hz), 3.27-3.17 (5H, m), 3.08 (2H, m), 2.85 (1H, dd, J=15.8, 8.2 Hz), 2.04 (2H, m), 1.90 (2H, m).

$^{13}$C NMR (DMSO$_{d6}$): 167.1, 160.2, 160.1, 158.5, 158.5, 156.6, 156.5, 155.2, 154.9, 154.9, 129.7, 129.6, 129.2, 118.8, 118.7, 118.6, 116.1, 116, 115.9, 115.9, 114.1, 113.3, 113.2, 113.1, 113.1, 48.5, 48.3, 43.9, 35.6, 31.4, 29.3, 29.1.

Example 113: (S)-2-(6-(3-chloro-2,6-difluorophenyl)-3-thioxo-2,5,6,7-tetrahydro-3H-pyrrolo[1,2-c]imidazol-1-yl)-N-(2,2,2-trifluoroethyl)acetamide

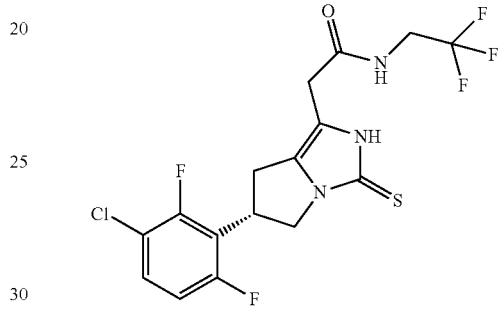

Compound was prepared analogous manner to Example 32 from (S)-1-(1H-imidazol-1-yl)-2-(6-(3-chloro-2,6-difluorophenyl)-3-thioxo-3,5,6,7-tetrahydro-2H-pyrrolo[1,2-c]imidazol-1-yl)ethanone and isolated as an off-white solid.

$^1$H NMR (DMSO$_{d6}$): 1.79 (1H, s), 8.64 (1H, br t, J=6.3 Hz), 7.61 (1H, m), 7.21 (1H, m), 4.44 (1H, quin, J=8.7 Hz), 4.16 (1H, dd, J=11.2, 9.3 Hz), 3.90 (2H, qd, J=9.8, 6.5 Hz), 3.74 (1H, dd, J=11.5, 8.0 Hz), 3.36 (2H, m), 3.21 (1H, dd, J=15.8, 9.3 Hz), 2.84 (1H, dd, J=15.8, 8.3 Hz).

$^{13}$C NMR (DMSO$_{d6}$): 168.6, 160.2, 160.1, 158.5, 158.5, 156.6, 156.5, 155.3, 154.9, 154.9, 129.7, 129.7, 129.4, 127.5, 125.6, 123.8, 121.9, 118.7, 118.6, 118.5, 116.1, 116, 115.9, 115.9, 113.5, 113.2, 113.2, 113.1, 113.1, 48.5, 35.6, 31.1, 29.2.

Example 114: (S)-2-(6-(3-chloro-2,6-difluorophenyl)-3-thioxo-2,5,6,7-tetrahydro-3H-pyrrolo[1,2-c]imidazol-1-yl)-N-(2-(methylsulfonyl)ethyl)acetamide

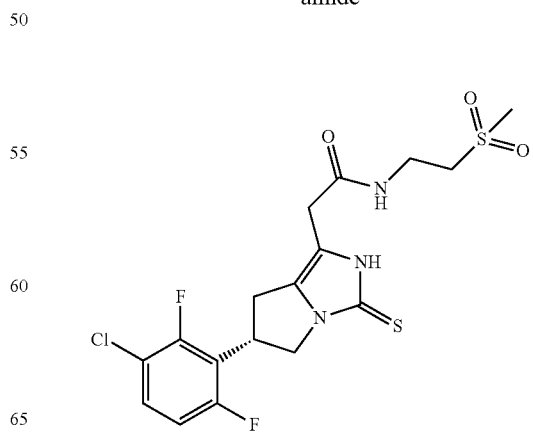

Compound was prepared analogous manner to Example 32 from (S)-1-(1H-imidazol-1-yl)-2-(6-(3-chloro-2,6-difluorophenyl)-3-thioxo-3,5,6,7-tetrahydro-2H-pyrrolo[1,2-c]imidazol-1-yl)ethanone and isolated as an off-white solid.

¹H NMR (DMSO$_{d6}$): 11.74 (1H, s), 8.20 (1H, t, J=5.6 Hz), 7.62 (1H, m), 7.22 (1H, m), 4.44 (1H, quin, J=8.7 Hz), 4.15 (1H, dd, J=11.4, 9.2 Hz), 3.74 (1H, dd, J=11.7, 8.1 Hz), 3.46 (2H, m), 3.27 (2H, m), 3.24 (2H, t, J=6.9 Hz), 3.23 (1H, m), 2.99 (3H, s), 2.87 (1H, dd, J=15.8, 8.4 Hz).

¹³C NMR (DMSO$_{d6}$): 168.1, 160.2, 160.1, 158.5, 158.5, 156.6, 156.5, 155.3, 154.9, 154.9, 129.7, 129.6, 129.5, 118.6, 118.5, 118.4, 116.1, 115.9, 113.8, 113.2, 113.1, 53, 48.5, 40.8, 35.6, 33, 31.3, 29.2.

Example 115: (S)-2-(6-(3-chloro-2,6-difluorophenyl)-3-thioxo-2,5,6,7-tetrahydro-3H-pyrrolo[1,2-c]imidazol-1-yl)-N-(2-(4,4-difluoropiperidin-1-yl)ethyl)acetamide Hydrochloride

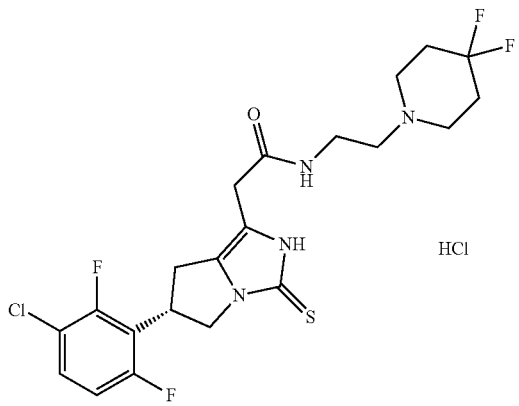 [SMILES: O=C(Cc1[nH]c(=S)n2c1C[C@@H](c1c(F)ccc(Cl)c1F)C2)NCCN1CCC(F)(F)CC1 ; Cl]

Compound was prepared analogous manner to Example 32 from (S)-1-(1H-imidazol-1-yl)-2-(6-(3-chloro-2,6-difluorophenyl)-3-thioxo-3,5,6,7-tetrahydro-2H-pyrrolo[1,2-c]imidazol-1-yl)ethanone and isolated as an off-white solid.

¹H NMR (DMSO$_{d6}$): 1.75 (1H, s), 10.88 (1H, br s), 8.28 (1H, br t, J=5.3 Hz), 7.62 (1H, m), 7.22 (1H, m), 4.45 (1H, quin, J=8.7 Hz), 4.15 (1H, dd, J=9.4, 11.4 Hz), 3.75 (1H, dd, J=8.2, 11.5 Hz), 3.64 (2H, br s), 3.46 (2H, q, J=5.9 Hz), 3.33 (2H, m), 3.24 (1H, dd, J=9.2, 15.8 Hz), 3.20 (2H, br s), 3.15 (2H, br s), 2.88 (1H, dd, J=15.8, 8.5 Hz), 2.46-2.24 (4H, 2 br s).

¹³C NMR (DMSO$_{d6}$): 168.5, 160.2, 160.1, 158.5, 158.5, 156.6, 155.3, 155, 129.8, 129.7, 129.6, 118.6, 118.5, 118.4, 116.2, 116.1, 116.1, 116, 113.8, 113.3, 113.3, 113.1, 113.1, 54.2, 48.7, 48.5, 35.6, 33.9, 31.5, 30.4, 29.3.

Example 116: 2-((R)-6-(3-bromo-2,6-difluorophenyl)-3-thioxo-2,5,6,7-tetrahydro-3H-pyrrolo[1,2-c]imidazol-1-yl)-N—((R)-tetrahydrofuran-3-yl)acetamide

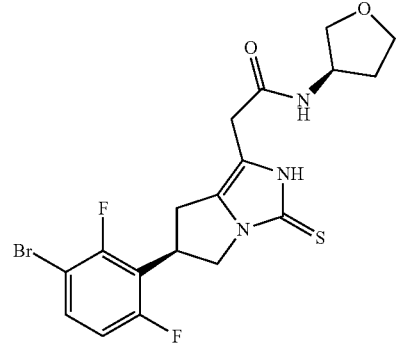 [SMILES: O=C(Cc1[nH]c(=S)n2c1C[C@H](c1c(F)ccc(Br)c1F)C2)N[C@@H]1CCOC1]

Compound was prepared analogous manner to Example 32 from (R)-1-(H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a light cream powder.

¹H NMR (DMSO$_{d6}$): 1.74 (1H, s), 8.22 (1H, d, J=6.6 Hz), 7.72 (1H, m), 7.16 (1H, m), 4.44 (1H, quin, J=8.6 Hz), 4.21 (1H, m), 4.14 (1H, dd, J=11.4, 9.2 Hz), 3.76 (1H, m), 3.71 (2H, m), 3.65 (1H, td, J=8.2, 5.6 Hz), 3.45 (1H, dd, J=8.9, 3.7 Hz), 3.24 (2H, s), 3.22 (1H, dd, J=9.4, 15.8 Hz), 2.83 (1H, dd, J=15.8, 8.1 Hz), 2.06 (1H, m), 1.71 (1H, m).

¹³C NMR (DMSO$_{d6}$): 167.5, 160.8, 160.8, 159.2, 159.1, 157.5, 157.5, 155.9, 155.9, 155.1, 132.5, 132.4, 129.1, 118.8, 118.7, 118.5, 114.2, 113.8, 113.8, 113.6, 113.6, 104.1, 104, 103.9, 103.9, 72.4, 66.3, 49.7, 48.6, 35.6, 32, 31.3, 29.3.

Example 117: (R)-2-(6-(3-bromo-2,6-difluorophenyl)-3-thioxo-2,5,6,7-tetrahydro-3H-pyrrolo[1,2-c]imidazol-1-yl)-1-(4,4-difluoropiperidin-1-yl)ethan-1-one

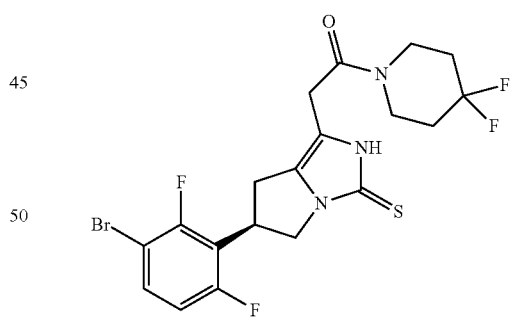

Compound was prepared analogous manner to Example 32 from (R)-1-(H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a cream powder.

¹H NMR (DMSO$_{d6}$): 11.68 (1H, s), 7.72 (1H, ddd, J=9.0, 8.0, 5.7 Hz), 7.16 (1H, m), 4.45 (1H, quin, J=8.5 Hz), 4.16 (1H, dd, J=11.5, 9.2 Hz), 3.73 (1H, dd, J=11.6, 7.8 Hz), 3.56 (6H, m), 3.22 (1H, dd, J=15.8, 9.3 Hz), 2.82 (1H, dd, J=15.8, 8.1 Hz), 2.02 (2H, m), 1.91 (2H, m).

¹³C NMR (DMSO$_{d6}$): 166.8, 160.8, 160.7, 159.2, 159.1, 157.5, 157.5, 155.9, 155.8, 155.2, 132.5, 132.4, 129.4, 124.2, 122.6, 121, 118.8, 118.7, 118.6, 114, 113.8, 113.7, 113.6, 113.6, 104, 104, 103.9, 103.9, 48.6, 42.1, 42.1, 42.1, 38.5, 38.4, 38.4, 35.7, 33.9, 33.8, 33.6, 33.3, 33.2, 33, 29.3, 28.9.

Example 118: (R)-2-(6-(3-bromo-2,6-difluorophenyl)-3-thioxo-2,5,6,7-tetrahydro-3H-pyrrolo[1,2-c]imidazol-1-yl)-N-(2-(methylsulfonyl)ethyl)acetamide

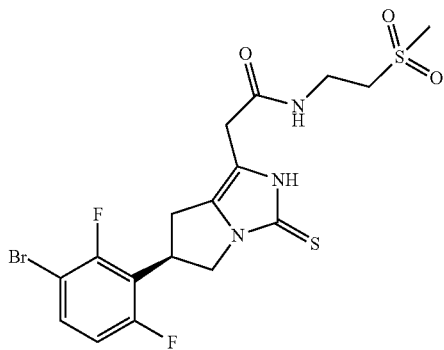 [SMILES: CS(=O)(=O)CCNC(=O)Cc1[nH]c(=S)n2c1C[C@H](c1c(F)ccc(Br)c1F)C2]

Compound was prepared analogous manner to Example 32 from (R)-1-(H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a light brown powder.

$^1$H NMR (DMSO$_{d6}$): 11.74 (1H, s), 8.19 (1H, t, J=5.7 Hz), 7.72 (1H, ddd, J=8.9, 8.1, 5.8 Hz), 7.17 (1H, m), 4.44 (1H, quin, J=8.7 Hz), 4.15 (1H, dd, J=11.4, 9.2 Hz), 3.73 (1H, dd, J=11.6, 8.2 Hz), 3.46 (2H, m), 3.30-3.18 (5H, m), 2.99 (3H, s), 2.86 (1H, dd, J=15.8, 8.4 Hz).

$^{13}$C NMR (DMSO$_{d6}$): 168.1, 160.8, 160.8, 159.2, 159.1, 157.6, 157.5, 155.9, 155.9, 155.3, 132.5, 132.4, 129.5, 118.6, 118.5, 118.4, 113.8, 113.6, 113.6, 104.1, 104, 103.9, 103.9, 53, 48.5, 40.8, 35.7, 33, 31.3, 29.2.

Example 119: (R)-2-(6-(3-bromo-2,6-difluorophenyl)-3-thioxo-2,5,6,7-tetrahydro-3H-pyrrolo[1,2-c]imidazol-1-yl)-N-(2-hydroxyethyl)acetamide

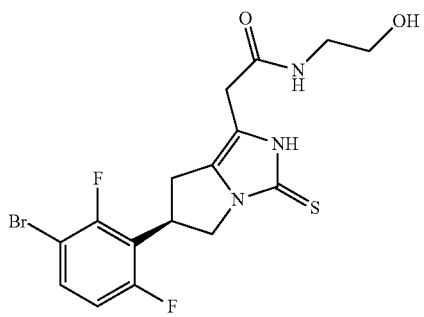 [SMILES: O=C(Cc1[nH]c(=S)n2c1C[C@H](c1c(F)ccc(Br)c1F)C2)NCCO]

Compound was prepared analogous manner to Example 32 from (R)-1-(H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a light cream powder.

$^1$H NMR (DMSO$_{d6}$): 11.72 (1H, s), 7.95 (1H, t, J=5.5 Hz), 7.72 (1H, m), 7.16 (1H, m), 4.66 (1H, t, J=5.4 Hz), 4.44 (1H, quin, J=8.7 Hz), 4.14 (1H, dd, J=11.4, 9.3 Hz), 3.72 (1H, dd, J=11.6, 8.1 Hz), 3.39 (2H, q, J=5.9 Hz), 3.24 (2H, m), 3.21 (1H, dd, J=15.8, 9.5 Hz), 3.11 (2H, q, J=6.0 Hz), 2.84 (1H, dd, J=15.8, 8.4 Hz).

$^{13}$C NMR (DMSO$_{d6}$): 167.7, 160.8, 160.8, 159.2, 159.1, 157.6, 157.5, 155.9, 155.9, 155.1, 132.5, 132.4, 129.1, 118.7, 118.6, 118.4, 114.3, 113.8, 113.8, 113.6, 113.6, 104.1, 104, 103.9, 103.9, 59.7, 48.5, 41.7, 35.7, 31.5, 29.3.

Example 120: 2-((R)-6-(3-bromo-2,6-difluorophenyl)-3-thioxo-2,5,6,7-tetrahydro-3H-pyrrolo[1,2-c]imidazol-1-yl)-N-(2-(hydroxymethyl)cyclopentyl)acetamide

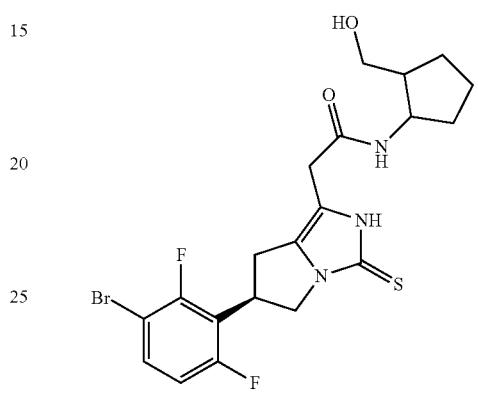

Compound was prepared analogous manner to Example 32 from (R)-1-(H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a light brown powder.

$^1$H NMR (DMSO$_{d6}$): 1.76 (1H, br s), 7.80 (0.5H, d, J=4.5 Hz), 7.80 (0.5H, d, J=4.5 Hz), 7.72 (1H, m), 7.16 (1H, m), 4.44 (1H, m), 4.32 (1H, m), 4.15 (1H, dd, J=11.1, 9.8 Hz), 4.08 (1H, m), 3.72 (1H, dd, J=11.0, 8.2 Hz), 3.33 (1H, m), 3.27 (2H, s), 3.25 (1H, m), 3.24 (1H, m), 2.84 (1H, m), 1.98 (1H, m), 1.80 (1H, m), 1.65 (2H, m), 1.47 (2H, m), 1.33 (1H, m).

$^{13}$C NMR (DMSO$_{d6}$): 167.8, 160.8, 160.8, 159.2, 159.1, 157.5, 157.5, 155.9, 155.9, 155.1, 132.5, 132.4, 129, 129, 118.8, 118.7, 118.5, 114.4, 113.8, 113.8, 113.6, 113.6, 104.1, 104, 103.9, 103.9, 60.9, 51.5, 51.5, 48.6, 45, 45, 35.7, 35.6, 31.4, 31.3, 31.3, 29.3, 26.2, 26.2, 21.5.

Example 121: 2-((R)-6-(3-bromo-2,6-difluorophenyl)-3-thioxo-2,5,6,7-tetrahydro-3H-pyrrolo[1,2-c]imidazol-1-yl)-1-(3-hydroxypiperidin-1-yl)ethan-1-one

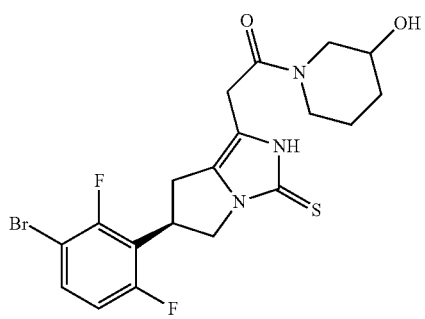 [SMILES: O=C(Cc1[nH]c(=S)n2c1C[C@H](c1c(F)ccc(Br)c1F)C2)N1CCCC(O)C1]

Compound was prepared analogous manner to Example 32 from (R)-1-(H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a light brown powder.

$^1$H NMR (DMSO$_{d6}$): 11.68 (1H, m), 7.72 (1H, ddd, J=8.7, 8.1, 5.8 Hz), 7.16 (1H, m), 4.89 (1H, m), 4.44 (1H, quin, J=8.6 Hz), 4.15 (1H, m), 4.08 (0.5H, m), 3.72 (1H, dd, J=11.5, 8.0 Hz), 3.64-3.43 (4H, m), 3.35 (0.5H, m), 3.26-3.13 (1.5H, m), 3.10 (0.5H, m), 3.00 (0.5H, m), 2.81 (1H, m), 2.57 (0.5H, m), 1.87-1.72 (1H, 2 m), 1.65 (1H, m), 1.44 (0.5H, m), 1.31 (1.5H, m).

$^{13}$C NMR (DMSO$_{d6}$): 166.7, 166.7, 166.4, 166.4, 160.8, 160.8, 159.2, 159.1, 157.5, 157.5, 155.9, 155.8, 155.1, 132.5, 132.4, 129.1, 118.9, 118.8, 118.7, 118.6, 118.6, 118.5, 114.4, 114.3, 114.3, 114.2, 113.8, 113.8, 113.6, 113.6, 104.1, 104, 103.9, 103.9, 65, 64.9, 54.9, 52.3, 48.6, 45.4, 45.4, 41.7, 41.7, 35.7, 32.8, 32.8, 32.3, 32.3, 29.3, 29.2, 29.1, 29, 23.4, 23.4, 21.7, 21.7.

Example 122: tert-butyl (R)-2-((2-((S)-6-(3-bromo-2,6-difluorophenyl)-3-thioxo-2,5,6,7-tetrahydro-3H-pyrrolo[1,2-c]imidazol-1-yl)acetamido)methyl)pyrrolidine-1-carboxylate

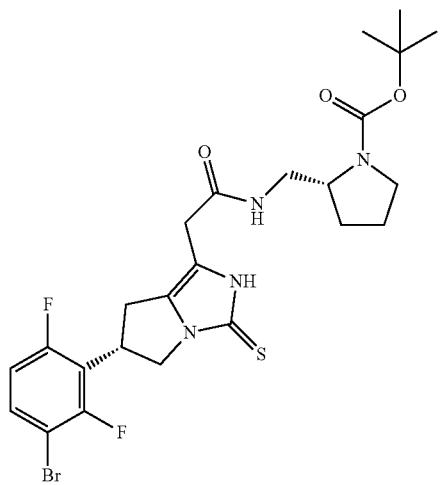 [SMILES: CC(C)(C)OC(=O)N1CCC[C@@H]1CNC(=O)Cc1[nH]c(=S)n2c1C[C@@H](c1c(F)ccc(Br)c1F)C2]

Compound was prepared analogous manner to Example 32 from (S)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a light brown powder.

$^1$H NMR (DMSO$_{d6}$): 1.74 (1H, 2 s), 8.00 (1H, m), 7.72 (1H, td, J=8.4, 5.8 Hz), 7.16 (1H, m), 4.44 (1H, quin, J=8.6 Hz), 4.15 (1H, dd, J=9.5, 11.4 Hz), 3.72 (1H, dd, J=8.0, 11.5 Hz), 3.71 (1H, m), 3.25 (2H, s), 3.20 (3H, m), 3.07, 2.96 (1H, 2 m), 2.83 (1H, m), 1.87-1.58 (5H, m), 1.38 (9H, s).

$^{13}$C NMR (DMSO$_{d6}$): 167.8, 160.8, 160.8, 159.2, 159.1, 157.6, 157.5, 155.9, 155.9, 155.2, 153.9, 153.4, 132.5, 132.4, 129.2, 129, 118.7, 118.6, 118.5, 118.5, 114.3, 114.3, 114.2, 113.8, 113.8, 113.6, 113.6, 104.1, 104, 103.9, 103.9, 78.4, 56.4, 48.5, 46.4, 46.1, 40.9, 35.7, 31.5, 29.3, 28.1, 27.6, 23.1, 22.2.

Example 123: (S)-2-(6-(3-bromo-2,6-difluorophenyl)-3-thioxo-2,5,6,7-tetrahydro-3H-pyrrolo[1,2-c]imidazol-1-yl)-1-(4-(methylsulfonyl)piperidin-1-yl)ethan-1-one

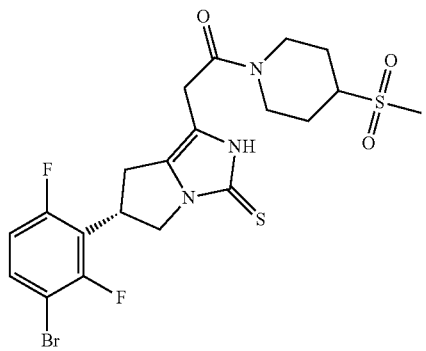 [SMILES: CS(=O)(=O)C1CCN(C(=O)Cc2[nH]c(=S)n3c2C[C@@H](c2c(F)ccc(Br)c2F)C3)CC1]

Compound was prepared analogous manner to Example 32 from (S)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a beige solid.

$^1$H NMR (DMSO$_{d6}$): 1.69 (1H, 2 s), 7.72 (1H, m), 7.16 (1H, m), 4.48 (1H, m), 4.44 (1H, quin, J=8.5 Hz), 4.15 (1H, dd, J=11.4, 9.2 Hz), 4.01 (1H, br d, J=13.6 Hz), 3.72 (1H, dd, J=11.6, 7.9 Hz), 3.54 (2H, m), 3.36 (1H, m), 3.21 (1H, m), 3.07 (1H, m), 2.94 (3H, s), 2.82 (1H, m), 2.61 (1H, m), 2.04 (2H, br d, J=12.5 Hz), 1.56 (1H, m), 1.42 (1H, m).

$^{13}$C NMR (DMSO$_{d6}$): 166.5, 166.5, 160.8, 160.8, 159.2, 159.1, 157.5, 157.5, 155.9, 155.8, 155.2, 132.5, 132.4, 129.3, 129.2, 118.7, 118.6, 118.5, 114.2, 113.8, 113.8, 113.6, 113.6, 104, 104, 103.9, 103.9, 58.4, 58.4, 48.6, 43.9, 37.5, 35.7, 29.2, 29, 29, 24.7, 24.1.

Example 124: (S)-2-(6-(3-bromo-2,6-difluorophenyl)-3-thioxo-2,5,6,7-tetrahydro-3H-pyrrolo[1,2-c]imidazol-1-yl)-N-(pyridin-3-ylmethyl)acetamide

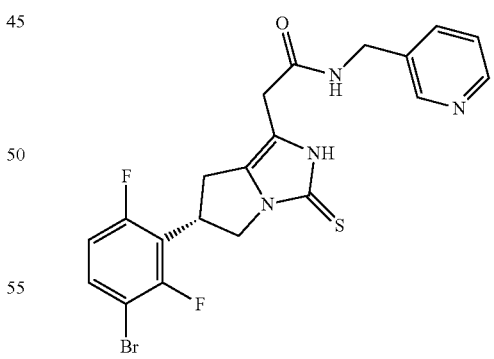

Compound was prepared analogous manner to Example 32 from (S)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a tan solid.

$^1$H NMR (DMSO$_{d6}$): 1.80 (1H, br s), 8.51 (1H, t, J=5.6 Hz), 8.48 (1H, s), 8.41 (1H, d, J=3.7 Hz), 7.73 (1H, m), 7.65 (1H, d, J=7.8 Hz), 7.31 (1H, dd, J=7.6, 4.8 Hz), 7.17 (1H, t, J=9.3 Hz), 4.42 (1H, quin, J=8.7 Hz), 4.29 (2H, d, J=5.7 Hz), 4.14 (1H, t, J=10.3 Hz), 3.72 (1H, dd, J=11.3, 8.4 Hz), 3.33 (2H, m), 3.13 (1H, br dd, J=15.7, 9.2 Hz), 2.75 (1H, br dd, J=15.7, 8.4 Hz).

$^{13}$C NMR (DMSO$_{d6}$): 167.9, 160.8, 160.8, 159.2, 159.1, 157.6, 157.5, 155.9, 155.9, 155.3, 148.8, 148.1, 135.1, 134.7, 132.5, 132.4, 129.3, 123.3, 118.6, 118.5, 118.3, 114, 113.8, 113.8, 113.6, 113.6, 104.1, 104, 103.9, 103.9, 48.5, 39.8, 35.6, 31.4, 29.2.

Example 125: (R)-2-(6-(3-bromo-2,6-difluorophenyl)-3-thioxo-2,5,6,7-tetrahydro-3H-pyrrolo[1,2-c]imidazol-1-yl)-1-(1,1-dioxidothiomorpholino)ethan-1-one

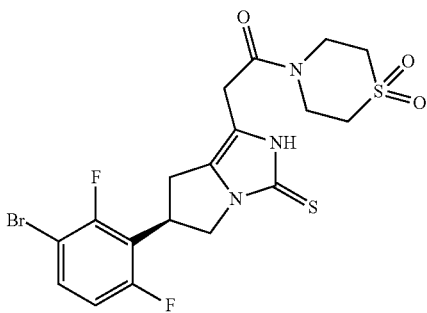 [SMILES: O=C(Cc1[nH]c(=S)n2c1C[C@H](c1c(F)ccc(Br)c1F)C2)N1CCS(=O)(=O)CC1]

Compound was prepared analogous manner to Example 32 from (R)-1-(H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a light cream powder.

$^1$H NMR (DMSO$_{d6}$): 1.63 (1H, s), 7.72 (1H, ddd, J=8.7, 8.1, 5.8 Hz), 7.17 (1H, m), 4.46 (1H, quin, J=8.6 Hz), 4.16 (1H, dd, J=11.3, 9.4 Hz), 3.87 (4H, m), 3.73 (1H, dd, J=11.6, 7.9 Hz), 3.62 (2H, s), 3.26 (2H, br m), 3.23 (1H, dd, J=15.9, 9.3 Hz), 3.10 (2H, br t, J=4.9 Hz), 2.84 (1H, dd, J=15.8, 8.1 Hz).

$^{13}$C NMR (DMSO$_{d6}$): 167.4, 160.8, 160.8, 159.2, 159.1, 157.5, 157.5, 155.9, 155.8, 155.2, 132.5, 132.4, 129.5, 118.8, 118.7, 118.6, 113.8, 113.8, 113.8, 113.6, 113.6, 104.1, 104, 103.9, 103.9, 51.3, 51.1, 48.6, 43.8, 40.3, 35.7, 29.2, 28.7.

Example 126: (R)-2-(6-(3-bromo-2,6-difluorophenyl)-3-thioxo-2,5,6,7-tetrahydro-3H-pyrrolo[1,2-c]imidazol-1-yl)-1-(4-(methylsulfonyl)piperidin-1-yl)ethan-1-one

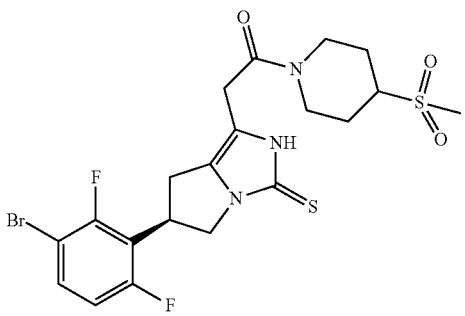 [SMILES: CS(=O)(=O)C1CCN(C(=O)Cc2[nH]c(=S)n3c2C[C@H](c2c(F)ccc(Br)c2F)C3)CC1]

Compound was prepared analogous manner to Example 32 from (R)-1-(H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a cream powder.

$^1$H NMR (DMSO$_{d6}$): 1.69 (1H, 2 s), 7.72 (1H, m), 7.16 (1H, m), 4.48 (1H, m), 4.44 (1H, quin, J=8.5 Hz), 4.15 (1H, dd, J=11.4, 9.2 Hz), 4.01 (1H, br d, J=13.6 Hz), 3.72 (1H, dd, J=11.6, 7.9 Hz), 3.54 (2H, m), 3.36 (1H, m), 3.21 (1H, m), 3.07 (1H, m), 2.94 (3H, s), 2.82 (1H, m), 2.61 (1H, m), 2.04 (2H, br d, J=12.5 Hz), 1.56 (1H, m), 1.42 (1H, m).

$^{13}$C NMR (DMSO$_{d6}$): 166.5, 166.5, 160.8, 160.8, 159.2, 159.1, 157.5, 157.5, 155.9, 155.8, 155.2, 132.5, 132.4, 129.3, 129.2, 118.7, 118.6, 118.5, 114.2, 113.8, 113.8, 113.6, 113.6, 104, 104, 103.9, 103.9, 58.4, 58.4, 48.6, 43.9, 37.5, 35.7, 29.2, 29, 29, 24.7, 24.1.

Example 127: 2-((R)-6-(3-bromo-2,6-difluorophenyl)-3-thioxo-2,5,6,7-tetrahydro-3H-pyrrolo[1,2-c]imidazol-1-yl)-N—((R)-1-cyclohexylethyl)acetamide

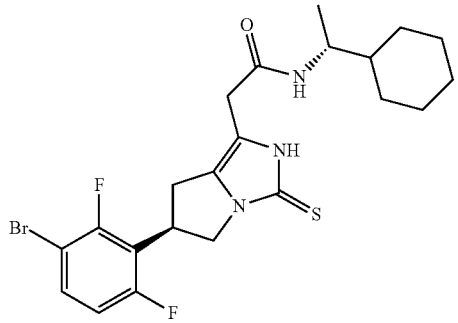 [SMILES: C[C@@H](NC(=O)Cc1[nH]c(=S)n2c1C[C@H](c1c(F)ccc(Br)c1F)C2)C1CCCCC1]

Compound was prepare analogous manner to Example 32 from (R)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a light cream powder.

$^1$H NMR (DMSO$_{d6}$): 1.76 (1H, s), 7.73 (2H, m), 7.16 (1H, m), 4.44 (1H, quin, J=8.6 Hz), 4.14 (1H, dd, J=11.4, 9.2 Hz), 3.72 (1H, dd, J=11.6, 7.9 Hz), 3.57 (1H, m), 3.22 (3H, m), 2.81 (1H, dd, J=15.7, 8.2 Hz), 1.64 (4.7H, m), 1.23 (1.3H, m), 1.09 (3H, m), 0.97 (3H, d, J=6.7 Hz), 0.88 (2H, m).

$^{13}$C NMR (DMSO$_{d6}$): 166.7, 160.8, 160.7, 159.1, 159.1, 157.6, 157.5, 155.9, 155.9, 155, 132.5, 132.4, 128.8, 118.8, 118.7, 118.6, 114.6, 113.8, 113.7, 113.6, 113.6, 104.1, 104, 103.9, 103.9, 48.7, 48.5, 42.3, 35.6, 31.6, 29.5, 28.8, 28.5, 26, 25.7, 25.7, 17.5.

Example 128: (R)-2-(6-(3-bromo-2,6-difluorophenyl)-3-thioxo-2,5,6,7-tetrahydro-3H-pyrrolo[1,2-c]imidazol-1-yl)-N-methyl-N-(tetrahydro-2H-pyran-4-yl)acetamide

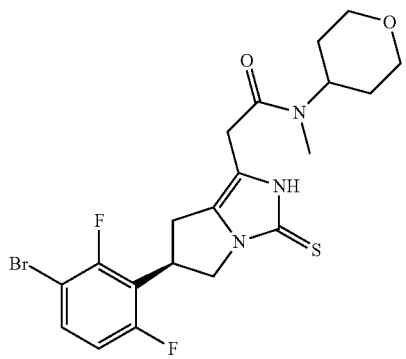 [SMILES: CN(C(=O)Cc1[nH]c(=S)n2c1C[C@H](c1c(F)ccc(Br)c1F)C2)C1CCOCC1]

Compound was prepared analogous manner to Example 32 from (R)-1-(H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a green powder.

¹H NMR (DMSO$_{d6}$): 1.69 (1H, br s), 7.72 (1H, m), 7.16 (1H, m), 4.45 (1.6H, m), 4.15 (1H, m), 3.88 (2.4H, m), 3.73 (1H, br dd, J=11.5, 7.8 Hz), 3.57, 3.48 (2H, 2 m), 3.40 (1H, m), 3.34 (1H, m), 3.21 (1H, m), 2.84, 2.71 (3H, 2 s), 2.80 (1H, dd, J=7.4, 15.3 Hz), 1.82-1.61 (2H, m), 1.52 (1H, m), 1.38 (1H, m).

¹³C NMR (DMSO$_{d6}$): 167.6, 167.6, 160.8, 160.7, 159.1, 159.1, 157.5, 157.5, 155.9, 155.8, 155.1, 155, 132.4, 132.4, 129.3, 129.2, 118.9, 118.8, 118.7, 114.4, 114.2, 113.8, 113.8, 113.6, 113.6, 104.1, 104, 103.9, 103.9, 66.5, 66.5, 66.2, 49.6, 48.6, 35.7, 30.2, 30.2, 30, 29.5, 29.4, 29.3, 29.2, 27.

Example 129: (R)—N-(1,1-dioxidotetrahydro-2H-thiopyran-4-yl)-2-(6-(2,3,5,6-tetrafluorophenyl)-3-thioxo-2,5,6,7-tetrahydro-3H-pyrrolo[1,2-c]imidazol-1-yl)acetamide

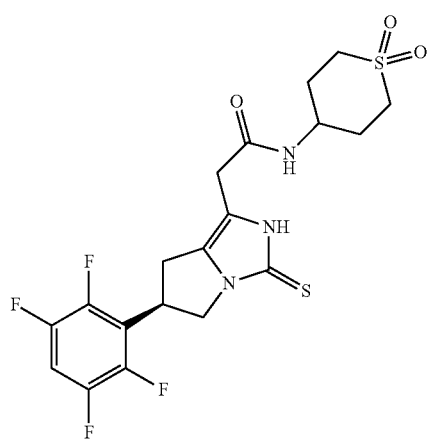 [SMILES: O=C(Cc1[nH]c(=S)n2c1C[C@H](c1c(F)c(F)cc(F)c1F)C2)NC1CCS(=O)(=O)CC1]

Compound was prepared analogous manner to Example 32 from (R)-1-(H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone and isolated as a cream powder.

¹H NMR (DMSO$_{d6}$): 11.78 (1H, s), 8.10 (1H, d, J=7.6 Hz), 7.85 (1H, m), 4.48 (1H, quin, J=8.6 Hz), 4.17 (1H, dd, J=11.4, 9.2 Hz), 3.93 (1H, m), 3.77 (1H, dd, J=11.6, 7.8 Hz), 3.28-3.17 (3H, m), 3.26 (2H, s), 3.08 (2H, m), 2.89 (1H, dd, J=8.0, 15.8 Hz), 2.04 (2H, br d, J=11.3 Hz), 1.90 (2H, m).

¹³C NMR (DMSO$_{d6}$): 167.1, 155.2, 146.4, 146.3, 146.2, 145.3, 145.2, 144.8, 144.7, 144.6, 143.7, 143.6, 129, 120.4, 120.3, 120.2, 114.2, 105.9, 105.7, 105.6, 48.4, 48.3, 43.9, 35.7, 31.4, 29.2, 29.1.

Example 130: (R)-2-(6-(3-bromo-2,6-difluorophenyl)-3-thioxo-2,5,6,7-tetrahydro-3H-pyrrolo[1,2-c]imidazol-1-yl)-N-(1,1-dioxidotetrahydro-2H-thiopyran-4-yl)acetamide

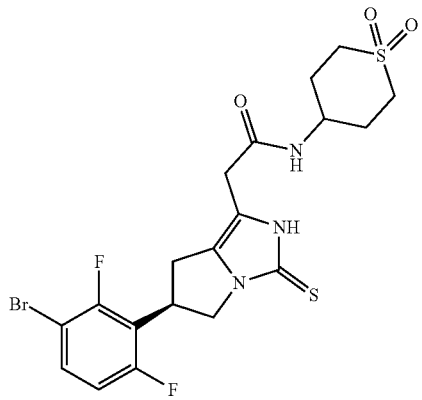 [SMILES: O=C(Cc1[nH]c(=S)n2c1C[C@H](c1c(F)ccc(Br)c1F)C2)NC1CCS(=O)(=O)CC1]

Compound was prepared analogous manner to Example 32 from (R)-1-(H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a cream powder.

¹H NMR (DMSO$_{d6}$): 1.77 (1H, s), 8.09 (1H, d, J=7.6 Hz), 7.72 (1H, ddd, J=8.8, 8.2, 5.9 Hz), 7.17 (1H, m), 4.44 (1H, quin, J=8.6 Hz), 4.15 (1H, dd, J=11.2, 9.5 Hz), 3.93 (1H, m), 3.72 (1H, dd, J=11.6, 7.9 Hz), 3.24 (2H, s), 3.22 (3H, m), 3.08 (2H, m), 2.84 (1H, dd, J=15.7, 8.1 Hz), 2.04 (2H, m), 1.90 (2H, m).

¹³C NMR (DMSO$_{d6}$): 167.1, 160.8, 160.8, 159.2, 159.1, 157.5, 157.5, 155.9, 155.8, 155.1, 132.5, 132.4, 129.2, 118.8, 118.7, 118.5, 114.1, 113.8, 113.8, 113.6, 113.6, 104.1, 104, 103.9, 103.9, 48.6, 48.3, 43.9, 35.6, 31.4, 29.3, 29.1.

Example 131: (R)-2-(6-(3-bromo-2,6-difluorophenyl)-3-thioxo-2,5,6,7-tetrahydro-3H-pyrrolo[1,2-c]imidazol-1-yl)-N-(2-hydroxyethyl)-N-methylacetamide

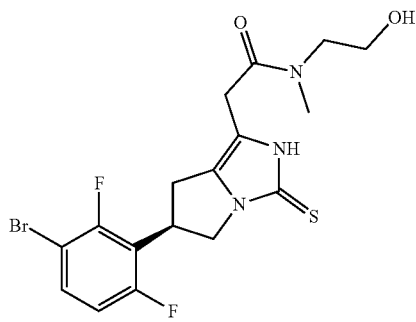 [SMILES: CN(CCO)C(=O)Cc1[nH]c(=S)n2c1C[C@H](c1c(F)ccc(Br)c1F)C2]

Compound was prepared analogous manner to Example 32 from (R)-1-(H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a pale brown powder.

¹H NMR (DMSO$_{d6}$): 11.69 (1H, 2 s), 7.72 (1H, ddd, J=8.6, 8.1, 5.9 Hz), 7.16 (1H, m), 4.87 (0.6H, t, J=5.4 Hz), 4.64 (0.4H, t, J=5.4 Hz), 4.44 (1H, 2 quin, J=8.7 Hz), 4.15 (1H, m), 3.72 (1H, dd, J=11.5, 8.0 Hz), 3.54 (2H, m), 3.46 (2H, m), 3.40-3.29 (2H, m), 3.20 (1H, m), 3.02 (1.2H, s), 2.82 (1.8H, s), 2.81 (1H, m).

¹³C NMR (DMSO$_{d6}$): 168.2, 167.9, 160.8, 160.8, 159.2, 159.1, 157.5, 157.5, 155.9, 155.8, 155, 132.5, 132.4, 129.2, 129.1, 118.8, 118.8, 118.7, 118.6, 118.6, 118.5, 114.5, 114.2, 113.8, 113.8, 113.6, 113.6, 104, 104, 103.9, 103.9, 58.5, 58.4, 51.6, 50, 48.6, 36.4, 35.6, 33.4, 29.4, 29.3, 29.2, 29.1, 29.

Example 132: (R)-2-(6-(3-bromo-2,6-difluorophenyl)-3-thioxo-2,5,6,7-tetrahydro-3H-pyrrolo[1,2-c]imidazol-1-yl)-N-cyclohexyl-N-methylacetamide

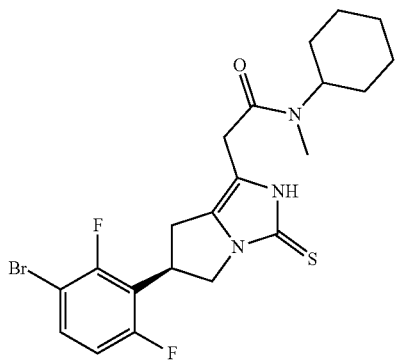 [SMILES: CN(C(=O)Cc1[nH]c(=S)n2c1C[C@H](c1c(F)ccc(Br)c1F)C2)C1CCCCC1]

Compound was prepared analogous manner to Example 32 from (R)-1-(H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a brown powder.

¹H NMR (DMSO$_{d6}$): 1.69 (1H, s), 7.72 (1H, m), 7.16 (1H, m), 4.44 (1H, quin, J=8.4 Hz), 4.20 (0.6H, tt, J=3.8, 11.8 Hz), 4.15 (1H, m), 3.72 (1H, br dd, J=11.5, 7.7 Hz), 3.58 (0.4H, tt, J=11.6, 3.5 Hz), 3.51 (0.8H, m), 3.46 (1.2H, m), 3.21 (1H, br dd, J=15.8, 9.3 Hz), 2.80 (1H, m), 2.81, 2.69 (3H, 2 s), 1.84-0.97 (10H, m).

¹³C NMR (DMSO$_{d6}$): 167.3, 167.3, 160.8, 160.7, 159.1, 159.1, 157.5, 157.5, 155.9, 155.8, 155, 155, 132.4, 132.4, 129.2, 129.1, 118.9, 118.8, 118.8, 114.5, 114.3, 113.8, 113.7, 113.6, 113.6, 104.1, 104, 103.9, 103.9, 55.7, 52, 48.6, 35.7, 30.2, 30.2, 30, 29.4, 29.4, 29.3, 29.2, 29.2, 29.2, 26.9, 25.3, 25.1, 25.1, 25, 24.8.

Example 133: (R)-2-(6-(3-bromo-2,6-difluorophenyl)-3-thioxo-2,5,6,7-tetrahydro-3H-pyrrolo[1,2-c]imidazol-1-yl)-N-isopropylacetamide

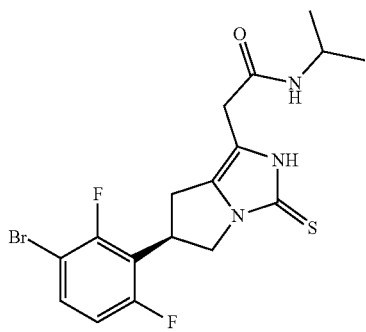 [SMILES: CC(C)NC(=O)Cc1[nH]c(=S)n2c1C[C@H](c1c(F)ccc(Br)c1F)C2]

Compound was prepared analogous manner to Example 32 rom (R)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a cream powder.

¹H NMR (DMSO$_{d6}$): 1.74 (1H, s), 7.84 (1H, br d, J=7.5 Hz), 7.72 (1H, ddd, J=5.8, 8.1, 8.8 Hz), 7.16 (1H, m), 4.44 (1H, quin, J=8.6 Hz), 4.14 (1H, dd, J=11.4, 9.2 Hz), 3.80 (1H, hep, J=6.7 Hz), 3.72 (1H, dd, J=11.6, 7.9 Hz), 3.21 (1H, dd, J=9.2, 15.8 Hz), 3.19 (2H, s), 2.83 (1H, dd, J=15.7, 8.2 Hz), 1.04 (6H, d, J=6.6 Hz).

¹³C NMR (DMSO$_{d6}$): 166.5, 160.8, 160.8, 159.2, 159.1, 157.5, 157.5, 155.9, 155.8, 155, 132.5, 132.4, 129, 118.8, 118.7, 118.5, 114.4, 113.8, 113.8, 113.6, 113.6, 104.1, 104, 103.9, 103.9, 48.6, 40.6, 35.6, 31.5, 29.4, 22.3.

Example 134: (S)-2-(6-(3-chloro-2,6-difluorophenyl)-3-thioxo-2,5,6,7-tetrahydro-3H-pyrrolo[1,2-c]imidazol-1-yl)-N-methyl-N-(pyridin-3-ylmethyl)acetamide

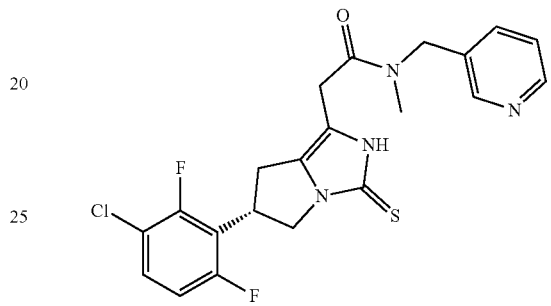

Compound was prepared analogous manner to Example 32 from (S)-1-(1H-imidazol-1-yl)-2-(6-(3-chloro-2,6-difluorophenyl)-3-thioxo-3,5,6,7-tetrahydro-2H-pyrrolo[1,2-c]imidazol-1-yl)ethanone and isolated as a beige solid.

¹H NMR (DMSO$_{d6}$): 1.76, 1.75 (1H, 2 br s), 8.52 (0.7H, m), 8.49 (0.7H, d, J=1.8 Hz), 8.44 (0.7H, dd, J=4.8, 1.7 Hz), 7.69-7.58 (2H, m), 7.40 (0.3H, dd, J=7.6, 4.9 Hz), 7.33 (1H, ddd, J=0.7, 4.8, 7.8 Hz), 7.22 (1H, m), 4.65 (0.6H, s), 4.53 (1.4H, m), 4.43 (1H, m), 4.16 (1H, m), 3.73 (1H, dd, J=11.6, 7.9 Hz), 3.59 (2H, m), 3.31-3.13 (1H, m), 2.98 (2H, s), 2.79 (1H, s), 2.85-2.73 (1H, m).

¹³C NMR (DMSO$_{d6}$): 168.4, 155.2, 149.1, 148.7, 148.5, 148.3, 135.4, 134.7, 133.1, 132.7, 129.7, 129.6, 129.3, 129.3, 123.7, 123.5, 118.7, 118.6, 116.1, 116, 115.9, 115.9, 114.1, 114.1, 113.2, 113.2, 113.1, 113.1, 50.2, 48.5, 48, 35.6, 35.1, 33.4, 29.6, 29.3, 29.2, 29.1.

Example 135: 2-((R)-6-(3-bromo-2,6-difluorophenyl)-3-thioxo-2,5,6,7-tetrahydro-3H-pyrrolo[1,2-c]imidazol-1-yl)-1-(3-(methylsulfonyl)pyrrolidin-1-yl)ethan-1-one

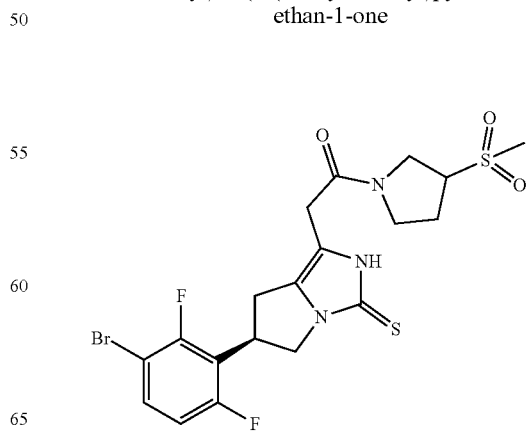

Compound was prepared analogous manner to Example 32 from (R)-1-(H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a light brown powder.

¹H NMR (DMSO_{d6}): 1.73 (1H, s), 7.72 (1H, m), 7.16 (1H, m), 4.45 (1H, 2 quin, J=8.6 Hz), 4.15 (1H, m), 4.06 (0.4H, m), 3.95 (0.6H, m), 3.88 (0.4H, m), 3.83 (0.4H, m), 3.72 (1H, dd, J=11.6, 7.9 Hz), 3.70-3.61 (1.8H, m), 3.56 (0.6H, m), 3.52-3.46 (1.4H, m), 3.45 (1H, s), 3.39 (0.4H, m), 3.22 (1H, m), 3.06, 3.06, 3.04, 3.04 (3H, 4 s), 2.84 (1H, m), 2.33 (1H, m), 2.22 (1H, m).

¹³C NMR (DMSO_{d6}): 166.4, 166.3, 160.8, 160.8, 159.2, 159.1, 157.5, 157.5, 155.9, 155.8, 155.2, 155.2, 132.5, 132.4, 129.4, 129.4, 118.8, 118.8, 118.7, 118.6, 118.5, 118.5, 113.8, 113.8, 113.7, 113.6, 113.6, 104.1, 104, 103.9, 103.9, 60.6, 60.6, 58.9, 58.9, 48.6, 45.4, 45.4, 45.3, 45.3, 45.1, 44.9, 35.7, 30.3, 30.2, 30.2, 30.2, 29.3, 25.7, 24.1, 24.1.

Example 136: (S)-2-(6-(3-bromo-2,6-difluorophenyl)-3-thioxo-2,5,6,7-tetrahydro-3H-pyrrolo[1,2-c]imidazol-1-yl)-1-(1,1-dioxidothiomorpholino)ethan-1-one

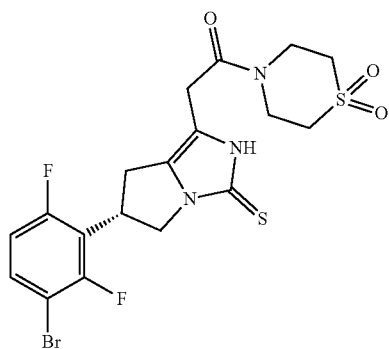 [SMILES: O=C(Cc1[nH]c(=S)n2c1C[C@@H](c1c(F)ccc(Br)c1F)C2)N1CCS(=O)(=O)CC1]

Compound was prepared analogous manner to Example 32 from (S)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as an off-white solid.

¹H NMR (DMSO_{d6}): 11.63 (1H, s), 7.72 (1H, td, J=8.4, 5.8 Hz), 7.17 (1H, m), 4.46 (1H, quin, J=8.6 Hz), 4.16 (1H, dd, J=9.3, 11.1 Hz), 3.87 (4H, m), 3.73 (1H, dd, J=11.5, 7.8 Hz), 3.62 (2H, s), 3.26 (2H, m), 3.23 (1H, dd, J=9.3, 15.8 Hz), 3.10 (2H, m), 2.84 (1H, dd, J=15.8, 8.1 Hz).

¹³C NMR (DMSO_{d6}): 167.4, 160.8, 160.8, 159.2, 159.1, 157.5, 157.5, 155.9, 155.8, 155.2, 132.5, 132.4, 129.5, 118.7, 113.8, 113.8, 113.8, 113.6, 113.6, 104.1, 104, 103.9, 103.9, 51.3, 51.1, 48.6, 43.8, 40.3, 35.7, 29.2, 28.7.

Example 137: (S)-2-(6-(3-bromo-2,6-difluorophenyl)-3-thioxo-2,5,6,7-tetrahydro-3H-pyrrolo[1,2-c]imidazol-1-yl)-1-thiomorpholinoethan-1-one

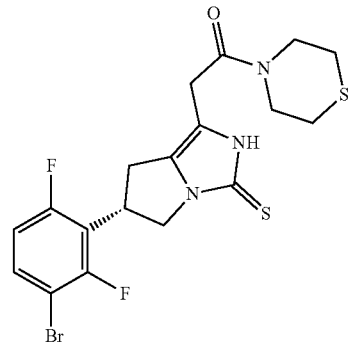 [SMILES: O=C(Cc1[nH]c(=S)n2c1C[C@@H](c1c(F)ccc(Br)c1F)C2)N1CCSCC1]

Compound was prepared analogous manner to Example 32 from (S)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as an off-white solid.

¹H NMR (DMSO_{d6}): 11.69 (1H, s), 7.72 (1H, ddd, J=5.8, 8.1, 8.8 Hz), 7.16 (1H, m), 4.45 (1H, quin, J=8.6 Hz), 4.15 (1H, dd, J=11.2, 9.3 Hz), 3.73 (1H, dd, J=8.0, 11.6 Hz), 3.71 (4H, m), 3.51 (2H, m), 3.21 (1H, dd, J=15.8, 9.3 Hz), 2.81 (1H, dd, J=15.9, 8.0 Hz), 2.61 (2H, m), 2.55-2.50 (2H, m).

¹³C NMR (DMSO_{d6}): 166.6, 160.8, 160.8, 159.2, 159.1, 157.5, 157.5, 155.9, 155.8, 155.1, 132.5, 132.4, 129.3, 118.9, 118.7, 118.6, 114.1, 113.8, 113.8, 113.6, 113.6, 104.1, 104, 103.9, 103.9, 48.6, 48.1, 44, 35.7, 29.3, 29.1, 26.9, 26.4.

Example 138: 2-((S)-6-(3-bromo-2,6-difluorophenyl)-3-thioxo-2,5,6,7-tetrahydro-3H-pyrrolo[1,2-c]imidazol-1-yl)-1-(2-oxa-7-azaspiro[4.4]nonan-7-yl)ethan-1-one

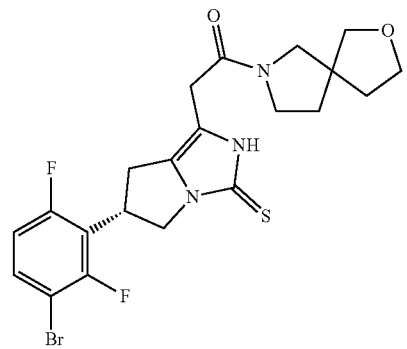 [SMILES: O=C(Cc1[nH]c(=S)n2c1C[C@@H](c1c(F)ccc(Br)c1F)C2)N1CCC2(CCOC2)C1]

Compound was prepared analogous manner to Example 32 from (S)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a white solid.

¹H NMR (DMSO_{d6}): 1.71 (1H, s), 7.72 (1H, m), 7.16 (1H, m), 4.45 (1H, quin, J=8.6 Hz), 4.15 (1H, dd, J=11.3, 9.4 Hz), 3.81-3.69 (3H, m), 3.59-3.47 (3H, m), 3.44-3.40 (3H, m), 3.36 (1H, m), 3.30-3.18 (2H, m), 2.82 (1H, m), 1.96-1.73 (4H, m).

¹³C NMR (DMSO_{d6}): 166.4, 166.4, 160.8, 159.2, 157.5, 157.5, 155.9, 155.8, 155.1, 132.4, 132.4, 129.3, 118.9, 118.8, 118.7, 114, 114, 113.8, 113.8, 113.6, 113.6, 104, 104, 103.9, 103.9, 75.2, 75.2, 75.1, 66.9, 66.9, 55, 54.2, 49.6, 48.6, 47.8, 45.6, 45, 35.8, 35.8, 35.8, 35.6, 34.7, 33.2, 30.3, 30.3, 30, 30, 29.3.

Example 139: (R)-2-(6-(3-bromo-2,6-difluorophenyl)-3-thioxo-2,5,6,7-tetrahydro-3H-pyrrolo[1,2-c]imidazol-1-yl)-N-(pyridin-2-ylmethyl)acetamide

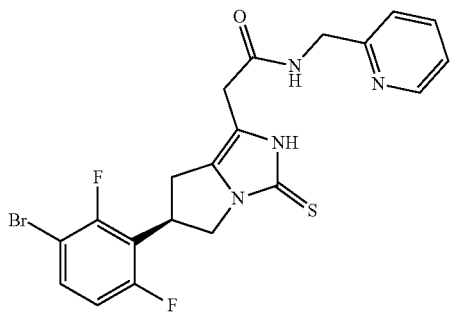 [SMILES: O=C(Cc1[nH]c(=S)n2c1C[C@H](c1c(F)ccc(Br)c1F)C2)NCc1ccccn1]

Compound was prepared analogous manner to Example 32 from (R)-1-(H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a cream powder.

$^1$H NMR (DMSO$_{d6}$): 11.84 (1H, s), 8.58 (1H, t, J=5.9 Hz), 8.50 (1H, m), 7.73 (2H, m), 7.30 (1H, d, J=7.8 Hz), 7.23 (1H, dd, J=6.9, 5.0 Hz), 7.17 (1H, m), 4.43 (1H, quin, J=m), 4.36 (2H, m), 4.14 (1H, dd, J=9.6, 11.3 Hz), 3.73 (1H, dd, J=11.5, 8.1 Hz), 3.36 (2H, m), 3.17 (1H, dd, J=15.8, 9.3 Hz), 2.78 (1H, dd, J=15.7, 8.4 Hz).

$^{13}$C NMR (DMSO$_{d6}$): 167.9, 160.8, 160.7, 159.1, 159.1, 158.2, 157.5, 157.5, 155.9, 155.9, 155.3, 148.8, 136.7, 132.5, 132.4, 129.2, 122.1, 121.2, 118.6, 118.5, 118.4, 114.1, 113.8, 113.7, 113.6, 113.6, 104, 104, 103.9, 103.9, 48.5, 44.3, 35.6, 31.5, 29.2.

Example 140: (S)-2-(6-(3-bromo-2,6-difluorophenyl)-3-thioxo-2,5,6,7-tetrahydro-3H-pyrrolo[1,2-c]imidazol-1-yl)-1-morpholinoethan-1-one

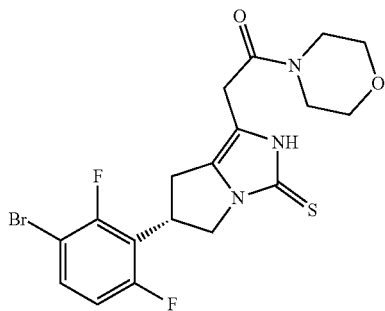

Compound was prepared analogous manner to Example 32 from (S)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a light brown powder.

$^1$H NMR (DMSO$_{d6}$): 11.70 (1H, s), 7.72 (1H, ddd, J=5.8, 8.1, 8.7 Hz), 7.17 (1H, m), 4.45 (1H, quin, J=8.5 Hz), 4.15 (1H, dd, J=11.5, 9.2 Hz), 3.73 (1H, dd, J=11.7, 7.8 Hz), 3.60-3.52 (4H, m), 3.51 (2H, s), 3.48-3.40 (4H, m), 3.21 (1H, dd, J=15.8, 9.3 Hz), 2.82 (1H, dd, J=15.8, 8.1 Hz)

$^{13}$C NMR (DMSO$_{d6}$): 166.8, 160.8, 160.8, 159.2, 159.1, 157.5, 157.5, 155.9, 155.9, 155.2, 132.5, 132.4, 129.3, 118.9, 118.7, 118.6, 114, 113.8, 113.6, 104.1, 104, 103.9, 103.9, 66, 66, 48.6, 45.7, 41.7, 35.7, 29.3, 28.9.

Example 141: (R)-2-(6-(3-bromo-2,6-difluorophenyl)-3-thioxo-2,5,6,7-tetrahydro-3H-pyrrolo[1,2-c]imidazol-1-yl)-1-morpholinoethan-1-one

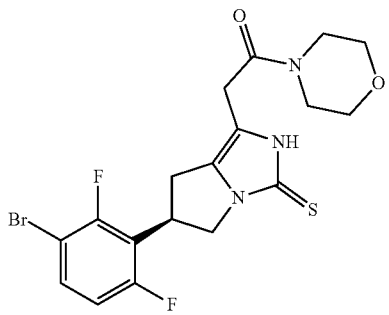

Compound was prepared analogous manner to Example 32 from (R)-1-(H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a light brown powder.

$^1$H NMR (DMSO$_{d6}$): 11.70 (1H, s), 7.72 (1H, ddd, J=5.8, 8.1, 8.7 Hz), 7.17 (1H, m), 4.45 (1H, quin, J=8.5 Hz), 4.15 (1H, dd, J=11.5, 9.2 Hz), 3.73 (1H, dd, J=11.7, 7.8 Hz), 3.60-3.52 (4H, m), 3.51 (2H, s), 3.48-3.40 (4H, m), 3.21 (1H, dd, J=15.8, 9.3 Hz), 2.82 (1H, dd, J=15.8, 8.1 Hz).

$^{13}$C NMR (DMSO$_{d6}$): 166.8, 160.8, 160.8, 159.2, 159.1, 157.5, 157.5, 155.9, 155.9, 155.2, 132.5, 132.4, 129.3, 118.9, 118.7, 118.6, 114, 113.8, 113.6, 104.1, 104, 103.9, 103.9, 66, 66, 48.6, 45.7, 41.7, 35.7, 29.3, 28.9.

Example 142: N-(2-(1H-pyrazol-1-yl)ethyl)-2-((5aS,6aR)-5a-(3-chloro-2,6-difluorophenyl)-3-thioxo-2,3,5,5a,6,6a-hexahydrocyclopropa[3,4]pyrrolo[1,2-c]imidazol-1-yl)acetamide

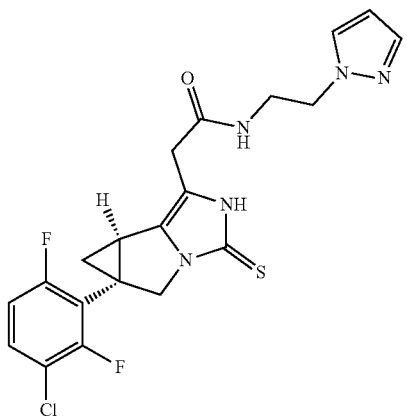 [SMILES: O=C(Cc1[nH]c(=S)n2c1[C@@H]1C[C@]1(c1c(F)ccc(Cl)c1F)C2)NCCn1cccn1]

Compound was prepared analogous manner to Example 25 from 2-((5aS,6aR)-5a-(3-chloro-2,6-difluorophenyl)-3-thioxo-2,3,5,5a,6,6a-hexahydrocyclopropa[3,4]pyrrolo[1,2- c]imidazol-1-yl)-1-(1H-imidazol-1-yl)ethan-1-one (prepared analogous to Example 23 step 1) and isolated as a light yellow solid. 20 $^1$H NMR (DMSO$_{d6}$): 1.68 (1H, s), 8.09 (1H, t, J=5.6 Hz), 7.68 (1H, dd, J=2.2, 0.6 Hz), 7.63 (1H, td, J=8.7, 5.6 Hz), 7.43 (1H, dd, J=0.6, 1.8 Hz), 7.21 (1H, dt, J=1.4, 9.2 Hz), 6.20 (1H, m), 4.17 (2H, t, J=6.3 Hz), 4.02 (1H, d, J=12.2 Hz), 3.74 (1H, d, J=12.2 Hz), 3.44 (2H, m), 3.31 (2H, m), 2.70 (1H, dd, J=8.4, 4.4 Hz), 1.65 (1H, dd, J=8.2, 5.4 Hz), 1.26 (1H, t, J=5.0 Hz).

$^{13}$C NMR (DMSO$_{d6}$): 168.1, 161.2, 161.2, 159.6, 159.5, 157.8, 157.8, 156.1, 156.1, 155.9, 138.8, 131.5, 130.3, 130.2, 130.1, 117.2, 117.1, 116.9, 115.7, 115.7, 115.6, 115.6, 114, 112.9, 112.9, 112.8, 112.7, 105, 51.4, 50.2, 39.4, 31.3, 26.3, 21.6, 21.2.

Example 143: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-(cyclopropylmethyl)acetamide

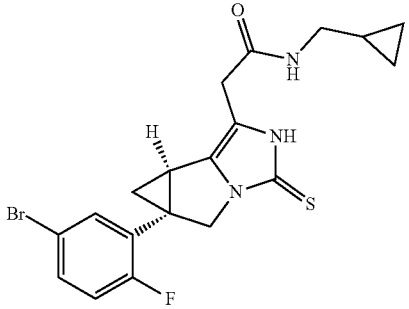 [SMILES: O=C(Cc1[nH]c(=S)n2c1[C@@H]1C[C@]1(c1cc(Br)ccc1F)C2)NCC1CC1]

Compound was prepared analogous manner to Example 32 from 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a yellow solid.

$^1$H NMR (DMSO$_{d6}$): 11.65 (1H, s), 8.03 (1H, br t, J=5.5 Hz), 7.58-7.53 (2H, m), 7.24 (1H, dd, J=10.1, 8.7 Hz), 4.07 (1H, d, J=12.0 Hz), 3.79 (1H, d, J=12.2 Hz), 3.30 (2H, m), 2.96 (2H, t, J=6.2 Hz), 2.82 (1H, dd, J=8.4, 4.3 Hz), 1.66 (1H, dd, J=8.4, 5.3 Hz), 1.15 (1H, t, J=4.8 Hz), 0.90 (1H, m), 0.40 (2H, m), 0.16 (2H, m).

$^{13}$C NMR (DMSO$_{d6}$): 167.5, 161.7, 160.1, 155.9, 133, 132.9, 132.3, 132.2, 131.7, 129.3, 129.2, 118, 117.8, 116.2, 116.2, 114, 51.6, 43.2, 31.4, 22, 20.7, 10.7, 3.3, 3.2

Example 144: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-(cyanomethyl)acetamide

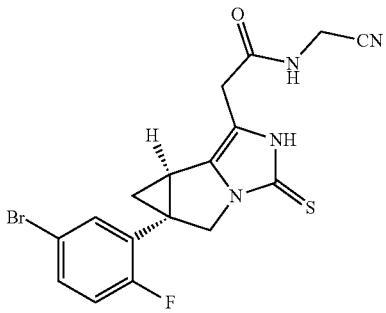 [SMILES: N#CCNC(=O)Cc1[nH]c(=S)n2c1[C@@H]1C[C@]1(c1cc(Br)ccc1F)C2]

Compound was prepared analogous manner to Example 32 from 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a white solid.

$^1$H NMR (DMSO$_{d6}$): 11.72 (1H, s), 8.66 (1H, br t, J=5.4 Hz), 7.62-7.51 (2H, m), 7.24 (1H, dd, J=10.0, 8.8 Hz), 4.16 (2H, m), 4.09 (1H, dd, J=11.8 Hz), 3.80 (1H, d, J=12.0 Hz), 3.39 (2H, m), 2.85 (1H, dd, J=8.3, 4.2 Hz), 1.64 (1H, dd, J=8.4, 5.3 Hz), 1.18 (1H, t, J=4.8 Hz).

$^{13}$C NMR (DMSO$_{d6}$): 168.6, 161.7, 160.1, 156.2, 132.9, 132.9, 132.3, 132.3, 129.3, 129.2, 118, 117.8, 117.6, 116.2, 112.9, 51.6, 32.3, 30.9, 27.3, 22.1, 20.6.

Example 145: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-(2-(pyridin-2-yl)ethyl)acetamide

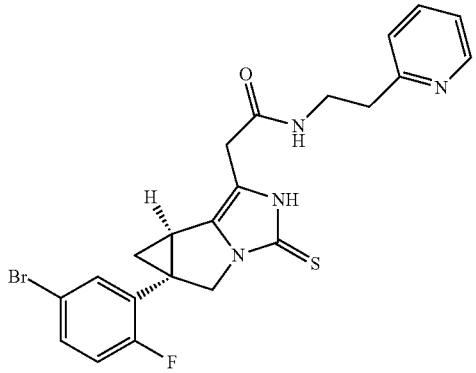 [SMILES: O=C(Cc1[nH]c(=S)n2c1[C@@H]1C[C@]1(c1cc(Br)ccc1F)C2)NCCc1ccccn1]

Compound was prepared analogous manner to Example 32 from 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a yellow solid.

$^1$H NMR (DMSO$_{d6}$): 1.66 (1H, br s), 8.48 (1H, ddd, J=0.8, 1.8, 4.8 Hz), 8.03 (1H, t, J=5.6 Hz), 7.68 (1H, td, J=7.6, 1.9 Hz), 7.56 (2H, m), 7.24 (2H, m), 7.19 (1H, ddd, J=7.5, 4.9, 1.1 Hz), 4.07 (1H, d, J=12.2 Hz), 3.79 (1H, d, J=12.0 Hz), 3.43 (2H, m), 3.28 (2H, m), 2.88 (2H, t, J=7.3 Hz), 2.79 (1H, dd, J=8.4, 4.3 Hz), 1.64 (1H, dd, J=8.4, 5.3 Hz), 1.14 (1H, t, J=4.8 Hz).

$^{13}$C NMR (DMSO$_{d6}$): 167.7, 161.8, 160.1, 159, 156, 149, 136.5, 133, 133, 132.3, 132.3, 131.8, 129.3, 129.2, 123.2, 121.5, 118, 117.8, 116.2, 116.2, 113.8, 51.6, 38.8, 37.2, 32.2, 31.5, 22, 20.7.

Example 146: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-(3-(dimethylamino)propyl)acetamide hydrochloride

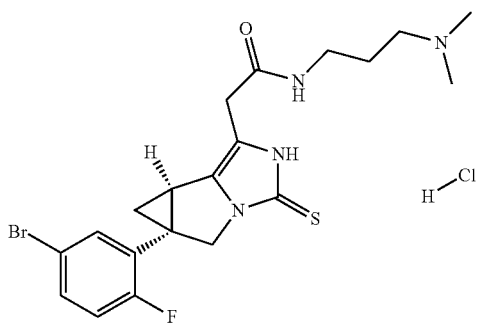 [SMILES: CN(C)CCCNC(=O)Cc1[nH]c(=S)n2c1[C@@H]1C[C@]1(c1cc(Br)ccc1F)C2 ; Cl]

Compound was prepared analogous manner to Example 32 from 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a dark yellow solid.

$^1$H NMR (D$_2$O): 7.52 (1H, dd, J=6.6, 2.3 Hz), 7.43 (1H, m), 7.03 (1H, t, J=9.4 Hz), 4.20 (1H, d, J=12.2 Hz), 3.92 (1H, d, J=12.2 Hz), 3.58 (2H, s), 3.30 (2H, t, J=6.7 Hz), 3.14 (2H, m), 2.87 (6H, s), 2.73 (1H, dd, J=8.4, 4.3 Hz), 1.95 (2H, m), 1.66 (1H, dd, J=8.1, 5.8 Hz), 1.19 (1H, t, J=4.8 Hz).

$^{13}$C NMR (D$_2$O): 171.6, 162, 160.3, 151.4, 134.7, 133.1, 132.5, 132.4, 128.3, 128.2, 117.6, 117.4, 116.1, 114.3, 55.3, 52.2, 42.7, 36.3, 32.4, 31.3, 24.1, 21.5, 20.5.

Example 147: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-1-(4-(pyridin-2-yl)piperazin-1-yl)ethan-1-one

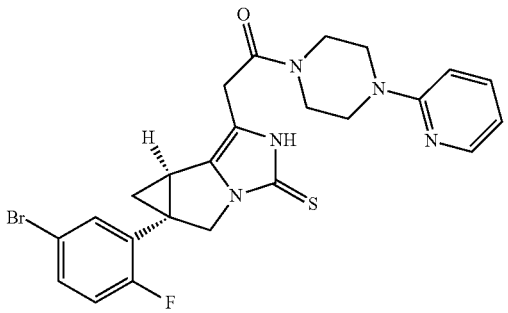 [SMILES: O=C(Cc1[nH]c(=S)n2c1[C@@H]1C[C@]1(c1cc(Br)ccc1F)C2)N1CCN(c2ccccn2)CC1]

Compound was prepared analogous manner to Example 32 from 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a yellow solid.

$^1$H NMR (DMSO$_{d6}$): 11.63 (1H, s), 8.11 (1H, dd, J=5.1, 1.2 Hz), 7.68 (1H, br d, J=18.6 Hz), 7.56 (2H, m), 7.23 (1H, dd, J=10.1, 8.8 Hz), 6.99 (1H, br s), 6.75 (1H, br s), 4.08 (1H, br d, J=12.2 Hz), 3.79 (1H, d, J=12.0 Hz), 3.69-3.51 (10H, m), 2.80 (1H, dd, J=8.3, 4.2 Hz), 1.68 (1H, dd, J=8.4, 5.3 Hz), 1.11 (1H, br t, J=4.8 Hz).

$^{13}$C NMR (DMSO$_{d6}$): 167, 161.8, 160.1, 156, 133, 133, 132.3, 132.3, 131.8, 129.3, 129.2, 118, 117.8, 116.2, 116.2, 113.7, 113.2, 51.6, 44.9, 44.6, 44.4, 40.8, 32.3, 29.2, 22.1, 20.7.

Example 148: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-(tetrahydrofuran-3-yl)acetamide

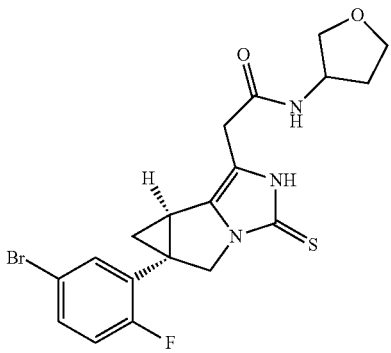 [SMILES: O=C(Cc1[nH]c(=S)n2c1[C@@H]1C[C@]1(c1cc(Br)ccc1F)C2)NC1CCOC1]

Compound was prepared analogous manner to Example 32 from 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige foam.

$^1$H NMR (DMSO$_{d6}$): 11.66 (1H, s), 8.23 (1H, d, J=6.7 Hz), 7.56 (2H, m), 7.24 (1H, dd, J=10.1, 8.6 Hz), 4.24 (1H, tt, J=10.2, 3.8 Hz), 4.07 (1H, d, J=12.0 Hz), 3.78 (2H, m), 3.74 (1H, dd, J=8.9, 6.0 Hz), 3.67 (1H, td, J=8.2, 5.6 Hz), 3.49 (1H, dd, J=8.8, 3.7 Hz), 3.30 (2H, m), 2.81 (1H, dd, J=8.4, 4.2 Hz), 2.08 (1H, dq, J=12.6, 7.6 Hz), 1.75 (1H, m), 1.66 (1H, dd, J=8.4, 5.4 Hz), 1.12 (1H, t, J=4.8 Hz).

$^{13}$C NMR (DMSO$_{d6}$): 167.6, 161.8, 160.1, 155.9, 133, 133, 132.3, 132.2, 131.7, 129.3, 129.2, 118, 117.8, 116.2, 116.2, 113.9, 72.4, 66.3, 51.6, 49.8, 32.2, 32, 31.2, 22.1, 20.7.

Example 149: 2-((5aS,6aR)-5a-(3-chloro-2,6-difluorophenyl)-3-thioxo-2,3,5,5a,6,6a-hexahydrocyclopropa[3,4]pyrrolo[1,2-c]imidazol-1-yl)-1-(4,4-difluoropiperidin-1-yl)ethan-1-one

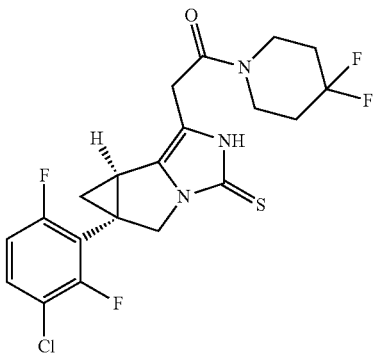 [SMILES: O=C(Cc1[nH]c(=S)n2c1[C@@H]1C[C@]1(c1c(F)ccc(Cl)c1F)C2)N1CCC(F)(F)CC1]

Compound was prepared analogous manner to Example 32 from 2-((5aS,6aR)-5a-(3-chloro-2,6-difluorophenyl)-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a brown solid.

$^1$H NMR (DMSO$_{d6}$): 11.63 (1H, br s), 7.63 (1H, td, J=8.7, 5.7 Hz), 7.20 (1H, dt, J=9.3 Hz, 1.3 Hz), 4.04 (1H, d, J=12.2 Hz), 3.74 (1H, d, J=12.2 Hz), 3.66 (2H, m), 3.59 (4H, m), 2.69 (1H, dd, J=8.4, 4.4 Hz), 2.04 (2H, m), 1.93 (2H, m), 1.68 (1H, dd, J=8.2, 5.4 Hz), 1.24 (1H, t, J=5.0 Hz).

$^{13}$C NMR (DMSO$_{d6}$): 166.8, 161.2, 161.2, 159.6, 159.5, 157.8, 157.7, 156.1, 156.1, 156, 131.5, 130.3, 130.2, 124.3, 122.7, 121.1, 117.1, 117, 116.9, 115.7, 115.7, 115.6, 115.6, 114, 112.9, 112.9, 112.8, 112.7, 51.4, 42.2, 42.1, 42.1, 38.5, 38.5, 38.4, 33.9, 33.8, 33.6, 33.3, 33.2, 33, 29.1, 26.4, 21.7, 21.2.

Example 150: 2-((5aS,6aR)-5a-(3-chloro-2,6-difluorophenyl)-3-thioxo-2,3,5,5a,6,6a-hexahydrocyclopropa[3,4]pyrrolo[1,2-c]imidazol-1-yl)-N-(2,2,2-trifluoroethyl)acetamide

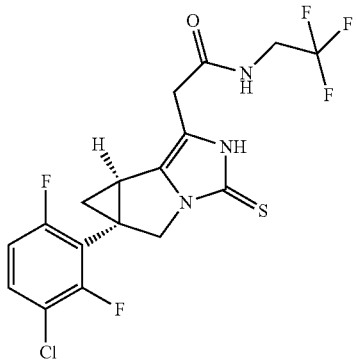 [SMILES: O=C(Cc1[nH]c(=S)n2c1[C@@H]1C[C@]1(c1c(F)ccc(Cl)c1F)C2)NCC(F)(F)F]

Compound was prepared analogous manner to Example 32 from 2-((5aS,6aR)-5a-(3-chloro-2,6-difluorophenyl)-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a light brown solid.

$^1$H NMR (DMSO$_{d6}$): 11.73 (1H, s), 8.67 (1H, t, J=6.3 Hz), 7.63 (1H, td, J=8.7, 5.6 Hz), 7.21 (1H, dt, J=1.4, 9.2 Hz), 4.03 (1H, d, J=12.2 Hz), 3.93 (2H, qd, J=9.8, 6.5 Hz), 3.74 (1H, d, J=12.2 Hz), 3.43 (2H, m), 2.72 (1H, dd, J=8.4, 4.4 Hz), 1.65 (1H, dd, J=8.4, 5.4 Hz), 1.26 (1H, t, J=5.0 Hz).

$^{13}$C NMR (DMSO$_{d6}$): 169.2, 161.7, 161.6, 160, 160, 158.3, 158.2, 156.6, 156.5, 132.2, 130.8, 130.7, 127.9, 126.1, 124.2, 122.4, 117.6, 117.5, 117.4, 116.2, 116.2, 116.1, 116.1, 114, 113.4, 113.4, 113.2, 113.2, 51.9, 40.1, 31.5, 26.8, 22.1, 21.7.

Example 151: 2-((5aS,6aR)-5a-(3-chloro-2,6-difluorophenyl)-3-thioxo-2,3,5,5a,6,6a-hexahydrocyclopropa[3,4]pyrrolo[1,2-c]imidazol-1-yl)-N-(pyridin-3-ylmethyl)acetamide

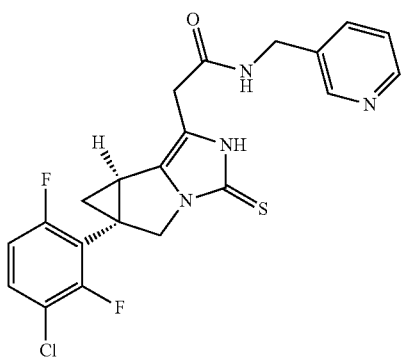 [SMILES: O=C(Cc1[nH]c(=S)n2c1[C@@H]1C[C@]1(c1c(F)ccc(Cl)c1F)C2)NCc1cccnc1]

Compound was prepared analogous manner to Example 32 from 2-((5aS,6aR)-5a-(3-chloro-2,6-difluorophenyl)-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a white solid.

$^1$H NMR (DMSO$_{d6}$): 1.75 (1H, s), 8.55-8.48 (2H, m), 8.43 (1H, dd, J=4.7, 1.6 Hz), 7.67 (1H, dt, J=7.8, 2.0 Hz), 7.64 (1H, td, J=8.7, 5.7 Hz), 7.34 (1H, ddd, J=0.7, 4.8, 7.8 Hz), 7.21 (1H, dt, J=1.0, 9.1 Hz), 4.32 (2H, m), 4.02 (1H, d, J=12.2 Hz), 3.74 (1H, d, J=12.2 Hz), 3.40 (2H, m), 2.68 (1H, dd, J=8.4, 4.4 Hz), 1.62 (1H, dd, J=8.3, 5.5 Hz), 1.27 (1H, t, J=5.0 Hz).

$^{13}$C NMR (DMSO$_{d6}$): 168, 161.2, 161.2, 159.6, 159.5, 157.8, 157.7, 156.1, 156, 148.8, 148.1, 135.1, 134.7, 131.6, 130.3, 130.2, 123.4, 117.2, 117, 116.9, 115.7, 115.6, 114, 112.9, 112.9, 112.8, 112.8, 51.4, 39.8, 31.3, 26.3, 21.5, 21.2.

Example 152: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-(2,2,2-trifluoroethyl)acetamide

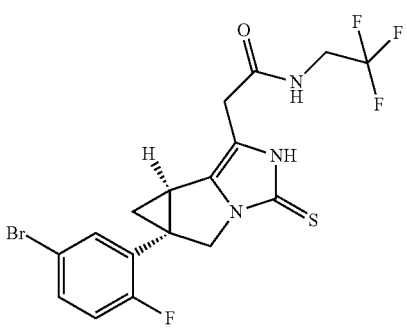 [SMILES: O=C(Cc1[nH]c(=S)n2c1[C@@H]1C[C@]1(c1cc(Br)ccc1F)C2)NCC(F)(F)F]

Compound was prepared analogous manner to Example 32 from 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a light beige solid.

$^1$H NMR (DMSO$_{d6}$): 1.75 (1H, s), 8.55-8.48 (2H, m), 8.43 (1H, dd, J=4.7, 1.6 Hz), 7.67 (1H, dt, J=7.8, 2.0 Hz), 7.64 (1H, td, J=8.7, 5.7 Hz), 7.34 (1H, ddd, J=0.7, 4.8, 7.8 Hz), 7.21 (1H, dt, J=1.0, 9.1 Hz), 4.32 (2H, m), 4.02 (1H, d, J=12.2 Hz), 3.74 (1H, d, J=12.2 Hz), 3.40 (2H, m), 2.68 (1H, dd, J=8.4, 4.4 Hz), 1.62 (1H, dd, J=8.3, 5.5 Hz), 1.27 (1H, t, J=5.0 Hz).

$^{13}$C NMR (DMSO$_{d6}$): 168, 161.2, 161.2, 159.6, 159.5, 157.8, 157.7, 156.1, 156, 148.8, 148.1, 135.1, 134.7, 131.6, 130.3, 130.2, 123.4, 117.2, 117, 116.9, 115.7, 115.6, 114, 112.9, 112.9, 112.8, 112.8, 51.4, 39.8, 31.3, 26.3, 21.5, 21.2.

Example 153: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-cyclobutylacetamide

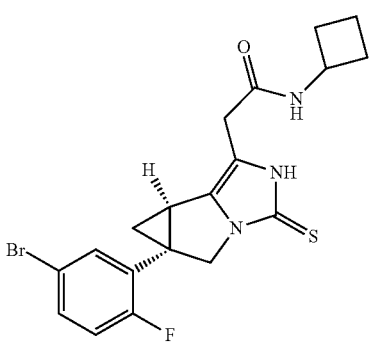 [SMILES: O=C(Cc1[nH]c(=S)n2c1[C@@H]1C[C@]1(c1cc(Br)ccc1F)C2)NC1CCC1]

Compound was prepared analogous manner to Example 32 from 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a yellow solid.

$^1$H NMR (DMSO$_{d6}$): 1.63 (1H, s), 8.20 (1H, br d, J=7.8 Hz), 7.56 (2H, m), 7.24 (1H, dd, J=9.9, 8.7 Hz), 4.20 (1H, sxt, J=8.1 Hz), 4.07 (1H, d, J=12.0 Hz), 3.78 (1H, d, J=12.0 Hz), 3.25 (2H, m), 2.80 (1H, dd, J=8.4, 4.3 Hz), 2.14 (2H, m), 1.90 (2H, m), 1.63 (3H, m), 1.13 (1H, t, J=4.8 Hz).

$^{13}$C NMR (DMSO$_{d6}$): 166.6, 161.7, 160.1, 155.9, 133, 132.9, 132.3, 132.2, 131.7, 129.3, 129.2, 118, 117.8, 116.2, 113.9, 51.5, 44.1, 32.2, 31.3, 30.2, 30.2, 22, 20.7, 14.6.

Example 154: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-cyclopropylacetamide

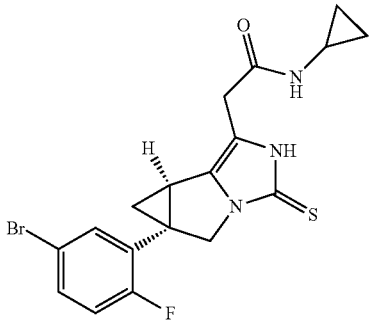 [SMILES: O=C(Cc1[nH]c(=S)n2c1[C@@H]1C[C@]1(c1cc(Br)ccc1F)C2)NC1CC1]

Compound was prepared analogous manner to Example 32 from 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a yellow solid.

$^1$H NMR (DMSO$_{d6}$): 1.63 (1H, s), 8.04 (1H, br d, J=3.8 Hz), 7.56 (2H, m), 7.24 (1H, dd, J=10.1, 8.7 Hz), 4.07 (1H, d, J=11.9 Hz), 3.78 (1H, d, J=12.0 Hz), 3.25 (2H, m), 2.81 (1H, dd, J=8.3, 4.2 Hz), 2.62 (1H, m), 1.65 (1H, dd, J=8.4, 5.3 Hz), 1.13 (1H, t, J=4.8 Hz), 0.62 (2H, m), 0.42 (2H, m).

$^{13}$C NMR (DMSO$_{d6}$): 168.8, 161.7, 160.1, 155.9, 133, 132.9, 132.3, 132.2, 131.7, 129.3, 129.2, 118, 117.8, 116.2, 116.2, 113.8, 51.6, 32.2, 31.2, 22.5, 22, 20.7, 5.6, 5.6.

Example 155: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-cyclopentyl-N-methylacetamide

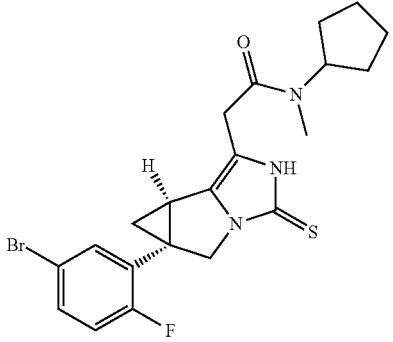 [SMILES: CN(C(=O)Cc1[nH]c(=S)n2c1[C@@H]1C[C@]1(c1cc(Br)ccc1F)C2)C1CCCC1]

Compound was prepared analogous manner to Example 32 from 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a brown solid.

$^1$H NMR (DMSO$_{d6}$): 1.59 (1H, br s), 7.55 (2H, m), 7.24 (1H, t, J=9.4 Hz), 4.82, 4.28 (1H, 2 m), 4.07 (1H, d, J=12.0 Hz), 3.78 (1H, d, J=12.0 Hz), 3.61, 3.52 (2H, 2 m), 2.85, 2.70 (3H, 2 s), 2.77 (1H, m), 1.85-1.40 (9H, m), 1.10 (1H, m).

$^{13}$C NMR (DMSO$_{d6}$): 167.9, 167.7, 161.7, 160.1, 155.9, 155.9, 133, 132.9, 132.3, 132.2, 131.6, 131.6, 129.3, 129.2, 118, 117.8, 116.2, 116.1, 114.1, 114, 57.6, 53.7, 51.5, 32.3, 32.2, 30.1, 29.5, 29.4, 28.5, 27.8, 27.7, 27.1, 23.9, 23.8, 22.1, 20.7, 20.6.

Example 156: N-benzyl-2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)acetamide

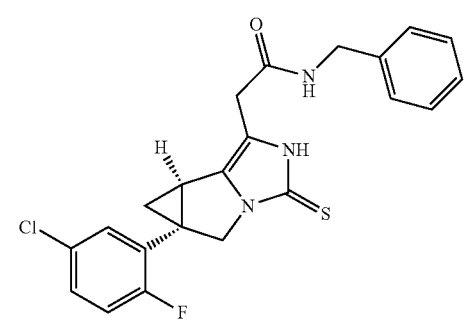 [SMILES: O=C(Cc1[nH]c(=S)n2c1[C@@H]1C[C@]1(c1cc(Cl)ccc1F)C2)NCc1ccccc1]

Compound was prepare analogous manner to Example 32 from 2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a brown solid.

$^1$H NMR (DMSO$_{d6}$): 11.72 (1H, s), 8.45 (1H, t, J=5.9 Hz), 7.47-7.40 (2H, m), 7.35-7.25 (5H, m), 7.22 (1H, m), 4.29 (2H, m), 4.07 (1H, d, J=12.0 Hz), 3.80 (1H, d, J=12.2 Hz), 3.38 (2H, m), 2.77 (1H, dd, J=8.4, 4.3 Hz), 1.62 (1H, dd, J=8.4, 5.3 Hz), 1.16 (1H, m).

$^{13}$C NMR (DMSO$_{d6}$): 167.8, 161.2, 159.6, 156, 139.3, 131.8, 130.1, 130, 129.3, 129.2, 128.9, 128.8, 128.2, 128.2, 128.2, 127.3, 126.8, 117.6, 117.4, 113.7, 51.5, 42.3, 32.3, 31.4, 22, 20.7.

Example 157: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl-1-morpholinoethan-1-one

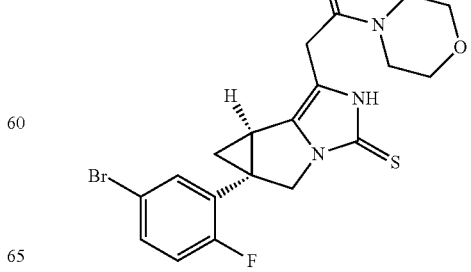

Compound was prepared analogous manner to Example 32 from 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a green solid.

¹H NMR (DMSO$_{d6}$): 11.61 (1H, s), 7.65-7.46 (2H, m), 7.24 (1H, dd, J=10.0, 8.7 Hz), 4.08 (1H, d, J=12.0 Hz), 3.79 (1H, d, J=12.0 Hz), 3.63-3.52 (6H, m), 3.49 (2H, m), 3.46 (2H, m), 2.78 (1H, dd, J=8.4, 4.3 Hz), 1.68 (1H, dd, J=8.3, 5.4 Hz), 1.11 (1H, t, J=4.8 Hz).

¹³C NMR (DMSO$_{d6}$): 166.9, 161.8, 160.1, 156, 133, 133, 132.3, 132.3, 131.7, 129.3, 129.2, 118, 117.8, 116.2, 116.2, 113.7, 66, 51.6, 51.6, 45.7, 41.7, 32.3, 29, 22.1, 20.7.

Example 158: 2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)-1-(piperidin-1-yl)ethan-1-one

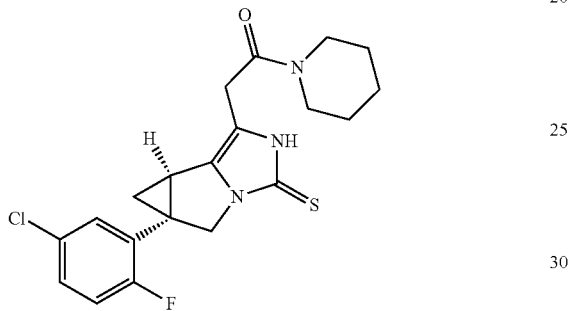

Compound was prepared analogous manner to Example 32 from 2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a dark yellow solid.

¹H NMR (DMSO$_{d6}$): 11.60 (1H, s), 7.47-7.40 (2H, m), 7.30 (1H, dd, J=9.9, 8.7 Hz), 4.08 (1H, d, J=12.2 Hz), 3.79 (1H, d, J=12.2 Hz), 3.54 (2H, m), 3.44 (4H, m), 2.78 (1H, dd, J=8.3, 4.2 Hz), 1.68 (1H, dd, J=8.4, 5.3 Hz), 1.58 (2H, m), 1.50 (2H, m), 1.44 (2H, m), 1.10 (1H, t, J=4.8 Hz).

¹³C NMR (DMSO$_{d6}$): 166.2, 161.2, 159.6, 155.9, 131.6, 130.1, 130.1, 129.3, 129.3, 128.9, 128.7, 128.3, 128.2, 117.6, 117.4, 114, 51.5, 51.5, 46.2, 42.2, 32.3, 29.3, 25.9, 25.2, 23.9, 22.1, 20.7.

Example 159: (R)-2-(6-(3-bromo-2,6-difluorophenyl)-3-thioxo-2,5,6,7-tetrahydro-3H-pyrrolo[1,2-c]imidazol-1-yl)-N-(cyanomethyl)acetamide

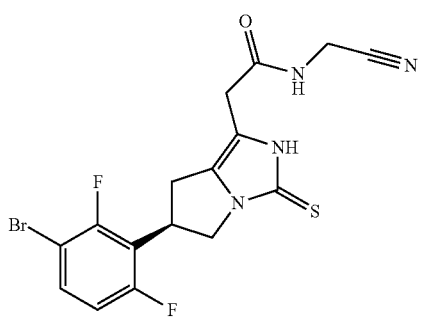 [SMILES: N#CCNC(=O)Cc1[nH]c(=S)n2c1C[C@H](c1c(F)ccc(Br)c1F)C2]

Compound was prepared analogous manner to Example 34 from (R)-2-(6-(3-bromo-2,6-difluorophenyl)-3-thioxo-2,5,6,7-tetrahydro-3H-pyrrolo[1,2-c]imidazol-1-yl)acetic acid (Example 13) and isolated as a grey powder.

¹H NMR (DMSO$_{d6}$): 11.80 (1H, s), 8.65 (1H, t, J=5.5 Hz), 7.72 (1H, m), 7.17 (1H, m), 4.45 (1H, quin, J=8.7 Hz), 4.15 (1H, dd, J=9.4, 11.5 Hz), 4.14 (2H, d, J=5.6 Hz), 3.74 (1H, dd, J=11.5, 8.1 Hz), 3.34 (2H, m), 3.22 (1H, dd, J=15.8, 9.3 Hz), 2.86 (1H, dd, J=15.8, 8.4 Hz).

¹³C NMR (DMSO$_{d6}$): 168.6, 160.8, 160.8, 159.2, 159.1, 157.6, 157.5, 155.9, 155.9, 155.4, 132.5, 132.4, 129.7, 118.6, 118.5, 118.3, 117.5, 113.8, 113.8, 113.6, 113.6, 113.3, 104.1, 104, 103.9, 103.9, 48.6, 35.7, 31, 29.2, 27.2.

Example 160: 2-((R)-6-(3-bromo-2,6-difluorophenyl)-3-thioxo-2,5,6,7-tetrahydro-3H-pyrrolo[1,2-c]imidazol-1-yl)-N-((1R,2R)-2-hydroxycyclohexyl)acetamide

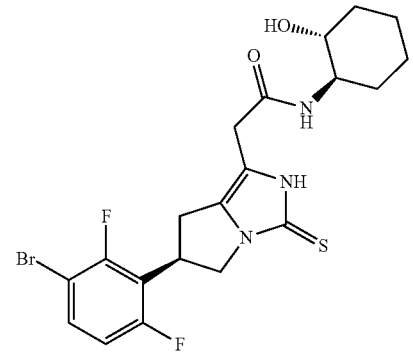 [SMILES: O=C(Cc1[nH]c(=S)n2c1C[C@H](c1c(F)ccc(Br)c1F)C2)N[C@@H]1CCCC[C@H]1O]

Compound was prepared analogous manner to Example 34 from (R)-2-(6-(3-bromo-2,6-difluorophenyl)-3-thioxo-2,5,6,7-tetrahydro-3H-pyrrolo[1,2-c]imidazol-1-yl)acetic acid (Example 13) and isolated as a beige powder.

¹H NMR (DMSO$_{d6}$): 1.71 (1H, 2 s), 7.80 (1H, 2 d, J=2.1 Hz), 7.72 (1H, m), 7.16 (1H, m), 4.52 (1H, 2 dd, J=4.8 Hz), 4.43 (1H, 2 quin, J=8.6 Hz), 4.14 (1H, dd, J=11.4, 9.5 Hz), 3.72 (1H, dd, J=11.6, 7.9 Hz), 3.37 (1H, m), 3.29-3.18 (4H, m), 2.86 (0.5H, dd, J=8.2, 16.2 Hz), 2.82 (0.5H, dd, J=8.3, 16.0 Hz), 1.83 (1H, m), 1.75 (1H, m), 1.64-1.50 (2H, 2 m), 1.22-1.01 (4H, m).

¹³C NMR (DMSO$_{d6}$): 167.2, 167.2, 160.8, 160.8, 159.2, 159.1, 157.6, 157.5, 155.9, 155.9, 155, 155, 132.5, 132.4, 129, 129, 118.8, 118.8, 118.7, 118.6, 118.6, 118.5, 114.6, 113.8, 113.8, 113.6, 113.6, 104.1, 104, 103.9, 103.9, 71.1, 54.5, 48.5, 35.6, 33.9, 31.8, 31.7, 30.9, 29.4, 29.4, 24.1, 23.7.

Example 161: 2-((R)-6-(3-bromo-2,6-difluorophenyl)-3-thioxo-2,5,6,7-tetrahydro-3H-pyrrolo[1,2-c]imidazol-1-yl)-N-((1S,2S)-2-hydroxycyclopentyl)acetamide

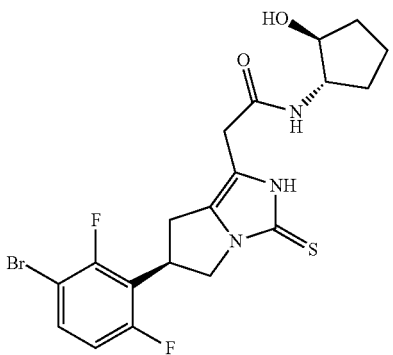 [SMILES: O=C(Cc1[nH]c(=S)n2c1C[C@H](c1c(F)ccc(Br)c1F)C2)N[C@H]1CCC[C@@H]1O]

Compound was prepared analogous manner to Example 34 from (R)-2-(6-(3-bromo-2,6-difluorophenyl)-3-thioxo-2,5,6,7-tetrahydro-3H-pyrrolo[1,2-c]imidazol-1-yl)acetic acid (Example 13) and isolated as a light brown powder.

$^1$H NMR (DMSO$_{d6}$): 1.74 (1H, s), 7.89 (1H, d, J=7.2 Hz), 7.72 (1H, m), 7.16 (1H, m), 4.70 (1H, d, J=4.3 Hz), 4.44 (1H, quin, J=8.6 Hz), 4.14 (1H, dd, J=11.4, 9.3 Hz), 3.79 (1H, m), 3.73 (2H, m), 3.22 (2H, s), 3.22 (1H, m), 2.83 (1H, dd, J=15.8, 8.2 Hz), 1.90 (1H, m), 1.76 (1H, m), 1.59 (2H, m), 1.41 (1H, m), 1.30 (1H, m).

$^{13}$C NMR (DMSO$_{d6}$): 167.3, 160.8, 160.8, 159.2, 159.1, 157.5, 157.5, 155.9, 155.9, 155.1, 132.5, 132.4, 128.9, 118.8, 118.7, 118.5, 114.4, 113.8, 113.8, 113.6, 113.6, 104.1, 104, 103.9, 103.9, 76, 57.7, 48.5, 35.6, 32.1, 31.5, 29.4, 29.3, 20.4.

Example 162: (S)—N-(2-(1H-pyrazol-1-yl)ethyl)-2-(6-(3-chloro-2,6-difluorophenyl)-3-thioxo-2,5,6,7-tetrahydro-3H-pyrrolo[1,2-c]imidazol-1-yl)acetamide

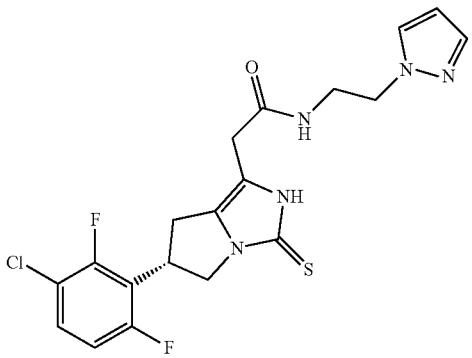 [SMILES: O=C(Cc1[nH]c(=S)n2c1C[C@@H](c1c(F)ccc(Cl)c1F)C2)NCCn1cccn1]

Compound was prepared analogous manner to Example 34 from (S)-2-(6-(3-chloro-2,6-difluorophenyl)-3-thioxo-2,5,6,7-tetrahydro-3H-pyrrolo[1,2-c]imidazol-1-yl)acetic acid and isolated as a beige solid.

$^1$H NMR (DMSO$_{d6}$): 11.74 (1H, s), 8.06 (1H, t, J=5.6 Hz), 7.66 (1H, d, J=2.1 Hz), 7.62 (1H, m), 7.40 (1H, d, J=1.3 Hz), 7.23 (1H, m), 6.17 (1H, t, J=2.1 Hz), 4.42 (1H, quin, J=8.7 Hz), 4.15 (3H, m), 3.73 (1H, dd, J=11.4, 8.2 Hz), 3.43 (2H, q, J=6.0 Hz), 3.22 (2H, m), 3.13 (1H, dd, J=15.7, 9.2 Hz), 2.79 (1H, dd, J=15.8, 8.4 Hz).

$^{13}$C NMR (DMSO$_{d6}$): 168, 160.2, 160.1, 158.5, 158.5, 156.6, 156.5, 155.2, 155, 154.9, 138.7, 130.1, 129.7, 129.6, 129.2, 118.4, 116.1, 116, 115.9, 115.9, 114, 113.2, 113.2, 113.1, 113.1, 104.9, 50.2, 48.4, 39.8, 35.6, 31.4, 29.1.

Example 163: (S)-2-(6-(3-chloro-2,6-difluorophenyl)-3-thioxo-2,5,6,7-tetrahydro-3H-pyrrolo[1,2-c]imidazol-1-yl)-N-(1,1-dioxidotetrahydro-2H-thiopyran-4-yl)-N-methylacetamide

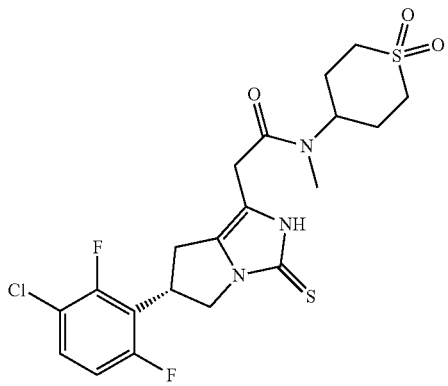 [SMILES: CN(C(=O)Cc1[nH]c(=S)n2c1C[C@@H](c1c(F)ccc(Cl)c1F)C2)C1CCS(=O)(=O)CC1]

Compound was prepare analogous manner to Example 34 from (S)-2-(6-(3-chloro-2,6-difluorophenyl)-3-thioxo-2,5,6,7-tetrahydro-3H-pyrrolo[1,2-c]imidazol-1-yl)acetic acid and isolated as an orange solid.

$^1$H NMR (DMSO$_{d6}$): 1.70 (1H, s), 7.61 (1H, m), 7.22 (1H, m), 4.58 (0.65H, tt, J=12.3, 3.4 Hz), 4.45 (1H, m), 4.16 (1.35H, m), 3.74 (1H, m), 3.58 (0.7H, m), 3.49 (1.3H, m), 3.43-3.35 (2H, m), 3.22 (1H, m), 3.12 (0.7H, m), 3.04 (1.3H, m), 2.85 (1.95H, s), 2.83 (1H, m), 2.70 (1.05H, s), 2.24-2.07 (2H, m), 1.93 (0.7H, m), 1.79 (1.3H, m).

$^{13}$C NMR (DMSO$_{d6}$): 167.8, 167.6, 160.1, 160.1, 158.5, 158.4, 156.6, 156.5, 155.1, 155.1, 154.9, 154.8, 129.7, 129.6, 129.5, 129.3, 118.9, 118.8, 118.7, 116.1, 116, 115.9, 115.9, 114.2, 114.1, 113.2, 113.2, 113.1, 113.1, 49.4, 49.3, 49.2, 48.6, 35.7, 35.6, 29.9, 29.4, 29.2, 29.1, 27.7, 27.7, 26.9, 26.6.

Example 164: 2-((S)-6-(3-bromo-2,6-difluorophenyl)-3-thioxo-2,5,6,7-tetrahydro-3H-pyrrolo[1,2-c]imidazol-1-yl)-1-(3-(methylsulfonyl)pyrrolidin-1-yl)ethan-1-one

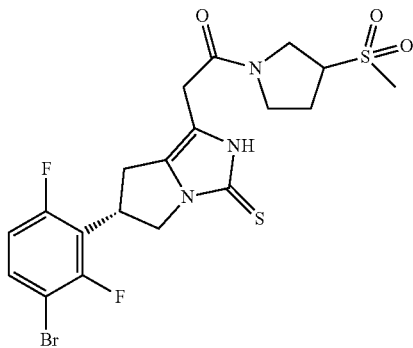 [SMILES: CS(=O)(=O)C1CCN(C(=O)Cc2[nH]c(=S)n3c2C[C@@H](c2c(F)ccc(Br)c2F)C3)C1]

Compound was prepared analogous manner to Example 34 from (S)-2-(6-(3-bromo-2,6-difluorophenyl)-3-thioxo-2,5,6,7-tetrahydro-3H-pyrrolo[1,2-c]imidazol-1-yl)acetic acid (Example 12) and isolated as a beige solid.

¹H NMR (DMSO$_{d6}$): 1.73 (1H, 2 s), 7.72 (1H, m), 7.16 (1H, m), 4.44 (1H, m), 4.15 (1H, m), 4.06, 3.94 (1H, 2 m), 3.88, 3.83, 3.70-3.61, 3.56, 3.50, 3.38 (4H, several mult.), 3.72 (1H, dd, J=11.4, 8.0 Hz), 3.48, 3.45 (2H, 2 m), 3.22 (1H, dd, J=15.6, 9.4 Hz), 3.07, 3.05 (3H, 2s), 2.84 (1H, m), 2.33 (1H, m), 2.22 (1H, m).

¹³C NMR (DMSO$_{d6}$): 166.4, 166.3, 160.8, 160.8, 159.2, 159.1, 157.5, 157.5, 155.9, 155.8, 155.2, 155.2, 132.5, 132.4, 129.4, 129.4, 118.8, 118.8, 118.7, 118.6, 118.5, 118.5, 113.8, 113.8, 113.7, 113.6, 113.6, 104.1, 104, 103.9, 103.9, 60.6, 60.6, 58.9, 58.9, 48.6, 45.4, 45.4, 45.3, 45.3, 45.1, 44.9, 35.7, 30.3, 30.2, 30.2, 30.2, 29.3, 25.7, 24.1, 24.1.

Example 165: (S)-2-(6-(3-bromo-2,6-difluorophenyl)-3-thioxo-2,5,6,7-tetrahydro-3H-pyrrolo[1,2-c]imidazol-1-yl)-1-(2-oxa-8-azaspiro[4.5]decan-8-yl)ethan-1-one

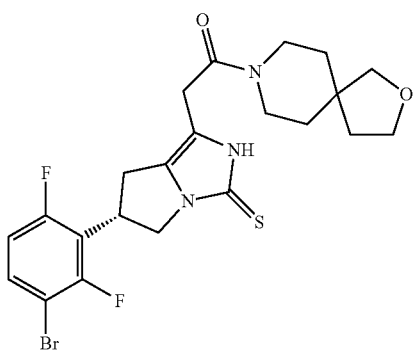 [SMILES: O=C(Cc1[nH]c(=S)n2c1C[C@@H](c1c(F)ccc(Br)c1F)C2)N1CCC2(CCOC2)CC1]

Compound was prepared analogous manner to Example 34 from (S)-2-(6-(3-bromo-2,6-difluorophenyl)-3-thioxo-2,5,6,7-tetrahydro-3H-pyrrolo[1,2-c]imidazol-1-yl)acetic acid (Example 12) and isolated as a beige solid.

¹H NMR (DMSO$_{d6}$): 1.70 (1H, s), 7.72 (1H, m), 7.16 (1H, m), 4.45 (1H, quin, J=8.3 Hz), 4.15 (1H, br t, J=10 Hz), 3.73 (3H, m), 3.60-3.27 (8H, m), 3.21 (1H, br dd, J=15.7, 9.2 Hz), 2.80 (1H, br dd, J=15.8, 7.6 Hz), 1.72 (2H, m), 1.47 (2H, m), 1.42 (2H, m).

¹³C NMR (DMSO$_{d6}$): 166.4, 166.4, 160.8, 159.2, 157.5, 157.5, 155.9, 155.8, 155.1, 132.4, 132.4, 129.1, 118.9, 118.8, 118.7, 114, 114, 113.8, 113.8, 113.6, 113.6, 104, 104, 103.9, 103.9, 76.9, 76.7, 66.4, 66.4, 48.6, 43.4, 41.6, 36.5, 36.3, 35.6, 34.7, 34, 29.3, 29.2.

Example 166: (S)-2-(6-(3-bromo-2,6-difluorophenyl)-3-thioxo-2,5,6,7-tetrahydro-3H-pyrrolo[1,2-c]imidazol-1-yl)-1-(1-oxidothiomorpholino)ethan-1-one

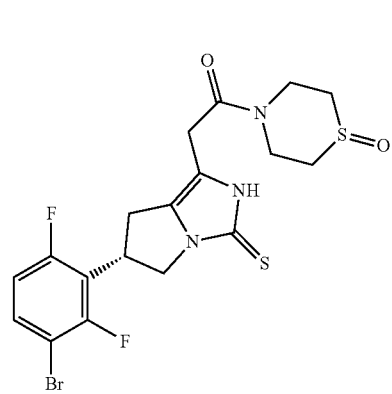 [SMILES: O=C(Cc1[nH]c(=S)n2c1C[C@@H](c1c(F)ccc(Br)c1F)C2)N1CCS(=O)CC1]

Compound was prepared analogous manner to Example 34 from (S)-2-(6-(3-bromo-2,6-difluorophenyl)-3-thioxo-2,5,6,7-tetrahydro-3H-pyrrolo[1,2-c]imidazol-1-yl)acetic acid (Example 12) and isolated as a beige solid.

¹H NMR (DMSO$_{d6}$): 1.68 (1H, s), 7.72 (1H, m), 7.17 (1H, m), 4.46 (1H, quin, J=8.4 Hz), 4.16 (2H, m), 3.88 (1H, m), 3.82 (1H, m), 3.73 (1H, dd, J=11.3, 8.1 Hz), 3.57 (3H, m), 3.23 (1H, dd, J=15.7, 9.4 Hz), 2.90 (1H, m), 2.83 (1H, dd, J=15.8, 8.2 Hz), 2.76 (3H, m).

¹³C NMR (DMSO$_{d6}$): 167, 160.8, 160.8, 159.2, 159.1, 157.5, 157.5, 155.9, 155.8, 155.1, 132.5, 132.4, 129.4, 118.9, 118.7, 118.6, 113.9, 113.8, 113.8, 113.6, 113.6, 104.1, 104, 103.9, 103.9, 48.6, 45.1, 45, 44.7, 44.6, 37, 37, 37, 35.7, 33.1, 33.1, 29.3, 29.3, 29.2, 28.8, 28.8.

Example 167: 2-((S)-6-(3-bromo-2,6-difluorophenyl)-3-thioxo-2,5,6,7-tetrahydro-3H-pyrrolo[1,2-c]imidazol-1-yl)-N-methyl-N-(tetrahydrofuran-3-yl)acetamide

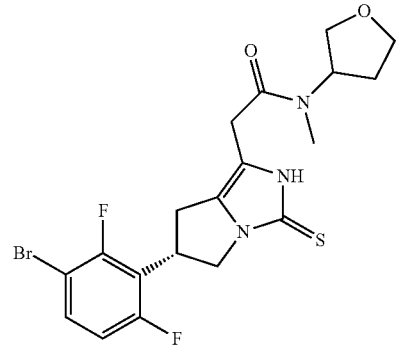 [SMILES: CN(C(=O)Cc1[nH]c(=S)n2c1C[C@@H](c1c(F)ccc(Br)c1F)C2)C1CCOC1]

Compound was prepared analogous manner to Example 34 from (S)-2-(6-(3-bromo-2,6-difluorophenyl)-3-thioxo-2,5,6,7-tetrahydro-3H-pyrrolo[1,2-c]imidazol-1-yl)acetic acid (Example 12) and isolated as a brown powder.

¹H NMR (DMSO$_{d6}$): 1.68 (1H, 2 s), 7.72 (1H, m), 7.16 (1H, m), 5.08 (0.6H, m), 4.61 (0.4H, m), 4.45 (1H, quin, J=8.6 Hz), 4.15 (1H, dd, J=9.6, 11.5 Hz), 3.91 (1H, m), 3.72 (1H, dd, J=11.7, 7.8 Hz), 3.66 (0.8H, m), 3.63-3.52 (3H, m), 3.48 (1.2H, m), 3.20 (1H, m), 2.88 (1.8H, m), 2.81 (1H, m), 2.72 (1.2H, s), 2.21-2.02 (1H, m), 1.88-1.69 (1H, m).

$^{13}$C NMR (DMSO$_{d6}$): 168.2, 168.2, 167.7, 160.8, 160.7, 159.1, 159.1, 157.5, 157.5, 155.9, 155.8, 155.1, 155.1, 132.4, 132.4, 129.3, 129.2, 118.8, 118.7, 118.6, 114.2, 114.2, 114.1, 113.8, 113.8, 113.6, 113.6, 104.1, 104, 103.9, 103.9, 69.3, 69.3, 69.2, 67.1, 67, 56.5, 56.5, 52.9, 48.6, 35.7, 30, 29.8, 29.8, 29.7, 29.7, 29.5, 29.5, 29.3, 29.2, 27.6.

Example 168: (S)-2-(6-(3-chloro-2,6-difluorophenyl)-3-thioxo-2,5,6,7-tetrahydro-3H-pyrrolo[1,2-c]imidazol-1-yl)-N-(1,3,4-thiadiazol-2-yl)acetamide

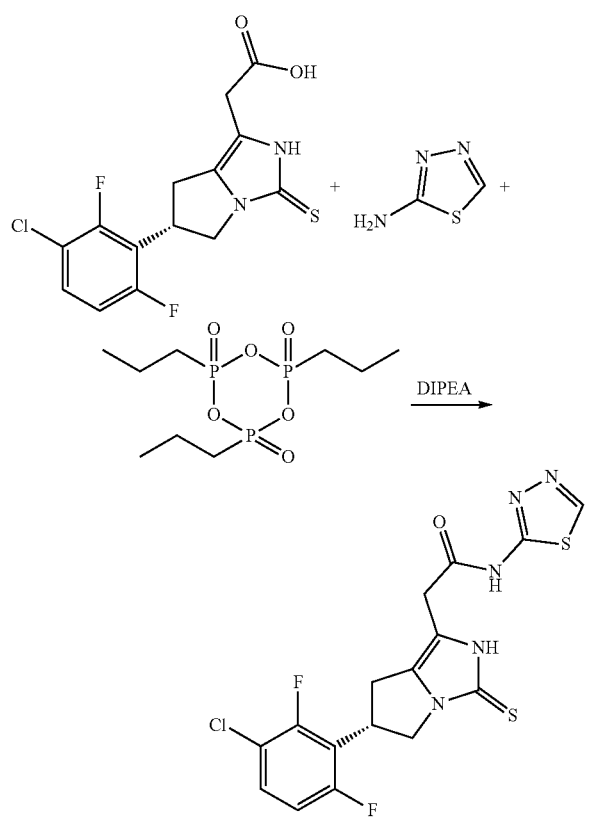

To a stirred mixture of 1,3,4-thiadiazol-2-amine (35.2 mg, 0.348 mmol) and N-ethyl-N-isopropylpropan-2-amine (DIPEA) (0.06 ml, 0.348 mmol). in dichloromethane (2 mL) was added (S)-2-(6-(3-chloro-2,6-difluorophenyl)-3-thioxo-3,5,6,7-tetrahydro-2H-pyrrolo[1,2-c]imidazol-1-yl)acetic acid (100 mg, 0.290 mmol) followed by addition of 2,4,6-tripropyl-1,3,5,2,4,6-trioxatriphosphinane 2,4,6-trioxide (0.180 ml, 0.290 mmol). The reaction was stirred at room temperature overnight. Thereupon, the organic was removed under vacuum and the residue was purified by column chromatography in a mixture of dichloromethane-methanol. Recrystallization from isopropanol afforded the titled product as an off-white solid.

Yield: 76 mg, 61%.

$^1$H NMR (DMSO$_{d6}$): 12.72 (1H, s), 11.81 (1H, s), 9.17 (1H, s), 7.61 (1H, m), 7.22 (1H, m), 4.47 (1H, quin, J=8.6 Hz), 4.17 (1H, dd, J=9.5, 11.2 Hz), 3.75 (1H, dd, J=11.7, 8.1 Hz), 3.71 (2H, m), 3.26 (1H, dd, J=15.8, 9.2 Hz), 2.88 (1H, dd, J=15.8, 8.2 Hz).

$^{13}$C NMR (DMSO$_{d6}$): 167.5, 160.2, 160.1, 158.5, 158.5, 158.5, 156.6, 156.5, 155.6, 154.9, 154.9, 148.8, 130.2, 129.7, 129.6, 118.7, 118.6, 118.5, 116.1, 116, 115.9, 115.9, 113.3, 113.2, 113.1, 113.1, 112.5, 48.6, 35.6, 31.1, 29.2.

Example 169: (S)-2-(6-(3-chloro-2,6-difluorophenyl)-3-thioxo-2,5,6,7-tetrahydro-3H-pyrrolo[1,2-c]imidazol-1-yl)-N-(pyridin-2-yl)acetamide

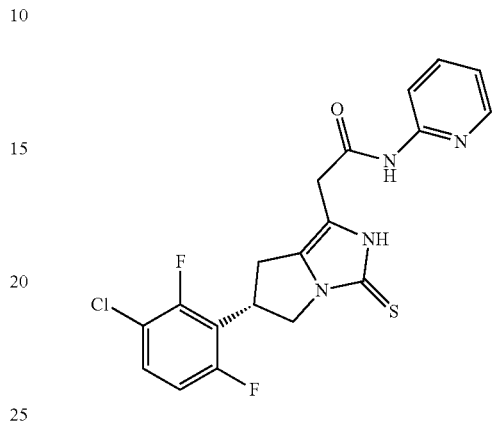

Compound was prepared analogous manner to Example 168 from (S)-2-(6-(3-chloro-2,6-difluorophenyl)-3-thioxo-2,5,6,7-tetrahydro-3H-pyrrolo[1,2-c]imidazol-1-yl)acetic acid and isolated as an off-white powder.

$^1$H NMR (DMSO$_{d6}$): 11.81 (1H, s), 10.61 (1H, s), 8.31 (1H, ddd, J=0.8, 1.8, 4.8 Hz), 8.04 (1H, br d, J=8.2 Hz), 7.77 (1H, m), 7.61 (1H, m), 7.21 (1H, m), 7.10 (1H, ddd, J=7.3, 4.9, 0.9 Hz), 4.46 (1H, quin, J=8.6 Hz), 4.17 (1H, dd, J=11.3, 9.4 Hz), 3.75 (1H, dd, J=11.6, 7.9 Hz), 3.58 (2H, m), 3.26 (1H, dd, J=15.8, 9.3 Hz), 2.88 (1H, dd, J=8.3, 15.8 Hz).

$^{13}$C NMR (DMSO$_{d6}$): 167.6, 160.1, 160.1, 158.5, 158.5, 156.6, 156.5, 155.4, 154.9, 154.9, 151.9, 148, 138.2, 129.7, 129.6, 119.5, 118.8, 118.6, 118.5, 116.1, 116, 115.9, 115.9, 113.6, 113.4, 113.2, 113.1, 113.1, 48.6, 35.6, 32.2, 29.2.

Example 170: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-(pyridin-2-yl)acetamide

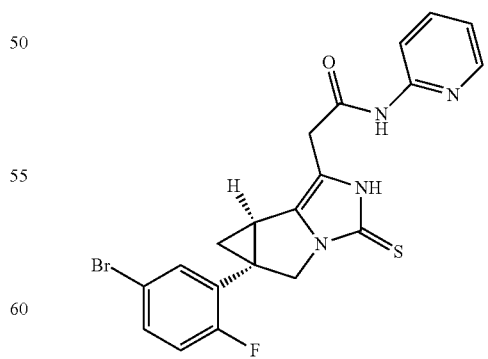

Compound was prepared analogous manner to Example 168 from 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)acetic acid and isolated as a brown solid.

¹H NMR (DMSO$_{d6}$): 11.71 (1H, s), 10.62 (1H, s), 8.33 (1H, dd, J=4.7, 1.0 Hz), 8.06 (1H, br d, J=8.1 Hz), 7.79 (1H, m), 7.56 (2H, m), 7.24 (1H, dd, J=10.0, 8.8 Hz), 7.11 (1H, ddd, J=6.7, 5.6, 0.7 Hz), 4.09 (1H, d, J=12.0 Hz), 3.81 (1H, d, J=12.2 Hz), 3.65 (2H, m), 2.88 (1H, dd, J=8.4, 4.3 Hz), 1.66 (1H, dd, J=8.3, 5.4 Hz), 1.14 (1H, t, J=4.8 Hz).

¹³C NMR (DMSO$_{d6}$): 167.7, 161.7, 160.1, 156.1, 151.9, 148, 138.2, 132.9, 132.9, 132.3, 132.3, 129.3, 129.2, 119.5, 118, 117.8, 116.2, 116.2, 113.4, 113.2, 51.6, 32.3, 32.2, 22.2, 20.6.

Example 171: 2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)-N-(pyridin-3-yl)acetamide

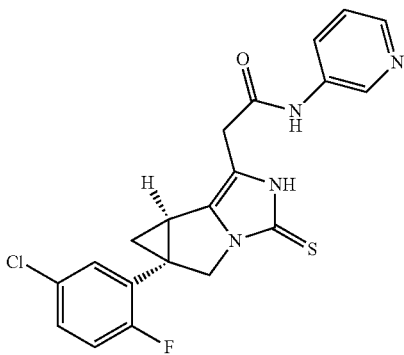 [SMILES: O=C(Cc1[nH]c(=S)n2c1[C@@H]1C[C@]1(c1cc(Cl)ccc1F)C2)Nc1cccnc1]

Compound was prepared analogous manner to Example 168 from 2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)acetic acid and isolated as a beige solid.

¹H NMR (DMSO$_{d6}$): 11.75 (1H, br s), 10.33 (1H, br s), 8.75 (1H, br s), 8.27 (1H, d, J=4.1 Hz), 8.04 (1H, d, J=7.9 Hz), 7.46 (1H, dd, J=6.5, 2.6 Hz), 7.43 (1H, ddd, J=8.7, 4.3, 2.6 Hz), 7.37 (1H, dd, J=8.2, 4.7 Hz), 7.30 (1H, dd, J=9.0, 10.0 Hz), 4.10 (1H, d, J=12.0 Hz), 3.82 (1H, d, J=12.0 Hz), 3.61 (2H, br s), 2.88 (1H, dd, J=8.2, 4.1 Hz), 1.67 (1H, dd, J=8.4, 5.4 Hz), 1.16 (1H, t, J=4.8 Hz).

¹³C NMR (DMSO$_{d6}$): 167.4, 161.3, 159.6, 156.2, 144.3, 140.8, 135.7, 132.3, 130.2, 130.1, 129.4, 129.3, 128.9, 128.7, 128.3, 126.3, 123.7, 117.6, 117.4, 113.2, 51.6, 32.4, 32.1, 22.1, 20.7.

Example 172: (R)-1-(2-hydroxyethyl)-6-(2,3,5,6-tetrafluorophenyl)-2,5,6,7-tetrahydro-3H-pyrrolo[1,2-c]imidazole-3-thione

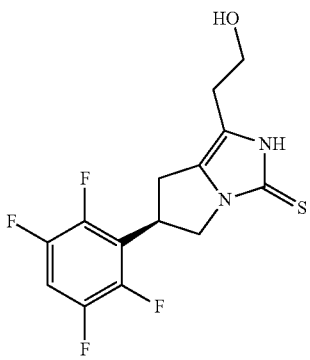 [SMILES: OCCc1[nH]c(=S)n2c1C[C@H](c1c(F)c(F)cc(F)c1F)C2]

Compound was prepared analogous manner to Example 8 from ethyl (R)-2-(6-(2,3,5,6-tetrafluorophenyl)-3-thioxo-2,5,6,7-tetrahydro-3H-pyrrolo[1,2-c]imidazol-1-yl)acetate and isolated as a cream powder.

¹H NMR (DMSO$_{d6}$): 1.73 (1H, s), 7.85 (1H, m), 4.69 (1H, t, J=5.3 Hz), 4.48 (1H, quin, J=8.6 Hz), 4.16 (1H, dd, J=11.5, 9.2 Hz), 3.76 (1H, dd, J=11.6, 8.1 Hz), 3.55 (2H, m), 3.29 (1H, dd, J=15.6, 9.2 Hz), 2.93 (1H, dd, J=15.6, 8.2 Hz), 2.49 (2H, t, J=6.8 Hz).

¹³C NMR (DMSO$_{d6}$): 155, 146.4, 146.4, 146.4, 146.3, 146.3, 146.2, 145.4, 145.3, 145.3, 145.3, 145.2, 145.2, 145.2, 144.8, 144.8, 144.7, 144.7, 144.7, 144.6, 144.6, 143.7, 143.7, 143.7, 143.7, 143.6, 143.6, 143.6, 143.6, 128.2, 120.4, 120.3, 120.2, 117.6, 105.9, 105.7, 105.5, 59.2, 48.3, 35.8, 29, 28.

Example 173: (R)-6-(3-bromo-2,6-difluorophenyl)-1-(2-hydroxyethyl)-2,5,6,7-tetrahydro-3H-pyrrolo[1,2-c]imidazole-3-thione

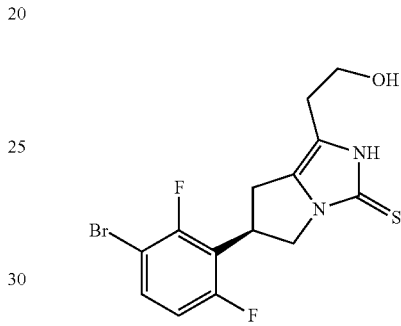

Compound was prepared analogous manner to Example 8 from ethyl (R)-2-(6-(3-bromo-2,6-difluorophenyl)-3-thioxo-2,5,6,7-tetrahydro-3H-pyrrolo[1,2-c]imidazol-1-yl)acetate and isolated as a light cream powder.

¹H NMR (DMSO$_{d6}$): 11.72 (1H, s), 7.72 (1H, ddd, J=9.0, 8.0, 5.8 Hz), 7.16 (1 Hm), 4.69 (1H, br t, J=5.1 Hz), 4.43 (1H, quin, J=8.7 Hz), 4.13 (1H, dd, J=11.6, 9.1 Hz), 3.71 (1H, dd, J=11.6, 8.1 Hz), 3.54 (2H, m), 3.25 (1H, dd, J=15.6, 9.2 Hz), 2.89 (1H, dd, J=15.6, 8.4 Hz), 2.48 (2H, t, J=6.7 Hz).

¹³C NMR (DMSO$_{d6}$): 160.8, 160.8, 159.2, 159.1, 157.6, 157.5, 155.9, 155.9, 154.9, 132.5, 132.4, 128.3, 118.7, 118.6, 118.4, 117.5, 113.8, 113.8, 113.6, 113.6, 104.1, 104, 103.9, 103.9, 59.2, 48.4, 35.7, 29.1, 28.

Example 174: (5aS,6aR)-5a-(5-chloro-2-fluorophenyl)-1-(2-morpholinoethyl)-5,5a,6,6a-tetrahydrocyclopropa[3,4]pyrrolo[1,2-c]imidazole-3(2H)-thione hydrochloride

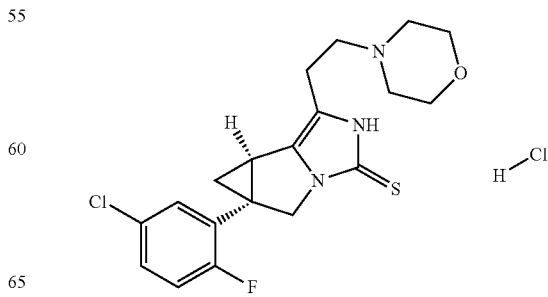

Compound was prepared analogous manner to Example 35 from 2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)-1-morpholinoethan-1-one (Example 66) and isolated as a beige solid.

¹H NMR (CD₃OD): 7.44 (1H, dd, J=6.4, 2.7 Hz), 7.36 (1H, ddd, J=8.8, 4.4, 2.6 Hz), 7.17 (1H, dd, J=9.8, 8.8 Hz), 4.20 (1H, d, J=12.3 Hz), 3.93 (1H, d, J=12.2 Hz), 3.86 (4H, br), 3.28-3.0 (6H, m), 2.94 (2H, m), 2.85 (1H, dd, J=8.3, 4.0 Hz), 1.71 (1H, dd, J=8.2, 5.6 Hz), 1.18 (1H, dd, J=5.5, 4.2 Hz).

¹³C NMR (CD₃OD): 163.3, 161.6, 157.1, 134.2, 131.5, 131.4, 131, 130.9, 130.7, 130.7, 130, 129.9, 118.6, 118.4, 66.2, 57.3, 54, 53.5, 53.5, 34.2, 23.2, 22.1, 21.3.

Example 175: (5aS,6aR)-5a-(5-chloro-2-fluorophenyl)-1-(2-(isopropylamino)ethyl)-5,5a,6,6a-tetrahydrocyclopropa[3,4]pyrrolo[1,2-c]imidazole-3(2H)-thione hydrochloride

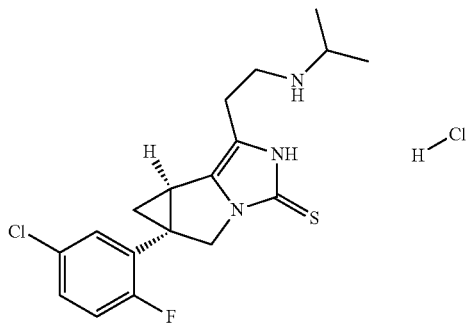 [SMILES: CC(C)NCCc1[nH]c(=S)n2c1[C@@H]1C[C@]1(c1cc(Cl)ccc1F)C2 ; Cl]

Compound was prepared analogous manner to Example 35 from 2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)-N-isopropylacetamide (Example 67) and isolated as a light beige solid.

¹H NMR (DMSO$_{d6}$): 1.80 (1H, br s), 8.48 (2H, br s), 7.48 (1H, dd, J=6.5, 2.7 Hz), 7.44 (1H, ddd, J=8.7, 4.3, 2.8 Hz), 7.31 (1H, dd, J=9.9, 8.9 Hz), 4.08 (1H, d, J=12.2 Hz), 3.80 (1H, d, J=12.0 Hz), 3.31 (1H, m), 3.16 (2H, br t, J=7.5 Hz), 2.97 (1H, dd, J=8.4, 4.3 Hz), 2.80 (2H, m), 1.67 (1H, dd, J=8.2, 5.3 Hz), 1.23 (6H, d, J=6.5 Hz), 1.20 (1H, t, J=4.8 Hz).

¹³C NMR (DMSO$_{d6}$): 161.2, 159.6, 156.5, 131.7, 130.1, 130.1, 129.4, 129.3, 128.8, 128.7, 128.3, 128.3, 117.6, 117.4, 114.6, 51.5, 51.5, 49.4, 42.3, 32.5, 22.1, 21.4, 20.3, 18.8, 18.8.

Example 176: (R)-6-(3-bromo-2,6-difluorophenyl)-1-(2-(((R)-tetrahydrofuran-3-yl)amino)ethyl)-2,5,6,7-tetrahydro-3H-pyrrolo[1,2-c]imidazole-3-thione

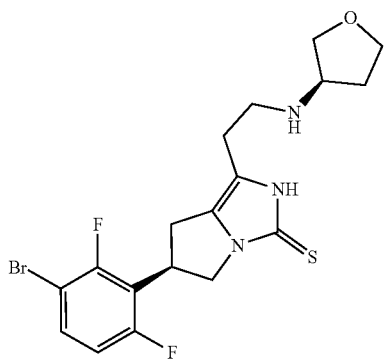 [SMILES: Fc1ccc(Br)c(F)c1[C@H]1Cc2c(CCN[C@@H]3CCOC3)[nH]c(=S)n2C1]

Compound was prepared analogous manner to Example 35 from 2-((R)-6-(3-bromo-2,6-difluorophenyl)-3-thioxo-2,5,6,7-tetrahydro-3H-pyrrolo[1,2-c]imidazol-1-yl)-N—((R)-tetrahydrofuran-3-yl)acetamide (Example 116) and isolated as a cream powder.

¹H NMR (DMSO$_{d6}$): 1.72 (1H, br s), 7.72 (1H, m), 7.16 (1H, m), 4.45 (1H, quin, J=8.5 Hz), 4.13 (1H, dd, J=11.0, 9.7 Hz), 3.74-3.68 (2H, m), 3.66 (1H, dd, J=8.6, 5.8 Hz), 3.61 (1H, m), 3.33 (1H, m), 3.31-3.21 (2H, m), 2.88 (1H, dd, J=15.6, 8.2 Hz), 2.67 (2H, m), 2.46 (2H, t, J=7.1 Hz), 1.91 (1H, m), 1.59 (1H, m).

¹³C NMR (DMSO$_{d6}$): 160.8, 160.8, 159.2, 159.2, 159.1, 157.6, 157.5, 155.9, 155.9, 154.9, 132.4, 132.4, 128.1, 118.9, 118.7, 118.6, 118.2, 113.8, 113.8, 113.6, 113.6, 104.1, 104, 103.9, 103.9, 72.5, 66.3, 57.9, 48.4, 46.3, 35.7, 32.5, 29.2, 25.

Example 177: (R)-6-(3-bromo-2,6-difluorophenyl)-1-(2-(4,4-difluoropiperidin-1-yl)ethyl)-2,5,6,7-tetrahydro-3H-pyrrolo[1,2-c]imidazole-3-thione

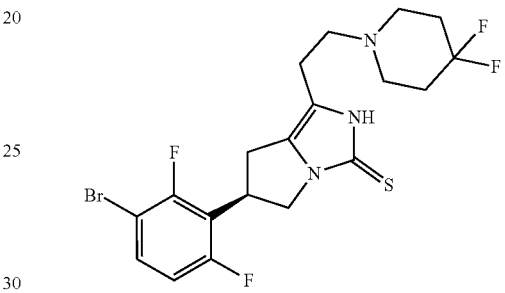

Compound was prepared analogous manner to Example 35 from 2-((R)-6-(3-bromo-2,6-difluorophenyl)-3-thioxo-2,5,6,7-tetrahydro-3H-pyrrolo[1,2-c]imidazol-1-yl)-N—((R)-tetrahydrofuran-3-yl)acetamide (Example 117) and isolated as a white powder.

¹H NMR (DMSO$_{d6}$): 1.74 (1H, s), 7.72 (1H, m), 7.16 (1H, m), 4.45 (1H, quin, J=8.5 Hz), 4.13 (1H, dd, J=11.3, 9.4 Hz), 3.71 (1H, dd, J=11.6, 7.8 Hz), 3.29 (1H, dd, J=15.6, 9.4 Hz), 2.88 (1H, dd, J=15.7, 7.9 Hz), 2.58-2.46 (8H, m), 1.91 (4H, m).

¹³C NMR (DMSO$_{d6}$): 160.8, 160.7, 159.1, 159.1, 157.5, 157.5, 155.9, 155.8, 154.9, 132.4, 132.4, 128.1, 124.4, 122.8, 121.2, 119, 118.9, 118.7, 118, 113.8, 113.7, 113.6, 113.6, 104.1, 104, 103.9, 103.9, 54.9, 49.2, 49.2, 49.1, 48.5, 35.7, 33.5, 33.4, 33.2, 29.2, 22.1.

Example 178: (R)-6-(3-bromo-2,6-difluorophenyl)-1-(2-((1,1-dioxidotetrahydro-2H-thiopyran-4-yl)amino)ethyl)-2,5,6,7-tetrahydro-3H-pyrrolo[1,2-c]imidazole-3-thione

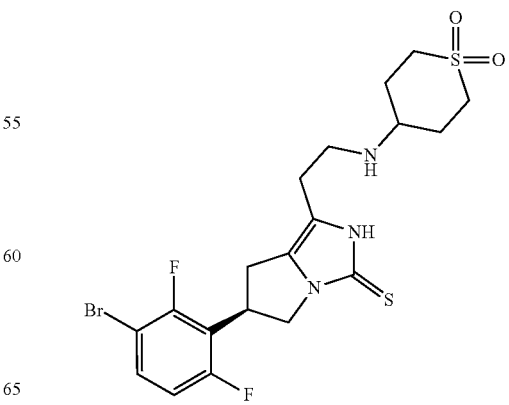

Compound was prepared analogous manner to Example 35 from 2-((R)-6-(3-bromo-2,6-difluorophenyl)-3-thioxo-2,5,6,7-tetrahydro-3H-pyrrolo[1,2-c]imidazol-1-yl)-N—((R)-tetrahydrofuran-3-yl)acetamide (Example 130) and isolated as a cream powder.

$^1$H NMR (DMSO$_{d6}$): 1.74 (1H, s), 7.72 (1H, m), 7.16 (1H, m), 4.45 (1H, quin, J=8.5 Hz), 4.13 (1H, dd, J=9.7, 11.1 Hz), 3.71 (1H, dd, J=11.4, 7.9 Hz), 3.27 (1H, dd, J=15.5, 9.2 Hz), 3.08 (2H, m), 2.98 (2H, m), 2.89 (1H, dd, J=15.6, 8.1 Hz), 2.73 (1H, m), 2.68 (2H, t, J=7.2 Hz), 2.46 (2H, t, J=7.1 Hz), 2.01 (2H, m), 1.83 (2H, m).

$^{13}$C NMR (DMSO$_{d6}$): 160.8, 160.8, 159.2, 159.1, 157.6, 157.5, 155.9, 155.9, 155, 132.5, 132.4, 128.1, 118.9, 118.7, 118.6, 118.2, 113.8, 113.8, 113.6, 113.6, 104.1, 104, 103.9, 103.9, 54.9, 50.4, 48.4, 47.7, 44.8, 35.7, 29.1, 29, 29, 25.

Example 179: (R)-6-(3-bromo-2,6-difluorophenyl)-1-(2-(4-(methylsulfonyl)piperidin-1-yl)ethyl)-2,5,6,7-tetrahydro-3H-pyrrolo[1,2-c]imidazole-3-thione

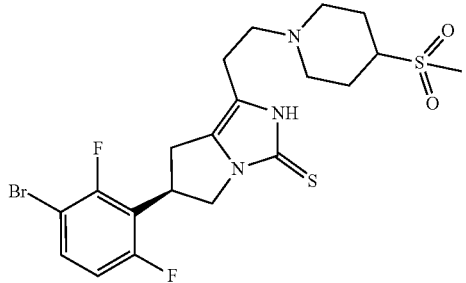 [SMILES: CS(=O)(=O)C1CCN(CCc2[nH]c(=S)n3c2C[C@H](c2c(F)ccc(Br)c2F)C3)CC1]

Compound was prepare analogous manner to Example 35 from 2-((R)-6-(3-bromo-2,6-difluorophenyl)-3-thioxo-2,5,6,7-tetrahydro-3H-pyrrolo[1,2-c]imidazol-1-yl)-N—((R)-tetrahydrofuran-3-yl)acetamide (Example 126) and isolated as a white powder.

$^1$H NMR (DMSO$_{d6}$): 1.74 (1H, s), 7.72 (1H, m), 7.16 (1H, m), 4.45 (1H, quin, J=8.5 Hz), 4.13 (1H, dd, J=11.3, 9.4 Hz), 3.70 (1H, dd, J=11.7, 7.8 Hz), 3.28 (1H, dd, J=15.6, 9.4 Hz), 3.01 (1H, tt, J=3.6, 12.4 Hz), 3.0-2.94 (2H, m), 2.90 (3H, s), 2.89 (1H, dd, J=8.0, 15.4 Hz), 2.50 (4H, m), 1.94 (4H, m), 1.55 (2H, m).

$^{13}$C NMR (DMSO$_{d6}$): 160.8, 160.8, 159.2, 159.1, 157.5, 157.5, 155.9, 155.8, 154.9, 132.4, 132.4, 128.1, 118.9, 118.8, 118.7, 118.1, 113.8, 113.8, 113.6, 113.6, 104.1, 104, 103.9, 103.9, 58.8, 55.7, 51.4, 51.3, 48.5, 37.4, 35.7, 29.2, 24.4, 24.4, 22.

Example 180: (5aS,6aR)-5a-(5-bromo-2-fluorophenyl)-1-(2-((2,2,2-trifluoroethyl)amino)ethyl)-5,5a,6,6a-tetrahydrocyclopropa[3,4]pyrrolo[1,2-c]imidazole-3(2H)-thione

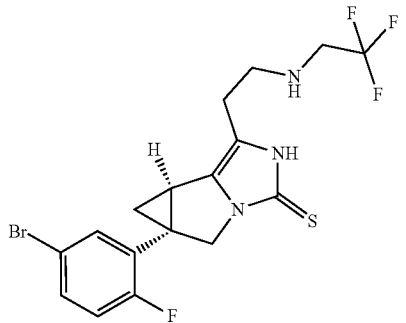 [SMILES: Fc1ccc(Br)cc1[C@]12C[C@H]1c1c(CCNCC(F)(F)F)[nH]c(=S)n1C2]

Compound was prepared analogous manner to Example 35 from 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-(2,2,2-trifluoroethyl)acetamide (Example 152) and isolated as a yellow solid.

$^1$H NMR (DMSO$_{d6}$): 11.65 (1H, s), 7.59 (1H, dd, J=6.7, 2.6 Hz), 7.55 (1H, ddd, J=8.7, 4.5, 2.5 Hz), 7.24 (1H, dd, J=10.2, 8.7 Hz), 4.06 (1H, d, J=11.4 Hz), 3.77 (1H, d, J=12.0 Hz), 3.26 (2H, m), 2.90 (1H, dd, J=8.4, 4.3 Hz), 2.84 (2H, m), 2.54 (2H, m), 1.62 (1H, dd, J=8.3, 5.4 Hz), 1.16 (1H, t, J=4.8 Hz).

$^{13}$C NMR (DMSO$_{d6}$): 161.8, 160.1, 155.8, 132.8, 132.8, 132.2, 132.2, 130.7, 129.5, 129.4, 129, 127.2, 125.3, 123.5, 118, 117.8, 117.5, 116.2, 116.2, 51.4, 49.3, 49.1, 48.9, 48.7, 47.7, 32.2, 24.8, 22.3, 20.4.

Example 181: (S)-6-(3-bromo-2,6-difluorophenyl)-1-(2-(cyclobutylamino)ethyl)-2,5,6,7-tetrahydro-3H-pyrrolo[1,2-c]imidazole-3-thione

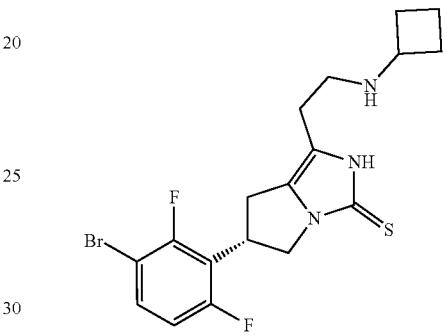

Compound was prepared analogous manner to Example 35 from (S)-2-(6-(3-bromo-2,6-difluorophenyl)-3-thioxo-2,5,6,7-tetrahydro-3H-pyrrolo[1,2-c]imidazol-1-yl)-N-cyclobutylacetamide (Example 102) and isolated as a white powder.

$^1$H NMR (DMSO$_{d6}$): 1.73 (1H, m), 7.72 (1H, m), 7.16 (1H, m), 4.45 (1H, t, J=8.7 Hz), 4.13 (1H, dd, J=11.3, 9.4 Hz), 3.71 (1H, dd, J=11.6, 7.9 Hz), 3.26 (1H, dd, J=15.6, 9.4 Hz), 3.18 (1H, quin, J=7.5 Hz), 2.88 (1H, dd, J=15.6, 8.1 Hz), 2.64 (2H, t, J=7.1 Hz), 2.45 (2H, t, J=7.0 Hz), 2.07 (2H, m), 1.75-1.45 (4H, m).

$^{13}$C NMR (DMSO$_{d6}$): 160.8, 160.8, 159.2, 159.1, 157.6, 157.5, 155.9, 155.9, 155, 132.5, 132.4, 128.1, 118.8, 118.7, 118.6, 118, 113.8, 113.8, 113.6, 113.6, 104.1, 104, 103.9, 103.9, 53.2, 48.4, 44.6, 35.7, 30, 29.1, 24.7, 14.5.

Example 182: (R)-6-(3-bromo-2,6-difluorophenyl)-1-(2-((2-(methylsulfonyl)ethyl)amino)ethyl)-2,5,6,7-tetrahydro-3H-pyrrolo[1,2-c]imidazole-3-thione

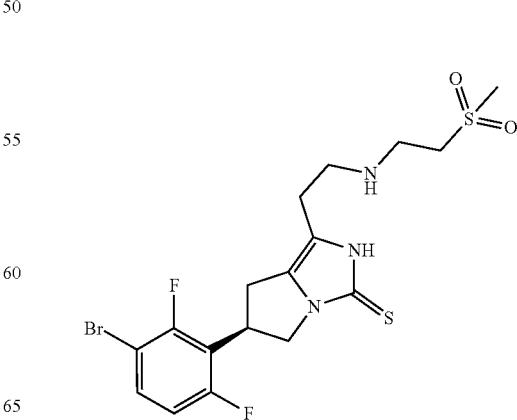

Compound was prepared analogous manner to Example 35 from (R)-2-(6-(3-bromo-2,6-difluorophenyl)-3-thioxo-2,5,6,7-tetrahydro-3H-pyrrolo[1,2-c]imidazol-1-yl)-N-(2-(methylsulfonyl)ethyl)acetamide (Example 118) and isolated as a yellow powder.

$^1$H NMR (DMSO$_{d6}$): 1.73 (1H, br s), 7.73 (1H, m), 7.17 (1H, m), 4.44 (1H, quin, J=8.7 Hz), 4.14 (1H, dd, J=9.5, 11.5 Hz), 3.71 (1H, dd, J=11.5, 8.1 Hz), 3.26 (1H, dd, J=15.5, 9.2 Hz), 3.20 (2H, t, J=6.7 Hz), 2.97 (3H, s), 2.91 (2H, t, J=6.7 Hz), 2.91 (1H, m), 2.70 (2H, t, J=7.0 Hz), 2.47 (2H, t, J=7.0 Hz).

$^{13}$C NMR (DMSO$_{d6}$): 160.8, 160.8, 159.2, 159.1, 157.6, 157.5, 155.9, 155.9, 155, 132.5, 132.4, 128.2, 118.7, 118.6, 118.5, 118, 113.8, 113.8, 113.6, 113.6, 104.1, 104, 103.9, 103.9, 53.6, 48.4, 47, 42.4, 41.4, 35.7, 29, 24.7.

Example 183: (R)-6-(3-bromo-2,6-difluorophenyl)-1-(2-((2-hydroxyethyl)(methyl)amino)ethyl)-2,5,6,7-tetrahydro-3H-pyrrolo[1,2-c]imidazole-3-thione

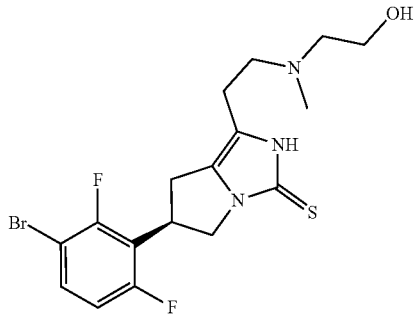 [SMILES: CN(CCO)CCc1[nH]c(=S)n2c1C[C@H](c1c(F)ccc(Br)c1F)C2]

Compound was prepared analogous manner to Example 35 from (R)-2-(6-(3-bromo-2,6-difluorophenyl)-3-thioxo-2,5,6,7-tetrahydro-3H-pyrrolo[1,2-c]imidazol-1-yl)-N-(2-hydroxyethyl)-N-methylacetamide (Example 131) and isolated as a brown powder.

$^1$H NMR (DMSO$_{d6}$): 1.72 (1H, s), 7.72 (1H, m), 7.17 (1H, m), 4.44 (1H, quin, J=8.7 Hz), 4.41 (1H, t, br, J=5.5 Hz), 4.13 (1H, dd, J=11.2, 9.5 Hz), 3.70 (1H, dd, J=11.6, 8.1 Hz), 3.44 (2H, q, J=6.1 Hz), 3.27 (1H, dd, J=15.5, 9.3 Hz), 2.88 (1H, dd, J=15.6, 8.3 Hz), 2.52 (2H, m), 2.48 (2H, t, J=7.1 Hz), 2.41 (2H, t, J=6.2 Hz), 2.18 (3H, s).

$^{13}$C NMR (DMSO$_{d6}$): 160.8, 160.8, 159.2, 159.1, 157.6, 157.5, 155.9, 155.9, 154.9, 132.5, 132.4, 127.9, 118.8, 118.6, 118.5, 118.3, 113.8, 113.8, 113.6, 113.6, 104.1, 104, 103.9, 103.9, 58.9, 58.8, 55.8, 48.4, 42, 35.7, 29.1, 22.1.

Example 184: (R)-6-(3-bromo-2,6-difluorophenyl)-1-(2-(((R)-1-cyclohexylethyl)amino)ethyl)-2,5,6,7-tetrahydro-3H-pyrrolo[1,2-c]imidazole-3-thione

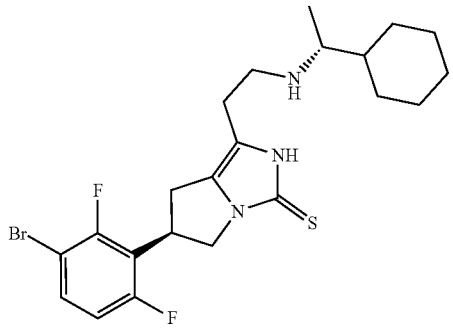 [SMILES: C[C@@H](NCCc1[nH]c(=S)n2c1C[C@H](c1c(F)ccc(Br)c1F)C2)C1CCCCC1]

Compound was prepared analogous manner to Example 35 from 2-((R)-6-(3-bromo-2,6-difluorophenyl)-3-thioxo-2,5,6,7-tetrahydro-3H-pyrrolo[1,2-c]imidazol-1-yl)-N—((R)-1-cyclohexylethyl)acetamide (Example 127) and isolated as a cream powder.

$^1$H NMR (DMSO$_{d6}$): 11.84 (1H, br), 7.73 (1H, m), 7.17 (1H, m), 4.45 (1H, quin, J=8.6 Hz), 4.13 (1H, dd, J=11.2, 9.4 Hz), 3.71 (1H, dd, J=11.6, 7.8 Hz), 3.28 (1H, dd, J=15.7, 9.5 Hz), 2.88 (1H, dd, J=15.6, 8.2 Hz), 2.83, 2.71 (2H, 2 br s), 2.50 (3H, m), 1.68 (2H, br d, J=12.6 Hz), 1.60 (3H, m), 1.38-1.0 (5H, m), 0.94 (4H, m).

$^{13}$C NMR (DMSO$_{d6}$): 160.8, 160.7, 159.1, 159.1, 157.6, 157.5, 155.9, 155.9, 155.1, 132.5, 132.4, 128.2, 118.8, 118.7, 118.6, 113.8, 113.6, 104.1, 103.9, 57, 48.4, 44.8, 41.8, 35.7, 29.2, 29.2, 27.1, 26.2, 26.1, 25.9, 24.6, 15.7.

Example 185: (5aS,6aR)-5a-(5-bromo-2-fluorophenyl)-1-(2-(pyrrolidin-1-yl)ethyl)-5,5a,6,6a-tetrahydrocyclopropa[3,4]pyrrolo[1,2-c]imidazole-3(2H)-thione hydrochloride

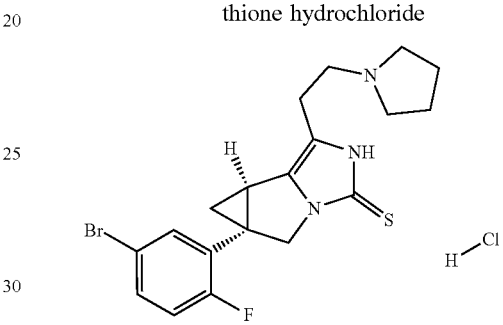

Compound was prepared analogous manner to Example 35 from 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-1-(pyrrolidin-1-yl)ethan-1-one (Example 70) and isolated as a beige solid.

$^1$H NMR (DMSO$_{d6}$): 11.80 (1H, br s), 9.60 (1H, br s), 7.59 (1H, dd, J=6.7, 2.5 Hz), 7.56 (1H, ddd, J=8.7, 4.5, 2.6 Hz), 7.25 (1H, dd, J=10.0, 8.8 Hz), 4.08 (1H, d, J=12.0 Hz), 3.80 (1H, d, J=12.2 Hz), 3.39-3.05 (6H, m), 2.97 (1H, dd, J=8.4, 4.3 Hz), 2.83 (2H, m), 1.91 (4H, br s), 1.67 (1H, dd, J=8.2, 5.3 Hz), 1.19 (1H, t, J=4.7 Hz).

$^{13}$C NMR (DMSO$_{d6}$): 161.8, 160.1, 156.5, 132.9, 132.9, 132.4, 132.3, 131.7, 129.2, 129.1, 118, 117.9, 116.2, 116.2, 114.6, 53.4, 52.4, 51.5, 32.4, 22.7, 22.1, 21.3, 20.3.

Example 186: (5aS,6aR)-5a-(5-bromo-2-fluorophenyl)-1-(2-((cyclopropylmethyl)amino)ethyl)-5,5a,6,6a-tetrahydrocyclopropa[3,4]pyrrolo[1,2-c]imidazole-3(2H)-thione hydrochloride

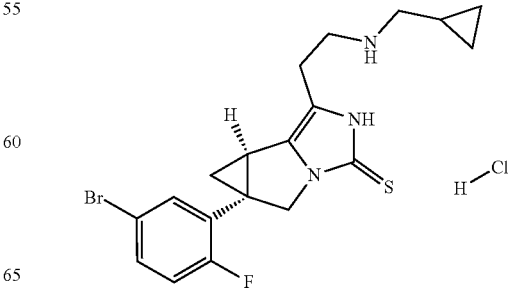

Compound was prepared analogous manner to Example 35 from 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-(cyclopropylmethyl)acetamide (Example 143) and isolated as a beige solid.

$^1$H NMR (DMSO$_{d6}$): 11.79 (1H, s br), 8.39 (2H, s br), 7.59 (1H, dd, J=6.7, 2.5 Hz), 7.56 (1H, ddd, J=8.6, 4.4, 2.6 Hz), 7.25 (1H, dd, J=9.9, 8.9 Hz), 4.08 (1H, br d, J=12.0 Hz), 3.79 (1H, d, J=12.0 Hz), 3.17 (2H, t, J=7.3 Hz), 2.93 (1H, dd, J=8.2, 4.3 Hz), 2.87-2.73 (4H, m), 1.67 (1H, dd, J=8.1, 5.4 Hz), 1.20 (1H, t, J=4.8 Hz), 1.02 (1H, m), 0.58 (2H, m), 0.34 (2H, m).

$^{13}$C NMR (DMSO$_{d6}$): 161.8, 160.1, 156.5, 133, 132.9, 132.4, 132.3, 131.7, 129.3, 129.2, 118, 117.9, 116.2, 116.2, 114.7, 51.5, 51.4, 44.8, 32.4, 22.1, 21.3, 20.3, 7.3, 3.9, 3.8.

Example 187: (5aS,6aR)-5a-(5-bromo-2-fluorophenyl)-1-(2-(cyclopropylamino)ethyl)-5,5a,6,6a-tetrahydrocyclopropa[3,4]pyrrolo[1,2-c]imidazole-3(2H)-thione hydrofluoride

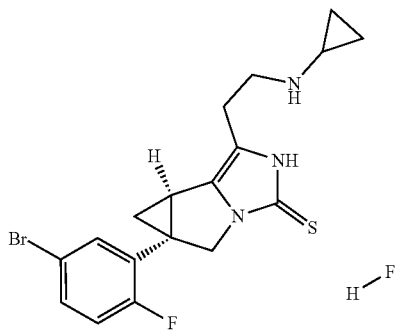

Compound was prepared analogous manner to Example 35 from 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-cyclopropylacetamide (Example 154) and isolated as a beige solid.

$^1$H NMR (DMSO$_{d6}$): 11.76 (1H, br s), 7.59 (1H, dd, J=6.6, 2.5 Hz), 7.56 (1H, ddd, J=8.6, 4.5, 2.6 Hz), 7.25 (1H, dd, J=10.0, 8.9 Hz), 4.07 (1H, d, J=12.0 Hz), 3.78 (1H, d, J=12.0 Hz), 3.14 (2H, m), 2.93 (1H, dd, J=8.3, 4.2 Hz), 2.73 (2H, m), 2.52 (1H, m), 1.65 (1H, dd, J=8.2, 5.3 Hz), 1.19 (1H, t, J=4.8 Hz), 0.70-0.57 (4H, m).

$^{13}$C NMR (DMSO$_{d6}$): 161.8, 160.1, 156.3, 132.9, 132.9, 132.3, 132.3, 131.4, 129.3, 129.2, 118, 117.8, 116.2, 116.2, 115.4, 51.5, 46.2, 32.4, 29.5, 22.2, 22.2, 20.4, 4.1, 4.

Example 188: (5aS,6aR)-5a-(5-bromo-2-fluorophenyl)-1-(2-(cyclobutylamino)ethyl)-5,5a,6,6a-tetrahydrocyclopropa[3,4]pyrrolo[1,2-c]imidazole-3(2H)-thione hydrofluoride

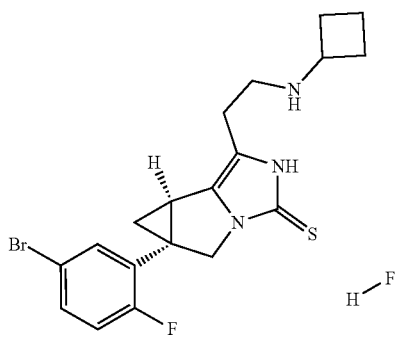

Compound was prepared analogous manner to Example 35 from 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-cyclobutylacetamide (Example 153) and isolated as a beige solid.

$^1$H NMR (DMSO$_{d6}$): 1.80 (1H, s br), 8.44 (1H, s br), 7.59 (1H, dd, J=6.7, 2.5 Hz), 7.56 (1H, ddd, J=8.7, 4.4, 2.6 Hz), 7.25 (1H, dd, J=10.0, 8.9 Hz), 4.07 (1H, d, J=12.0 Hz), 3.78 (1H, d, J=12.0 Hz), 3.65 (1H, quin, J=8.0 Hz), 3.02 (2H, t, J=7.2 Hz), 2.94 (1H, dd, J=8.3, 4.2 Hz), 2.74 (2H, m), 2.18 (2H, m), 2.08 (2H, m), 1.77 (2H, m), 1.66 (1H, dd, J=8.2, 5.3 Hz), 1.20 (1H, t, J=4.7 Hz).

$^{13}$C NMR (DMSO$_{d6}$): 161.8, 160.1, 156.5, 133, 133, 132.4, 132.3, 131.8, 129.3, 129.2, 118, 117.9, 116.2, 116.2, 114.6, 51.6, 51.6, 51.1, 42.8, 32.4, 26.4, 22.1, 21.6, 20.3, 14.5.

Example 189: (5aS,6aR)-1-(2-(benzylamino)ethyl)-5a-(5-chloro-2-fluorophenyl)-5,5a,6,6a-tetrahydrocyclopropa[3,4]pyrrolo[1,2-c]imidazole-3(2H)-thione hydrofluoride

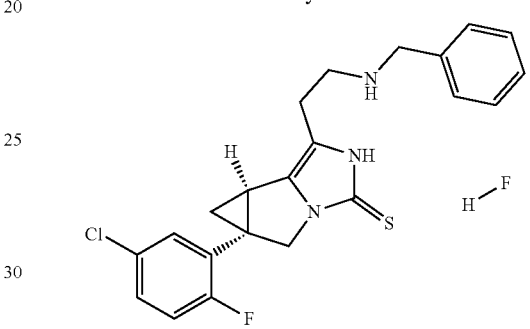

Compound was prepared analogous manner to Example 35 from N-benzyl-2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)acetamide (Example 156) and isolated as a beige solid.

$^1$H NMR (DMSO$_{d6}$): 1.79 (1H, br s), 8.28 (2H, br m), 7.50-7.41 (6H, m), 7.39 (1H, m), 7.31 (1H, dd, J=9.0, 9.9 Hz), 4.10 (2H, s), 4.08 (1H, d, J=12.3 Hz), 3.79 (1H, d, J=12.2 Hz), 3.12 (2H, t, J=6.8 Hz), 2.90 (1H, dd, J=8.4, 4.3 Hz), 2.78 (2H, m), 1.66 (1H, dd, J=8.2, 5.3 Hz), 1.19 (1H, t, J=4.7 Hz).

$^{13}$C NMR (DMSO$_{d6}$): 161.2, 159.6, 156.4, 133.6, 131.5, 130.1, 130.1, 129.5, 129.4, 129.3, 128.9, 128.8, 128.6, 128.6, 128.3, 117.6, 117.4, 115.1, 51.5, 50.6, 45.5, 32.4, 22.1, 21.8, 20.4.

Example 190: (5aS,6aR)-5a-(5-bromo-2-fluorophenyl)-1-(2-(cyclopentyl(methyl)amino)ethyl)-5,5a,6,6a-tetrahydrocyclopropa[3,4]pyrrolo[1,2-c]imidazole-3(2H)-thione hydrofluoride

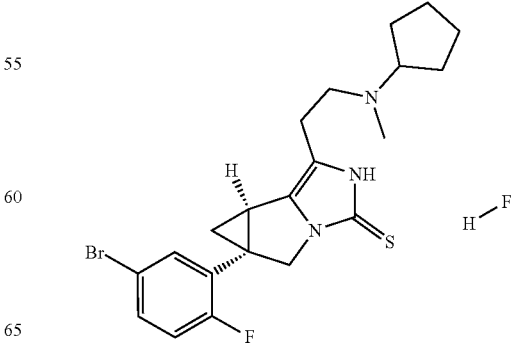

Compound was prepared analogous manner to Example 35 from 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-cyclopentyl-N-methylacetamide (Example 155) and isolated as a beige solid.

¹H NMR (DMSO$_{d6}$): 1.81 (1H, br s), 9.42 (1H, m), 7.63-7.49 (2H, m), 7.25 (1H, t, J=9.3 Hz), 4.08 (1H, d, J=12.0 Hz), 3.79 (1H, d, J=12.2 Hz), 3.29 (2H, m), 2.95 (2H, dd, J=7.8, 3.9 Hz), 2.78 (4H, br m), 1.97 (2H, br m), 1.78-1.37 (7H, m), 1.17 (1H, m), 1H (br).

¹³C NMR (DMSO$_{d6}$): 161.7, 160.1, 156.4, 132.9, 132.8, 132.3, 132.3, 131.4, 129.2, 129.1, 118, 117.8, 116.2, 116.2, 66.1, 52.6, 51.5, 37.8, 32.4, 27.9, 23.7, 22.2, 20.3, 19.6.

Example 191: (5aS,6aR)-5a-(5-bromo-2-fluorophenyl)-1-(2-morpholinoethyl)-5,5a,6,6a-tetrahydrocyclopropa[3,4]pyrrolo[1,2-c]imidazole-3(2H)-thione hydrofluoride

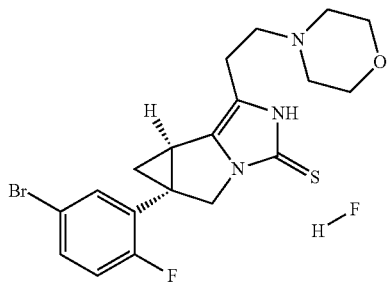

Compound was prepared analogous manner to Example 35 from 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-1-morpholinoethan-1-one (Example 157) and isolated as an off-white solid.

¹H NMR (DMSO$_{d6}$): 1.85 (1H, br s), 11.05 (1H, br s), 7.64-7.52 (2H, m), 7.25 (1H, br t, J=9.3 Hz), 4.08 (1H, d, J=11.9 Hz), 3.98 (2H, br m), 3.79 (3H, m), 3.44 (2H, m), 3.35 (2H, m), 3.10 (2H, br s), 2.97 (3H, br s), 1.67 (1H, m), 1.19 (1H, br s).

¹³C NMR (DMSO$_{d6}$): 161.8, 160.1, 156.6, 132.9, 132.4, 132.3, 131.5, 129.2, 129.1, 118, 117.8, 116.2, 114.3, 63.1, 53.9, 51.5, 51.2, 50.9, 32.4, 22.1, 20.4, 18.7.

Example 192: (5aS,6aR)-5a-(5-bromo-2-fluorophenyl)-1-(2-(pyridin-2-ylamino)ethyl)-5,5a,6,6a-tetrahydrocyclopropa[3,4]pyrrolo[1,2-c]imidazole-3(2H)-thione hydrofluoride

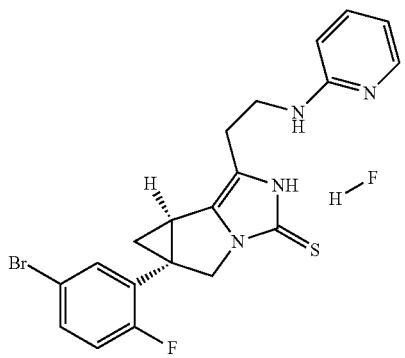

Compound was prepared analogous manner to Example 35 from 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N-(pyridin-2-yl)acetamide (Example 170) and isolated as a dark beige solid.

¹H NMR (DMSO$_{d6}$): 11.75 (1H, s), 7.95 (1H, dd, J=5.4, 1.5 Hz), 7.64-7.43 (3H, m), 7.23 (1H, t, J=9.8 Hz), 6.66 (1H, br s), 6.58 (1H, br s), 4.05 (1H, d, J=11.9 Hz), 3.76 (1H, d, J=12.1 Hz), 3.50 (2H, m), 2.73 (1H, dd, J=8.1, 4.2 Hz), 2.69 (2H, t, J=6.9 Hz), 1.54 (1H, dd, J=8.2, 5.3 Hz), 1.11 (1H, t, J=4.8 Hz).

¹³C NMR (DMSO$_{d6}$): 161.7, 160.1, 157.3, 155.9, 145.6, 137.9, 132.8, 132.8, 132.2, 132.2, 131.1, 129.4, 129.3, 118, 117.8, 117.1, 116.1, 111.6, 109.2, 51.4, 39.4, 32.2, 24, 22.4, 20.3.

Example 193: (S)-6-(3-chloro-2,6-difluorophenyl)-1-(2-(methylamino)ethyl)-2,5,6,7-tetrahydro-3H-pyrrolo[1,2-c]imidazole-3-thione Hydrochloride

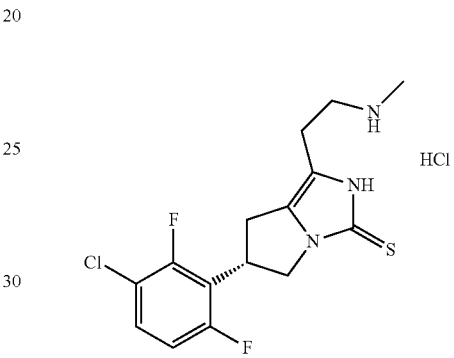

Compound was prepared analogous manner to Example 35 from (S)-2-(6-(3-chloro-2,6-difluorophenyl)-3-thioxo-2,5,6,7-tetrahydro-3H-pyrrolo[1,2-c]imidazol-1-yl)-N-methylacetamide and isolated as a white solid.

¹H NMR (DMSO$_{d6}$): 1.89 (1H, s), 8.93 (2H, m), 7.63 (1H, m), 7.23 (1H, m), 4.44 (1H, quin, J=8.8 Hz), 4.14 (1H, dd, J=11.3, 9.4 Hz), 3.75 (1H, dd, J=11.5, 8.4 Hz), 3.31 (1H, dd, J=9.1, 15.6 Hz), 3.09 (2H, br s), 2.94 (1H, dd, J=15.6, 8.7 Hz), 2.76 (2H, m), 2.52 (3H, br s).

¹³C NMR (DMSO$_{d6}$): 160.2, 160.1, 158.5, 158.5, 156.6, 156.6, 155.9, 155, 154.9, 129.8, 129.7, 129.5, 118.4, 118.2, 118.1, 116.1, 116.1, 116, 115.9, 114.7, 113.3, 113.2, 113.1, 113.1, 48.3, 46.4, 35.8, 32.3, 29, 21.

Example 194: (5aS,6aR)-5a-(5-chloro-2-fluorophenyl)-1-(2-(piperidin-1-yl)ethyl)-5,5a,6,6a-tetrahydrocyclopropa[3,4]pyrrolo[1,2-c]imidazole-3(2H)-thione Hydrofluoride

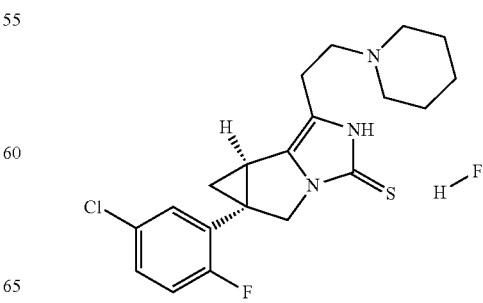

Compound was prepared analogous manner to Example 35 from 2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)-1-(piperidin-1-yl)ethan-1-one (Example 158) and isolated as a beige solid.

¹H NMR (DMSO_d6): 1.80 (1H, br s), 9.08 (2H, br s), 7.47 (1H, dd, J=6.5, 2.6 Hz), 7.44 (1H, ddd, J=8.6, 4.3, 2.8 Hz), 7.31 (1H, dd, J=9.1, 9.9 Hz), 4.08 (1H, d, J=11.9 Hz), 3.80 (1H, d, J=12.0 Hz), 3.50-2.63 (8H, m), 2.94 (1H, dd, J=8.3, 4.2 Hz), 2.0-1.25 (6H, m), 1.68 (1H, dd, J=8.3, 5.4 Hz), 1.18 (1H, t, J=4.5 Hz).

¹³C NMR (DMSO_d6): 161.2, 159.6, 156.4, 131.4, 130, 129.4, 129.3, 128.8, 128.7, 128.3, 117.6, 117.4, 114.7, 54.4, 52.6, 51.5, 32.4, 23, 22.1, 21.7, 20.4, 19.6.

Example 195: (S)-6-(3-bromo-2,6-difluorophenyl)-1-(2-morpholinoethyl)-2,5,6,7-tetrahydro-3H-pyrrolo[1,2-c]imidazole-3-thione

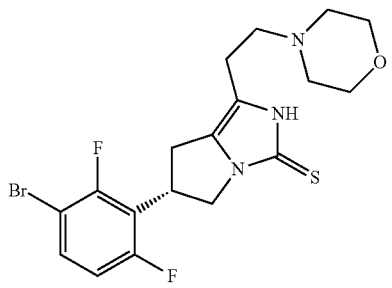 [SMILES: Fc1ccc(Br)c(F)c1[C@@H]1Cc2c(CCN3CCOCC3)[nH]c(=S)n2C1]

Compound was prepared analogous manner to Example 35 from (S)-2-(6-(3-bromo-2,6-difluorophenyl)-3-thioxo-2,5,6,7-tetrahydro-3H-pyrrolo[1,2-c]imidazol-1-yl)-1-morpholinoethan-1-one (Example 140) and isolated as a beige powder.

¹H NMR (DMSO_d6): 11.73 (1H, s), 7.72 (1H, ddd, J=5.8, 8.1, 8.7 Hz), 7.16 (1H, m), 4.45 (1H, quin, J=8.5 Hz), 4.13 (1H, dd, J=11.5, 9.2 Hz), 3.70 (1H, dd, J=11.6, 7.8 Hz), 3.53 (4H, br t, J=4.5 Hz), 3.28 (1H, dd, J=15.6, 9.4 Hz), 2.89 (1H, dd, J=15.6, 8.0 Hz), 2.51 (2H, m) 2.46 (2H, m), 2.34 (4H, br s).

¹³C NMR (DMSO_d6): 160.8, 160.7, 159.1, 159.1, 157.6, 157.5, 155.9, 155.9, 154.8, 132.4, 132.4, 128.1, 119, 118.8, 118.7, 118.1, 113.8, 113.8, 113.6, 113.6, 104.1, 104, 103.9, 103.9, 66.2, 56.3, 53, 48.5, 35.7, 29.3, 21.5.

Example 196: (S)-6-(3-chloro-2,6-difluorophenyl)-1-(2-morpholinoethyl)-2,5,6,7-tetrahydro-3H-pyrrolo[1,2-c]imidazole-3-thione Hydrochloride

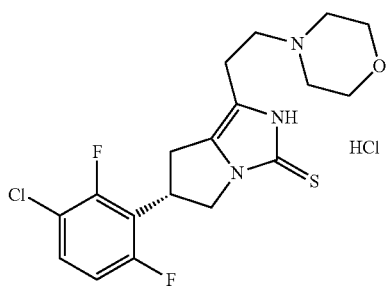 [SMILES: Fc1ccc(Cl)c(F)c1[C@@H]1Cc2c(CCN3CCOCC3)[nH]c(=S)n2C1 ; Cl]

Compound was prepared analogous manner to Example 35 from (S)-2-(6-(3-chloro-2,6-difluorophenyl)-3-thioxo-2,5,6,7-tetrahydro-3H-pyrrolo[1,2-c]imidazol-1-yl)-1-morpholinoethan-1-one and isolated as a white solid.

¹H NMR (DMSO_d6): 1.93 (1H, s), 11.01 (1H, br s), 7.63 (1 Hm), 7.23 (1H, m), 4.47 (1H, quin, J=8.5 Hz), 4.16 (1H, dd, J=11.4, 9.2 Hz), 3.96 (2H, br d, J=12.2 Hz), 3.76 (3H, m), 3.40 (2H, br d, J=12.0 Hz), 3.31 (2H, m), 3.05 (2H, m), 2.94 (1H, br dd, J=15.8, 8.1 Hz), 2.89 (2H, br t, J=7.5 Hz).

¹³C NMR (DMSO_d6): 160.1, 160.1, 158.5, 158.4, 156.6, 156.5, 155.8, 154.9, 154.9, 129.8, 129.7, 129.1, 118.7, 118.6, 118.5, 116.1, 116.1, 116, 115.9, 114.7, 113.3, 113.2, 113.1, 113.1, 63.1, 53.8, 51.1, 48.5, 35.7, 29.1, 18.8.

Example 197: (5aS,6aR)-5a-(5-chloro-2-fluorophenyl)-1-(2-(pyridin-3-ylamino)ethyl)-5,5a,6,6a-tetrahydrocyclopropa[3,4]pyrrolo[1,2-c]imidazole-3(2H)-thione

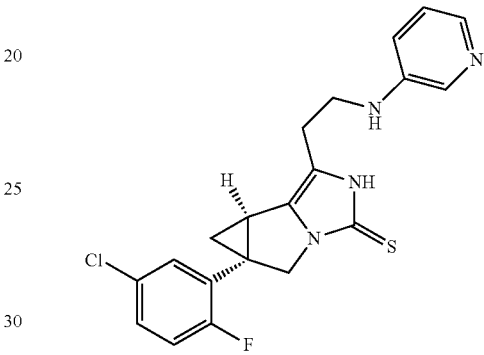

Compound was prepared analogous manner to Example 35 from 2-((5aS,6aR)-5a-(5-chloro-2-fluorophenyl)-3-thioxo-2,3,5,5a,6,6a-hexahydrocyclopropa[3,4]pyrrolo[1,2-c]imidazol-1-yl)-N-(pyridin-3-yl)acetamide (Example 171) and isolated as a beige solid.

¹H NMR (DMSO_d6): 11.78 (1H, br s), 8.00 (1H, d, J=2.8 Hz), 7.75 (1H, dd, J=4.5, 1.2 Hz), 7.46 (1H, dd, J=6.5, 2.6 Hz), 7.42 (1H, ddd, J=8.7, 4.3, 2.8 Hz), 7.29 (1H, dd, J=9.0, 9.9, Hz), 7.07 (1H, dd, J=8.3, 4.6 Hz), 6.96 (1H, ddd, J=1.2, 2.7, 8.3 Hz), 5.93 (1H, t, J=5.9 Hz), 4.06 (1H, d, J=11.9 Hz), 3.77 (1H, d, J=12.2 Hz), 3.30 (2H, m), 2.81 (1H, dd, J=8.2, 4.3 Hz), 2.66 (2H, m), 1.56 (1H, dd, J=8.2, 5.3 Hz), 1.14 (1H, t, J=4.8 Hz).

¹³C NMR (DMSO_d6): 161.2, 159.6, 155.9, 144.4, 135.3, 131.1, 130, 129.9, 129.3, 129.2, 129, 128.9, 128.3, 128.2, 123.6, 117.5, 117.4, 117.4, 117, 51.4, 51.4, 41.2, 32.3, 23.9, 22.3, 20.3.

Example 198: (R)-1-(2-(pyrrolidin-1-yl)ethyl)-6-(2,3,5,6-tetrafluorophenyl)-2,5,6,7-tetrahydro-3H-pyrrolo[1,2-c]imidazole-3-thione Hydrochloride

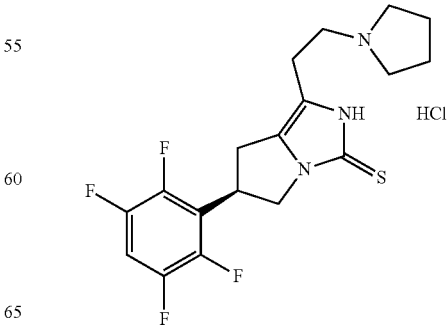

231

Compound was prepared analogous manner to Example 35 from (R)-1-(pyrrolidin-1-yl)-2-(6-(2,3,5,6-tetrafluorophenyl)-3-thioxo-2,5,6,7-tetrahydro-3H-pyrrolo[1,2-c]imidazol-1-yl)ethan-1-one (Example 104) and isolated as a light yellow solid.

$^{1}$H NMR (DMSO$_{d6}$): 1.92 (1H, s), 10.90 (1H, br s), 7.87 (1H, m), 4.51 (1H, quin, J=8.5 Hz), 4.17 (1H, dd, J=11.5, 9.2 Hz), 3.78 (1H, dd, J=11.6, 7.8 Hz), 3.47 (2H, m), 3.37 (1H, m), 3.32 (2H, m), 2.98 (3H, m), 2.85 (2H, br t, J=7.8 Hz), 1.98 (2H, m), 1.86 (2H, m).

$^{13}$C NMR (DMSO$_{d6}$): 155.9, 146.4, 146.4, 146.4, 146.3, 146.3, 146.3, 146.3, 146.3, 146.2, 145.3, 145.3, 145.3, 145.3, 145.2, 145.2, 145.2, 144.8, 144.7, 144.7, 144.6, 144.6, 143.7, 143.7, 143.7, 143.6, 143.6, 143.6, 143.6, 143.6, 129, 120.4, 120.3, 120.2, 114.9, 105.9, 105.8, 105.6, 53, 52, 48.4, 35.8, 29, 22.7, 20.8.

Example 199: (R)-1-(2-morpholinoethyl)-6-(2,3,5,6-tetrafluorophenyl)-2,5,6,7-tetrahydro-3H-pyrrolo[1,2-c]imidazole-3-thione Hydrochloride

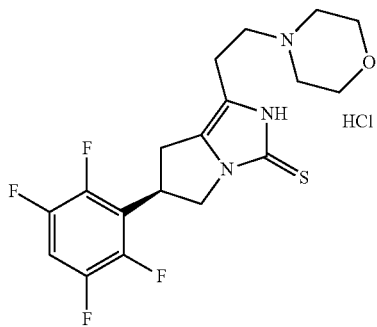 [SMILES: Fc1cc(F)c(F)c([C@H]2Cc3c(CCN4CCOCC4)[nH]c(=S)n3C2)c1F ; Cl]

Compound was prepared analogous manner to Example from (R)-1-morpholino-2-(6-(2,3,5,6-tetrafluorophenyl)-3-thioxo-2,5,6,7-tetrahydro-3H-pyrrolo[1,2-c]imidazol-1-yl)ethan-1-one and isolated as a light cream powder.

$^{1}$H NMR (DMSO$_{d6}$): 11.95 (1H, s), 11.05 (1H, br s), 7.88 (1H, m), 4.51 (1H, quin, J=8.4 Hz), 4.17 (1H, br dd, J=11.4, 9.4 Hz), 3.96 (2H, br d, J=12.2 Hz), 3.78 (3H, m), 3.41 (2H, m), 3.36 (1H, m), 3.30 (2H, m), 3.06 (2H, m), 2.98 (1H, br dd, J=15.7, 7.9 Hz), 2.89 (2H, m).

$^{13}$C NMR (DMSO$_{d6}$): 155.9, 146.4, 146.3, 146.3, 145.3, 145.3, 145.3, 145.3, 145.2, 145.2, 145.2, 144.8, 144.8, 144.8, 144.7, 144.7, 144.7, 144.6, 143.7, 143.7, 143.7, 143.6, 143.6, 143.6, 128.9, 120.4, 120.3, 120.2, 114.8, 106, 105.8, 105.6, 63.1, 53.8, 51.1, 48.4, 35.8, 29, 18.8.

Example 200: (R)-diethyl 2-((6-(2,3,5,6-tetrafluorophenyl)-3-thioxo-3,5,6,7-tetrahydro-2H-pyrrolo[1,2-c]imidazol-1-yl)methyl)malonate Step 1: tert-butyl (4R)-2-(2-diazoacetyl)-4-(2,3,5,6-tetrafluorophenyl)pyrrolidine-1-carboxylate

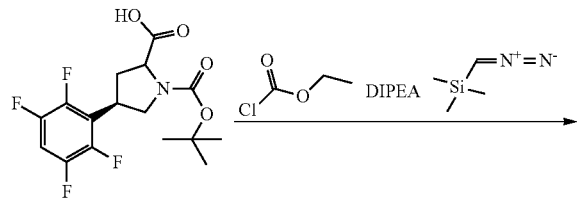

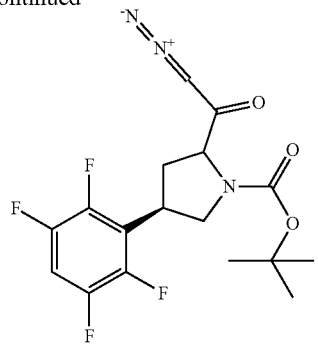

To a solution of (4R)-1-(tert-butoxycarbonyl)-4-(2,3,5,6-tetrafluorophenyl)pyrrolidine-2-carboxylic acid (2 g, 5.51 mmol) and N-ethyl-N-isopropylpropan-2-amine (DIPEA) (1.68 mL, 9.63 mmol) in dry tetrahydrofuran (20 mL) was added ethyl chloroformate (0.793 mL, 8.26 mmol) at 0-5° C. The mixture was stirred for 4 h in the cold, and then diluted with acetonitrile (10 mL) followed by addition of 2 M (diazomethyl)trimethylsilane (5.51 mL 11.01 mmol) in diethyl ether. The stirring was continued for additional 3 h at 0-5° C. and the mixture was allowed to warm up naturally overnight with stirring under N$_2$. Thereupon, the solvents were removed under vacuum and the residue was purified by column chromatography in a mixture of petroleumether-ethyl acetate. to give (4R)-tert-butyl 2-(2-diazoacetyl)-4-(2,3,5,6-tetrafluorophenyl)pyrrolidine-1-carboxylate as a yellow oil. Yield: 1.99 g, 93%.

Step 2: tert-butyl(4R)-2-(2-bromoacetyl)-4-(2,3,5,6-tetrafluorophenyl)pyrrolidine-1-carboxylate

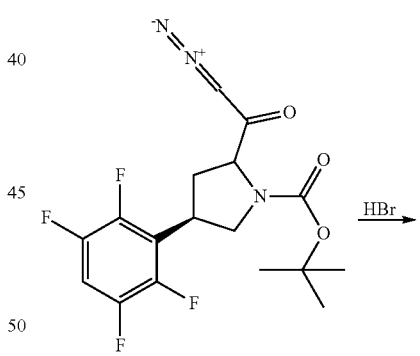

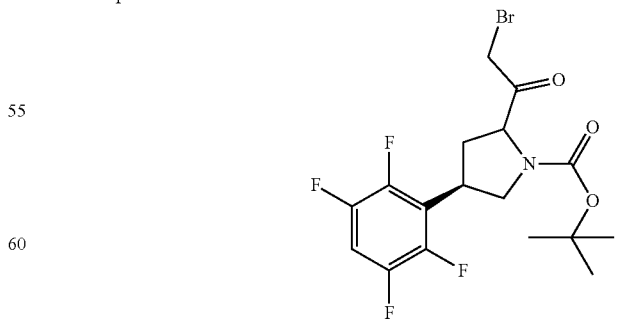

To a solution of (4R)-tert-butyl 2-(2-diazoacetyl)-4-(2,3,5,6-tetrafluorophenyl)pyrrolidine-1-carboxylate (1.98 g, 5.11 mmol) in diethyl ether (15 mL) was added 48% HBr (0.61 mL, 5.37 mmol) at 0-5° C. with stirring. After 5 min. the mixture was diluted with ethyl acetate (20 mL) and then washed with sodium bicarbonate solution. The organic phase was dried (MgSO₄), filtered, evaporated to dryness to give (4R)-tert-butyl 2-(2-bromoacetyl)-4-(2,3,5,6-tetrafluorophenyl)pyrrolidine-1-carboxylate as a yellowish oil. Yield: 1.83 g, 81%.

Step 3: diethyl 2-(2-((4R)-1-(tert-butoxycarbonyl)-4-(2,3,5,6-tetrafluorophenyl)pyrrolidin-2-yl)-2-oxo-ethyl)malonate

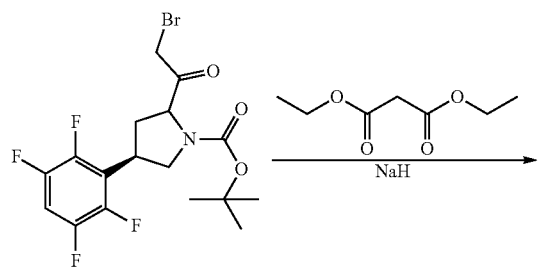

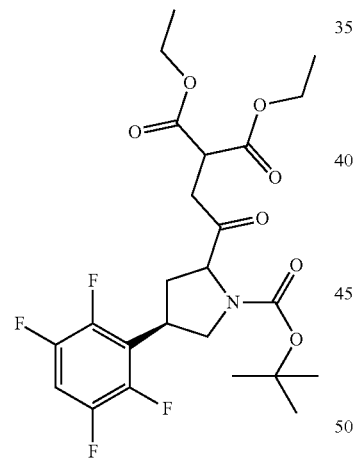

To a solution of diethyl malonate (0.83 mL, 5.45 mmol) in N,N-dimethyl formamide (7 mL) was added sodium hydride (60% in minar oil) (0.174 g, 4.36 mmol) with ice cooling and the solution was stirred for 30 min. Thereupon, (4R)-tert-butyl 2-(2-bromoacetyl)-4-(2,3,5,6-tetrafluorophenyl)pyrrolidine-1-carboxylate (1.6 g, 3.63 mmol) in dry tetrahydrofuran (3.50 mL) was added to the above reaction mixture with ice cooling and the mixture was stirred in the cold for 30 min. The reaction was then diluted with a mixture of ethyl acetate-petroleumether (2:1), washed with NaHSO₄ solution (40 mL), dried over MgSO₄, filtered and evaporated to dryness. Chromatography in a mixture of ethyl acetate-petroleumether afforded the titled product as a white powder. Yield: 1.15 g, 60%.

Step 4: diethyl 2-(2-oxo-2-((4R)-4-(2,3,5,6-tetrafluorophenyl)pyrrolidin-2-yl)ethyl)malonate Hydrochloride

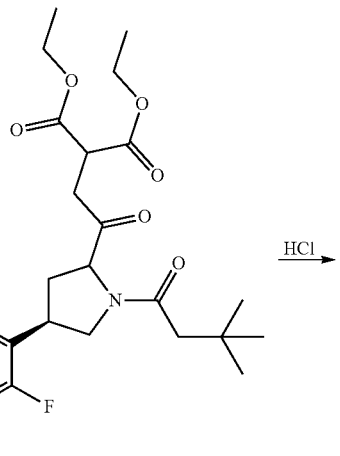

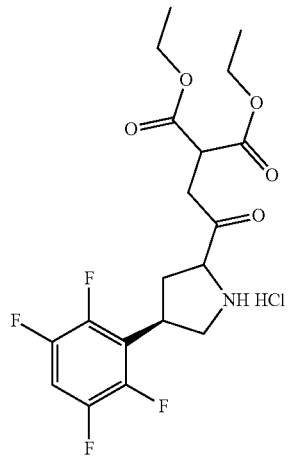

Diethyl 2-(2-((4R)-1-(tert-butoxycarbonyl)-4-(2,3,5,6-tetrafluorophenyl)pyrrolidin-2-yl)-2-oxoethyl)malonate (1.3 g, 2.502 mmol) was dissolved in 4 M HCl (9.38 mL, 37.5 mmol) in dioxane and the solution was stirred for 2 h. Thereupon, the mixture was diluted with diethyl ether (ca. 150 mL) The resulting crystals were collected, washed with diethyl ether and dried under vacuum at 50° C. to give diethyl 2-(2-oxo-2-((4R)-4-(2,3,5,6-tetrafluorophenyl)pyrrolidin-2-yl)ethyl)malonate hydrochloride as a white powder. Yield: 1.02 g, 89%.

Step 5: diethyl (R)-2-((6-(2,3,5,6-tetrafluorophenyl)-3-thioxo-2,5,6,7-tetrahydro-3H-pyrrolo[1,2-c]imidazol-1-yl)methyl)malonate

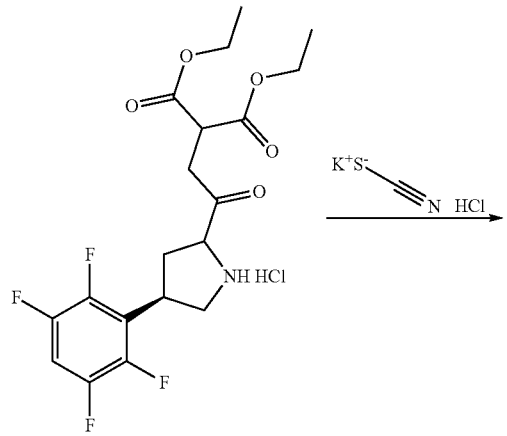

Example 201: (R)-2-((6-(2,3,5,6-tetrafluorophenyl)-3-thioxo-2,5,6,7-tetrahydro-3H-pyrrolo[1,2-c]imidazol-1-yl)methyl)malonic Acid

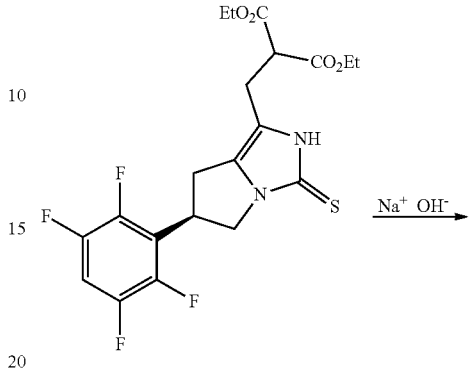

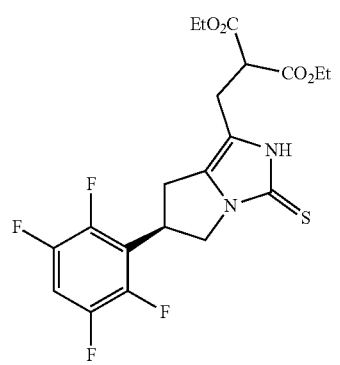

A mixture of diethyl 2-(2-oxo-2-((4R)-4-(2,3,5,6-tetrafluorophenyl)pyrrolidin-2-yl)ethyl)malonate hydrochloride (1.01 g, 2.216 mmol), potassium isothiocyanate (0.237 g, 2.437 mmol) and cc. HCl (0.092 mL, 1.108 mmol) in abs. ethanol (22 mL) was stirred under reflux for 30 min. The suspension was then cooled to room temperature, evaporated to dryness and the residue was partitioned between dichloromethane and water. The organic phase was dried (MgSO$_4$), filtered and evaporated to dryness to give the titled product as a yellow powder.

Yield: 0.94 g, 92% yield.

$^1$H NMR (DMSO$_{d6}$): 1.80 (1H, s), 7.85 (1H, m), 4.47 (1H, quin, J=8.4 Hz), 4.20-4.05 (5H, m), 3.81 (1H, t, J=8.0 Hz), 3.74 (1H, dd, J=11.8, 7.4 Hz), 3.28 (1H, dd, J=15.8, 9.4 Hz), 2.93-2.80 (3H, m), 1.14 (6H, q, J=7.3 Hz).

$^{13}$C NMR (DMSO$_{d6}$): 168, 167.9, 155.7, 146.4, 146.3, 146.3, 146.3, 146.2, 145.3, 145.3, 145.3, 145.2, 145.2, 145.2, 145.2, 144.8, 144.8, 144.7, 144.7, 144.6, 144.6, 143.7, 143.6, 143.6, 143.6, 143.5, 143.5, 143.5, 129.1, 120.6, 120.5, 120.4, 115.6, 105.9, 105.7, 105.6, 61.3, 61.2, 50.1, 48.5, 35.7, 29, 23.5, 13.8, 13.8.

To a solution of (R)-diethyl 2-((6-(2,3,5,6-tetrafluorophenyl)-3-thioxo-3,5,6,7-tetrahydro-2H-pyrrolo[1,2-c]imidazol-1-yl)methyl)malonate (Example 200) (0.9 g, 1.955 mmol) in methanol (20 mL) was added 1 M sodium hydroxide solution (11.72 mL, 11.72 mmol) and the mixture was stirred at room temperature overnight. Thereupon, methanol was removed by vacuum, the residue was diluted with water (20 mL) and then acidified to pH=1 by addition of 2 M HCl solution with ice cooling. The mixture was then extracted with 50 mL of mixture of dichloromethane-isopropanol (9:1), the organic phase was dried over MgSO$_4$, filtered and evaporated to 5 mL volume. The resulting precipitate was collected by filtration washed with petroleum ether and dried under vacuum at 50° C. to give (R)-2-((6-(2,3,5,6-tetrafluorophenyl)-3-thioxo-3,5,6,7-tetrahydro-2H-pyrrolo[1,2-c]imidazol-1-yl)methyl)malonic acid as a yellow powder.

Yield: 0.74 g, 94%.

$^1$H NMR (DMSO$_{d6}$): 12.93 (1H, br s), 11.79 (1H, s), 7.85 (1H, m), 4.45 (1H, quin, J=8.6 Hz), 4.16 (1H, dd, J=11.6, 9.2 Hz), 3.75 (1H, dd, J=8.0, 11.5 Hz), 3.56 (1H, t, J=8.0 Hz), 3.26 (1H, dd, J=15.8, 9.3 Hz), 2.89 (1H, dd, J=15.8, 8.2 Hz), 2.80 (2H, dd, J=7.9, 2.9 Hz).

$^{13}$C NMR (DMSO$_{d6}$): 169.8, 169.8, 155.5, 146.4, 146.4, 146.4, 146.3, 146.3, 146.3, 146.2, 145.3, 145.3, 145.2, 145.2, 145.2, 144.8, 144.8, 144.7, 144.7, 144.7, 144.6, 144.6, 143.7, 143.7, 143.7, 143.6, 143.6, 143.6, 143.6, 143.6, 143.6, 128.8, 120.3, 120.2, 120.1, 116.4, 105.9, 105.8, 105.6, 50.6, 48.3, 35.7, 29, 23.7.

Example 202: (R)-3-(6-(2,3,5,6-tetrafluorophenyl)-3-thioxo-2,5,6,7-tetrahydro-3H-pyrrolo[1,2-c]imidazol-1-yl)propanoic Acid

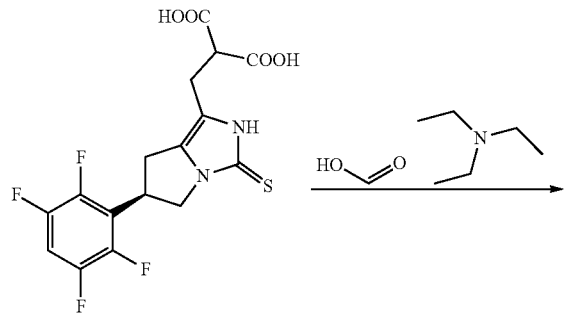

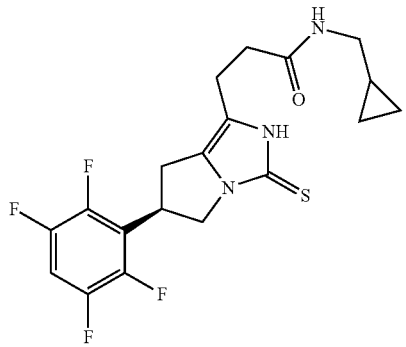 [SMILES: O=C(CCc1[nH]c(=S)n2c1C[C@H](c1c(F)c(F)cc(F)c1F)C2)NCC1CC1]

To a solution of (R)-2-((6-(2,3,5,6-tetrafluorophenyl)-3-thioxo-3,5,6,7-tetrahydro-2H-pyrrolo[1,2-c]imidazol-1-yl)methyl)malonic acid (0.1 g, 0.247 mmol) in formic acid (0.237 mL, 6.18 mmol) was added triethylamine (0.345 mL, 2.473 mmol) dropwise with stirring (exothermic reaction), and then the resulting solution was stirred at 115° C. for 1 h. Thereupon, the mixture was diluted with water to 4 mL, the resulting oily mixture treated with 2 M HCl (0.5 mL) and then aged for 30 min. The resultant solid was collected washed with water and dried under vacuum at 50° C. to give (R)-3-(6-(2,3,5,6-tetrafluorophenyl)-3-thioxo-3,5,6,7-tetrahydro-2H-pyrrolo[1,2-c]imidazol-1-yl)propanoic acid as a beige powder. Yield: 0.051 g, 57%.

$^1$H NMR (DMSO$_{d6}$): 12.22 (1H, br), 11.78 (1H, s), 7.85 (1H, m), 4.47 (1H, quin, J=8.6 Hz), 4.15 (1H, dd, J=11.7, 9.2 Hz), 3.75 (1H, dd, J=11.7, 7.8 Hz), 3.30 (1H, br dd, J=15.7, 9.4 Hz), 2.92 (1H, dd, J=15.7, 8.1 Hz), 2.63-2.54 (2H, m), 2.5 (2H, m).

$^{13}$C NMR (DMSO$_{d6}$): 173.4, 155.2, 146.4, 146.4, 146.3, 146.3, 146.2, 145.3, 145.3, 145.3, 145.3, 145.2, 145.2, 144.8, 144.8, 144.7, 144.7, 144.6, 144.6, 143.7, 143.7, 143.7, 143.6, 143.6, 143.6, 143.6, 128, 127.7, 120.4, 120.3, 120.2, 118.7, 105.9, 105.7, 105.6, 48.3, 35.8, 32.2, 29, 19.7.

Example 203: (R)—N-(cyclopropylmethyl)-3-(6-(2,3,5,6-tetrafluorophenyl)-3-thioxo-2,5,6,7-tetrahydro-3H-pyrrolo[1,2-c]imidazol-1-yl)propanamide Compound was prepared analogous manner to Example 32 from (R)-3-(6-(2,3,5,6-tetrafluorophenyl)-3-thioxo-2,5,6,7-tetrahydro-3H-pyrrolo[1,2-c]imidazol-1-yl)propanoic acid (Example 202) and isolated as an off-white powder.

$^1$H NMR (DMSO$_{d6}$): 1.72 (1H, br s), 7.90 (1H, br t, J=5.5 Hz), 7.86 (1H, m), 4.46 (1H, quin, J=8.5 Hz), 4.14 (1H, dd, J=11.5, 9.2 Hz), 3.74 (1H, dd, J=11.7, 7.8 Hz), 3.29 (1H, dd, J=15.7, 9.2 Hz), 2.91 (1H, m), 2.89 (2H, br t, J=6.2 Hz), 2.57 (2H, m), 2.34 (2H, t, J=7.4 Hz), 0.83 (1H, m), 0.35 (2H, m), 0.09 (2H, m).

$^{13}$C NMR (DMSO$_{d6}$): 170.5, 155, 146.4, 146.4, 146.3, 146.3, 146.3, 146.2, 146.2, 145.3, 145.3, 145.3, 145.2, 145.2, 145.2, 145.2, 145.2, 144.8, 144.8, 144.7, 144.7, 144.7, 144.6, 144.6, 143.7, 143.6, 143.6, 143.6, 143.6, 143.6, 143.5, 127.5, 120.5, 120.4, 120.3, 119.1, 105.9, 105.7, 105.5, 48.2, 42.8, 35.8, 33.4, 29.1, 20, 10.7, 3.1.

Example 204: (R)-1-(pyrrolidin-1-yl)-3-(6-(2,3,5,6-tetrafluorophenyl)-3-thioxo-2,5,6,7-tetrahydro-3H-pyrrolo[1,2-c]imidazol-1-yl)propan-1-one

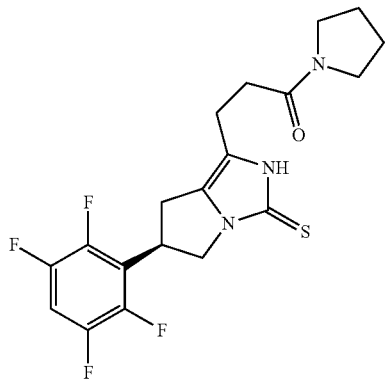 [SMILES: O=C(CCc1[nH]c(=S)n2c1C[C@H](c1c(F)c(F)cc(F)c1F)C2)N1CCCC1]

Compound was prepared analogous manner to Example 32 from (R)-3-(6-(2,3,5,6-tetrafluorophenyl)-3-thioxo-2,5,6,7-tetrahydro-3H-pyrrolo[1,2-c]imidazol-1-yl)propanoic acid (Example 202) and isolated as an off-white powder.

$^1$H NMR (DMSO$_{d6}$): 1.73 (1H, br s), 7.85 (1H, t, J=9.0 Hz), 4.46 (1H, quin, J=8.6 Hz), 4.15 (1H, dd, J=11.5, 9.2 Hz), 3.74 (1H, dd, J=11.7, 7.8 Hz), 3.36 (2H, t, J=6.8 Hz), 3.30 (1H, br dd, J=15.7, 9.4 Hz), 3.25 (2H, t, J=6.9 Hz), 2.93 (1H, dd, J=15.7, 8.1 Hz), 2.56 (2H, m), 2.51 (2H, m), 1.84 (2H, m), 1.74 (2H, m).
$^{13}$C NMR (DMSO$_{d6}$): 169, 155, 146.4, 146.3, 146.3, 145.3, 145.2, 144.8, 144.7, 144.6, 143.7, 143.6, 127.6, 120.5, 120.4, 120.3, 119.2, 105.8, 105.7, 105.5, 48.2, 45.7, 45.3, 35.8, 32.2, 28.9, 25.5, 23.9, 19.5.

Example 205: (R)-1-morpholino-3-(6-(2,3,5,6-tetrafluorophenyl)-3-thioxo-2,5,6,7-tetrahydro-3H-pyrrolo[1,2-c]imidazol-1-yl)propan-1-one

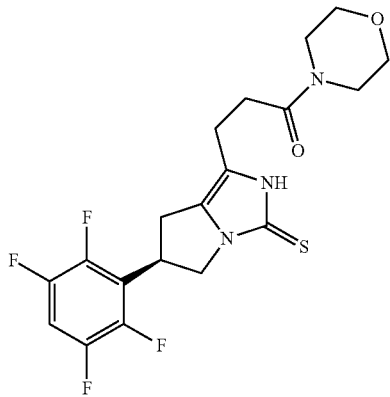 [SMILES: O=C(CCc1[nH]c(=S)n2c1C[C@H](c1c(F)c(F)cc(F)c1F)C2)N1CCOCC1]

Compound was prepared analogous manner to Example 32 from (R)-3-(6-(2,3,5,6-tetrafluorophenyl)-3-thioxo-2,5,6,7-tetrahydro-3H-pyrrolo[1,2-c]imidazol-1-yl)propanoic acid (Example 202) and isolated as a beige powder.
$^1$H NMR (DMSO$_{d6}$): 1.73 (1H, br s), 7.86 (1H, m), 4.47 (1H, quin, J=8.6 Hz), 4.15 (1H, dd, J=11.4, 9.3 Hz), 3.75 (1H, dd, J=11.6, 7.9 Hz), 3.52 (4H, dt, J=13.2, 4.7 Hz), 3.42 (4H, m), 3.31 (1H, dd, J=9.3, 15.7 Hz), 2.94 (1H, dd, J=15.6, 8.1 Hz), 2.58 (4H, m).
$^{13}$C NMR (DMSO$_{d6}$): 169.6, 155.1, 146.4, 146.3, 146.2, 145.3, 145.2, 144.8, 144.7, 144.6, 143.7, 143.6, 127.6, 120.4, 120.3, 120.2, 119.1, 105.9, 105.7, 105.5, 66.1, 66.1, 48.2, 45.2, 41.5, 35.8, 30.5, 28.9, 19.8.

Example 206: (R)-1-(4,4-difluoropiperidin-1-yl)-3-(6-(2,3,5,6-tetrafluorophenyl)-3-thioxo-2,5,6,7-tetrahydro-3H-pyrrolo[1,2-c]imidazol-1-yl)propan-1-one

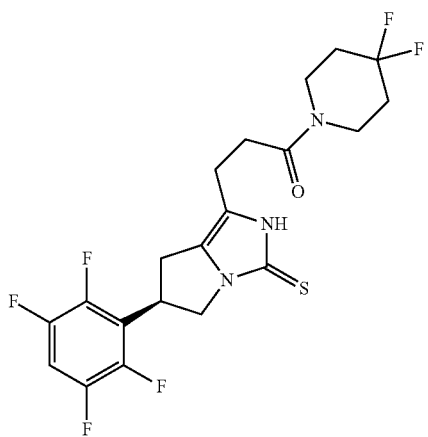 [SMILES: O=C(CCc1[nH]c(=S)n2c1C[C@H](c1c(F)c(F)cc(F)c1F)C2)N1CCC(F)(F)CC1]

Compound was prepared analogous manner to Example 32 from (R)-3-(6-(2,3,5,6-tetrafluorophenyl)-3-thioxo-2,5,6,7-tetrahydro-3H-pyrrolo[1,2-c]imidazol-1-yl)propanoic acid (Example 202) and isolated as a light yellow powder.
$^1$H NMR (DMSO$_{d6}$): 11.74 (1H, s), 7.86 (1H, m), 4.47 (1H, quin, J=8.6 Hz), 4.15 (1H, dd, J=11.5, 9.3 Hz), 3.75 (1H, dd, J=11.6, 7.9 Hz), 3.54 (4H, m), 3.31 (1H, m), 2.94 (1H, dd, J=15.7, 8.2 Hz), 2.66 (2H, m), 2.57 (2H, m), 1.98 (2H, m), 1.88 (2H, m).
$^{13}$C NMR (DMSO$_{d6}$): 169.5, 155.1, 146.4, 146.3, 146.2, 145.3, 145.2, 144.8, 144.7, 143.7, 143.6, 127.6, 124.3, 122.7, 121.1, 120.4, 120.3, 120.2, 119, 105.9, 105.7, 105.6, 48.2, 41.6, 41.5, 41.5, 38.1, 38, 38, 35.8, 34, 33.8, 33.7, 33.3, 33.2, 33, 30.5, 28.9, 19.9.

Example 207: (R)-1-(piperidin-1-yl)-3-(6-(2,3,5,6-tetrafluorophenyl)-3-thioxo-2,5,6,7-tetrahydro-3H-pyrrolo[1,2-c]imidazol-1-yl)propan-1-one

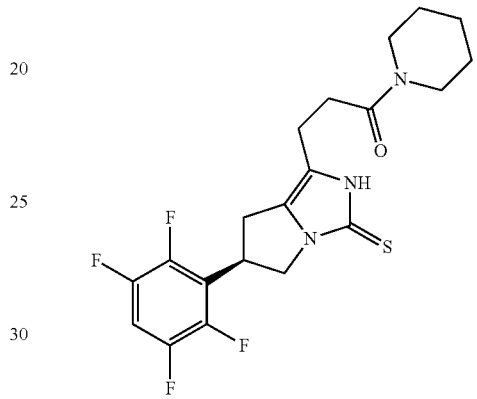

Compound was prepared analogous manner to Example 32 from (R)-3-(6-(2,3,5,6-tetrafluorophenyl)-3-thioxo-2,5,6,7-tetrahydro-3H-pyrrolo[1,2-c]imidazol-1-yl)propanoic acid (Example 202) and isolated as a beige powder.
$^1$H NMR (DMSO$_{d6}$): 1.72 (1H, br s), 7.86 (1H, m), 4.46 (1H, quin, J=8.6 Hz), 4.15 (1H, dd, J=11.6, 9.2 Hz), 3.75 (1H, dd, J=11.7, 7.8 Hz), 3.37 (4H, m), 3.30 (1H, dd, J=9.3, 11.8 Hz), 2.93 (1H, dd, J=15.6, 8.1 Hz), 2.57 (4H, m), 1.55 (2H, m), 1.45 (2H, m), 1.38 (2H, m).
$^{13}$C NMR (DMSO$_{d6}$): 168.9, 155, 146.4, 146.3, 146.2, 145.3, 145.2, 145.2, 144.8, 144.7, 144.6, 143.6, 143.6, 127.6, 120.4, 120.3, 120.2, 119.2, 105.8, 105.7, 105.5, 48.2, 45.7, 41.9, 35.8, 30.7, 28.9, 26, 25.3, 24, 20.

Example 208: (R)-1-(4-methylpiperidin-1-yl)-3-(6-(2,3,5,6-tetrafluorophenyl)-3-thioxo-2,5,6,7-tetrahydro-3H-pyrrolo[1,2-c]imidazol-1-yl)propan-1-one

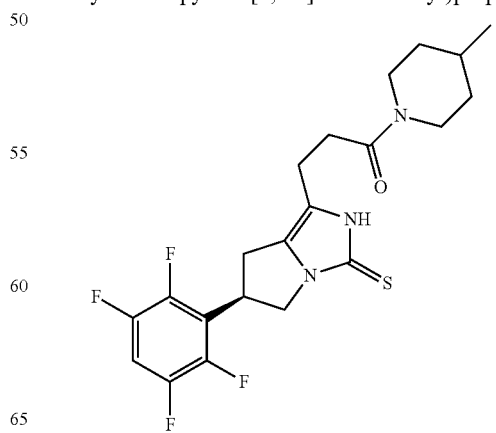

Compound was prepared analogous manner to Example 32 from (R)-3-(6-(2,3,5,6-tetrafluorophenyl)-3-thioxo-2,5,6,7-tetrahydro-3H-pyrrolo[1,2-c]imidazol-1-yl)propanoic acid (Example 202) and isolated as a beige powder.

$^1$H NMR (DMSO$_{d6}$): 11.73 (1H, s), 7.86 (1H, m), 4.46 (1H, quin, J=8.6 Hz), 4.32 (1H, br d, J=13.2 Hz), 4.14 (1H, m), 3.81 (1H, br d, J=13.5 Hz), 3.74 (1H, dd, J=11.7, 8.0 Hz), 3.30 (1H, m), 2.92 (2H, br dd, J=15.1, 8.8 Hz), 2.56 (4H, m), 2.47 (1H, m), 1.57 (3H, m), 0.95 (1H, m), 0.87 (4H, m).

$^{13}$C NMR (DMSO$_{d6}$): 168.9, 155.1, 146.4, 146.3, 146.2, 145.3, 145.2, 144.8, 144.7, 144.6, 143.7, 143.6, 127.5, 127.5, 120.4, 120.4, 120.3, 120.3, 120.2, 120.2, 119.2, 119.2, 105.9, 105.7, 105.6, 48.2, 45, 44.9, 41.3, 35.8, 34.2, 33.5, 30.7, 30.6, 30.3, 29, 29, 21.6, 20.

Example 209: (R)-1-(morpholinomethyl)-6-(2,3,5,6-tetrafluorophenyl)-6,7-dihydro-2H-pyrrolo[1,2-c]imidazole-3(5H)-thione Hydrochloride Step 1: tert-butyl(4R)-2-(2-morpholinoacetyl)-4-(2,3,5,6-tetrafluorophenyl)pyrrolidine-1-carboxylate Hydrobromide

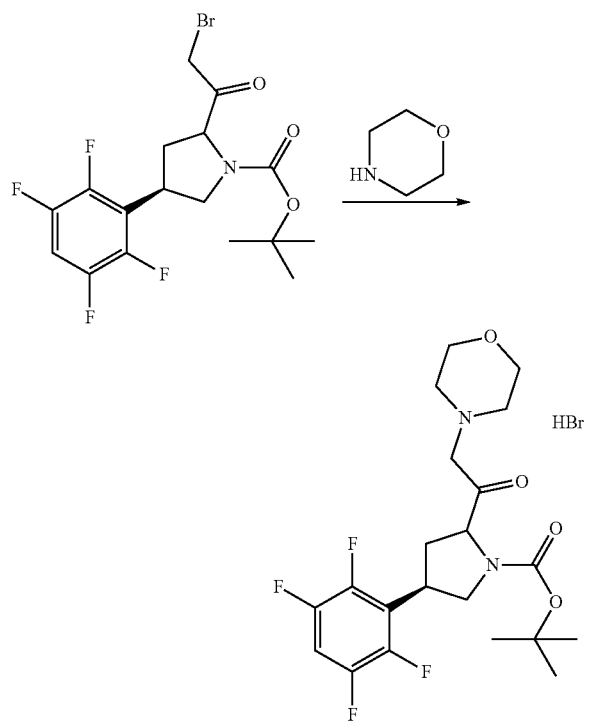

To a solution of (4R)-tert-butyl 2-(2-bromoacetyl)-4-(2,3,5,6-tetrafluorophenyl)pyrrolidine-1-carboxylate (Example 200 step 2) (0.1 g, 0.227 mmol) in dry tetrahydrofuran (1 mL) was added morpholine (0.020 mL, 0.227 mmol) at room temperature in one portion. The reaction was stirred for 15 min. and then diluted with diethyl ether (1 mL). The resulting solid was filtered off and the filtrate was evaporated to dryness to give (4R)-tert-butyl 2-(2-morpholinoacetyl)-4-(2,3,5,6-tetrafluorophenyl)pyrrolidine-1-carboxylate hydrobromide as viscous oil. Yield: 0.105 g, 88%.

Step 2: 2-morpholino-1-((4R)-4-(2,3,5,6-tetrafluorophenyl)pyrrolidin-2-yl)ethan-1-one Dihydrochloride

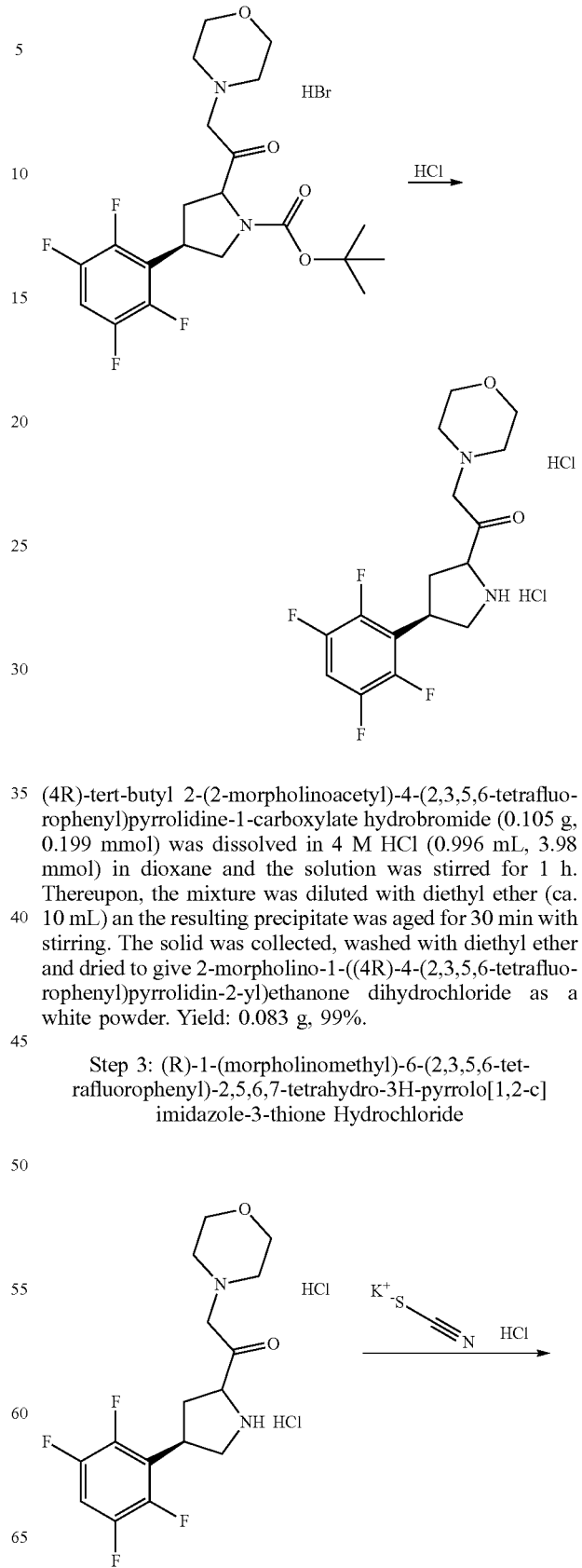

(4R)-tert-butyl 2-(2-morpholinoacetyl)-4-(2,3,5,6-tetrafluorophenyl)pyrrolidine-1-carboxylate hydrobromide (0.105 g, 0.199 mmol) was dissolved in 4 M HCl (0.996 mL, 3.98 mmol) in dioxane and the solution was stirred for 1 h. Thereupon, the mixture was diluted with diethyl ether (ca. 10 mL) an the resulting precipitate was aged for 30 min with stirring. The solid was collected, washed with diethyl ether and dried to give 2-morpholino-1-((4R)-4-(2,3,5,6-tetrafluorophenyl)pyrrolidin-2-yl)ethanone dihydrochloride as a white powder. Yield: 0.083 g, 99%.

Step 3: (R)-1-(morpholinomethyl)-6-(2,3,5,6-tetrafluorophenyl)-2,5,6,7-tetrahydro-3H-pyrrolo[1,2-c]imidazole-3-thione Hydrochloride

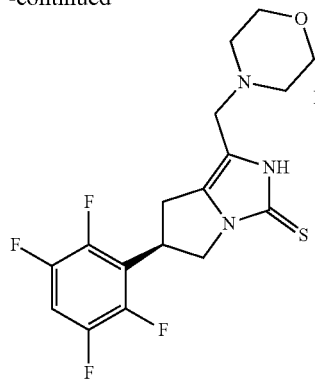

A mixture of 2-morpholino-1-((4R)-4-(2,3,5,6-tetrafluorophenyl)pyrrolidin-2-yl)ethanone dihydrochloride (0.078 g, 0.186 mmol), potassium isothiocyanate (0.027 g, 0.279 mmol) and cc. HCl (0.022 mL, 0.130 mmol) in a mixture of ethanol (1 mL) and water (1 mL) was stirred under reflux for 30 min. Thereupon, the mixture was diluted with water (ca. 2 mL) and then ethanol was removed under vacuum. The aqueous residue was neutralized by addition of sodium bicarbonate solution and then extracted with dichloromethane. The organic phase was dried (MgSO$_4$), filtered and evaporated to dryness. The oily residue was taken up in isopropanol (ca. 1 mL), acidified by addition of 2 M HCl in diethyl ether, and then diluted with diethyl ether to 10 mL. The resulting precipitate was collected, washed with diethyl ether and dried in vacuum at 50° C. to give (R)-1-(morpholinomethyl)-6-(2,3,5,6-tetrafluorophenyl)-6,7-dihydro-2H-pyrrolo[1,2-c]imidazole-3(5H)-thione hydrochloride as an off-white powder, Yield: 0.050 g, 63%.

$^1$H NMR (DMSO$_{d6}$): 12.07 (1H, s), 11.58 (1H, br s), 7.88 (1H, m), 4.54 (1H, quin, J=8.5 Hz), 4.23 (1H, dd, J=11.7, 9.2 Hz), 4.15 (2H, m), 3.97 (2H, br d, J=12.5 Hz), 3.85 (1H, dd, J=11.7, 7.8 Hz), 3.78 (2H, br t, J=12.0 Hz), 3.52 (1H, dd, J=9.4, 16.3 Hz), 3.29 (2H, br dd, J=18.0, 13.4 Hz), 3.12 (1H, dd, J=16.4, 8.1 Hz), 3.04 (2H, m).

$^{13}$C NMR (DMSO$_{d6}$): 157.4, 146.4, 146.4, 146.3, 145.3, 145.2, 144.8, 144.7, 144.7, 143.7, 143.6, 135.6, 120, 108.2, 106, 105.9, 105.7, 63.1, 50.2, 48.9, 48.5, 35.6, 29.6.

Example 210: (R)-1-(pyrrolidin-1-ylmethyl)-6-(2,3,5,6-tetrafluorophenyl)-2,5,6,7-tetrahydro-3H-pyrrolo[1,2-c]imidazole-3-thione hydrochloride

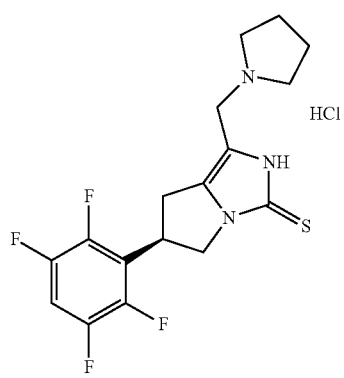 [SMILES: Fc1cc(F)c(F)c([C@H]2Cc3c(CN4CCCC4)[nH]c(=S)n3C2)c1F ; Cl]

Compound was prepared analogous manner to Example 209 and isolated as an off-white powder.

$^1$H NMR (DMSO$_{d6}$): 12.11 (1H, s), 11.13 (1H, br s), 7.87 (1H, m), 4.53 (1H, quin, J=8.4 Hz), 4.23 (1H, dd, J=11.4, 9.4 Hz), 4.15 (2H, br s), 3.84 (1H, dd, J=11.7, 7.6 Hz), 3.52 (1H, br dd, J=16.2, 9.3 Hz), 3.38 (2H, m), 3.12 (1H, br dd, J=16.3, 7.8 Hz), 3.03 (2H, br s), 1.99 (2H, br s), 1.88 (2H, br s).

$^{13}$C NMR (DMSO$_{d6}$): 157, 146.4, 146.3, 146.3, 145.3, 145.2, 144.8, 144.7, 144.6, 143.7, 143.6, 134.1, 120.3, 120.2, 111.1, 106, 105.8, 105.7, 52.2, 48.9, 46.1, 35.6, 29.5, 22.7.

Example 211: (R)-1-(((2-hydroxyethyl)(methyl)amino)methyl)-6-(2,3,5,6-tetrafluorophenyl)-2,5,6,7-tetrahydro-3H-pyrrolo[1,2-c]imidazole-3-thione hydrochloride

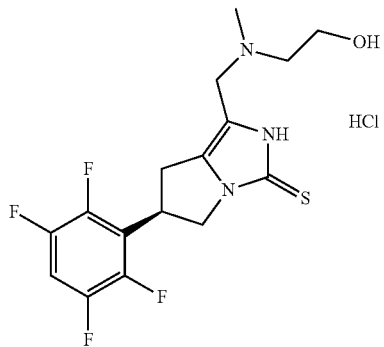 [SMILES: CN(CCO)Cc1[nH]c(=S)n2c1C[C@H](c1c(F)c(F)cc(F)c1F)C2 ; Cl]

Compound was prepared analogous manner to Example 209 and isolated as a cream powder.

$^1$H NMR (DMSO$_{d6}$): 12.10 (1H, br s), 10.45 (1H, br s), 7.88 (1H, br s), 5.35 (1H, br), 4.55 (1H, m), 4.23 (1H, dd, J=11.5, 9.3 Hz), 4.17 (2H, m), 3.85 (1H, m), 3.77 (2H, br t, J=5.2 Hz), 3.49 (1H, dt, J=9.9, 16.3 Hz), 3.19 (1H, m), 3.09 (1H, m), 3.04 (1H, m), 2.81 (0.5H, br s), 2.72 (2.5H, br t, J=5.6 Hz).

$^{13}$C NMR (DMSO$_{d6}$): 157.4, 146.4, 146.3, 146.2, 145.3, 145.2, 144.8, 144.7, 144.6, 143.7, 143.6, 135.6, 120.2, 120.1, 120.1, 108.5, 108.5, 106, 105.8, 105.7, 56, 56, 55.2, 48.9, 48.6, 48.6, 42.4, 39, 35.6, 35.6, 29.6.

Example 212: (R)-1-(2-(pyridin-3-yl)ethyl)-6-(2,3,5,6-tetrafluorophenyl)-6,7-dihydro-2H-pyrrolo[1,2-c]imidazole-3(5H)-thione Step 1: tert-butyl (4R)-2-(2-(dimethoxyphosphoryl)acetyl)-4-(2,3,5,6-tetrafluorophenyl)pyrrolidine-1-carboxylate

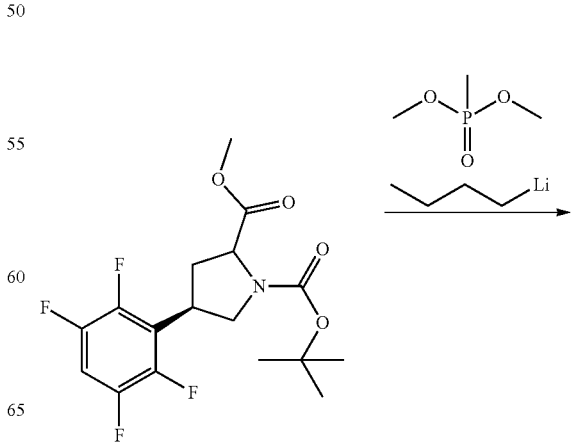

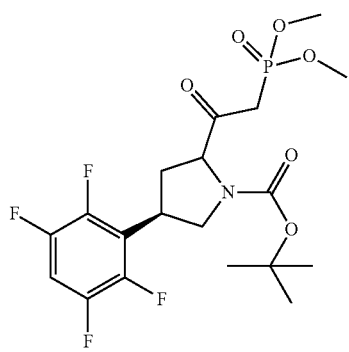

To a solution of dimethyl methylphosphonate (0.655 mL, 6.04 mmol) in dry tetrahydrofuran (12 mL) was added N-butyllithium (4.15 mL, 6.65 mmol) (1.6 M in hexane) at −78° C., and the mixture was stirred for 30 min in the cold. Thereupon, a solution of (4R)-1-tert-butyl 2-methyl 4-(2,3,5,6-tetrafluorophenyl)pyrrolidine-1,2-dicarboxylate (1.14 g, 3.02 mmol) in tetrahydrofuran (12 mL) was added, and the reaction mixture was stirred for 2 h in the cold. The reaction mixture was quenched with saturated ammonium chloride solution and then extracted with ethyl acetate (20 mL). The organic phase was dried over MgSO₄, filtered and evaporated to leave a colorless oil which was purified by column chromatography in a mixture of petroleumether-ethyl acetate to give (4R)-tert-butyl 2-(2-(dimethoxyphosphoryl)acetyl)-4-(2,3,5,6-tetrafluorophenyl)pyrrolidine-1-carboxylate as a colorless oil. (Yield: 0.86 g, 60% yield).

Step 2: tert-butyl (4R)-2-((E)-3-(pyridin-3-yl)acryloyl)-4-(2,3,5,6-tetrafluorophenyl)pyrrolidine-1-carboxylate

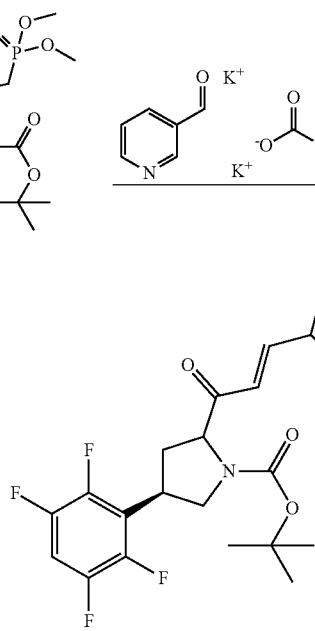

To a solution of (4R)-tert-butyl 2-(2-(dimethoxyphosphoryl)acetyl)-4-(2,3,5,6-tetrafluorophenyl)pyrrolidine-1-carboxylate (0.2 g, 0.426 mmol) in ethanol (2.5 mL) was added potassium carbonate (0.065 g, 0.469 mmol) and the mixture was stirred at room temperature for 15 min. Thereupon, 3-pyridinecarboxaldehyde (0.044 mL, 0.469 mmol) was added and the stirring was continued for 2 h. The resulting solid was filtered off, the filtrate was evaporated to dryness, and then purified by column chromatography in a mixture of petroleumether-ethyl acetate to give (4R)-tert-butyl 2-((E)-3-(pyridin-3-yl)acryloyl)-4-(2,3,5,6-tetrafluorophenyl)pyrrolidine-1-carboxylate as an oil. Yield: 0.19 g, 99%.

Step 3: tert-butyl(4R)-2-(3-(pyridin-3-yl)propanoyl)-4-(2,3,5,6-tetrafluorophenyl)pyrrolidine-1-carboxylate

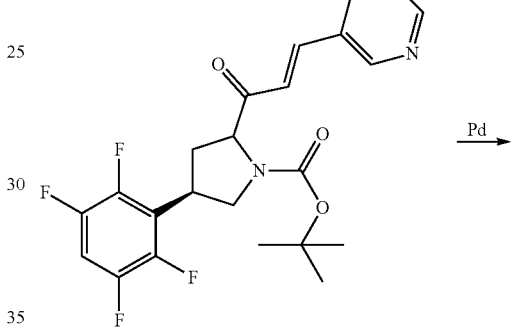

A solution of (4R)-tert-butyl 2-((E)-3-(pyridin-3-yl)acryloyl)-4-(2,3,5,6-tetrafluorophenyl)pyrrolidine-1-carboxylate (0.18 g, 0.400 mmol) in ethyl acetate (5 mL) was hydrogenated over 10% palladium on charcoal (0.043 g, 0.040 mmol) for 7 h with a H₂ balloon. Thereupon, the catalyst was filtered through a celite pad and the filtrate was evaporated to give (4R)-tert-butyl 2-(3-(pyridin-3-yl)propanoyl)-4-(2,3,5,6-tetrafluorophenyl)pyrrolidine-1-carboxylate as an oil. Yield: 0.16 g, 88%.

Step 4: (R)-1-(2-(pyridin-3-yl)ethyl)-6-(2,3,5,6-tetrafluorophenyl)-2,5,6,7-tetrahydro-3H-pyrrolo[1,2-c]imidazole-3-thione

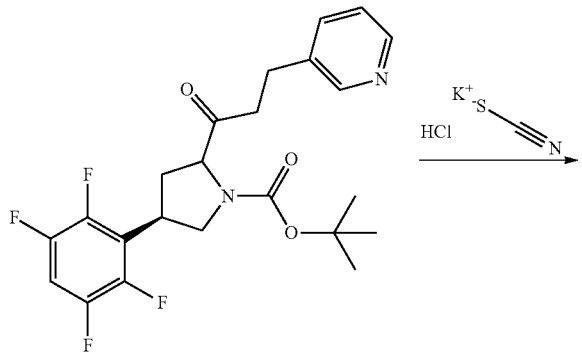

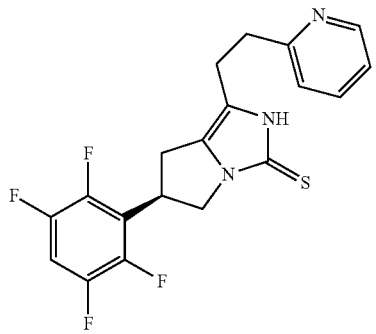 [SMILES: Fc1cc(F)c(F)c([C@H]2Cc3c(CCc4ccccn4)[nH]c(=S)n3C2)c1F]

Example 213: (R)-1-(2-(pyridin-2-yl)ethyl)-6-(2,3,5,6-tetrafluorophenyl)-2,5,6,7-tetrahydro-3H-pyrrolo[1,2-c]imidazole-3-thione Compound was prepared analogous manner to Example 212 and isolated as an off-white powder.

¹H NMR (DMSO$_{d6}$): 11.85 (1H, s), 8.45 (1H, m), 7.84 (1H, m), 7.66 (1H, td, J=7.6, 1.9 Hz), 7.20 (1H, d, J=7.8 Hz), 7.17 (1H, ddd, J=7.4, 4.9, 1.0 Hz), 4.39 (1H, quin, J=8.4 Hz), 4.11 (1H, dd, J=11.6, 9.1 Hz), 3.71 (1H, dd, J=11.7, 7.6 Hz), 3.11 (1H, dd, J=15.6, 9.3 Hz), 2.98 (2H, m), 2.78 (2H, m), 2.66 (1H, dd, J=15.6, 7.8 Hz).

¹³C NMR (DMSO$_{d6}$): 159.9, 155.1, 148.9, 146.4, 146.3, 146.2, 145.2, 145.1, 145.1, 145.1, 145.1, 144.8, 144.7, 144.7, 144.6, 144.6, 144.6, 143.6, 143.6, 143.5, 143.5, 143.5, 143.5, 136.4, 127.7, 122.8, 121.4, 120.5, 120.4, 120.3, 119, 105.8, 105.7, 105.5, 48.2, 35.8, 35.7, 28.9, 23.6.

(4R)-tert-butyl 2-(3-(pyridin-3-yl)propanoyl)-4-(2,3,5,6-tetrafluorophenyl)pyrrolidine-1-carboxylate (0.16 g, 0.354 mmol) was dissolved in 4 M HCl (1.33 mL, 5.30 mmol) in dioxane and the solution was stirred for 1 h. The mixture was then diluted with diethyl ether ether (ca. 10 mL) to give a semi-solid precipitate. Thereupon, diethyl ether was decanted and the residue was dissolved in mixture of ethanol (2 mL) and water (2 mL) followed by addition of 6 M HCl (0.03 mL, 0.177 mmol) and potassium isothiocyanate (0.052 g, 0.530 mmol). The mixture was stirred under reflux for 30 min. After being cooled to room temperature, the pH was set to 7-8 by addition of 1 M sodium hydroxide solution. The aqueous mixture was extracted with dichloromethane, the organic phase was dried (MgSO$_4$), filtered and evaporated to dryness. The residue was purified by chromatography in a mixture of dichloromethane-methanol to give (R)-1-(2-(pyridin-3-yl)ethyl)-6-(2,3,5,6-tetrafluorophenyl)-6,7-dihydro-2H-pyrrolo[1,2-c]imidazole-3(5H)-thione as an off-white powder. Yield: 0.049 g, 35%.

¹H NMR (DMSO$_{d6}$): 11.87 (1H, s), 8.38 (2H, m), 7.84 (1H, m), 7.57 (1H, dt, J=7.8, 2.0 Hz), 7.28 (1H, dd, J=7.8, 4.8 Hz), 4.40 (1H, quin, J=8.4 Hz), 4.12 (1H, dd, J=11.6, 9.1 Hz), 3.73 (1H, dd, J=11.7, 7.6 Hz), 3.08 (1H, dd, J=15.6, 9.2 Hz), 2.85 (2H, m), 2.67 (2H, t, J=7.7 Hz), 2.65 (1H, m).

¹³C NMR (DMSO$_{d6}$): 155.3, 149.6, 147.3, 146.4, 146.4, 146.3, 146.2, 146.2, 145.3, 145.2, 145.2, 145.2, 145.1, 144.8, 144.8, 144.7, 144.7, 144.6, 144.6, 143.6, 143.6, 143.6, 143.5, 143.5, 143.5, 143.5, 136.1, 135.8, 127.9, 123.3, 120.4, 120.3, 120.2, 118.6, 105.8, 105.7, 105.5, 48.2, 35.8, 30.8, 28.8, 25.4.

Example 214: (R)-6-(3-bromo-2,6-difluorophenyl)-1-(2-(pyridin-3-yl)ethyl)-2,5,6,7-tetrahydro-3H-pyrrolo[1,2-c]imidazole-3-thione

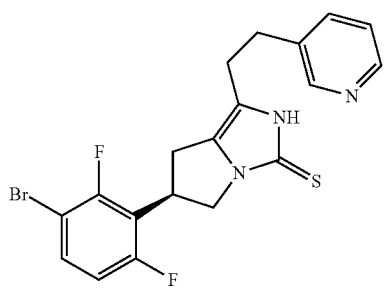 [SMILES: Fc1ccc(Br)c(F)c1[C@H]1Cc2c(CCc3cccnc3)[nH]c(=S)n2C1]

Compound was prepared analogous manner to Example 212 and isolated as a cream powder.

¹H NMR (DMSO$_{d6}$): 11.86 (1H, s), 8.39 (2H, m), 7.71 (1H, ddd, J=5.9, 8.1, 8.7 Hz), 7.57 (1H, dt, J=7.9, 2.0 Hz), 7.28 (1H, ddd, J=7.8, 4.8, 0.8 Hz), 7.15 (1H, m), 4.36 (1H, m), 4.10 (1H, m), 3.67 (1H, dd, J=11.6, 7.8 Hz), 3.04 (1H, dd, J=15.6, 9.2 Hz), 2.85 (2H, m), 2.67 (2H, t, J=7.7 Hz), 2.61 (1H, dd, J=15.6, 8.2 Hz).

¹³C NMR (DMSO$_{d6}$): 160.7, 160.7, 159.1, 159, 157.5, 157.4, 155.9, 155.8, 155.2, 149.6, 147.3, 136.1, 135.8, 132.4, 132.4, 128.1, 123.3, 118.7, 118.6, 118.5, 113.8, 113.7, 113.6, 113.6, 104, 104, 103.9, 103.9, 48.4, 35.7, 30.8, 28.9, 25.4.

Example 215: (S)-6-(3-chloro-2,6-difluorophenyl)-1-(2-(pyridin-3-yl)ethyl)-2,5,6,7-tetrahydro-3H-pyrrolo[1,2-c]imidazole-3-thione Hydrochloride

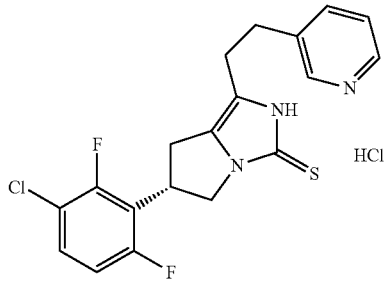 [SMILES: Fc1ccc(Cl)c(F)c1[C@@H]1Cc2c(CCc3cccnc3)[nH]c(=S)n2C1 ; Cl]

Compound was prepared analogous manner to Example 212 and isolated as an off-white solid.

$^1$H NMR (DMSO$_{d6}$): 1.86 (1H, s), 8.64 (2H, m), 8.09 (1H, br d, J=7.8 Hz), 7.73 (1H, dd, J=7.7, 5.5 Hz), 7.61 (1H, m), 7.21 (1H, m), 4.38 (1H, quin, J=8.5 Hz), 4.11 (1H, dd, J=11.2, 9.4 Hz), 3.68 (1H, dd, J=11.6, 7.6 Hz), 3.11 (1H, br dd, J=15.6, 9.3 Hz), 2.99 (2H, m), 2.73 (2H, t, J=7.5 Hz), 2.67 (1H, dd, J=15.7, 7.9 Hz).

$^{13}$C NMR (DMSO$_{d6}$): 160.1, 160, 158.4, 158.4, 156.5, 156.4, 155.3, 154.9, 154.8, 144.5, 142.7, 142, 138.8, 129.7, 129.6, 128.3, 125.5, 118.9, 118.8, 118.6, 118, 116.1, 116, 115.9, 115.9, 113.2, 113.2, 113.1, 113.1, 48.4, 35.6, 30.5, 28.9, 24.9.

Example 216: (R)-1-(3-ethoxypropyl)-6-(2,3,5,6-tetrafluorophenyl)-2,5,6,7-tetrahydro-3H-pyrrolo[1,2-c]imidazole-3-thione

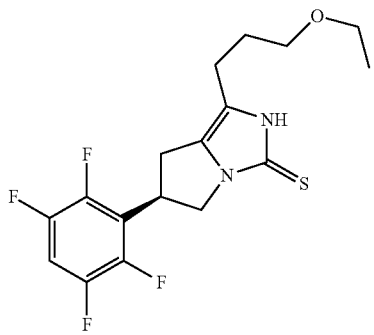 [SMILES: CCOCCCc1[nH]c(=S)n2c1C[C@H](c1c(F)c(F)cc(F)c1F)C2]

Compound was prepared analogous manner to Example 212 and isolated as a white powder.

$^1$H NMR (DMSO$_{d6}$): 1.77 (1H, s), 7.85 (1H, m), 4.50 (1H, quin, J=8.4 Hz), 4.16 (1H, dd, J=11.5, 9.2 Hz), 3.76 (1H, dd, J=11.7, 7.6 Hz), 3.36 (2H, m), 3.31 (3H, m), 2.90 (1H, dd, J=15.7, 7.8 Hz), 2.38 (2H, t, J=7.5 Hz), 1.73 (2H, quin, J=6.9 Hz), 1.07 (3H, t, J=7.0 Hz).

$^{13}$C NMR (DMSO$_{d6}$): 155.1, 146.4, 146.4, 146.3, 146.3, 146.2, 146.2, 145.3, 145.3, 145.3, 145.2, 145.2, 145.2, 144.8, 144.8, 144.7, 144.6, 144.6, 143.7, 143.6, 143.6, 127.5, 120.6, 120.5, 120.4, 119.2, 105.8, 105.7, 105.5, 68.5, 65.2, 48.3, 35.8, 28.9, 27.7, 20.8, 15.1.

Example 217: (R)-1-(2-(1-methyl-1H-imidazol-2-yl)ethyl)-6-(2,3,5,6-tetrafluorophenyl)-2,5,6,7-tetrahydro-3H-pyrrolo[1,2-c]imidazole-3-thione

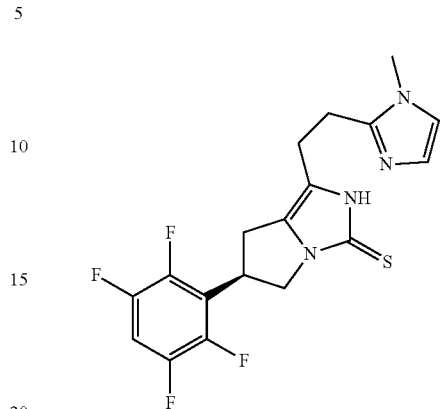

Compound was prepared analogous manner to Example 212 and isolated as a light beige powder.

$^1$H NMR (DMSO$_{d6}$): 11.89 (1H, br s), 7.85 (1H, m), 6.99 (1H, s), 6.72 (1H, s), 4.43 (1H, quin, J=8.5 Hz), 4.14 (1H, dd, J=9.4, 11.3 Hz), 3.75 (1H, br dd, J=11.5, 8.0 Hz), 3.51 (3H, s), 3.18 (1H, br dd, J=15.6, 9.4 Hz), 2.85 (2H, dd, J=7.1, 8.8 Hz), 2.79 (1H, br dd, J=15.6, 8.1 Hz), 2.73 (2H, dd, J=7.1, 8.8 Hz).

$^{13}$C NMR (DMSO$_{d6}$): 155.1, 146.4, 146.4, 146.3, 146.3, 146.2, 145.3, 145.3, 145.3, 145.2, 145.2, 144.8, 144.7, 144.6, 143.7, 143.7, 143.6, 143.6, 143.6, 143.5, 127.9, 126.1, 121, 120.3, 119, 105.9, 105.7, 105.6, 48.2, 35.8, 32, 28.7, 24.9, 22.2.

Example 218: (R)-1-(2-(pyridin-4-yl)ethyl)-6-(2,3,5,6-tetrafluorophenyl)-2,5,6,7-tetrahydro-3H-pyrrolo[1,2-c]imidazole-3-thione

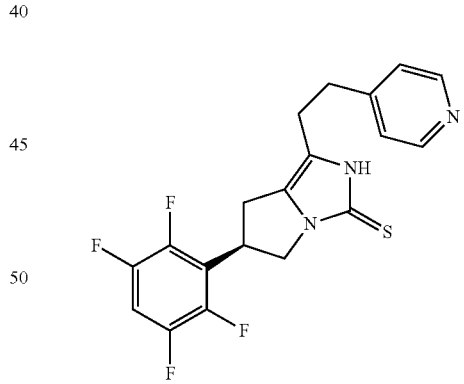

Compound was prepared analogous manner to Example 212 and isolated as a light yellow powder.

$^1$H NMR (DMSO$_{d6}$): 11.87 (1H, s), 8.43 (2H, m), 7.84 (1H, m), 7.19 (2H, m), 4.41 (1H, quin, J=8.4 Hz), 4.13 (1H, dd, J=11.6, 9.1 Hz), 3.73 (1H, dd, J=11.7, 7.5 Hz), 3.13 (1H, dd, J=15.7, 9.4 Hz), 2.85 (2H, m), 2.68 (3H, m).

$^{13}$C NMR (DMSO$_{d6}$): 155.3, 149.6, 149.5, 146.4, 146.4, 146.3, 146.3, 146.3, 146.2, 146.2, 145.3, 145.2, 145.2, 145.2, 145.2, 145.1, 145.1, 144.8, 144.8, 144.7, 144.7, 144.7, 144.6, 144.6, 143.6, 143.6, 143.6, 143.5, 143.5, 143.5, 143.5, 127.9, 123.8, 120.5, 120.4, 120.3, 118.5, 105.9, 105.7, 105.6, 48.3, 35.8, 32.8, 28.9, 24.6.

Example 219: (R)-1-(3-(pyrrolidin-1-yl)propyl)-6-(2,3,5,6-tetrafluorophenyl)-2,5,6,7-tetrahydro-3H-pyrrolo[1,2-c]imidazole-3-thione hydrochloride

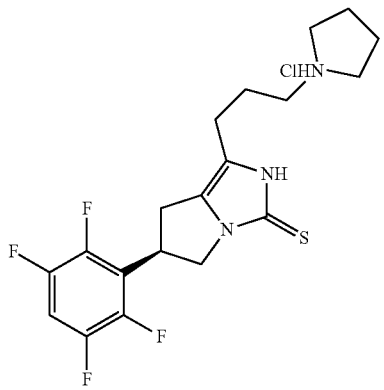

Compound was prepared analogous manner to Example 35 from (R)-1-(pyrrolidin-1-yl)-3-(6-(2,3,5,6-tetrafluorophenyl)-3-thioxo-2,5,6,7-tetrahydro-3H-pyrrolo[1,2-c]imidazol-1-yl)propan-1-one (Example 204) and isolated as a yellowish powder.

$^1$H NMR (DMSO$_{d6}$): 1.86 (1H, br s), 10.76 (1H, br s), 7.87 (1H, m), 4.51 (1H, quin, J=8.5 Hz), 4.16 (1H, dd, J=11.4, 9.3 Hz), 3.77 (1H, br dd, J=11.6, 7.8 Hz), 3.49 (2H, m), 3.34 (1H, dd, J=6.4, 11.7 Hz), 3.05 (2H, m), 2.96 (1H, dd, J=8.0, 15.8 Hz), 2.93 (2H, m), 2.46 (2H, br t, J=7.4 Hz), 1.95 (4H, m), 1.87 (2H, m).

$^{13}$C NMR (DMSO$_{d6}$): 155.4, 146.4, 146.4, 146.4, 146.3, 146.3, 146.3, 146.2, 145.3, 145.3, 145.3, 145.3, 145.2, 145.2, 145.2, 144.8, 144.7, 144.7, 144.7, 144.6, 144.6, 143.7, 143.7, 143.7, 143.6, 143.6, 143.6, 143.6, 143.5, 128, 120.4, 120.3, 120.2, 118.2, 105.9, 105.7, 105.6, 53, 52.8, 48.3, 35.8, 28.9, 23.9, 22.6, 21.3.

Example 220: (S)—N-((6-(3-chloro-2,6-difluorophenyl)-3-thioxo-3,5,6,7-tetrahydro-2H-pyrrolo[1,2-c]imidazol-1-yl)methyl)cyclopropanecarboxamide Step 1: (S)-1-(aminomethyl)-6-(3-chloro-2,6-difluorophenyl)-2,5,6,7-tetrahydro-3H-pyrrolo[1,2-c]imidazole-3-thione

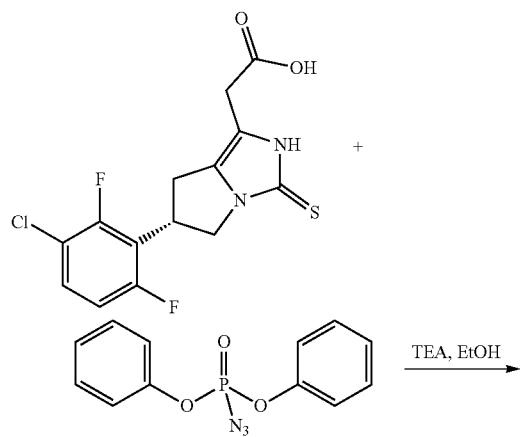

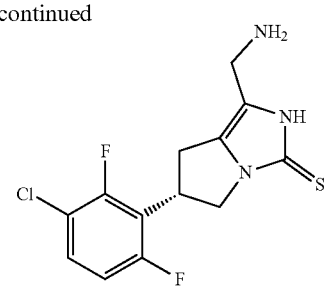

To a stirred solution of (S)-2-(6-(3-chloro-2,6-difluorophenyl)-3-thioxo-3,5,6,7-tetrahydro-2H-pyrrolo[1,2-c]imidazol-1-yl)acetic acid (1 g, 2.90 mmol) in a mixture of Toluene (20 mL) and ethanol (0.85 mL, 14.50 mmol) was added triethylamine (0.48 mL, 3.48 mmol) followed by dropwise addition of diphenyl phosphorazidate (0.75 mL 3.48 mmol) at room temperature. The reaction mixture was heated at reflux for 3 h. The solvent was then removed under reduced pressure and the obtained crude oil was purified by column chromatography in a mixture of dichloromethane-methanol. The obtained oil was dissolved in 2 mL of methanol and treated with 2 mL of 1 M potassium hydroxide solution and the reaction was stirred at room temperature overnight. Thereupon, the mixture was diluted with water and extracted with a mixture of dichloromethane:isopropanol (7:3). The organic phase was evaporated to dryness and the product was purified by chromatography. Yield: 74 mg, 8%.

Step 2: (S)—N-((6-(3-chloro-2,6-difluorophenyl)-3-thioxo-2,5,6,7-tetrahydro-3H-pyrrolo[1,2-c]imidazol-1-yl)methyl)cyclopropanecarboxamide

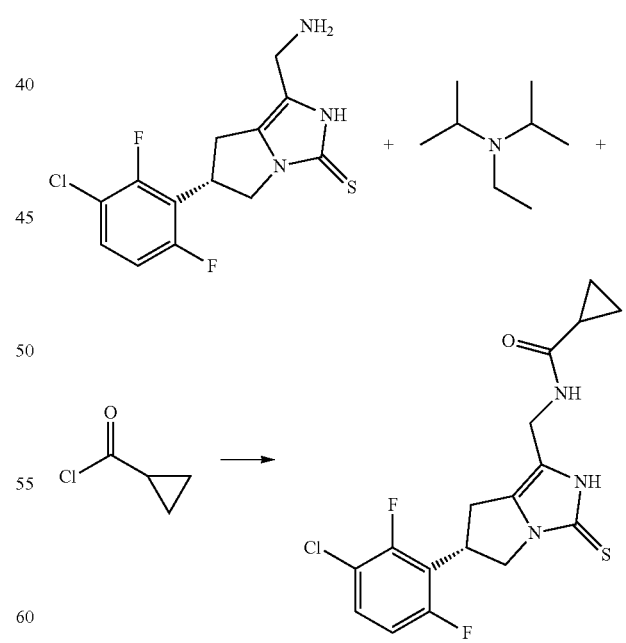

To a stirred solution of (S)-1-(aminomethyl)-6-(3-chloro-2,6-difluorophenyl)-6,7-dihydro-2H-pyrrolo[1,2-c]imidazole-3(5H)-thione (70 mg, 0.222 mmol) and N-ethyl-N-isopropylpropan-2-amine (0.042 mL, 0.244 mmol) was added cyclopropanecarbonyl chloride (0.024 mL, 0.266 mmol) and the reaction was stirred for 1 h at room temperature. The reaction was then diluted with 10 mL of dichloromethane, washed with 1 M HCl and concentrated NaHCO₃, respectively. The organic phase was dried over MgSO₄, filtered and evaporated to dryness. The residue was dissolved in 2 mL of 4 N HCl in dioxane and stirred overnight at room temperature. Thereupon, the solvent was removed under vacuum and the crude product was purified by column chromatography in a mixture of dichloromethane-methanol. Trituration in diethyl ether afforded (S)—N-((6-(3-chloro-2,6-difluorophenyl)-3-thioxo-3,5,6,7-tetrahydro-2H-pyrrolo[1,2-c]imidazol-1-yl)methyl)cyclopropanecarboxamide as an off-white solid. Yield: 16 mg, 18%.

¹H NMR (DMSO$_{d6}$): 11.81 (1H, br s), 8.40 (1H, t, J=5.4 Hz), 7.62 (1H, m), 7.22 (1H, m), 4.44 (1H, quin, J=8.6 Hz), 4.14 (1H, dd, J=11.5, 9.2 Hz), 4.02 (2H, m), 3.72 (1H, dd, J=11.7, 7.8 Hz), 3.24 (1H, dd, J=15.8, 9.4 Hz), 2.87 (1H, dd, J=15.8, 8.1 Hz), 1.55 (1H, m), 0.64 (4H, m).

¹³C NMR (DMSO$_{d6}$): 172.7, 160.1, 160.1, 158.5, 158.4, 156.6, 156.5, 155.5, 154.9, 154.9, 129.7, 129.7, 128.9, 118.8, 118.7, 118.6, 117.5, 116.1, 116, 115.9, 115.9, 113.3, 113.2, 113.1, 113.1, 48.5, 35.6, 33.2, 29.2, 13.4, 6.3, 6.3.

Example 221: (S)—N-((6-(3-chloro-2,6-difluorophenyl)-3-thioxo-3,5,6,7-tetrahydro-2H-pyrrolo[1,2-c]imidazol-1-yl)methyl)cyclopropanecarboxamide Step 1: (S)-1-(aminomethyl)-6-(3-chloro-2,6-difluorophenyl)-2,5,6,7-tetrahydro-3H-pyrrolo[1,2-c]imidazole-3-thione Hydrochloride

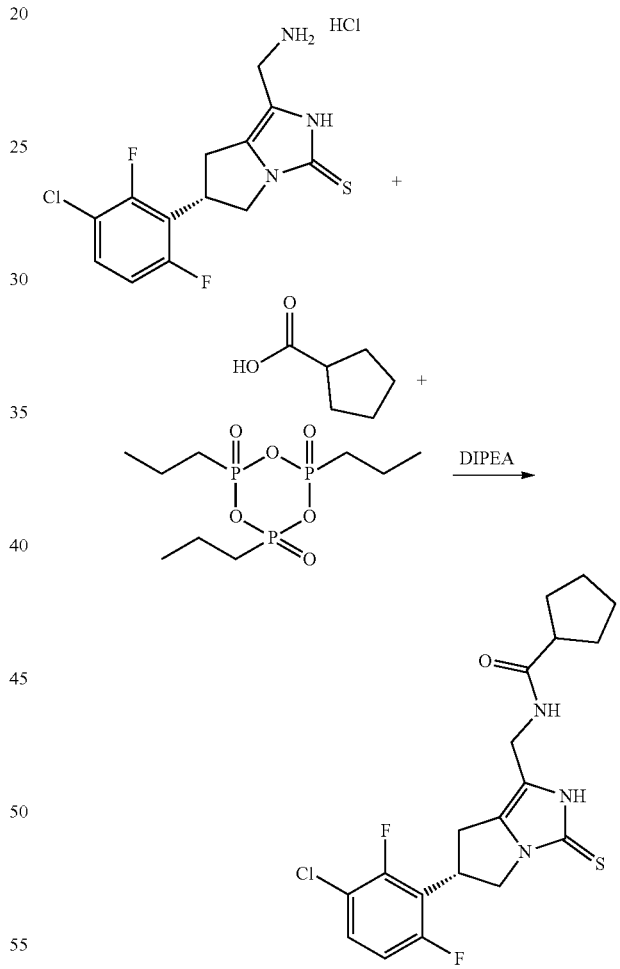

To a stirred solution of (S)-2-(6-(3-chloro-2,6-difluorophenyl)-3-thioxo-3,5,6,7-tetrahydro-2H-pyrrolo[1,2-c]imidazol-1-yl)acetic acid (1 g, 2.90 mmol) in 1,4-Dioxane (100 ml) was added in triethylamine (0.404 ml, 2.90 mmol) followed by addition of diphenyl phosphorazidate (0.686 ml, 3.19 mmol) and the reaction was stirred at room temperature for 30 min. The above mixture was added dropwise to a pre-heated (80° C.) solution of formic acid (0.657 mL, 17.40 mmol) and hydrogen chloride (5.80 mL, 5.80 mmol) in 1,4-Dioxane (100 mL). The reaction was stirred in the warm 90 min. and then cooled to room temperature. The solvent was removed under vacuum and the residue was azeotroped with isopropanol. Recrystallization from a mixture of isopropanol-diethyl ether afforded yield (S)-1-(aminomethyl)-6-(3-chloro-2,6-difluorophenyl)-6,7-dihydro-2H-pyrrolo[1,2-c]imidazole-3(5H)-thione hydrochloride. Yield: 395 mg, 38%.

Step 2: (S)—N-((6-(3-chloro-2,6-difluorophenyl)-3-thioxo-2,5,6,7-tetrahydro-3H-pyrrolo[1,2-c]imidazol-1-yl)methyl)cyclopentanecarboxamide

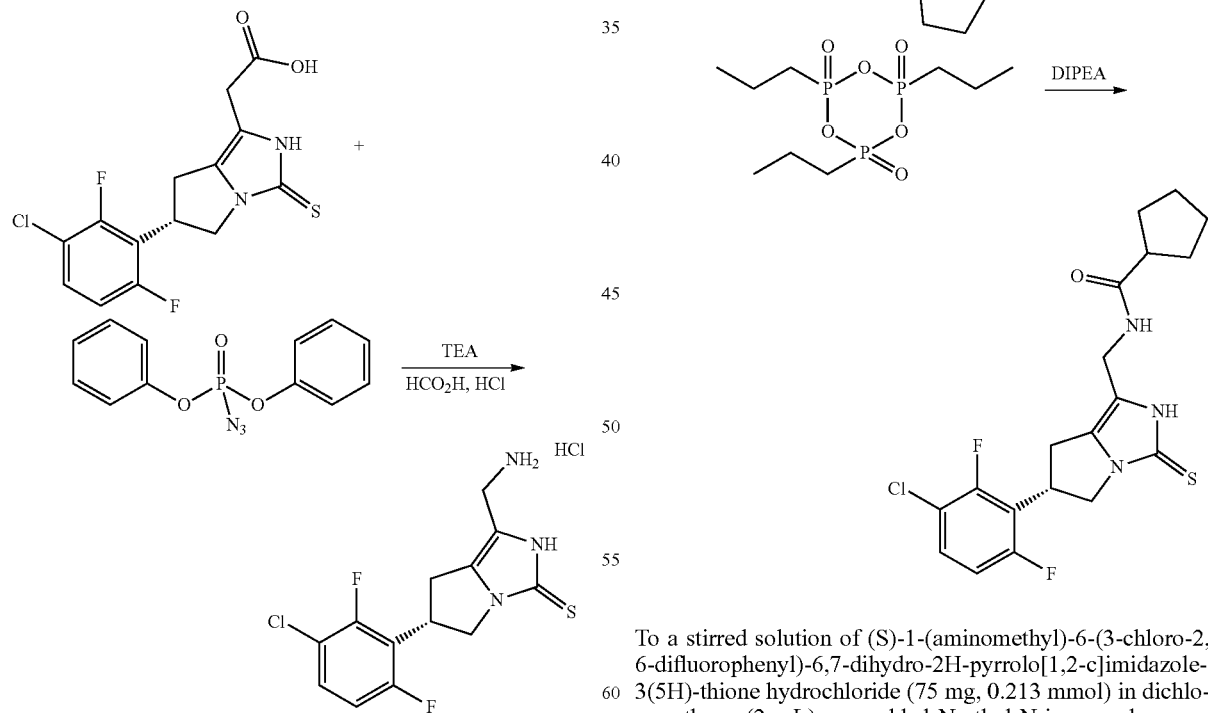

To a stirred solution of (S)-1-(aminomethyl)-6-(3-chloro-2,6-difluorophenyl)-6,7-dihydro-2H-pyrrolo[1,2-c]imidazole-3(5H)-thione hydrochloride (75 mg, 0.213 mmol) in dichloromethane (2 mL) was added N-ethyl-N-isopropylpropan-2-amine (DIPEA) (0.076 mL, 0.426 mmol). After being stirred for 15 min. at room temperature, cyclopentanecarboxylic acid (36.5 mg, 0.319 mmol) was added followed by addition of 2,4,6-tripropyl-1,3,5,2,4,6-trioxatriphosphinane 2,4,6-trioxide (0.198 ml, 0.319 mmol). The reaction was stirred overnight at room temperature. Thereupon, the mixture was diluted with 10 mL of dichloromethane, washed with 1 M HCl, saturated NaHCO₃ and brine, respectively. The organics were dried over MgSO₄, filtered and evaporated to dryness. Chromatography in a mixture of dichloromethane-isopropanol afforded (S)—N-((6-(3-chloro-2,6-difluorophenyl)-3-thioxo-3,5,6,7-tetrahydro-2H-pyrrolo[1,2-c]imidazol-1-yl)methyl)cyclopentanecarboxamide as an off-white solid. Yield: 31 mg, 35%.

$^1$H NMR (DMSO$_{d6}$): 11.79 (1H, s), 8.11 (1H, t, J=5.5 Hz), 7.61 (1H, m), 7.21 (1H, m), 4.44 (1H, quin, J=8.5 Hz), 4.14 (1H, dd, J=11.3, 9.4 Hz), 4.01 (2H, m), 3.71 (1H, dd, J=11.7, 7.8 Hz), 3.24 (1H, dd, J=15.8, 9.4 Hz), 2.85 (1H, dd, J=15.8, 7.9 Hz), 2.50 (1H, m), 1.70 (2H, m), 1.58 (4H, m), 1.47 (2H, m).

$^{13}$C NMR (DMSO$_{d6}$): 175.4, 160.1, 160.1, 158.5, 158.4, 156.6, 156.5, 155.3, 154.9, 154.9, 129.7, 129.6, 128.7, 118.9, 118.7, 118.6, 117.7, 116.1, 116.1, 116, 115.9, 113.3, 113.2, 113.1, 113.1, 48.5, 44.1, 35.6, 33, 29.9, 29.9, 29.3, 25.6.

Example 222: (S)—N-((6-(3-chloro-2,6-difluorophenyl)-3-thioxo-2,5,6,7-tetrahydro-3H-pyrrolo[1,2-c]imidazol-1-yl)methyl)tetrahydro-2H-pyran-4-carboxamide

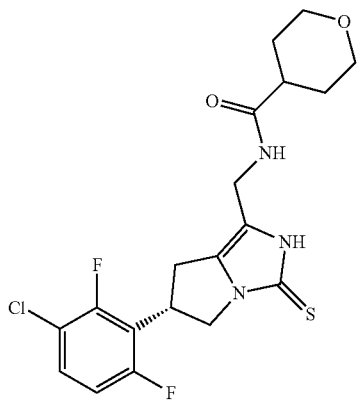 [SMILES: O=C(NCc1[nH]c(=S)n2c1C[C@@H](c1c(F)ccc(Cl)c1F)C2)C1CCOCC1]

Compound was prepared analogous manner to Example 221 from (S)-1-(aminomethyl)-6-(3-chloro-2,6-difluorophenyl)-2,5,6,7-tetrahydro-3H-pyrrolo[1,2-c]imidazole-3-thione hydrochloride and isolated as an off-white solid.

$^1$H NMR (DMSO$_{d6}$): 11.80 (1H, br s), 8.14 (1H, br t, J=5.4 Hz), 7.61 (1H, m), 7.22 (1H, m), 4.44 (1H, quin, J=8.6 Hz), 4.14 (1H, dd, J=11.5, 9.3 Hz), 4.02 (2H, m), 3.83 (2H, m), 3.71 (1H, dd, J=11.6, 7.8 Hz), 3.25 (3H, m), 2.85 (1H, dd, J=15.8, 8.1 Hz), 2.35 (1H, m), 1.54 (4H, m).

$^{13}$C NMR (DMSO$_{d6}$): 174, 160.1, 160.1, 158.5, 158.4, 156.6, 156.5, 155.3, 154.9, 154.9, 129.7, 129.6, 128.7, 118.9, 118.8, 118.7, 117.5, 116, 115.9, 113.3, 113.2, 113.1, 113.1, 66.4, 48.5, 40.6, 35.6, 33, 29.2, 28.8.

Example 223: (S)—N-((6-(3-chloro-2,6-difluorophenyl)-3-thioxo-2,5,6,7-tetrahydro-3H-pyrrolo[1,2-c]imidazol-1-yl)methyl)nicotinamide

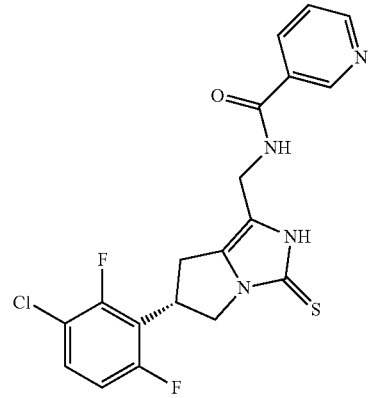 [SMILES: O=C(NCc1[nH]c(=S)n2c1C[C@@H](c1c(F)ccc(Cl)c1F)C2)c1cccnc1]

Compound was prepared analogous manner to Example 221 from (S)-1-(aminomethyl)-6-(3-chloro-2,6-difluorophenyl)-2,5,6,7-tetrahydro-3H-pyrrolo[1,2-c]imidazole-3-thione hydrochloride and isolated as an off-white solid.

$^1$H NMR (DMSO$_{d6}$): 11.90 (1H, br s), 9.03 (1H, t, J=5.4 Hz), 9.00 (1H, dd, J=2.3, 0.8 Hz), 8.70 (1H, dd, J=4.8, 1.7 Hz), 8.18 (1H, dt, J=8.1, 1.9 Hz), 7.60 (1H, m), 7.50 (1H, ddd, J=7.9, 4.8, 0.7 Hz), 7.20 (1H, m), 4.44 (1H, quin, J=8.6 Hz), 4.27 (2H, m), 4.15 (1H, dd, J=11.4, 9.2 Hz), 3.72 (1H, dd, J=11.7, 7.9 Hz), 3.26 (1H, dd, J=15.8, 9.4 Hz), 2.88 (1H, dd, J=15.8, 8.1 Hz).

$^{13}$C NMR (DMSO$_{d6}$): 165, 160.1, 160.1, 158.5, 158.4, 156.6, 156.5, 155.6, 154.9, 154.9, 152, 148.4, 135, 129.7, 129.6, 129.5, 129, 123.5, 118.7, 118.6, 118.5, 117, 116.1, 116, 115.9, 115.9, 113.2, 113.2, 113.1, 113.1, 48.5, 35.6, 33.7, 29.2.

Example 224: 2-{[(6S)-6-(3-bromo-2,6-difluorophenyl)-3-thioxo-2,5,6,7-tetrahydro-3H-pyrrolo[1,2-c]imidazol-1-yl]methyl}-1-cyanoguanidine

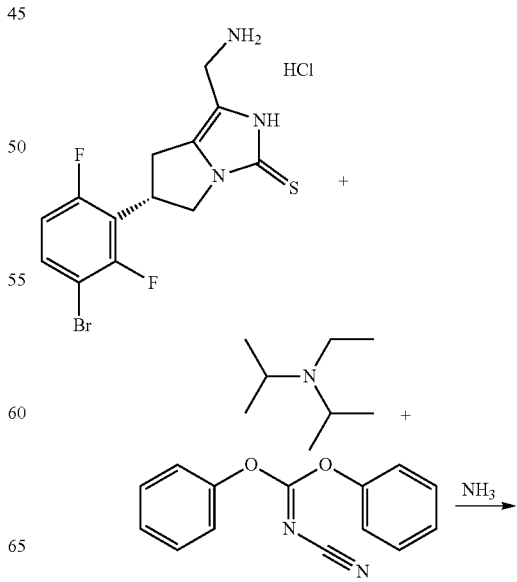

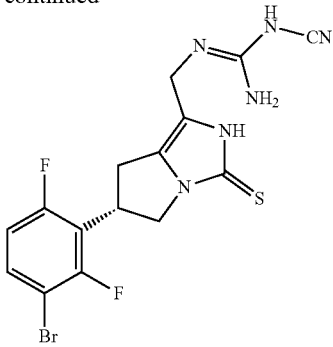

To a stirred suspension of (S)-1-(aminomethyl)-6-(3-bromo-2,6-difluorophenyl)-6,7-dihydro-2H-pyrrolo[1,2-c]imidazole-3(5H)-thione hydrochloride (prepared analogous manner to Example 221 step 1) (0.23 g, 0.580 mmol) in tetrahydrofuran (29.0 mL) was added N-ethyl-N-isopropylpropan-2-amine (DIPEA) (0.203 mL, 1.160 mmol), followed by quick addition of diphenyl N-cyanocarbonimidate (0.276 g, 1.160 mmol), and then the reaction was stirred for 30 min. at room temperature. Thereupon, 7 M ammonia in methanol (4.14 mL, 29.0 mmol) was added and the mixture was heated at 80° C. overnight in a sealed tube. Thereupon, the reaction was cooled to room temperature and evaporated to dryness under reduced pressure. Chromatography in a mixture of dichloromethane-methanol afforded the product as a light yellow solid.

$^1$H NMR (DMSO$_{d6}$): 11.83 (1H, s), 7.73 (1H, m), 7.17 (1H, m), 6.97 (1H, s br), 6.81 (2H, s br), 4.47 (1H, quin, J=8.6 Hz), 4.15 (1H, m), 4.03 (2H, m), 3.72 (1H, dd, J=11.6, 7.9 Hz), 3.25 (1H, dd, J=9.4, 15.7 Hz), 2.86 (1H, dd, J=15.8, 8.1 Hz).

$^{13}$C NMR (DMSO$_{d6}$): 161.1, 160.8, 160.7, 159.1, 159.1, 157.5, 157.5, 155.9, 155.8, 155.7, 132.5, 132.4, 129.2, 118.8, 118.6, 118.5, 117.8, 116.9, 113.8, 113.8, 113.6, 113.6, 104.1, 103.9, 48.5, 35.6, 35, 29.3.

Example 225: (S,Z)—N-((6-(3-bromo-2,6-difluorophenyl)-3-thioxo-2,5,6,7-tetrahydro-3H-pyrrolo[1,2-c]imidazol-1-yl)methyl)-N'-cyanopyrrolidine-1-carboximidamide

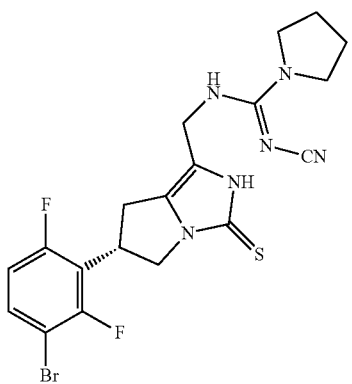 [SMILES: N#C/N=C(/NCc1[nH]c(=S)n2c1C[C@@H](c1c(F)ccc(Br)c1F)C2)N1CCCC1]

Compound was prepared analogous manner to Example 224 and isolated as a dark yellow solid.

$^1$H NMR (DMSO$_{d6}$): 1.74 (1H, s), 7.73 (1H, m), 7.17 (1H, m), 7.04 (0.8H, t, J=5.6 Hz), 6.87 (0.2H, s), 4.45 (1H, quin, J=8.7 Hz), 4.24-4.09 (2.6H, m), 3.98 (0.4H, t, J=6.1 Hz), 3.71 (1H, dd, J=11.7, 8.0 Hz), 3.47 (3.2H, br s), 3.30-3.16 (1.8H, m), 2.90 (1H, m), 1.84, 1.77 (4H, m).

$^{13}$C NMR (DMSO$_{d6}$):160.8, 160.8, 159.2, 159.1, 158.6, 157.5, 157.5, 156.3, 155.9, 155.9, 155.6, 155.5, 132.5, 132.4, 129, 119.1, 118.7, 118.6, 118.6, 118.5, 118.3, 117.4, 117.3, 113.8, 113.8, 113.6, 113.6, 104.1, 104, 103.9, 103.9, 48.5, 47.8, 36.2, 35.6, 29.2, 24.8.

Example 226: (S)—N-(2-(6-(3-chloro-2,6-difluorophenyl)-3-thioxo-2,5,6,7-tetrahydro-3H-pyrrolo[1,2-c]imidazol-1-yl)ethyl)-N-methylnicotinamide

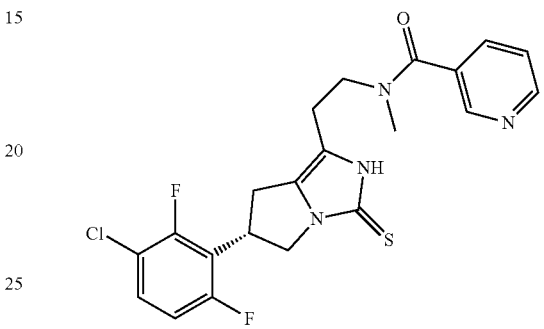

Compound was prepared analogous manner to Example 168 from (S)-6-(3-chloro-2,6-difluorophenyl)-1-(2-(methylamino)ethyl)-6,7-dihydro-2H-pyrrolo[1,2-c]imidazole-3(5H)-thione hydrochloride (Example 193) and isolated as an off-white solid.

$^1$H NMR (DMSO$_{d6}$): 1.93 (0.5H, br s), 11.64 (0.5H, br s), 8.63 (0.5H, br d, J=4.0 Hz), 8.59 (0.5H, br d, J=4.0 Hz), 8.57 (0.5H, br s), 8.43 (0.5H, s), 7.78 (05H, br d, J=7.6 Hz), 7.62 (1H, m), 7.51 (0.5H, br d, J=7.6 Hz), 7.45 (0.5H, br dd, J=7.0, 5.3 Hz), 7.42 (0.5H, m), 7.21 (1H, m), 4.46 (0.5H, m), 4.37 (0.5H, quin, J=8.5 Hz), 4.15 (1H, m), 3.73 (1H, m), 3.65 (1H, m), 3.41 (1H, m), 3.31 (0.5H, m), 3.01 (0.5H, dd, J=9.2, 15.8 Hz), 2.97 (1.5H, s), 2.91 (1H, dd, J=7.9, 15.6 Hz), 2.87 (1.5H, s), 2.70 (1H, m), 2.53 (1H, m).

$^{13}$C NMR (DMSO$_{d6}$): 168.3, 167.8, 160.1, 160.1, 158.5, 158.4, 156.5, 156.5, 155.5, 155.5, 155.4, 154.9, 154.8, 150.3, 150, 147.5, 146.9, 134.5, 134.2, 132.2, 132.1, 129.7, 129.7, 129.6, 128.9, 128.8, 128.7, 123.5, 123.4, 118.8, 118.7, 118.6, 118.5, 118.4, 118.3, 116.9, 116.1, 116.1, 116, 115.9, 115.9, 113.2, 113.1, 49.9, 48.5, 48.3, 45.9, 37.3, 35.7, 32.5, 28.9, 28.6, 22.7, 21.9.

Example 227: (S)—N-(2-(6-(3-chloro-2,6-difluorophenyl)-3-thioxo-2,5,6,7-tetrahydro-3H-pyrrolo[1,2-c]imidazol-1-yl)ethyl)-N-methylpyrrolidine-1-carboxamide

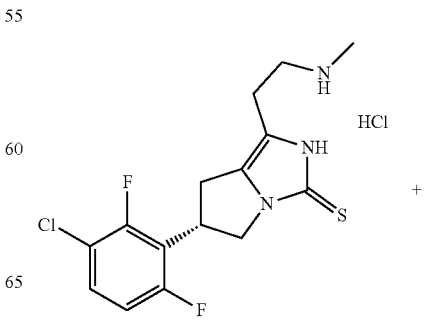

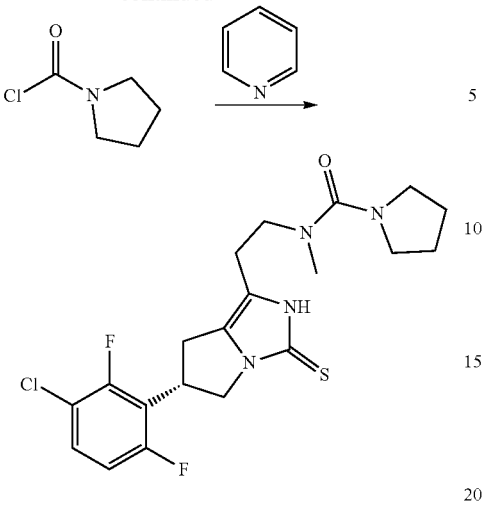

To a stirred suspension of (S)-6-(3-chloro-2,6-difluorophenyl)-1-(2-(methylamino)ethyl)-6,7-dihydro-2H-pyrrolo[1,2-c]imidazole-3(5H)-thione hydrochloride (Example 193) (87 mg, 0.229 mmol in pyridine (2 mL) was added pyrrolidine-1-carbonyl chloride (0.030 mL, 0.275 mmol) an the reaction was stirred at room temperature overnight. The reaction was diluted with dichloromethane (10 mL) and washed three times with 5 mL of 1 M HCl. The organic phase was dried over MgSO$_4$, filtered and evaporated to dryness. The crude product was purified by chromatography in a mixture of dichloromethane-methanol. Crystallization from ethyl acetate afforded (S)—N-(2-(6-(3-chloro-2,6-difluorophenyl)-3-thioxo-3,5,6,7-tetrahydro-2H-pyrrolo[1,2-c]imidazol-1-yl)ethyl)-N-methylpyrrolidine-1-carboxamide as a white solid.

Yield: 23 mg, 22%.

$^1$H NMR (DMSO$_{d6}$): 1.82 (1H, s), 7.62 (1H, m), 7.22 (1H, m), 4.42 (1H, quin, J=8.7 Hz), 4.12 (1H, dd, J=9.5, 11.2 Hz), 3.72 (1H, dd, J=11.5, 8.1 Hz), 3.30 (2H, t, J=7.0 Hz), 3.24 (1H, dd, J=15.6, 9.2 Hz), 3.16 (4H, m), 2.86 (1H, dd, J=15.6, 8.4 Hz), 2.71 (3H, s), 2.56 (2H, br t, J=7.0 Hz), 1.71 (4H, m).

$^{13}$C NMR (DMSO$_{d6}$): 161.8, 160.1, 160.1, 158.5, 158.5, 156.6, 156.5, 155.2, 155, 154.9, 129.7, 129.7, 128.5, 118.7, 118.5, 118.4, 117.3, 116.1, 116.1, 116, 115.9, 113.3, 113.2, 113.1, 113.1, 48.3, 48.1, 47.9, 36, 35.7, 28.9, 25.1, 22.4.

Example 228: (S)-6-(3-chloro-2,6-difluorophenyl)-1-((3-methyl-1,2,4-oxadiazol-5-yl)methyl)-6,7-dihydro-2H-pyrrolo[1,2-c]imidazole-3(5H)-thione

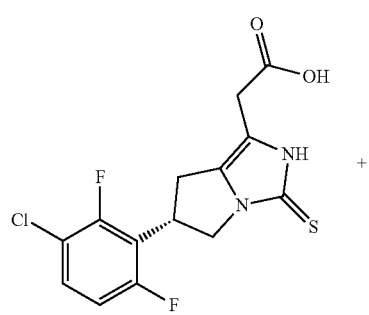

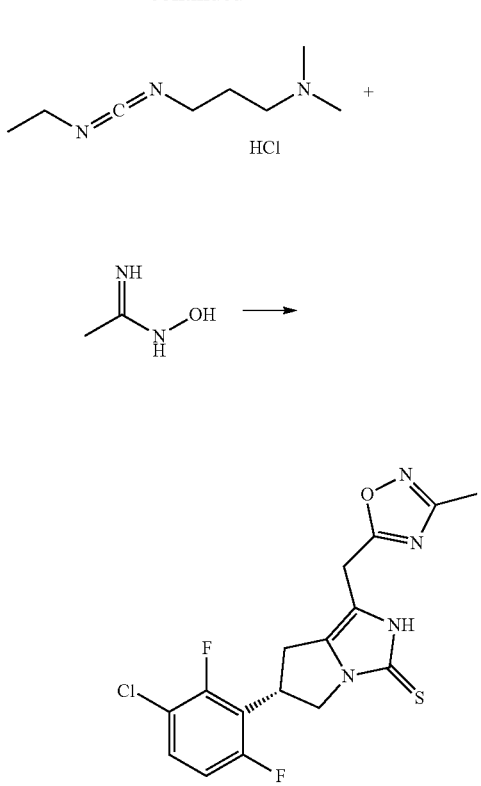

To a stirred suspension of (S)-2-(6-(3-chloro-2,6-difluorophenyl)-3-thioxo-3,5,6,7-tetrahydro-2H-pyrrolo[1,2-c]imidazol-1-yl)acetic acid (150 mg, 0.435 mmol) in dioxane (3 mL) was added 3-(((ethylimino)methylene)amino)-N,N-dimethylpropan-1-amine hydrochloride (113 mg, 0.592 mmol) in one portion and the reaction mixture was stirred for 30 min. at room temperature. Thereupon, the obtained solution was treated with N-hydroxyacetimidamide (32.2 mg, 0.435 mmol) and the reaction mixture was stirred for 1 h at room temperature followed by stirring at 110° C. for additional 3.5 h. The solvent was then removed under vacuum and the residue was diluted with ethyl acetate (25 mL), twice with sodium bicarbonate solution (25 mL) and water (25 mL), respectively. The organic phase was dried over MgSO$_4$, filtered and evaporated to dryness. Purification by chromatography (reversed phase, acetonitrile-water mixture) followed by recrystallization from isopropanol afforded (S)-6-(3-chloro-2,6-difluorophenyl)-1-((3-methyl-1,2,4-oxadiazol-5-yl)methyl)-6,7-dihydro-2H-pyrrolo[1,2-c]imidazole-3(5H)-thione as an off-white solid. Yield: 0.058 g, 34%.

$^1$H NMR (DMSO$_{d6}$): 11.97 (1H, s), 7.61 (1H, m), 7.21 (1H, m), 4.48 (1H, quin, J=8.5 Hz), 4.18 (1H, dd, J=9.3, 11.7 Hz), 4.15 (2H, m), 3.75 (1H, dd, J=11.6, 7.8 Hz), 3.25 (1H, dd, J=15.9, 9.3 Hz), 2.86 (1H, dd, J=15.9, 8.0 Hz), 2.31 (3H, s).

$^{13}$C NMR (DMSO$_{d6}$): 175.9, 167.1, 160.1, 160.1, 158.5, 158.4, 156.6, 156.5, 156.1, 154.9, 154.9, 130.2, 129.7, 129.7, 118.8, 118.6, 118.5, 116.1, 116, 115.9, 115.9, 113.2, 113.2, 113.1, 113.1, 112, 48.7, 35.6, 29, 22, 11.1.

Example 229: (R)-2-(2-methyl-6-(2,3,5,6-tetrafluorophenyl)-3-thioxo-3,5,6,7-tetrahydro-2H-pyrrolo[1,2-c]imidazol-1-yl)acetic Acid Step 1: ethyl (R)-2-(2-methyl-6-(2,3,5,6-tetrafluorophenyl)-3-thioxo-2,5,6,7-tetrahydro-3H-pyrrolo[1,2-c]imidazol-1-yl)acetate

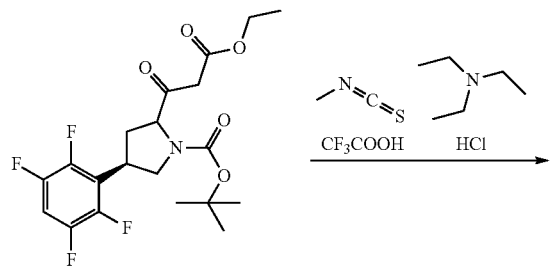

Step 2: (R)-2-(2-methyl-6-(2,3,5,6-tetrafluorophenyl)-3-thioxo-2,5,6,7-tetrahydro-3H-pyrrolo[1,2-c]imidazol-1-yl)acetic Acid

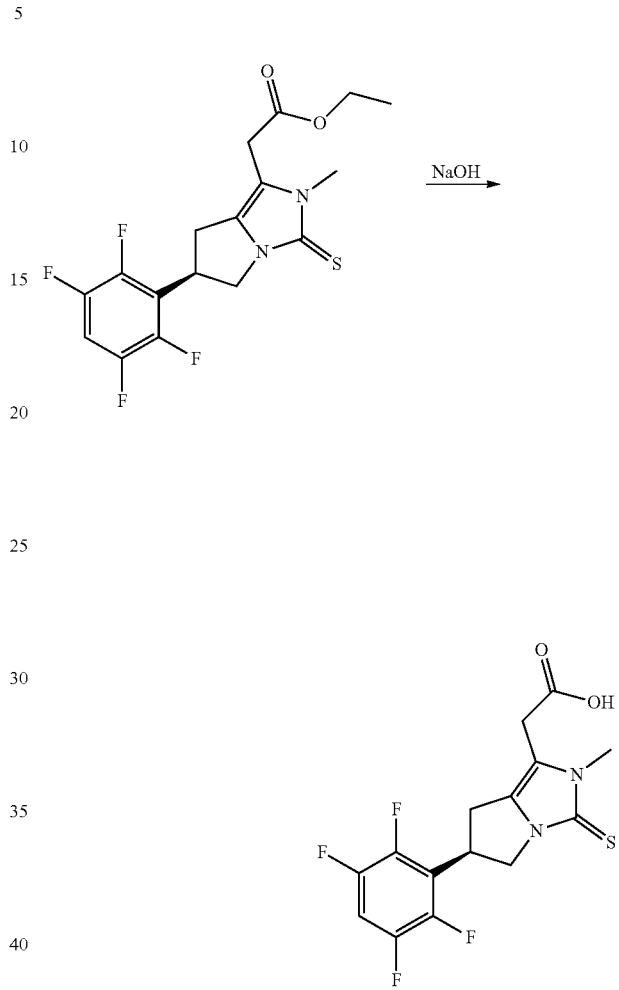

To a solution of (4R)-tert-butyl 2-(3-ethoxy-3-oxopropanoyl)-4-(2,3,5,6-tetrafluorophenyl)pyrrolidine-1-carboxylate (3.22 g, 5.57 mmol) in dichloromethane (50 mL) was added trifluoroacetic acid (8.59 mL, 111 mmol) in one portion and the solution was stirred for 5 h at room temperature. Thereupon, the mixture was quenched with sodium bicarbonate solution with ice cooling. The organic phase was dried over MgSO$_4$, filtered and treated with methyl isothiocyanate (0.489 g, 6.69 mmol) followed by addition of triethyl amine (0.78 mL, 5.57 mmol). The solution was stirred for 64 h at room temperature, and then evaporated to dryness. The residue was dissolved in abs. ethanol (50 mL) followed by addition of cc. HCl (1.39 mL, 16.72 mmol) and the mixture was stirred under reflux for 1 h. Thereupon the solvent was removed and the residue was partitioned between dichloromethane and water. The organic phase was dried (MgSO$_4$), filtered and evaporated. Chromatography in a mixture of petroleumether-ethyl acetate followed by slurring in petroleum ether afforded (R)-ethyl 2-(2-methyl-6-(2,3,5,6-tetrafluorophenyl)-3-thioxo-3,5,6,7-tetrahydro-2H-pyrrolo[1,2-c]imidazol-1-yl)acetate as colorless solid. Yield: 0.25 g, 11%.

To a solution of (R)-ethyl 2-(2-methyl-6-(2,3,5,6-tetrafluorophenyl)-3-thioxo-3,5,6,7-tetrahydro-2H-pyrrolo[1,2-c]imidazol-1-yl)acetate (0.25 g, 0.644 mmol) in methanol (7 mL) was added 1 N NaOH (0.97 mL, 0.966 mmol) (gentle heating and sonication to get clear solution) and the mixture was stirred for 3 h at room temperature. Methanol was then removed under vacuum, the residue was diluted with water to approx. 10 mL, acidified by addition of 6 M HCl to pH=1-2. The resulting precipitate was collected, washed with water, dried in vacuum at 50° C. to give (R)-2-(2-methyl-6-(2,3,5,6-tetrafluorophenyl)-3-thioxo-3,5,6,7-tetrahydro-2H-pyrrolo[1,2-c]imidazol-1-yl)acetic acid as an off-white powder. Yield: 0.21 g, 91%.

$^1$H NMR (DMSO$_{d6}$): 12.74 (1H, s br), 7.86 (1H, m), 4.49 (1H, quin, J=8.5 Hz), 4.25 (1H, dd, J=11.6, 9.2 Hz), 3.85 (1H, dd, J=11.7, 7.6 Hz), 3.65 (2H, s), 3.40 (3H, s), 3.35 (1H, m), 2.95 (1H, dd, J=16.0, 7.8 Hz).

$^{13}$C NMR (DMSO$_{d6}$): 170.8, 156.4, 146.4, 146.3, 146.3, 146.2, 145.3, 145.2, 144.8, 144.8, 144.7, 144.7, 144.6, 144.6, 143.7, 143.6, 143.6, 143.6, 128.5, 120.5, 120.4, 120.3, 115.6, 105.9, 105.7, 105.6, 49.5, 34.8, 31.4, 29.8, 29.

Example 230: (S)-2-(6-(5-chloro-2-fluorophenyl)-2-methyl-3-thioxo-2,5,6,7-tetrahydro-3H-pyrrolo[1,2-c]imidazol-1-yl)acetic acid

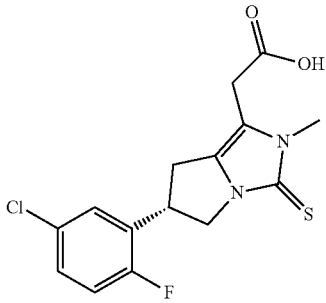 [SMILES: Cn1c(CC(=O)O)c2n(c1=S)C[C@H](c1cc(Cl)ccc1F)C2]

Compound was prepared in an analogous manner to Example 229 from (4S)-tert-butyl 2-(3-ethoxy-3-oxopropanoyl)-4-(5-chloro-2-fluorophenyl)pyrrolidine-1-carboxylate and isolated as a beige solid.

$^1$H NMR (DMSO$_{d6}$): 12.70 (1H, br s), 7.47 (1H, dd, J=6.5, 2.6 Hz), 7.40 (1H, ddd, J=8.7, 4.4, 2.6 Hz), 7.29 (1H, dd, J=9.9, 8.9 Hz), 4.21 (2H, m), 3.81 (1H, m), 3.67 (2H, s), 3.39 (3H, m), 3.27 (1H, br dd, J=15.6, 7.5 Hz), 2.93 (1H, dd, J=15.5, 7.3 Hz).

$^{13}$C NMR (DMSO$_{d6}$): 170.8, 159.8, 158.2, 156.6, 130.2, 130.1, 128.9, 128.9, 128.7, 128.5, 128.5, 128.5, 117.6, 117.4, 115.8, 50.2, 31.4, 29.8, 29.3.

Example 231: 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)acetic Acid

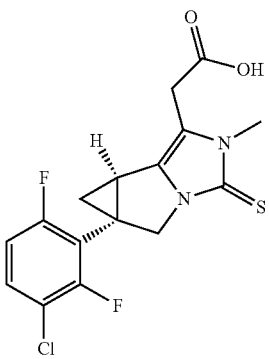 [SMILES: Cn1c(CC(=O)O)c2n(c1=S)C[C@@]1(c3c(F)ccc(Cl)c3F)C[C@@H]21]

Compound was prepared in an analogous manner to Example 229 from tert-butyl (1S,5R)-1-(3-chloro-2,6-difluorophenyl)-4-(3-ethoxy-3-oxopropanoyl)-3-azabicyclo[3.1.0]hexane-3-carboxylate and isolated as a beige solid.

$^1$H NMR (DMSO$_{d6}$): 12.78 (1H, br s), 7.64 (1H, m), 7.21 (1H, t, J=8.9 Hz), 4.12 (1H, d, J=12.2 Hz), 3.81 (1H, d, J=12.0 Hz), 3.74 (2H, m), 3.36 (3H, s), 2.85 (1H, dd, J=8.2, 4.4 Hz), 1.70 (1H, dd, J=8.1, 5.6 Hz), 1.27 (1H, t, J=5.0 Hz).

$^{13}$C NMR (DMSO$_{d6}$): 170.9, 161.2, 161.2, 159.6, 159.6, 157.8, 157.8, 157, 157, 156.2, 156.1, 117, 116.9, 116.8, 115.8, 115.7, 115.6, 115.6, 115.6, 112.9, 112.9, 112.8, 112.8, 52.3, 31.4, 29.8, 25.7, 21.7, 21.1.

Example 232: 2-((S)-6-(3-bromo-2,6-difluorophenyl)-2-methyl-3-thioxo-2,5,6,7-tetrahydro-3H-pyrrolo[1,2-c]imidazol-1-yl)-N—((R)-tetrahydrofuran-3-yl)acetamide

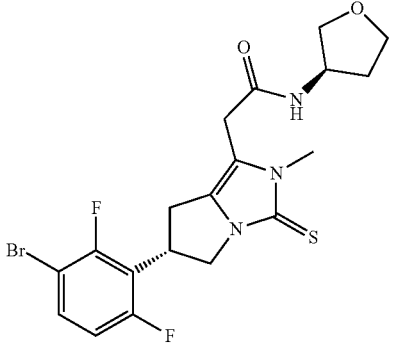 [SMILES: Cn1c(CC(=O)N[C@@H]2CCOC2)c2n(c1=S)C[C@H](c1c(F)ccc(Br)c1F)C2]

Compound was prepared analogous manner to Example 32 from (S)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a light cream powder.

$^1$H NMR (DMSO$_{d6}$): 8.38 (1H, br d, J=6.6 Hz), 7.73 (1H, m), 7.17 (1H, m), 4.44 (1H, quin, J=8.6 Hz), 4.22 (2H, m), 3.78 (2H, m), 3.72 (1H, dd, J=8.9, 6.0 Hz), 3.66 (1H, m), 3.46 (1H, dd, J=8.9, 3.5 Hz), 3.43 (2H, m), 3.40 (3H, s), 3.28 (1H, dd, J=15.8, 9.5 Hz), 2.88 (1H, dd, J=15.8, 8.1 Hz), 2.07 (1H, m), 1.71 (1H, m).

$^{13}$C NMR (DMSO$_{d6}$): 167.6, 160.8, 160.8, 159.2, 159.1, 157.6, 157.5, 156.2, 155.9, 155.9, 132.5, 132.4, 128.4, 118.8, 118.7, 118.6, 116.4, 113.8, 113.8, 113.6, 113.6, 104.1, 104.1, 103.9, 103.9, 72.4, 66.3, 49.8, 49.6, 34.8, 32, 31.5, 31.1, 29.2.

Example 233: (S)-2-(6-(3-bromo-2,6-difluorophenyl)-2-methyl-3-thioxo-2,5,6,7-tetrahydro-3H-pyrrolo[1,2-c]imidazol-1-yl)-1-morpholinoethan-1-one

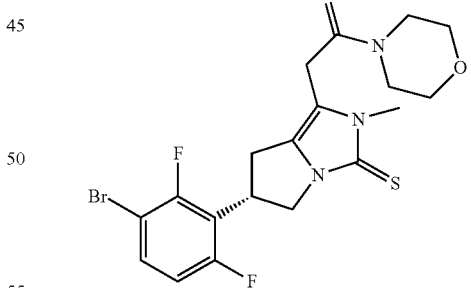

Compound was prepared analogous manner to Example 32 from (S)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a light cream powder.

$^1$H NMR (DMSO$_{d6}$): 7.72 (1H, m), 7.16 (1H, m), 4.44 (1H, quin, J=8.5 Hz), 4.22 (1H, dd, J=9.3, 11.2 Hz), 3.79 (1H, br dd, J=11.6, 7.6 Hz), 3.75 (2H, s), 3.59 (2H, m), 3.55 (2H, m), 3.49 (2H, m), 3.45 (2H, m), 3.36 (3H, m), 3.27 (1H, dd, J=15.8, 9.4 Hz), 2.85 (1H, dd, J=15.8, 7.8 Hz).

$^{13}$C NMR (DMSO$_{d6}$): 166.8, 160.8, 160.7, 159.2, 159.1, 157.5, 157.5, 156.2, 155.9, 155.9, 132.5, 132.4, 128.3, 118.9, 118.8, 118.6, 116.2, 113.8, 113.8, 113.6, 113.6, 104.1, 104, 103.9, 103.9, 66, 66, 49.5, 45.6, 41.7, 34.8, 31.5, 29.2, 28.8.

Example 234: 1-((S)-6-(3-bromo-2,6-difluorophenyl)-2-methyl-3-thioxo-2,5,6,7-tetrahydro-3H-pyrrolo[1,2-c]imidazol-1-yl)-N—((R)-tetrahydrofuran-3-yl)cyclopropane-1-carboxamide

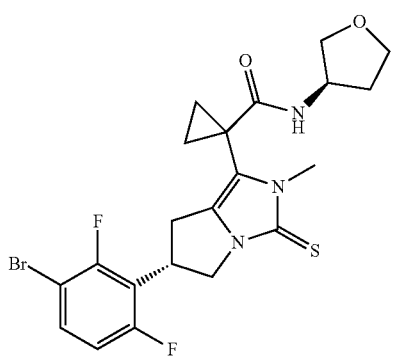 [SMILES: Cn1c(C2(C(=O)N[C@@H]3CCOC3)CC2)c2n(c1=S)C[C@H](c1c(F)ccc(Br)c1F)C2]

Compound was prepared analogous manner to Example 32 from (S)-(1-(6-(3-bromo-2,6-difluorophenyl)-2-methyl-3-thioxo-2,5,6,7-tetrahydro-3H-pyrrolo[1,2-c]imidazol-1-yl)cyclopropyl)(1H-imidazol-1-yl)methanone and isolated as a white powder.

$^1$H NMR (DMSO$_{d6}$): 7.74 (1H, m), 7.63 (1H, d, J=6.9 Hz), 7.18 (1H, m), 4.41 (1H, quin, J=8.9 Hz), 4.32 (1H, m), 4.21 (1H, dd, J=9.3, 11.3 Hz), 3.84-3.74 (2H, m), 3.72 (1H, dd, J=8.8, 6.7 Hz), 3.63 (1H, m), 3.46 (1H, dd, J=8.8, 4.8 Hz), 3.35 (3H, s), 3.24 (1H, dd, J=15.6, 9.0 Hz), 2.97 (1H, dd, J=15.6, 9.0 Hz), 2.04 (1H, m), 1.76 (1H, m), 1.43 (1H, m), 1.35 (1H, m), 1.02 (2H, m).

$^{13}$C NMR (DMSO$_{d6}$): 170.4, 161, 160.9, 159.3, 159.3, 157.7, 157.6, 156.5, 156.1, 156, 132.6, 132.5, 130.9, 119.3, 118, 117.9, 117.7, 113.8, 113.8, 113.6, 113.6, 104.1, 103.9, 71.5, 66.6, 50.3, 49.2, 35.1, 32, 31.4, 29, 22.1, 15.5, 15.1.

Example 235: (S)-2-(6-(3-bromo-2,6-difluorophenyl)-2-methyl-3-thioxo-2,5,6,7-tetrahydro-3H-pyrrolo[1,2-c]imidazol-1-yl)-1-(1,1-dioxidothiomorpholino)ethan-1-one

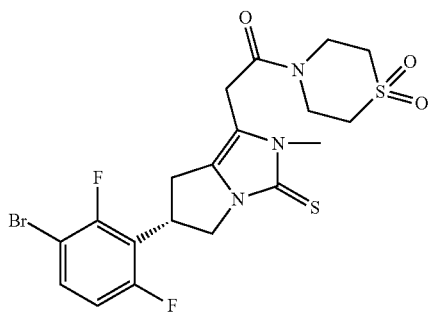 [SMILES: Cn1c(CC(=O)N2CCS(=O)(=O)CC2)c2n(c1=S)C[C@H](c1c(F)ccc(Br)c1F)C2]

Compound was prepared analogous manner to Example 32 from (S)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a white solid.

$^1$H NMR (DMSO$_{d6}$): 7.73 (1H, ddd, J=8.8, 8.1, 5.8 Hz), 7.17 (1H, m), 4.44 (1H, quin, J=8.5 Hz), 4.23 (1H, dd, J=11.2, 9.5 Hz), 3.90 (2H, m), 3.87 (2H, m), 3.85 (2H, s), 3.80 (1H, dd, J=11.6, 7.8 Hz), 3.36 (3H, s), 3.31 (2H, m), 3.28 (1H, dd, J=9.3, 15.8 Hz), 3.13 (2H, m), 2.86 (1H, dd, J=15.9, 8.0 Hz).

$^{13}$C NMR (DMSO$_{d6}$): 167.2, 160.8, 160.8, 159.2, 159.1, 157.6, 157.5, 156.3, 155.9, 155.9, 132.5, 132.4, 128.5, 118.8, 118.7, 118.6, 116, 113.8, 113.8, 113.6, 113.6, 104.1, 104, 103.9, 103.9, 51.1, 51, 49.6, 43.7, 40.2, 34.8, 31.6, 29.2, 28.8.

Example 236: (S)-2-(6-(3-chloro-2,6-difluorophenyl)-2-methyl-3-thioxo-2,5,6,7-tetrahydro-3H-pyrrolo[1,2-c]imidazol-1-yl)-N-isopropylacetamide

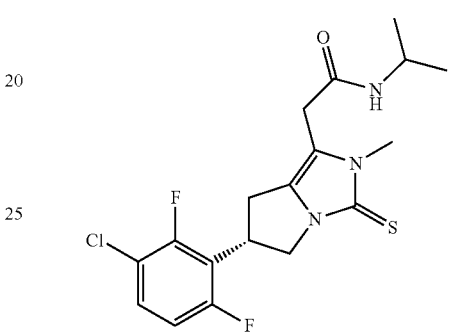

Compound was prepared analogous manner to Example 32 from (S)-1-(1H-imidazol-1-yl)-2-(6-(3-chloro-2,6-difluorophenyl)-3-thioxo-3,5,6,7-tetrahydro-2H-pyrrolo[1,2-c]imidazol-1-yl)ethanone and isolated as an off-white solid.

$^1$H NMR (DMSO$_{d6}$): 7.99 (1H, br d, J=7.5 Hz), 7.62 (1H, m), 7.22 (1H, m), 4.44 (1H, quin, J=8.6 Hz), 4.22 (1H, dd, J=11.3, 9.4 Hz), 3.81 (2H, m), 3.40 (3H, s), 3.38 (2H, m), 3.29 (1H, dd, J=15.8, 9.3 Hz), 2.89 (1H, dd, J=15.8, 8.0 Hz), 1.05 (6H, d, J=6.5 Hz).

$^{13}$C NMR (DMSO$_{d6}$): 166.6, 160.1, 160.1, 158.5, 158.5, 156.6, 156.5, 156.2, 156.1, 154.9, 154.9, 129.7, 129.6, 128.3, 118.8, 118.7, 118.6, 116.6, 116.1, 116, 115.9, 113.2, 113.2, 113.1, 113.1, 49.5, 40.7, 34.7, 31.4, 31.3, 29.2, 22.3, 22.3.

Example 237: (R)-2-(2-methyl-3-thioxo-6-(2,3,6-trifluorophenyl)-2,5,6,7-tetrahydro-3H-pyrrolo[1,2-c]imidazol-1-yl)-1-morpholinoethan-1-one

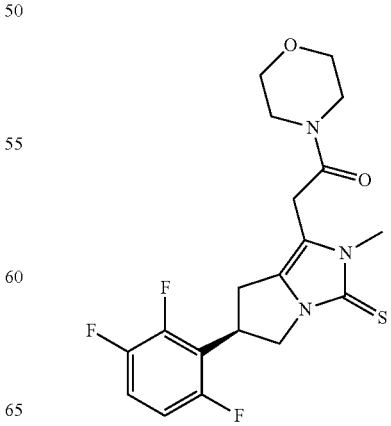

Compound was prepared analogous manner to Example 32 from (R)-1-(H-imidazol-1-yl)-2-(6-(2,3,6-trifluorophenyl)-3-thioxo-3,5,6,7-tetrahydro-2H-pyrrolo[1,2-c]imidazol-1-yl)ethanone and isolated as a beige powder.

¹H NMR (DMSO$_{d6}$): 7.47 (1H, qd, J=9.4, 4.9 Hz), 7.18 (1H, m), 4.44 (1H, quin, J=8.5 Hz), 4.24 (1H, dd, J=9.4, 11.2 Hz), 3.81 (1H, dd, J=11.4, 7.9 Hz), 3.75 (2H, s), 3.59 (2H, m), 3.56 (2H, m), 3.49 (2H, m), 3.45 (2H, m), 3.36 (3H, s), 3.28 (1H, dd, J=15.7, 9.2 Hz), 2.88 (1H, dd, J=15.8, 8.1 Hz).

¹³C NMR (DMSO$_{d6}$): 166.8, 157, 156.9, 156.3, 155.3, 155.3, 149, 149, 147.6, 147.5, 147.4, 147.4, 145.9, 145.9, 145.9, 145.8, 128.2, 118.9, 118.8, 118.8, 118.7, 116.5, 116.4, 116.4, 116.3, 116.3, 112, 112, 112, 111.9, 111.8, 111.8, 66, 66, 49.4, 45.6, 41.7, 34.8, 31.5, 29.2, 28.8.

Example 238: (S)-1-(6-(3-bromo-2,6-difluorophenyl)-2-methyl-3-thioxo-2,5,6,7-tetrahydro-3H-pyrrolo[1,2-c]imidazol-1-yl)-N-(2-(methylsulfonyl)ethyl)cyclopropane-1-carboxamide

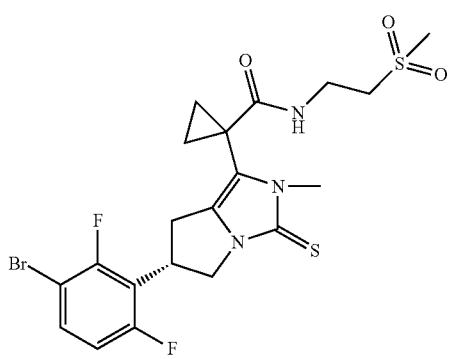 [SMILES: Cn1c(C2(C(=O)NCCS(C)(=O)=O)CC2)c2n(c1=S)C[C@H](c1c(F)ccc(Br)c1F)C2]

Compound was prepared analogous manner to Example 32 from (S)-(1-(6-(3-bromo-2,6-difluorophenyl)-2-methyl-3-thioxo-2,5,6,7-tetrahydro-3H-pyrrolo[1,2-c]imidazol-1-yl)cyclopropyl)(1H-imidazol-1-yl)methanone and isolated as a light cream solid.

¹H NMR (DMSO$_{d6}$): 7.84 (1H, t, J=5.6 Hz), 7.74 (1H, m), 7.18 (1H, m), 4.41 (1H, quin, J=8.9 Hz), 4.21 (1H, dd, J=9.4, 10.9 Hz), 3.81 (1H, dd, J=11.2, 9.1 Hz), 3.45 (2H, q, J=6.5 Hz), 3.37 (3H, s), 3.24 (3H, m), 2.98 (3H, s), 2.98 (1H, dd, J=9.4, 15.4 Hz), 1.43 (1H, m), 1.34 (1H, m), 1.08 (1H, m), 1.04 (1H, m).

¹³C NMR (DMSO$_{d6}$): 170.7, 160.9, 160.9, 159.3, 159.3, 157.7, 157.6, 156.7, 156.1, 156, 132.6, 132.5, 131.2, 119.1, 117.8, 117.7, 117.6, 113.8, 113.7, 113.6, 113.6, 104.1, 104, 103.9, 103.9, 52.7, 49.2, 40.6, 35.1, 33.4, 31.5, 28.9, 19.2, 15.4, 14.8.

Example 239: (R)—N-(1,1-dioxidotetrahydro-2H-thiopyran-4-yl)-2-(2-methyl-3-thioxo-6-(2,3,6-trifluorophenyl)-2,5,6,7-tetrahydro-3H-pyrrolo[1,2-c]imidazol-1-yl)acetamide

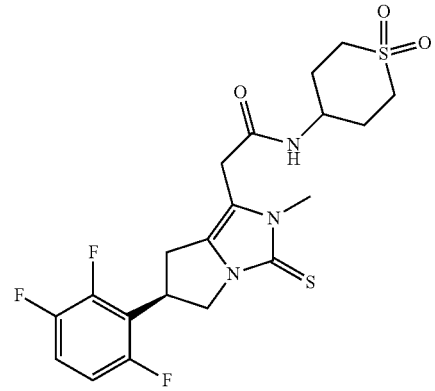 [SMILES: Cn1c(CC(=O)NC2CCS(=O)(=O)CC2)c2n(c1=S)C[C@@H](c1c(F)ccc(F)c1F)C2]

Compound was prepared analogous manner to Example 32 from (R)-1-(H-imidazol-1-yl)-2-(6-(2,3,6-trifluorophenyl)-3-thioxo-3,5,6,7-tetrahydro-2H-pyrrolo[1,2-c]imidazol-1-yl)ethanone and isolated as a beige powder.

¹H NMR (DMSO$_{d6}$): 8.23 (1H, d, J=7.6 Hz), 7.48 (1H, qd, J=9.4, 4.8 Hz), 7.18 (1H, m), 4.43 (1H, quin, J=8.7 Hz), 4.23 (1H, dd, J=9.7, 11.5 Hz), 3.95 (1H, m), 3.81 (1H, dd, J=11.4, 7.9 Hz), 3.44 (2H, m), 3.39 (3H, s), 3.29 (1H, dd, J=15.8, 9.4 Hz), 3.23 (2H, m), 3.06 (2H, m), 2.90 (1H, dd, J=8.3, 15.8 Hz), 2.05 (2H, m), 1.90 (2H, m).

¹³C NMR (DMSO$_{d6}$): 167.2, 157, 156.9, 156.3, 155.4, 155.3, 149.1, 149, 149, 147.6, 147.5, 147.5, 147.4, 147.4, 147.3, 146, 145.9, 145.9, 145.8, 128.5, 118.9, 118.8, 118.7, 118.6, 116.5, 116.5, 116.4, 116.3, 116.3, 112, 112, 112, 111.8, 111.8, 111.8, 111.8, 49.5, 48.4, 44.1, 34.7, 31.5, 31.2, 29.2, 29.1.

Example 240: (S)-2-(6-(3-bromo-2,6-difluorophenyl)-2-methyl-3-thioxo-2,5,6,7-tetrahydro-3H-pyrrolo[1,2-c]imidazol-1-yl)acetamide

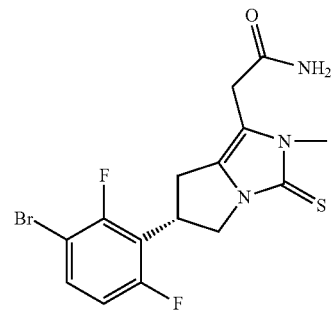 [SMILES: Cn1c(CC(N)=O)c2n(c1=S)C[C@H](c1c(F)ccc(Br)c1F)C2]

Compound was prepared analogous manner to Example 32 from (S)-1-(1H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a brown powder.

¹H NMR (DMSO$_{d6}$): 7.73 (1H, m), 7.51 (1H, br s), 7.17 (1H, m), 7.10 (1H, br s), 4.44 (1H, quin, J=8.7 Hz), 4.21 (1H, dd, J=9.4, 11.4 Hz), 3.80 (1H, dd, J=11.6, 7.9 Hz), 3.40 (2H, m), 3.39 (3H, s), 3.29 (1H, dd, J=15.7, 9.4 Hz), 2.90 (1H, dd, J=15.8, 8.3 Hz).

$^{13}$C NMR (DMSO$_{d6}$): 169.9, 160.8, 160.8, 159.2, 159.1, 157.6, 157.5, 156.2, 155.9, 155.9, 132.5, 132.4, 128.5, 118.7, 118.5, 118.4, 116.5, 113.8, 113.8, 113.6, 113.6, 104.1, 104, 103.9, 103.9, 49.5, 34.8, 31.4, 31, 29.1.

Example 241: 2-((S)-6-(3-bromo-2,6-difluorophenyl)-2-methyl-3-thioxo-2,5,6,7-tetrahydro-3H-pyrrolo[1,2-c]imidazol-1-yl)-1-((S)-2-(hydroxymethyl)pyrrolidin-1-yl)ethan-1-one

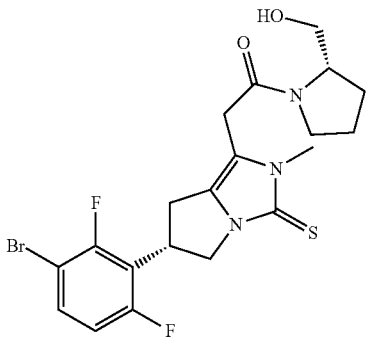 [SMILES: Cn1c(CC(=O)N2CCC[C@H]2CO)c2n(c1=S)C[C@H](c1c(F)ccc(Br)c1F)C2]

Compound was prepared analogous manner to Example 32 from (S)-1-(1-H-imidazol-1-yl)-2-(6-(3-bromo-2,6-difluorophenyl)-3-thioxo-3,5,6,7-tetrahydro-2H-pyrrolo[1,2-c]imidazol-1-yl)ethanone and isolated as a brown powder.

$^1$H NMR (DMSO$_{d6}$): 7.72 (1H, m), 7.16 (1H, t, J=9.4 Hz), 5.04 (0.3H, t, J=5.5 Hz), 4.72 (0.7H, t, J=5.6 Hz), 4.44 (1H, m), 4.22 (1H, dd, J=9.5, 11.1 Hz), 4.02 (0.3H, q, J=6.6 Hz), 3.93 (0.7H, m), 3.79 (1.6H, m), 3.64 (1.4H, m), 3.48 (2.1H, m), 3.43-3.36 (3.9H, m), 3.27 (2H, m), 2.86 (1H, m), 1.85 (4H, m).

$^{13}$C NMR (DMSO$_{d6}$): 166.8, 166.7, 160.8, 160.7, 159.1, 159.1, 157.6, 157.5, 156.1, 156, 155.9, 155.9, 132.5, 132.4, 128.3, 128.2, 118.9, 118.8, 118.8, 118.7, 116.7, 116.2, 113.8, 113.8, 113.6, 113.6, 104.1, 104, 103.9, 103.9, 62.8, 62.8, 60.8, 58.8, 58.7, 49.6, 49.5, 46.9, 45.5, 34.8, 31.6, 31.5, 30.6, 30, 29.2, 27.8, 26.7, 23.5, 21.4.

Example 242: (R)-2-(2-methyl-6-(2,3,5,6-tetrafluorophenyl)-3-thioxo-2,5,6,7-tetrahydro-3H-pyrrolo[1,2-c]imidazol-1-yl)-1-morpholinoethan-1-one

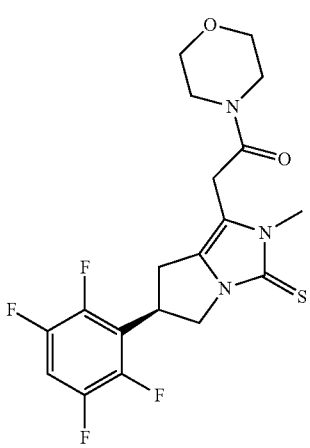 [SMILES: Cn1c(CC(=O)N2CCOCC2)c2n(c1=S)C[C@@H](c1c(F)c(F)cc(F)c1F)C2]

Compound was prepared analogous manner to Example 32 from (S)-1-(1H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone and isolated as an off-white powder.

$^1$H NMR (DMSO$_{d6}$): 7.86 (1H, m), 4.49 (1H, quin, J=8.5 Hz), 4.25 (1H, dd, J=11.6, 9.2 Hz), 3.84 (1H, dd, J=11.6, 7.6 Hz), 3.75 (2H, s), 3.59 (2H, m), 3.55 (2H, m), 3.49 (2H, m), 3.45 (2H, m), 3.36 (3H, s), 3.30 (1H, dd, J=15.9, 9.3 Hz), 2.90 (1H, dd, J=15.8, 7.8 Hz).

$^{13}$C NMR (DMSO$_{d6}$): 166.8, 156.3, 146.4, 146.3, 146.2, 145.4, 145.3, 145.3, 145.3, 145.2, 145.2, 144.8, 144.8, 144.7, 144.6, 144.6, 143.7, 143.7, 143.6, 143.6, 143.6, 128, 120.5, 120.4, 120.3, 116.3, 105.9, 105.7, 105.6, 66, 66, 49.4, 45.6, 41.7, 34.9, 31.5, 29.1, 28.8.

Example 243: 2-((R)-2-methyl-6-(2,3,5,6-tetrafluorophenyl)-3-thioxo-2,5,6,7-tetrahydro-3H-pyrrolo[1,2-c]imidazol-1-yl-N—((R)-tetrahydrofuran-3-yl)acetamide

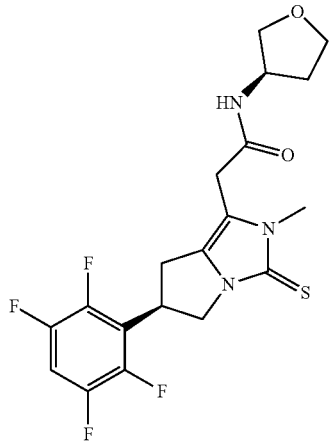 [SMILES: Cn1c(CC(=O)N[C@@H]2CCOC2)c2n(c1=S)C[C@@H](c1c(F)c(F)cc(F)c1F)C2]

Compound was prepared analogous manner to Example 32 from (S)-1-(1H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone and isolated as an off-white powder.

$^1$H NMR (DMSO$_{d6}$): 8.37 (1H, d, J=6.6 Hz), 7.86 (1H, m), 4.48 (1H, quin, J=8.5 Hz), 4.27-4.19 (2H, m), 3.84 (1H, dd, J=11.7, 7.6 Hz), 3.77 (1H, q, J=7.3 Hz), 3.72 (1H, dd, J=8.9, 5.9 Hz), 3.66 (1H, td, J=8.2, 5.6 Hz), 3.46 (1H, br dd, J=8.9, 3.6 Hz), 3.44 (2H, s), 3.40 (3H, s), 3.31 (1H, dd, J=9.4, 16.1 Hz), 2.93 (1H, dd, J=15.8, 7.9 Hz), 2.08 (1H, m), 1.71 (1H, m).

$^{13}$C NMR (DMSO$_{d6}$): 167.6, 156.2, 146.4, 146.4, 146.3, 146.3, 146.2, 145.3, 145.3, 145.3, 145.3, 145.2, 145.2, 144.8, 144.7, 144.6, 144.6, 143.7, 143.7, 143.7, 143.6, 143.6, 143.6, 128.2, 120.5, 120.4, 120.3, 116.4, 105.9, 105.7, 105.6, 72.4, 66.3, 49.8, 49.4, 34.9, 32, 31.5, 31, 29.1.

Example 244: 2-((R)-2-methyl-3-thioxo-6-(2,3,6-trifluorophenyl)-2,5,6,7-tetrahydro-3H-pyrrolo[1,2-c]imidazol-1-yl)-N—((R)-tetrahydrofuran-3-yl)acetamide

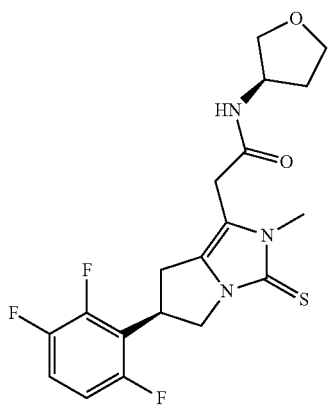 [SMILES: Cn1c(CC(=O)N[C@@H]2CCOC2)c2n(c1=S)C[C@@H](c1c(F)ccc(F)c1F)C2]

Compound was prepared analogous manner to Example 32 from (S)-1-(1H-imidazol-1-yl)-2-(6-(2,3,6-trifluorophenyl)-3-thioxo-3,5,6,7-tetrahydro-2H-pyrrolo[1,2-c]imidazol-1-yl)ethanone and isolated as a light beige powder.

$^1$H NMR (DMSO$_{d6}$): 8.36 (1H, br d, J=6.5 Hz), 7.47 (1H, m), 7.18 (1H, t br), 4.43 (1H, quin, J=8.6 Hz), 4.29-4.16 (2H, m), 3.81 (1H, dd, J=11.6, 8.1 Hz), 3.77 (1H, m), 3.72 (1H, dd, J=9.0, 5.9 Hz), 3.66 (1H, td, J=8.2, 5.6 Hz), 3.46 (1H, dd, J=8.9, 3.6 Hz), 3.43 (2H, s), 3.40 (3H, s), 3.29 (1H, dd, J=15.8, 9.3 Hz), 2.90 (1H, dd, J=15.8, 8.2 Hz), 2.08 (1H, m), 1.71 (1H, m).

$^{13}$C NMR (DMSO$_{d6}$): 167.6, 157, 156.9, 156.9, 156.9, 156.2, 155.3, 155.3, 155.3, 155.3, 149, 147.5, 147.5, 147.4, 145.9, 145.8, 145.8, 128.4, 118.9, 118.8, 118.8, 118.7, 116.5, 116.4, 116.4, 116.3, 112, 112, 111.9, 111.9, 111.8, 111.8, 111.8, 111.8, 72.3, 66.2, 49.8, 49.4, 34.7, 32, 31.5, 31.1, 29.1.

Example 245: (R)-2-(6-(5-chloro-2-fluorophenyl)-2-methyl-3-thioxo-2,5,6,7-tetrahydro-3H-pyrrolo[1,2-c]imidazol-1-yl)-N-cyclopentylacetamide

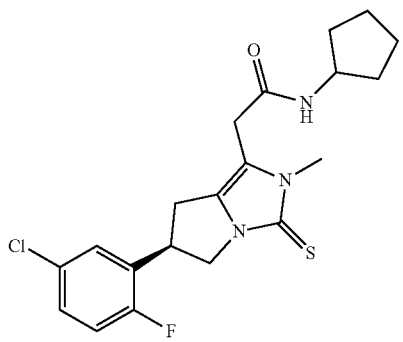 [SMILES: Cn1c(CC(=O)NC2CCCC2)c2n(c1=S)C[C@@H](c1cc(Cl)ccc1F)C2]

Compound was prepared analogous manner to Example 32 from (R)-1-(H-imidazol-1-yl)-2-(6-(5-chloro-2-fluorophenyl)-3-thioxo-3,5,6,7-tetrahydro-2H-pyrrolo[1,2-c]imidazol-1-yl)ethanone and isolated as a beige solid.

$^1$H NMR (DMSO$_{d6}$): 8.08 (1H, br d, J=7.0 Hz), 7.46 (1H, dd, J=6.5, 2.5 Hz), 7.41 (1H, ddd, J=8.7, 4.3, 2.7 Hz), 7.30 (1H, dd, J=9.0, 10.0 Hz), 4.20 (2H, m), 3.98 (1H, m), 3.80 (1H, m), 3.41 (2H, s), 3.39 (3H, s), 3.24 (1H, br dd, J=15.6, 7.5 Hz), 2.89 (1H, br dd, J=15.4, 7.0 Hz), 1.79 (2H, m), 1.62 (2H, m), 1.49 (2H, m), 1.36 (2H, m).

$^{13}$C NMR (DMSO$_{d6}$): 167, 159.8, 158.2, 156.3, 130.3, 130.2, 128.9, 128.9, 128.5, 128.5, 128.5, 128.2, 117.6, 117.4, 116.9, 50.5, 50.1, 39.8, 32.2, 32.2, 31.4, 31.2, 29.5, 23.4.

Example 246: 2-((R)-6-(5-chloro-2-fluorophenyl)-2-methyl-3-thioxo-2,5,6,7-tetrahydro-3H-pyrrolo[1,2-c]imidazol-1-yl)-N—((R)-tetrahydrofuran-3-yl)acetamide

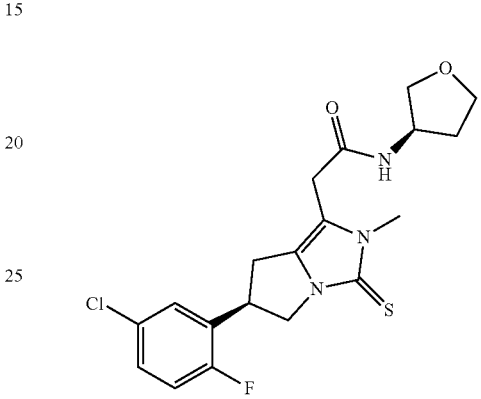

Compound was prepared analogous manner to Example 32 from (R)-1-(1H-imidazol-1-yl)-2-(6-(5-chloro-2-fluorophenyl)-3-thioxo-3,5,6,7-tetrahydro-2H-pyrrolo[1,2-c]imidazol-1-yl)ethanone and isolated as a beige solid.

$^1$H NMR (DMSO$_{d6}$): 8.37 (1H, br d, J=6.6 Hz), 7.46 (1H, dd, J=6.5, 2.6 Hz), 7.41 (1H, ddd, J=8.7, 4.3, 2.8 Hz), 7.30 (1H, dd, J=10.0, 8.9 Hz), 4.28-4.15 (3H, m), 3.78 (2H, m), 3.73 (1H, dd, J=8.9, 5.9 Hz), 3.66 (1H, td, J=8.2, 5.6 Hz), 3.47 (1H, dd, J=8.9, 3.5 Hz), 3.45 (2H, s), 3.40 (3H, s), 3.24 (1H, dd, J=15.5, 7.6 Hz), 2.90 (1H, dd, J=15.4, 7.2 Hz), 2.08 (1H, m), 1.71 (1H, m).

$^{13}$C NMR (DMSO$_{d6}$): 167.6, 159.8, 158.2, 156.4, 130.2, 130.1, 128.9, 128.9, 128.5, 128.5, 128.4, 117.6, 117.4, 116.7, 72.4, 66.3, 50.1, 49.8, 39.8, 32, 31.5, 31, 29.4.

Example 247: 1-((S)-2-(methoxymethyl)pyrrolidin-1-yl)-2-((R)-2-methyl-3-thioxo-6-(2,3,6-trifluorophenyl)-2,5,6,7-tetrahydro-3H-pyrrolo[1,2-c]imidazol-1-yl)ethan-1-one

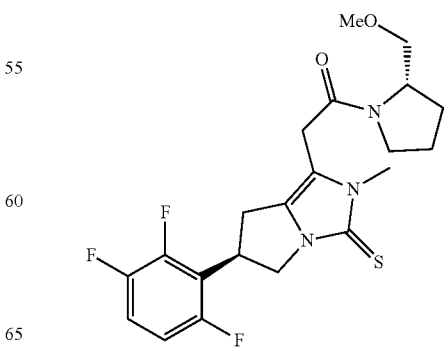

Compound was prepared analogous manner to Example 32 from (R)-1-(1H-imidazol-1-yl)-2-(6-(2,3,6-trifluorophenyl)-3-thioxo-3,5,6,7-tetrahydro-2H-pyrrolo[1,2-c]imidazol-1-yl)ethanone and isolated as a white powder.

¹H NMR (DMSO$_{d6}$): 7.47 (1H, m), 7.18 (1H, m), 4.43 (1H, m), 4.23 (1.35H, m), 4.04 (0.65H, m), 3.82 (1H, m), 3.79 (0.7H, m), 3.65 (1.3H, s), 3.53-3.37 (2.3H, m), 3.36, 3.35 (3H, 2 s), 3.34-3.22 (3.75H, m), 3.21 (1.95H, s), 2.92-2.84 (1H, m), 2.0-1.73 (4H, m).

¹³C NMR (DMSO$_{d6}$): 166.9, 166.6, 156.9, 156.9, 156.9, 156.9, 156.2, 156.1, 155.3, 155.3, 155.3, 149.1, 149, 149, 147.6, 147.5, 147.5, 147.4, 147.4, 147.3, 145.9, 145.9, 145.9, 145.8, 129.5, 128.2, 128.2, 118.9, 118.9, 118.8, 118.7, 116.7, 116.5, 116.4, 116.4, 116.3, 116.3, 112, 112, 112, 111.8, 111.8, 111.8, 111.8, 73.8, 71.6, 58.5, 58.3, 56.3, 56.2, 49.4, 46.8, 45.4, 34.8, 31.5, 30.6, 29.9, 29.1, 29.1, 28.2, 27.2, 23.5, 21.5.

Example 248: 2-((R)-2-methyl-3-thioxo-6-(2,3,6-trifluorophenyl)-2,5,6,7-tetrahydro-3H-pyrrolo[1,2-c]imidazol-1-yl)-1-((S)-2-(trifluoromethyl)pyrrolidin-1-yl)ethan-1-one

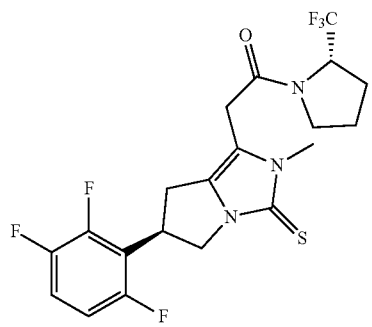 [SMILES: Cn1c(CC(=O)N2CCC[C@H]2C(F)(F)F)c2n(c1=S)C[C@@H](c1c(F)ccc(F)c1F)C2]

Compound was prepared analogous manner to Example 32 from (R)-1-(H-imidazol-1-yl)-2-(6-(2,3,6-trifluorophenyl)-3-thioxo-3,5,6,7-tetrahydro-2H-pyrrolo[1,2-c]imidazol-1-yl)ethanone and isolated as a light cream powder.

¹H NMR (DMSO$_{d6}$): 7.47 (1H, m), 7.18 (1H, m), 5.03 (0.3H, m), 4.76 (0.7H, quin, J=8.3 Hz), 4.43 (1H, quin, J=8.6 Hz), 4.25 (1H, m), 3.94 (0.3H, br d, J=17.5 Hz), 3.83 (1H, dd, J=11.5, 7.8 Hz), 3.79 (1.4H, m), 3.64 (1.7H, m), 3.35 (3H, s), 3.30 (1.6H, m), 2.90 (1H, m), 2.28-1.85 (4H, m).

¹³C NMR (DMSO$_{d6}$): 168.6, 168.1, 156.9, 156.9, 156.4, 156.3, 155.3, 155.3, 149.1, 149, 149, 148.9, 147.6, 147.5, 147.5, 147.4, 147.4, 147.3, 147.3, 145.9, 145.9, 145.9, 145.8, 128.8, 128.6, 128.5, 127, 125.1, 123.2, 118.9, 118.8, 118.7, 116.5, 116.4, 116.4, 116.3, 116, 115.8, 111.9, 111.8, 56.6, 56.4, 56.2, 56, 49.5, 47, 46.5, 34.8, 34.7, 31.4, 31.4, 30.4, 29.6, 29.2, 26.2, 24.8, 23.6, 21.3.

Example 249: (S)-2-(6-(3-chloro-2,6-difluorophenyl)-2-methyl-3-thioxo-2,5,6,7-tetrahydro-3H-pyrrolo[1,2-c]imidazol-1-yl)acetamide

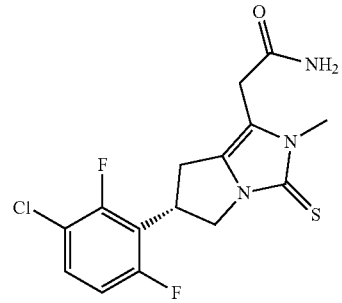 [SMILES: Cn1c(CC(N)=O)c2n(c1=S)C[C@H](c1c(F)ccc(Cl)c1F)C2]

Compound was prepared analogous manner to Example 32 from (R)-1-(H-imidazol-1-yl)-2-(6-(3-chloro-2,6-difluorophenyl)-3-thioxo-3,5,6,7-tetrahydro-2H-pyrrolo[1,2-c]imidazol-1-yl)ethanone and isolated as an off-white solid.

¹H NMR (DMSO$_{d6}$): 7.62 (1H, m), 7.51 (1H, br s), 7.22 (1H, m), 7.10 (1H, br s), 4.44 (1H, quin, J=8.6 Hz), 4.22 (1H, dd, J=9.3, 11.3 Hz), 3.81 (1H, dd, J=11.5, 8.0 Hz), 3.41 (2H, m), 3.40 (3H, s), 3.30 (1H, dd, J=15.9, 9.3 Hz), 2.91 (1H, dd, J=15.8, 8.3 Hz).

¹³C NMR (DMSO$_{d6}$): 169.9, 160.2, 160.1, 158.5, 158.5, 156.6, 156.6, 156.2, 155, 154.9, 129.7, 129.7, 128.5, 118.7, 118.6, 118.4, 116.5, 116.1, 116.1, 116, 115.9, 113.3, 113.2, 113.1, 113.1, 49.4, 34.8, 31.4, 31, 29.1.

Example 250: 2-((S)-6-(3-chloro-2,6-difluorophenyl)-2-methyl-3-thioxo-2,5,6,7-tetrahydro-3H-pyrrolo[1,2-c]imidazol-1-yl)-N—((R)-tetrahydrofuran-3-yl)acetamide

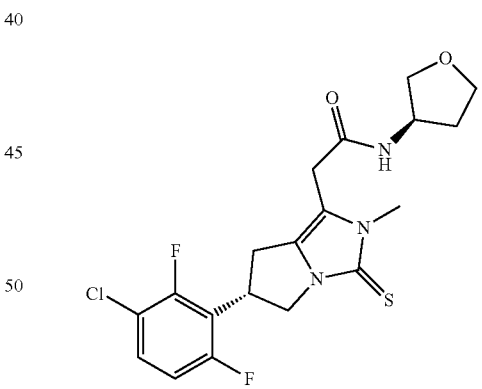

Compound was prepared analogous manner to Example 32 from (R)-1-(H-imidazol-1-yl)-2-(6-(3-chloro-2,6-difluorophenyl)-3-thioxo-3,5,6,7-tetrahydro-2H-pyrrolo[1,2-c]imidazol-1-yl)ethanone and isolated as an off-white solid.

¹H NMR (DMSO$_{d6}$): 8.37 (1H, br d, J=6.6 Hz), 7.61 (1H, m), 7.21 (1H, m), 4.44 (1H, quin, J=8.5 Hz), 4.22 (2H, m), 3.78 (2H, m), 3.72 (1H, dd, J=8.9, 6.0 Hz), 3.66 (1H, td, J=8.2, 5.6 Hz), 3.45 (1H, dd, J=9.0, 3.4 Hz), 3.43 (2H, m), 3.40 (3H, s), 3.29 (1H, dd, J=15.8, 9.4 Hz), 2.89 (1H, dd, J=15.8, 8.1 Hz), 2.07 (1H, dq, J=12.7, 7.6 Hz), 1.71 (1H, m).

¹³C NMR (DMSO$_{d6}$): 167.6, 160.2, 160.1, 158.5, 158.5, 156.6, 156.5, 156.2, 154.9, 154.9, 129.7, 129.7, 128.4, 118.8, 118.7, 118.6, 116.4, 116.1, 116, 115.9, 115.9, 113.3, 113.2, 113.1, 113.1, 72.4, 66.3, 49.8, 49.5, 34.7, 32, 31.5, 31.1, 29.2.

Example 251: 2-((S)-6-(5-chloro-2-fluorophenyl)-2-methyl-3-thioxo-2,5,6,7-tetrahydro-3H-pyrrolo[1,2-c]imidazol-1-yl)-N—((R)-tetrahydrofuran-3-yl)acetamide

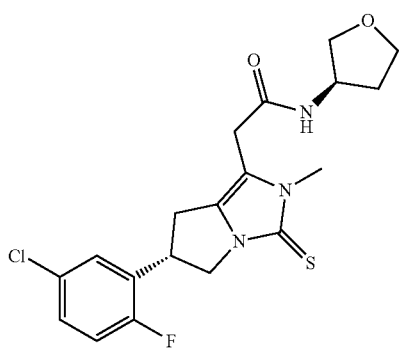 [SMILES: Cn1c(CC(=O)N[C@@H]2CCOC2)c2n(c1=S)C[C@H](c1cc(Cl)ccc1F)C2]

Compound was prepared analogous manner to Example 32 from (R)-1-(H-imidazol-1-yl)-2-(6-(5-chloro-2-fluorophenyl)-3-thioxo-3,5,6,7-tetrahydro-2H-pyrrolo[1,2-c]imidazol-1-yl)ethanone and isolated as an off-white solid.

$^1$H NMR (DMSO$_{d6}$): 8.37 (1H, d, J=6.6 Hz), 7.47 (1H, dd, J=6.5, 2.7 Hz), 7.41 (1H, ddd, J=8.8, 4.4, 2.7 Hz), 7.30 (1H, dd, J=10.1, 8.8 Hz), 4.22 (3H, m), 3.79 (2H, m), 3.73 (1H, dd, J=8.9, 5.9 Hz), 3.66 (1H, td, J=8.2, 5.6 Hz), 3.46 (2H, m), 3.46 (1H, dd, J=3.6, 9.0 Hz), 3.40 (3H, s), 3.24 (1H, dd, J=15.6, 7.6 Hz), 2.90 (1H, dd, J=15.5, 7.3 Hz), 2.08 (1H, m), 1.72 (1H, m).

$^{13}$C NMR (DMSO$_{d6}$): 167.6, 159.8, 158.2, 156.4, 130.2, 130.1, 128.9, 128.9, 128.5, 128.5, 128.5, 128.3, 117.6, 117.4, 116.7, 72.4, 66.3, 50.1, 49.8, 39.8, 32, 31.5, 31, 29.4.

Example 252: 2-((S)-6-(3-bromo-2,6-difluorophenyl)-2-methyl-3-thioxo-2,5,6,7-tetrahydro-3H-pyrrolo[1,2-c]imidazol-1-yl)-N-methyl-N-(tetrahydrofuran-3-yl)acetamide

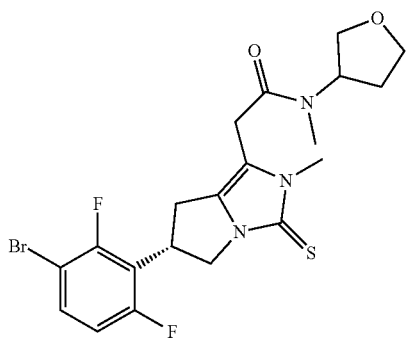 [SMILES: CN(C(=O)Cc1c2n(c(=S)n1C)C[C@H](c1c(F)ccc(Br)c1F)C2)C1CCOC1]

Compound was prepared analogous manner to Example 34 from (S)-2-(6-(3-bromo-2,6-difluorophenyl)-3-thioxo-2,5,6,7-tetrahydro-3H-pyrrolo[1,2-c]imidazol-1-yl)acetic acid (Example 12) and isolated as a yellow powder.

$^1$H NMR (DMSO$_{d6}$): 7.72 (1H, m), 7.16 (1H, m), 5.09 (0.6H, m), 4.65 (0.4H, m), 4.44 (1H, quin, J=8.5 Hz), 4.22 (1H, dd, J=9.7, 11.2 Hz), 3.91 (1H, m), 3.81 (1H, m), 3.80 (1H, dd, J=7.7, 11.6 Hz), 3.71 (1H, m), 3.69 (1H, m), 3.62 (1H, m), 3.56 (1H, m), 3.34 (3H, m), 3.26 (1H, m), 2.93 (1.8H, m), 2.84 (1H, m), 2.74 (1.2H, s), 2.25-2.04 (1H, m), 1.90-1.72 (1H, m).

$^{13}$C NMR (DMSO$_{d6}$): 168.2, 167.6, 160.8, 160.7, 159.1, 159.1, 157.5, 157.5, 156.2, 156.2, 155.9, 155.8, 132.5, 132.4, 128.3, 128.1, 118.9, 118.8, 118.6, 116.5, 116.4, 113.8, 113.8, 113.6, 113.6, 104.1, 104, 103.9, 103.9, 69.4, 69.3, 69.3, 69.2, 67.1, 67, 56.5, 56.5, 53, 49.5, 34.8, 31.5, 31.5, 31.2, 29.9, 29.8, 29.7, 29.7, 29.4, 29.4, 29.3, 29.2, 29.2, 27.6.

Example 253: (S)-2-(6-(3-bromo-2,6-difluorophenyl)-2-methyl-3-thioxo-2,5,6,7-tetrahydro-3H-pyrrolo[1,2-c]imidazol-1-yl)-N-(cyanomethyl)acetamide

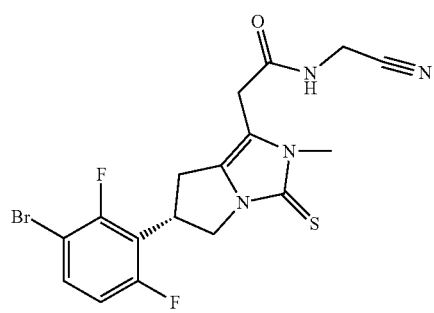 [SMILES: Cn1c(CC(=O)NCC#N)c2n(c1=S)C[C@H](c1c(F)ccc(Br)c1F)C2]

Compound was prepared analogous manner to Example 34 from (S)-2-(6-(3-bromo-2,6-difluorophenyl)-3-thioxo-2,5,6,7-tetrahydro-3H-pyrrolo[1,2-c]imidazol-1-yl)acetic acid (Example 12) and isolated as a cream powder.

$^1$H NMR (DMSO$_{d6}$): 8.78 (1H, t, J=5.5 Hz), 7.72 (1H, m), 7.16 (1H, m), 4.44 (1H, quin, J=8.6 Hz), 4.23 (1H, dd, J=9.7, 11.2 Hz), 4.16 (2H, d, J=5.6 Hz), 3.81 (1H, dd, J=11.4, 8.1 Hz), 3.55 (2H, m), 3.39 (3H, s), 3.29 (1H, dd, J=15.8, 9.3 Hz), 2.90 (1H, dd, J=15.8, 8.2 Hz).

$^{13}$C NMR (DMSO$_{d6}$): 168.6, 160.8, 160.8, 159.2, 159.1, 157.6, 157.5, 156.5, 155.9, 155.9, 132.5, 132.4, 128.9, 118.6, 118.5, 118.4, 117.5, 115.5, 113.8, 113.8, 113.6, 113.6, 104.1, 104.1, 103.9, 103.9, 49.5, 34.8, 31.4, 30.8, 29.1, 27.3.

Example 254: (R)—N-(1-cyanocyclopropyl)-2-(2-methyl-3-thioxo-6-(2,3,6-trifluorophenyl)-2,5,6,7-tetrahydro-3H-pyrrolo[1,2-c]imidazol-1-yl)acetamide

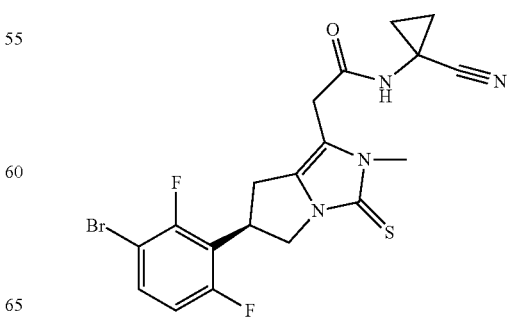

Compound was prepared analogous manner to Example 34 from (R)-2-(2-methyl-3-thioxo-6-(2,3,6-trifluorophenyl)-2,5,6,7-tetrahydro-3H-pyrrolo[1,2-c]imidazol-1-yl)acetic acid and isolated as a cream powder.

¹H NMR (DMSO$_{d6}$): 9.03 (1H, s), 7.48 (1H, m), 7.18 (1H, br t, J=9.4 Hz), 4.43 (1H, quin, J=8.6 Hz), 4.24 (1H, dd, J=9.5, 11.3 Hz), 3.82 (1H, dd, J=11.4, 8.1 Hz), 3.48 (2H, m), 3.37 (3H, s), 3.30 (1H, dd, J=9.2, 11.9 Hz), 2.92 (1H, dd, J=15.8, 8.3 Hz), 1.48 (2H, m), 1.14 (2H, m).

¹³C NMR (DMSO$_{d6}$): 169.3, 156.9, 156.5, 155.3, 149, 149, 148.9, 147.5, 147.5, 147.4, 147.4, 147.4, 147.3, 145.9, 145.9, 145.8, 128.8, 120.6, 118.8, 118.7, 118.7, 118.6, 116.5, 116.5, 116.4, 116.3, 115.5, 112, 112, 112, 111.9, 111.8, 111.8, 111.8, 111.8, 49.5, 34.7, 31.4, 30.8, 29.1, 19.9, 15.6, 15.6.

Example 255: 2-((R)-2-methyl-3-thioxo-6-(2,3,6-trifluorophenyl)-2,5,6,7-tetrahydro-3H-pyrrolo[1,2-c]imidazol-1-yl)-N—((R)-tetrahydro-2H-pyran-3-yl)acetamide

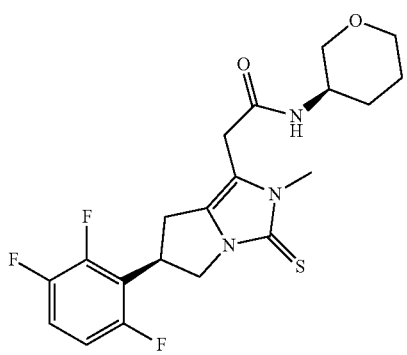 [SMILES: Cn1c(CC(=O)N[C@@H]2CCCOC2)c2n(c1=S)C[C@@H](c1c(F)ccc(F)c1F)C2]

Compound was prepared analogous manner to Example 34 from (R)-2-(2-methyl-3-thioxo-6-(2,3,6-trifluorophenyl)-2,5,6,7-tetrahydro-3H-pyrrolo[1,2-c]imidazol-1-yl)acetic acid and isolated as a white powder.

¹H NMR (DMSO$_{d6}$): 8.12 (1H, br d, J=7.3 Hz), 7.47 (1H, m), 7.18 (1H, br t, J=9.6 Hz), 4.43 (1H, quin, J=8.6 Hz), 4.23 (1H, dd, J=9.6, 11.3 Hz), 3.81 (1H, dd, J=11.5, 8.0 Hz), 3.72-3.59 (3H, m), 3.45 (2H, s), 3.39 (3H, s), 3.36 (1H, m), 3.29 (1H, dd, J=15.8, 9.3 Hz), 3.12 (1H, m), 2.90 (1H, dd, J=15.7, 8.2 Hz), 1.80 (1H, m), 1.66 (1H, m), 1.46 (2H, m).

¹³C NMR (DMSO$_{d6}$): 167.3, 157, 156.9, 156.9, 156.2, 155.3, 155.3, 149.1, 149, 149, 148.9, 147.5, 147.5, 147.5, 147.4, 147.4, 147.4, 147.3, 145.9, 145.9, 145.9, 145.8, 128.3, 118.9, 118.8, 118.8, 118.7, 116.5, 116.4, 116.4, 116.3, 111.9, 111.8, 70.1, 67, 49.4, 45.1, 34.7, 31.5, 31.2, 29.1, 28.5, 23.8.

Example 256: (S)-6-(3-bromo-2,6-difluorophenyl)-2-methyl-1-(2-(((R)-tetrahydrofuran-3-yl)amino)ethyl)-2,5,6,7-tetrahydro-3H-pyrrolo[1,2-c]imidazole-3-thione hydrochloride

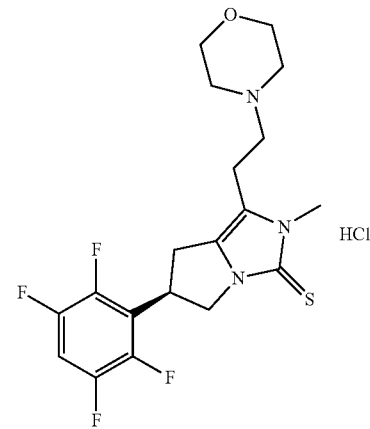 [SMILES: Cn1c(CCN2CCOCC2)c2n(c1=S)C[C@@H](c1c(F)c(F)cc(F)c1F)C2 ; Cl]

Compound was prepared analogous manner to Example 35 from 1-((S)-6-(3-bromo-2,6-difluorophenyl)-2-methyl-3-thioxo-2,5,6,7-tetrahydro-3H-pyrrolo[1,2-c]imidazol-1-yl)-N—((R)-tetrahydrofuran-3-yl)acetamide (Example 234) and isolated as a light cream powder.

¹H NMR (DMSO$_{d6}$): 9.20 (2H, m), 7.74 (1H, m), 7.18 (1H, m), 4.44 (1H, quin, J=8.7 Hz), 4.22 (1H, dd, J=9.5, 11.1 Hz), 3.91 (2H, m), 3.84 (1H, s br), 3.80 (1H, dd, J=8.1, 11.4 Hz), 3.75 (1H, dd, J=6.0, 10.2 Hz), 3.64 (1H, m), 3.47 (3H, s), 3.40 (1H, dd, J=9.6, 15.9 Hz), 3.13 (2H, br s), 3.00 (1H, dd, J=15.7, 8.4 Hz), 2.94 (2H, t, J=7.6 Hz), 2.20 (1H, m), 2.03 (1H, m).

¹³C NMR (DMSO$_{d6}$): 160.8, 160.8, 159.2, 159.1, 157.6, 157.6, 156.6, 156, 155.9, 132.6, 132.5, 128.5, 118.5, 118.4, 118.3, 116.5, 113.8, 113.8, 113.7, 113.6, 104.1, 104.1, 104, 104, 68.9, 66.4, 57.5, 49.4, 43.5, 34.9, 31.4, 29.2, 28.9, 21.1.

Example 257: (R)-2-methyl-1-(2-morpholinoethyl)-6-(2,3,5,6-tetrafluorophenyl)-2,5,6,7-tetrahydro-3H-pyrrolo[1,2-c]imidazole-3-thione Hydrochloride Compound was prepared analogous manner to Example 35 from (R)-2-(2-methyl-6-(2,3,5,6-tetrafluorophenyl)-3-thioxo-2,5,6,7-tetrahydro-3H-pyrrolo[1,2-c]imidazol-1-yl)-1-morpholinoethan-1-one (Example 242) and isolated as a pale yellow powder.

¹H NMR (DMSO_{d6}): 1.61 (1H, br s), 7.88 (1H, m), 4.51 (1H, quin, J=8.4 Hz), 4.24 (1H, dd, J=11.3, 9.5 Hz), 3.97 (2H, br d, J=11.7 Hz), 3.85 (1H, dd, J=7.7, 11.7 Hz), 3.82 (2H, m), 3.48 (3H, s), 3.47 (2H, m), 3.43 (1H, dd, J=15.6, 8.6 Hz), 3.30 (2H, m), 3.13-2.98 (5H, m).
¹³C NMR (DMSO_{d6}): 156.7, 146.4, 146.4, 146.3, 146.3, 146.3, 146.3, 146.2, 145.3, 145.3, 145.3, 145.2, 144.8, 144.8, 144.7, 144.7, 144.6, 144.6, 143.7, 143.7, 143.7, 143.6, 143.6, 143.6, 143.6, 127.9, 120.4, 120.3, 120.2, 116.6, 105.9, 105.8, 105.6, 63.1, 52.9, 50.8, 49.3, 34.9, 31.4, 29.2, 18.6.

Example 258: (S)-2-amino-3-(2-((R)-6-(2,3,5,6-tetrafluorophenyl)-3-thioxo-2,5,6,7-tetrahydro-3H-pyrrolo[1,2-c]imidazol-1-yl)acetamido)propanoic Acid

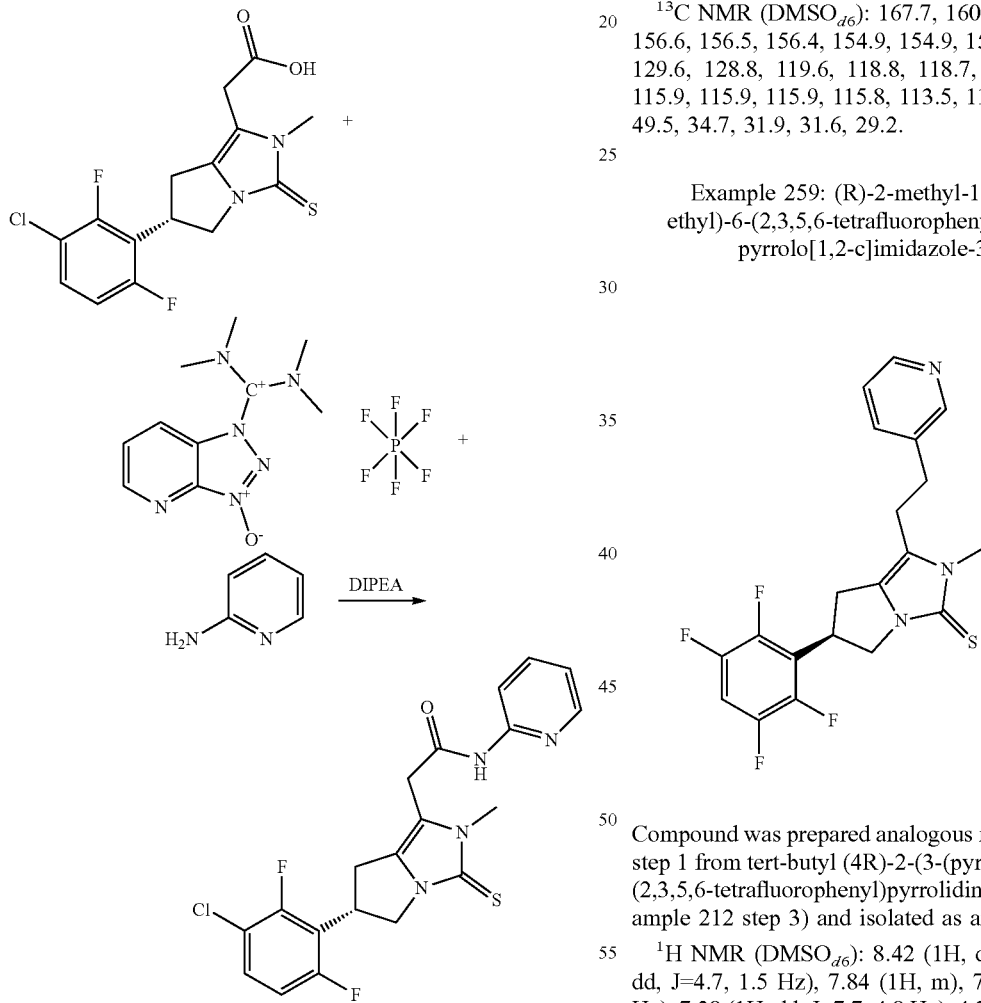

To a solution of pyridin-2-amine (28.9 mg, 0.307 mmol) in N,N-dimethyl formamide (0.93 mL) was added N-ethyl-N-isopropylpropan-2-amine (0.10 mL, 0.557 mmol). The reaction mixture was cooled in an ice bath and 1-(bis(dimethylamino)methylene)-1H-[1,2,3]triazolo[4,5-b]pyridine-1-ium 3-oxide hexafluorophosphate(V) (HATU) (117 mg, 0.307 mmol) and (S)-2-(6-(3-chloro-2,6-difluorophenyl)-2-methyl-3-thioxo-3,5,6,7-tetrahydro-2H-pyrrolo[1,2-c]imidazol-1-yl)acetic acid (100 mg, 0.279 mmol) were added in one portion. The reaction mixture was allowed to warm up to room temperature and stirred for 2 h. The reaction mixture was then transferred to a separatory funnel, diluted with 30 mL of water and 40 mL of ethyl acetate. The aqueous layer was extracted twice with 40 mL of ethyl acetate. The organic layer was washed with brine, dried over MgSO_4, filtered and evaporated to dryness. Chromatography afforded (S)-2-(6-(3-chloro-2,6-difluorophenyl)-2-methyl-3-thioxo-3,5,6,7-tetrahydro-2H-pyrrolo[1,2-c]imidazol-1-yl)-N-(pyridin-2-yl)acetamide as an off-white solid.

Yield: 31 mg, 25%.

¹H NMR (DMSO_{d6}): 10.76 (1H, s), 8.32 (1H, dd, J=4.8, 1.0 Hz), 8.04 (1H, br d, J=8.1 Hz), 7.78 (1H, m), 7.61 (1H, m), 7.21 (1H, m), 7.11 (1H, dd, J=7.0, 5.2 Hz), 4.46 (1H, quin, J=8.5 Hz), 4.24 (1H, dd, J=9.7, 11.1 Hz), 3.81 (1H, dd, J=7.9, 11.7 Hz), 3.79 (2H, m), 3.44 (3H, m), 3.31 (1H, m), 2.92 (1H, dd, J=16.0, 8.1 Hz).
¹³C NMR (DMSO_{d6}): 167.7, 160.1, 160.1, 158.5, 158.4, 156.6, 156.5, 156.4, 154.9, 154.9, 151.7, 148, 138.2, 129.7, 129.6, 128.8, 119.6, 118.8, 118.7, 118.5, 116, 116, 116, 115.9, 115.9, 115.9, 115.8, 113.5, 113.2, 113.2, 113.1, 113, 49.5, 34.7, 31.9, 31.6, 29.2.

Example 259: (R)-2-methyl-1-(2-(pyridin-3-yl)ethyl)-6-(2,3,5,6-tetrafluorophenyl)-6,7-dihydro-2H-pyrrolo[1,2-c]imidazole-3(5H)-thione

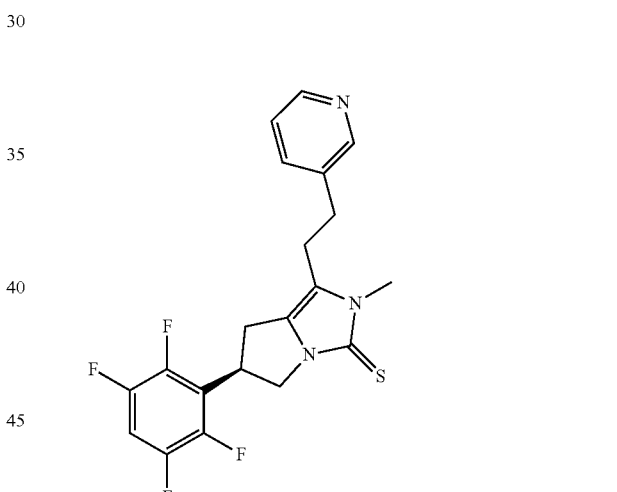

Compound was prepared analogous manner to Example 229 step 1 from tert-butyl (4R)-2-(3-(pyridin-3-yl)propanoyl)-4-(2,3,5,6-tetrafluorophenyl)pyrrolidine-1-carboxylate (Example 212 step 3) and isolated as an off-white powder.

¹H NMR (DMSO_{d6}): 8.42 (1H, d, J=1.8 Hz), 8.38 (1H, dd, J=4.7, 1.5 Hz), 7.84 (1H, m), 7.62 (1H, dt, J=7.8, 1.8 Hz), 7.28 (1H, dd, J=7.7, 4.8 Hz), 4.38 (1H, quin, J=8.4 Hz), 4.19 (1H, br dd, J=11.4, 9.2 Hz), 3.79 (1H, dd, J=11.7, 7.4 Hz), 3.45 (3H, s), 3.13 (1H, dd, J=15.7, 9.4 Hz), 2.86 (4H, m), 2.67 (1H, dd, J=15.6, 7.6 Hz).
¹³C NMR (DMSO_{d6}): 156.1, 149.7, 147.4, 146.4, 146.3, 146.2, 145.3, 145.2, 145.2, 145.2, 145.2, 145.1, 145.1, 145.1, 144.8, 144.7, 144.7, 144.7, 144.6, 144.6, 143.6, 143.6, 143.6, 143.6, 143.5, 143.5, 143.5, 136, 135.9, 127.1, 123.3, 120.4, 120.3, 120.2, 120.2, 105.8, 105.7, 105.5, 49.1, 34.9, 31.2, 30.1, 29.1, 25.2.

Example 260: (R)-3-(2-methyl-6-(2,3,5,6-tetrafluorophenyl)-3-thioxo-2,5,6,7-tetrahydro-3H-pyrrolo[1,2-c]imidazol-1-yl)propanoic Acid

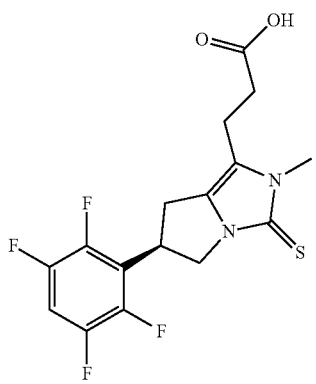 [SMILES: Cn1c(CCC(=O)O)c2n(c1=S)C[C@@H](c1c(F)c(F)cc(F)c1F)C2]

Compound was prepared analogous manner to Example 229 step 1 from ethyl oxoacetate and (4R)-tert-butyl 2-(2-(dimethoxyphosphoryl)acetyl)-4-(2,3,5,6-tetrafluorophenyl)pyrrolidine-1-carboxylate (Example 212 step 3) and isolated as an off-white powder.

$^1$H NMR (DMSO$_{d6}$): 12.33 (1H, br s), 7.86 (1H, m), 4.46 (1H, quin, J=8.5 Hz), 4.22 (1H, dd, J=11.4, 9.3 Hz), 3.81 (1H, dd, J=11.7, 7.7 Hz), 3.44 (3H, s), 3.38 (1H, dd, J=9.4, 15.2 Hz), 2.99 (1H, dd, J=15.7, 7.9 Hz), 2.73 (2H, t, J=7.3 Hz), 2.54 (2H, t, J=7.3 Hz).

$^{13}$C NMR (DMSO$_{d6}$): 173.4, 156, 146.4, 146.3, 146.3, 145.3, 145.3, 145.3, 145.2, 145.2, 145.2, 144.8, 144.8, 144.7, 144.7, 144.7, 144.6, 144.6, 143.7, 143.7, 143.7, 143.6, 143.6, 143.6, 143.6, 143.5, 126.8, 120.5, 120.4, 120.4, 120.3, 105.9, 105.7, 105.6, 49.1, 34.9, 31.4, 31.1, 29.3, 19.5.

Example 261: (R)-3-(2-methyl-6-(2,3,5,6-tetrafluorophenyl)-3-thioxo-2,5,6,7-tetrahydro-3H-pyrrolo[1,2-c]imidazol-1-yl)-1-(pyrrolidin-1-yl)propan-1-one

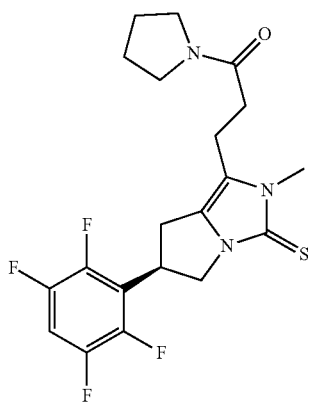 [SMILES: Cn1c(CCC(=O)N2CCCC2)c2n(c1=S)C[C@@H](c1c(F)c(F)cc(F)c1F)C2]

Compound was prepared analogous manner to Example 32 from (R)-1-(H-imidazol-1-yl)-3-(6-(2,3,5,6-tetrafluorophenyl)-3-thioxo-2,5,6,7-tetrahydro-3H-pyrrolo[1,2-c]imidazol-1-yl)propan-1-one and isolated as an off-white powder.

$^1$H NMR (DMSO$_{d6}$): 7.86 (1H, m), 4.45 (1H, quin, J=8.5 Hz), 4.22 (1H, dd, J=11.2, 9.5 Hz), 3.80 (1H, dd, J=11.6, 7.8 Hz), 3.45 (3H, s), 3.37 (3H, m), 3.25 (2H, t, J=6.9 Hz), 3.00 (1H, br dd, J=15.7, 7.9 Hz), 2.72 (2H, m), 2.53 (2H, t, J=7.7 Hz), 1.83 (2H, quin, J=6.7 Hz), 1.74 (2H, m).

$^{13}$C NMR (DMSO$_{d6}$): 168.9, 155.8, 146.4, 146.4, 146.3, 146.3, 146.3, 146.3, 146.2, 145.3, 145.3, 145.3, 145.2, 145.2, 145.2, 144.8, 144.8, 144.7, 144.7, 144.6, 143.7, 143.7, 143.7, 143.6, 143.6, 143.6, 143.6, 143.6, 126.7, 120.9, 120.6, 120.4, 120.3, 105.8, 105.7, 105.5, 49.1, 45.7, 45.3, 34.9, 31.5, 31.1, 29.2, 25.5, 23.9, 19.3.

Example 262: (S)-3-(6-(3-chloro-2,6-difluorophenyl)-2-methyl-3-thioxo-2,5,6,7-tetrahydro-3H-pyrrolo[1,2-c]imidazol-1-yl)propanamide

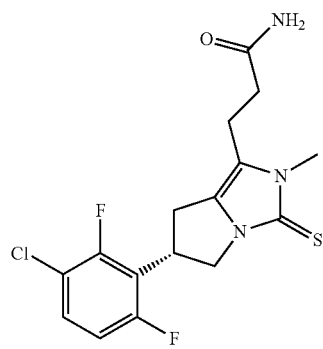 [SMILES: Cn1c(CCC(N)=O)c2n(c1=S)C[C@H](c1c(F)ccc(Cl)c1F)C2]

Compound was prepared analogous manner to Example 32 from (S)-1-(1H-imidazol-1-yl)-3-(6-(3-chloro-2,6-difluorophenyl)-3-thioxo-2,5,6,7-tetrahydro-3H-pyrrolo[1,2-c]imidazol-1-yl)propan-1-one and isolated as an off-white solid.

$^1$H NMR (DMSO$_{d6}$): 7.62 (1H, m), 7.31 (1H, br s), 7.21 (1H, m), 6.86 (1H, br s), 4.42 (1H, quin, J=8.7 Hz), 4.20 (1H, dd, J=9.3, 11.1 Hz), 3.77 (1H, dd, J=11.6, 7.9 Hz), 3.44 (3H, s), 3.32 (1H, m), 2.94 (1H, dd, J=15.7, 8.2 Hz), 2.71 (2H, t, J=7.3 Hz), 2.35 (2H, t, J=7.4 Hz).

$^{13}$C NMR (DMSO$_{d6}$): 172.8, 160.1, 160.1, 158.5, 158.5, 156.6, 156.5, 155.8, 155, 154.9, 129.7, 129.7, 126.8, 120.8, 118.8, 118.7, 118.6, 116.1, 116.1, 116, 115.9, 113.3, 113.2, 113.1, 113.1, 49.2, 34.8, 32.5, 31.1, 29.4, 19.8.

Example 263: (R)-3-(6-(2,6-difluorophenyl)-2-methyl-3-thioxo-2,5,6,7-tetrahydro-3H-pyrrolo[1,2-c]imidazol-1-yl)propanamide

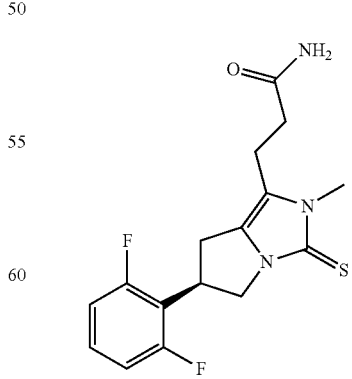

Compound was prepared analogous manner to Example 32 from (R)-1-(H-imidazol-1-yl)-3-(6-(2,6-difluorophenyl)-3- thioxo-2,5,6,7-tetrahydro-3H-pyrrolo[1,2-c]imidazol-1-yl)propan-1-one and isolated as an off-white solid.

¹H NMR (DMSO_{d6}): 7.41 (1H, m), 7.31 (1H, br s), 7.14 (1H, m), 6.87 (1H, br s), 4.39 (1H, quin, J=8.8 Hz), 4.19 (1H, dd, J=10.6, 9.9 Hz), 3.75 (1H, dd, J=11.3, 8.4 Hz), 3.44 (3H, s), 3.31 (1H, br dd, J=15.5, 9.3 Hz), 2.93 (1H, dd, J=15.6, 8.7 Hz), 2.71 (2H, t, J=7.3 Hz), 2.36 (2H, t, J=7.3 Hz).

¹³C NMR (DMSO_{d6}): 172.9, 161.6, 161.6, 160, 159.9, 155.8, 129.8, 129.8, 129.7, 126.9, 120.8, 116.6, 116.5, 116.3, 112.3, 112.2, 112.1, 112.1, 49.2, 34.5, 32.5, 31.1, 29.6, 19.8.

Example 264: (R)-3-(6-(2,6-difluorophenyl)-2-methyl-3-thioxo-2,5,6,7-tetrahydro-3H-pyrrolo[1,2-c]imidazol-1-yl)-1-(pyrrolidin-1-yl)propan-1-one

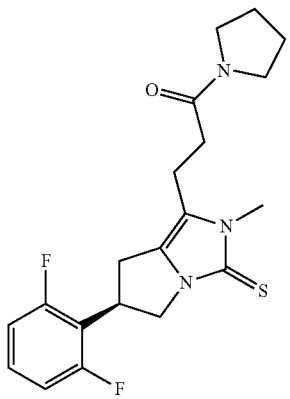 [SMILES: Cn1c(CCC(=O)N2CCCC2)c2n(c1=S)C[C@@H](c1c(F)cccc1F)C2]

Compound was prepared analogous manner to Example 32 from (R)-1-(H-imidazol-1-yl)-3-(6-(2,6-difluorophenyl)-3-thioxo-2,5,6,7-tetrahydro-3H-pyrrolo[1,2-c]imidazol-1-yl)propan-1-one and isolated as an off-white solid.

¹H NMR (DMSO_{d6}): 7.41 (1H, m), 7.14 (2H, m), 4.38 (1H, quin, J=8.8 Hz), 4.19 (1H, m), 3.75 (1H, dd, J=11.2, 8.4 Hz), 3.45 (3H, s), 3.37 (2H, m), 3.32 (1H, m), 3.25 (2H, t, J=6.8 Hz), 2.95 (1H, dd, J=15.6, 8.7 Hz), 2.72 (2H, t, J=7.7 Hz), 2.54 (2H, t, J=7.5 Hz), 1.83 (2H, m), 1.74 (2H, m).

¹³C NMR (DMSO_{d6}): 168.9, 161.6, 161.6, 160, 159.9, 155.8, 129.8, 129.7, 129.7, 127, 120.9, 116.6, 116.5, 116.3, 112.2, 112.2, 112.1, 49.2, 45.7, 45.3, 34.4, 31.5, 31.1, 29.4, 25.5, 23.9, 19.3.

Example 265: 3-((R)-2-methyl-3-thioxo-6-(2,3,6-trifluorophenyl)-2,5,6,7-tetrahydro-3H-pyrrolo[1,2-c]imidazol-1-yl)-N—((R)-tetrahydrofuran-3-yl)propanamide

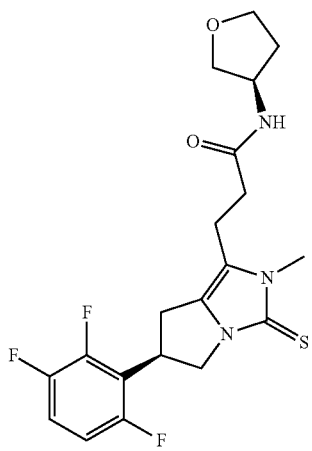 [SMILES: Cn1c(CCC(=O)N[C@@H]2CCOC2)c2n(c1=S)C[C@@H](c1c(F)ccc(F)c1F)C2]

Compound was prepared analogous manner to Example 32 from (R)-1-(H-imidazol-1-yl)-3-(6-(2,3,6-trifluorophenyl)-3-thioxo-2,5,6,7-tetrahydro-3H-pyrrolo[1,2-c]imidazol-1-yl)propan-1-one and isolated as a beige powder.

¹H NMR (DMSO_{d6}): 8.09 (1H, d, J=6.6 Hz), 7.48 (1H, m), 7.18 (1H, br t, J=9.5 Hz), 4.40 (1H, quin, J=8.6 Hz), 4.20 (1H, dd, J=9.4, 11.5 Hz), 4.19 (1H, m), 3.78 (1H, dd, J=11.4, 7.9 Hz), 3.74-3.66 (2H, m), 3.63 (1H, m), 3.44 (3H, s), 3.38 (1H, dd, J=8.9, 3.6 Hz), 3.33 (1H, m), 2.92 (1H, dd, J=15.6, 8.1 Hz), 2.72 (2H, t, J=7.3 Hz), 2.37 (2H, t, J=7.3 Hz), 2.03 (1H, m), 1.62 (1H, m).

¹³C NMR (DMSO_{d6}): 170.5, 156.9, 156.9, 155.9, 155.3, 155.3, 149.1, 149, 149, 148.9, 147.5, 147.4, 147.4, 147.3, 145.9, 145.9, 145.8, 145.8, 126.8, 120.6, 119, 118.9, 118.8, 118.7, 116.5, 116.4, 116.4, 116.3, 112, 112, 111.9, 111.9, 111.8, 111.8, 111.8, 111.8, 72.4, 66.2, 49.5, 49.1, 34.7, 32.6, 32.1, 31.1, 29.5, 19.9.

Example 266: (R)-3-(2-methyl-3-thioxo-6-(2,3,6-trifluorophenyl)-2,5,6,7-tetrahydro-3H-pyrrolo[1,2-c]imidazol-1-yl)-1-morpholinopropan-1-one Compound was prepared analogous manner to Example 32 from (R)-1-(H-imidazol-1-yl)-3-(6-(2,3,6-trifluorophenyl)-3-thioxo-2,5,6,7-tetrahydro-3H-pyrrolo[1,2-c]imidazol-1-yl)propan-1-one and isolated as a cream powder.

¹H NMR (DMSO_{d6}): 7.48 (1H, m), 7.18 (1H, t, J=9.4 Hz), 4.40 (1H, quin, J=8.7 Hz), 4.21 (1H, dd, J=9.4, 11.3 Hz), 3.78 (1H, dd, J=11.5, 8.1 Hz), 3.51 (4H, m), 3.45 (3H, s), 3.41 (4H, m), 3.38 (1H, m), 2.98 (1H, dd, J=15.6, 8.4 Hz), 2.72 (2H, m), 2.63 (2H, m).

¹³C NMR (DMSO_{d6}): 169.6, 157, 156.9, 155.8, 155.3, 155.3, 149.1, 149.1, 149, 149, 147.6, 147.5, 147.5, 147.4, 147.4, 147.4, 147.3, 145.9, 145.8, 126.8, 120.8, 118.9, 118.8, 118.7, 116.5, 116.4, 116.4, 116.3, 112, 112, 112, 111.9, 111.8, 111.8, 111.8, 111.8, 66.1, 66, 49.1, 45.1, 41.5, 34.8, 31.1, 29.7, 29.3, 19.6.

Example 267: 1-((S)-2-(hydroxymethyl)pyrrolidin-1-yl)-3-((R)-2-methyl-3-thioxo-6-(2,3,6-trifluorophenyl)-2,5,6,7-tetrahydro-3H-pyrrolo[1,2-c]imidazol-1-yl)propan-1-one

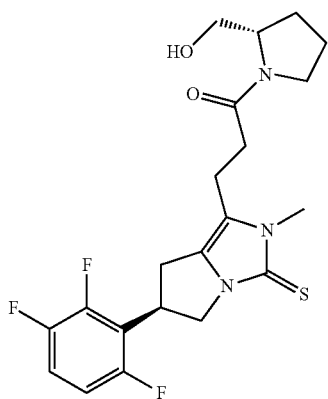 [SMILES: Cn1c(CCC(=O)N2CCC[C@H]2CO)c2n(c1=S)C[C@@H](c1c(F)ccc(F)c1F)C2]

Compound was prepared analogous manner to Example 32 from (R)-1-(H-imidazol-1-yl)-3-(6-(2,3,6-trifluorophenyl)-3-thioxo-2,5,6,7-tetrahydro-3H-pyrrolo[1,2-c]imidazol-1-yl)propan-1-one and isolated as a white powder.

$^1$H NMR (DMSO$_{d6}$): 7.47 (1H, m), 7.18 (1H, br t, J=9.5 Hz), 4.92 (0.35H, t, J=5.7 Hz), 4.72 (0.65H, t, J=5.7 Hz), 4.40 (1H, m), 4.20 (1H, br t, J=10.3 Hz), 3.90 (1H, m), 3.77 (1H, m), 3.46 (0.65H, m), 3.45 (3H, s), 3.42-3.27 (3H, m), 3.26-3.15 (1.35H, m), 2.97 (1H, m), 2.71 (2H, m), 2.68-2.51 (2H, m), 1.94-1.68 (4H, m).

$^{13}$C NMR (DMSO$_{d6}$): 169.6, 169.6, 156.9, 156.9, 155.8, 155.8, 155.3, 155.3, 149.1, 149, 147.5, 147.5, 145.9, 145.9, 145.8, 145.8, 126.8, 126.8, 120.9, 120.9, 118.9, 118.8, 118.8, 118.7, 116.5, 116.4, 116.4, 116.3, 112, 112, 112, 111.9, 111.9, 111.8, 111.8, 111.8, 111.7, 62.6, 61, 58.6, 58.5, 49.1, 46.5, 45.3, 34.8, 31.6, 31.3, 31.1, 29.3, 26.6, 23.3, 21.3, 19.2.

Example 268: (S)-3-(6-(3-chloro-2,6-difluorophenyl)-2-methyl-3-thioxo-2,5,6,7-tetrahydro-3H-pyrrolo[1,2-c]imidazol-1-yl)-N-(pyridin-2-yl)propanamide

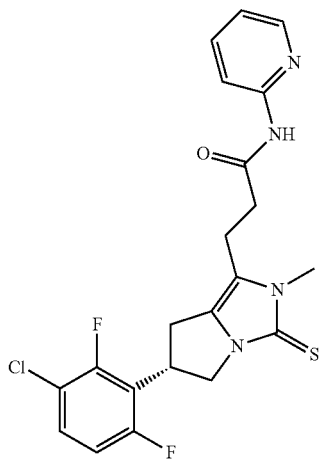 [SMILES: Cn1c(CCC(=O)Nc2ccccn2)c2n(c1=S)C[C@H](c1c(F)ccc(Cl)c1F)C2]

Compound was prepared analogous manner to Example 168 from (S)-3-(6-(3-chloro-2,6-difluorophenyl)-2-methyl-3-thioxo-2,5,6,7-tetrahydro-3H-pyrrolo[1,2-c]imidazol-1-yl)propanoic acid and isolated as an off-white solid.

$^1$H NMR (DMSO$_{d6}$): 10.54 (1H, s), 8.27 (1H, ddd, J=0.7, 1.8, 4.8 Hz), 8.01 (1H, br d, J=8.4 Hz), 7.75 (1H, m), 7.57 (1H, m), 7.12 (1H, m), 7.08 (1H, ddd, J=7.3, 4.9, 1.0 Hz), 4.38 (1H, quin, J=8.5 Hz), 4.17 (1H, dd, J=11.4, 9.4 Hz), 3.74 (1H, dd, J=11.7, 7.6 Hz), 3.47 (3H, s), 3.33 (1H, dd, J=15.8, 9.5 Hz), 2.90 (1H, dd, J=15.6, 7.7 Hz), 2.82 (2H, m), 2.69 (2H, m).

$^{13}$C NMR (DMSO$_{d6}$): 170.8, 160, 160, 158.4, 158.3, 156.5, 156.4, 155.9, 154.8, 154.8, 151.8, 147.6, 138.4, 129.6, 129.6, 127.1, 120.3, 119.3, 118.9, 118.8, 118.7, 116, 116, 115.9, 115.9, 113.4, 113.1, 113.1, 113, 113, 49.3, 34.7, 33.8, 31.1, 29.4, 21.6, 19.7.

Example 269: (R)-3-(6-(2,6-difluorophenyl)-2-methyl-3-thioxo-2,5,6,7-tetrahydro-3H-pyrrolo[1,2-c]imidazol-1-yl)-N-(pyridin-2-yl)propanamide

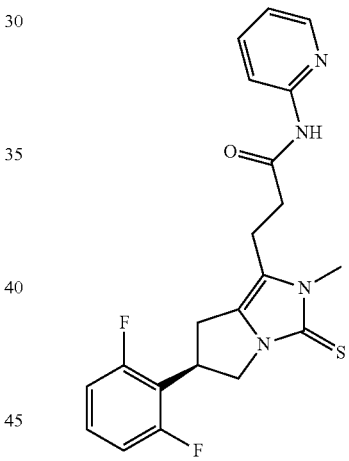

Compound was prepared analogous manner to Example 168 from (R)-3-(6-(2,6-difluorophenyl)-2-methyl-3-thioxo-2,5,6,7-tetrahydro-3H-pyrrolo[1,2-c]imidazol-1-yl)propanoic acid and isolated as an off-white solid.

$^1$H NMR (DMSO$_{d6}$): 10.52 (1H, s), 8.28 (1H, ddd, J=0.9, 1.9, 4.9 Hz), 8.03 (1H, br d, J=8.2 Hz), 7.75 (1H, m), 7.38 (1H, m), 7.09 (1H, ddd, J=1.0, 4.9, 7.4 Hz), 7.06 (2H, m), 4.36 (1H, quin, J=8.7 Hz), 4.17 (1H, dd, J=9.7, 11.3 Hz), 3.73 (1H, dd, J=11.4, 8.0 Hz), 3.48 (3H, s), 3.31 (1H, dd, J=15.6, 9.4 Hz), 2.90 (1H, dd, J=15.7, 8.4 Hz), 2.82 (2H, m), 2.70 (2H, m).

$^{13}$C NMR (DMSO$_{d6}$): 170.8, 161.5, 161.4, 159.9, 159.8, 155.9, 151.9, 147.8, 138.2, 129.7, 129.7, 129.6, 127.2, 120.3, 119.3, 116.6, 113.3, 112.1, 112.1, 112, 112, 49.4, 34.3, 33.8, 31.1, 29.6, 19.7.

Example 270: (R)—N-(cyanomethyl)-3-(2-methyl-3-thioxo-6-(2,3,6-trifluorophenyl)-2,5,6,7-tetrahydro-3H-pyrrolo[1,2-c]imidazol-1-yl)propanamide

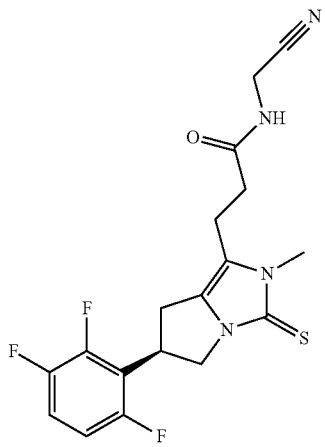 [SMILES: Cn1c(CCC(=O)NCC#N)c2n(c1=S)C[C@@H](c1c(F)ccc(F)c1F)C2]

Compound was prepared analogous manner to Example 34 from (R)-3-(2-methyl-3-thioxo-6-(2,3,6-trifluorophenyl)-2,5,6,7-tetrahydro-3H-pyrrolo[1,2-c]imidazol-1-yl)propanoic acid and isolated as a cream powder.

$^1$H NMR (DMSO$_{d6}$): 8.60 (1H, t, J=5.6 Hz), 7.47 (1H, m), 7.17 (1H, t, J=9.6 Hz), 4.41 (1H, quin, J=8.6 Hz), 4.19 (1H, dd, J=9.7, 11.3 Hz), 4.11 (2H, m), 3.77 (1H, dd, J=11.5, 8.0 Hz), 3.44 (3H, s), 3.31 (1H, dd, J=9.2, 15.5 Hz), 2.93 (1H, dd, J=15.6, 8.1 Hz), 2.76 (2H, t, J=7.3 Hz), 2.45 (2H, t, J=7.3 Hz).

$^{13}$C NMR (DMSO$_{d6}$): 171.5, 156.9, 156.9, 156, 155.3, 155.3, 149.1, 149, 149, 148.9, 147.5, 147.5, 147.4, 147.4, 147.3, 147.3, 145.9, 145.9, 145.8, 145.8, 127, 120.2, 118.9, 118.8, 118.8, 118.7, 117.6, 116.5, 116.4, 116.4, 116.3, 112, 111.9, 111.9, 111.9, 111.8, 111.8, 111.8, 111.7, 49.2, 34.7, 32.4, 31.1, 29.3, 27, 19.6.

Example 271: 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-N-cyclopentylacetamide

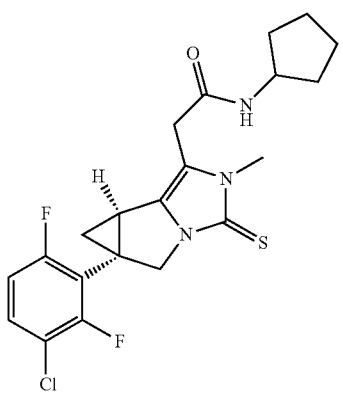 [SMILES: Cn1c(CC(=O)NC2CCCC2)c2n(c1=S)C[C@@]1(c3c(F)ccc(Cl)c3F)C[C@@H]21]

Compound was prepared analogous manner to Example 32 from 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

$^1$H NMR (DMSO$_{d6}$): 8.12 (1H, br d, J=7.0 Hz), 7.64 (1H, td, J=8.6, 5.6 Hz), 7.21 (1H, td, J=1.0, 9.0 Hz), 4.10 (1H, d, J=12.0 Hz), 4.00 (1H, sxt, J=6.8 Hz), 3.79 (1H, d, J=12.2 Hz), 3.47 (2H, m), 3.35 (3H, s), 2.78 (1H, dd, J=8.4, 4.4 Hz), 1.80 (2H, m), 1.69 (1H, dd, J=8.2, 5.6 Hz), 1.63 (2H, m), 1.50 (2H, m), 1.39 (2H, m), 1.25 (1H, t, J=4.9 Hz).

$^{13}$C NMR (DMSO$_{d6}$): 167.1, 161.3, 161.2, 159.6, 159.6, 157.8, 157.8, 156.7, 156.2, 156.1, 130.5, 130.3, 130.2, 117.1, 116.9, 116.8, 116.7, 115.8, 115.7, 115.6, 115.6, 112.9, 112.9, 112.8, 112.8, 52.2, 50.5, 32.2, 32.2, 31.4, 31.2, 25.6, 23.4, 21.7, 21.3.

Example 272: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-cyclopentylacetamide

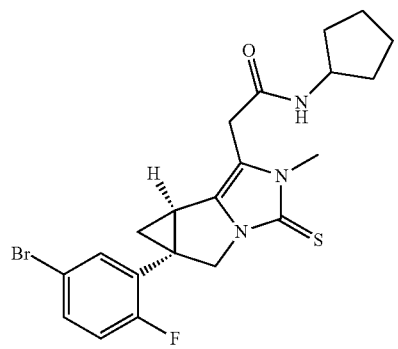

Compound was prepared analogous manner to Example 32 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

$^1$H NMR (DMSO$_{d6}$): 8.10 (1H, d, J=7.2 Hz), 7.58 (1H, dd, J=2.5, 6.7 Hz), 7.56 (1H, ddd, J=6.5, 4.4, 2.2 Hz), 7.24 (1H, dd, J=10.1, 8.8 Hz), 4.14 (1H, d, J=12.0 Hz), 4.00 (1H, sxt, J=6.8 Hz), 3.85 (1H, d, J=12.0 Hz), 3.47 (2H, m), 3.34 (3H, s), 2.87 (1H, dd, J=8.4, 4.1 Hz), 1.81 (2H, m), 1.70 (1H, dd, J=8.3, 5.4 Hz), 1.63 (2H, m), 1.51 (2H, m), 1.39 (2H, m), 1.13 (1H, t, J=4.8 Hz).

$^{13}$C NMR (DMSO$_{d6}$): 167.1, 161.8, 160.1, 156.8, 133.1, 133, 132.4, 132.3, 130.9, 129.2, 129.1, 118, 117.8, 116.3, 116.2, 116.2, 52.4, 50.5, 32.2, 32.2, 31.5, 31.4, 23.4, 22.1, 20.7.

Example 273: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-cyclopentylacetamide

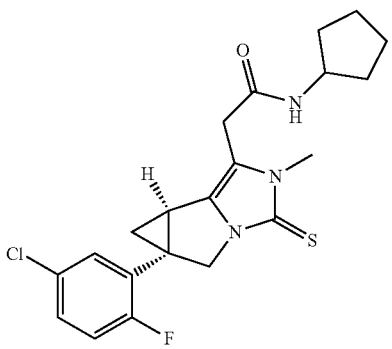 [SMILES: Cn1c(CC(=O)NC2CCCC2)c2n(c1=S)C[C@@]1(c3cc(Cl)ccc3F)C[C@@H]21]

Compound was prepared analogous manner to Example 32 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as an off-white solid.

$^{1}$H NMR (DMSO$_{d6}$): 8.11 (1H, d, J=7.2 Hz), 7.46 (1H, dd, J=6.5, 2.7 Hz), 7.43 (1H, ddd, J=8.7, 4.3, 2.6 Hz), 7.30 (1H, dd, J=9.9, 8.9 Hz), 4.14 (1H, d, J=12.0 Hz), 4.00 (1H, sxt, J=6.8 Hz), 3.85 (1H, d, J=12.0 Hz), 3.47 (2H, d, J=5.6 Hz), 3.35 (3H, s), 2.87 (1H, dd, J=8.3, 4.2 Hz), 1.81 (2H, m), 1.70 (1H, dd, J=8.3, 5.4 Hz), 1.63 (2H, m), 1.51 (2H, m), 1.39 (2H, dq, J=12.9, 6.4 Hz), 1.13 (1H, t, J=4.8 Hz).

$^{13}$C NMR (DMSO$_{d6}$): 167.1, 161.3, 159.6, 156.8, 130.9, 130.2, 130.2, 129.4, 129.3, 128.8, 128.7, 128.3, 117.6, 117.4, 116.3, 52.4, 50.6, 32.2, 32.2, 31.5, 31.4, 31.2, 23.4, 22.1, 20.8.

Example 274: 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-N—((R)-tetrahydrofuran-3-yl)acetamide

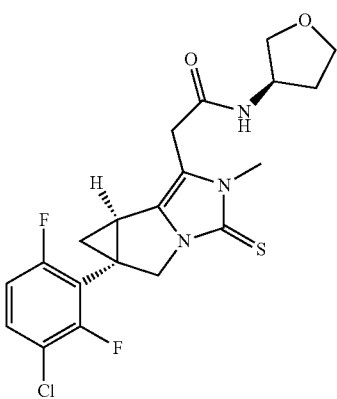 [SMILES: Cn1c(CC(=O)N[C@@H]2CCOC2)c2n(c1=S)C[C@@]1(c3c(F)ccc(Cl)c3F)C[C@@H]21]

Compound was prepared analogous manner to Example 32 from 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

$^{1}$H NMR (DMSO$_{d6}$): 8.42 (1H, d, J=6.6 Hz), 7.64 (1H, td, J=8.6, 5.8 Hz), 7.21 (1H, dt, J=1.0, 9.1 Hz), 4.25 (1H, m), 4.10 (1H, d, J=12.0 Hz), 3.79 (2H, m), 3.74 (1H, dd, J=8.9, 5.9 Hz), 3.68 (1H, td, J=8.2, 5.6 Hz), 3.50 (2H, m), 3.48 (1H, dd, J=3.6, 8.9 Hz), 3.35 (3 H, s), 2.78 (1H, dd, J=8.4, 4.4 Hz), 2.09 (1H, dq, J=12.7, 7.6 Hz), 1.73 (1H, m), 1.69 (1H, dd, J=8.4, 5.6 Hz), 1.26 (1H, t, J=4.9 Hz).

$^{13}$C NMR (DMSO$_{d6}$): 167.6, 161.3, 161.2, 159.6, 159.6, 157.8, 157.8, 156.8, 156.2, 156.1, 130.6, 130.3, 130.2, 117.1, 116.9, 116.8, 116.5, 115.8, 115.7, 115.6, 115.6, 112.9, 112.9, 112.8, 112.8, 72.3, 66.3, 52.2, 49.8, 32.1, 31.5, 31, 25.6, 21.7, 21.2.

Example 275: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)acetic acid

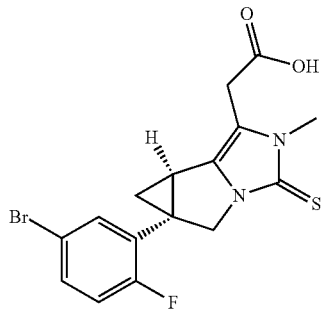 [SMILES: Cn1c(CC(=O)O)c2n(c1=S)C[C@@]1(c3cc(Br)ccc3F)C[C@@H]21]

Compound was prepared in an analogous manner to Example 229 from tert-butyl (1S,5R)-1-(5-bromo-2-fluorophenyl)-4-(3-ethoxy-3-oxopropanoyl)-3-azabicyclo[3.1.0]hexane-3-carboxylate and isolated as a beige solid.

$^{1}$H NMR (DMSO$_{d6}$): 12.79 (1H, br s), 7.58 (1H, dd, J=6.7, 2.6 Hz), 7.56 (1H, m), 7.24 (1H, dd, J=10.1, 8.7 Hz), 4.16 (1H, d, J=12.0 Hz), 3.86 (1H, d, J=12.0 Hz), 3.73 (2H, m), 3.35 (3H, s), 2.97 (1H, dd, J=8.4, 4.3 Hz), 1.70 (1H, dd, J=8.4, 5.4 Hz), 1.13 (1H, t, J=4.8 Hz).

$^{13}$C NMR (DMSO$_{d6}$): 170.9, 161.8, 160.2, 157.1, 133, 133, 132.4, 132.3, 131.2, 129.1, 129, 118, 117.8, 116.2, 116.2, 115.2, 52.5, 52.5, 31.5, 31.4, 29.7, 22.1, 20.5.

Example 276: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)acetic Acid

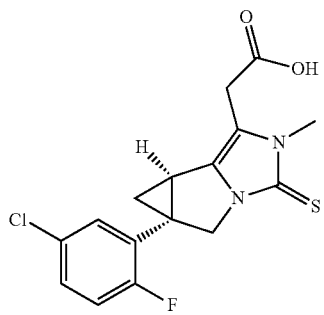 [SMILES: Cn1c(CC(=O)O)c2n(c1=S)C[C@@]1(c3cc(Cl)ccc3F)C[C@@H]21]

Compound was prepared in an analogous manner to Example 229 from tert-butyl (1S,5R)-1-(5-chloro-2-fluorophenyl)-4-(3-ethoxy-3-oxopropanoyl)-3-azabicyclo[3.1.0]hexane-3-carboxylate and isolated as a beige solid.

$^1$H NMR (DMSO$_{d6}$): 12.77 (1H, m), 7.47 (1H, dd, J=6.5, 2.7 Hz), 7.43 (1H, ddd, J=8.7, 4.3, 2.8 Hz), 7.30 (1H, dd, J=9.9, 8.9 Hz), 4.16 (1H, d, J=12.0 Hz), 3.87 (1H, d, J=12.0 Hz), 3.73 (2H, m), 3.36 (3H, s), 2.97 (1H, dd, J=8.4, 4.2 Hz), 1.70 (1H, dd, J=8.4, 5.4 Hz), 1.13 (1H, t, J=4.8 Hz).

$^{13}$C NMR (DMSO$_{d6}$): 170.9, 161.3, 159.6, 157.1, 131.2, 130.2, 130.1, 129.4, 129.3, 128.7, 128.6, 128.3, 128.3, 117.6, 117.4, 115.2, 52.4, 52.4, 31.6, 31.4, 29.7, 22.1, 20.6.

Example 277: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N—((R)-tetrahydro-2H-pyran-3-yl)acetamide

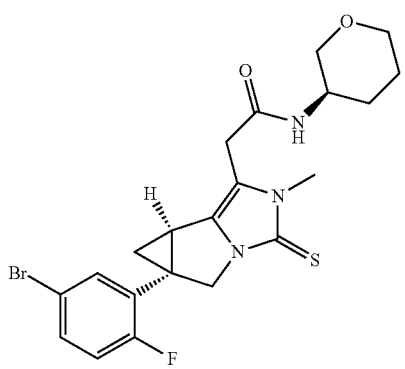

Compound was prepared analogous manner to Example 34 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)acetic acid and isolated as an off-white solid.

$^1$H NMR (DMSO$_{d6}$): 8.15 (1H, br d, J=7.3 Hz), 7.58 (1H, dd, J=6.7, 2.6 Hz), 7.56 (1H, ddd, J=2.5, 4.5, 8.5 Hz), 7.24 (1H, dd, J=8.8, 10.1 Hz), 4.14 (1H, d, J=12.0 Hz), 3.85 (1H, d, J=12.2 Hz), 3.73-3.67 (2H, m), 3.65 (1H, m), 3.52 (2H, m), 3.37 (1H, m), 3.14 (1H, m), 3.34 (3H, s), 2.88 (1H, dd, J=8.4, 4.3 Hz), 1.83 (1H, m), 1.70 (1H, dd, J=8.3, 5.4 Hz), 1.69 (1H, m), 1.49 (2H, m), 1.12 (1H, t, J=4.8 Hz).

$^{13}$C NMR (DMSO$_{d6}$): 167.4, 161.8, 160.1, 156.8, 133.1, 133, 132.4, 132.3, 130.9, 129.2, 129.1, 118, 117.8, 116.2, 116.2, 70.1, 67, 52.4, 45.2, 31.5, 31.4, 31.1, 28.6, 23.9, 22.1, 20.7.

Example 278: 2-((R)-2-methyl-6-(2,3,5,6-tetrafluorophenyl)-3-thioxo-2,5,6,7-tetrahydro-3H-pyrrolo[1,2-c]imidazol-1-yl)-N—((R)-tetrahydro-2H-pyran-3-yl)acetamide

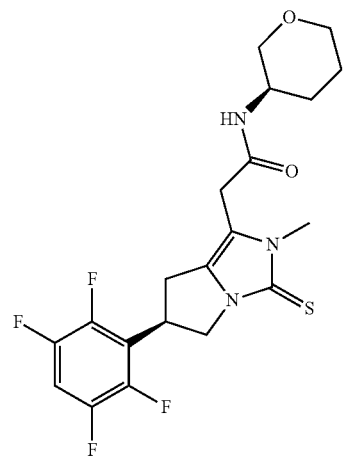 [SMILES: Cn1c(CC(=O)N[C@@H]2CCCOC2)c2n(c1=S)C[C@@H](c1c(F)c(F)cc(F)c1F)C2]

Compound was prepared analogous manner to Example 34 from (R)-2-(2-methyl-3-thioxo-6-(2,3,5,6-tetrafluorophenyl)-2,5,6,7-tetrahydro-3H-pyrrolo[1,2-c]imidazol-1-yl)acetic acid and isolated as an off-white powder.

$^1$H NMR (DMSO$_{d6}$): 8.13 (1H, br d, J=7.3 Hz), 7.85 (1H, m), 4.48 (1H, quin, J=8.5 Hz), 4.24 (1H, dd, J=11.4, 9.2 Hz), 3.84 (1H, dd, J=11.7, 7.7 Hz), 3.72-3.59 (3H, m), 3.45 (2H, s), 3.40 (3H, s), 3.36 (1H, m), 3.30 (1H, dd, J=9.4, 16.0 Hz), 3.12 (1H, m), 2.92 (1H, dd, J=15.9, 7.8 Hz), 1.80 (1H, m), 1.66 (1H, m), 1.46 (2H, m).

$^{13}$C NMR (DMSO$_{d6}$): 167.3, 156.2, 146.4, 146.3, 146.3, 145.4, 145.3, 145.3, 145.2, 144.9, 144.8, 144.8, 144.7, 144.7, 144.7, 144.7, 144.6, 144.6, 144.6, 143.8, 143.7, 143.7, 143.7, 143.7, 143.6, 143.6, 143.6, 128.2, 120.5, 120.4, 120.3, 116.5, 105.9, 105.7, 105.6, 70.1, 67, 49.4, 45.1, 34.9, 31.5, 31.2, 29.1, 28.5, 23.8.

Example 279: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N—((R)-tetrahydrofuran-3-yl)acetamide

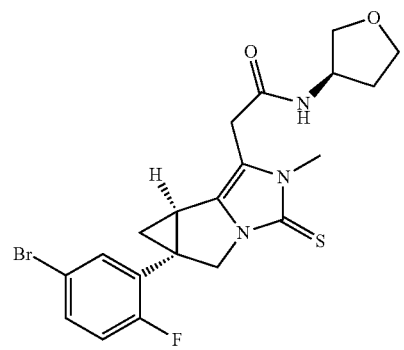 [SMILES: Cn1c(CC(=O)N[C@@H]2CCOC2)c2n(c1=S)C[C@@]1(c3cc(Cl)ccc3F)C[C@@H]21]

Compound was prepared analogous manner to Example 32 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

¹H NMR (DMSO$_{d6}$): 8.40 (1H, d, J=6.6 Hz), 7.58 (1H, dd, J=6.6, 2.5 Hz), 7.56 (1H, ddd, J=8.6, 4.5, 2.6 Hz), 7.24 (1H, dd, J=10.1, 8.8 Hz), 4.26 (1H, m), 4.14 (1H, d, J=12.0 Hz), 3.85 (1H, d, J=12.0 Hz), 3.79 (1H, q, J=7.3 Hz), 3.74 (1H, dd, J=8.9, 5.9 Hz), 3.68 (1H, td, J=8.2, 5.6 Hz), 3.56-3.45 (3H, m), 3.35 (3H, s), 2.88 (1H, dd, J=8.4, 4.3 Hz), 2.10 (1H, m), 1.74 (1H, m), 1.70 (1H, dd, J=8.4, 5.3 Hz), 1.13 (1H, t, J=4.8 Hz).
¹³C NMR (DMSO$_{d6}$): 167.7, 161.8, 160.1, 156.8, 133.1, 133, 132.4, 132.3, 131, 129.2, 129.1, 118, 117.8, 116.2, 116.2, 116.1, 72.3, 66.3, 52.4, 49.8, 32.1, 31.5, 31.4, 31, 22.1, 20.7.

Example 280: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)acetamide

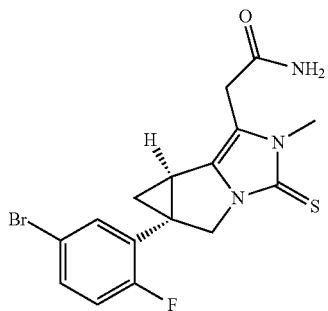 [SMILES: Cn1c(CC(N)=O)c2n(c1=S)C[C@@]1(c3cc(Cl)ccc3F)C[C@@H]21]

Compound was prepared analogous manner to Example 32 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.
¹H NMR (DMSO$_{d6}$): 7.59 (1H, dd, J=6.7, 2.6 Hz), 7.56 (1H, ddd, J=8.7, 4.4, 2.6 Hz), 7.53 (1H, br s), 7.24 (1H, dd, J=10.0, 8.8 Hz), 7.14 (1H, br s), 4.14 (1H, d, J=11.9 Hz), 3.85 (1H, d, J=12.0 Hz), 3.49 (2H, m), 3.35 (3H, s), 2.93 (1H, dd, J=8.4, 4.1 Hz), 1.67 (1H, dd, J=8.3, 5.4 Hz), 1.17 (1H, t, J=4.8 Hz).
¹³C NMR (DMSO$_{d6}$): 170, 161.8, 160.1, 156.8, 133, 133, 132.3, 132.3, 131.1, 129.2, 129.1, 118, 117.8, 116.2, 116.2, 52.5, 52.4, 31.5, 31.4, 30.9, 22.1, 20.6.

Example 281: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N—((R)-tetrahydrofuran-3-yl)acetamide

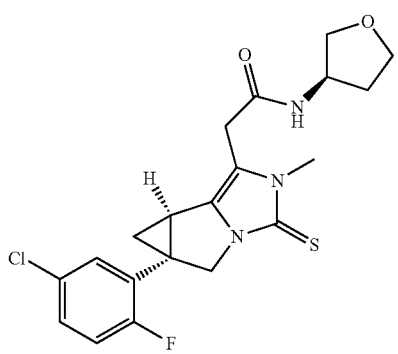

Compound was prepared analogous manner to Example 32 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.
¹H NMR (DMSO$_{d6}$): 8.41 (1H, br d, J=6.6 Hz), 7.47 (1H, dd, J=6.6, 2.6 Hz), 7.43 (1H, ddd, J=8.7, 4.3, 2.8 Hz), 7.30 (1H, dd, J=8.9, 9.8 Hz), 4.26 (1H, m), 4.14 (1H, d, J=12.0 Hz), 3.85 (1H, d, J=12.0 Hz), 3.79 (1H, q, J=7.5 Hz), 3.74 (1H, dd, J=8.9, 6.0 Hz), 3.68 (1H, m), 3.56-3.46 (3H, m), 3.35 (3H, s), 2.88 (1H, dd, J=8.3, 4.2 Hz), 2.10 (1H, dq, J=12.7, 7.6 Hz), 1.74 (1H, m), 1.70 (1H, dd, J=8.3, 5.4 Hz), 1.13 (1H, t, J=4.8 Hz).
¹³C NMR (DMSO$_{d6}$): 167.7, 161.3, 159.6, 156.8, 131, 130.2, 130.2, 129.4, 129.3, 128.8, 128.6, 128.3, 128.3, 117.6, 117.4, 116.1, 72.3, 66.3, 52.4, 49.8, 32.1, 31.6, 31.5, 31, 22.1, 20.7.

Example 282: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)acetamide

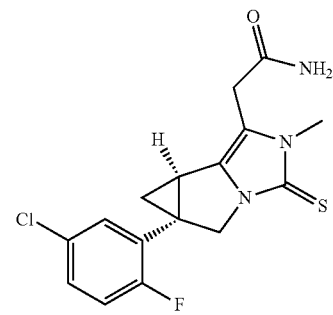

Compound was prepared analogous manner to Example 32 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as an off-white solid.
¹H NMR (DMSO$_{d6}$): 7.53 (1H, br s), 7.48 (1H, dd, J=6.5, 2.6 Hz), 7.43 (1H, ddd, J=8.7, 4.3, 2.6 Hz), 7.30 (1H, dd, J=9.8, 9.0 Hz), 7.14 (1H, br s), 4.14 (1H, d, J=12.0 Hz), 3.85 (1H, d, J=12.0 Hz), 3.49 (2H, m), 3.35 (3H, s), 2.93 (1H, dd, J=8.4, 4.1 Hz), 1.68 (1H, dd, J=8.4, 5.3 Hz), 1.17 (1H, m).
¹³C NMR (DMSO$_{d6}$): 170, 161.3, 159.6, 156.8, 131.1, 130.2, 130.2, 129.4, 129.3, 128.8, 128.7, 128.3, 128.3, 117.6, 117.4, 116.2, 52.4, 31.5, 31.4, 30.9, 22.1, 20.6.

Example 283: 1-((S)-2-(methoxymethyl)pyrrolidin-1-yl)-2-((R)-2-methyl-6-(2,3,5,6-tetrafluorophenyl)-3-thioxo-2,5,6,7-tetrahydro-3H-pyrrolo[1,2-c]imidazol-1-yl)ethan-1-one

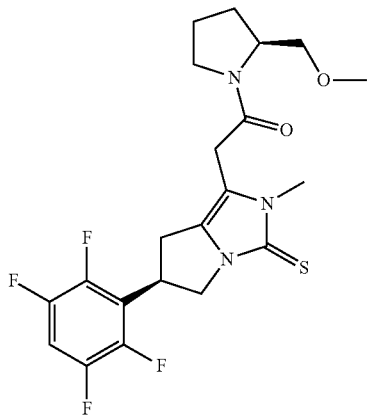 [SMILES: COC[C@@H]1CCCN1C(=O)Cc1c2n(c(=S)n1C)C[C@@H](c1c(F)c(F)cc(F)c1F)C2]

Compound was prepared analogous manner to Example 32 from (R)-1-(H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone and isolated as an off-white powder.

$^1$H NMR (DMSO$_{d6}$): 7.86 (1H, m), 4.48 (1H, quin, J=8.4 Hz), 4.29-4.18 (1.35H, m), 4.04 (0.65H, m), 3.88-3.82 (1H, m), 3.79 (0.65H, m), 3.66 (1.35H, s), 3.54-3.41 (1.65H, m), 3.40 (1H, m), 3.37, 3.36 (3H, 2 s), 3.32-3.23 (3.4H, m), 3.22 (1.95H, s), 2.91 (1H, m), 2.0-1.73 (4H, m).

$^{13}$C NMR (DMSO$_{d6}$): 166.9, 166.6, 156.3, 156.1, 146.4, 146.3, 146.3, 146.3, 146.2, 146.2, 145.3, 145.3, 145.2, 145.2, 145.2, 144.8, 144.8, 144.7, 144.6, 144.6, 143.7, 143.7, 143.6, 143.6, 128.1, 128, 120.5, 120.4, 120.3, 116.8, 116.3, 105.9, 105.7, 105.6, 73.8, 71.6, 58.5, 58.3, 56.3, 56.2, 49.4, 46.8, 45.4, 34.9, 31.5, 30.6, 29.8, 29, 29, 28.2, 27.1, 23.5, 21.5.

Example 284: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-isopropylacetamide

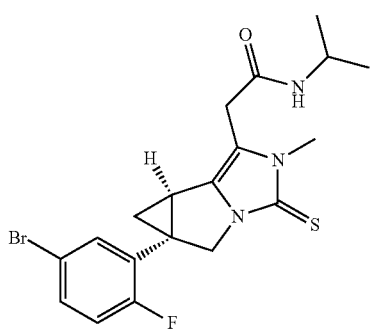

Compound was prepared analogous manner to Example 32 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as an off-white solid.

$^1$H NMR (DMSO$_{d6}$): 8.01 (1H, br d, J=7.6 Hz), 7.58 (1H, dd, J=6.7, 2.6 Hz), 7.57 (1H, ddd, J=2.6, 4.5, 8.5 Hz), 7.24 (1H, dd, J=10.1, 8.9 Hz), 4.14 (1H, d, J=12.0 Hz), 3.90-3.80 (2H, m), 3.46 (2H, m), 3.35 (3H, s), 2.88 (1H, dd, J=8.3, 4.2 Hz), 1.70 (1H, dd, J=8.3, 5.4 Hz), 1.13 (1H, t, J=4.8 Hz), 1.07 (6H, d, J=6.6 Hz).

$^{13}$C NMR (DMSO$_{d6}$): 166.7, 161.8, 160.1, 156.8, 133.1, 133, 132.3, 132.3, 130.9, 129.2, 129.1, 118, 117.8, 116.3, 116.2, 116.2, 52.4, 52.4, 40.7, 31.5, 31.4, 31.2, 22.3, 22.3, 22, 20.7.

Example 285: (S)-2-(6-(3-chloro-2,6-difluorophenyl)-2-methyl-3-thioxo-2,5,6,7-tetrahydro-3H-pyrrolo[1,2-c]imidazol-1-yl)-N-(1,3,4-thiadiazol-2-yl)acetamide

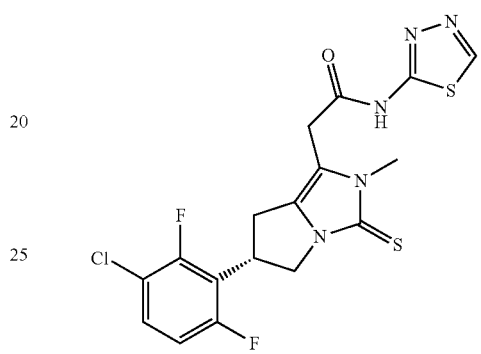

Compound was prepared analogous manner to Example 258 from (S)-2-(6-(3-chloro-2,6-difluorophenyl)-2-methyl-3-thioxo-2,5,6,7-tetrahydro-3H-pyrrolo[1,2-c]imidazol-1-yl)acetic acid and isolated as an off-white solid.

$^1$H NMR (DMSO$_{d6}$): 9.17 (1H, s), 7.61 (1H, m), 7.21 (1H, m), 4.45 (1H, quin, J=8.5 Hz), 4.24 (1H, dd, J=11.4, 9.5 Hz), 3.90 (2H, m), 3.82 (1H, dd, J=11.6, 7.8 Hz), 3.42 (3H, s), 3.31 (1H, m), 2.92 (1H, dd, J=16.0, 8.1 Hz).

$^{13}$C NMR (DMSO$_{d6}$): 167.6, 160.2, 160.1, 158.7, 158.5, 158.5, 156.6, 156.5, 154.9, 154.9, 148.9, 129.7, 129.7, 129.3, 118.8, 118.6, 118.5, 116.1, 116.1, 116, 115.9, 114.7, 113.3, 113.2, 113.1, 113.1, 49.6, 34.7, 31.6, 30.9, 29.1.

Example 286: (R)-2-(2-methyl-3-thioxo-6-(2,3,6-trifluorophenyl)-2,5,6,7-tetrahydro-3H-pyrrolo[1,2-c]imidazol-1-yl)-N-(oxazol-2-yl)acetamide

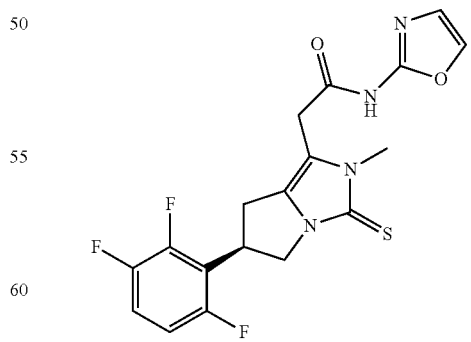

Compound was prepared analogous manner to Example 32 from (R)-1-(H-imidazol-1-yl)-2-(6-(2,3,6-trifluorophenyl)-3-thioxo-3,5,6,7-tetrahydro-2H-pyrrolo[1,2-c]imidazol-1-yl)ethanone and isolated as a light cream powder.

¹H NMR (DMSO$_{d6}$): 1.45 (1H, br s), 7.87 (1H, s), 7.47 (1H, m), 7.18 (1H, m), 7.10 (1H, s), 4.44 (1H, quin, J=8.6 Hz), 4.25 (1H, dd, J=9.6, 11.2 Hz), 3.83 (1H, dd, J=11.5, 8.0 Hz), 3.79 (2H, br s), 3.41 (3H, s), 3.33 (1H, m), 2.94 (1H, dd, J=15.8, 8.2 Hz).

¹³C NMR (DMSO$_{d6}$): 166.7, 157, 156.9, 156.5, 155.3, 155.3, 155.3, 153, 149.1, 149, 149, 149, 148.9, 147.5, 147.5, 147.5, 147.4, 147.4, 147.4, 147.4, 147.3, 145.9, 145.9, 145.9, 145.8, 136.2, 129.1, 126.7, 118.8, 118.8, 118.7, 118.7, 118.6, 116.5, 116.5, 116.4, 116.3, 115.1, 112, 112, 112, 111.8, 111.8, 111.8, 49.5, 34.7, 31.6, 31.4, 29.1.

Example 287: (S)-2-(6-(3-chloro-2,6-difluorophenyl)-2-methyl-3-thioxo-2,5,6,7-tetrahydro-3H-pyrrolo[1,2-c]imidazol-1-yl)-N-(pyridin-4-yl)acetamide Hydrochloride

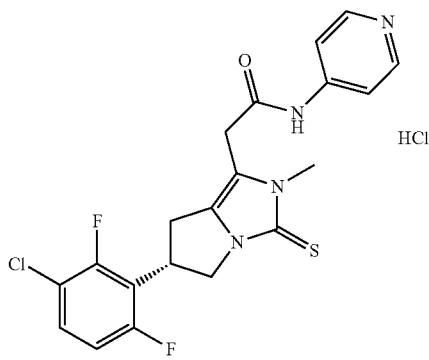 [SMILES: Cn1c(CC(=O)Nc2ccncc2)c2n(c1=S)C[C@H](c1c(F)ccc(Cl)c1F)C2 ; Cl]

Compound was prepared analogous manner to Example 168 from (S)-2-(6-(3-chloro-2,6-difluorophenyl)-2-methyl-3-thioxo-2,5,6,7-tetrahydro-3H-pyrrolo[1,2-c]imidazol-1-yl)acetic acid and isolated as an off-white solid.

¹H NMR (DMSO$_{d6}$): 12.16 (1H, s), 8.71 (2H, d, J=7.2 Hz), 8.13 (2H, d, J=7.2 Hz), 7.62 (1H, m), 7.22 (1H, m), 4.46 (1H, quin, J=8.5 Hz), 4.25 (1H, dd, J=9.6, 11.3 Hz), 3.97 (2H, m), 3.83 (1H, dd, J=11.6, 7.8 Hz), 3.45 (3H, s), 3.37 (1H, dd, J=9.3, 16.0 Hz), 2.95 (1H, dd, J=16.0, 7.9 Hz).

¹³C NMR (DMSO$_{d6}$): 169.6, 160.1, 160.1, 158.5, 158.4, 156.6, 156.6, 156.5, 154.9, 154.9, 152.6, 142.6, 129.7, 129.7, 129.4, 118.8, 118.7, 118.5, 116.1, 116, 115.9, 115.9, 114.7, 114.4, 113.3, 113.2, 113.1, 113.1, 49.6, 34.7, 32.5, 31.7, 29.3.

Example 288: 3-((R)-2-methyl-3-thioxo-6-(2,3,6-trifluorophenyl)-2,5,6,7-tetrahydro-3H-pyrrolo[1,2-c]imidazol-1-yl)-N—((R)-tetrahydro-2H-pyran-3-yl)propanamide

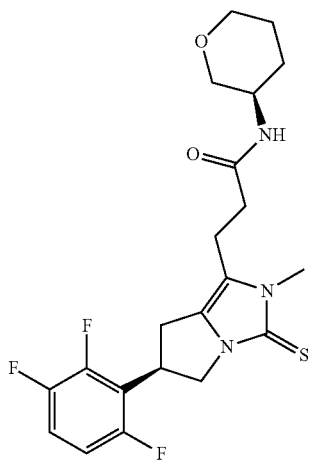 [SMILES: Cn1c(CCC(=O)N[C@@H]2CCCOC2)c2n(c1=S)C[C@@H](c1c(F)ccc(F)c1F)C2]

Compound was prepared analogous manner to Example 34 from (R)-3-(2-methyl-3-thioxo-6-(2,3,6-trifluorophenyl)-2,5,6,7-tetrahydro-3H-pyrrolo[1,2-c]imidazol-1-yl)propanoic acid and isolated as an off-white solid.

¹H NMR (DMSO$_{d6}$): 7.82 (1H, d, J=7.5 Hz), 7.48 (1H, m), 7.18 (1H, br t, J=9.4 Hz), 4.40 (1H, quin, J=8.6 Hz), 4.20 (1H, dd, J=11.2, 9.3 Hz), 3.78 (1H, dd, J=11.6, 7.9 Hz), 3.66-3.58 (3H, m), 3.44 (3H, m), 3.34 (1H, m), 3.32 (1H, m), 3.04 (1H, m), 2.92 (1H, dd, J=15.7, 8.2 Hz), 2.72 (2H, t, J=7.3 Hz), 2.38 (2H, m), 1.74 (1H, m), 1.61 (1H, m), 1.40 (2H, m).

¹³C NMR (DMSO$_{d6}$): 170.3, 156.9, 156.9, 156.9, 155.9, 155.5, 155.3, 155.3, 149.1, 149, 149, 148.9, 147.5, 147.5, 147.5, 147.4, 147.4, 147.3, 147.3, 145.9, 145.9, 145.8, 145.8, 126.8, 120.6, 118.9, 118.9, 118.8, 118.7, 116.5, 116.5, 116.4, 116.3, 112, 112, 112, 111.9, 111.8, 111.8, 111.8, 111.8, 70.2, 67, 49.1, 44.8, 34.8, 32.6, 31.1, 29.5, 28.6, 23.8, 19.9.

Example 289: 2-((R)-2-methyl-3-thioxo-6-(2,3,6-trifluorophenyl)-2,5,6,7-tetrahydro-3H-pyrrolo[1,2-c]imidazol-1-yl)-N—((S)-tetrahydrofuran-3-yl)acetamide

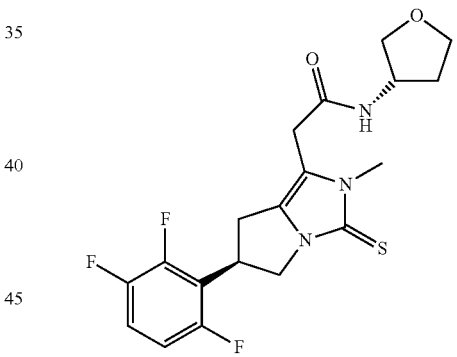

Compound was prepared analogous manner to Example 32 from (R)-1-(1H-imidazol-1-yl)-2-(6-(2,3,6-trifluorophenyl)-3-thioxo-3,5,6,7-tetrahydro-2H-pyrrolo[1,2-c]imidazol-1-yl)ethanone and isolated as a white powder.

¹H NMR (DMSO$_{d6}$): 8.37 (1H, d, J=6.6 Hz), 7.47 (1H, m), 7.18 (1H, br t, J=9.6 Hz), 4.43 (1H, quin, J=8.7 Hz), 4.23 (2H, m), 3.81 (1H, dd, J=10.9, 7.4 Hz), 3.77 (1H, m), 3.72 (1H, dd, J=8.9, 6.0 Hz), 3.66 (1H, td, J=8.2, 5.6 Hz), 3.46 (1H, dd, J=8.9, 3.7 Hz), 3.43 (2H, m), 3.40 (3H, s), 3.29 (1H, dd, J=15.7, 9.4 Hz), 2.90 (1H, dd, J=15.8, 8.3 Hz), 2.08 (1H, m), 1.71 (1H, m).

¹³C NMR (DMSO$_{d6}$): 167.6, 157, 156.9, 156.9, 156.9, 156.2, 155.3, 155.3, 149.1, 149, 147.6, 147.5, 147.5, 147.4, 147.4, 147.4, 145.9, 145.9, 145.9, 145.8, 128.4, 118.9, 118.8, 118.7, 118.6, 116.5, 116.4, 116.4, 116.3, 112, 112, 112, 111.9, 111.8, 111.8, 111.8, 111.8, 72.4, 66.3, 49.8, 49.4, 34.7, 32, 31.5, 31.1, 29.1.

Example 290: (S)-2-(6-(3-chloro-2,6-difluorophenyl)-2-methyl-3-thioxo-2,5,6,7-tetrahydro-3H-pyrrolo[1,2-c]imidazol-1-yl)-N-(pyridin-3-ylmethyl)acetamide

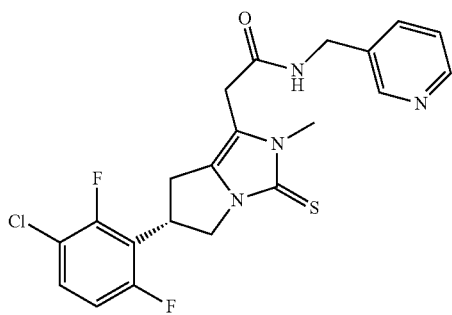 [SMILES: Cn1c(CC(=O)NCc2cccnc2)c2n(c1=S)C[C@H](c1c(F)ccc(Cl)c1F)C2]

Compound was prepared analogous manner to Example 32 from (S)-2-(6-(3-chloro-2,6-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as an off-white solid.

$^1$H NMR (DMSO$_{d6}$): 8.67 (1H, br t, J=5.9 Hz), 8.50 (1H, d, J=1.8 Hz), 8.44 (1H, dd, J=4.7, 1.3 Hz), 7.70 (1H, m), 7.62 (1H, m), 7.37 (1H, dd, J=7.8, 4.8 Hz), 7.22 (1H, m), 4.41 (1H, quin, J=8.6 Hz), 4.31 (2H, m), 4.22 (1H, dd, J=9.5, 11.0 Hz), 3.80 (1H, dd, J=11.5, 8.0 Hz), 3.52 (2H, m), 3.38 (3H, m), 3.22 (1H, dd, J=15.8, 9.3 Hz), 2.82 (1H, dd, J=15.8, 8.3 Hz).

$^{13}$C NMR (DMSO$_{d6}$): 168, 160.1, 160.1, 158.5, 158.5, 156.6, 156.5, 156.3, 154.9, 154.9, 148.4, 147.7, 135.7, 135, 129.7, 129.7, 128.5, 123.6, 118.6, 118.5, 118.4, 116.1, 116.1, 116, 115.9, 115.9, 113.3, 113.2, 113.1, 113.1, 49.4, 39.8, 34.7, 31.4, 31.2, 29.1.

Example 291: (S)—N-(benzo[d][1,3]dioxol-5-ylmethyl)-2-(6-(3-chloro-2,6-difluorophenyl)-2-methyl-3-thioxo-2,5,6,7-tetrahydro-3H-pyrrolo[1,2-c]imidazol-1-yl)acetamide

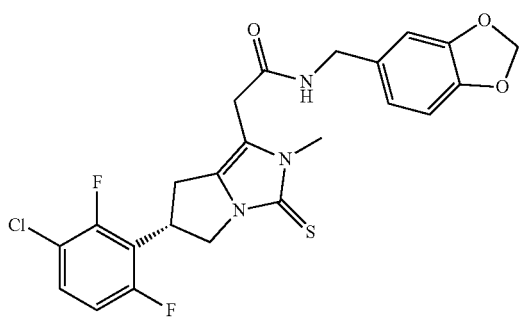 [SMILES: Cn1c(CC(=O)NCc2ccc3c(c2)OCO3)c2n(c1=S)C[C@H](c1c(F)ccc(Cl)c1F)C2]

Compound was prepared analogous manner to Example 32 from (S)-2-(6-(3-chloro-2,6-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as an off-white solid.

$^1$H NMR (DMSO$_{d6}$): 8.52 (1H, t, J=5.9 Hz), 7.62 (1H, m), 7.22 (1H, m), 6.81 (2H, m), 6.72 (1H, m), 5.95 (2H, m), 4.41 (1H, quin, J=8.7 Hz), 4.21 (1H, dd, J=9.4, 11.4 Hz), 4.17 (2H, m), 3.79 (1H, dd, J=11.6, 8.1 Hz), 3.49 (2H, m), 3.39 (3H, s), 3.22 (1H, dd, J=15.8, 9.3 Hz), 2.83 (1H, dd, J=15.8, 8.2 Hz).

$^{13}$C NMR (DMSO$_{d6}$): 167.6, 160.1, 160.1, 158.5, 158.5, 156.6, 156.5, 156.3, 154.9, 154.9, 147.2, 146.1, 133, 129.7, 129.7, 128.4, 120.6, 118.6, 118.5, 118.4, 116.3, 116.1, 116, 115.9, 115.9, 113.2, 113.2, 113.1, 113.1, 108.1, 108, 100.8, 49.4, 42.2, 34.7, 31.4, 31.3, 29.1.

Example 292: 1-((R)-3-fluoropyrrolidin-1-yl)-2-((R)-2-methyl-3-thioxo-6-(2,3,6-trifluorophenyl)-2,5,6,7-tetrahydro-3H-pyrrolo[1,2-c]imidazol-1-yl)ethan-1-one

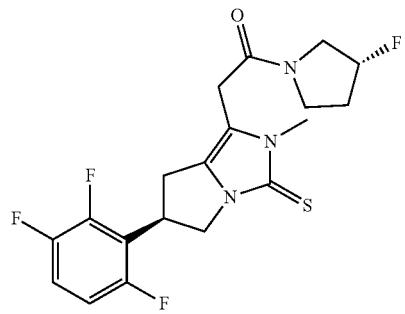 [SMILES: Cn1c(CC(=O)N2CC[C@@H](F)C2)c2n(c1=S)C[C@@H](c1c(F)ccc(F)c1F)C2]

Compound was prepared analogous manner to Example 34 from (R)-2-(2-methyl-3-thioxo-6-(2,3,6-trifluorophenyl)-2,5,6,7-tetrahydro-3H-pyrrolo[1,2-c]imidazol-1-yl)acetic acid and isolated as a white solid.

$^1$H NMR (DMSO$_{d6}$): 7.47 (1H, m), 7.18 (1H, m), 5.36 (1H, m t, J=52 Hz), 4.44 (1H, m), 4.24 (1H, m), 3.87-3.52 (6H, m), 3.51-3.40 (0.5H, m), 3.37 (3H, s), 3.31-3.24 (1.5H, m), 2.88 (1H, m), 2.29-1.92 (2H, m).

$^{13}$C NMR (DMSO$_{d6}$): 166.6, 166.5, 156.9, 156.9, 156.3, 155.3, 155.3, 155.3, 155.3, 149.1, 149, 149, 148.9, 147.5, 147.4, 147.4, 147.4, 147.3, 145.9, 145.9, 145.9, 145.8, 128.3, 128.2, 118.9, 118.8, 118.8, 118.7, 116.5, 116.4, 116.4, 116.3, 116.1, 116, 112, 111.8, 94.2, 93, 92.6, 91.4, 62.8, 54.9, 52.8, 52.6, 52.4, 52.3, 49.4, 43.8, 43.5, 34.7, 32.1, 32, 31.5, 30.5, 30.4, 30.2, 29.1, 29.1.

Example 293: (R)—N-(2-hydroxyethyl)-N-methyl-2-(2-methyl-3-thioxo-6-(2,3,6-trifluorophenyl)-2,5,6,7-tetrahydro-3H-pyrrolo[1,2-c]imidazol-1-yl)acetamide

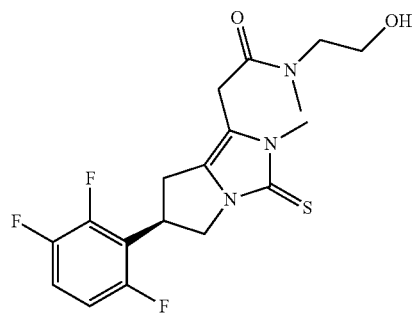 [SMILES: CN(CCO)C(=O)Cc1c2n(c(=S)n1C)C[C@@H](c1c(F)ccc(F)c1F)C2]

Compound was prepared analogous manner to Example 32 from (R)-1-(H-imidazol-1-yl)-2-(2-methyl-3-thioxo-6-(2,3, 6-trifluorophenyl)-2,5,6,7-tetrahydro-3H-pyrrolo[1,2-c]imidazol-1-yl)ethan-1-one and isolated as a cream powder.

¹H NMR (DMSO$_{d6}$): 7.47 (1H, m), 7.18 (1H, br t, J=9.7 Hz), 4.93 (0.6H, t, J=5.3 Hz), 4.67 (0.4H, t, J=5.4 Hz), 4.43 (1H, m), 4.24 (1H, brt, J=10.3 Hz), 3.81 (1H, dd, J=11.6, 8.1 Hz), 3.79 (1.2H, s), 3.71 (0.8H, s), 3.56 (1.2H, q, J=5.3 Hz), 3.47 (0.8H, q, J=5.8 Hz), 3.42 (1.2H, m), 3.35 (0.8H, m), 3.35 (3H, s), 3.32-3.21 (1H, m), 3.06 (1.2H, s), 2.88 (1H, m), 2.84 (1.8H, s).

¹³C NMR (DMSO$_{d6}$): 168.3, 167.9, 157, 156.9, 156.2, 156.1, 155.3, 155.3, 155.3, 155.3, 149.1, 149, 149, 149, 148.9, 147.5, 147.5, 147.5, 147.4, 147.4, 147.4, 147.4, 147.3, 145.9, 145.9, 145.9, 145.8, 128.2, 128.1, 118.9, 118.9, 118.8, 118.8, 118.8, 118.7, 118.7, 118.6, 116.9, 116.6, 116.5, 116.4, 116.4, 116.3, 112, 112, 111.9, 111.9, 111.8, 111.8, 111.8, 111.8, 58.5, 58.3, 51.4, 50, 49.4, 36.3, 34.7, 33.2, 31.5, 29.4, 29.1, 29, 29.

Example 294: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-cyclohexylacetamide

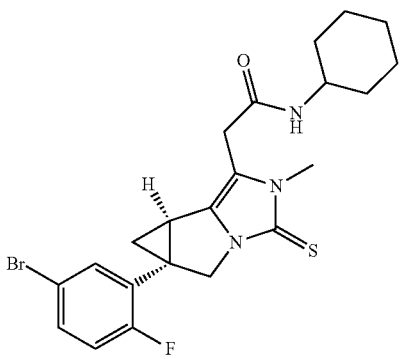

Compound was prepared analogous manner to Example 32 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

¹H NMR (DMSO$_{d6}$): 8.01 (1H, d, J=7.8 Hz), 7.58 (1H, dd, J=2.5, 8.9 Hz), 7.55 (1H, m), 7.24 (1H, dd, J=10.1, 8.7 Hz), 4.14 (1H, d, J=12.0 Hz), 3.85 (1H, d, J=12.0 Hz), 3.55 (1H, m), 3.47 (2H, m), 3.34 (3H, s), 2.87 (1H, dd, J=8.3, 4.2 Hz), 1.75 (2H, m), 1.70 (1H, dd, J=5.5, 8.4 Hz), 1.67 (2H, m), 1.55 (1H, m), 1.25 (2H, m), 1.21-1.08 (4H, m).

¹³C NMR (DMSO$_{d6}$): 166.6, 161.8, 160.1, 156.8, 133.1, 133, 132.4, 132.3, 130.9, 129.2, 129.1, 118, 117.8, 116.3, 116.2, 116.2, 52.4, 52.4, 47.8, 32.4, 32.3, 31.5, 31.4, 31.2, 25.2, 24.5, 22, 20.7.

Example 295: 2-((R)-2-methyl-3-thioxo-6-(2,3,5,6-tetrafluorophenyl)-2,5,6,7-tetrahydro-3H-pyrrolo[1,2-c]imidazol-1-yl)-N—((S)-tetrahydrofuran-3-yl) acetamide

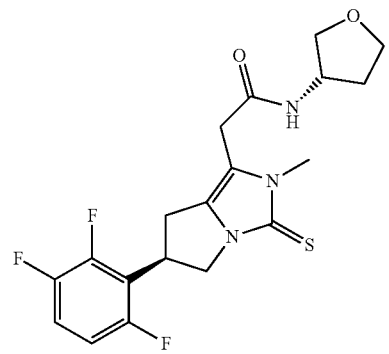

Compound was prepared analogous manner to Example 32 from (R)-1-(1H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone and isolated as an off-white powder.

¹H NMR (DMSO$_{d6}$): 8.37 (1H, br d, J=6.6 Hz), 7.85 (1H, m), 4.48 (1H, quin, J=8.5 Hz), 4.23 (2H, m), 3.84 (1H, dd, J=11.6, 7.6 Hz), 3.78 (1H, q, J=7.3 Hz), 3.72 (1H, dd, J=8.9, 6.0 Hz), 3.66 (1H, td, J=8.2, 5.6 Hz), 3.46 (1H, dd, J=9.0, 3.6 Hz), 3.43 (2H, m), 3.40 (3H, m), 3.31 (1H, dd, J=9.2, 15.8 Hz), 2.93 (1H, dd, J=16.0, 7.9 Hz), 2.08 (1H, m), 1.71 (1H, m).

¹³C NMR (DMSO$_{d6}$): 167.6, 156.2, 146.4, 146.4, 146.3, 146.3, 146.3, 146.2, 145.3, 145.3, 145.3, 145.2, 145.2, 144.8, 144.7, 144.6, 143.7, 143.7, 143.7, 143.7, 143.6, 143.6, 143.6, 128.2, 120.4, 116.4, 105.9, 105.7, 105.6, 72.4, 66.3, 49.8, 49.4, 34.9, 32, 31.5, 31.1, 29.1.

Example 296: 1-((S)-2-(fluoromethyl)pyrrolidin-1-yl)-2-((R)-2-methyl-3-thioxo-6-(2,3,6-trifluorophenyl)-2,5,6,7-tetrahydro-3H-pyrrolo[1,2-c]imidazol-1-yl)ethan-1-one

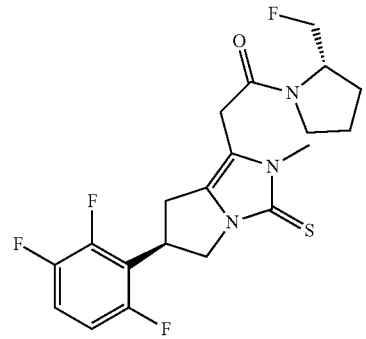 [SMILES: Cn1c(CC(=O)N2CCC[C@H]2CF)c2n(c1=S)C[C@@H](c1c(F)ccc(F)c1F)C2]

Compound was prepared analogous manner to Example 34 from (R)-2-(2-methyl-3-thioxo-6-(2,3,6-trifluorophenyl)-2,5,6,7-tetrahydro-3H-pyrrolo[1,2-c]imidazol-1-yl)acetic acid and isolated as a white solid.

¹H NMR (DMSO$_{d6}$): 7.47 (1H, m), 7.18 (1H, br t, J=9.6 Hz), 4.53-4.30 (3.25H, m), 4.24 (1H, m), 4.13 (0.75H, m), 3.82 (1.25H, m), 3.70 (1.5H, s), 3.70 (0.25H, m), 3.56-3.42 (1.75H, m), 3.37, 3.36 (3H, 2 s), 3.32-3.24 (1.25H, m), 2.89 (1H, m), 2.05-1.77 (4H, m).

$^{13}$C NMR (DMSO$_{d6}$): 167.1, 167, 156.9, 156.9, 156.3, 156.2, 155.3, 155.3, 155.3, 149.1, 149, 149, 148.9, 147.5, 147.5, 147.4, 147.3, 147.3, 145.9, 145.9, 145.9, 145.8, 128.3, 128.3, 118.9, 118.8, 118.8, 118.7, 116.5, 116.5, 116.4, 116.4, 116.3, 116.1, 112, 112, 111.9, 111.9, 111.8, 111.8, 111.8, 111.8, 84.6, 83.5, 83.1, 82, 56.4, 56.3, 56.2, 56.1, 49.5, 46.9, 45.7, 34.8, 34.7, 31.5, 30.5, 29.7, 29.7, 29.1, 27.3, 27.3, 26.5, 26.5, 23.8, 21.5.

Example 297: (R)-2-(2-methyl-6-(2,3,5,6-tetrafluorophenyl)-3-thioxo-2,5,6,7-tetrahydro-3H-pyrrolo[1,2-c]imidazol-1-yl)-N-(tetrahydro-2H-pyran-4-yl)acetamide

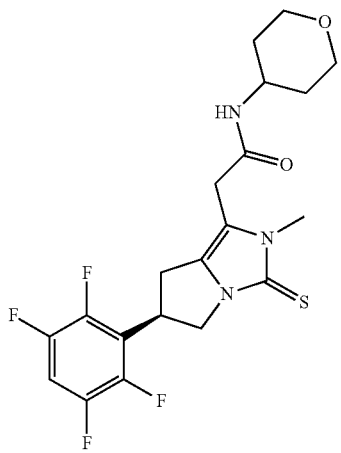 [SMILES: Cn1c(CC(=O)NC2CCOCC2)c2n(c1=S)C[C@@H](c1c(F)c(F)cc(F)c1F)C2]

Compound was prepared analogous manner to Example 32 from (R)-1-(1H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone and isolated as an off-white powder.

$^1$H NMR (DMSO$_{d6}$): 8.12 (1H, d, J=7.6 Hz), 7.86 (1H, m), 4.48 (1H, quin, J=8.5 Hz), 4.24 (1H, dd, J=11.6, 9.2 Hz), 3.84 (1H, dd, J=7.6, 11.7 Hz), 3.81 (2H, m), 3.75 (1H, m), 3.42 (2H, s), 3.40 (3H, s), 3.36-3.28 (3H, m), 2.93 (1H, dd, J=15.8, 7.9 Hz), 1.69 (2H, m), 1.38 (2H, m).

$^{13}$C NMR (DMSO$_{d6}$): 166.8, 156.2, 146.4, 146.3, 146.3, 146.3, 146.2, 146.2, 145.3, 145.3, 145.3, 145.2, 145.2, 145.2, 144.8, 144.8, 144.7, 144.7, 144.7, 144.6, 143.7, 143.7, 143.6, 143.6, 143.6, 143.6, 128.2, 120.5, 120.4, 120.3, 116.5, 105.9, 105.7, 105.6, 65.8, 49.4, 45.2, 34.9, 32.4, 32.4, 31.5, 31.3, 29.1.

Example 298: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-(2,2,2-trifluoroethyl)acetamide

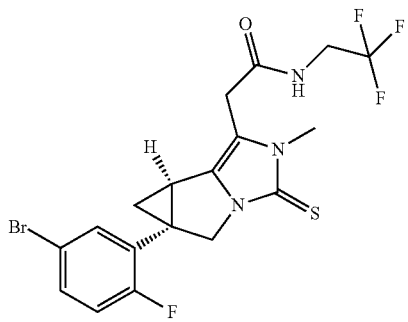

Compound was prepared analogous manner to Example 32 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

$^1$H NMR (DMSO$_{d6}$): 8.80 (1H, t, J=6.3 Hz), 7.58 (1H, dd, J=2.5, 6.7 Hz), 7.56 (1H, ddd, J=6.5, 4.4, 2.2 Hz), 7.24 (1H, dd, J=10.0, 8.8 Hz), 4.15 (1H, d, J=12.0 Hz), 3.95 (2H, m), 3.86 (1H, d, J=12.0 Hz), 3.64 (2H, m), 3.34 (3H, s), 2.91 (1H, dd, J=8.4, 4.3 Hz), 1.69 (1H, dd, J=8.3, 5.4 Hz), 1.15 (1H, t, J=4.8 Hz).

$^{13}$C NMR (DMSO$_{d6}$): 168.9, 161.8, 160.1, 157.1, 133, 133, 132.4, 132.3, 131.4, 129.1, 129, 127.5, 125.6, 123.8, 121.9, 118, 117.8, 116.2, 116.2, 115.3, 52.5, 52.4, 31.5, 31.3, 30.8, 22.8, 22, 20.6.

Example 299: (R)-2-(2-methyl-6-(2,3,6-trifluorophenyl)-3-thioxo-2,5,6,7-tetrahydro-3H-pyrrolo[1,2-c]imidazol-1-yl)-N-(tetrahydro-2H-pyran-4-yl)acetamide

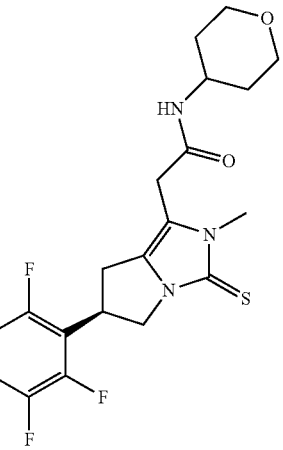

Compound was prepared analogous manner to Example 32 from (R)-1-(H-imidazol-1-yl)-2-(6-(2,3,6-trifluorophenyl)-3-thioxo-3,5,6,7-tetrahydro-2H-pyrrolo[1,2-c]imidazol-1-yl)ethanone and isolated as a white powder.

$^1$H NMR (DMSO$_{d6}$): 8.12 (1H, d, J=7.6 Hz), 7.47 (1H, m), 7.18 (1H, br t, J=9.6 Hz), 4.43 (1H, quin, J=8.6 Hz), 4.23 (1H, dd, J=9.7, 11.3 Hz), 3.79 (3H, m), 3.75 (1H, m), 3.42 (2H, m), 3.40 (3H, s), 3.33 (2H, m), 3.29 (1H, dd, J=9.3, 15.7 Hz), 2.90 (1H, dd, J=15.7, 8.2 Hz), 1.69 (2H, m d), 1.38 (2H, m q).

$^{13}$C NMR (DMSO$_{d6}$): 166.8, 156.9, 156.9, 156.2, 155.3, 155.3, 155.3, 155.3, 149.1, 149, 149, 148.9, 147.5, 147.5, 147.4, 147.4, 147.4, 147.3, 145.9, 145.9, 145.9, 145.8, 145.8, 128.3, 118.9, 118.8, 118.8, 118.7, 116.5, 116.4, 116.4, 116.3, 112, 112, 111.9, 111.9, 111.8, 111.8, 111.8, 65.8, 49.4, 45.2, 34.7, 32.4, 31.5, 31.3, 29.2.

Example 300: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-(2,2,2-trifluoroethyl)acetamide

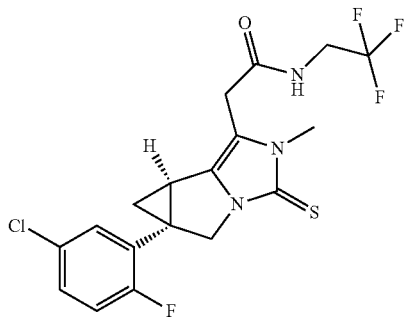 [SMILES: Cn1c(CC(=O)NCC(F)(F)F)c2n(c1=S)C[C@@]1(c3cc(Cl)ccc3F)C[C@@H]21]

Compound was prepared analogous manner to Example 32 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

$^1$H NMR (DMSO$_{d6}$): 8.80 (1H, t, J=6.3 Hz), 7.46 (1H, dd, J=6.5, 2.7 Hz), 7.43 (1H, ddd, J=8.8, 4.4, 2.7 Hz), 7.30 (1H, dd, J=9.9, 8.7 Hz), 4.15 (1H, d, J=12.0 Hz), 3.95 (2H, m), 3.86 (1H, d, J=12.0 Hz), 3.64 (2H, m), 3.34 (3H, s), 2.91 (1H, dd, J=8.4, 4.3 Hz), 1.69 (1H, dd, J=8.4, 5.3 Hz), 1.16 (1H, t, J=4.8 Hz).

$^{13}$C NMR (DMSO$_{d6}$): 168.9, 161.3, 159.6, 157.1, 131.4, 130.2, 130.2, 129.4, 129.3, 128.7, 128.6, 128.3, 128.3, 127.5, 125.6, 123.8, 121.9, 117.6, 117.4, 115.3, 52.4, 52.4, 39.9, 31.5, 31.3, 30.8, 22, 20.6.

Example 301: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N—((R)-tetrahydro-2H-pyran-3-yl)acetamide

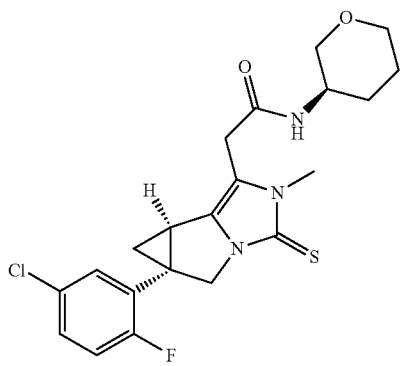 [SMILES: Cn1c(CC(=O)N[C@@H]2CCCOC2)c2n(c1=S)C[C@@]1(c3cc(Cl)ccc3F)C[C@@H]21]

Compound was prepared analogous manner to Example 34 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)acetic acid and isolated as a beige solid.

$^1$H NMR (DMSO$_{d6}$): 8.15 (1H, d, J=7.3 Hz), 7.47 (1H, dd, J=6.5, 2.6 Hz), 7.43 (1H, ddd, J=8.7, 4.3, 2.8 Hz), 7.30 (1H, dd, J=10.0, 8.8 Hz), 4.14 (1H, d, J=12.0 Hz), 3.85 (1H, d, J=12.0 Hz), 3.70 (2H, m), 3.65 (1H, m), 3.52 (2H, m), 3.38 (1H, m), 3.34 (3H, s), 3.14 (1H, m), 2.88 (1H, dd, J=8.4, 4.1 Hz), 1.83 (1H, m), 1.70 (1H, dd, J=5.5, 8.4 Hz), 1.68 (1H, m), 1.49 (2H, m), 1.13 (1H, t, J=4.8 Hz).

$^{13}$C NMR (DMSO$_{d6}$): 167.4, 161.3, 159.6, 156.8, 130.9, 130.2, 130.2, 129.4, 129.3, 128.7, 128.6, 128.3, 128.3, 117.6, 117.4, 116.2, 70.1, 67, 52.4, 52.4, 45.2, 31.5, 31.4, 31.1, 28.6, 23.9, 22.1, 20.7.

Example 302: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-cyclohexylacetamide

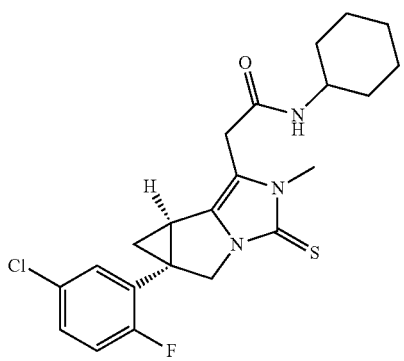 [SMILES: Cn1c(CC(=O)NC2CCCCC2)c2n(c1=S)C[C@@]1(c3cc(Cl)ccc3F)C[C@@H]21]

Compound was prepared analogous manner to Example 32 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

$^1$H NMR (DMSO$_{d6}$): 8.01 (1H, d, J=7.8 Hz), 7.46 (1H, dd, J=6.5, 2.6 Hz), 7.43 (1H, ddd, J=8.7, 4.3, 2.7 Hz), 7.30 (1H, dd, J=9.9, 8.9 Hz), 4.14 (1H, d, J=12.0 Hz), 3.85 (1H, d, J=12.0 Hz), 3.55 (1H, m), 3.48 (2H, m), 3.35 (3H, s), 2.88 (1H, dd, J=8.3, 4.2 Hz), 1.75 (2H, br d, J=11.2 Hz), 1.70 (1H, dd, J=5.4, 8.3 Hz), 1.69 (2H, m), 1.55 (1H, m), 1.25 (2H, m), 1.15 (4H, m). 166.6, 161.3, 159.6, 156.8, 130.9, 130.2, 130.2, 129.4, 129.3, 128.8, 128.6, 128.3, 128.3, 117.6, 117.4, 116.3, 52.4, 52.4, 47.8, 32.4, 32.3, 31.5, 31.4, 31.2, 25.2, 24.5, 22, 20.8.

Example 303: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-isopropylacetamide

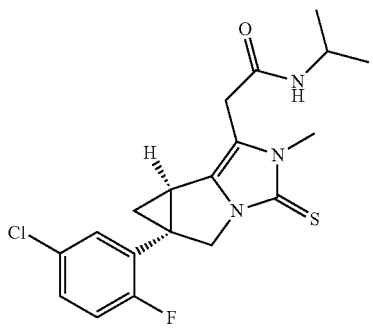 [SMILES: CC(C)NC(=O)Cc1c2n(c(=S)n1C)C[C@@]1(c3cc(Cl)ccc3F)C[C@@H]21]

Compound was prepared analogous manner to Example 32 from 2-((5aS,6aR)-5a-(5-chloro-2-fluorophenyl)-2-methyl- 3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a grey solid.

¹H NMR (DMSO_d6): 8.02 (1H, d, J=7.6 Hz), 7.47 (1H, dd, J=6.5, 2.7 Hz), 7.43 (1H, ddd, J=8.7, 4.4, 2.7 Hz), 7.30 (1H, dd, J=10.0, 8.8 Hz), 4.14 (1H, d, J=12.0 Hz), 3.85 (2H, m), 3.46 (2H, d, J=7.3 Hz), 3.35 (3H, s), 2.88 (1H, dd, J=8.4, 4.2 Hz), 1.70 (1H, dd, J=8.4, 5.4 Hz), 1.14 (1H, t, J=4.8 Hz), 1.07 (6H, d, J=6.6 Hz).

¹³C NMR (DMSO_d6): 166.7, 161.3, 159.6, 156.8, 130.9, 130.2, 130.2, 129.4, 129.3, 128.8, 128.7, 128.3, 128.3, 117.6, 117.4, 116.3, 52.4, 52.4, 40.7, 31.5, 31.4, 31.2, 22.3, 22.3, 22.1, 20.7.

Example 304: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-(cyanomethyl)acetamide

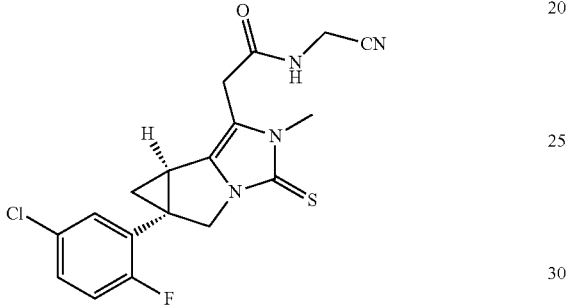

Compound was prepared analogous manner to Example 32 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

¹H NMR (DMSO_d6): 8.77 (1H, t, J=5.6 Hz), 7.47 (1H, dd, J=6.5, 2.6 Hz), 7.43 (1H, ddd, J=8.7, 4.3, 2.8 Hz), 7.30 (1H, dd, J=9.8, 8.9 Hz), 4.18 (2H, d, J=5.6 Hz), 4.16 (1H, d, J=12.0 Hz), 3.87 (1H, d, J=12.0 Hz), 3.63 (2H, m), 3.34 (3H, s), 2.92 (1H, dd, J=8.4, 4.3 Hz), 1.68 (1H, dd, J=8.3, 5.4 Hz), 1.18 (1H, t, J=4.8 Hz).

¹³C NMR (DMSO_d6): 168.7, 161.2, 159.6, 157.1, 131.4, 130.2, 130.1, 129.4, 129.3, 128.7, 128.6, 128.3, 128.3, 117.6, 117.5, 117.4, 115.1, 52.4, 31.6, 31.3, 30.7, 27.3, 22.1, 20.6.

Example 305: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-(cyanomethyl)acetamide

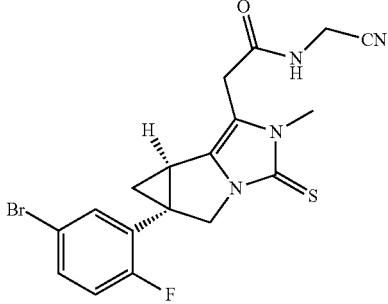 [SMILES: Cn1c(CC(=O)NCC#N)c2n(c1=S)C[C@@]1(c3cc(Cl)ccc3F)C[C@@H]21]

Compound was prepared analogous manner to Example 32 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a white solid.

¹H NMR (DMSO_d6): 8.77 (1H, t, J=5.6 Hz), 7.59 (1H, dd, J=6.7, 2.6 Hz), 7.56 (1H, ddd, J=8.6, 4.5, 2.6 Hz), 7.24 (1H, dd, J=8.7, 10.2 Hz), 4.18 (2H, d, J=5.6 Hz), 4.15 (1H, d, J=12.0 Hz), 3.86 (1H, d, J=12.0 Hz), 3.63 (2H, m), 3.34 (3H, s), 2.92 (1H, dd, J=8.4, 4.2 Hz), 1.68 (1H, dd, J=8.4, 5.4 Hz), 1.18 (1H, t, J=4.8 Hz).

¹³C NMR (DMSO_d6): 168.7, 161.8, 160.1, 157.1, 133, 133, 132.4, 132.3, 131.4, 129.1, 129, 118, 117.8, 117.5, 116.2, 116.2, 115.1, 52.5, 31.5, 31.3, 30.7, 27.3, 22.1, 20.6.

Example 306: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N—((S)-tetrahydrofuran-3-yl)acetamide

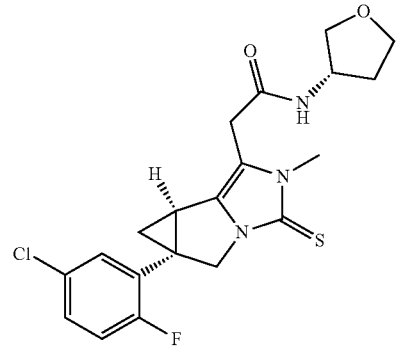 [SMILES: Cn1c(CC(=O)N[C@H]2CCOC2)c2n(c1=S)C[C@@]1(c3cc(Cl)ccc3F)C[C@@H]21]

Compound was prepared analogous manner to Example 32 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a light beige solid.

¹H NMR (DMSO_d6): 8.39 (1H, br d, J=6.6 Hz), 7.47 (1H, dd, J=6.5, 2.7 Hz), 7.43 (1H, ddd, J=8.7, 4.3, 2.7 Hz), 7.30 (1H, dd, J=9.1, 9.9 Hz), 4.26 (1H, m), 4.15 (1H, d, J=12.0 Hz), 3.86 (1H, d, J=12.0 Hz), 3.80 (1H, q, J=7.3 Hz), 3.74 (1H, dd, J=9.0, 5.9 Hz), 3.67 (1H, td, J=8.2, 5.6 Hz), 3.51 (2H, m), 3.49 (1H, dd, J=3.6, 9.0 Hz), 3.34 (3H, s), 2.89 (1H, dd, J=8.3, 4.2 Hz), 2.10 (1H, dq, J=12.7, 7.6 Hz), 1.75 (1H, m), 1.70 (1H, dd, J=8.3, 5.4 Hz), 1.13 (1H, t, J=4.8 Hz).

¹³C NMR (DMSO_d6): 167.7, 161.3, 159.6, 156.8, 131, 130.2, 130.2, 129.4, 129.3, 128.8, 128.6, 128.3, 128.3, 117.6, 117.4, 116.1, 72.4, 66.3, 52.4, 52.4, 49.8, 32, 31.5, 31.4, 31, 22.1, 20.7.

Example 307: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-N—((R)-tetrahydrofuran-3-yl)acetamide

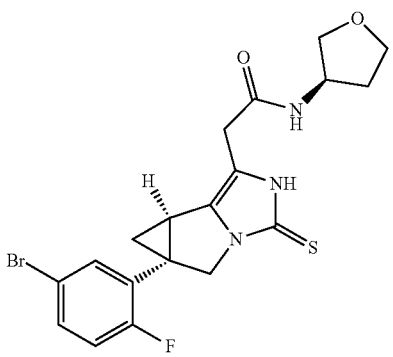 [SMILES: O=C(Cc1[nH]c(=S)n2c1[C@@H]1C[C@]1(c1cc(Br)ccc1F)C2)N[C@@H]1CCOC1]

Compound was prepared analogous manner to Example 32 from 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a brown solid.

$^1$H NMR (DMSO$_{d6}$): 11.66 (1H, s), 8.23 (1H, br d, J=6.6 Hz), 7.56 (3H, m), 7.24 (2H, dd, J=10.1, 8.5 Hz), 4.24 (1H, m), 4.07 (1H, d, J=12.0 Hz), 3.78 (2H, m), 3.74 (1H, dd, J=8.9, 5.9 Hz), 3.67 (1H, td, J=8.2, 5.6 Hz), 3.49 (1H, dd, J=8.9, 3.7 Hz), 3.30 (2H, m), 2.81 (1H, dd, J=8.4, 4.1 Hz), 2.08 (1H, m), 1.75 (1H, m), 1.66 (1H, dd, J=8.3, 5.4 Hz), 1.12 (1H, t, J=4.8 Hz).

$^{13}$C NMR (DMSO$_{d6}$): 167.6, 161.8, 160.1, 155.9, 133, 132.3, 132.3, 131.7, 129.3, 129.2, 118, 117.8, 116.2, 113.9, 72.4, 66.3, 51.5, 49.8, 32.2, 32, 31.2, 22.1, 20.7.

Example 308: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N—((S)-tetrahydrofuran-3-yl)acetamide

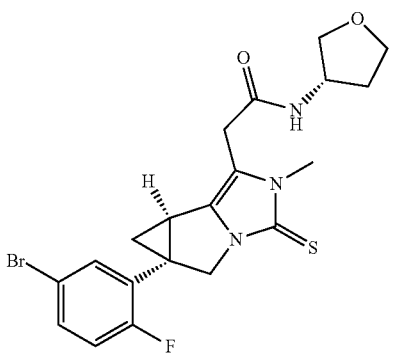

Compound was prepared analogous manner to Example 32 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

$^1$H NMR (DMSO$_{d6}$): 8.39 (1H, d, J=6.6 Hz), 7.58 (1H, dd, J=6.6, 2.5 Hz), 7.56 (1H, ddd, J=8.7, 4.5, 2.6 Hz), 7.24 (1H, dd, J=10.1, 8.8 Hz), 4.26 (1H, m), 4.14 (1H, d, J=12.0 Hz), 3.85 (1H, d, J=12.2 Hz), 3.80 (1H, q, J=7.3 Hz), 3.74 (1H, dd, J=8.9, 6.0 Hz), 3.67 (1H, td, J=8.2, 5.6 Hz), 3.51 (2H, m), 3.49 (1H, dd, J=3.7, 9.0 Hz), 3.35 (3H, s), 2.89 (1H, dd, J=8.3, 4.2 Hz), 2.09 (1H, m), 1.75 (1H, m), 1.70 (1H, dd, J=8.3, 5.4 Hz), 1.13 (1H, t, J=4.8 Hz).

$^{13}$C NMR (DMSO$_{d6}$): 167.7, 161.8, 160.1, 156.8, 133, 133, 132.3, 132.3, 131, 129.2, 129.1, 118, 117.8, 116.2, 116.2, 116.1, 72.4, 66.3, 52.4, 49.8, 32, 31.5, 31.4, 31, 22.1, 20.7.

Example 309: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(pyrrolidin-1-yl)ethan-1-one

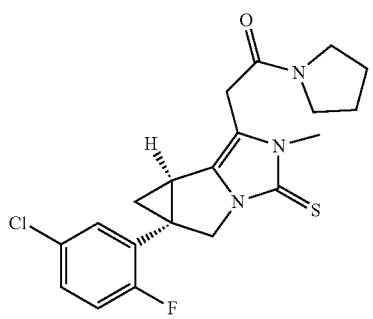

Compound was prepared analogous manner to Example 32 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

$^1$H NMR (DMSO$_{d6}$): 7.46 (1H, dd, J=6.5, 2.6 Hz), 7.43 (1H, ddd, J=8.7, 4.3, 2.8 Hz), 7.30 (1H, dd, J=8.9, 9.8 Hz), 4.15 (1H, d, J=12.0 Hz), 3.86 (1H, d, J=12.0 Hz), 3.72 (2H, m), 3.52 (2H, t, J=6.8 Hz), 3.34 (3H, s), 3.32 (2H, t, J=7.1 Hz), 2.87 (1H, dd, J=8.2, 4.3 Hz), 1.91 (2H, quin, J=6.7 Hz), 1.79 (2H, quin, J=6.8 Hz), 1.69 (1H, dd, J=8.3, 5.4 Hz), 1.12 (1H, t, J=4.8 Hz).

$^{13}$C NMR (DMSO$_{d6}$): 166.2, 161.3, 159.6, 156.8, 130.7, 130.2, 130.2, 129.4, 129.3, 128.7, 128.6, 128.3, 128.3, 117.6, 117.4, 116, 52.4, 52.4, 46.1, 45.6, 31.6, 31.5, 30.4, 25.6, 24, 22.1, 20.7.

Example 310: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(pyrrolidin-1-yl)ethan-1-one

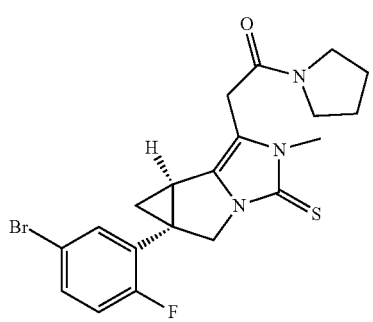 [SMILES: Cn1c(CC(=O)N2CCCC2)c2n(c1=S)C[C@@]1(c3cc(Cl)ccc3F)C[C@@H]21]

Compound was prepared analogous manner to Example 32 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

$^{1}$H NMR (DMSO$_{d6}$): 7.43 (2H, m), 7.00 (1H, dd, J=9.8, 8.6 Hz), 4.23 (1H, d, J=12.2 Hz), 3.99 (1H, d, J=12.0 Hz), 3.53 (2H, s), 3.46 (3H, s), 3.43 (4H, m), 2.59 (1H, dd, J=8.3, 4.2 Hz), 1.98 (2H, m), 1.87 (2H, m), 1.61 (1H, dd, J=8.2, 5.6 Hz), 1.15 (1H, m).

$^{13}$C NMR (DMSO$_{d6}$): 166.4, 162.7, 161.1, 158.7, 133.8, 133.8, 133, 132.9, 131.4, 129.4, 129.3, 118.2, 118.1, 117.1, 117.1, 116, 53.4, 53.4, 47.4, 46.7, 32.4, 32.3, 32.1, 26.8, 24.9, 22.6, 21.7.

Example 311: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(piperidin-1-yl)ethan-1-one

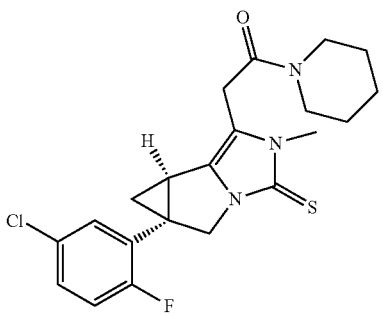 [SMILES: Cn1c(CC(=O)N2CCCCC2)c2n(c1=S)C[C@@]1(c3cc(Cl)ccc3F)C[C@@H]21]

Compound was prepared analogous manner to Example 32 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as an off-white solid.

$^{1}$H NMR (DMSO$_{d6}$): 7.46 (1H, dd, J=6.5, 2.7 Hz), 7.43 (1H, ddd, J=8.7, 4.3, 2.8 Hz), 7.30 (1H, dd, J=10.1, 8.7 Hz), 4.15 (1H, d, J=12.0 Hz), 3.86 (1H, d, J=12.0 Hz), 3.79 (2H, m), 3.51-3.40 (4H, m), 3.32 (3H, s), 2.87 (1H, dd, J=8.4, 4.1 Hz), 1.71 (1H, dd, J=8.3, 5.4 Hz), 1.59 (2H, m), 1.53 (2H, m), 1.45 (2H, m), 1.12 (1H, t, J=4.8 Hz).

$^{13}$C NMR (DMSO$_{d6}$): 166.2, 161.3, 159.6, 156.9, 130.6, 130.2, 130.2, 129.4, 129.3, 128.7, 128.6, 128.3, 128.3, 117.6, 117.4, 116.3, 52.4, 52.4, 46.2, 42.3, 31.6, 31.5, 29.1, 26, 25.2, 23.9, 22.1, 20.7.

Example 312: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(piperidin-1-yl)ethan-1-one

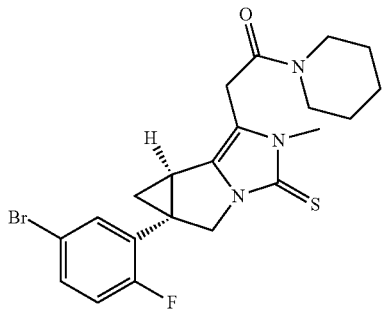

Compound was prepared analogous manner to Example 32 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as an off-white solid.

$^{1}$H NMR (DMSO$_{d6}$): 7.56 (2H, m), 7.24 (1H, dd, J=10.0, 8.7 Hz), 4.15 (1H, d, J=12.0 Hz), 3.85 (1H, d, J=12.0 Hz), 3.79 (2H, m), 3.46 (4H, m), 3.32 (3H, s), 2.87 (1H, dd, J=8.3, 4.2 Hz), 1.71 (1H, dd, J=8.2, 5.4 Hz), 1.59 (2H, m), 1.53 (2H, m), 1.45 (2H, m), 1.11 (1H, t, J=4.8 Hz).

$^{13}$C NMR (DMSO$_{d6}$): 166.2, 161.8, 160.1, 156.9, 133, 133, 132.3, 132.3, 130.6, 129.1, 129, 118, 117.8, 116.3, 116.2, 116.2, 52.4, 52.4, 46.2, 42.3, 31.5, 31.4, 29.1, 26, 25.2, 23.9, 22.1, 20.7.

Example 313: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-(tetrahydro-2H-pyran-4-yl)acetamide

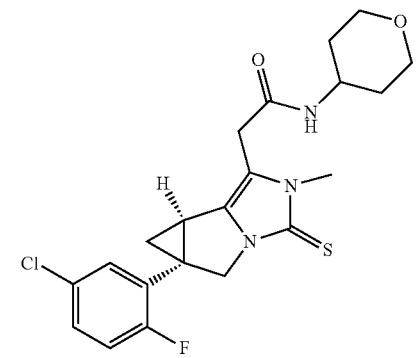 [SMILES: Cn1c(CC(=O)NC2CCOCC2)c2n(c1=S)C[C@@]1(c3cc(Cl)ccc3F)C[C@@H]21]

Compound was prepared analogous manner to Example 32 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a light beige solid.

$^{1}$H NMR (DMSO$_{d6}$): 8.14 (1H, d, J=7.6 Hz), 7.46 (1H, dd, J=6.6, 2.6 Hz), 7.43 (1H, ddd, J=8.7, 4.4, 2.8 Hz), 7.30 (1H, t, J=9.3 Hz), 4.14 (1H, d, J=12.0 Hz), 3.86 (1H, d, J=12.0 Hz), 3.82 (2H, dt, J=11.2, 3.1 Hz), 3.78 (1H, m), 3.50

(2H, m), 3.35 (2H, m), 3.35 (3H, s), 2.88 (1H, dd, J=8.4, 4.3 Hz), 1.71 (3H, m), 1.41 (2H, m), 1.13 (1H, t, J=4.8 Hz).

$^{13}$C NMR (DMSO$_{d6}$): 166.9, 161.3, 159.6, 156.8, 130.9, 130.2, 130.2, 129.4, 129.3, 128.7, 128.6, 128.3, 128.3, 117.6, 117.4, 116.2, 65.8, 52.4, 52.4, 45.2, 32.4, 32.4, 31.5, 31.4, 31.2, 22, 21.6, 20.8.

Example 314: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-(tetrahydro-2H-pyran-4-yl)acetamide

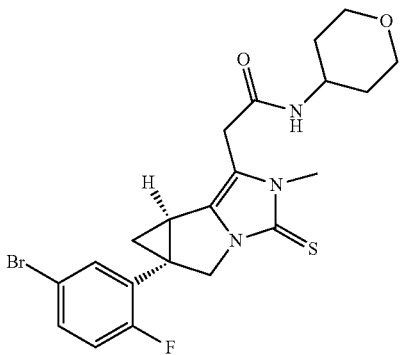

Compound was prepared analogous manner to Example 32 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

$^{1}$H NMR (DMSO$_{d6}$): 8.14 (1H, d, J=7.6 Hz), 7.58 (1H, m), 7.56 (1H, ddd, J=6.5, 4.4, 2.2 Hz), 7.24 (1H, dd, J=10.1, 8.7 Hz), 4.14 (1H, d, J=12.0 Hz), 3.85 (1H, d, J=12.2 Hz), 3.82 (2H, m), 3.77 (1H, m), 3.50 (2H, m), 3.35 (3H, s), 3.34 (2H, m), 2.88 (1H, dd, J=8.4, 4.1 Hz), 1.72 (2H, m), 1.71 (1H, dd, J=5.4, 8.5 Hz), 1.41 (2H, m), 1.13 (1H, t, J=4.8 Hz).

$^{13}$C NMR (DMSO$_{d6}$): 166.9, 161.8, 160.1, 156.8, 133.1, 133, 132.3, 132.3, 130.9, 129.2, 129.1, 118, 117.8, 116.2, 116.2, 65.8, 52.4, 52.4, 45.2, 32.4, 32.3, 31.5, 31.4, 31.2, 22, 20.7.

Example 315: (R)-2-(2-methyl-6-(2,3,5,6-tetrafluorophenyl)-3-thioxo-2,5,6,7-tetrahydro-3H-pyrrolo[1,2-c]imidazol-1-yl)-N-(2,2,2-trifluoroethyl)acetamide

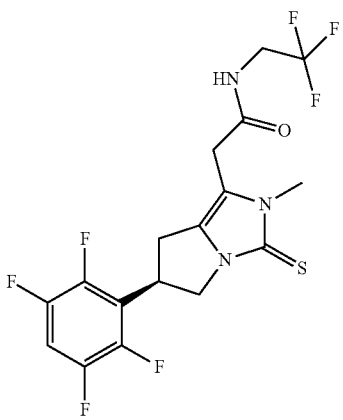 [SMILES: Cn1c(CC(=O)NCC(F)(F)F)c2n(c1=S)C[C@@H](c1c(F)c(F)cc(F)c1F)C2]

Compound was prepared analogous manner to Example 32 from (R)-1-(1H-imidazol-1-yl)-2-(2-methyl-6-(2,3,5,6-tetrafluorophenyl)-3-thioxo-2,5,6,7-tetrahydro-3H-pyrrolo[1,2-c]imidazol-1-yl)ethan-1-one and isolated as a light cream powder.

$^{1}$H NMR (DMSO$_{d6}$): 8.77 (1H, br t, J=6.2 Hz), 7.85 (1H, m), 4.48 (1H, quin, J=8.5 Hz), 4.25 (1H, dd, J=11.4, 9.3 Hz), 3.93 (2H, m), 3.85 (1H, dd, J=11.6, 7.6 Hz), 3.57 (2H, m), 3.39 (3H, s), 3.32 (1H, dd, J=9.2, 16.0 Hz), 2.93 (1H, dd, J=15.9, 8.0 Hz).

$^{13}$C NMR (DMSO$_{d6}$): 168.7, 156.5, 146.4, 146.4, 146.3, 146.3, 146.3, 146.3, 146.2, 145.3, 145.3, 145.3, 145.3, 145.2, 145.2, 145.2, 145.2, 144.8, 144.8, 144.7, 144.7, 144.6, 144.6, 143.7, 143.7, 143.7, 143.7, 143.6, 143.6, 143.6, 143.6, 128.6, 127.5, 125.6, 123.8, 121.9, 120.4, 120.3, 120.2, 115.7, 105.9, 105.7, 105.6, 49.4, 39.5, 34.9, 31.4, 30.9, 29.

Example 316: (R)-2-(2-methyl-3-thioxo-6-(2,3,5,6-tetrafluorophenyl)-2,5,6,7-tetrahydro-3H-pyrrolo[1,2-c]imidazol-1-yl)-N-(oxazol-2-yl)acetamide

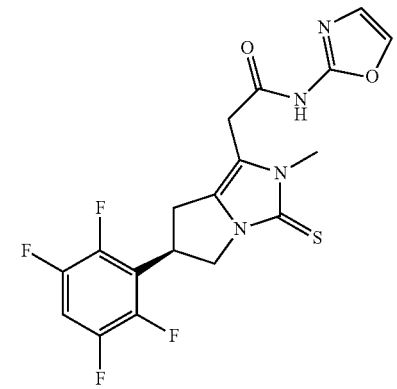 [SMILES: Cn1c(CC(=O)Nc2ncco2)c2n(c1=S)C[C@@H](c1c(F)c(F)cc(F)c1F)C2]

Compound was prepared analogous manner to Example 32 from (R)-1-(H-imidazol-1-yl)-2-(2-methyl-6-(2,3,5,6-tetrafluorophenyl)-3-thioxo-2,5,6,7-tetrahydro-3H-pyrrolo[1,2-c]imidazol-1-yl)ethan-1-one and isolated as a cream powder.

$^{1}$H NMR (DMSO$_{d6}$): 1.45 (1H, br s), 7.87 (1H, d, J=0.9 Hz), 7.85 (1H, m), 7.10 (1H, d, J=0.9 Hz), 4.49 (1H, quin, J=8.5 Hz), 4.26 (1H, dd, J=11.4, 9.3 Hz), 3.86 (1H, dd, J=11.7, 7.7 Hz), 3.74 (2H, m), 3.41 (3H, m), 3.37 (1H, dd, J=16.0, 8.4 Hz), 2.96 (1H, dd, J=16.0, 7.9 Hz).

$^{13}$C NMR (DMSO$_{d6}$): 156.5, 152.9, 146.4, 146.4, 146.3, 146.3, 146.3, 146.3, 146.2, 145.3, 145.3, 145.3, 145.3, 145.2, 145.2, 145.2, 144.8, 144.8, 144.7, 144.7, 144.7, 144.6, 144.6, 143.7, 143.7, 143.7, 143.7, 143.6, 143.6, 136.2, 128.9, 126.6, 120.4, 120.3, 120.2, 115.2, 105.9, 105.7, 105.6, 49.5, 34.8, 31.6, 31.4, 29.1, 29.

Example 317: (S)-2-(6-(3-chloro-2,6-difluorophenyl)-2-methyl-3-thioxo-2,5,6,7-tetrahydro-3H-pyrrolo[1,2-c]imidazol-1-yl)-N-(oxazol-2-yl)acetamide

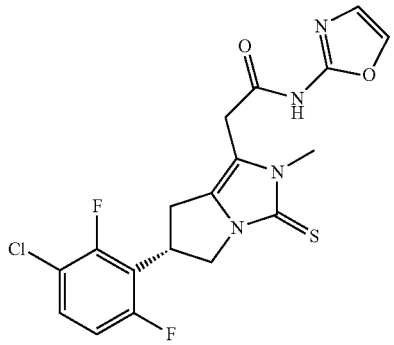 [SMILES: Cn1c(CC(=O)Nc2ncco2)c2n(c1=S)C[C@H](c1c(F)ccc(Cl)c1F)C2]

Compound was prepared analogous manner to Example 32 from (S)-2-(6-(3-chloro-2,6-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as an off-white solid.

$^1$H NMR (DMSO$_{d6}$): 1.44 (1H, br s), 7.87 (1H, s), 7.61 (1H, td, J=8.7, 5.6 Hz), 7.21 (1H, t, J=9.3 Hz), 7.10 (1H, s), 4.45 (1H, quin, J=8.6 Hz), 4.24 (1H, m), 3.82 (1H, dd, J=11.6, 7.8 Hz), 3.78 (2H, br), 3.41 (3H, s), 3.31 (1H, m), 2.92 (1H, dd, J=16.0, 8.1 Hz).

$^{13}$C NMR (DMSO$_{d6}$): 166.6, 160.1, 160.1, 158.5, 158.5, 156.6, 156.5, 156.5, 154.9, 154.9, 152.9, 152.9, 136.2, 129.7, 129.7, 129.1, 126.6, 118.8, 118.6, 118.5, 116.1, 116, 115.9, 115.9, 115.1, 113.2, 113.2, 113.1, 113.1, 49.6, 34.7, 31.6, 31.4, 29.1.

Example 318: (R)-3-(2-methyl-3-thioxo-6-(2,3,5,6-tetrafluorophenyl)-2,5,6,7-tetrahydro-3H-pyrrolo[1,2-c]imidazol-1-yl)-1-morpholinopropan-1-one

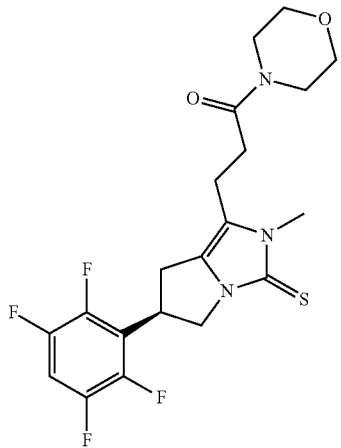 [SMILES: Cn1c(CCC(=O)N2CCOCC2)c2n(c1=S)C[C@@H](c1c(F)c(F)cc(F)c1F)C2]

Compound was prepared analogous manner to Example 32 from (R)-1-(1H-imidazol-1-yl)-3-(2-methyl-6-(2,3,5,6-tetrafluorophenyl)-3-thioxo-2,5,6,7-tetrahydro-3H-pyrrolo[1,2-c]imidazol-1-yl)propan-1-one and isolated as a yellowish powder.

$^1$H NMR (DMSO$_{d6}$): 7.86 (1H, m), 4.45 (1H, quin, J=8.6 Hz), 4.22 (1H, br dd, J=11.4, 9.2 Hz), 3.81 (1H, dd, J=11.7, 7.8 Hz), 3.52 (4H, m), 3.45 (3H, s), 3.41 (4H, m), 3.38 (1H, m), 3.01 (1H, br dd, J=15.6, 8.0 Hz), 2.72 (2H, br t, J=7.3 Hz), 2.62 (2H, t, J=7.6 Hz).

$^{13}$C NMR (DMSO$_{d6}$): 169.5, 155.8, 146.4, 146.4, 146.3, 146.3, 146.3, 146.2, 146.2, 145.3, 145.3, 145.3, 145.3, 145.2, 145.2, 145.2, 145.2, 144.8, 144.8, 144.7, 144.7, 144.6, 143.7, 143.7, 143.7, 143.6, 143.6, 143.6, 143.6, 143.6, 126.7, 120.8, 120.5, 120.4, 120.3, 105.9, 105.7, 105.5, 66, 66, 49.1, 45.1, 41.5, 34.9, 31.1, 29.7, 29.2, 19.6.

Example 319: 1-(6,6-dimethyl-3-azabicyclo[3.1.0]hexan-3-yl)-3-((R)-2-methyl-6-(2,3,5,6-tetrafluorophenyl)-3-thioxo-2,5,6,7-tetrahydro-3H-pyrrolo[1,2-c]imidazol-1-yl)propan-1-one

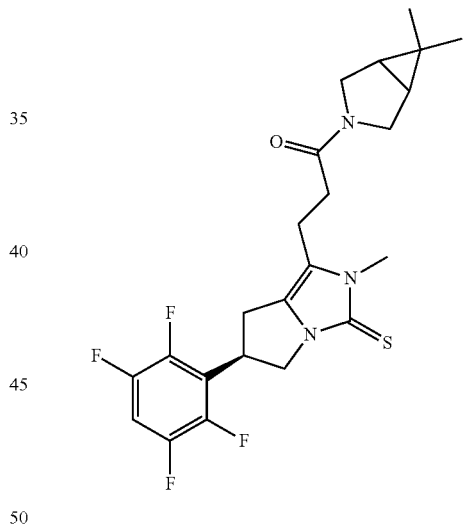

Compound was prepared analogous manner to Example 32 from (R)-1-(1H-imidazol-1-yl)-3-(2-methyl-6-(2,3,5,6-tetrafluorophenyl)-3-thioxo-2,5,6,7-tetrahydro-3H-pyrrolo[1,2-c]imidazol-1-yl)propan-1-one and isolated as a light beige solid.

$^1$H NMR (DMSO$_{d6}$): 7.86 (1H, m), 4.43 (1H, m), 4.20 (1H, m), 3.79 (1H, m), 3.60 (1H, m), 3.44 (3H, s), 3.40-3.29 (3H, m), 3.26 (1H, dd, J=12.4, 7.8 Hz), 2.97 (1H, m), 2.69 (2H, m), 2.49 (2H, m), 1.42 (1H, m), 1.36 (1H, m), 0.98 (3H, 2 s), 0.77 (3H, 2 s).

$^{13}$C NMR (DMSO$_{d6}$): 168.7, 155.9, 155.8, 146.4, 146.3, 145.3, 145.3, 144.8, 144.7, 143.7, 143.7, 143.6, 126.6, 126.5, 120.8, 120.8, 120.5, 120.4, 120.3, 120.2, 120.1, 105.9, 105.7, 105.6, 49, 49, 45.8, 45.8, 45.5, 34.9, 34.9, 31.3, 31.2, 31.1, 29.3, 29.2, 27.4, 27.3, 25.9, 25.9, 25.9, 19.2, 18.5, 18.5, 12.1, 12.1.

Example 320: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(piperazin-1-yl)ethan-1-one

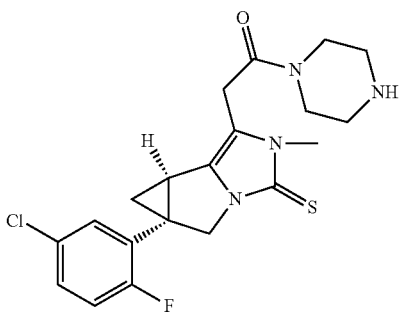 [SMILES: Cn1c(CC(=O)N2CCNCC2)c2n(c1=S)C[C@@]1(c3cc(Cl)ccc3F)C[C@@H]21]

Compound was prepared analogous manner to Example 32 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

$^1$H NMR (DMSO$_{d6}$): 7.46 (1H, dd, J=6.6, 2.6 Hz), 7.43 (1H, ddd, J=8.7, 4.4, 2.8 Hz), 7.30 (1H, dd, J=8.9, 9.9 Hz), 4.15 (1H, d, J=12.0 Hz), 3.86 (1H, d, J=12.0 Hz), 3.79 (2H, m), 3.44 (2H, m), 3.40 (2H, m), 3.32 (3H, s), 2.86 (1H, dd, J=8.3, 4.2 Hz), 2.72 (2H, m), 2.65 (2H, m), 1.71 (1H, dd, J=8.3, 5.4 Hz), 1.12 (1H, t, J=4.8 Hz).

$^{13}$C NMR (DMSO$_{d6}$): 166.5, 161.3, 159.6, 156.9, 130.6, 130.2, 130.2, 129.4, 129.3, 128.7, 128.6, 128.3, 128.3, 117.6, 117.4, 116.2, 64.9, 62.8, 52.4, 46.5, 45.8, 45.3, 42.5, 31.6, 31.5, 29, 22.1, 20.7, 15.2.

Example 321: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(piperazin-1-yl)ethan-1-one Hydrochloride

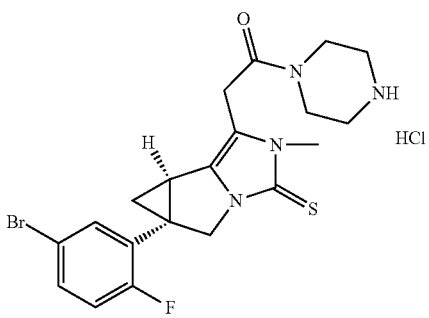 [SMILES: Cn1c(CC(=O)N2CCNCC2)c2n(c1=S)C[C@@]1(c3cc(Br)ccc3F)C[C@@H]21 ; Cl]

Compound was prepared analogous manner to Example 32 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one on the reaction with piperazine followed by salt formation in a mixture of ethyl acetate and 2M HCl in diethyl ether. The product was isolated as a yellow solid.

$^1$H NMR (DMSO$_{d6}$): 9.30 (2H, m), 7.61-7.53 (2H, m), 7.24 (1H, dd, J=9.9, 8.7 Hz), 4.15 (1H, d, J=12.0 Hz), 3.89 (2H, s), 3.86 (1H, d, J=12.2 Hz), 3.78 (2H, m), 3.70 (2H, m), 3.32 (3H, s), 3.17 (2H, m), 3.08 (2H, m), 2.85 (1H, dd, J=8.3, 4.2 Hz), 1.71 (1H, dd, J=8.3, 5.4 Hz), 1.13 (1H, t, J=4.8 Hz).

$^{13}$C NMR (DMSO$_{d6}$): 167, 161.8, 160.1, 157, 133.1, 133.1, 132.4, 132.3, 130.9, 129.1, 129, 118, 117.9, 116.2, 116.2, 115.7, 52.4, 42.6, 42.4, 42.1, 38.1, 31.6, 31.5, 28.8, 22.1, 20.7.

Example 322: (5aS,6aR)-5a-(5-chloro-2-fluorophenyl)-1-(2-(cyclopentylamino)ethyl)-2-methyl-5,5a,6,6a-tetrahydrocyclopropa[3,4]pyrrolo[1,2-c]imidazole-3(2H)-thione Hydrochloride

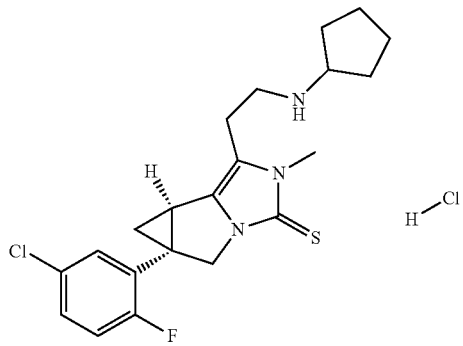 [SMILES: Cn1c(CCNC2CCCC2)c2n(c1=S)C[C@@]1(c3cc(Cl)ccc3F)C[C@@H]21 ; Cl]

Compound was prepared analogous manner to Example 35 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-cyclopentylacetamide (Example 273) and isolated as a yellow solid.

$^1$H NMR (DMSO$_{d6}$): 8.71 (1H, br s), 8.64 (1H, br s), 7.49 (1H, dd, J=6.4, 2.6 Hz), 7.45 (1H, m), 7.31 (1H, t, J=9.3 Hz), 4.15 (1H, d, J=12.2 Hz), 3.86 (1H, d, J=12.0 Hz), 3.55 (1H, m), 3.44 (3H, s), 3.18 (2H, br s), 3.03 (1H, dd, J=8.4, 4.3 Hz), 2.97 (2H, m), 1.99 (2H, m), 1.71 (3H, m), 1.62 (2H, td, J=12.8, 6.4 Hz), 1.56 (2H, m), 1.21 (1H, t, J=4.8 Hz).

$^{13}$C NMR (DMSO$_{d6}$): 161.3, 159.6, 157.3, 130.9, 130.2, 130.2, 129.4, 129.4, 128.7, 128.6, 128.3, 128.3, 117.6, 117.5, 116.3, 58.2, 52.4, 43.8, 31.7, 31.3, 29.2, 29.1, 23.6, 22, 21, 20.6.

Example 323: (R)-4-(2-(2-methyl-6-(2,3,5,6-tetrafluorophenyl)-3-thioxo-2,5,6,7-tetrahydro-3H-pyrrolo[1,2-c]imidazol-1-yl)acetyl)piperazin-2-one

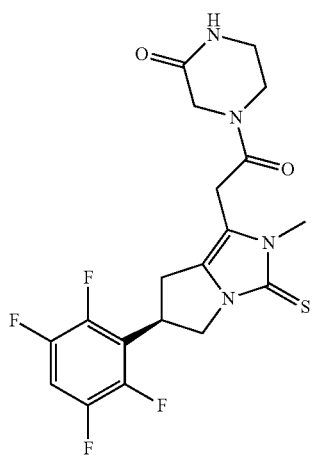 [SMILES: Cn1c(CC(=O)N2CCNC(=O)C2)c2n(c1=S)C[C@@H](c1c(F)c(F)cc(F)c1F)C2]

Compound was prepared analogous manner to Example 32 from (R)-1-(H-imidazol-1-yl)-2-(2-methyl-6-(2,3,5,6-tetrafluorophenyl)-3-thioxo-2,5,6,7-tetrahydro-3H-pyrrolo[1,2-c]imidazol-1-yl)ethan-1-one and isolated as a beige powder.

¹H NMR (DMSO$_{d6}$): 8.17, 8.11 (1H, 2 s), 7.85 (1H, m), 4.48 (1H, quin, J=8.5 Hz), 4.25 (1H, dd, J=9.7, 11.1 Hz), 4.11 (1H, s), 3.94 (1H, s), 3.84 (1H, dd, J=11.7, 7.7 Hz), 3.79 (2H, m), 3.66 (1H, m), 3.61 (1H, m), 3.36 (3H, 2 s), 3.32-3.25 (2H, m), 3.17 (1H, m), 2.90 (1H, br dd, J=15.8, 7.8 Hz).

¹³C NMR (DMSO$_{d6}$): 166.9, 166.7, 166.4, 165.8, 156.3, 156.3, 146.4, 146.4, 146.3, 146.2, 146.2, 145.3, 145.3, 145.3, 145.3, 145.2, 145.2, 144.8, 144.8, 144.7, 144.6, 143.7, 143.7, 143.7, 143.6, 143.6, 143.6, 143.6, 128.2, 128.1, 120.5, 120.4, 120.4, 120.3, 120.3, 120.2, 116.1, 116, 105.9, 105.7, 105.5, 49.4, 48.2, 45.7, 42.1, 38.4, 34.9, 34.9, 31.5, 29, 29.

Example 324: (R)-1-methyl-4-(2-(2-methyl-6-(2,3,5,6-tetrafluorophenyl)-3-thioxo-2,5,6,7-tetrahydro-3H-pyrrolo[1,2-c]imidazol-1-yl)acetyl)piperazin-2-one

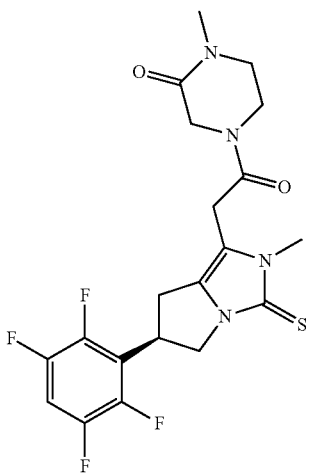 [SMILES: CN1CCN(C(=O)Cc2c3n(c(=S)n2C)C[C@@H](c2c(F)c(F)cc(F)c2F)C3)CC1=O]

Compound was prepared analogous manner to Example 32 from (R)-1-(1H-imidazol-1-yl)-2-(2-methyl-6-(2,3,5,6-tetrafluorophenyl)-3-thioxo-2,5,6,7-tetrahydro-3H-pyrrolo[1,2-c]imidazol-1-yl)ethan-1-one and isolated as a cream powder.

¹H NMR (DMSO$_{d6}$): 7.86 (1H, m), 4.48 (1H, quin, J=8.1 Hz), 4.25 (1H, br t, J=10.3 Hz), 4.16 (1H, s), 4.00 (1H, s), 3.90-3.73 (4H, m), 3.69 (1H, m), 3.41 (1H, m), 3.39-3.34 (3H, m), 3.32-3.25 (2H, m), 2.90 (1H, m), 2.86 (3H, s).

¹³C NMR (DMSO$_{d6}$): 166.6, 166.5, 164.6, 164, 156.3, 156.3, 146.4, 146.4, 146.3, 146.2, 146.2, 145.3, 145.3, 145.3, 145.3, 145.2, 145.2, 145.2, 145.2, 144.8, 144.8, 144.7, 144.7, 144.7, 144.6, 144.6, 143.7, 143.7, 143.7, 143.6, 143.6, 143.6, 128.1, 120.5, 120.4, 120.3, 116.1, 116, 105.9, 105.7, 105.5, 49.4, 48.4, 47.5, 47, 45.8, 42.1, 38.3, 34.9, 33.7, 33.5, 31.5, 29, 29, 28.8.

Example 325: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-((1r,4R)-4-hydroxycyclohexyl)acetamide

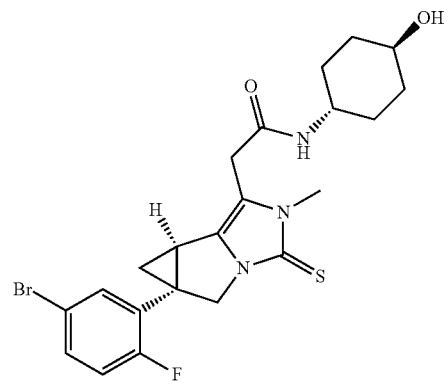 [SMILES: Cn1c(CC(=O)N[C@H]2CC[C@H](O)CC2)c2n(c1=S)C[C@@]1(c3cc(Br)ccc3F)C[C@@H]21]

Compound was prepared analogous manner to Example 25 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one using DIPEA as base and isolated as a beige solid.

¹H NMR (DMSO$_{d6}$): 7.98 (1H, d, J=7.8 Hz), 7.90-7.53 (2H, m), 7.24 (1H, dd, J=10.1, 8.7 Hz), 4.54 (1H, d, J=4.4 Hz), 4.14 (1H, d, J=12.0 Hz), 3.84 (1H, d, J=12.0 Hz), 3.47 (3H, m), 3.37 (1H, m), 3.34 (3H, s), 2.87 (1H, dd, J=8.4, 4.3 Hz), 1.79 (4H, m), 1.69 (1H, dd, J=8.4, 5.4 Hz), 1.19 (4H, m), 1.12 (1H, t, J=4.8 Hz).

¹³C NMR (DMSO$_{d6}$): 166.8, 161.8, 160.1, 156.8, 133.1, 133, 132.3, 132.3, 130.9, 129.2, 129.1, 118, 117.8, 116.3, 116.2, 116.2, 68.1, 62.8, 52.4, 47.5, 33.9, 31.5, 31.4, 31.3, 30.2, 30.1, 22, 20.7.

Example 326: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(4-methylpiperazin-1-yl)ethan-1-one

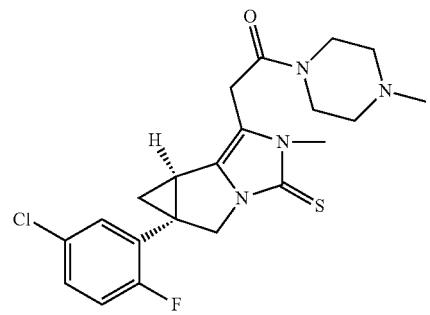 [SMILES: CN1CCN(C(=O)Cc2c3n(c(=S)n2C)C[C@@]2(c4cc(Cl)ccc4F)C[C@@H]32)CC1]

Compound was prepared analogous manner to Example 32 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

¹H NMR (DMSO$_{d6}$): 7.46 (1H, dd, J=6.5, 2.7 Hz), 7.44 (1H, ddd, J=8.7, 4.3, 2.8 Hz), 7.30 (1H, dd, J=9.9, 8.9 Hz), 4.15 (1H, d, J=12.0 Hz), 3.86 (1H, d, J=12.0 Hz), 3.82 (2H, m), 3.58 (4H, m), 3.32 (3H, s), 2.85 (1H, dd, J=8.3, 4.2 Hz), 2.65-2.36 (4H, m br), 2.30 (3H, br s), 1.71 (1H, dd, J=8.3, 5.4 Hz), 1.12 (1H, t, J=4.8 Hz).
$^{13}$C NMR (DMSO$_{d6}$): 166.6, 161.3, 159.6, 156.9, 130.7, 130.2, 130.2, 129.4, 129.3, 128.7, 128.6, 128.3, 128.3, 117.6, 117.4, 116, 54.3, 53.9, 52.4, 45.1, 44.6, 40.8, 31.6, 31.5, 29, 22.1, 20.7.

Example 327: 2-((S)-6-(3-chloro-2,6-difluorophenyl)-2-methyl-3-thioxo-2,5,6,7-tetrahydro-3H-pyrrolo[1,2-c]imidazol-1-yl)-N—((R)-tetrahydro-2H-pyran-3-yl)acetamide

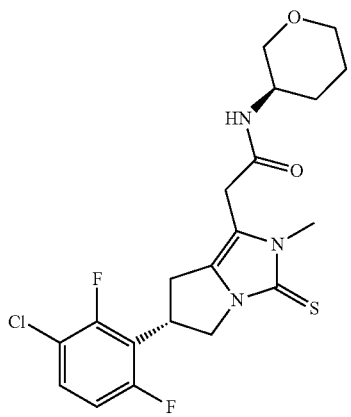 [SMILES: Cn1c(CC(=O)N[C@@H]2CCCOC2)c2n(c1=S)C[C@H](c1c(F)ccc(Cl)c1F)C2]

Compound was prepared analogous manner to Example 34 from (S)-2-(2-methyl-3-thioxo-6-(3-chloro-2,6-difluorophenyl)-2,5,6,7-tetrahydro-3H-pyrrolo[1,2-c]imidazol-1-yl)acetic acid and isolated as an off-white solid.

$^1$H NMR (DMSO$_{d6}$): 8.11 (1H, br d, J=7.3 Hz), 7.61 (1H, td, J=8.7, 5.6 Hz), 7.22 (1H, t, J=9.4 Hz), 4.44 (1H, quin, J=8.5 Hz), 4.22 (1H, dd, J=11.3, 9.4 Hz), 3.80 (1H, dd, J=11.5, 7.8 Hz), 3.65 (3H, m), 3.44 (2H, m), 3.39 (3H, s), 3.33 (1H, m), 3.29 (1H, m), 3.11 (1H, m), 2.88 (1H, dd, J=15.8, 8.1 Hz), 1.80 (1H, m), 1.66 (1H, m), 1.46 (2H, m).
$^{13}$C NMR (DMSO$_{d6}$): 167.3, 160.1, 160.1, 158.5, 158.5, 156.6, 156.5, 156.2, 154.9, 154.9, 129.7, 129.6, 128.4, 118.8, 118.7, 118.6, 116.4, 116.1, 116, 115.9, 115.9, 113.2, 113.2, 113.1, 113.1, 70.1, 67, 49.5, 45.1, 34.7, 31.5, 31.2, 29.2, 28.5, 23.8

Example 328: (S)-2-(6-(3-chloro-2,6-difluorophenyl)-2-methyl-3-thioxo-2,5,6,7-tetrahydro-3H-pyrrolo[1,2-c]imidazol-1-yl)-N-(pyrazin-2-ylmethyl)acetamide

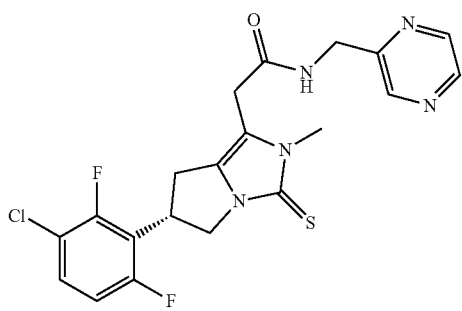 [SMILES: Cn1c(CC(=O)NCc2cnccn2)c2n(c1=S)C[C@H](c1c(F)ccc(Cl)c1F)C2]

Compound was prepared analogous manner to Example 32 from (S)-2-(6-(3-chloro-2,6-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as an off-white solid.

$^1$H NMR (DMSO$_{d6}$): 8.74 (1H, br t, J=5.7 Hz), 8.59 (1H, s), 8.55 (1H, dd, J=2.4, 1.5 Hz), 8.51 (1H, d, J=2.5 Hz), 7.62 (1H, td, J=8.7, 5.6 Hz), 7.22 (1H, t, J=9.4 Hz), 4.43 (3H, m), 4.22 (1H, m), 3.80 (1H, dd, J=11.5, 8.0 Hz), 3.56 (2H, d, J=5.9 Hz), 3.40 (3H, m), 3.25 (1H, dd, J=15.8, 9.3 Hz), 2.85 (1H, dd, J=15.8, 8.3 Hz).
$^{13}$C NMR (DMSO$_{d6}$): 168.2, 160.1, 160.1, 158.5, 158.5, 156.6, 156.5, 156.3, 154.9, 154.9, 153.9, 143.9, 143.5, 143.2, 129.7, 129.7, 128.6, 118.6, 118.5, 118.4, 116.1, 116.1, 116, 115.9, 115.9, 113.3, 113.2, 113.1, 113.1, 49.4, 42.4, 34.7, 31.4, 31.2, 29.1.

Example 329: (S)-2-(6-(3-chloro-2,6-difluorophenyl)-2-methyl-3-thioxo-2,5,6,7-tetrahydro-3H-pyrrolo[1,2-c]imidazol-1-yl)-1-morpholinoethan-1-one

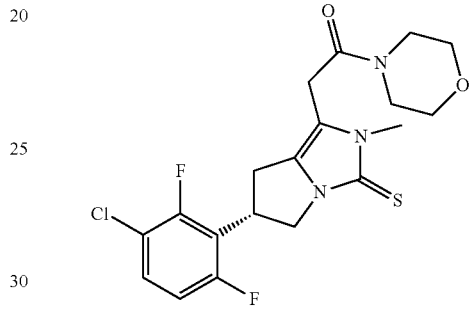

Compound was prepared analogous manner to Example 32 from (S)-2-(6-(3-chloro-2,6-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as an off-white solid.

$^1$H NMR (DMSO$_{d6}$): 7.61 (1H, td, J=8.7, 5.6 Hz), 7.22 (1H, t, J=9.4 Hz), 4.44 (1H, quin, J=8.5 Hz), 4.23 (1H, m), 3.80 (1H, dd, J=11.5, 7.7 Hz), 3.75 (2H, s), 3.59 (2H, m), 3.55 (2H, m), 3.49 (2H, m), 3.45 (2H, m), 3.36 (3H, m), 3.27 (1H, dd, J=15.9, 9.3 Hz), 2.86 (1H, dd, J=15.9, 7.8 Hz).
$^{13}$C NMR (DMSO$_{d6}$): 166.8, 160.1, 160.1, 158.5, 158.5, 156.6, 156.5, 156.2, 154.9, 154.9, 129.7, 129.6, 128.2, 118.9, 118.8, 118.6, 116.2, 116.1, 116, 115.9, 115.9, 113.2, 113.2, 113.1, 113.1, 66, 66, 49.5, 45.6, 41.7, 34.8, 31.5, 29.2, 28.8.

Example 330: (5aS,6aR)-5a-(5-bromo-2-fluorophenyl)-1-(2-(cyclopentylamino)ethyl)-2-methyl-5,5a,6,6a-tetrahydrocyclopropa[3,4]pyrrolo[1,2-c]imidazole-3(2H)-thione Hydrochloride

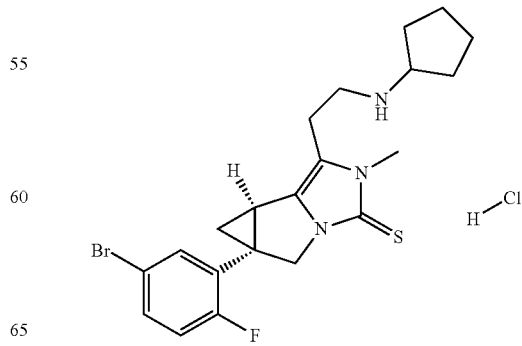

Compound was prepared analogous manner to Example 35 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-cyclopentylacetamide (Example 272) and isolated as a beige solid.

$^1$H NMR (DMSO$_{d6}$): 8.77 (2H, m), 7.61 (1H, dd, J=6.7, 2.6 Hz), 7.57 (1H, ddd, J=8.7, 4.5, 2.5 Hz), 7.25 (1H, dd, J=10.1, 8.8 Hz), 4.14 (1H, d, J=11.9 Hz), 3.85 (1H, d, J=12.0 Hz), 3.54 (1H, m), 3.43 (3H, s), 3.17 (2H, br s), 3.04 (1H, dd, J=8.4, 4.3 Hz), 2.98 (2H, m), 1.99 (2H, m), 1.71 (3H, m), 1.63 (2H, m), 1.55 (2H, m), 1.20 (1H, t, J=4.8 Hz).

$^{13}$C NMR (DMSO$_{d6}$): 161.8, 160.2, 157.2, 133.1, 133, 132.4, 132.4, 130.9, 129.2, 129.1, 118, 117.9, 116.3, 116.2, 58.2, 52.4, 43.8, 31.7, 31.3, 29.2, 29.1, 23.7, 22, 21, 20.6.

Example 331: (5aS,6aR)-5a-(5-bromo-2-fluorophenyl)-2-methyl-1-(2-(((R)-tetrahydro-2H-pyran-3-yl)amino)ethyl)-5,5a,6,6a-tetrahydrocyclopropa[3,4]pyrrolo[1,2-c]imidazole-3(2H)-thione Hydrochloride

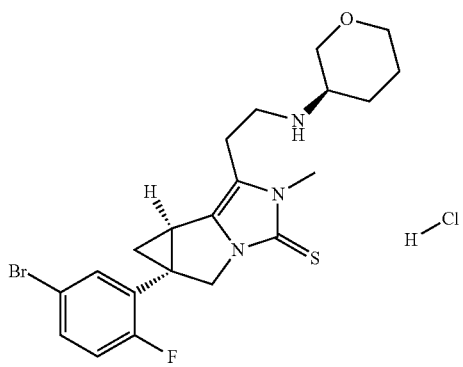 [SMILES: Cn1c(CCN[C@@H]2CCCOC2)c2n(c1=S)C[C@@]1(c3cc(Br)ccc3F)C[C@@H]21 ; Cl]

Compound was prepared analogous manner to Example 35 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N—((R)-tetrahydro-2H-pyran-3-yl)acetamide (Example 277) and isolated as a beige solid.

$^1$H NMR (DMSO$_{d6}$): 9.05 (2H, m), 7.61 (1H, dd, J=6.7, 2.6 Hz), 7.57 (1H, ddd, J=8.7, 4.5, 2.6 Hz), 7.25 (1H, dd, J=10.1, 8.8 Hz), 4.14 (1H, d, J=12.0 Hz), 3.90 (1H, dd, J=11.6, 2.6 Hz), 3.85 (1H, d, J=12.0 Hz), 3.66 (1H, m), 3.59 (1H, dd, J=11.7, 7.1 Hz), 3.49 (1H, ddd, J=11.2, 8.2, 2.9 Hz), 3.43 (3H, s), 3.22 (3H, m), 3.03 (3H, m), 2.07 (1H, td, J=8.9, 4.4 Hz), 1.77 (2H, m), 1.69 (1H, dd, J=8.3, 5.4 Hz), 1.52 (1H, m), 1.19 (1H, t, J=4.8 Hz).

$^{13}$C NMR (DMSO$_{d6}$): 161.8, 160.2, 157.2, 133, 133, 132.4, 132.4, 130.7, 129.2, 129.1, 118, 117.9, 116.4, 116.2, 116.2, 67.3, 66.7, 52.4, 52.4, 42.4, 31.7, 31.4, 24.7, 22.4, 22.1, 20.9, 20.6.

Example 332: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-(pyridin-2-ylmethyl)acetamide Hydrochloride

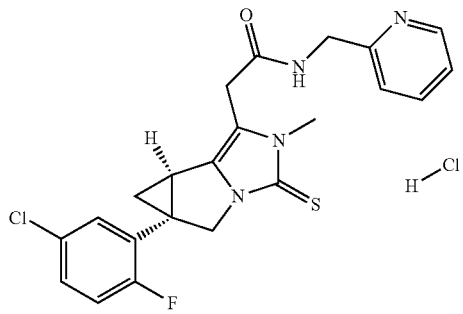 [SMILES: Cn1c(CC(=O)NCc2ccccn2)c2n(c1=S)C[C@@]1(c3cc(Cl)ccc3F)C[C@@H]21 ; Cl]

Compound was prepared analogous manner to Example 32 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a light green solid.

$^1$H NMR (DMSO$_{d6}$): 8.99 (1H, br t, J=5.6 Hz), 8.74 (1H, br d, J=5.3 Hz), 8.32 (1H, br t, J=7.5 Hz), 7.75 (2H, m), 7.47 (1H, dd, J=6.5, 2.6 Hz), 7.44 (1H, ddd, J=8.7, 4.3, 2.7 Hz), 7.31 (1H, dd, J=9.8, 8.9 Hz), 4.61 (2H, br d, J=5.6 Hz), 4.15 (1H, br d, J=11.9 Hz), 3.86 (1H, br d, J=12.0 Hz), 3.71 (2H, br m), 3.36 (3H, s), 2.94 (1H, dd, J=8.3, 4.2 Hz), 1.68 (1H, dd, J=8.4, 5.4 Hz), 1.16 (1H, m).

$^{13}$C NMR (DMSO$_{d6}$): 168.8, 161.2, 159.6, 156.8, 155.5, 143.7, 143.3, 131.4, 130.2, 130.2, 129.4, 129.3, 128.7, 128.6, 128.3, 128.3, 124.4, 124, 117.6, 117.4, 115.7, 52.5, 41.7, 31.6, 31.5, 30.9, 22.1, 20.7.

Example 333: (S)-2-(6-(3-chloro-2,6-difluorophenyl)-2-methyl-3-thioxo-2,5,6,7-tetrahydro-3H-pyrrolo[1,2-c]imidazol-1-yl)-N-(oxetan-3-yl)acetamide

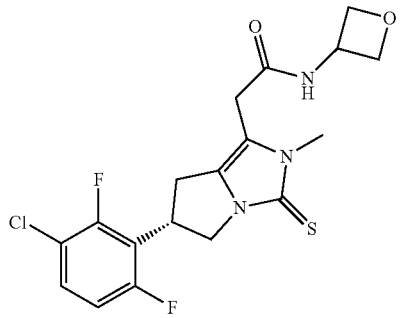 [SMILES: Cn1c(CC(=O)NC2COC2)c2n(c1=S)C[C@H](c1c(F)ccc(Cl)c1F)C2]

Compound was prepared analogous manner to Example 32 from (S)-2-(6-(3-chloro-2,6-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as an off-white solid.

$^1$H NMR (DMSO$_{d6}$): 8.84 (1H, d, J=6.6 Hz), 7.62 (1H, td, J=8.7, 5.6 Hz), 7.22 (1H, t, J=9.4 Hz), 4.78 (1H, m), 4.70 (2H, m), 4.42 (3H, m), 4.22 (1H, dd, J=11.4, 9.3 Hz), 3.80 (1H, dd, J=11.7, 7.7 Hz), 3.47 (2H, m), 3.39 (3H, s), 3.29 (1H, dd, J=15.8, 9.4 Hz), 2.90 (1H, dd, J=15.8, 8.1 Hz).

$^{13}$C NMR (DMSO$_{d6}$): 167.4, 160.1, 160.1, 158.5, 158.5, 156.6, 156.5, 156.3, 154.9, 154.9, 129.7, 129.6, 128.6, 118.7, 118.6, 118.5, 116.1, 116, 116, 115.9, 115.9, 113.2, 113.2, 113.1, 113.1, 77, 76.9, 49.5, 44.2, 34.7, 31.5, 31, 29.1.

Example 334: (5aS,6aR)-5a-(5-bromo-2-fluorophenyl)-2-methyl-1-(2-((2,2,2-trifluoroethyl)amino)ethyl)-5,5a,6,6a-tetrahydrocyclopropa[3,4]pyrrolo[1,2-c]imidazole-3(2H)-thione Hydrochloride

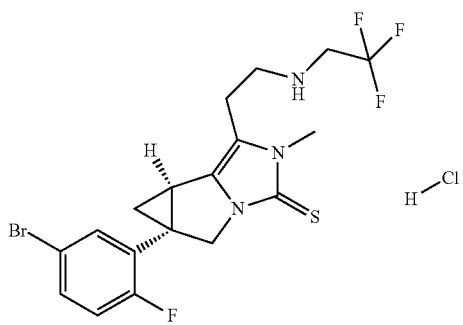 [SMILES: Cn1c(CCNCC(F)(F)F)c2n(c1=S)C[C@@]1(c3cc(Br)ccc3F)C[C@@H]21 ; Cl]

Compound was prepared analogous manner to Example 35 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-(2,2,2-trifluoroethyl)acetamide (Example 298) and isolated as a beige solid.

$^1$H NMR (DMSO$_{d6}$): 10.19 (2H, m), 7.61 (1H, dd, J=6.7, 2.6 Hz), 7.57 (1H, ddd, J=8.7, 4.5, 2.6 Hz), 7.25 (1H, dd, J=10.1, 8.8 Hz), 4.14 (1H, br d, J=11.9 Hz), 4.09 (2H, m), 3.84 (1H, d, J=12.0 Hz), 3.42 (3H, s), 3.27 (2H, br d, J=7.5 Hz), 3.08 (2H, m), 2.99 (1H, dd, J=8.3, 4.2 Hz), 1.69 (1H, dd, J=8.4, 5.4 Hz), 1.20 (1H, t, J=4.8 Hz).

$^{13}$C NMR (DMSO$_{d6}$): 161.8, 160.1, 157.2, 133, 133, 132.4, 132.4, 130.8, 129.1, 129, 126.1, 124.3, 122.4, 120.6, 118, 117.8, 116.4, 116.2, 116.2, 52.4, 46.7, 46.5, 46.2, 46, 45.9, 31.6, 31.3, 22, 20.8, 20.6.

Example 335: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-(pyrazin-2-ylmethyl)acetamide Hydrochloride

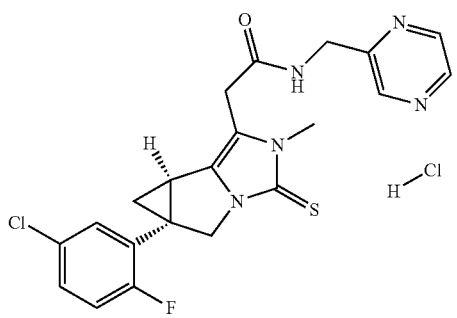 [SMILES: Cn1c(CC(=O)NCc2cnccn2)c2n(c1=S)C[C@@]1(c3cc(Cl)ccc3F)C[C@@H]21 ; Cl]

Compound was prepared analogous manner to Example 32 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as an orange solid.

$^1$H NMR (DMSO$_{d6}$): 8.79 (1H, t, J=5.7 Hz), 8.61 (1H, d, J=1.3 Hz), 8.58 (1H, dd, J=2.4, 1.5 Hz), 8.53 (1H, d, J=2.6 Hz), 7.46 (1H, dd, J=6.5, 2.7 Hz), 7.44 (1H, ddd, J=8.7, 4.3, 2.8 Hz), 7.30 (1H, dd, J=9.8, 8.9 Hz), 4.46 (2H, m), 4.16 (1H, br d, J=12.2 Hz), 3.87 (1H, d, J=12.0 Hz), 3.66 (2H, m), 3.37 (3H, s), 2.92 (1H, dd, J=8.4, 4.3 Hz), 1.67 (1H, dd, J=8.3, 5.4 Hz), 1.17 (1H, m).

$^{13}$C NMR (DMSO$_{d6}$): 168.2, 161.2, 159.6, 153.9, 144, 143.9, 143.4, 143.2, 131.8, 130.2, 130.2, 129.4, 129.4, 128.7, 128.6, 128.3, 128.3, 117.6, 117.4, 116.2, 52.5, 42.4, 31.6, 31.5, 31, 22.1, 20.7.

Example 336: 2-((S)-6-(3-chloro-2,6-difluorophenyl)-2-methyl-3-thioxo-2,5,6,7-tetrahydro-3H-pyrrolo[1,2-c]imidazol-1-yl)-N—(((S)-tetrahydrofuran-2-yl)methyl)acetamide

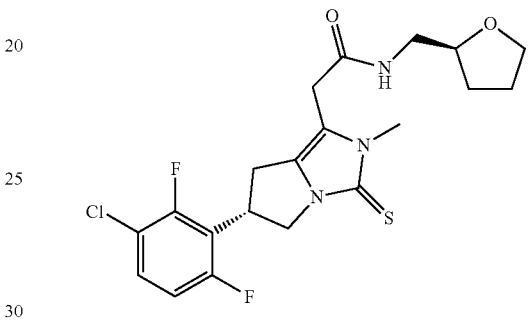

Compound was prepared analogous manner to Example 32 from (S)-2-(6-(3-chloro-2,6-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as an off-white solid.

$^1$H NMR (DMSO$_{d6}$): 8.18 (1H, br t, J=5.6 Hz), 7.62 (1H, td, J=8.7, 5.6 Hz), 7.22 (1H, t, J=9.4 Hz), 4.43 (1H, quin, J=8.6 Hz), 4.22 (1H, m), 3.81 (2H, m), 3.72 (1H, m), 3.58 (1H, m), 3.45 (2H, m), 3.40 (3H, s), 3.28 (1H, dd, J=15.8, 9.3 Hz), 3.17 (1H, m), 3.08 (1H, m), 2.89 (1H, dd, J=15.8, 8.1 Hz), 1.85 (1H, m), 1.78 (2H, m), 1.46 (1H, m).

$^{13}$C NMR (DMSO$_{d6}$): 167.8, 160.1, 160.1, 158.5, 158.5, 156.6, 156.5, 156.2, 154.9, 154.9, 129.7, 129.6, 128.4, 118.8, 118.6, 118.5, 116.4, 116.1, 116, 115.9, 115.9, 113.2, 113.2, 113.1, 113.1, 77, 67.1, 49.4, 42.9, 34.7, 31.4, 31.2, 29.1, 28.4, 25.1.

Example 337: 2-((S)-6-(3-chloro-2,6-difluorophenyl)-2-methyl-3-thioxo-2,5,6,7-tetrahydro-3H-pyrrolo[1,2-c]imidazol-1-yl)-N—(((R)-tetrahydrofuran-2-yl)methyl)acetamide

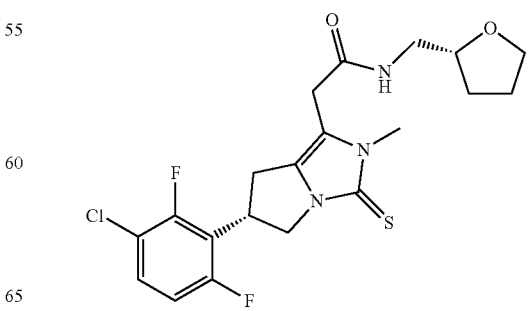

Compound was prepared analogous manner to Example 32 from (S)-2-(6-(3-chloro-2,6-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as an off-white solid.

¹H NMR (DMSO$_{d6}$): 8.18 (1H, br t, J=5.6 Hz), 7.62 (1H, td, J=8.7, 5.6 Hz), 7.21 (1H, m), 4.43 (1H, quin, J=8.5 Hz), 4.22 (1H, m), 3.81 (2H, m), 3.72 (1H, m), 3.58 (1H, m), 3.45 (2H, m), 3.40 (3H, s), 3.28 (1H, dd, J=15.8, 9.4 Hz), 3.16 (1H, m), 3.10 (1H, m), 2.89 (1H, dd, J=15.8, 8.1 Hz), 1.85 (1H, m), 1.78 (2H, m), 1.46 (1H, m).

¹³C NMR (DMSO$_{d6}$): 167.8, 160.1, 160.1, 158.5, 158.5, 156.6, 156.5, 156.2, 154.9, 154.9, 129.7, 129.6, 128.4, 118.8, 118.6, 118.5, 116.4, 116.1, 116, 115.9, 115.9, 113.2, 113.2, 113.1, 113.1, 77, 67.1, 49.5, 42.9, 34.7, 31.4, 31.2, 29.1, 28.4, 25.1.

Example 338: (S)-2-(6-(3-chloro-2,6-difluorophenyl)-2-methyl-3-thioxo-2,5,6,7-tetrahydro-3H-pyrrolo[1,2-c]imidazol-1-yl)-N-((1-methyl-1H-pyrazol-4-yl)methyl)acetamide

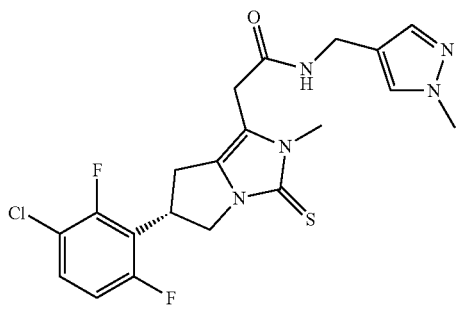 [SMILES: Cn1cc(CNC(=O)Cc2c3n(c(=S)n2C)C[C@H](c2c(F)ccc(Cl)c2F)C3)cn1]

Compound was prepared analogous manner to Example 32 from (S)-2-(6-(3-chloro-2,6-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as an off-white solid.

¹H NMR (DMSO$_{d6}$): 8.36 (1H, t, J=5.5 Hz), 7.62 (1H, td, J=8.7, 5.6 Hz), 7.54 (1H, s), 7.29 (1H, s), 7.22 (1H, m), 4.42 (1H, quin, J=8.6 Hz), 4.22 (1H, m), 4.08 (2H, m), 3.80 (1H, dd, J=11.5, 8.0 Hz), 3.75 (3H, s), 3.44 (2H, m), 3.38 (3H, s), 3.23 (1H, dd, J=15.8, 9.3 Hz), 2.85 (1H, dd, J=15.8, 8.3 Hz).

¹³C NMR (DMSO$_{d6}$): 167.3, 160.2, 160.1, 158.5, 158.5, 156.6, 156.5, 156.2, 154.9, 154.9, 137.9, 129.7, 129.7, 129.4, 128.4, 118.7, 118.5, 118.4, 116.4, 116.1, 116, 115.9, 115.9, 113.2, 113.2, 113.1, 113.1, 49.4, 38.3, 34.7, 33.2, 31.4, 31.2, 29.1.

Example 339: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-((1-methyl-1H-pyrazol-4-yl)methyl)acetamide

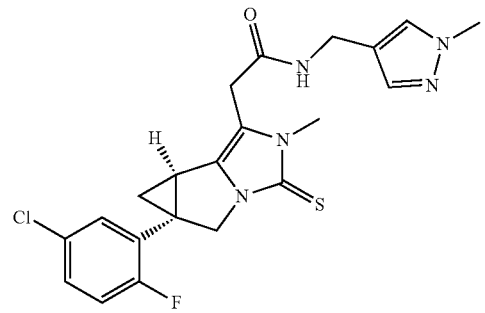 [SMILES: Cn1cc(CNC(=O)Cc2c3n(c(=S)n2C)C[C@@]2(c4cc(Cl)ccc4F)C[C@@H]32)cn1]

Compound was prepared analogous manner to Example 32 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

¹H NMR (DMSO$_{d6}$): 8.39 (1H, br t, J=5.5 Hz), 7.56 (1H, s), 7.46 (1H, dd, J=6.5, 2.6 Hz), 7.43 (1H, ddd, J=8.6, 4.3, 2.8 Hz), 7.31 (2H, m), 4.12 (3H, m), 3.85 (1H, d, J=12.0 Hz), 3.77 (3H, s), 3.52 (2H, m), 3.33 (3H, m), 2.87 (1H, dd, J=8.4, 4.1 Hz), 1.67 (1H, dd, J=8.3, 5.4 Hz), 1.15 (1H, t, J=4.8 Hz).

¹³C NMR (DMSO$_{d6}$): 167.5, 161.3, 159.6, 156.9, 137.9, 131.1, 130.2, 130.2, 129.4, 129.4, 129.3, 128.8, 128.7, 128.3, 128.3, 118.5, 117.6, 117.4, 116, 52.4, 38.4, 33.2, 31.5, 31.4, 31.1, 22, 20.7.

Example 340: (R)-2-(2-methyl-6-(2,3,5,6-tetrafluorophenyl)-3-thioxo-2,5,6,7-tetrahydro-3H-pyrrolo[1,2-c]imidazol-1-yl)-N-(thiazol-2-yl)acetamide

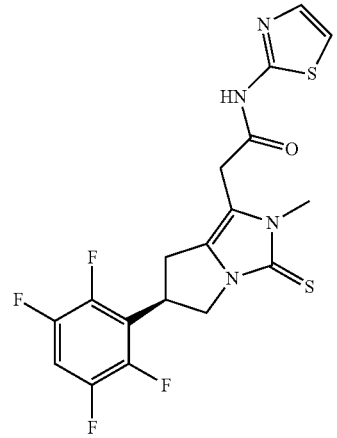 [SMILES: Cn1c(CC(=O)Nc2nccs2)c2n(c1=S)C[C@@H](c1c(F)c(F)cc(F)c1F)C2]

Compound was prepared analogous manner to Example 32 from (R)-1-(1H-imidazol-1-yl)-2-(2-methyl-6-(2,3,5,6-tetrafluorophenyl)-3-thioxo-2,5,6,7-tetrahydro-3H-pyrrolo[1,2-c]imidazol-1-yl)ethan-1-one and isolated as an off-white powder.

¹H NMR (DMSO$_{d6}$): 12.39 (1H, s), 7.85 (1H, m), 7.48 (1H, d, J=3.5 Hz), 7.23 (1H, d, J=3.5 Hz), 4.50 (1H, quin, J=8.5 Hz), 4.26 (1H, dd, J=11.4, 9.3 Hz), 3.86 (1H, dd, J=7.7, 11.4 Hz), 3.84 (2H, m), 3.43 (3H, s), 3.36 (1H, m), 2.96 (1H, dd, J=16.0, 7.9 Hz).

$^{13}$C NMR (DMSO$_{d6}$): 167, 157.8, 156.6, 146.4, 146.4, 146.3, 146.3, 146.2, 145.4, 145.3, 145.3, 145.3, 145.3, 145.2, 145.2, 145.2, 144.8, 144.8, 144.8, 144.7, 144.7, 144.6, 144.6, 143.7, 143.7, 143.7, 143.7, 143.6, 143.6, 143.6, 143.6, 137.7, 129, 120.4, 120.3, 120.2, 115.1, 113.8, 105.9, 105.7, 105.6, 49.5, 34.8, 31.6, 30.8, 29.1.

Example 341: (5aS,6aR)-5a-(5-bromo-2-fluorophenyl)-1-(2-(cyclohexylamino)ethyl)-2-methyl-5,5a,6,6a-tetrahydrocyclopropa[3,4]pyrrolo[1,2-c]imidazole-3(2H)-thione hydrochloride

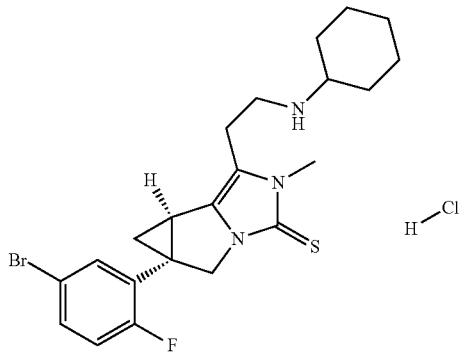 [SMILES: Cn1c(CCNC2CCCCC2)c2n(c1=S)C[C@@]1(c3cc(Br)ccc3F)C[C@@H]21 ; Cl]

Compound was prepared analogous manner to Example 35 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-cyclohexylacetamide (Example 294) and isolated as a beige solid.

$^1$H NMR (DMSO$_{d6}$): 8.69 (2H, m), 7.61 (1H, dd, J=6.7, 2.6 Hz), 7.57 (1H, ddd, J=8.7, 4.5, 2.6 Hz), 7.25 (1H, dd, J=10.1, 8.7 Hz), 4.14 (1H, d, J=12.0 Hz), 3.85 (1H, d, J=12.0 Hz), 3.43 (3H, s), 3.20 (2H, m), 3.01 (4H, m), 2.06 (2H, m), 1.77 (2H, m), 1.70 (1H, dd, J=8.2, 5.3 Hz), 1.61 (1H, m), 1.27 (4H, m), 1.19 (1H, t, J=4.8 Hz), 1.12 (1H, m).

$^{13}$C NMR (DMSO$_{d6}$): 161.8, 160.2, 157.2, 133.1, 132.4, 132.4, 130.8, 129.1, 129, 118, 117.9, 116.4, 116.2, 116.2, 55.8, 52.4, 41.6, 31.7, 31.3, 28.7, 28.5, 24.7, 23.9, 23.9, 22, 21, 20.6.

Example 342: 2-((S)-6-(3-bromo-2,6-difluorophenyl)-2-methyl-3-thioxo-2,5,6,7-tetrahydro-3H-pyrrolo[1,2-c]imidazol-1-yl)-N—((R)-2-oxopyrrolidin-3-yl)acetamide

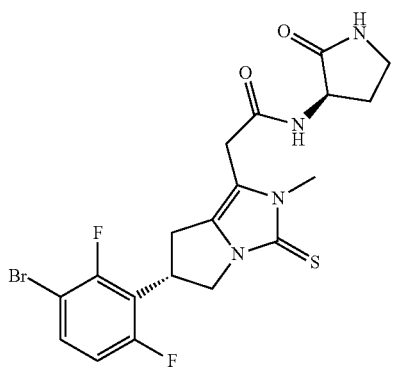 [SMILES: Cn1c(CC(=O)N[C@@H]2CCNC2=O)c2n(c1=S)C[C@H](c1c(F)ccc(Br)c1F)C2]

Compound was prepared analogous manner to Example 22 from (S)-2-(6-(3-bromo-2,6-difluorophenyl)-2-methyl-3-thioxo-2,5,6,7-tetrahydro-3H-pyrrolo[1,2-c]imidazol-1-yl) acetic acid and isolated as a cream powder.

$^1$H NMR (DMSO$_{d6}$): 8.37 (1H, d, J=8.1 Hz), 7.84 (1H, s), 7.72 (1H, m), 7.16 (1H, t, J=9.2 Hz), 4.43 (1H, quin, J=8.4 Hz), 4.28 (1H, m), 4.22 (1H, br t, J=10.3 Hz), 3.80 (1H, dd, J=11.4, 8.1 Hz), 3.47 (2H, s), 3.42 (3H, s), 3.16 (2H, m), 2.89 (1H, br dd, J=15.8, 8.3 Hz), 2.29 (1H, m), 1.81 (1H, m).

$^{13}$C NMR (DMSO$_{d6}$): 174.2, 167.8, 160.9, 160.8, 159.2, 159.2, 157.6, 157.5, 156.2, 156, 155.9, 132.5, 132.5, 128.6, 118.6, 118.5, 118.4, 116.2, 113.8, 113.8, 113.7, 113.6, 104.1, 104.1, 103.9, 103.9, 49.9, 49.5, 38, 34.8, 31.4, 31.3, 29.1, 28.2.

Example 343: (5aS,6aR)-5a-(5-chloro-2-fluorophenyl)-2-methyl-1-(2-((pyridin-2-ylmethyl)amino)ethyl)-5,5a,6,6a-tetrahydrocyclopropa[3,4]pyrrolo[1,2-c]imidazole-3(2H)-thione Hydrochloride

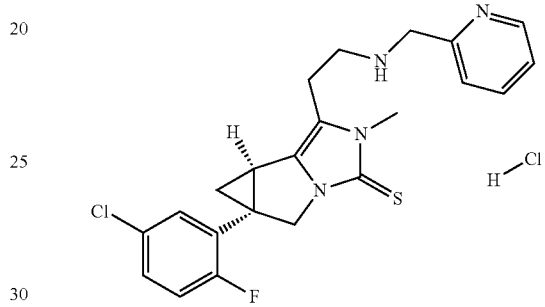

Compound was prepared analogous manner to Example 35 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-(pyridin-2-ylmethyl)acetamide hydrochloride (Example 332) and isolated as a light yellow solid.

$^1$H NMR (DMSO$_{d6}$): 9.45 (2H, br s), 8.66 (1H, br d, J=4.7 Hz), 7.92 (1H, td, J=7.7, 1.5 Hz), 7.57 (1H, d, J=7.8 Hz), 7.47 (3H, m), 7.32 (1H, t, J=9.3 Hz), 4.39 (2H, br s), 4.15 (1H, br d, J=11.9 Hz), 3.86 (1H, m), 3.43 (3H, s), 3.29 (2H, m), 3.07 (3H, m), 1.69 (1H, dd, J=8.1, 5.4 Hz), 1.21 (1H, br t, J=4.6 Hz).

$^{13}$C NMR (DMSO$_{d6}$): 161.3, 159.6, 157.4, 151.9, 148.9, 137.6, 131.1, 130.2, 130.2, 129.5, 129.4, 128.7, 128.6, 128.3, 128.3, 123.8, 123.3, 117.6, 117.4, 116.3, 52.4, 50.1, 44.9, 31.7, 31.4, 22.1, 20.8, 20.6.

Example 344: 2-((R)-2-methyl-3-thioxo-6-(2,3,6-trifluorophenyl)-2,5,6,7-tetrahydro-3H-pyrrolo[1,2-c]imidazol-1-yl)-1-((R)-2-(trifluoromethyl)pyrrolidin-1-yl)ethan-1-one

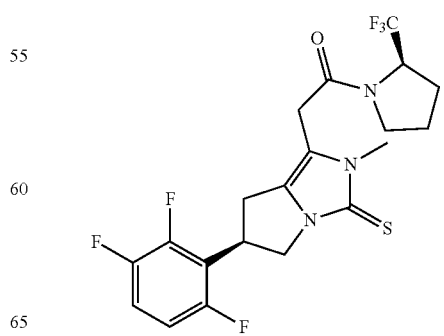

Compound was prepared analogous manner to Example 25 from (R)-1-(1H-imidazol-1-yl)-2-(2-methyl-3-thioxo-6-(2,3,6-trifluorophenyl)-2,5,6,7-tetrahydro-3H-pyrrolo[1,2-c]imidazol-1-yl)ethan-1-one and isolated as a cream powder.

$^1$H NMR (DMSO$_{d6}$): 7.47 (1H, m), 7.18 (1H, m), 5.04 (0.2H, quin, J=7.8 Hz), 4.76 (0.8H, quin, J=8.2 Hz), 4.45 (1H, m), 4.24 (1H, dd, J=9.5, 11.3 Hz), 3.82 (1H, dd, J=7.7, 11.5 Hz), 3.79 (2H, m), 3.64 (2H, m), 3.35 (3H, m), 3.30 (1H, dd, J=15.8, 9.7 Hz), 2.89 (1H, br dd, J=15.8, 8.1 Hz), 2.15-1.84 (4H, m).

$^{13}$C NMR (DMSO$_{d6}$): 168.6, 168.1, 156.9, 156.9, 156.9, 156.4, 156.3, 155.3, 155.3, 155.3, 149, 148.9, 147.5, 147.5, 147.5, 147.4, 145.9, 145.9, 145.9, 145.8, 128.6, 127, 125.1, 119, 118.9, 118.9, 118.8, 118.7, 116.5, 116.4, 116.4, 116.3, 116, 115.8, 112, 112, 112, 111.9, 111.8, 111.8, 111.8, 111.8, 57.5, 57.3, 56.7, 56.5, 56.3, 56.1, 49.5, 46.9, 34.7, 31.5, 31.4, 30.5, 29.5, 29.2, 29.1, 26.2, 24.8, 23.6, 21.3.

Example 345: N-(2-cyanocyclopentyl)-2-((R)-2-methyl-3-thioxo-6-(2,3,6-trifluorophenyl)-2,5,6,7-tetrahydro-3H-pyrrolo[1,2-c]imidazol-1-yl)acetamide

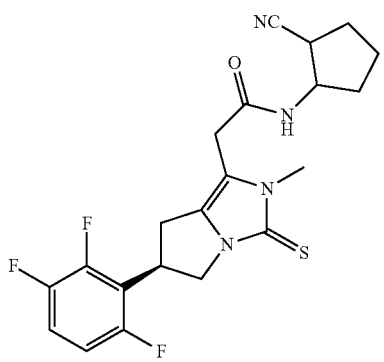 [SMILES: Cn1c(CC(=O)NC2CCCC2C#N)c2n(c1=S)C[C@@H](c1c(F)ccc(F)c1F)C2]

Compound was prepared analogous manner to Example 25 from (R)-1-(1H-imidazol-1-yl)-2-(2-methyl-3-thioxo-6-(2,3,6-trifluorophenyl)-2,5,6,7-tetrahydro-3H-pyrrolo[1,2-c]imidazol-1-yl)ethan-1-one and isolated as a cream powder.

$^1$H NMR (DMSO$_{d6}$): 8.55 (0.5H, d, J=7.6 Hz), 8.39 (0.5H, dd, J=7.6, 2.4 Hz), 7.47 (1H, m), 7.18 (1H, m), 4.43 (1H, m), 4.24 (2H, m), 3.82 (1H, m), 3.52 (1H, m), 3.47 (1H, s), 3.42, 3.40 (3H, 2 s), 3.32-3.23 (1.5H, m), 2.93 (1H, m), 2.83 (0.5H, m), 2.15-2.0 (1H, m), 1.99-1.88 (1H, m), 1.89-1.74 (1.5H, m), 1.74-1.64 (1H, m), 1.62-1.52 (1H, m), 1.47 (0.5H, m).

$^{13}$C NMR (DMSO$_{d6}$): 167.8, 167.7, 157, 156.9, 156.3, 156.2, 156.2, 155.4, 155.3, 155.3, 149.1, 149.1, 149, 147.6, 147.5, 147.5, 147.3, 145.9, 145.9, 145.9, 145.8, 128.5, 122, 120.7, 120.7, 118.8, 118.7, 118.7, 118.6, 116.5, 116.5, 116.4, 116.3, 116.3, 116.3, 116.1, 116.1, 112, 112, 112, 111.9, 111.8, 111.8, 111.8, 111.8, 54.4, 54.4, 51.4, 49.4, 34.7, 33.9, 33.9, 33.7, 33.7, 31.5, 31.4, 31.3, 31.2, 30.9, 30.9, 30.1, 29.1, 29.1, 28.8, 28.6, 28.6, 22.3, 22.3, 22.1.

Example 346: (5aS,6aR)-5a-(5-chloro-2-fluorophenyl)-2-methyl-1-(2-(((1-methyl-1H-pyrazol-4-yl)methyl)amino)ethyl)-5,5a,6,6a-tetrahydrocyclopropa[3,4]pyrrolo[1,2-c]imidazole-3(2H)-thione Hydrochloride

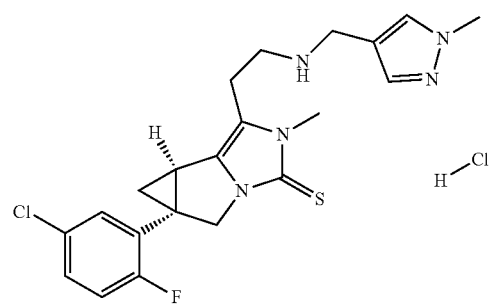 [SMILES: Cn1cc(CNCCc2c3n(c(=S)n2C)C[C@@]2(c4cc(Cl)ccc4F)C[C@@H]32)cn1 ; Cl]

Compound was prepared analogous manner to Example 35 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-((1-methyl-1H-pyrazol-4-yl)methyl)acetamide (Example 339) and isolated as a beige solid.

$^1$H NMR (DMSO$_{d6}$): 9.25 (2H, m), 7.84 (1H, s), 7.58 (1H, s), 7.50 (1H, dd, J=6.5, 2.6 Hz), 7.44 (1H, m), 7.31 (1H, t, J=9.4 Hz), 4.14 (1H, br d, J=12.0 Hz), 4.05 (2H, br t, J=5.5 Hz), 3.84 (4H, m), 3.42 (3H, s), 3.15 (2H, m), 3.03 (3H, m), 1.67 (1H, dd, J=8.2, 5.4 Hz), 1.20 (1H, t, J=4.7 Hz).

$^{13}$C NMR (DMSO$_{d6}$): 159.6, 157.2, 139.7, 131.8, 130.9, 130.2, 130.2, 129.4, 129.4, 128.7, 128.6, 128.3, 117.6, 117.4, 116.5, 111.2, 52.4, 43.9, 40.5, 38.6, 31.7, 31.4, 22.8, 22.1, 20.7.

Example 347: (R)—N-(isoxazol-4-yl)-2-(2-methyl-3-thioxo-6-(2,3,6-trifluorophenyl)-2,5,6,7-tetrahydro-3H-pyrrolo[1,2-c]imidazol-1-yl)acetamide

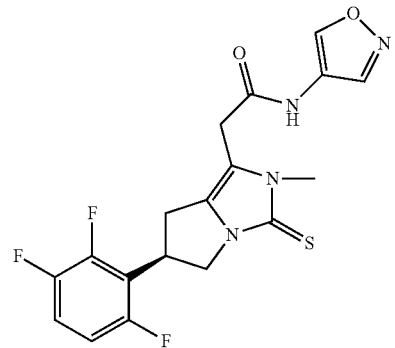 [SMILES: Cn1c(CC(=O)Nc2cnoc2)c2n(c1=S)C[C@@H](c1c(F)ccc(F)c1F)C2]

Compound was prepared analogous manner to Example 32 from (R)-1-(H-imidazol-1-yl)-2-(2-methyl-3-thioxo-6-(2,3,6-trifluorophenyl)-2,5,6,7-tetrahydro-3H-pyrrolo[1,2-c]imidazol-1-yl)ethan-1-one and isolated as a cream powder.

$^1$H NMR (DMSO$_{d6}$): 10.49 (1H, s), 9.11 (1H, s), 8.63 (1H, s), 7.47 (1H, m), 7.18 (1H, m), 4.44 (1H, quin, J=8.7 Hz), 4.25 (1H, dd, J=9.6, 11.2 Hz), 3.83 (1H, dd, J=11.4, 8.1 Hz), 3.71 (2H, m), 3.43 (3H, s), 3.32 (1H, dd, J=9.3, 16.1 Hz), 2.94 (1H, dd, J=15.9, 8.3 Hz).

$^{13}$C NMR (DMSO$_{d6}$): 166.3, 159.2, 157, 157, 156.9, 156.9, 156.5, 155.3, 155.3, 149.1, 149, 149, 149, 147.5, 147.5, 147.5, 147.4, 147.4, 147.2, 145.9, 145.9, 145.9, 145.8, 144.3, 144.3, 128.9, 119.6, 118.8, 118.7, 118.7, 118.6, 116.5, 116.5, 116.4, 116.3, 115.5, 112, 112, 112, 111.9, 111.8, 111.8, 111.8, 111.8, 49.5, 34.7, 31.6, 31.1, 29.1.

Example 348: (S)-1-(2-((R)-2-methyl-3-thioxo-6-(2,3,6-trifluorophenyl)-2,5,6,7-tetrahydro-3H-pyrrolo[1,2-c]imidazol-1-yl)acetyl)pyrrolidine-3-carbonitrile

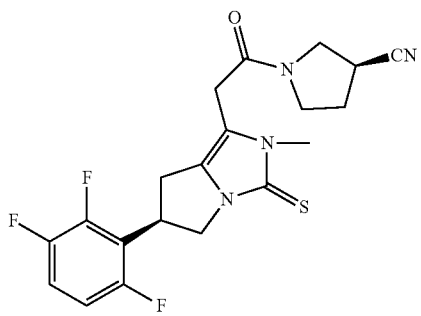 [SMILES: Cn1c(CC(=O)N2CC[C@H](C#N)C2)c2n(c1=S)C[C@@H](c1c(F)ccc(F)c1F)C2]

Compound was prepared analogous manner to Example 25 from (R)-1-(H-imidazol-1-yl)-2-(2-methyl-3-thioxo-6-(2,3,6-trifluorophenyl)-2,5,6,7-tetrahydro-3H-pyrrolo[1,2-c]imidazol-1-yl)ethan-1-one and isolated as a cream powder.

¹H NMR (DMSO$_{d6}$): 7.47 (1H, m), 7.18 (1H, t, J=9.6 Hz), 4.45 (1H, quin, J=8.6 Hz), 4.24 (1H, dd, J=9.5, 11.3 Hz), 3.88-3.40 (8H, several mult.), 3.37 (3H, s), 3.29 (1H, dd, J=9.2, 15.8 Hz), 2.90 (1H, m), 2.32 (0.5H, m), 2.21 (1H, m), 2.10 (0.5H, m).

¹³C NMR (DMSO$_{d6}$): 166.6, 166.4, 156.9, 156.9, 156.9, 156.9, 156.3, 155.3, 155.3, 149.1, 149, 149, 149, 148.9, 147.5, 147.5, 147.4, 147.4, 147.4, 147.3, 145.9, 145.9, 145.8, 145.8, 128.4, 121.1, 120.9, 118.9, 118.8, 118.8, 118.7, 116.5, 116.4, 116.4, 116.3, 115.9, 115.9, 112, 112, 112, 111.9, 111.8, 111.8, 111.8, 49.5, 48.7, 48.6, 44.8, 44.6, 34.7, 31.5, 30.2, 30.1, 29.6, 29.1, 28.1, 28, 26.5.

Example 349: (S)-2-(6-(3-chloro-2,6-difluorophenyl)-2-methyl-3-thioxo-2,5,6,7-tetrahydro-3H-pyrrolo[1,2-c]imidazol-1-yl)-N-(5-methyl-1,3,4-oxadiazol-2-yl)acetamide

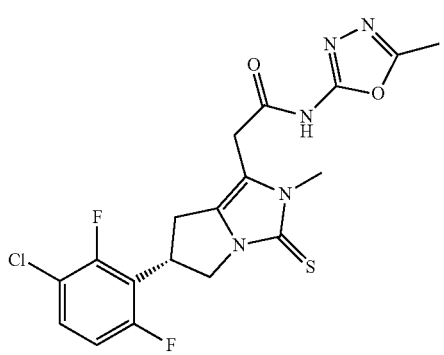 [SMILES: Cc1nnc(NC(=O)Cc2c3n(c(=S)n2C)C[C@H](c2c(F)ccc(Cl)c2F)C3)o1]

Compound was prepared analogous manner to Example 168 from (S)-2-(6-(3-chloro-2,6-difluorophenyl)-2-methyl-3-thioxo-2,5,6,7-tetrahydro-3H-pyrrolo[1,2-c]imidazol-1-yl) acetic acid and isolated as an off-white solid.

¹H NMR (DMSO$_{d6}$): 11.78 (1H, m), 7.61 (1H, td, J=8.7, 5.6 Hz), 7.22 (1H, m), 4.45 (1H, quin, J=8.5 Hz), 4.24 (1H, dd, J=11.3, 9.4 Hz), 3.82 (3H, br dd, J=11.4, 7.7 Hz), 3.41 (3H, m), 3.33 (1H, m), 2.93 (1H, dd, J=15.9, 8.0 Hz), 2.43 (3H, s).

¹³C NMR (DMSO$_{d6}$): 166.8, 160.5, 160.1, 160.1, 158.5, 158.4, 157, 156.6, 156.5, 154.9, 154.9, 129.7, 129.7, 129.3, 118.8, 118.6, 118.5, 116.1, 116, 115.9, 115.9, 114.8, 113.2, 113.2, 113.1, 113.1, 49.6, 34.7, 31.6, 31.5, 29.2, 10.6.

Example 350: (S)-2-(6-(3-chloro-2,6-difluorophenyl)-2-methyl-3-thioxo-2,5,6,7-tetrahydro-3H-pyrrolo[1,2-c]imidazol-1-yl)-N-(1-methyl-1H-pyrazol-4-yl)acetamide

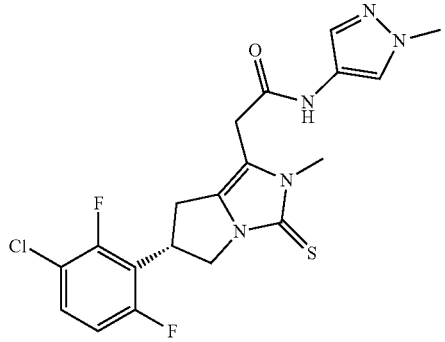 [SMILES: Cn1cc(NC(=O)Cc2c3n(c(=S)n2C)C[C@H](c2c(F)ccc(Cl)c2F)C3)cn1]

Compound was prepared analogous manner to Example 168 from (S)-2-(6-(3-chloro-2,6-difluorophenyl)-2-methyl-3-thioxo-2,5,6,7-tetrahydro-3H-pyrrolo[1,2-c]imidazol-1-yl) acetic acid and isolated as an off-white solid.

¹H NMR (DMSO$_{d6}$): 10.16 (1H, s), 7.85 (1H, s), 7.61 (1H, td, J=8.7, 5.6 Hz), 7.39 (1H, s), 7.21 (1H, t, J=9.4 Hz), 4.45 (1H, quin, J=8.5 Hz), 4.23 (1H, m), 3.81 (1H, br dd, J=11.4, 7.9 Hz), 3.77 (3H, s), 3.62 (2H, m), 3.42 (3H, s), 3.29 (1H, m), 2.90 (1H, br dd, J=15.8, 8.1 Hz).

¹³C NMR (DMSO$_{d6}$): 165, 160.1, 160.1, 158.5, 158.5, 156.6, 156.5, 156.3, 154.9, 154.9, 129.7, 129.7, 129.6, 128.7, 128.6, 121.4, 121.2, 118.7, 118.6, 118.5, 116.1, 113.3, 113.2, 113.1, 113.1, 49.5, 38.6, 34.7, 31.5, 31.3, 29.1.

Example 351: (R)—N-(isothiazol-4-yl)-2-(2-methyl-3-thioxo-6-(2,3,6-trifluorophenyl)-2,5,6,7-tetrahydro-3H-pyrrolo[1,2-c]imidazol-1-yl)acetamide

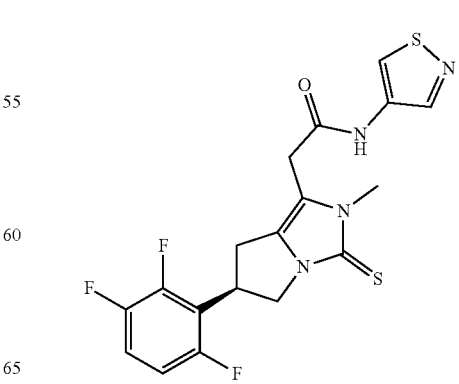

Compound was prepared analogous manner to Example 168 from (S)-2-(2-methyl-3-thioxo-6-(2,3,6-trifluorophenyl)-2,5,6,7-tetrahydro-3H-pyrrolo[1,2-c]imidazol-1-yl)acetic acid and isolated as a cream powder.

¹H NMR (DMSO_{d6}): 10.87 (1H, s), 8.88 (1H, s), 8.59 (1H, s), 7.47 (1H, m), 7.18 (1H, m), 4.45 (1H, quin, J=8.7 Hz), 4.25 (1H, dd, J=9.5, 11.4 Hz), 3.83 (1H, dd, J=11.5, 8.0 Hz), 3.72 (2H, m), 3.44 (3H, s), 3.33 (1H, dd, J=9.5, 15.8 Hz), 2.94 (1H, dd, J=15.8, 8.4 Hz).

¹³C NMR (DMSO_{d6}): 166.2, 157, 157, 156.9, 156.5, 155.3, 155.3, 155.3, 150.8, 149.1, 149, 149, 149, 147.5, 147.5, 147.5, 147.4, 147.4, 147.4, 147.3, 145.9, 145.9, 145.8, 145.8, 134.7, 132.6, 128.8, 118.8, 118.7, 118.7, 118.6, 116.5, 116.5, 116.4, 116.3, 115.7, 112, 112, 112, 111.9, 111.8, 111.8, 111.8, 111.8, 49.5, 34.7, 31.6, 31.4, 29.1.

Example 352: (S)-2-(6-(3-chloro-2,6-difluorophenyl)-2-methyl-3-thioxo-2,5,6,7-tetrahydro-3H-pyrrolo[1,2-c]imidazol-1-yl)-N-((tetrahydro-2H-pyran-4-yl)methyl)acetamide

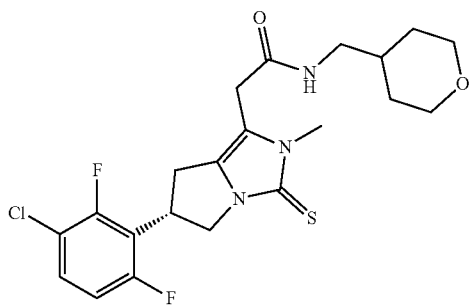 [SMILES: Cn1c(CC(=O)NCC2CCOCC2)c2n(c1=S)C[C@H](c1c(F)ccc(Cl)c1F)C2]

Compound was prepared analogous manner to Example 32 from (S)-2-(6-(3-chloro-2,6-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as an off-white solid.

¹H NMR (DMSO_{d6}): 8.09 (1H, br t, J=5.7 Hz), 7.62 (1H, td, J=8.8, 5.6 Hz), 7.22 (1H, m), 4.44 (1H, quin, J=8.6 Hz), 4.22 (1H, m), 3.81 (3H, m), 3.44 (2H, m), 3.40 (3H, s), 3.29 (1H, m), 3.22 (2H, tt, J=11.7, 2.3 Hz), 2.96 (2H, m), 2.88 (1H, dd, J=15.8, 8.1 Hz), 1.62 (1H, m), 1.51 (2H, br d, J=12.6 Hz), 1.13 (2H, m).

¹³C NMR (DMSO_{d6}): 167.8, 160.1, 160.1, 158.5, 158.4, 156.6, 156.5, 156.2, 154.9, 154.9, 129.7, 129.7, 128.4, 118.8, 118.7, 118.5, 116.5, 116.1, 116, 115.9, 115.9, 113.2, 113.2, 113.1, 113.1, 66.7, 49.5, 44.5, 34.7, 34.7, 31.5, 31.2, 30.3, 29.2.

Example 353: 1-(3-(fluoromethyl)pyrrolidin-1-yl)-2-((R)-2-methyl-3-thioxo-6-(2,3,6-trifluorophenyl)-2,5,6,7-tetrahydro-3H-pyrrolo[1,2-c]imidazol-1-yl)ethan-1-one

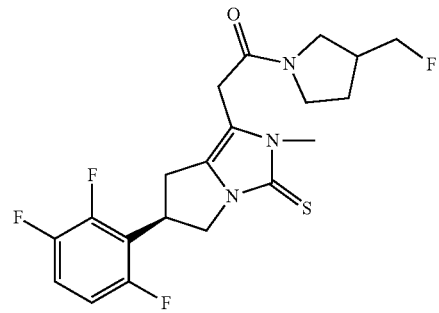 [SMILES: Cn1c(CC(=O)N2CCC(CF)C2)c2n(c1=S)C[C@@H](c1c(F)ccc(F)c1F)C2]

Compound was prepared analogous manner to Example 32 from (S)-2-(6-(2,3,6-trifluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as a cream powder.

¹H NMR (DMSO_{d6}): 7.47 (1H, m), 7.18 (1H, m), 4.54-4.34 (3H, m), 4.24 (1H, dd, J=9.6, 11.0 Hz), 3.81 (1H, dd, J=11.6, 7.9 Hz), 3.75-3.58 (3H, m), 3.55-3.44 (1.5H, m), 3.37 (3H, m), 3.29 (2H, m), 3.12 (0.5H, m), 2.88 (1H, m), 2.67 (0.5H, m), 2.53 (0.5H, m), 2.05 (0.5H, m), 1.94 (0.5H, m), 1.77 (0.5H, m), 1.64 (0.5H, m).

¹³C NMR (DMSO_{d6}): 166.3, 166.2, 157, 156.9, 156.9, 156.9, 156.2, 155.3, 155.3, 155.3, 155.3, 149.1, 149, 149, 148.9, 147.5, 147.5, 147.5, 147.4, 147.4, 147.4, 147.3, 145.9, 145.9, 145.9, 145.8, 128.3, 128.2, 128.2, 118.9, 118.8, 118.8, 118.7, 116.5, 116.4, 116.4, 116.3, 116.2, 111.9, 111.8, 84.8, 84.8, 83.7, 83.7, 49.4, 48, 47.9, 47.9, 47.9, 47.2, 47.2, 47.2, 47.2, 45.4, 45, 37.3, 37.2, 37.1, 37.1, 34.7, 31.5, 30.3, 30.1, 30.1, 29.1, 27.2, 27.1, 25.4, 25.4, 25.4, 25.3.

Example 354: 2-((R)-2-methyl-3-thioxo-6-(2,3,6-trifluorophenyl)-2,5,6,7-tetrahydro-3H-pyrrolo[1,2-c]imidazol-1-yl)-N—((R)-2-oxopiperidin-3-yl)acetamide

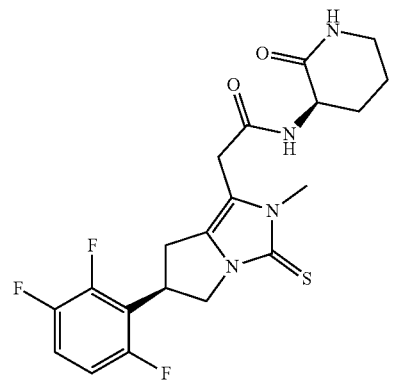 [SMILES: Cn1c(CC(=O)N[C@@H]2CCCNC2=O)c2n(c1=S)C[C@@H](c1c(F)ccc(F)c1F)C2]

Compound was prepared analogous manner to Example 22 from (R)-2-(6-(2,3,6-trifluorophenyl)-2-methyl-3-thioxo-2,5,6,7-tetrahydro-3H-pyrrolo[1,2-c]imidazol-1-yl)acetic acid and isolated as a cream powder.

¹H NMR (DMSO$_{d6}$): 8.30 (1H, d, J=8.3 Hz), 7.62 (1H, br s), 7.47 (1H, m), 7.18 (1H, m), 4.42 (1H, m), 4.23 (1H, dd, J=9.6, 11.3 Hz), 4.13 (1H, m), 3.81 (1H, dd, J=11.4, 8.1 Hz), 3.47 (2H, m), 3.42 (3H, s), 3.29 (1H, dd, J=15.7, 9.3 Hz), 3.11 (2H, m), 2.95 (1H, dd, J=16.0, 8.3 Hz), 1.94 (1H, m), 1.81-1.66 (2H, m), 1.60 (1H, m).

¹³C NMR (DMSO$_{d6}$): 169.5, 167.4, 157, 156.9, 156.9, 156.2, 155.4, 155.3, 155.3, 149.1, 149.1, 148.9, 147.5, 147.5, 147.5, 147.4, 147.4, 147.4, 145.9, 145.8, 128.6, 128.5, 118.8, 118.7, 118.7, 118.6, 116.5, 116.5, 116.4, 116.4, 116.3, 112, 112, 112, 111.8, 111.8, 111.8, 111.8, 49.4, 49.2, 41, 34.7, 31.4, 31.3, 29.1, 27.5, 21.

Example 355: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-((1r,4R)-4-hydroxycyclohexyl)acetamide

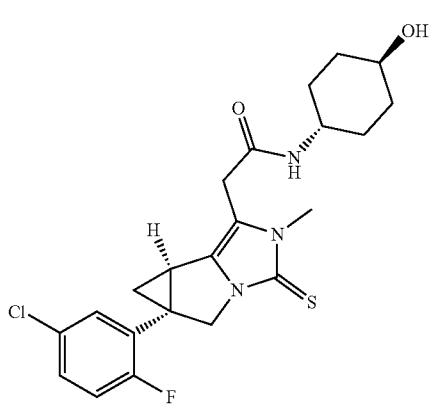 [SMILES: Cn1c(CC(=O)N[C@H]2CC[C@H](O)CC2)c2n(c1=S)C[C@@]1(c3cc(Cl)ccc3F)C[C@@H]21]

Compound was prepared analogous manner to Example 25 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one using DIPEA as base and isolated as a light beige solid.

¹H NMR (DMSO$_{d6}$): 7.44 (1H, dd, J=6.5, 2.6 Hz), 7.35 (1H, ddd, J=8.8, 4.4, 2.7 Hz), 7.16 (1H, dd, J=9.8, 8.9 Hz), 4.24 (1H, d, J=12.3 Hz), 3.97 (1H, d, J=12.2 Hz), 3.65 (1H, m), 3.56 (2H, s), 3.52 (1H, m), 3.48 (3H, s), 2.81 (1H, dd, J=8.3, 4.0 Hz), 1.95 (4H, m), 1.68 (1H, dd, J=8.4, 5.6 Hz), 1.34 (4H, m), 1.18 (1H, m).

¹³C NMR (DMSO$_{d6}$): 170.2, 163.3, 161.6, 157.7, 133.8, 131.5, 131.5, 130.9, 130.8, 130.7, 130.7, 130, 129.9, 118.5, 118.4, 118, 70.5, 54.3, 54.3, 49.3, 34.9, 33.3, 32.5, 32.4, 31.6, 23.3, 22.3.

Example 356: (S)-2-(6-(3-chloro-2,6-difluorophenyl)-2-methyl-3-thioxo-2,5,6,7-tetrahydro-3H-pyrrolo[1,2-c]imidazol-1-yl)-N-cyclohexylacetamide

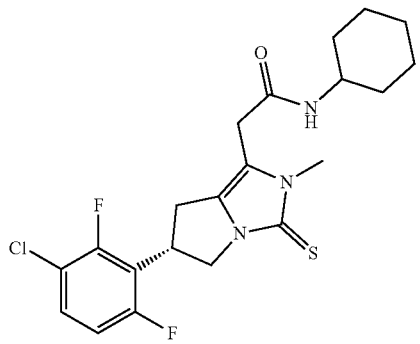 [SMILES: Cn1c(CC(=O)NC2CCCCC2)c2n(c1=S)C[C@H](c1c(F)ccc(Cl)c1F)C2]

Compound was prepared analogous manner to Example 32 from (S)-2-(6-(3-chloro-2,6-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as an off-white solid.

¹H NMR (DMSO$_{d6}$): 7.98 (1H, br d, J=7.8 Hz), 7.61 (1H, td, J=8.7, 5.6 Hz), 7.22 (1H, t, J=9.0 Hz), 4.44 (1H, quin, J=8.5 Hz), 4.22 (1H, m), 3.80 (1H, dd, J=11.6, 7.8 Hz), 3.51 (1H, m), 3.39 (3H, m), 3.28 (1H, br dd, J=15.9, 9.3 Hz), 2.88 (1H, br dd, J=15.8, 7.9 Hz), 1.80-1.40 (6H, m), 1.32-0.97 (6H, m).

¹³C NMR (DMSO$_{d6}$): 166.5, 160.1, 160.1, 158.5, 158.4, 156.6, 156.5, 156.1, 154.9, 154.9, 129.7, 129.6, 128.3, 118.9, 118.7, 118.6, 116.6, 116.1, 116, 115.9, 115.9, 113.2, 113.2, 113.1, 113.1, 49.5, 47.7, 34.7, 33.3, 32.3, 31.4, 31.3, 29.2, 25.2, 24.5.

Example 357: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-cyclopropylacetamide

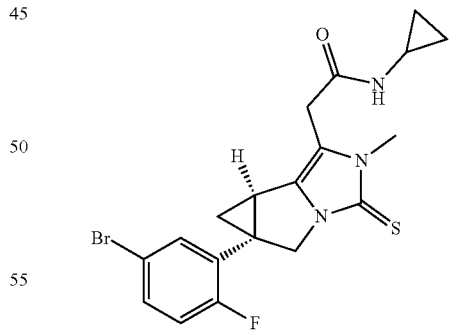

Compound was prepared analogous manner to Example 32 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

¹H NMR (DMSO$_{d6}$): 8.19 (1H, d, J=4.0 Hz), 7.59 (1H, dd, J=6.7, 2.6 Hz), 7.56 (1H, ddd, J=8.6, 4.5, 2.6 Hz), 7.24 (1H, dd, J=10.1, 8.7 Hz), 4.14 (1H, d, J=12.0 Hz), 3.85 (1H, d, J=12.0 Hz), 3.46 (2H, m), 3.34 (3H, s), 2.89 (1H, dd, J=8.4, 4.1 Hz), 2.64 (1H, m), 1.69 (1H, dd, J=8.3, 5.4 Hz), 1.14 (1H, t, J=4.8 Hz), 0.63 (2H, m), 0.42 (2H, m).

$^{13}$C NMR (DMSO$_{d6}$): 168.9, 161.8, 160.1, 156.8, 133, 133, 132.4, 132.3, 131, 129.2, 129.1, 118, 117.8, 116.2, 116.2, 116, 52.4, 52.4, 31.5, 31.4, 31, 22.5, 22.1, 20.7, 5.6.

Example 358: N,N-dimethyl-1-(2-((R)-2-methyl-3-thioxo-6-(2,3,6-trifluorophenyl)-2,5,6,7-tetrahydro-3H-pyrrolo[1,2-c]imidazol-1-yl)acetyl)pyrrolidine-3-carboxamide

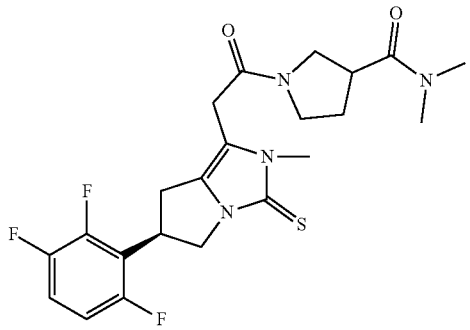 [SMILES: CN(C)C(=O)C1CCN(C(=O)Cc2c3n(c(=S)n2C)C[C@@H](c2c(F)ccc(F)c2F)C3)C1]

Compound was prepared analogous manner to Example 25 from (R)-1-(H-imidazol-1-yl)-2-(2-methyl-3-thioxo-6-(2,3,6-trifluorophenyl)-2,5,6,7-tetrahydro-3H-pyrrolo[1,2-c]imidazol-1-yl)ethan-1-one and isolated as a cream powder.

$^1$H NMR (DMSO$_{d6}$): 7.47 (1H, m), 7.18 (1H, m), 4.43 (1H, m), 4.24 (1H, dd, J=9.5, 11.2 Hz), 3.81 (1H, dd, J=11.4, 8.1 Hz), 3.75-3.42 (5.5H, several. mult.), 3.38 (3H, s), 3.37 (1H, m), 3.29 (1.5H, m), 3.03, 3.02 (3H, 3 s), 2.89 (1H, m), 2.82 (3H, 4 s), 2.12 (0.5H, m), 2.05 (0.5H, m), 1.97 (0.5H, m), 1.85 (0.5H, m).

$^{13}$C NMR (DMSO$_{d6}$): 171.7, 171.7, 171.3, 171.3, 166.1, 166, 166, 166, 156.9, 156.9, 156.2, 156.2, 155.3, 155.3, 155.3, 149.1, 149.1, 149, 149, 148.9, 147.5, 147.5, 147.5, 147.4, 147.4, 147.4, 147.3, 145.9, 145.9, 145.9, 145.8, 128.2, 119, 118.9, 118.9, 118.8, 118.8, 118.8, 117.7, 116.5, 116.4, 116.4, 116.3, 116.3, 116.2, 116.2, 116.2, 112, 111.9, 111.9, 111.8, 111.8, 111.8, 49.4, 48.6, 48.4, 45.8, 45.8, 45.3, 45.2, 40.2, 40, 38.3, 36.7, 35.1, 35.1, 35, 34.7, 34.7, 31.5, 30.3, 30.3, 30.2, 29.1, 29.1, 29, 27.5.

Example 359: (5aS,6aR)-5a-(5-bromo-2-fluorophenyl)-2-methyl-1-(2-(((R)-tetrahydrofuran-3-yl)amino)ethyl)-5,5a,6,6a-tetrahydrocyclopropa[3,4]pyrrolo[1,2-c]imidazole-3(2H)-thione

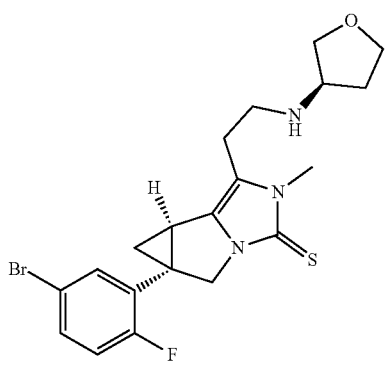 [SMILES: Cn1c(CCN[C@@H]2CCOC2)c2n(c1=S)C[C@@]1(c3cc(Br)ccc3F)C[C@@H]21]

Compound was prepared analogous manner to Example 35 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N—((R)-tetrahydrofuran-3-yl)acetamide (Example 279) and isolated as a beige solid.

$^1$H NMR (DMSO$_{d6}$): 7.58 (1H, dd, J=6.6, 2.5 Hz), 7.50 (1H, m), 7.11 (1H, t, J=9.4 Hz), 4.23 (1H, d, J=12.2 Hz), 3.95 (2H, m), 3.83 (1H, dd, J=9.2, 5.9 Hz), 3.76 (1H, td, J=8.3, 6.4 Hz), 3.65 (1H, dd, J=9.2, 4.0 Hz), 3.52 (4H, s), 3.04-2.77 (5H, m), 2.19 (1H, td, J=13.4, 7.6 Hz), 1.81 (1H, m), 1.70 (1H, dd, J=8.2, 5.6 Hz), 1.16 (1H, m).

$^{13}$C NMR (DMSO$_{d6}$): 163.8, 162.2, 157.5, 134.5, 134.5, 134, 133.9, 132.7, 130.5, 130.4, 121, 119, 118.8, 118, 118, 73.5, 68.3, 59.7, 54.2, 54.1, 47.1, 33.3, 33.2, 32.2, 25.4, 23.3, 22.4.

Example 360: 2-((R)-6-(2,3,5,6-tetrafluorophenyl)-3-thioxo-2,5,6,7-tetrahydro-3H-pyrrolo[1,2-c]imidazol-1-yl)-N—((R)-tetrahydrofuran-3-yl)acetamide

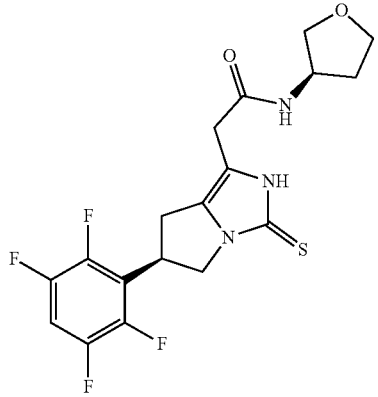 [SMILES: O=C(Cc1[nH]c(=S)n2c1C[C@H](c1c(F)c(F)cc(F)c1F)C2)N[C@@H]1CCOC1]

Compound was prepared analogous manner to Example 32 from (R)-1-(1H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone and isolated as a khaki powder.

$^1$H NMR (DMSO$_{d6}$): 11.76 (1H, s), 8.23 (1H, d, J=6.6 Hz), 7.85 (1H, m), 4.48 (1H, quin, J=8.5 Hz), 4.21 (1H, m), 4.17 (1H, dd, J=11.6, 9.1 Hz), 3.77 (2H, m), 3.71 (1H, dd, J=8.9, 5.9 Hz), 3.65 (1H, td, J=8.2, 5.6 Hz), 3.45 (1H, dd, J=8.9, 3.7 Hz), 3.25 (1H, m), 3.25 (2H, s), 2.88 (1H, dd, J=15.8, 8.3 Hz), 2.06 (1H, dq, J=12.7, 7.6 Hz), 1.71 (1H, m).

$^{13}$C NMR (DMSO$_{d6}$): 167.5, 155.2, 146.4, 146.4, 146.3, 146.3, 146.2, 145.3, 145.3, 145.3, 145.3, 145.2, 145.2, 144.8, 144.8, 144.7, 144.6, 144.6, 143.7, 143.7, 143.7, 143.7, 143.6, 143.6, 143.6, 143.6, 128.9, 120.5, 120.3, 120.2, 114.3, 105.9, 105.7, 105.6, 72.4, 66.3, 49.8, 48.4, 35.7, 32, 31.3, 29.2.

Example 361: 2-((5aS,6aR)-5a-(5-bromo-2-fluorophenyl)-3-thioxo-2,3,5,5a,6,6a-hexahydrocyclopropa[3,4]pyrrolo[1,2-c]imidazol-1-yl)acetic Acid

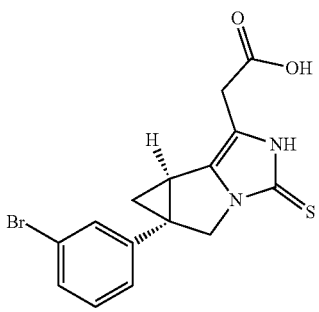 [SMILES: O=C(O)Cc1[nH]c(=S)n2c1[C@@H]1C[C@]1(c1cccc(Br)c1)C2]

Compound was prepared analogous manner to Example 2 from (1R,5S)-3-(tert-butoxycarbonyl)-5-(5-bromo-2-fluorophenyl)-3-azabicyclo[3.1.0]hexane-2-carboxylic acid. The product was isolated as a light yellow solid.

$^1$H NMR (DMSO$_{d6}$): 1.65 (1H, br s), 7.56 (2H, m), 7.24 (1H, t, J=9.3 Hz), 4.08 (1H, br d, J=11.9 Hz), 3.79 (1H, d, J=12.2 Hz), 3.42 (2H, m), 2.88 (1H, dd, J=8.3, 4.2 Hz), 1.66 (1H, dd, J=8.1, 5.4 Hz), 1.10 (1H, m).

$^{13}$C NMR (DMSO$_{d6}$): 171.1, 161.8, 160.1, 155.9, 132.9, 132.9, 132.3, 132.3, 131.8, 129.3, 129.2, 118, 117.8, 116.2, 116.2, 113.7, 51.6, 51.6, 32.3, 30.5, 22.2, 20.6.

Example 362: 2-((S)-6-(3-chloro-2,6-difluorophenyl)-3-thioxo-2,5,6,7-tetrahydro-3H-pyrrolo[1,2-c]imidazol-1-yl)-N—((R)-tetrahydrofuran-3-yl)acetamide

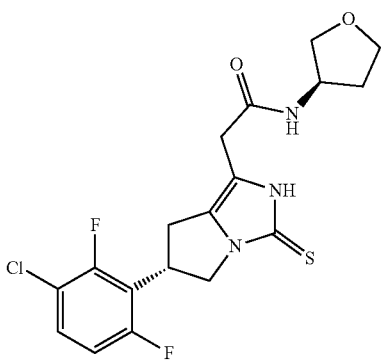 [SMILES: O=C(Cc1[nH]c(=S)n2c1C[C@@H](c1c(F)ccc(Cl)c1F)C2)N[C@@H]1CCOC1]

Compound was prepared analogous manner to Example 32 from (S)-2-(6-(3-chloro-2,6-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as an off-white solid.

$^1$H NMR (DMSO$_{d6}$): 11.75 (1H, s), 8.22 (1H, br d, J=6.6 Hz), 7.61 (1H, td, J=8.7, 5.6 Hz), 7.22 (1H, t, J=8.9 Hz), 4.44 (1H, quin, J=8.6 Hz), 4.21 (1H, m), 4.15 (1H, dd, J=11.2, 9.5 Hz), 3.73 (3H, m), 3.65 (1H, td, J=8.2, 5.6 Hz), 3.45 (1H, dd, J=8.9, 3.7 Hz), 3.24 (2H, s), 3.21 (1H, dd, J=9.0, 15.6 Hz), 2.84 (1H, dd, J=15.6, 8.1 Hz), 2.06 (1H, m), 1.71 (1H, m).

$^{13}$C NMR (DMSO$_{d6}$): 167.5, 160.1, 160.1, 158.5, 158.5, 156.6, 156.5, 155.1, 154.9, 154.9, 129.7, 129.6, 129.1, 118.8, 118.7, 118.5, 116, 116, 115.9, 115.9, 114.2, 113.2, 113.2, 113.1, 113.1, 72.4, 72.4, 66.3, 49.7, 48.5, 35.6, 32, 31.9, 31.3, 29.3.

Example 363: (S)-2-(6-(3-chloro-2,6-difluorophenyl)-3-thioxo-2,5,6,7-tetrahydro-3H-pyrrolo[1,2-c]imidazol-1-yl)-1-morpholinoethan-1-one

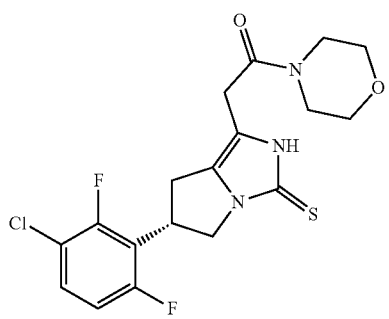 [SMILES: O=C(Cc1[nH]c(=S)n2c1C[C@@H](c1c(F)ccc(Cl)c1F)C2)N1CCOCC1]

Compound was prepared analogous manner to Example 32 from (S)-2-(6-(3-chloro-2,6-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as an off-white solid.

$^1$H NMR (DMSO$_{d6}$): 1.69 (1H, br s), 7.61 (1H, td, J=8.7, 5.6 Hz), 7.22 (1H, t, J=8.9 Hz), 4.45 (1H, quin, J=8.5 Hz), 4.16 (1H, dd, J=11.1, 9.6 Hz), 3.73 (1H, dd, J=11.4, 7.9 Hz), 3.55 (4H, m), 3.51 (2H, s), 3.44 (4H, m), 3.22 (1H, dd, J=15.8, 9.3 Hz), 2.83 (1H, dd, J=15.7, 8.1 Hz).

$^{13}$C NMR (DMSO$_{d6}$): 166.8, 160.1, 160.1, 158.5, 158.5, 156.6, 156.5, 155.2, 154.9, 154.9, 129.7, 129.6, 129.3, 118.8, 118.7, 118.6, 116.1, 116, 115.9, 115.9, 114, 113.2, 113.2, 113.1, 113.1, 66, 66, 48.6, 45.7, 41.7, 35.6, 29.3, 28.8.

Example 364: N-methyl-N-(tetrahydrofuran-3-yl)-2-((R)-3-thioxo-6-(2,3,6-trifluorophenyl)-2,5,6,7-tetrahydro-3H-pyrrolo[1,2-c]imidazol-1-yl)acetamide

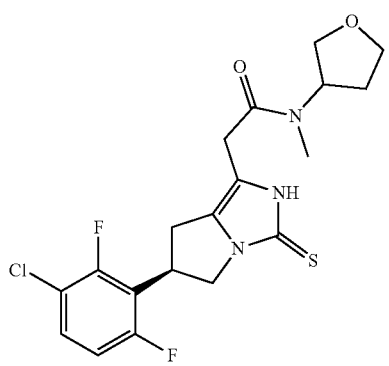 [SMILES: CN(C(=O)Cc1[nH]c(=S)n2c1C[C@H](c1c(F)ccc(Cl)c1F)C2)C1CCOC1]

Compound was prepared analogous manner to Example 34 from (R)-2-(3-thioxo-6-(2,3,6-trifluorophenyl)-2,5,6,7-tetrahydro-3H-pyrrolo[1,2-c]imidazol-1-yl)acetic acid and isolated as a cream powder.

$^1$H NMR (DMSO$_{d6}$): 11.68 (1H, m), 7.47 (1H, qd, J=9.4, 5.1 Hz), 7.18 (1H, t, J=9.5 Hz), 5.08 (0.6H, m), 4.61 (0.4H, m), 4.43 (1H, quin, J=8.6 Hz), 4.16 (1H, m), 3.92 (1H, m), 3.74 (1H, dd, J=11.5, 8.0 Hz), 3.67 (0.8H, m), 3.64-3.53

(3H, m), 3.48 (1.2H, s), 3.21 (1H, m), 2.88 (1.8H, s), 2.83 (1H, m), 2.72 (1.2H, s), 2.10 (1H, m), 1.78 (1H, m).

$^{13}$C NMR (DMSO$_{d6}$): 168.3, 167.7, 157, 156.9, 156.9, 155.3, 155.3, 155.2, 155.1, 149.1, 149, 149, 147.6, 147.5, 147.5, 147.4, 147.4, 147.4, 147.3, 145.9, 145.9, 145.9, 145.8, 129.2, 129.2, 119, 118.9, 118.8, 118.8, 118.7, 118.7, 116.5, 116.4, 116.4, 116.3, 114.3, 114.2, 112, 112, 112, 111.9, 111.8, 111.8, 111.8, 111.8, 69.3, 69.3, 69.3, 67.1, 67.1, 56.5, 52.9, 48.5, 35.6, 30, 29.8, 29.8, 29.7, 29.5, 29.5, 29.3, 29.2, 29.2, 27.6.

Example 365: N—((R)-tetrahydro-2H-pyran-3-yl)-2-((R)-3-thioxo-6-(2,3,6-trifluorophenyl)-2,5,6,7-tetrahydro-3H-pyrrolo[1,2-c]imidazol-1-yl)acetamide

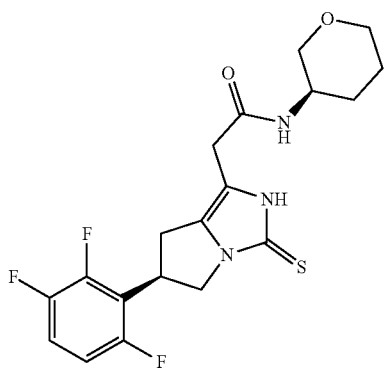 [SMILES: O=C(Cc1[nH]c(=S)n2c1C[C@H](c1c(F)ccc(F)c1F)C2)N[C@@H]1CCCOC1]

Compound was prepared analogous manner to Example 34 from (R)-2-(3-thioxo-6-(2,3,6-trifluorophenyl)-2,5,6,7-tetrahydro-3H-pyrrolo[1,2-c]imidazol-1-yl)acetic acid and isolated as a cream powder.

$^1$H NMR (DMSO$_{d6}$): 11.75 (1H, s), 7.96 (1H, br d, J=7.5 Hz), 7.47 (1H, qd, J=9.4, 5.1 Hz), 7.18 (1H, m), 4.43 (1H, quin, J=8.7 Hz), 4.16 (1H, m), 3.74 (1H, dd, J=11.5, 8.1 Hz), 3.65 (3H, m), 3.33 (1H, m), 3.25 (2H, s), 3.22 (1H, dd, J=16.0, 9.5 Hz), 3.09 (1H, m), 2.85 (1H, dd, J=15.7, 8.4 Hz), 1.80 (1H, m), 1.66 (1H, m), 1.45 (2H, m).

$^{13}$C NMR (DMSO$_{d6}$): 167.2, 157, 156.9, 155.3, 155.3, 155.1, 149.1, 149, 149, 148.9, 147.6, 147.5, 147.5, 147.4, 147.4, 147.3, 145.9, 145.9, 145.9, 145.8, 129, 118.9, 118.8, 118.8, 118.7, 116.5, 116.4, 116.4, 116.3, 114.4, 112, 112, 112, 111.9, 111.8, 111.8, 111.8, 111.8, 70.2, 67, 48.5, 45.1, 35.6, 31.4, 29.3, 28.6, 23.9.

Example 366: (R)-2-(6-(2,3,6-trifluorophenyl)-3-thioxo-2,5,6,7-tetrahydro-3H-pyrrolo[1,2-c]imidazol-1-yl)-1-morpholinoethan-1-one

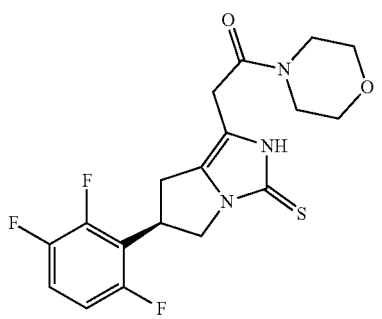 [SMILES: O=C(Cc1[nH]c(=S)n2c1C[C@H](c1c(F)ccc(F)c1F)C2)N1CCOCC1]

Compound was prepared analogous manner to Example 32 from (R)-1-(H-imidazol-1-yl)-2-(6-(2,3,6-trifluorophenyl)-3-thioxo-3,5,6,7-tetrahydro-2H-pyrrolo[1,2-c]imidazol-1-yl)ethanone and isolated as a cream powder.

$^1$H NMR (DMSO$_{d6}$): 11.70 (1H, s), 7.47 (1H, qd, J=9.4, 4.9 Hz), 7.18 (1H, m), 4.44 (1H, quin, J=8.7 Hz), 4.17 (1H, dd, J=11.1, 9.5 Hz), 3.74 (1H, dd, J=11.6, 8.1 Hz), 3.55 (4H, m), 3.51 (2H, s), 3.45 (4H, m), 3.22 (1H, dd, J=15.7, 9.2 Hz), 2.85 (1H, dd, J=15.8, 8.3 Hz).

$^{13}$C NMR (DMSO$_{d6}$): 166.8, 157, 157, 156.9, 156.9, 155.4, 155.3, 155.3, 155.2, 149.1, 149, 149, 148.9, 147.6, 147.5, 147.4, 147.4, 147.3, 146, 145.9, 145.9, 145.8, 129.2, 118.9, 118.8, 118.8, 118.7, 116.5, 116.4, 116.4, 116.3, 114.1, 112, 112, 112, 111.9, 111.8, 111.8, 111.8, 111.8, 66, 66, 48.5, 45.7, 41.7, 35.6, 29.2, 28.8.

Example 367: (S)-2-(6-(3-chloro-2,6-difluorophenyl)-2-methyl-3-thioxo-2,5,6,7-tetrahydro-3H-pyrrolo[1,2-c]imidazol-1-yl)-N-(tetrahydro-2H-pyran-4-yl)acetamide

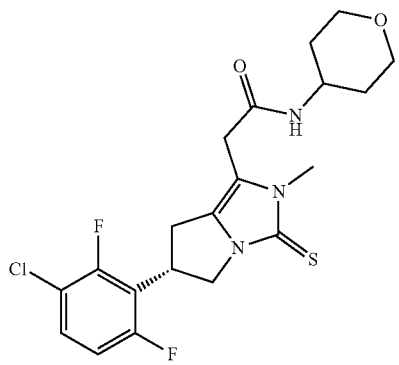 [SMILES: Cn1c(CC(=O)NC2CCOCC2)c2n(c1=S)C[C@H](c1c(F)ccc(Cl)c1F)C2]

Compound was prepared analogous manner to Example 32 from (S)-2-(6-(3-chloro-2,6-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as an off-white powder.

$^1$H NMR (DMSO$_{d6}$): 8.11 (1H, d, J=7.6 Hz), 7.61 (1H, td, J=8.7, 5.6 Hz), 7.22 (1H, m), 4.44 (1H, quin, J=8.5 Hz), 4.22 (1H, dd, J=11.4, 9.3 Hz), 3.80 (3H, m), 3.75 (1H, m), 3.42 (2H, d, J=2.2 Hz), 3.40 (3H, s), 3.33 (2H, m), 3.29 (1H, dd, J=9.2, 15.8 Hz), 2.89 (1H, dd, J=15.8, 8.1 Hz), 1.69 (2H, dt, J=12.7, 2.2 Hz), 1.38 (2H, m).

$^{13}$C NMR (DMSO$_{d6}$): 166.8, 160.1, 160.1, 158.5, 158.4, 156.6, 156.5, 156.2, 154.9, 154.9, 129.7, 129.6, 128.4, 118.8, 118.7, 118.6, 116.5, 116.1, 116, 115.9, 115.9, 113.2, 113.2, 113.1, 113.1, 65.8, 49.5, 45.2, 34.7, 32.4, 32.4, 31.5, 31.3, 29.2.

Example 368: 2-((R)-6-(2,3,6-trifluorophenyl)-3-thioxo-2,5,6,7-tetrahydro-3H-pyrrolo[1,2-c]imidazol-1-yl)-N—((R)-tetrahydrofuran-3-yl)acetamide

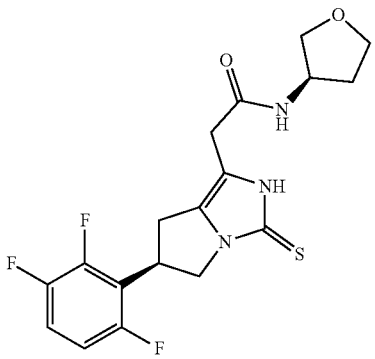 [SMILES: O=C(Cc1[nH]c(=S)n2c1C[C@H](c1c(F)ccc(F)c1F)C2)N[C@@H]1CCOC1]

Compound was prepared analogous manner to Example 32 from (R)-1-(H-imidazol-1-yl)-2-(6-(2,3,6-trifluorophenyl)-3-thioxo-3,5,6,7-tetrahydro-2H-pyrrolo[1,2-c]imidazol-1-yl)ethanone and isolated as a cream powder.

$^1$H NMR (DMSO$_{d6}$): 11.75 (1H, s), 8.22 (1H, d, J=6.6 Hz), 7.47 (1H, qd, J=9.5, 5.1 Hz), 7.18 (1H, tdd, J=9.6, 9.6, 3.7, 1.8 Hz), 4.43 (1H, quin, J=8.7 Hz), 4.21 (1H, tt, J=10.2, 3.9 Hz), 4.16 (1H, dd, J=11.4, 9.3 Hz), 3.73 (3H, m), 3.65 (1H, td, J=8.2, 5.6 Hz), 3.45 (1H, dd, J=8.9, 3.6 Hz), 3.24 (2H, s), 3.22 (1H, m), 2.86 (1H, dd, J=15.8, 8.4 Hz), 2.06 (1H, dq, J=12.7, 7.6 Hz), 1.71 (1H, m).

$^{13}$C NMR (DMSO$_{d6}$): 167.5, 157, 156.9, 156.9, 155.4, 155.3, 155.3, 155.1, 149.1, 149, 149, 148.9, 147.6, 147.5, 147.5, 147.4, 147.4, 147.4, 147.3, 145.9, 145.9, 145.9, 145.8, 129.1, 118.9, 118.8, 118.7, 118.7, 116.5, 116.4, 116.4, 116.3, 114.3, 112, 112, 112, 111.9, 111.8, 111.8, 111.8, 111.8, 72.4, 66.3, 49.8, 48.5, 35.6, 32, 31.3, 29.3.

Example 369: 2-((R)-6-(2,3,5,6-tetrafluorophenyl)-3-thioxo-2,5,6,7-tetrahydro-3H-pyrrolo[1,2-c]imidazol-1-yl)-N—((S)-tetrahydrofuran-3-yl)acetamide

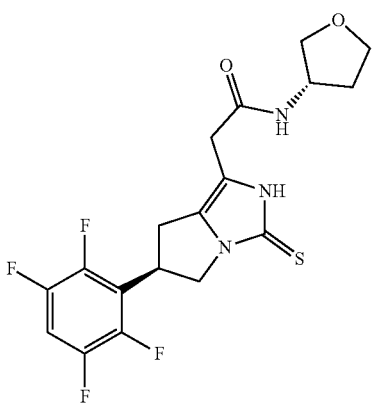 [SMILES: O=C(Cc1[nH]c(=S)n2c1C[C@H](c1c(F)c(F)cc(F)c1F)C2)N[C@H]1CCOC1]

Compound was prepared analogous manner to Example 32 from (R)-1-(H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone and isolated as a khaki powder.

$^1$H NMR (DMSO$_{d6}$): 1.76 (1H, br s), 8.23 (1H, br d, J=6.6 Hz), 7.85 (1H, m), 4.48 (1H, quin, J=8.5 Hz), 4.21 (1H, m), 4.17 (1H, dd, J=11.7, 9.2 Hz), 3.77 (2H, m), 3.71 (1H, dd, J=8.9, 6.0 Hz), 3.65 (1H, td, J=8.3, 5.5 Hz), 3.45 (1H, dd, J=8.9, 3.7 Hz), 3.25 (2H, s), 3.25 (1H, dd, J=9.4, 15.8 Hz), 2.88 (1H, dd, J=15.8, 8.1 Hz), 2.06 (1H, dq, J=12.7, 7.6 Hz), 1.71 (1H, m).

$^{13}$C NMR (DMSO$_{d6}$): 167.5, 155.2, 146.4, 146.4, 146.3, 146.3, 146.2, 145.3, 145.3, 145.3, 145.3, 145.2, 145.2, 145.2, 144.8, 144.8, 144.8, 144.7, 144.7, 144.7, 144.6, 144.6, 143.7, 143.7, 143.7, 143.6, 143.6, 143.6, 143.6, 143.6, 128.9, 120.4, 120.3, 120.2, 114.3, 105.8, 105.7, 105.5, 72.4, 66.3, 49.8, 48.4, 35.7, 31.9, 31.3, 29.2.

Example 370: 2-((R)-6-(2,3,6-trifluorophenyl)-3-thioxo-2,5,6,7-tetrahydro-3H-pyrrolo[1,2-c]imidazol-1-yl)-N—((S)-tetrahydrofuran-3-yl)acetamide

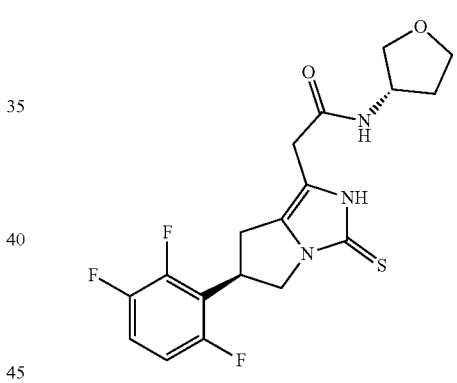

Compound was prepared analogous manner to Example 32 from (R)-1-(H-imidazol-1-yl)-2-(6-(2,3,6-trifluorophenyl)-3-thioxo-3,5,6,7-tetrahydro-2H-pyrrolo[1,2-c]imidazol-1-yl)ethanone and isolated as a cream powder.

$^1$H NMR (DMSO$_{d6}$): 1.75 (1H, br s), 8.22 (1H, br d, J=6.6 Hz), 7.47 (1H, qd, J=9.4, 4.9 Hz), 7.18 (1H, m), 4.43 (1H, quin, J=8.7 Hz), 4.21 (1H, m), 4.16 (1H, m), 3.82-3.69 (3H, m), 3.65 (1H, td, J=8.2, 5.6 Hz), 3.45 (1H, dd, J=8.9, 3.7 Hz), 3.24 (2H, s), 3.22 (1H, m), 2.86 (1H, dd, J=15.7, 8.5 Hz), 2.06 (1H, m), 1.71 (1H, m).

$^{13}$C NMR (DMSO$_{d6}$): 167.5, 157, 157, 156.9, 156.9, 155.4, 155.3, 155.3, 155.1, 149.1, 149, 149, 149, 148.9, 147.6, 147.5, 147.5, 147.4, 147.4, 147.4, 147.3, 145.9, 145.9, 145.9, 145.8, 129.1, 118.9, 118.8, 118.7, 118.7, 116.5, 116.4, 116.4, 116.3, 114.3, 112, 112, 112, 111.9, 111.8, 111.8, 111.8, 111.8, 72.4, 66.3, 49.8, 48.5, 35.6, 32, 31.3, 29.3.

Example 371: 2-((R)-2-methyl-3-thioxo-6-(2,3,6-trifluorophenyl)-2,5,6,7-tetrahydro-3H-pyrrolo[1,2-c]imidazol-1-yl)-N-(1-methyl-6-oxopiperidin-3-yl)acetamide

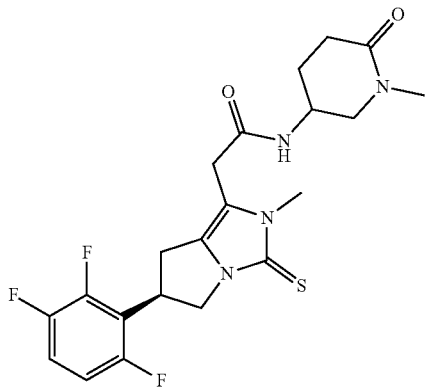 [SMILES: CN1CC(NC(=O)Cc2c3n(c(=S)n2C)C[C@@H](c2c(F)ccc(F)c2F)C3)CCC1=O]

Compound was prepared analogous manner to Example 22 from (R)-2-(6-(2,3,6-trifluorophenyl)-2-methyl-3-thioxo-2,5,6,7-tetrahydro-3H-pyrrolo[1,2-c]imidazol-1-yl)acetic acid and isolated as a cream powder.

$^1$H NMR (DMSO$_{d6}$): 8.35 (1H, d, J=7.7 Hz), 7.47 (1H, qd, J=9.4, 5.0 Hz), 7.18 (1H, m), 4.43 (1H, quin, J=8.6 Hz), 4.24 (1H, dd, J=11.2, 9.4 Hz), 4.04 (1H, m), 3.81 (1H, dd, J=11.5, 8.0 Hz), 3.47 (2H, m), 3.40 (4H, m), 3.30 (1H, dd, J=9.3, 15.8 Hz), 3.07 (1H, ddd, J=12.1, 6.9, 2.2 Hz), 2.91 (1H, dd, J=15.8, 8.2 Hz), 2.77 (3H, 2 s), 2.28 (2H, m), 1.85 (1H, m), 1.75 (1H, m).

$^{13}$C NMR (DMSO$_{d6}$): 167.7, 167.6, 157, 156.9, 156.2, 155.3, 155.3, 149.1, 149, 149, 148.9, 147.6, 147.5, 147.5, 147.4, 147.4, 147.3, 145.9, 145.9, 145.9, 145.8, 128.4, 118.9, 118.8, 118.8, 118.7, 116.5, 116.5, 116.4, 116.4, 116.3, 112, 112, 112, 111.9, 111.8, 111.8, 111.8, 111.8, 52.9, 49.5, 43.4, 43.4, 34.7, 33.9, 31.5, 31.1, 31.1, 29.2, 29, 29, 26.1.

Example 372: (R)—N-methyl-2-(2-methyl-3-thioxo-6-(2,3,6-trifluorophenyl)-2,5,6,7-tetrahydro-3H-pyrrolo[1,2-c]imidazol-1-yl)-N-(tetrahydro-2H-pyran-4-yl)acetamide

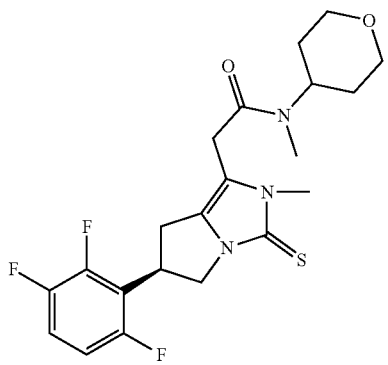 [SMILES: CN(C(=O)Cc1c2n(c(=S)n1C)C[C@@H](c1c(F)ccc(F)c1F)C2)C1CCOCC1]

Compound was prepared analogous manner to Example 32 from (R)-1-(H-imidazol-1-yl)-2-(2-methyl-3-thioxo-6-(2,3,6-trifluorophenyl)-2,5,6,7-tetrahydro-3H-pyrrolo[1,2-c]imidazol-1-yl)ethan-1-one and isolated as a cream powder.

$^1$H NMR (DMSO$_{d6}$): 7.47 (1H, qd, J=9.4, 5.0 Hz), 7.18 (1H, m), 4.45 (1.6H, m), 4.24 (1H, br t, J=10.3 Hz), 3.90 (2.4H, m), 3.82 (1.8H, m), 3.72 (1.2H, m), 3.40 (1.8H, m), 3.30 (1.2H, m), 2.96-2.84 (2.8H, m), 2.72 (1.2H, s), 1.84-1.63 (2H, m), 1.58 (0.8H, m), 1.41 (1.2H, m).

$^{13}$C NMR (DMSO$_{d6}$): 167.7, 167.5, 157, 156.9, 156.9, 156.9, 156.2, 156.2, 155.3, 155.3, 149.1, 149, 148.9, 147.5, 147.5, 147.4, 147.4, 147.3, 145.9, 145.9, 145.8, 128.2, 128.2, 119, 118.9, 118.9, 118.8, 116.8, 116.6, 116.5, 116.4, 116.4, 116.3, 112, 112, 112, 111.9, 111.8, 111.8, 111.8, 111.8, 66.5, 66.3, 53, 49.7, 49.4, 34.8, 31.5, 31.5, 30.2, 30.2, 29.9, 29.5, 29.2, 29.2, 29.2, 29, 27.1.

Example 373: (S)-2-(6-(3-chloro-2,6-difluorophenyl)-2-methyl-3-thioxo-2,5,6,7-tetrahydro-3H-pyrrolo[1,2-c]imidazol-1-yl)-N-methyl-N-(tetrahydro-2H-pyran-4-yl)acetamide

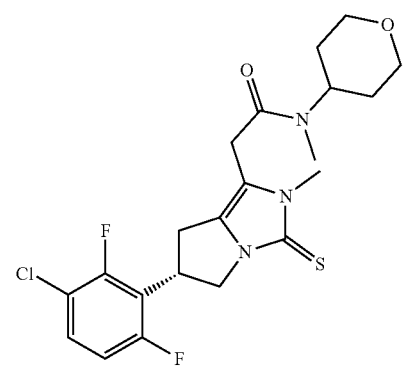 [SMILES: CN(C(=O)Cc1c2n(c(=S)n1C)C[C@H](c1c(F)ccc(Cl)c1F)C2)C1CCOCC1]

Compound was prepared analogous manner to Example 32 from (S)-1-(1H-imidazol-1-yl)-2-(2-methyl-3-thioxo-6-(3-chloro-2,6-difluorophenyl)-2,5,6,7-tetrahydro-3H-pyrrolo[1,2-c]imidazol-1-yl)ethan-1-one and isolated as an off-white powder.

$^1$H NMR (DMSO$_{d6}$): 7.61 (1H, td, J=8.7, 5.6 Hz), 7.21 (1H, t, J=9.5 Hz), 4.45 (1.6H, m), 4.23 (1H, br t, J=10.3 Hz), 3.98-3.84 (2.4H, m), 3.84-3.76 (1.8H, m), 3.72 (1.2H, m), 3.43-3.23 (3H, m), 3.35 (3H, s), 2.89 (1.8H, s), 2.86 (1H, m), 2.72 (1.2H, s), 1.83-1.64 (2H, m), 1.58 (0.8H, br t, J=10.9 Hz), 1.40 (1.2H, m).

$^{13}$C NMR (DMSO$_{d6}$): 167.7, 167.5, 160.1, 160.1, 158.5, 158.4, 156.6, 156.5, 156.2, 154.9, 154.9, 129.7, 129.6, 128.2, 128.2, 119, 118.9, 118.8, 118.8, 118.7, 118.7, 116.7, 116.5, 116.1, 116, 115.9, 115.9, 113.3, 113.2, 113.1, 113.1, 66.5, 66.3, 53, 49.7, 49.5, 34.8, 31.5, 31.5, 30.2, 30.2, 29.9, 29.5, 29.2, 29.2, 29.2, 29.1, 27.1.

Example 374: N-methyl-2-((R)-2-methyl-3-thioxo-6-(2,3,6-trifluorophenyl)-2,5,6,7-tetrahydro-3H-pyrrolo[1,2-c]imidazol-1-yl)-N-(tetrahydrofuran-3-yl)acetamide

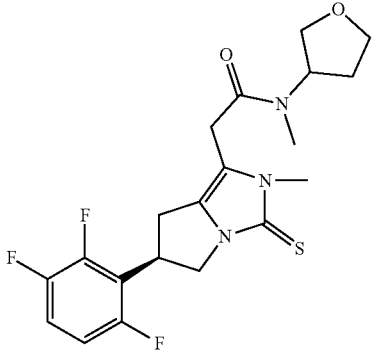 [SMILES: CN(C(=O)Cc1c2n(c(=S)n1C)C[C@@H](c1c(F)ccc(F)c1F)C2)C1CCOC1]

Compound was prepared analogous manner to Example 34 from (R)-2-(2-methyl-3-thioxo-6-(2,3,6-trifluorophenyl)-2,5,6,7-tetrahydro-3H-pyrrolo[1,2-c]imidazol-1-yl)acetic acid and isolated as a cream powder.

$^1$H NMR (DMSO$_{d6}$): 7.47 (1H, qd, J=9.4, 4.9 Hz), 7.18 (1H, m), 5.09 (0.6H, m), 4.65 (0.4H, m), 4.43 (1H, quin, J=8.6 Hz), 4.24 (1H, m), 3.92 (1H, m), 3.82 (1.8H, m), 3.71 (2H, s), 3.65-3.52 (2.2H, m), 3.27 (1H, m), 2.93 (1.8H, s), 2.87 (1H, m), 2.74 (1.2H, s), 2.20 (0.4H, m), 1.85 (0.4H, m), 1.77 (0.6H, m).

$^{13}$C NMR (DMSO$_{d6}$): 168.2, 167.6, 157, 156.9, 156.2, 156.2, 155.3, 155.3, 149.1, 149, 149, 148.9, 147.5, 147.5, 147.4, 147.4, 147.4, 147.3, 147.3, 145.9, 145.9, 145.9, 145.8, 128.2, 128.1, 118.9, 118.8, 118.8, 118.7, 116.6, 116.5, 116.4, 116.4, 116.3, 112, 111.8, 69.4, 69.4, 69.3, 69.2, 67.1, 67.1, 56.6, 56.5, 53, 49.4, 34.8, 31.5, 31.5, 30, 29.8, 29.7, 29.7, 29.4, 29.4, 29.3, 29.1, 29.1, 27.6.

Example 375: N-methyl-2-((R)-2-methyl-6-(2,3,5,6-tetrafluorophenyl)-3-thioxo-2,5,6,7-tetrahydro-3H-pyrrolo[1,2-c]imidazol-1-yl)-N-(tetrahydrofuran-3-yl)acetamide

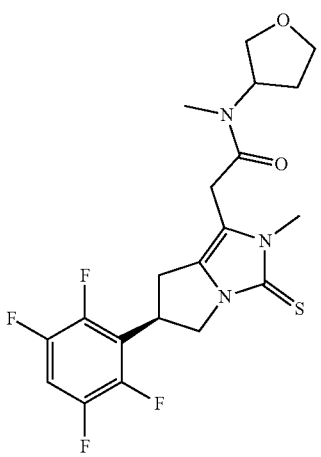 [SMILES: CN(C(=O)Cc1c2n(c(=S)n1C)C[C@@H](c1c(F)c(F)cc(F)c1F)C2)C1CCOC1]

Compound was prepared analogous manner to Example 34 from (R)-2-(2-methyl-6-(2,3,5,6-tetrafluorophenyl)-3-thioxo-2,5,6,7-tetrahydro-3H-pyrrolo[1,2-c]imidazol-1-yl)acetic acid and isolated as a yellowish powder.

$^1$H NMR (DMSO$_{d6}$): 7.86 (1H, m), 5.09 (0.6H, m), 4.65 (0.4H, m), 4.48 (1H, quin, J=8.4 Hz), 4.25 (1H, dd, J=11.3, 9.4 Hz), 3.92 (1H, m), 3.84 (1.8H, m), 3.76-3.65 (2H, s), 3.62 (1.2H, m), 3.56 (1H, m), 3.35 (3H, 2 s), 3.29 (1H, m), 2.93 (1.8H, m), 2.89 (1H, m), 2.74 (1.2H, s), 2.20 (0.4H, m), 2.10 (0.6H, m), 1.86 (0.4H, m), 1.78 (0.6H, m).

$^{13}$C NMR (DMSO$_{d6}$): 168.2, 167.6, 167.6, 156.2, 146.4, 146.4, 146.4, 146.4, 146.3, 146.2, 145.3, 145.3, 145.3, 145.2, 145.2, 144.8, 144.8, 144.7, 144.7, 144.6, 143.7, 143.7, 143.7, 143.6, 143.6, 143.6, 143.6, 128.1, 127.9, 120.5, 120.4, 120.3, 116.6, 116.5, 105.9, 105.7, 105.6, 69.4, 69.4, 69.3, 69.2, 67.1, 67, 56.6, 56.5, 53, 49.4, 34.9, 31.5, 31.5, 30, 29.8, 29.7, 29.7, 29.4, 29.4, 29.3, 29.1, 29, 27.6, 27.6.

Example 376: (R)—N-(tetrahydro-2H-pyran-4-yl)-2-(3-thioxo-6-(2,3,6-trifluorophenyl)-2,5,6,7-tetrahydro-3H-pyrrolo[1,2-c]imidazol-1-yl)acetamide

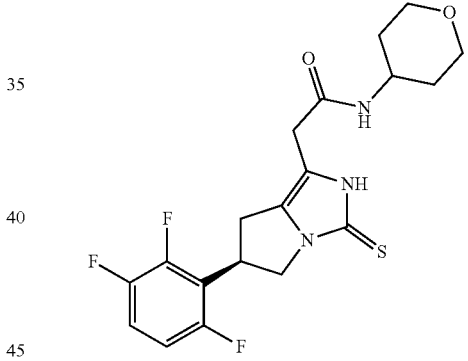

Compound was prepared analogous manner to Example 32 from (R)-2-(3-thioxo-6-(2,3,6-trifluorophenyl)-2,5,6,7-tetrahydro-3H-pyrrolo[1,2-c]imidazol-1-yl)acetic acid and isolated as a cream powder.

$^1$H NMR (DMSO$_{d6}$): 11.75 (1H, s), 7.98 (1H, br d, J=7.5 Hz), 7.47 (1H, qd, J=9.4, 4.9 Hz), 7.18 (1H, m), 4.43 (1H, quin, J=8.7 Hz), 4.16 (1H, dd, J=11.2, 9.5 Hz), 3.80 (2H, dt, J=11.3, 3.3 Hz), 3.73 (2H, m), 3.31 (2H, m), 3.23 (2H, s), 3.22 (1H, dd, J=9.1, 15.5 Hz), 2.86 (1H, dd, J=15.8, 8.3 Hz), 1.68 (2H, m), 1.37 (2H, m).

$^{13}$C NMR (DMSO$_{d6}$): 166.8, 157, 156.9, 155.4, 155.3, 155.1, 149.1, 149, 149, 148.9, 147.6, 147.5, 147.5, 147.5, 147.4, 147.4, 145.9, 145.9, 145.9, 145.8, 129, 118.9, 118.8, 118.8, 118.7, 116.5, 116.4, 116.4, 116.3, 114.4, 112, 112, 112, 111.9, 111.8, 111.8, 111.8, 111.8, 65.8, 48.5, 45.2, 35.6, 32.4, 31.5, 29.4.

Example 377: (R)—N-(tetrahydro-2H-pyran-4-yl)-2-(3-thioxo-6-(2,3,5,6-tetrafluorophenyl)-2,5,6,7-tetrahydro-3H-pyrrolo[1,2-c]imidazol-1-yl)acetamide

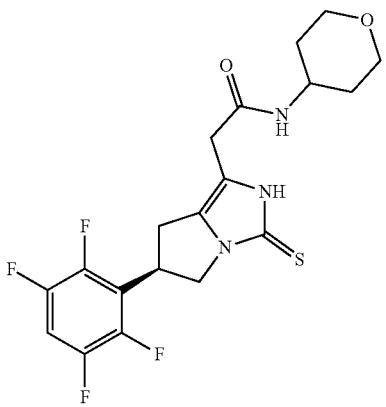 [SMILES: O=C(Cc1[nH]c(=S)n2c1C[C@H](c1c(F)c(F)cc(F)c1F)C2)NC1CCOCC1]

Compound was prepared analogous manner to Example 32 from (R)-2-(3-thioxo-6-(2,3,5,6-tetrafluorophenyl)-2,5,6,7-tetrahydro-3H-pyrrolo[1,2-c]imidazol-1-yl)acetic acid and isolated as beige powder.

$^1$H NMR (DMSO$_{d6}$): 11.76 (1H, s), 7.98 (1H, br d, J=7.5 Hz), 7.85 (1H, m), 4.48 (1H, quin, J=8.5 Hz), 4.17 (1H, dd, J=11.4, 9.3 Hz), 3.89-3.67 (4H, m), 3.32 (2H, m), 3.25 (1H, dd, J=9.2, 16.1 Hz), 3.24 (2H, s), 2.88 (1H, dd, J=8.1, 15.8 Hz), 1.67 (2H, m), 1.37 (2H, m).

$^{13}$C NMR (DMSO$_{d6}$): 166.8, 155.1, 146.4, 146.4, 146.4, 146.3, 146.3, 146.3, 145.4, 145.3, 145.3, 145.2, 145.2, 145.2, 145.2, 144.8, 144.8, 144.7, 144.7, 144.6, 144.6, 143.7, 143.7, 143.7, 143.7, 143.6, 143.6, 143.6, 143.6, 128.9, 120.5, 120.4, 120.3, 114.4, 105.9, 105.7, 105.6, 65.8, 48.4, 45.2, 35.7, 32.4, 31.5, 29.3.

Example 378: (R)—N-methyl-2-(6-(2,3,5,6-tetrafluorophenyl)-3-thioxo-2,5,6,7-tetrahydro-3H-pyrrolo[1,2-c]imidazol-1-yl)-N-(tetrahydro-2H-pyran-4-yl)acetamide

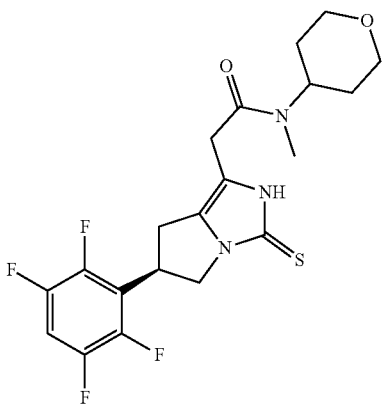 [SMILES: CN(C(=O)Cc1[nH]c(=S)n2c1C[C@H](c1c(F)c(F)cc(F)c1F)C2)C1CCOCC1]

Compound was prepared analogous manner to Example 32 from (R)-1-(H-imidazol-1-yl)-2-(6-(2,3,5,6-tetrafluorophenyl)-3-thioxo-3,5,6,7-tetrahydro-2H-pyrrolo[1,2-c]imidazol-1-yl)ethanone and isolated as a beige powder.

$^1$H NMR (DMSO$_{d6}$): 1.71 (1H, br s), 7.85 (1H, m), 4.47 (1.6H, m), 4.18 (1H, br t, J=10.3 Hz), 3.88 (2.4H, m), 3.78 (1H, m), 3.58, 3.49 (2H, 2 s), 3.33 (2H, m), 3.25 (1H, m), 2.84 (2.8H, s), 2.70 (1.2H, s), 1.85-1.62 (2H, m), 1.51 (0.8H, m), 1.38 (1.2H, m).

$^{13}$C NMR (DMSO$_{d6}$): 167.7, 167.6, 155.1, 146.5, 146.4, 146.4, 146.4, 146.4, 146.4, 146.3, 146.3, 146.3, 146.2, 145.4, 145.3, 145.3, 145.3, 145.3, 145.2, 145.2, 145.2, 145.2, 144.9, 144.8, 144.8, 144.8, 144.8, 144.7, 144.7, 144.7, 144.6, 144.6, 143.7, 143.7, 143.7, 143.6, 143.6, 143.6, 143.6, 143.6, 129.1, 129, 120.5, 114.5, 114.3, 105.9, 105.7, 105.5, 66.5, 66.3, 53, 49.6, 48.5, 35.8, 30.3, 30.2, 30, 29.6, 29.3, 29.2, 29.2, 27.

Example 379: (R)—N-methyl-2-(6-(2,3,6-trifluorophenyl)-3-thioxo-2,5,6,7-tetrahydro-3H-pyrrolo[1,2-c]imidazol-1-yl)-N-(tetrahydro-2H-pyran-4-yl)acetamide

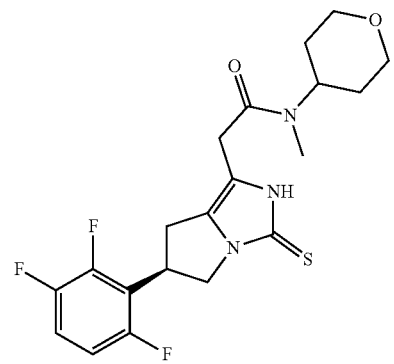 [SMILES: CN(C(=O)Cc1[nH]c(=S)n2c1C[C@H](c1c(F)ccc(F)c1F)C2)C1CCOCC1]

Compound was prepared analogous manner to Example 32 from (R)-1-(H-imidazol-1-yl)-2-(6-(2,3,6-trifluorophenyl)-3-thioxo-3,5,6,7-tetrahydro-2H-pyrrolo[1,2-c]imidazol-1-yl)ethanone and isolated as a cream powder.

$^1$H NMR (DMSO$_{d6}$): 11.69 (1H, s), 7.47 (1H, qd, J=9.4, 5.0 Hz), 7.18 (1H, m), 4.44 (1.6H, m), 4.17 (1H, br t, J=10.3 Hz), 3.88 (2.4H, m), 3.74 (1H, dd, J=11.3, 8.2 Hz), 3.57 (0.8H, m), 3.49 (1.2H, m), 3.40-3.30 (2H, m), 3.22 (1H, m), 2.84 (2.8H, m), 2.70 (1.2H, s), 1.83-1.62 (2H, m), 1.52 (0.8H, m), 1.37 (1.2H, m).

$^{13}$C NMR (DMSO$_{d6}$): 167.7, 167.6, 156.9, 156.9, 155.3, 155.3, 155.1, 155.1, 149.1, 149, 149, 147.6, 147.5, 147.5, 147.4, 147.4, 147.3, 145.9, 145.9, 145.9, 129.2, 129.2, 119, 119, 118.9, 118.9, 118.9, 118.9, 118.8, 118.8, 118.7, 116.5, 116.4, 116.4, 116.3, 116.3, 114.5, 114.3, 112, 112, 111.9, 111.9, 111.8, 111.8, 111.8, 111.8, 66.5, 66.2, 53, 49.6, 48.5, 35.6, 30.3, 30.2, 30, 29.6, 29.4, 29.2, 27.

Example 380: (S)-2-(6-(3-chloro-2,6-difluorophenyl)-3-thioxo-2,5,6,7-tetrahydro-3H-pyrrolo[1,2-c]imidazol-1-yl)-N-methyl-N-(tetrahydro-2H-pyran-4-yl)acetamide

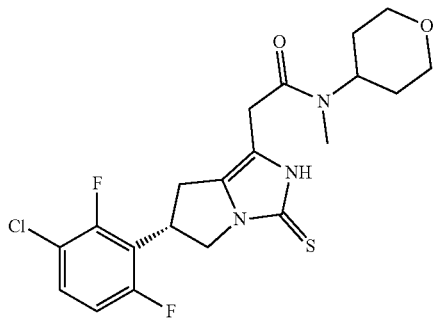 [SMILES: CN(C(=O)Cc1[nH]c(=S)n2c1C[C@@H](c1c(F)ccc(Cl)c1F)C2)C1CCOCC1]

Compound was prepared analogous manner to Example 32 from (S)-1-(1H-imidazol-1-yl)-2-(6-(3-chloro-2,6-difluorophenyl)-3-thioxo-3,5,6,7-tetrahydro-2H-pyrrolo[1,2-c]imidazol-1-yl)ethanone and isolated as an off-white solid.

¹H NMR (DMSO$_{d6}$): 1.69 (1H, br s), 7.61 (1H, td, J=8.6, 5.6 Hz), 7.21 (1H, t, J=9.5 Hz), 4.45 (1.6H, m), 4.16 (1H, br t, J=10.3 Hz), 3.88 (2.4H, m), 3.73 (1H, dd, J=11.4, 8.0 Hz), 3.57 (1.2H, m), 3.49 (1.8H, m), 3.39 (1H, m), 3.34 (1H, m), 3.31 (1H, dd, J=4.5, 2.2 Hz), 3.22 (1H, m), 2.84 (2H, s), 2.70 (1H, s), 1.71 (2H, m), 1.52 (1H, br t, J=12.5 Hz), 1.37 (1H, m).

¹³C NMR (DMSO$_{d6}$): 167.7, 167.6, 160.1, 160.1, 158.5, 158.4, 156.6, 156.5, 155.1, 155, 154.9, 154.9, 129.7, 129.6, 129.3, 129.2, 119, 118.9, 118.8, 118.8, 118.7, 118.7, 116.1, 116, 115.9, 115.9, 114.4, 114.2, 113.3, 113.2, 113.1, 113.1, 66.5, 66.5, 66.2, 53, 49.6, 48.6, 35.6, 30.3, 30.2, 30, 29.6, 29.4, 29.2, 29.2, 27.

Example 381: 2-((5aS,6aR)-5a-(3-chloro-2,6-difluorophenyl)-3-thioxo-2,3,5,5a,6,6a-hexahydrocyclopropa[3,4]pyrrolo[1,2-c]imidazol-1-yl)-N-methyl-N-(tetrahydro-2H-pyran-4-yl)acetamide

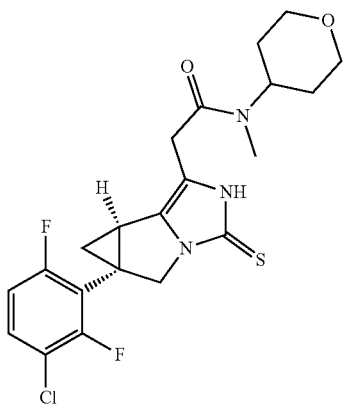 [SMILES: CN(C(=O)Cc1[nH]c(=S)n2c1[C@@H]1C[C@]1(c1c(F)ccc(Cl)c1F)C2)C1CCOCC1]

Compound was prepared analogous manner to Example 32 from 2-((5aS,6aR)-5a-(3-chloro-2,6-difluorophenyl)-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a yellow solid.

¹H NMR (DMSO$_{d6}$): 11.63 (1H, br d, J=13.5 Hz), 7.63 (1H, m), 7.20 (1H, br t, J=9.2 Hz), 4.49 (0.6H, m), 4.18-3.92 (1.8H, m), 3.89 (2H, m), 3.72 (0.6H, m), 3.70-3.48 (2H, m), 3.45-3.30 (2H, m), 2.90-2.63 (4H, m), 1.84-1.15 (6H, m).

¹³C NMR (DMSO$_{d6}$): 167.7, 167.6, 161.2, 159.6, 157.8, 157.7, 156.1, 156.1, 155.9, 155.8, 131.5, 131.3, 130.3, 130.3, 130.3, 130.3, 130.2, 117.1, 116.9, 115.7, 115.7, 115.6, 115.6, 114.5, 114.2, 112.9, 112.9, 112.8, 66.5, 66.5, 66.3, 64.9, 52.9, 51.4, 51.4, 49.6, 49.4, 30.2, 29.6, 29.3, 29.2, 29.2, 27.1, 26.5, 26.4, 21.8, 21.7, 21.3, 21.2.

Example 382: 2-((S)-6-(3-bromo-2,6-difluorophenyl)-2-methyl-3-thioxo-2,5,6,7-tetrahydro-3H-pyrrolo[1,2-c]imidazol-1-yl)-N-((R)-tetrahydro-2H-pyran-3-yl)acetamide

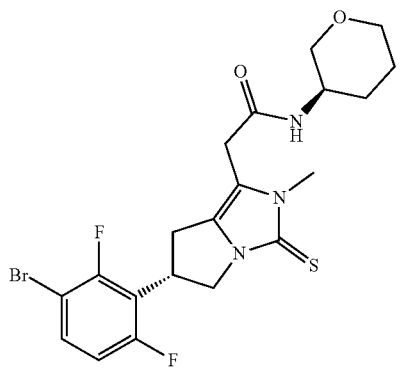 [SMILES: Cn1c(CC(=O)N[C@@H]2CCCOC2)c2n(c1=S)C[C@H](c1c(F)ccc(Br)c1F)C2]

Compound was prepared analogous manner to Example 34 from (S)-2-(2-methyl-3-thioxo-6-(3-bromo-2,6-difluorophenyl)-2,5,6,7-tetrahydro-3H-pyrrolo[1,2-c]imidazol-1-yl) acetic acid and isolated as a cream powder.

¹H NMR (DMSO$_{d6}$): 8.11 (1H, br d, J=7.5 Hz), 7.72 (1H, td, J=8.5, 5.8 Hz), 7.17 (1H, m), 4.44 (1H, quin, J=8.6 Hz), 4.22 (1H, m), 3.79 (1H, dd, J=11.6, 7.6 Hz), 3.65 (3H, m), 3.44 (2H, m), 3.39 (3H, s), 3.33 (1H, m), 3.28 (1H, dd, J=15.8, 9.4 Hz), 3.11 (1H, m), 2.87 (1H, dd, J=15.8, 7.9 Hz), 1.80 (1H, m), 1.66 (1H, m), 1.46 (2H, m).

¹³C NMR (DMSO$_{d6}$): 167.3, 160.8, 160.8, 159.2, 159.1, 157.6, 157.5, 156.1, 155.9, 155.9, 132.5, 132.4, 128.4, 118.8, 118.7, 118.6, 116.4, 113.8, 113.8, 113.6, 113.6, 113.6, 112.3, 112.1, 104.1, 104.1, 103.9, 103.9, 70.1, 67, 49.6, 45.1, 34.8, 31.5, 31.2, 29.2, 28.5, 23.8.

Example 383: 2-((S)-6-(3-chloro-2,6-difluorophenyl)-2-methyl-3-thioxo-2,5,6,7-tetrahydro-3H-pyrrolo[1,2-c]imidazol-1-yl)-N-methyl-N-(tetrahydrofuran-3-yl)acetamide

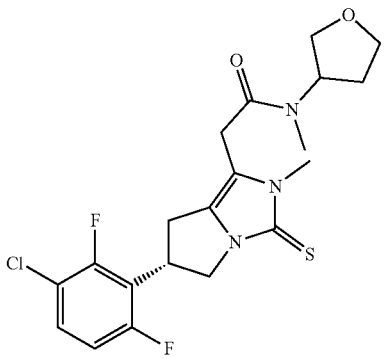 [SMILES: CN(C(=O)Cc1c2n(c(=S)n1C)C[C@H](c1c(F)ccc(Cl)c1F)C2)C1CCOC1]

Compound was prepared analogous manner to Example 34 from (S)-2-(6-(3-chloro-2,6-difluorophenyl)-2-methyl-3-thioxo-2,5,6,7-tetrahydro-3H-pyrrolo[1,2-c]imidazol-1-yl) acetic acid and isolated as an off-white solid.

$^1$H NMR (DMSO$_{d6}$): 7.61 (1H, td, J=8.7, 5.6 Hz), 7.22 (1H, m), 5.09 (0.6H, m), 4.65 (0.4H, m), 4.44 (1H, quin, J=8.5 Hz), 4.23 (1H, m), 3.91 (1H, m), 3.81 (1.8H, m), 3.75-3.65 (2H, m), 3.65-3.59 (1.2H, m), 3.56 (1H, m), 3.35 (3H, 2 s), 3.26 (1H, m), 2.93 (1.8H, s), 2.85 (1H, m), 2.74 (1.2H, s), 2.20 (0.4H, m), 2.10 (0.6H, m), 1.85 (0.4H, m), 1.77 (0.6H, m).

$^{13}$C NMR (DMSO$_{d6}$): 168.2, 167.6, 160.1, 160.1, 158.5, 158.4, 156.6, 156.5, 156.2, 156.2, 154.9, 154.9, 129.7, 129.6, 128.3, 128.1, 118.9, 118.8, 118.6, 116.5, 116.4, 116.1, 116, 115.9, 115.9, 113.3, 113.2, 113.1, 113.1, 69.4, 69.4, 69.3, 69.2, 67.1, 67, 56.6, 56.5, 53, 49.5, 34.8, 31.5, 31.5, 29.9, 29.8, 29.7, 29.7, 29.4, 29.4, 29.3, 29.2, 29.1, 27.6.

Example 384: 2-((S)-6-(3-chloro-2,6-difluorophenyl)-3-thioxo-2,5,6,7-tetrahydro-3H-pyrrolo[1,2-c]imidazol-1-yl)-N-methyl-N-(tetrahydrofuran-3-yl)acetamide

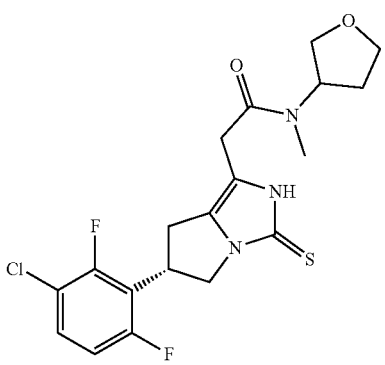 [SMILES: CN(C(=O)Cc1[nH]c(=S)n2c1C[C@@H](c1c(F)ccc(Cl)c1F)C2)C1CCOC1]

Compound was prepared analogous manner to Example 34 from (S)-2-(6-(3-chloro-2,6-difluorophenyl)-3-thioxo-2,5,6,7-tetrahydro-3H-pyrrolo[1,2-c]imidazol-1-yl)acetic acid and isolated as an off-white solid.

$^1$H NMR (DMSO$_{d6}$): 1.68 (1H, m), 7.61 (1H, td, J=8.7, 5.6 Hz), 7.21 (1H, m), 5.08 (0.6H, m), 4.61 (0.4H, m), 4.44 (1H, quin, J=8.5 Hz), 4.16 (1H, m), 3.91 (1H, m), 3.73 (1H, dd, J=11.6, 7.8 Hz), 3.66 (0.8H, dd, J=7.3, 5.9 Hz), 3.63-3.52 (3H, m), 3.48 (1.2H, s), 3.21 (1H, m), 2.88 (1.8H, d, J=1.5 Hz), 2.82 (1H, m), 2.72 (1.2H, s), 2.22-2.02 (1H, m), 1.88-1.67 (1H, m).

$^{13}$C NMR (DMSO$_{d6}$): 168.2, 167.7, 160.1, 160.1, 158.5, 158.5, 156.5, 155.1, 155.1, 154.9, 154.9, 129.7, 129.6, 129.3, 129.2, 118.9, 118.9, 118.9, 118.8, 118.8, 118.7, 118.6, 118.6, 116.1, 116, 115.9, 115.9, 114.3, 114.2, 114.2, 113.3, 113.2, 113.1, 113.1, 69.3, 69.3, 69.3, 67.1, 67.1, 67, 56.5, 52.9, 48.6, 35.6, 30, 29.8, 29.8, 29.8, 29.7, 29.5, 29.5, 29.3, 29.2, 27.6.

Example 385: 2-((S)-6-(3-chloro-2,6-difluorophenyl)-2-methyl-3-thioxo-2,5,6,7-tetrahydro-3H-pyrrolo[1,2-c]imidazol-1-yl)-N—((S)-tetrahydrofuran-3-yl)acetamide

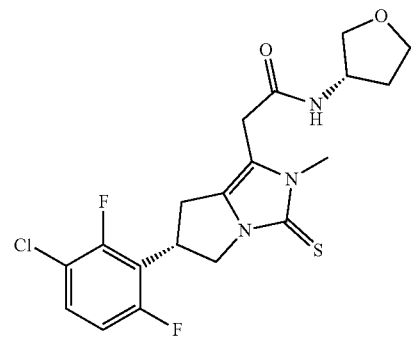 [SMILES: Cn1c(CC(=O)N[C@H]2CCOC2)c2n(c1=S)C[C@H](c1c(F)ccc(Cl)c1F)C2]

Compound was prepared analogous manner to Example 32 from (R)-2-(6-(3-chloro-2,6-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as an off-white solid.

$^1$H NMR (DMSO$_{d6}$): 8.37 (1H, br d, J=6.6 Hz), 7.61 (1H, td, J=8.7, 5.6 Hz), 7.22 (1H, m), 4.44 (1H, quin, J=8.5 Hz), 4.22 (2H, m), 3.78 (2H, m), 3.72 (1H, dd, J=9.0, 5.9 Hz), 3.66 (1H, td, J=8.2, 5.6 Hz), 3.46 (1H, dd, J=8.9, 3.5 Hz), 3.43 (2H, s), 3.40 (3H, s), 3.29 (1H, dd, J=15.9, 9.5 Hz), 2.89 (1H, dd, J=15.8, 8.1 Hz), 2.08 (1H, m), 1.71 (1H, m).

$^{13}$C NMR (DMSO$_{d6}$): 167.6, 160.1, 160.1, 158.5, 158.5, 156.6, 156.5, 156.2, 154.9, 154.9, 129.7, 129.6, 128.4, 118.8, 118.7, 118.6, 116.4, 116.1, 116, 115.9, 115.9, 113.2, 113.2, 113.1, 72.3, 66.3, 49.8, 49.5, 34.7, 32, 31.5, 31.1, 29.2.

Example 386: N—((R)-tetrahydro-2H-pyran-3-yl)-2-((R)-3-thioxo-6-(2,3,5,6-tetrafluorophenyl)-2,5,6,7-tetrahydro-3H-pyrrolo[1,2-c]imidazol-1-yl)acetamide

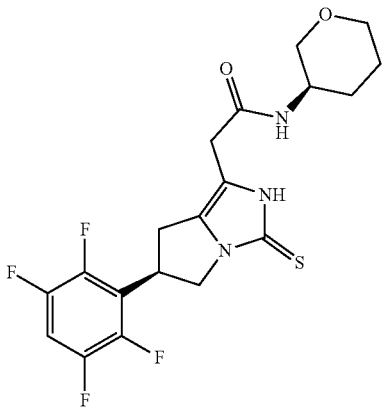 [SMILES: O=C(Cc1[nH]c(=S)n2c1C[C@H](c1c(F)c(F)cc(F)c1F)C2)N[C@@H]1CCCOC1]

Compound was prepared analogous manner to Example 34 from (R)-2-(3-thioxo-6-(2,3,5,6-tetrafluorophenyl)-2,5,6,7-tetrahydro-3H-pyrrolo[1,2-c]imidazol-1-yl)acetic acid and isolated as a light beige powder.

$^1$H NMR (DMSO$_{d6}$): 11.76 (1H, s), 7.97 (1H, br d, J=7.5 Hz), 7.85 (1H, m), 4.48 (1H, quin, J=8.5 Hz), 4.17 (1H, dd, J=11.4, 9.3 Hz), 3.77 (1H, dd, J=11.7, 7.8 Hz), 3.65 (3H, m), 3.34 (1H, m), 3.25 (2H, s), 3.25 (1H, dd, J=9.5, 15.6 Hz), 3.09 (1H, m), 2.88 (1H, br dd, J=15.7, 8.1 Hz), 1.80 (1H, m), 1.66 (1H, m), 1.45 (2H, m).

$^{13}$C NMR (DMSO$_{d6}$): 167.2, 155.1, 146.4, 146.4, 146.4, 146.4, 146.3, 146.3, 146.3, 146.3, 146.2, 145.3, 145.3, 145.3, 145.3, 145.3, 145.2, 145.2, 145.2, 145.2, 144.8, 144.8, 144.7, 144.7, 144.7, 144.6, 144.6, 143.7, 143.7, 143.7, 143.7, 143.6, 143.6, 128.8, 120.5, 120.4, 120.3, 114.4, 105.9, 105.7, 105.5, 70.2, 67, 48.4, 45.1, 35.7, 31.4, 29.2, 28.6, 23.9.

Example 387: 2-((R)-2-methyl-6-(2,3,5,6-tetrafluorophenyl)-3-thioxo-2,5,6,7-tetrahydro-3H-pyrrolo[1,2-c]imidazol-1-yl)-N—(((S)-tetrahydrofuran-2-yl)methyl)acetamide

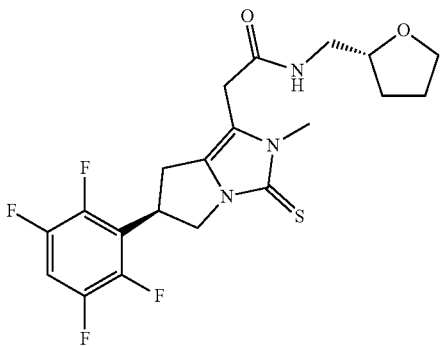 [SMILES: Cn1c(CC(=O)NC[C@H]2CCCO2)c2n(c1=S)C[C@@H](c1c(F)c(F)cc(F)c1F)C2]

Compound was prepared analogous manner to Example 32 from (R)-2-(6-(2,3,5,6-tetrafluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as a light beige powder.

$^1$H NMR (DMSO$_{d6}$): 8.18 (1H, t, J=5.7 Hz), 7.86 (1H, m), 4.48 (1H, quin, J=8.5 Hz), 4.24 (1H, dd, J=11.6, 9.2 Hz), 3.83 (2H, m), 3.73 (1H, m), 3.59 (1H, m), 3.46 (2H, m), 3.40 (3H, s), 3.31 (1H, dd, J=9.5, 16.0 Hz), 3.16 (1H, m), 3.10 (1H, m), 2.93 (1H, dd, J=15.9, 8.0 Hz), 1.92-1.72 (3H, m), 1.46 (1H, m).

$^{13}$C NMR (DMSO$_{d6}$): 167.8, 156.2, 146.4, 146.4, 146.4, 146.3, 146.3, 146.3, 146.2, 145.4, 145.3, 145.3, 145.3, 145.2, 145.2, 145.2, 144.8, 144.8, 144.7, 144.7, 144.7, 144.6, 144.6, 144.6, 143.7, 143.7, 143.7, 143.7, 143.7, 143.6, 143.6, 143.6, 143.6, 143.6, 128.2, 120.4, 120.3, 120.2, 116.5, 105.9, 105.7, 105.6, 77, 67.1, 49.4, 42.9, 34.9, 31.4, 31.2, 29, 28.4, 25.1.

Example 388: N-(1-methyl-2-oxopyrrolidin-3-yl)-2-((R)-2-methyl-3-thioxo-6-(2,3,6-trifluorophenyl)-2,5,6,7-tetrahydro-3H-pyrrolo[1,2-c]imidazol-1-yl)acetamide

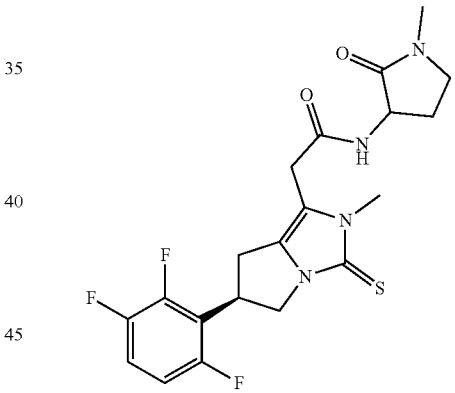

Compound was prepared analogous manner to Example 22 from (R)-2-(6-(2,3,6-trifluorophenyl)-2-methyl-3-thioxo-2,5,6,7-tetrahydro-3H-pyrrolo[1,2-c]imidazol-1-yl)acetic acid and isolated as a cream powder.

$^1$H NMR (DMSO$_{d6}$): 8.40 (1H, dd, J=14.0, 8.1 Hz), 7.48 (1H, qd, J=9.3, 5.0 Hz), 7.19 (1H, m), 4.42 (1H, m), 4.33 (1H, m), 4.23 (1H, m), 3.82 (1H, dd, J=11.4, 8.2 Hz), 3.53-3.43 (2H, m), 3.42 (3H, m), 3.37-3.28 (1H, m), 3.26 (2H, m), 2.93 (1H, m), 2.73 (3H, 2 s), 2.27 (1H, m), 1.76 (1H, m).

$^{13}$C NMR (DMSO$_{d6}$): 171.3, 167.7, 157, 156.9, 156.3, 155.4, 155.3, 149.1, 149.1, 149, 147.5, 147.5, 147.5, 147.4, 147.4, 147.4, 145.9, 145.9, 145.9, 145.8, 128.7, 128.6, 118.8, 118.7, 118.7, 118.6, 118.6, 118.5, 116.5, 116.5, 116.5, 116.5, 116.4, 116.4, 116.3, 116.3, 116.2, 116.1, 112, 112,112, 111.9, 111.8, 111.8, 111.8, 111.8, 111.8, 50.2, 50.1, 49.4, 45.3, 34.8, 31.4, 31.3, 31.3, 29.7, 29.1, 25.7, 25.7.

Example 389: 2-((R)-2-methyl-3-thioxo-6-(2,3,6-trifluorophenyl)-2,5,6,7-tetrahydro-3H-pyrrolo[1,2-c]imidazol-1-yl)-N—((S)-1-methyl-5-oxopyrrolidin-3-yl)acetamide

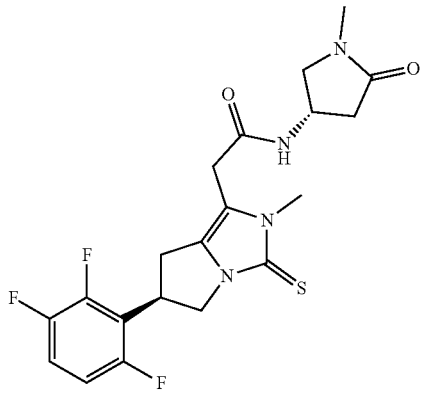 [SMILES: CN1C[C@@H](NC(=O)Cc2c3n(c(=S)n2C)C[C@@H](c2c(F)ccc(F)c2F)C3)CC1=O]

Compound was prepared analogous manner to Example 22 from (R)-2-(6-(2,3,6-trifluorophenyl)-2-methyl-3-thioxo-2,5,6,7-tetrahydro-3H-pyrrolo[1,2-c]imidazol-1-yl)acetic acid and isolated as a cream powder.

$^1$H NMR (DMSO$_{d6}$): 8.54 (1H, br d, J=6.6 Hz), 7.48 (1H, qd, J=9.4, 5.0 Hz), 7.19 (1H, m), 4.43 (1H, quin, J=8.6 Hz), 4.28 (1H, m), 4.23 (1H, m), 3.81 (1H, dd, J=11.4, 8.0 Hz), 3.61 (1H, dd, J=10.3, 7.0 Hz), 3.44 (2H, d, J=3.2 Hz), 3.40 (3H, s), 3.30 (1H, br dd, J=15.8, 9.4 Hz), 3.11 (1H, dd, J=10.2, 3.6 Hz), 2.90 (1H, br dd, J=15.8, 8.3 Hz), 2.70 (3H, s), 2.57 (1H, dd, J=16.8, 8.6 Hz), 2.11 (1H, dd, J=16.9, 4.1 Hz).

$^{13}$C NMR (DMSO$_{d6}$): 171.6, 167.7, 157, 156.9, 156.3, 155.3, 155.3, 149.1, 149.1, 149, 149, 147.6, 147.5, 147.4, 145.9, 145.8, 128.5, 118.9, 118.8, 118.7, 118.6, 116.5, 116.5, 116.4, 116.3, 116.2, 112, 112, 112, 111.9, 111.8, 111.8, 111.8, 111.8, 55.1, 49.5, 42.4, 36.8, 34.7, 31.5, 31.1, 29.1, 28.9.

Example 390: (R)-1-(2-((R)-2-methyl-3-thioxo-6-(2,3,6-trifluorophenyl)-2,5,6,7-tetrahydro-3H-pyrrolo[1,2-c]imidazol-1-yl)acetyl)pyrrolidine-3-carbonitrile

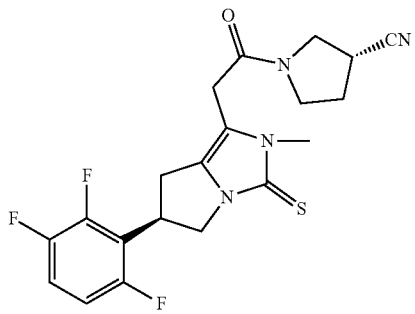 [SMILES: Cn1c(CC(=O)N2CC[C@@H](C#N)C2)c2n(c1=S)C[C@@H](c1c(F)ccc(F)c1F)C2]

Compound was prepared analogous manner to Example 25 from (R)-1-(H-imidazol-1-yl)-2-(2-methyl-3-thioxo-6-(2,3,6-trifluorophenyl)-2,5,6,7-tetrahydro-3H-pyrrolo[1,2-c]imidazol-1-yl)ethan-1-one and isolated as a cream powder.

$^1$H NMR (DMSO$_{d6}$): 7.48 (1H, qd, J=9.4, 5.0 Hz), 7.19 (1H, m), 4.44 (1H, m), 4.25 (1H, m), 3.91-3.38 (8H, m), 3.38 (3H, s), 3.29 (1H, m), 2.90 (1H, m), 2.32 (0.5H, m), 2.23 (1H, m), 2.10 (0.5H, m).

$^{13}$C NMR (DMSO$_{d6}$): 166.6, 166.4, 157, 156.9, 156.9, 156.3, 155.3, 155.3, 155.3, 155.3, 149.1, 149, 149, 148.9, 147.5, 147.5, 147.5, 147.4, 147.4, 147.3, 145.9, 145.9, 145.9, 145.8, 128.4, 128.3, 121.1, 120.9, 118.9, 118.9, 118.8, 118.8, 118.8, 118.8, 118.7, 118.7, 116.5, 116.4, 116.4, 116.3, 115.9, 115.9, 112, 112, 112, 111.9, 111.8, 111.8, 111.8, 111.8, 49.5, 48.7, 48.6, 44.8, 44.6, 34.7, 31.5, 30.2, 30.1, 29.6, 29.1, 28.1, 28, 26.5.

Example 391: 2-((R)-2-methyl-6-(2,3,5,6-tetrafluorophenyl)-3-thioxo-2,5,6,7-tetrahydro-3H-pyrrolo[1,2-c]imidazol-1-yl)-N—(((R)-tetrahydrofuran-2-yl)methyl)acetamide

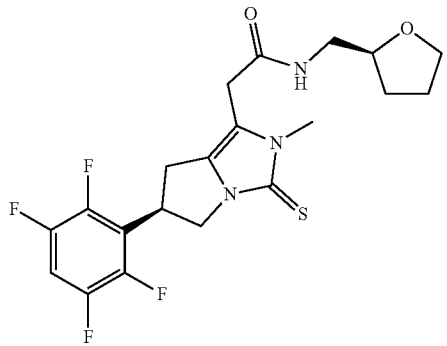 [SMILES: Cn1c(CC(=O)NC[C@@H]2CCCO2)c2n(c1=S)C[C@@H](c1c(F)c(F)cc(F)c1F)C2]

Compound was prepared analogous manner to Example 32 from (R)-2-(6-(2,3,5,6-tetrafluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as a cream powder.

$^1$H NMR (DMSO$_{d6}$): 8.18 (1H, t, J=5.7 Hz), 7.86 (1H, m), 4.48 (1H, quin, J=8.5 Hz), 4.24 (1H, dd, J=11.6, 9.2 Hz), 3.83 (2H, m), 3.73 (1H, m), 3.59 (1H, m), 3.46 (2H, m), 3.40 (3H, s), 3.31 (1H, dd, J=9.5, 16.0 Hz), 3.16 (1H, m), 3.10 (1H, m), 2.93 (1H, dd, J=15.9, 8.0 Hz), 1.92-1.72 (3H, m), 1.46 (1H, m).

$^{13}$C NMR (DMSO$_{d6}$): 167.8, 156.2, 146.4, 146.4, 146.3, 146.3, 146.3, 146.2, 145.3, 145.3, 145.3, 145.2, 145.2, 144.8, 144.8, 144.7, 144.7, 144.6, 144.6, 143.7, 143.7, 143.7, 143.7, 143.6, 143.6, 143.6, 128.2, 120.4, 120.3, 120.2, 116.5, 105.9, 105.7, 105.6, 77, 67.1, 49.4, 42.9, 34.9, 31.5, 31.2, 29, 28.4, 25.1.

Example 392: 2-((5aS,6aR)-5a-(3-chloro-2,6-difluorophenyl)-3-thioxo-2,3,5,5a,6,6a-hexahydrocyclopropa[3,4]pyrrolo[1,2-c]imidazol-1-yl)-N—((R)-tetrahydrofuran-3-yl)acetamide

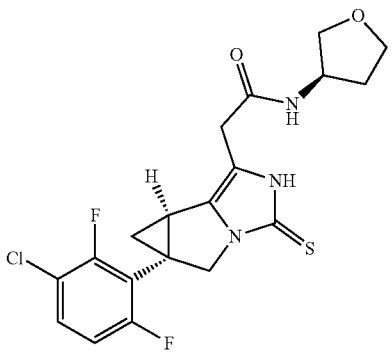 [SMILES: O=C(Cc1[nH]c(=S)n2c1[C@@H]1C[C@]1(c1c(F)ccc(Cl)c1F)C2)N[C@@H]1CCOC1]

Compound was prepared analogous manner to Example 32 from 2-((5aS,6aR)-5a-(3-chloro-2,6-difluorophenyl)-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a khaki solid.

$^1$H NMR (DMSO$_{d6}$): 11.69 (1H, s), 8.26 (1H, br d, J=6.6 Hz), 7.63 (1H, td, J=8.6, 5.6 Hz), 7.21 (1H, t, J=9.2 Hz), 4.24 (1H, m), 4.03 (1H, d, J=12.2 Hz), 3.78 (1H, q, J=7.4 Hz), 3.73 (2H, m), 3.67 (1H, td, J=8.2, 5.6 Hz), 3.48 (1H, dd, J=8.9, 3.7 Hz), 3.31 (2H, m), 2.72 (1H, dd, J=8.3, 4.5 Hz), 2.08 (1H, dq, J=12.7, 7.6 Hz), 1.74 (1H, m), 1.66 (1H, dd, J=8.1, 5.5 Hz), 1.24 (1H, t, J=4.9 Hz).

$^{13}$C NMR (DMSO$_{d6}$): 167.6, 161.2, 161.2, 159.6, 159.5, 157.8, 157.7, 156.1, 156.1, 155.8, 131.3, 130.3, 130.2, 117.2, 117.1, 117.1, 116.9, 115.7, 115.7, 115.6, 115.6, 114.3, 112.9, 112.9, 112.8, 112.8, 72.4, 66.3, 51.4, 49.8, 32, 31.3, 26.3, 21.6, 21.6, 21.3.

Example 393: (R)—N-(oxetan-3-yl)-2-(6-(2,3,5,6-tetrafluorophenyl)-3-thioxo-2,5,6,7-tetrahydro-3H-pyrrolo[1,2-c]imidazol-1-yl)acetamide

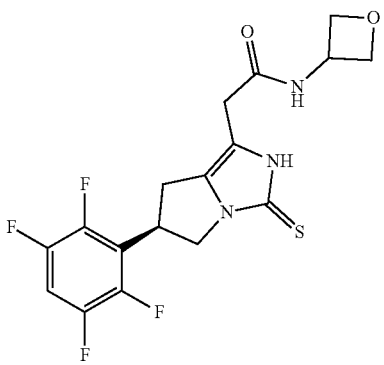 [SMILES: O=C(Cc1[nH]c(=S)n2c1C[C@H](c1c(F)c(F)cc(F)c1F)C2)NC1COC1]

Compound was prepared analogous manner to Example 32 from (R)-1-(1H-imidazol-1-yl)-2-(6-(2,3,5,6-tetrafluorophenyl)-3-thioxo-2,5,6,7-tetrahydro-3H-pyrrolo[1,2-c]imidazol-1-yl)ethan-1-one and isolated as a beige powder.

$^1$H NMR (DMSO$_{d6}$): 11.77 (1H, s), 8.72 (1H, br d, J=6.5 Hz), 7.85 (1H, m), 4.76 (1H, m), 4.69 (2H, t, J=6.8 Hz), 4.48 (1H, quin, J=8.5 Hz), 4.41 (2H, t, J=6.0 Hz), 4.17 (1H, dd, J=11.2, 9.5 Hz), 3.77 (1H, dd, J=11.6, 7.9 Hz), 3.28 (2H, s), 3.25 (1H, br dd, J=15.9, 9.5 Hz), 2.88 (1H, br dd, J=15.8, 8.0 Hz).

$^{13}$C NMR (DMSO$_{d6}$): 167.4, 155.3, 146.4, 146.4, 146.3, 146.3, 146.2, 145.3, 145.3, 145.2, 145.2, 144.8, 144.8, 144.7, 144.7, 144.7, 144.6, 144.6, 143.7, 143.7, 143.7, 143.6, 143.6, 143.6, 143.6, 129.2, 120.4, 120.3, 120.2, 114, 105.9, 105.7, 105.6, 77, 48.4, 44.1, 35.7, 31.2, 29.2.

Example 394: (R)-2-(2-methyl-6-(2,3,5,6-tetrafluorophenyl)-3-thioxo-2,5,6,7-tetrahydro-3H-pyrrolo[1,2-c]imidazol-1-yl)-N-(oxetan-3-yl)acetamide

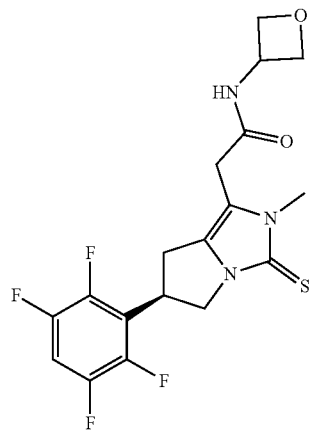 [SMILES: Cn1c(CC(=O)NC2COC2)c2n(c1=S)C[C@@H](c1c(F)c(F)cc(F)c1F)C2]

Compound was prepared analogous manner to Example 32 from (R)-1-(H-imidazol-1-yl)-2-(2-methyl-6-(2,3,5,6-tetrafluorophenyl)-3-thioxo-2,5,6,7-tetrahydro-3H-pyrrolo[1,2-c]imidazol-1-yl)ethan-1-one and isolated as a white powder.

$^1$H NMR (DMSO$_{d6}$): 8.85 (1H, br d, J=6.6 Hz), 7.86 (1H, m), 4.78 (1H, m), 4.70 (2H, m), 4.48 (1H, quin, J=8.5 Hz), 4.41 (2H, t, J=6.3 Hz), 4.26 (1H, dd, J=11.5, 9.3 Hz), 3.86 (1H, dd, J=11.7, 7.7 Hz), 3.48 (2H, m), 3.39 (3H, m), 3.33 (1H, dd, J=9.5, 16 Hz), 2.94 (1H, dd, J=15.8, 7.9 Hz).

$^{13}$C NMR (DMSO$_{d6}$): 167.4, 156.3, 146.4, 146.4, 146.4, 146.3, 146.3, 146.3, 146.2, 145.4, 145.3, 145.3, 145.3, 145.2, 145.2, 144.8, 144.8, 144.7, 144.7, 144.7, 144.6, 143.7, 143.7, 143.7, 143.7, 143.6, 143.6, 143.6, 128.4, 120.4, 120.3, 120.2, 116.1, 105.9, 105.7, 105.6, 77, 49.4, 44.2, 34.9, 31.5, 31, 29.

Example 395: 2-((R)-6-(2,3,5,6-tetrafluorophenyl)-3-thioxo-2,5,6,7-tetrahydro-3H-pyrrolo[1,2-c]imidazol-1-yl)-N—(((S)-tetrahydrofuran-2-yl)methyl)acetamide

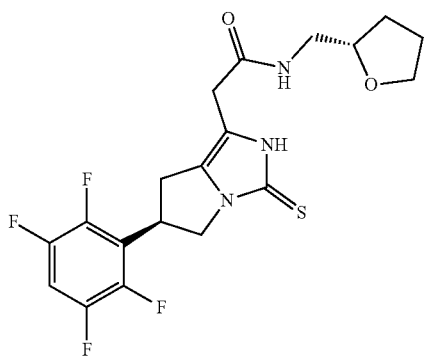 [SMILES: O=C(Cc1[nH]c(=S)n2c1C[C@H](c1c(F)c(F)cc(F)c1F)C2)NC[C@@H]1CCCO1]

Compound was prepared analogous manner to Example 32 from (R)-1-(H-imidazol-1-yl)-2-(6-(2,3,5,6-tetrafluorophenyl)-3-thioxo-2,5,6,7-tetrahydro-3H-pyrrolo[1,2-c]imidazol-1-yl)ethan-1-one and isolated as a beige powder.

$^1$H NMR (DMSO$_{d6}$): 1.75 (1H, s), 8.03 (1H, br t, J=5.6 Hz), 7.85 (1H, m), 4.48 (1H, quin, J=8.5 Hz), 4.17 (1H, dd, J=11.2, 9.5 Hz), 3.81 (1H, m), 3.77 (1H, dd, J=11.5, 7.8 Hz), 3.72 (1H, m), 3.58 (1H, m), 3.26 (2H, s), 3.24 (1H, m), 3.16 (1H, m), 3.09 (1H, m), 2.88 (1H, br dd, J=15.8, 8.1 Hz), 1.94-1.68 (3H, m), 1.46 (1H, m).

$^{13}$C NMR (DMSO$_{d6}$): 167.7, 155.2, 146.4, 146.4, 146.3, 146.3, 146.3, 145.3, 145.3, 145.3, 145.3, 145.2, 145.2, 144.8, 144.8, 144.7, 144.7, 144.6, 143.7, 143.7, 143.6, 143.6, 128.9, 120.4, 120.3, 120.2, 114.4, 105.9, 105.7, 105.6, 77, 67.1, 48.4, 42.9, 35.7, 31.4, 29.2, 28.5, 25.1.

Example 396: 2-((5aS,6aR)-5a-(3-chloro-2,6-difluorophenyl)-3-thioxo-2,3,5,5a,6,6a-hexahydrocyclopropa[3,4]pyrrolo[1,2-c]imidazol-1-yl)-N-methyl-N-(tetrahydrofuran-3-yl)acetamide

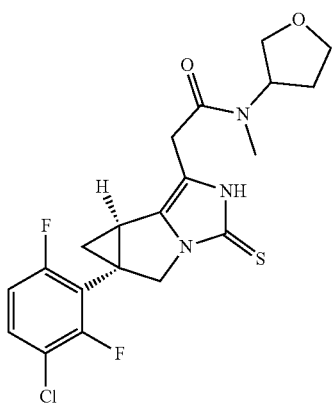 [SMILES: CN(C(=O)Cc1[nH]c(=S)n2c1[C@@H]1C[C@]1(c1c(F)ccc(Cl)c1F)C2)C1CCOC1]

Compound was prepared analogous manner to Example 221 step 2 from 2-((5aS,6aR)-5a-(3-chloro-2,6-difluorophenyl)-3-thioxo-2,3,5,5a,6,6a-hexahydrocyclopropa[3,4]pyrrolo[1,2-c]imidazol-1-yl)acetic acid and isolated as a yellow solid.

$^1$H NMR (DMSO$_{d6}$): 11.62 (1H, br s), 7.63 (1H, td, J=8.6, 5.9 Hz), 7.20 (1H, br t, J=8.9 Hz), 5.11 (0.6H, br s), 4.67 (0.4H, m), 4.04 (1H, br d, J=11.9 Hz), 3.92 (1H, m), 3.80-3.48 (6H, m), 2.90 (1.8H, br s), 2.71 (1.2H, m), 2.67 (1H, m), 2.25-2.01 (1H, m), 1.92-1.72 (1H, m), 1.67 (1H, m), 1.24 (1H, m).

$^{13}$C NMR (DMSO$_{d6}$): 168.3, 167.7, 161.2, 161.2, 159.6, 159.5, 157.8, 157.8, 156.1, 156.1, 156, 155.9, 155.9, 131.4, 130.3, 130.2, 117.1, 115.7, 115.7, 115.6, 115.6, 114.3, 114.2, 112.9, 112.9, 112.8, 112.8, 69.3, 69.3, 69.3, 67.1, 67.1, 67, 56.5, 52.9, 51.4, 29.9, 29.8, 29.7, 29.2, 29.2, 27.6, 26.4, 21.8, 21.7, 21.7, 21.7, 21.2, 21.1.

Example 397: (R)-2-(2-methyl-6-(2,3,5,6-tetrafluorophenyl)-3-thioxo-2,5,6,7-tetrahydro-3H-pyrrolo[1,2-c]imidazol-1-yl)-N-((tetrahydro-2H-pyran-4-yl)methyl)acetamide

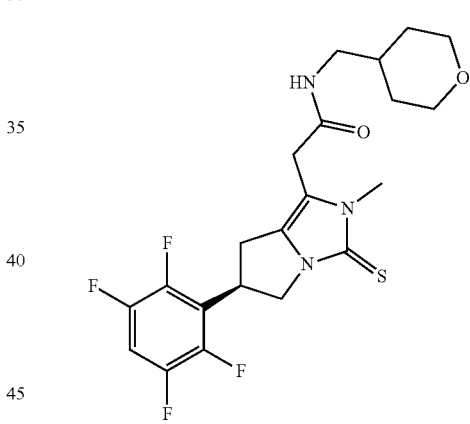

Compound was prepared analogous manner to Example 32 from (R)-1-(1H-imidazol-1-yl)-2-(2-methyl-6-(2,3,5,6-tetrafluorophenyl)-3-thioxo-2,5,6,7-tetrahydro-3H-pyrrolo[1,2-c]imidazol-1-yl)ethan-1-one and isolated as a light cream powder.

$^1$H NMR (DMSO$_{d6}$): 8.10 (1H, br t, J=5.7 Hz), 7.86 (1H, m), 4.48 (1H, quin, J=8.5 Hz), 4.24 (1H, dd, J=11.5, 9.3 Hz), 3.82 (3H, m), 3.44 (2H, m), 3.40 (3H, s), 3.31 (1H, m), 3.22 (2H, m), 2.95 (3H, m), 1.62 (1H, m), 1.51 (2H, br d, J=12.5 Hz), 1.12 (2H, m).

$^{13}$C NMR (DMSO$_{d6}$): 167.8, 156.2, 146.4, 146.4, 146.3, 146.3, 146.2, 145.4, 145.3, 145.3, 145.3, 145.2, 145.2, 144.8, 144.8, 144.8, 144.7, 144.7, 144.6, 144.6, 143.7, 143.7, 143.7, 143.7, 143.6, 143.6, 143.6, 143.6, 128.2, 120.4, 120.3, 120.2, 116.6, 105.9, 105.7, 105.6, 66.7, 49.4, 44.5, 34.9, 34.7, 31.5, 31.2, 30.4, 29.1.

Example 398: (R)—N-methyl-2-(2-methyl-6-(2,3,5,6-tetrafluorophenyl)-3-thioxo-2,5,6,7-tetrahydro-3H-pyrrolo[1,2-c]imidazol-1-yl)-N-(oxetan-3-yl)acetamide

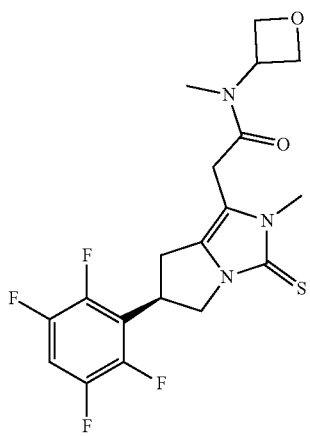 [SMILES: CN(C(=O)Cc1c2n(c(=S)n1C)C[C@@H](c1c(F)c(F)cc(F)c1F)C2)C1COC1]

Compound was prepared analogous manner to Example 32 from (R)-1-(H-imidazol-1-yl)-2-(2-methyl-6-(2,3,5,6-tetrafluorophenyl)-3-thioxo-2,5,6,7-tetrahydro-3H-pyrrolo[1,2-c]imidazol-1-yl)ethan-1-one and isolated as an off-white powder.

$^1$H NMR (DMSO$_{d6}$): 7.86 (1H, m), 5.24 (1H, m), 4.72 (1.4H, m), 4.65 (1.3H, br t, J=7.1 Hz), 4.59 (1.3H, m), 4.48 (1H, quin, J=8.3 Hz), 4.24 (1H, m), 3.84 (1H, m), 3.76, 3.73 (2H, 2 s), 3.33 (3H, s), 3.33 (1H, m), 3.11 (1.8H, s), 3.04 (1.2H, s), 2.88 (1H, m).

$^{13}$C NMR (DMSO$_{d6}$): 168.6, 167.8, 156.3, 146.4, 146.4, 146.4, 146.3, 146.3, 146.2, 145.3, 145.3, 145.3, 145.2, 145.2, 144.8, 144.8, 144.7, 144.6, 143.7, 143.7, 143.7, 143.7, 143.6, 143.6, 143.6, 143.6, 128.2, 128, 120.5, 120.4, 120.3, 116.3, 116.2, 105.9, 105.7, 105.6, 74.6, 74.6, 74.2, 74.2, 51, 49.4, 49.2, 34.9, 31.5, 31.5, 30.7, 29.6, 29.3, 29, 29, 27.9.

Example 399: 2-((S)-6-(3-chloro-2,6-difluorophenyl)-2-methyl-3-thioxo-2,5,6,7-tetrahydro-3H-pyrrolo[1,2-c]imidazol-1-yl)-N-methyl-N—((R)-tetrahydrofuran-3-yl)acetamide

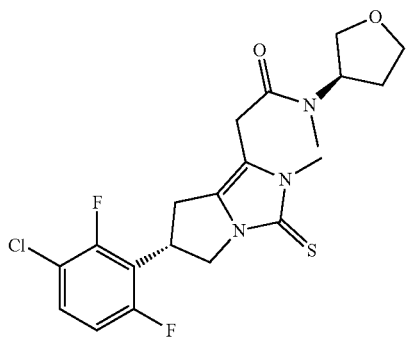 [SMILES: CN(C(=O)Cc1c2n(c(=S)n1C)C[C@H](c1c(F)ccc(Cl)c1F)C2)[C@@H]1CCOC1]

Compound was prepared analogous manner to Example 34 from (S)-2-(2-methyl-6-(3-chloro-2,6-difluorophenyl)-3-thioxo-2,5,6,7-tetrahydro-3H-pyrrolo[1,2-c]imidazol-1-yl) acetic acid and isolated as an off-white solid.

$^1$H NMR (DMSO$_{d6}$): 7.61 (1H, td, J=8.7, 5.6 Hz), 7.22 (1H, m), 5.09 (0.6H, m), 4.65 (0.4H, m), 4.44 (1H, quin, J=8.5 Hz), 4.23 (1H, m), 3.92 (1H, m), 3.82 (2H, m), 3.70 (2H, m), 3.63 (1H, m), 3.56 (1H, m), 3.35 (3H, 2 s), 3.26 (1H, m), 2.94 (1.8H, s), 2.86 (1H, m), 2.74 (1.2H, s), 2.21 (0.4H, m), 2.09 (0.6H, m), 1.86 (0.4H, m), 1.76 (0.6H, m).

$^{13}$C NMR (DMSO$_{d6}$): 168.2, 167.6, 160.1, 160.1, 158.5, 158.5, 156.6, 156.5, 156.2, 156.2, 154.9, 154.9, 129.7, 129.6, 128.3, 128.1, 118.9, 118.8, 118.7, 116.5, 116.4, 116.1, 116.1, 116, 115.9, 113.3, 113.2, 113.1, 113.1, 69.4, 69.2, 67.1, 67.1, 56.6, 53, 49.5, 34.8, 34.8, 31.5, 31.5, 30, 29.8, 29.7, 29.4, 29.3, 29.2, 27.6.

Example 400: 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-N-(oxetan-3-yl)acetamide

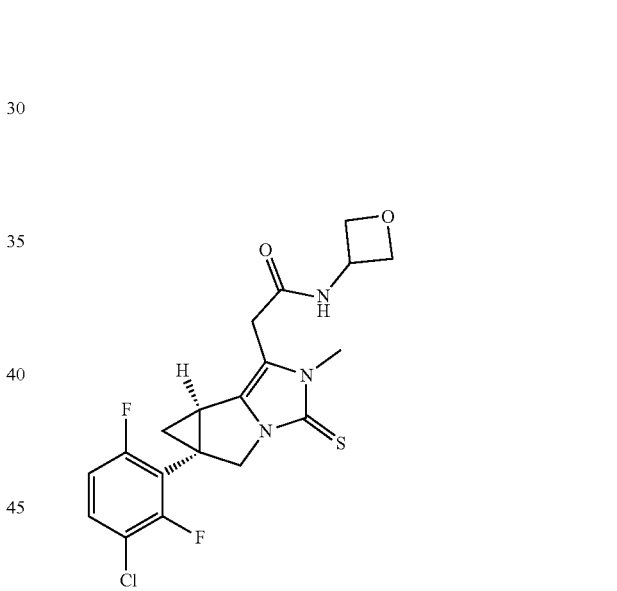

Compound was prepared analogous manner to Example 32 from 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

$^1$H NMR (DMSO$_{d6}$): 8.90 (1H, d, J=6.7 Hz), 7.64 (1H, td, J=8.7, 5.6 Hz), 7.21 (1H, m), 4.81 (1H, m), 4.72 (2H, m), 4.44 (2H, td, J=6.4, 1.5 Hz), 4.10 (1H, d, J=12.0 Hz), 3.80 (1H, d, J=12.2 Hz), 3.56 (2H, m), 3.35 (3H, s), 2.79 (1H, dd, J=8.4, 4.4 Hz), 1.69 (1H, dd, J=8.3, 5.5 Hz), 1.27 (1H, t, J=5.0 Hz).

$^{13}$C NMR (DMSO$_{d6}$): 167.5, 161.3, 161.2, 159.6, 159.6, 157.8, 157.8, 156.9, 156.2, 156.1, 130.8, 130.3, 130.2, 117, 116.9, 116.8, 116.1, 115.7, 115.6, 115.6, 112.9, 112.9, 112.8, 77, 77, 52.2, 44.2, 31.5, 31, 25.6, 21.6, 21.2.

Example 401: 2-((S)-6-(3-chloro-2,6-difluorophenyl)-3-thioxo-2,5,6,7-tetrahydro-3H-pyrrolo[1,2-c]imidazol-1-yl)-N—((R)-tetrahydro-2H-pyran-3-yl)acetamide

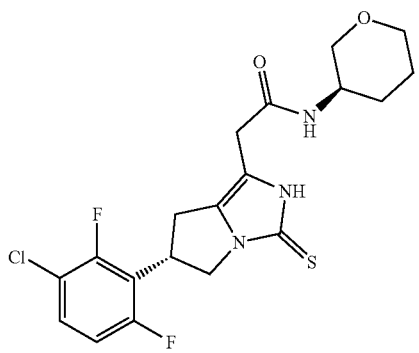

Compound was prepared analogous manner to Example 34 from (S)-2-(6-(3-chloro-2,6-difluorophenyl)-3-thioxo-2,5,6,7-tetrahydro-3H-pyrrolo[1,2-c]imidazol-1-yl)acetic acid and isolated as an off-white solid.

$^1$H NMR (DMSO$_{d6}$): 11.75 (1H, s), 7.96 (1H, br d, J=7.5 Hz), 7.61 (1H, m), 7.21 (1H, t, J=9.5 Hz), 4.44 (1H, quin, J=8.6 Hz), 4.15 (1H, dd, J=11.4, 9.2 Hz), 3.72 (1H, dd, J=11.6, 7.9 Hz), 3.65 (3H, m), 3.31 (1H, m), 3.26 (2H, s), 3.23 (1H, dd, J=9.4, 15.9 Hz), 3.08 (1H, m), 2.84 (1H, dd, J=15.8, 8.1 Hz), 1.80 (1H, m), 1.66 (1H, m), 1.45 (2H, m).

$^{13}$C NMR (DMSO$_{d6}$): 167.2, 160.2, 160.1, 158.5, 158.5, 156.6, 156.5, 155.1, 154.9, 154.9, 129.7, 129.6, 129, 118.8, 118.7, 118.6, 116.1, 116, 115.9, 115.9, 114.3, 113.2, 113.2, 113.1, 113.1, 70.2, 67, 48.5, 35.6, 31.4, 29.3, 28.6, 23.9.

Example 402: 2-((S)-6-(3-bromo-2,6-difluorophenyl)-3-thioxo-2,5,6,7-tetrahydro-3H-pyrrolo[1,2-c]imidazol-1-yl)-N—((R)-tetrahydro-2H-pyran-3-yl)acetamide

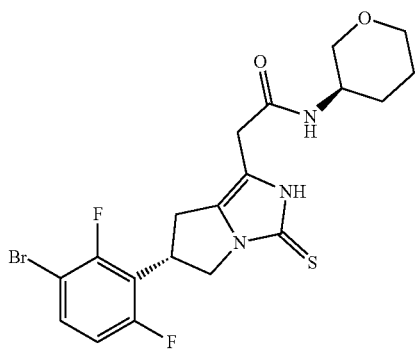 [SMILES: O=C(Cc1[nH]c(=S)n2c1C[C@@H](c1c(F)ccc(Cl)c1F)C2)N[C@@H]1CCCOC1]

Compound was prepared analogous manner to Example 34 from (S)-2-(6-(3-bromo-2,6-difluorophenyl)-3-thioxo-2,5,6,7-tetrahydro-3H-pyrrolo[1,2-c]imidazol-1-yl)acetic acid and isolated as a cream powder. $^1$H NMR (DMSO$_{d6}$): 11.74 (1H, s), 7.96 (1H, br d, J=7.6 Hz), 7.71 (1H, m), 7.17 (1H, m), 4.44 (1H, quin, J=8.6 Hz), 4.14 (1H, dd, J=11.5, 9.2 Hz), 3.72 (1H, dd, J=11.6, 7.9 Hz), 3.65 (3H, m), 3.34 (1H, m), 3.25 (2H, d, J=2.9 Hz), 3.21 (1H, dd, J=16.0, 9.1 Hz), 3.09 (1H, dd, J=10.5, 7.8 Hz), 2.83 (1H, dd, J=15.7, 8.2 Hz), 1.79 (1H, m), 1.65 (1H, m), 1.45 (2H, m).

$^{13}$C NMR (DMSO$_{d6}$): 167.2, 160.8, 160.8, 159.2, 159.1, 157.6, 157.5, 155.9, 155.9, 155.1, 132.5, 132.4, 129, 118.8, 118.7, 118.6, 114.3, 113.8, 113.8, 113.6, 113.6, 104.1, 104, 103.9, 103.9, 70.2, 67, 48.6, 45.1, 35.6, 31.4, 29.4, 28.6, 23.9.

Example 403: 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-N-methyl-N-(oxetan-3-yl)acetamide

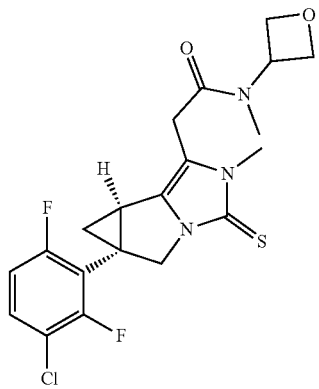 [SMILES: CN(C(=O)Cc1c2n(c(=S)n1C)C[C@@]1(c3c(F)ccc(Cl)c3F)C[C@@H]21)C1COC1]

Compound was prepared analogous manner to Example 32 from 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

$^1$H NMR (DMSO$_{d6}$): 7.64 (1H, td, J=8.7, 5.6 Hz), 7.21 (1H, m), 5.29 (1H, m), 4.76, 4.67, 4.60 (4H, 3 m), 4.11 (1H, m), 3.84 (3H, m), 3.29 (3H, 2 s), 3.16 (1.8H, m), 3.06 (1.2H, s), 2.76 (0.6H, dd, J=8.3, 4.3 Hz), 2.69 (0.4H, dd, J=8.4, 4.4 Hz), 1.68 (1H, m), 1.25 (0.6H, t, J=5.0 Hz), 1.22 (0.4H, t, J=5.0 Hz).

$^{13}$C NMR (DMSO$_{d6}$): 168.6, 167.8, 161.3, 161.2, 159.6, 159.6, 157.8, 157.8, 156.9, 156.2, 156.1, 130.6, 130.3, 130.3, 130.2, 117, 117, 116.9, 116.8, 116.8, 116.3, 116.2, 115.8, 115.7, 115.6, 115.6, 112.9, 112.9, 112.8, 112.8, 74.7, 74.6, 74.3, 74.2, 52.2, 52.2, 51.1, 49.1, 31.5, 31.5, 31.4, 30.7, 29.8, 29.4, 27.9, 25.7, 21.7, 21.2, 21.1.

Example 404: 2-((S)-6-(3-chloro-2,6-difluorophenyl)-3-thioxo-2,5,6,7-tetrahydro-3H-pyrrolo[1,2-c]imidazol-1-yl)-N—((S)-tetrahydrofuran-3-yl)acetamide

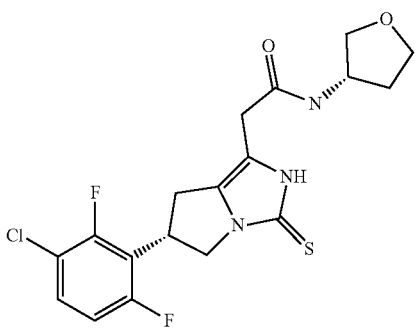 [SMILES: O=C(Cc1[nH]c(=S)n2c1C[C@@H](c1c(F)ccc(Cl)c1F)C2)N[C@H]1CCOC1]

Compound was prepared analogous manner to Example 32 from (S)-2-(6-(3-chloro-2,6-difluorophenyl)-3-thioxo-2,5,6,7-tetrahydro-3H-pyrrolo[1,2-c]imidazol-1-yl)-1-(1H-imidazol-1-yl)ethan-1-one and isolated as an off-white solid.

$^1$H NMR (DMSO$_{d6}$): 11.75 (1H, s), 8.22 (1H, br d, J=6.6 Hz), 7.61 (1H, td, J=8.8, 5.6 Hz), 7.21 (1H, t, J=9.4 Hz), 4.44 (1H, quin, J=8.6 Hz), 4.21 (1H, tt, J=10.1, 3.8 Hz), 4.15 (1H, dd, J=11.5, 9.2 Hz), 3.73 (3H, m), 3.65 (1H, td, J=8.2, 5.6 Hz), 3.45 (1H, dd, J=8.9, 3.7 Hz), 3.24 (2H, s), 3.22 (1H, dd, J=6.3, 11.7 Hz), 2.84 (1H, dd, J=15.6, 8.1 Hz), 2.07 (1H, m), 1.71 (1H, m).

$^{13}$C NMR (DMSO$_{d6}$): 167.5, 160.2, 160.1, 158.5, 158.5, 156.6, 156.5, 155.1, 154.9, 154.9, 129.7, 129.6, 129.1, 118.8, 118.7, 118.6, 116.1, 116, 115.9, 115.9, 114.2, 113.3, 113.2, 113.1, 113.1, 72.4, 66.3, 49.8, 48.5, 35.6, 32, 31.3, 29.3.

Example 405: (S)-2-(6-(3-bromo-2,6-difluorophenyl)-2-methyl-3-thioxo-2,5,6,7-tetrahydro-3H-pyrrolo[1,2-c]imidazol-1-yl)-N-methyl-N-(tetrahydro-2H-pyran-4-yl)acetamide

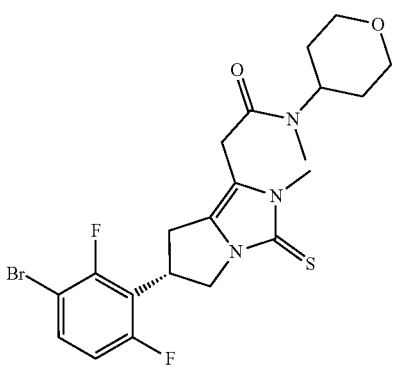

Compound was prepared analogous manner to Example 32 from (S)-2-(6-(3-bromo-2,6-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as a cream powder.

$^1$H NMR (DMSO$_{d6}$): 7.72 (1H, td, J=8.4, 5.8 Hz), 7.16 (1H, br t, J=9.4 Hz), 4.38-4.52 (1.6H, m), 4.22 (1H, m), 3.94 (0.4H, m), 3.90 (2H, m), 3.76-3.85 (1.8H, m), 3.72 (1.2H, s), 3.37 (2H, m), 3.35 (3H, s), 3.28 (1H, m), 2.89 (1.8H, s), 2.82-2.88 (1H, m), 2.72 (1.2H, s), 1.74-1.82 (0.8H, m), 1.64-1.74 (1.2H, m), 1.54-1.63 (0.8H, m), 1.37-1.46 (1.2H, m).

$^{13}$C NMR (DMSO$_{d6}$): 167.7, 167.5, 160.8, 160.7, 159.1, 159.1, 157.5, 157.5, 156.1, 155.9, 155.8, 132.5, 132.4, 128.2, 118.9, 118.8, 118.8, 118.7, 116.7, 116.5, 116.3, 113.8, 113.6, 104.1, 103.9, 66.5, 66.3, 52.9, 49.7, 49.6, 34.8, 31.5, 31.5, 30.2, 30.2, 29.9, 29.5, 29.2, 29.1, 27.1.

Example 406: (S)-2-(6-(3-bromo-2,6-difluorophenyl)-2-methyl-3-thioxo-2,5,6,7-tetrahydro-3H-pyrrolo[1,2-c]imidazol-1-yl)-N-(tetrahydro-2H-pyran-4-yl)acetamide

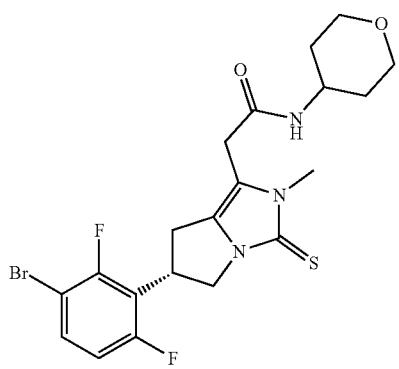

Compound was prepared analogous manner to Example 32 from (S)-2-(6-(3-bromo-2,6-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as a cream powder.

$^1$H NMR (DMSO$_{d6}$): 8.11 (1H, d, J=7.6 Hz), 7.68-7.79 (1H, m), 7.12-7.21 (1H, m), 4.44 (1H, quin, J=8.5 Hz), 4.22 (1H, dd, J=11.4, 9.3 Hz), 3.71-3.83 (4H, m), 3.42 (2H, d, J=2.3 Hz), 3.40 (3H, s), 3.33 (2H, m), 3.28 (1H, dd, J=15.9, 9.6 Hz), 2.88 (1H, dd, J=15.9, 8.0 Hz), 1.64-1.73 (2H, m), 1.30-1.46 (2H, m).

$^{13}$C NMR (DMSO$_{d6}$): 166.8, 160.8, 160.7, 159.2, 159.1, 157.6, 157.5, 156.2, 155.9, 155.9, 132.5, 132.4, 128.4, 118.8, 118.7, 118.6, 116.4, 113.8, 113.6, 104.1, 104.1, 103.9, 103.9, 65.8, 49.6, 45.2, 34.8, 32.4, 31.5, 31.3, 29.2.

Example 407: (S)-2-(6-(3-chloro-2,6-difluorophenyl)-3-thioxo-2,5,6,7-tetrahydro-3H-pyrrolo[1,2-c]imidazol-1-yl)acetic acid

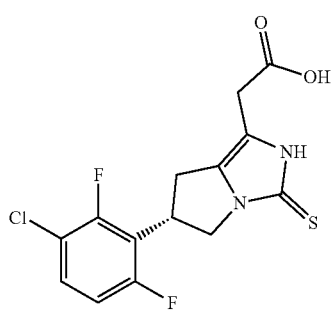 [SMILES: O=C(O)Cc1[nH]c(=S)n2c1C[C@@H](c1c(F)ccc(Cl)c1F)C2]

Compound was prepared analogous manner to Example 3 from tert-butyl (4S)-4-(3-chloro-2,6-difluorophenyl)-2-(3-ethoxy-3-oxopropanoyl)pyrrolidine-1-carboxylate and isolated as an off-white solid.

$^1$H NMR (DMSO$_{d6}$): 12.56 (1H, br s), 11.78 (1H, s), 7.61 (1H, td, J=8.7, 5.6 Hz), 7.21 (1H, t, J=8.9 Hz), 4.46 (1H, quin, J=8.6 Hz), 4.16 (1H, dd, J=11.4, 9.2 Hz), 3.74 (1H, dd, J=11.6, 7.9 Hz), 3.41 (2H, s), 3.26 (1H, dd, J=9.3, 15.8 Hz), 2.87 (1H, dd, J=15.8, 8.2 Hz).

$^{13}$C NMR (DMSO$_{d6}$): 170.7, 160.2, 160.1, 158.5, 158.5, 156.6, 156.5, 155.3, 154.9, 154.9, 129.7, 129.7, 129.6, 118.8, 118.7, 118.6, 116.1, 116.1, 116, 115.9, 113.4, 113.3, 113.2, 113.1, 113.1, 48.6, 35.6, 29.9, 29.2.

Example 408: (S)-2-(6-(3-bromo-2,6-difluorophenyl)-3-thioxo-2,5,6,7-tetrahydro-3H-pyrrolo[1,2-c]imidazol-1-yl)-N-methyl-N-(oxetan-3-yl)acetamide

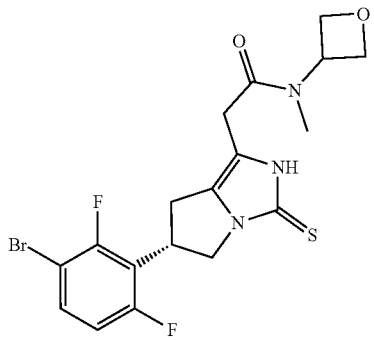 [SMILES: CN(C(=O)Cc1[nH]c(=S)n2c1C[C@@H](c1c(F)ccc(Br)c1F)C2)C1COC1]

Compound was prepared analogous manner to Example 32 from (S)-2-(6-(3-bromo-2,6-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as a cream powder.

$^1$H NMR (DMSO$_{d6}$): 11.67 (1H, br s), 7.72 (1H, td, J=8.4, 5.9 Hz), 7.18 (1H, m), 5.22 (1H, m), 4.70 (1.33H, m), 4.63 (1.3H, m), 4.58 (1.3H, m), 4.44 (1 Hm), 4.15 (1H, m), 3.69 (1H, m), 3.51, 3.48 (2H, m), 3.18 (1H, m), 3.06, 3.02 (3H, 2 s), 2.80 (1H, m).

$^{13}$C NMR (DMSO$_{d6}$): 168.6, 167.8, 160.8, 160.8, 159.2, 157.5, 157.5, 155.9, 155.8, 155.2, 155.1, 132.5, 132.4, 129.4, 129.3, 118.9, 118.7, 118.6, 114, 113.9, 113.8, 113.6, 104.1, 103.9, 74.6, 74.6, 74.2, 51, 49.1, 48.6, 35.7, 30.8, 29.7, 29.4, 29.3, 29.2, 28.

Example 409: (S)-2-(2-methyl-3-thioxo-6-(2,3,6-trifluorophenyl)-2,5,6,7-tetrahydro-3H-pyrrolo[1,2-c]imidazol-1-yl)acetic Acid

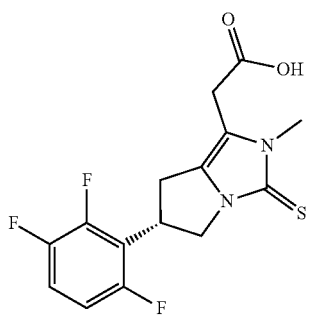 [SMILES: Cn1c(CC(=O)O)c2n(c1=S)C[C@H](c1c(F)ccc(F)c1F)C2]

Compound was prepared in an analogous manner to Example 229 from tert-butyl (4S)-2-(3-ethoxy-3-oxopropanoyl)-4-(2,3,6-trifluorophenyl)pyrrolidine-1-carboxylate and isolated as an off-white powder.

$^1$H NMR (DMSO$_{d6}$): 12.73 (1H, br s), 12.74 (1H, m), 7.53 (1H, m), 7.47 (1H, m), 7.18 (1H, m), 4.44 (1H, quin, J=8.6 Hz), 4.24 (1H, dd, J=11.4, 9.2 Hz), 3.82 (1H, dd, J=11.6, 7.8 Hz), 3.65 (2H, d, J=0.7 Hz), 3.40 (3H, s), 3.34 (1H, m), 2.92 (1H, dd, J=15.9, 8.1 Hz).

$^{13}$C NMR (DMSO$_{d6}$): 170.8, 156.9, 156.9, 156.4, 155.3, 155.3, 155.3, 155.3, 149.1, 149, 149, 148.9, 147.6, 147.5, 147.4, 147.4, 147.3, 145.9, 145.9, 145.9, 145.8, 128.7, 118.9, 118.8, 118.8, 118.7, 116.5, 116.5, 116.4, 116.3, 115.6, 112, 112, 112, 111.9, 111.8, 111.8, 111.8, 111.8, 49.5, 34.7, 31.4, 29.8, 29.1.

Example 410: (S)-2-(6-(3-bromo-2,6-difluorophenyl)-3-thioxo-2,5,6,7-tetrahydro-3H-pyrrolo[1,2-c]imidazol-1-yl)-N-(tetrahydro-2H-pyran-4-yl)acetamide

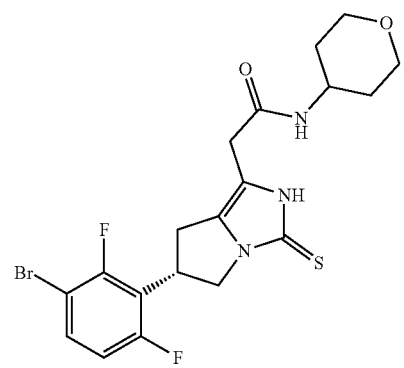 [SMILES: O=C(Cc1[nH]c(=S)n2c1C[C@@H](c1c(F)ccc(Br)c1F)C2)NC1CCOCC1]

Compound was prepared analogous manner to Example 32 from (R)-2-(3-thioxo-6-(3-bromo-2,6-difluorophenyl)-2,5,6,7-tetrahydro-3H-pyrrolo[1,2-c]imidazol-1-yl)acetic acid and isolated as a cream powder.

$^1$H NMR (DMSO$_{d6}$): 1.75 (1H, s), 7.97 (1H, d, J=7.5 Hz), 7.72 (1H, m), 7.16 (1H, m), 4.44 (1H, quin, J=8.6 Hz), 4.14 (1H, dd, J=11.4, 9.2 Hz), 3.80 (2H, dt, J=11.4, 3.6 Hz), 3.72 (2H, m), 3.31 (2H, m), 3.24 (2H, s), 3.23 (1H, dd, J=9.4, 16 Hz), 2.83 (1H, dd, J=15.9, 8.1 Hz), 1.67 (2H, m), 1.37 (2H, m).

$^{13}$C NMR (DMSO$_{d6}$): 166.8, 160.8, 160.8, 159.2, 159.1, 157.6, 157.5, 155.9, 155.9, 155.1, 132.5, 132.4, 129, 118.8, 118.7, 118.6, 114.3, 113.8, 113.8, 113.6, 113.6, 104.1, 104, 103.9, 103.9, 65.8, 48.6, 45.2, 35.6, 32.4, 31.5, 29.4.

Example 411: (S)-2-(2-methyl-3-thioxo-6-(2,3,6-trifluorophenyl)-2,5,6,7-tetrahydro-3H-pyrrolo[1,2-c]imidazol-1-yl)-1-morpholinoethan-1-one

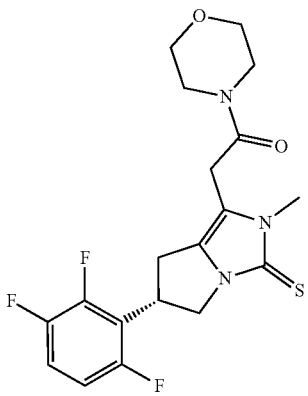 [SMILES: Cn1c(CC(=O)N2CCOCC2)c2n(c1=S)C[C@H](c1c(F)ccc(F)c1F)C2]

Compound was prepared analogous manner to Example 32 from (S)-2-(6-(2,3,6-trifluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as an off-white solid.

$^1$H NMR (DMSO$_{d6}$): 7.47 (1H, qd, J=9.4, 5.1 Hz), 7.18 (1H, m), 4.44 (1H, quin, J=8.6 Hz), 4.24 (1H, m), 3.81 (1H, dd, J=11.4, 7.9 Hz), 3.75 (2H, s), 3.59 (2H, m), 3.55 (2H, m), 3.49 (2H, m), 3.45 (2H, m), 3.36 (3H, s), 3.28 (1H, dd, J=15.8, 9.3 Hz), 2.88 (1H, dd, J=15.8, 8.1 Hz).

$^{13}$C NMR (DMSO$_{d6}$): 166.8, 157, 157, 156.9, 156.9, 156.3, 155.3, 155.3, 155.3, 155.3, 149.1, 149, 149, 148.9, 147.5, 147.5, 147.4, 147.4, 147.4, 147.3, 145.9, 145.9, 145.9, 145.8, 128.2, 118.9, 118.8, 118.8, 118.7, 116.5, 116.4, 116.4, 116.3, 116.3, 112, 112, 112, 111.9, 111.8, 111.8, 111.8, 111.8, 66, 66, 49.4, 45.6, 41.7, 34.8, 31.5, 29.2, 28.8.

Example 412: 2-((S)-2-methyl-3-thioxo-6-(2,3,6-trifluorophenyl)-2,5,6,7-tetrahydro-3H-pyrrolo[1,2-c]imidazol-1-yl)-N—((R)-tetrahydrofuran-3-yl)acetamide

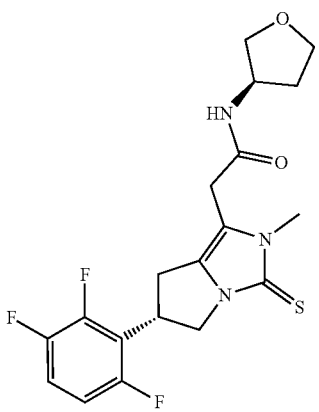 [SMILES: Cn1c(CC(=O)N[C@@H]2CCOC2)c2n(c1=S)C[C@H](c1c(F)ccc(F)c1F)C2]

Compound was prepared analogous manner to Example 32 from (S)-1-(1H-imidazol-1-yl)-2-(2-methyl-3-thioxo-6-(2,3,6-trifluorophenyl)-2,5,6,7-tetrahydro-3H-pyrrolo[1,2-c]imidazol-1-yl)ethan-1-one and isolated as an off-white powder.

$^1$H NMR (DMSO$_{d6}$): 8.37 (1H, br d, J=6.5 Hz), 7.47 (1H, qd, J=9.4, 5.0 Hz), 7.18 (1H, m), 4.43 (1H, quin, J=8.6 Hz), 4.23 (2H, m), 3.81 (1H, dd, J=11.0, 7.6 Hz), 3.78 (1H, q, J=7.1 Hz), 3.72 (1H, dd, J=8.9, 6.0 Hz), 3.66 (1H, td, J=8.2, 5.6 Hz), 3.46 (1H, dd, J=9.0, 3.5 Hz), 3.43 (2H, m), 3.40 (3H, s), 3.29 (1H, br dd, J 15.7, 9.2 Hz), 2.90 (1H, dd, J 15.8, 8.2 Hz), 2.08 (1H, dq, J=12.7, 7.6 Hz), 1.71 (1H, m).

$^{13}$C NMR (DMSO$_{d6}$): 167.6, 157, 156.9, 156.2, 155.3, 155.3, 149.1, 149, 149, 149, 147.6, 147.5, 147.4, 147.4, 147.3, 145.9, 145.9, 145.9, 145.8, 128.4, 118.9, 118.8, 118.7, 118.6, 116.5, 116.5, 116.4, 116.3, 112, 112, 112, 111.9, 111.8, 111.8, 111.8, 111.8, 72.4, 66.3, 49.8, 49.4, 34.7, 32, 31.5, 31.1, 29.1.

Example 413: (S)-2-(6-(3-bromo-2,6-difluorophenyl)-2-methyl-3-thioxo-2,5,6,7-tetrahydro-3H-pyrrolo[1,2-c]imidazol-1-yl)-N-(oxetan-3-yl)acetamide

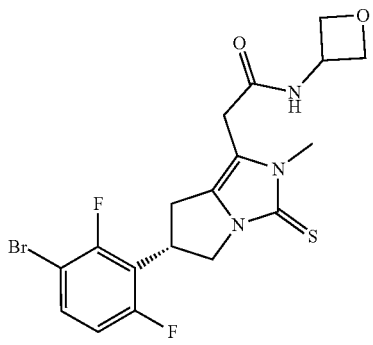 [SMILES: Cn1c(CC(=O)NC2COC2)c2n(c1=S)C[C@H](c1c(F)ccc(Br)c1F)C2]

Compound was prepared analogous manner to Example 32 from (S)-2-(6-(3-bromo-2,6-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as a cream powder.

$^1$H NMR (DMSO$_{d6}$): 8.84 (1H, br d, J=6.6 Hz), 7.72 (1H, m), 7.18 (1H, m), 4.78 (1H, m), 4.70 (2H, td, J=6.9, 2.2 Hz), 4.42 (3H, m), 4.22 (1H, dd, J=11.4, 9.2 Hz), 3.79 (1H, dd, J=11.6, 7.8 Hz), 3.47 (2H, m), 3.39 (3H, s), 3.28 (1H, dd, J=15.8, 9.3 Hz), 2.89 (1H, dd, J=15.8, 8.1 Hz).

$^{13}$C NMR (DMSO$_{d6}$): 167.5, 160.8, 160.8, 159.2, 159.1, 157.6, 157.5, 156.3, 155.9, 155.9, 132.5, 132.4, 128.7, 118.8, 118.6, 118.5, 116, 113.8, 113.6, 104.1, 104.1, 103.9, 103.9, 77, 77, 49.6, 44.2, 34.8, 31.5, 31, 29.2.

Example 414: (R)-2-(2-methyl-3-thioxo-6-(2,3,6-trifluorophenyl)-2,5,6,7-tetrahydro-3H-pyrrolo[1,2-c]imidazol-1-yl)-N-(oxetan-3-yl)acetamide

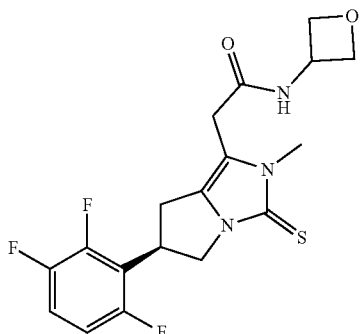

Compound was prepared analogous manner to Example 32 from (R)-1-(1H-imidazol-1-yl)-2-(2-methyl-3-thioxo-6-(2,3,6-trifluorophenyl)-2,5,6,7-tetrahydro-3H-pyrrolo[1,2-c]imidazol-1-yl)ethan-1-one and isolated as cream powder.

$^1$H NMR (DMSO$_{d6}$): 8.85 (1H, br d, J=6.6 Hz), 7.47 (1H, qd, J=9.4, 5.0 Hz), 7.19 (1H, m), 4.78 (1H, m), 4.70 (2H, m), 4.41 (3H, t, J=6.3 Hz), 4.23 (1H, m), 3.81 (1H, dd, J=11.5, 8.0 Hz), 3.48 (2H, m), 3.39 (3H, s), 3.29 (1H, dd, J=15.8, 9.3 Hz), 2.91 (1H, dd, J=15.8, 8.4 Hz).

$^{13}$C NMR (DMSO$_{d6}$): 167.5, 157, 156.9, 156.3, 155.4, 155.3, 149.1, 149.1, 149, 149, 147.6, 147.5, 147.5, 147.4, 147.4, 147.4, 147.3, 146, 145.9, 145.9, 145.8, 128.6, 118.8, 118.7, 118.7, 118.6, 116.5, 116.5, 116.4, 116.3, 116.1, 112, 112, 112, 112, 111.9, 111.8, 111.8, 111.8, 111.8, 77, 77, 49.5, 44.2, 34.7, 31.5, 31, 29.1.

Example 415: 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-N—((R)-tetrahydro-2H-pyran-3-yl)acetamide

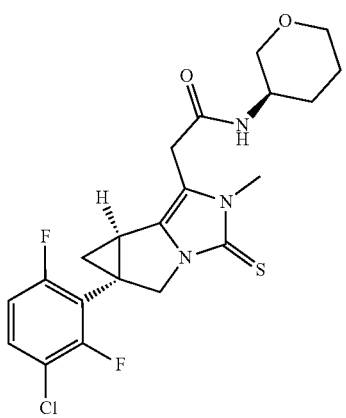 [SMILES: Cn1c(CC(=O)N[C@@H]2CCCOC2)c2n(c1=S)C[C@@]1(c3c(F)ccc(Cl)c3F)C[C@@H]21]

Compound was prepared analogous manner to Example 34 from 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)acetic acid and isolated as a beige solid.

$^1$H NMR (DMSO$_{d6}$): 8.17 (1H, br d, J=7.3 Hz), 7.64 (1H, td, J=8.7, 5.7 Hz), 7.21 (1H, m), 4.10 (1H, d, J=12.2 Hz), 3.80 (1H, d, J=12.0 Hz), 3.68 (3H, m), 3.53 (2H, m), 3.39 (1H, m), 3.35 (3H, s), 3.14 (1H, m), 2.78 (1H, dd, J=8.4, 4.4 Hz), 1.83 (1H, m), 1.69 (2H, m), 1.48 (2H, m), 1.25 (1H, t, J=5.0 Hz).

$^{13}$C NMR (DMSO$_{d6}$): 167.4, 161.3, 161.2, 159.6, 159.6, 157.8, 157.8, 156.8, 156.2, 156.1, 130.6, 130.3, 130.2, 117.1, 116.9, 116.8, 116.5, 115.7, 115.7, 115.6, 115.6, 112.9, 112.9, 112.8, 112.8, 70.1, 67, 52.2, 45.1, 31.4, 31.1, 28.6, 25.6, 23.9, 21.7, 21.2.

Example 416: (S)-2-(2-methyl-3-thioxo-6-(2,3,6-trifluorophenyl)-2,5,6,7-tetrahydro-3H-pyrrolo[1,2-c]imidazol-1-yl)-N-(tetrahydro-2H-pyran-4-yl)acetamide

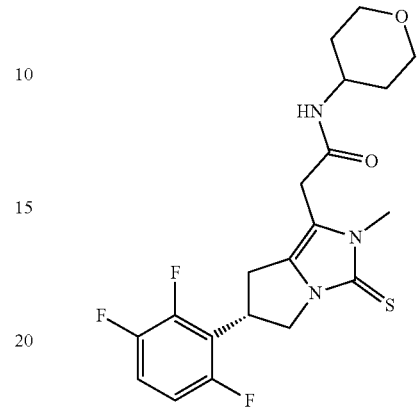

Compound was prepared analogous manner to Example 32 from (S)-2-(6-(2,3,6-trifluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as a light beige powder.

$^1$H NMR (DMSO$_{d6}$): 8.11 (1H, d, J=7.5 Hz), 7.47 (1H, qd, J=9.4, 5.0 Hz), 7.18 (1H, m), 4.43 (1H, quin, J=8.6 Hz), 4.23 (1H, dd, J=11.4, 9.4 Hz), 3.81 (3H, m), 3.75 (1H, m), 3.42 (2H, m), 3.40 (3H, s), 3.33 (2H, m), 3.29 (1H, dd, J=15.8, 9.2 Hz), 2.90 (1H, dd, J=15.8, 8.3 Hz), 1.69 (2H, m), 1.38 (2H, m).

$^{13}$C NMR (DMSO$_{d6}$): 166.8, 157, 156.9, 156.2, 155.3, 155.3, 155.3, 149.1, 149, 149, 148.9, 147.5, 147.5, 147.5, 147.4, 147.4, 147.3, 147.3, 145.9, 145.9, 145.9, 145.8, 128.3, 118.9, 118.8, 118.8, 118.7, 116.5, 116.5, 116.4, 116.4, 116.3, 112, 112, 112, 111.9, 111.8, 111.8, 111.8, 111.8, 65.8, 49.4, 45.2, 34.7, 32.4, 31.5, 31.3, 29.2.

Example 417: 2-((S)-2-methyl-3-thioxo-6-(2,3,6-trifluorophenyl)-2,5,6,7-tetrahydro-3H-pyrrolo[1,2-c]imidazol-1-yl)-N—((S)-tetrahydrofuran-3-yl)acetamide

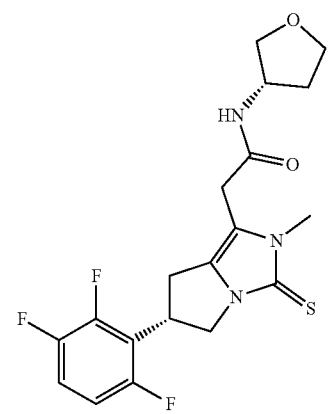 [SMILES: Cn1c(CC(=O)N[C@H]2CCOC2)c2n(c1=S)C[C@H](c1c(F)ccc(F)c1F)C2]

Compound was prepared analogous manner to Example 32 from (S)-1-(1H-imidazol-1-yl)-2-(2-methyl-3-thioxo-6-(2, 3,6-trifluorophenyl)-2,5,6,7-tetrahydro-3H-pyrrolo[1,2-c]imidazol-1-yl)ethan-1-one and isolated as an off-white powder.

¹H NMR (DMSO$_{d6}$): 8.37 (1H, d, J=6.6 Hz), 7.47 (1H, qd, J=9.4, 5.0 Hz), 7.16 (1H, t, J=9.6 Hz), 4.43 (1H, quin, J=8.6 Hz), 4.23 (2H, m), 3.77 (3H, m), 3.66 (1H, td, J=8.2, 5.6 Hz), 3.46 (1H, br dd, J=9.0, 3.6 Hz), 3.43 (2H, s), 3.40 (3H, m), 3.29 (1H, dd, J=15.8, 9.2 Hz), 2.90 (1H, dd, J=15.8, 8.2 Hz), 2.08 (1H, dq, J=12.7, 7.6 Hz), 1.71 (1H, m).

¹³C NMR (DMSO$_{d6}$): 167.6, 157, 156.9, 156.9, 156.2, 155.3, 155.3, 155.3, 149.1, 149, 149, 148.9, 147.5, 147.5, 147.5, 147.4, 147.4, 147.4, 147.3, 145.9, 145.9, 145.9, 145.8, 128.4, 118.9, 118.8, 118.8, 118.7, 116.5, 116.4, 116.4, 116.3, 112, 112, 112, 111.9, 111.8, 111.8, 111.8, 111.8, 72.4, 66.3, 49.8, 49.4, 34.7, 32, 31.5, 31.1, 29.1.

Example 418: 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-N—((S)-tetrahydrofuran-3-yl)acetamide

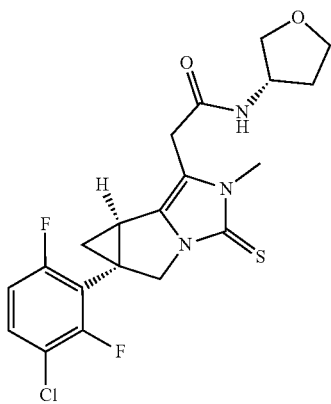 [SMILES: Cn1c(CC(=O)N[C@H]2CCOC2)c2n(c1=S)C[C@@]1(c3c(F)ccc(Cl)c3F)C[C@@H]21]

Compound was prepared analogous manner to Example 32 from 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a grey solid.

¹H NMR (DMSO$_{d6}$): 8.41 (1H, d, J=6.7 Hz), 7.64 (1H, td, J=8.7, 5.7 Hz), 7.21 (1H, td, J=9.1, 1.2 Hz), 4.25 (1H, m), 4.10 (1H, d, J=12.0 Hz), 3.80 (2H, m), 3.74 (1H, dd, J=8.9, 5.9 Hz), 3.67 (1H, td, J=8.2, 5.6 Hz), 3.52 (2H, m), 3.48 (1H, dd, J=8.9, 3.6 Hz), 3.36 (3H, s), 2.79 (1H, dd, J=8.4, 4.4 Hz), 2.09 (1H, dq, J=12.7, 7.6 Hz), 1.74 (1H, m), 1.69 (1H, dd, J=8.4, 5.6 Hz), 1.26 (1H, t, J=5.0 Hz).

¹³C NMR (DMSO$_{d6}$): 167.6, 161.3, 161.2, 159.6, 159.6, 157.8, 157.8, 156.8, 156.2, 156.1, 130.6, 130.3, 130.2, 117.1, 116.9, 116.8, 116.5, 115.7, 115.7, 115.6, 115.6, 112.9, 112.9, 112.8, 112.8, 72.4, 66.3, 52.2, 49.8, 32, 31.5, 31, 25.6, 21.7, 21.2.

Example 419: (S)-2-(6-(3,5-difluorophenyl)-2-methyl-3-thioxo-2,5,6,7-tetrahydro-3H-pyrrolo[1,2-c]imidazol-1-yl)-1-morpholinoethan-1-one

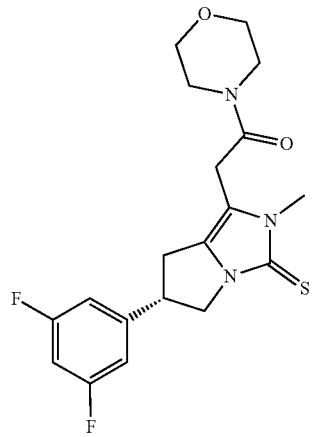 [SMILES: Cn1c(CC(=O)N2CCOCC2)c2n(c1=S)C[C@H](c1cc(F)cc(F)c1)C2]

Compound was prepared analogous manner to Example 32 from (S)-2-(6-(3,5-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as an off-white powder.

¹H NMR (DMSO$_{d6}$): 7.13 (3H, m), 4.23 (1H, dd, J=11.2, 7.8 Hz), 4.07 (1H, quin, J=8.0 Hz), 3.76 (3H, m), 3.60 (2H, br t, J=4.3 Hz), 3.56 (2H, br d, J=4.0 Hz), 3.51 (2H, m), 3.45 (2H, m), 3.36 (3H, s), 3.20 (1H, dd, J=15.3, 7.9 Hz), 2.84 (1H, dd, J=15.3, 8.4 Hz).

¹³C NMR (DMSO$_{d6}$): 166.8, 163.3, 163.2, 161.7, 161.6, 156.4, 145.8, 145.7, 145.7, 128.4, 116.6, 110.7, 110.7, 110.6, 110.6, 102.7, 102.5, 102.3, 66, 51, 45.6, 45.5, 41.7, 31.5, 30.4, 28.7.

Example 420: (R)—N-methyl-N-(oxetan-3-yl)-2-(3-thioxo-6-(2,3,6-trifluorophenyl)-2,5,6,7-tetrahydro-3H-pyrrolo[1,2-c]imidazol-1-yl)acetamide

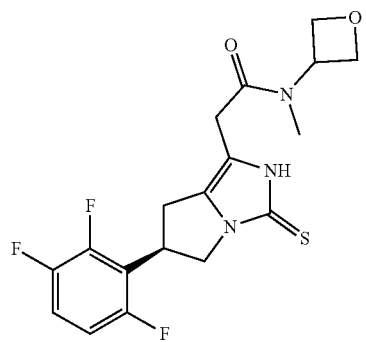 [SMILES: CN(C(=O)Cc1[nH]c(=S)n2c1C[C@H](c1c(F)ccc(F)c1F)C2)C1COC1]

Compound was prepared analogous manner to Example 32 from (R)-2-(6-(2,3,6-trifluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as a cream powder.

¹H NMR (DMSO$_{d6}$): 1.68 (1H, br s), 7.47 (1H, m), 7.17 (1H, m), 5.22 (1H, m), 4.70 (1.33H, m), 4.63 (1.33H, m), 4.58 (1.33H, m), 4.43 (1H, m), 4.16 (1H, m), 3.74 (1H, m), 3.52, 3.49 (2H, 2s), 3.19 (1H, m), 3.05, 3.01 (3H, 2 s), 2.82 (1H, m).

$^{13}$C NMR (DMSO$_{d6}$): 168.6, 167.8, 157, 155.3, 155.3, 155.2, 155.2, 149.1, 147.5, 147.5, 129.3, 129.2, 118.8, 116.5, 116.4, 116.4, 116.3, 114.1, 114, 112, 111.8, 74.6, 74.6, 74.2, 51, 49.1, 48.5, 35.6, 30.8, 29.7, 29.4, 29.2, 29.1, 28.

Example 421: 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-1-morpholinoethan-1-one

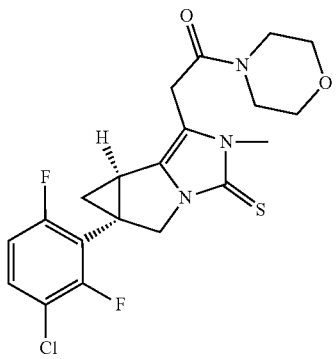 [SMILES: Cn1c(CC(=O)N2CCOCC2)c2n(c1=S)C[C@@]1(c3c(F)ccc(Cl)c3F)C[C@@H]21]

Compound was prepared analogous manner to Example 32 from 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as an off-white powder.

$^1$H NMR (DMSO$_{d6}$): 7.64 (1H, td, J=8.7, 5.7 Hz), 7.21 (1H, m), 4.11 (1H, d, J=12.2 Hz), 3.83 (2H, m), 3.80 (1H, d, J=12.2 Hz), 3.62 (2H, m), 3.57 (2H, m), 3.52 (2H, m), 3.47 (2H, m), 3.33 (3H, s), 2.75 (1H, dd, J=8.4, 4.4 Hz), 1.71 (1H, dd, J=8.3, 5.5 Hz), 1.26 (1H, t, J=5.0 Hz).

$^{13}$C NMR (DMSO$_{d6}$): 166.8, 161.2, 161.2, 159.6, 159.6, 157.8, 157.8, 156.9, 156.1, 156.1, 130.4, 130.3, 130.2, 117, 116.9, 116.8, 116.2, 115.7, 115.7, 115.6, 115.6, 112.9, 112.9, 112.8, 112.7, 66, 52.2, 45.7, 41.7, 31.5, 29, 25.7, 21.8, 21.2.

Example 422: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-morpholinoethan-1-one

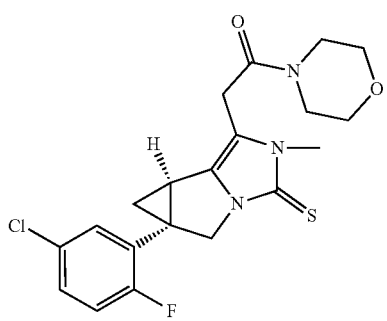 [SMILES: Cn1c(CC(=O)N2CCOCC2)c2n(c1=S)C[C@@]1(c3cc(Cl)ccc3F)C[C@@H]21]

Compound was prepared analogous manner to Example 32 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

$^1$H NMR (DMSO$_{d6}$): 7.45 (2H, m), 7.30 (1H, dd, J=10.0, 8.8 Hz), 4.15 (1H, d, J=12.0 Hz), 3.86 (1H, d, J=12 Hz), 3.82 (2H, m), 3.62 (2H, m), 3.58 (2H, br t, J=4.8 Hz), 3.53 (2H, m), 3.47 (2H, m), 3.33 (3H, s), 2.86 (1H, dd, J=8.3, 4.2 Hz), 1.72 (1H, dd, J=8.3, 5.4 Hz), 1.13 (1H, t, J=4.8 Hz).

$^{13}$C NMR (DMSO$_{d6}$): 166.8, 161.3, 159.6, 156.9, 130.7, 130.2, 130.2, 129.4, 129.3, 128.7, 128.6, 128.3, 128.2, 117.6, 117.4, 115.9, 66, 52.4, 52.4, 45.7, 41.7, 31.6, 31.5, 28.9, 22.1, 20.7.

Example 423: 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-N-(tetrahydro-2H-pyran-4-yl)acetamide

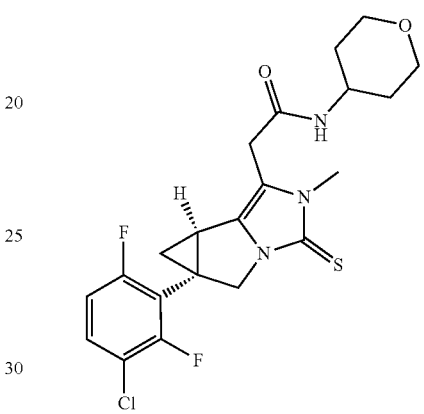

Compound was prepared analogous manner to Example 32 from 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a light grey solid.

$^1$H NMR (DMSO$_{d6}$): 8.16 (1H, d, J=7.6 Hz), 7.64 (1H, td, J=8.7, 5.6 Hz), 7.22 (1H, m), 4.10 (1H, d, J=12.0 Hz), 3.80 (4H, m), 3.50 (2H, m), 3.36 (3H, s), 3.34 (2H, m), 2.79 (1H, dd, J=8.4, 4.4 Hz), 1.71 (3H, m), 1.41 (2H, m), 1.26 (1H, t, J=5.0 Hz).

$^{13}$C NMR (DMSO$_{d6}$): 166.9, 161.3, 161.2, 159.6, 159.6, 157.8, 157.8, 156.8, 156.2, 156.1, 130.6, 130.3, 130.2, 117.1, 116.9, 116.8, 116.6, 115.7, 115.7, 115.6, 115.6, 112.9, 112.9, 112.8, 112.8, 65.8, 52.2, 45.2, 32.4, 32.3, 31.4, 31.3, 25.6, 21.7, 21.3.

Example 424: (S)-2-(6-(3-chloro-2,6-difluorophenyl)-2-methyl-3-thioxo-2,5,6,7-tetrahydro-3H-pyrrolo[1,2-c]imidazol-1-yl)acetic acid

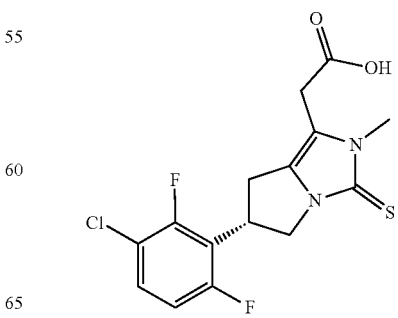

Compound was prepared in an analogous manner to Example 229 from tert-butyl (4S)-2-(3-ethoxy-3-oxopropanoyl)-4-(3-chloro-2,6-difluorophenyl)pyrrolidine-1-carboxylate and isolated as an off-white solid.

$^1$H NMR (DMSO$_{d6}$): 12.73 (1H, s), 7.62 (1H, td, J=8.8, 5.6 Hz), 7.22 (1H, m), 4.46 (1H, m), 4.24 (1H, dd, J=11.6, 9.2 Hz), 3.81 (1H, dd, J=11.6, 7.6 Hz), 3.65 (2H, m), 3.40 (3H, s), 3.33 (1H, dd, J=9.3, 15.9 Hz), 2.91 (1H, dd, J=16.1, 8.1 Hz).

$^{13}$C NMR (DMSO$_{d6}$): 170.8, 160.1, 160.1, 158.5, 158.5, 156.6, 156.5, 156.4, 154.9, 154.9, 129.7, 129.7, 128.7, 118.8, 118.7, 118.6, 116.1, 116, 116, 115.9, 115.5, 113.3, 113.2, 113.1, 113.1, 49.6, 34.7, 31.4, 29.8, 29.1.

Example 425: 2-((S)-6-(3,5-difluorophenyl)-2-methyl-3-thioxo-2,5,6,7-tetrahydro-3H-pyrrolo[1,2-c]imidazol-1-yl)-N—((R)-tetrahydrofuran-3-yl)acetamide

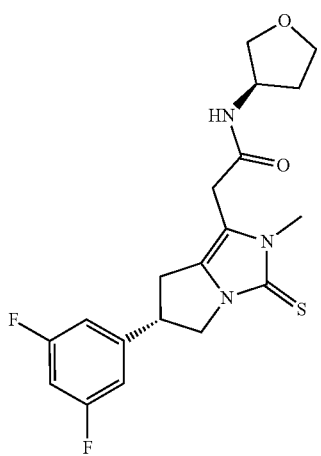 [SMILES: Cn1c(CC(=O)N[C@@H]2CCOC2)c2n(c1=S)C[C@H](c1cc(F)cc(F)c1)C2]

Compound was prepared analogous manner to Example 32 from (S)-1-(1H-imidazol-1-yl)-2-(2-methyl-3-thioxo-6-(3,5-difluorophenyl)-2,5,6,7-tetrahydro-3H-pyrrolo[1,2-c]imidazol-1-yl)ethan-1-one and isolated as an off-white powder.

$^1$H NMR (DMSO$_{d6}$): 8.37 (1H, br d, J=6.6 Hz), 7.13 (3H, m), 4.23 (2H, m), 4.07 (1H, quin, J=8.0 Hz), 3.76 (3H, m), 3.67 (1H, td, J=8.2, 5.6 Hz), 3.46 (3H, m), 3.40 (3H, s), 3.23 (1H, dd, J=15.4, 7.9 Hz), 2.86 (1H, dd, J=15.4, 8.4 Hz), 2.08 (1H, m), 1.72 (1H, m).

$^{13}$C NMR (DMSO$_{d6}$): 167.6, 163.3, 163.2, 161.7, 161.6, 156.4, 145.8, 145.8, 145.7, 128.5, 116.6, 110.7, 110.7, 110.6, 110.5, 102.6, 102.5, 102.3, 72.4, 66.3, 51.1, 49.8, 45.4, 32, 31.5, 31, 30.4.

Example 426: 2-((S)-6-(3,5-difluorophenyl)-2-methyl-3-thioxo-2,5,6,7-tetrahydro-3H-pyrrolo[1,2-c]imidazol-1-yl)-N—((S)-tetrahydrofuran-3-yl)acetamide

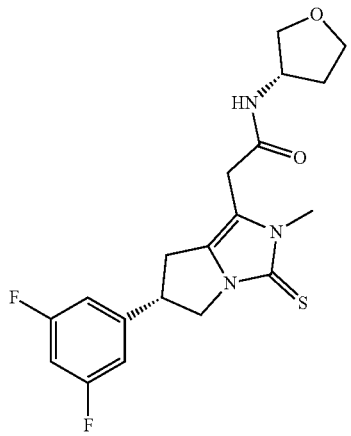 [SMILES: Cn1c(CC(=O)N[C@H]2CCOC2)c2n(c1=S)C[C@H](c1cc(F)cc(F)c1)C2]

Compound was prepared analogous manner to Example 32 from (S)-1-(1H-imidazol-1-yl)-2-(2-methyl-3-thioxo-6-(3,5-difluorophenyl)-2,5,6,7-tetrahydro-3H-pyrrolo[1,2-c]imidazol-1-yl)ethan-1-one and isolated as an off-white powder.

$^1$H NMR (DMSO$_{d6}$): 8.37 (1H, br d, J=6.6 Hz), 7.13 (3H, m), 4.23 (2H, m), 4.07 (1H, quin, J=8.0 Hz), 3.75 (3H, m), 3.67 (1H, td, J=8.3, 5.5 Hz), 3.48 (1H, br d, J=3.5 Hz), 3.45 (2H, s), 3.40 (3H, s), 3.23 (1H, dd, J=15.4, 7.9 Hz), 2.86 (1H, dd, J=15.3, 8.3 Hz), 2.08 (1H, m), 1.72 (1H, m).

$^{13}$C NMR (DMSO$_{d6}$): 167.6, 163.3, 163.2, 161.7, 161.6, 156.4, 145.9, 145.8, 145.7, 128.5, 116.6, 110.7, 110.7, 110.6, 110.5, 102.6, 102.5, 102.3, 72.4, 66.3, 51.1, 49.8, 45.4, 32, 31.5, 31, 30.4.

Example 427 (S)-2-(2-methyl-3-thioxo-6-(2,3,6-trifluorophenyl)-2,5,6,7-tetrahydro-3H-pyrrolo[1,2-c]imidazol-1-yl)-N-((tetrahydro-2H-pyran-4-yl)methyl)acetamide

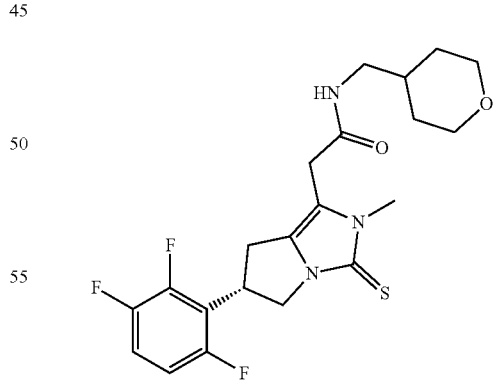

Compound was prepared analogous manner to Example 32 from (S)-1-(1H-imidazol-1-yl)-2-(2-methyl-6-(2,3,6-trifluorophenyl)-3-thioxo-2,5,6,7-tetrahydro-3H-pyrrolo[1,2-c]imidazol-1-yl)ethan-1-one and isolated as an off-white powder.

$^1$H NMR (DMSO$_{d6}$): 8.10 (1H, br t, J=5.8 Hz), 7.47 (1H, qd, J=9.5, 4.9 Hz), 7.18 (1H, m), 4.43 (1H, quin, J=8.7 Hz), 4.23 (1H, dd, J=11.3, 9.4 Hz), 3.81 (3H, m), 3.44 (2H, m), 3.40 (3H, s), 3.29 (1H, dd, J=15.9, 9.2 Hz), 3.22 (2H, tt, J=11.7, 2.3 Hz), 2.96 (2H, m), 2.90 (1H, dd, J=15.8, 8.3 Hz), 1.62 (1H, m), 1.51 (2H, m), 1.13 (2H, m).

$^{13}$C NMR (DMSO$_{d6}$): 167.8, 157, 156.9, 156.2, 155.3, 155.3, 149.1, 149, 149, 149, 147.5, 147.5, 147.5, 147.4, 147.4, 147.4, 147.3, 147.3, 145.9, 145.9, 145.9, 145.8, 128.4, 118.9, 118.8, 118.7, 118.6, 116.5, 116.5, 116.4, 116.3, 112, 112, 112, 111.9, 111.8, 111.8, 111.8, 111.8, 66.7, 49.4, 44.5, 34.7, 34.7, 31.5, 31.2, 30.4, 29.2.

Example 428: (S)-2-(6-(3,5-difluorophenyl)-2-methyl-3-thioxo-2,5,6,7-tetrahydro-3H-pyrrolo[1,2-c]imidazol-1-yl)-N-((tetrahydro-2H-pyran-4-yl)methyl)acetamide

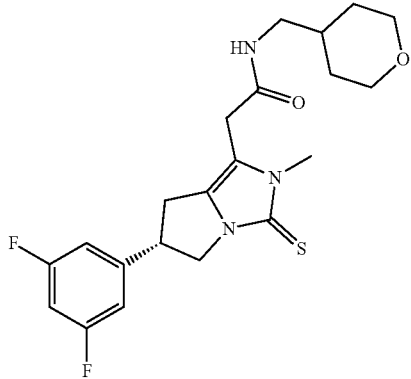 [SMILES: Cn1c(CC(=O)NCC2CCOCC2)c2n(c1=S)C[C@H](c1cc(F)cc(F)c1)C2]

Compound was prepared analogous manner to Example 32 from (S)-1-(1H-imidazol-1-yl)-2-(2-methyl-6-(3,5-difluorophenyl)-3-thioxo-2,5,6,7-tetrahydro-3H-pyrrolo[1,2-c]imidazol-1-yl)ethan-1-one and isolated as an off-white powder.

$^{1}$H NMR (DMSO$_{d6}$): 8.10 (1H, t, J=5.8 Hz), 7.13 (3H, m), 4.23 (1H, dd, J=11.2, 7.9 Hz), 4.07 (1H, quin, J=8.0 Hz), 3.82 (2H, m), 3.75 (1H, dd, J=11.2, 7.8 Hz), 3.46 (2H, m), 3.40 (3H, s), 3.22 (3H, m), 2.97 (2H, m), 2.85 (1H, dd, J=15.4, 8.2 Hz), 1.63 (1H, m), 1.51 (2H, m), 1.14 (2H, m).

$^{13}$C NMR (DMSO$_{d6}$): 167.8, 163.3, 163.2, 161.7, 161.6, 156.4, 145.9, 145.9, 145.8, 128.6, 116.7, 110.7, 110.7, 110.6, 110.6, 102.7, 102.5, 102.3, 66.7, 51.2, 45.4, 44.5, 34.8, 31.4, 31.1, 30.4, 30.4.

Example 429: (S)-2-(6-(3-chloro-2,6-difluorophenyl)-2-methyl-3-thioxo-2,5,6,7-tetrahydro-3H-pyrrolo[1,2-c]imidazol-1-yl)-N-methyl-N-(oxetan-3-yl)acetamide

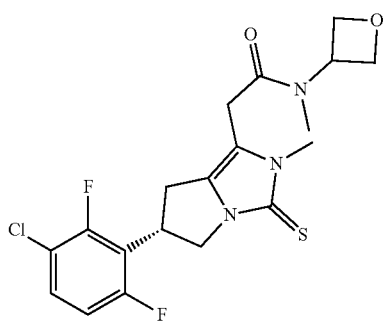 [SMILES: CN(C(=O)Cc1c2n(c(=S)n1C)C[C@H](c1c(F)ccc(Cl)c1F)C2)C1COC1]

Compound was prepared analogous manner to Example 32 from (S)-1-(1H-imidazol-1-yl)-2-(2-methyl-6-(3-chloro-2,6-difluorophenyl)-3-thioxo-2,5,6,7-tetrahydro-3H-pyrrolo[1,2-c]imidazol-1-yl)ethan-1-one and isolated as an off-white solid.

$^{1}$H NMR (DMSO$_{d6}$): 7.61 (1H, td, J=8.7, 5.6 Hz), 7.22 (1H, m), 5.24 (1H, m), 4.72, 4.64, 4.59 (4H, m), 4.43 (1H, m), 4.23 (1H, m), 3.80 (1H, m), 3.75, 3.72 (2H, m), 3.33 (3H, s), 3.24 (1H, m), 3.11 (1.8H, s), 3.03 (1.2H, s), 2.83 (1H, m).

$^{13}$C NMR (DMSO$_{d6}$): 168.6, 167.8, 160.1, 160.1, 158.5, 158.5, 156.6, 156.5, 156.2, 154.9, 154.9, 129.7, 129.6, 128.4, 128.1, 118.9, 118.8, 118.6, 116.3, 116.1, 116.1, 116, 115.9, 115.9, 113.3, 113.2, 113.1, 113.1, 74.6, 74.6, 74.2, 74.2, 51, 49.5, 49.2, 34.8, 31.5, 30.7, 29.6, 29.3, 29.1, 29.1, 27.9.

Example 430: (S)-2-(6-(3-chloro-2,6-difluorophenyl)-2-methyl-3-thioxo-2,5,6,7-tetrahydro-3H-pyrrolo[1,2-c]imidazol-1-yl)-N-methyl-N-((1-methyl-1H-pyrazol-4-yl)methyl)acetamide

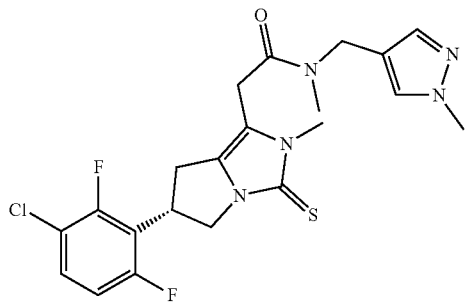 [SMILES: CN(Cc1cnn(C)c1)C(=O)Cc1c2n(c(=S)n1C)C[C@H](c1c(F)ccc(Cl)c1F)C2]

Compound was prepared analogous manner to Example 168 from (S)-2-(6-(3-chloro-2,6-difluorophenyl)-3-thioxo-2,5,6,7-tetrahydro-3H-pyrrolo[1,2-c]imidazol-1-yl)acetic acid and isolated as an off-white solid.

$^{1}$H NMR (DMSO$_{d6}$): 7.70 (0.4H, s), 7.62 (1H, td, J=8.7, 5.6 Hz), 7.59 (0.6H, s), 7.41 (0.4H, s), 7.31 (0.6H, s), 7.22 (1H, m), 4.42 (1.8H, m), 4.32 (0.6H, m), 4.27 (0.6H, m), 4.21 (1H, m), 3.80 (3H, m), 3.71 (3H, m), 3.36 (3H, 2 s), 3.21 (1H, m), 2.97 (1.8H, s), 2.81 (1.2H, s), 2.80 (1H, m).

$^{13}$C NMR (DMSO$_{d6}$): 167.6, 167.5, 160.1, 160.1, 158.5, 158.5, 156.6, 156.6, 156.5, 156.5, 156.2, 154.9, 154.9, 154.9, 154.9, 138.4, 137.8, 129.9, 129.7, 129.6, 129.5, 128.2, 128.2, 118.8, 118.8, 118.7, 118.6, 118.6, 116.7, 116.6, 116.5, 116.4, 116.1, 116, 115.9, 115.9, 113.3, 113.2, 113.1, 113.1, 49.5, 43.6, 41, 38.5, 38.3, 34.7, 34.7, 34.6, 33, 31.5, 31.5, 29.4, 29.1, 29.1, 29.

Example 431: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-methyl-N-(oxetan-3-yl)acetamide

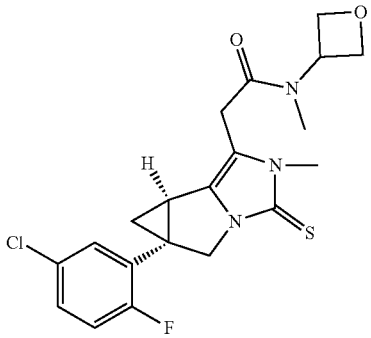 [SMILES: CN(C(=O)Cc1c2n(c(=S)n1C)C[C@@]1(c3cc(Cl)ccc3F)C[C@@H]21)C1COC1]

Compound was prepared analogous manner to Example 32 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

$^1$H NMR (DMSO$_{d6}$): 7.45 (2H, m), 7.30 (1H, dd, J=10.1, 8.7 Hz), 5.29 (1H, m), 4.77, 4.74, 4.66, 4.61 (4H, 4 m), 4.15 (1H, m), 3.83 (3H, m), 3.30 (3H, 2 s), 3.16 (1.8H, s), 3.06 (1.2H, s), 2.87 (0.6H, dd, J=8.4, 4.3 Hz), 2.79 (0.4H, dd, J=8.3, 4.2 Hz), 1.69 (1H, m), 1.12 (0.6H, t, J=4.8 Hz), 1.09 (0.4H, m).

$^{13}$C NMR (DMSO$_{d6}$): 168.6, 167.8, 161.3, 159.6, 156.9, 130.9, 130.6, 130.3, 130.2, 130.2, 129.4, 129.3, 128.7, 128.7, 128.6, 128.6, 128.3, 128.3, 117.6, 117.4, 116, 115.8, 74.7, 74.6, 74.3, 74.2, 52.4, 51.1, 49.1, 31.6, 31.5, 31.5, 30.7, 29.7, 29.4, 27.9, 22.1, 22, 20.7, 20.6.

Example 432: (S)-2-(2-methyl-3-thioxo-6-(2,3,6-trifluorophenyl)-2,5,6,7-tetrahydro-3H-pyrrolo[1,2-c]imidazol-1-yl)-N-(oxetan-3-yl)acetamide

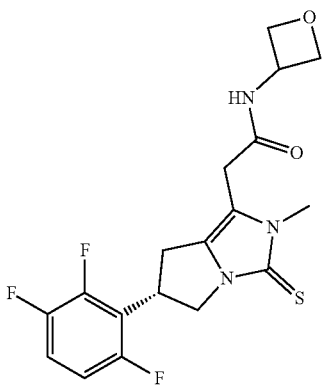 [SMILES: Cn1c(CC(=O)NC2COC2)c2n(c1=S)C[C@H](c1c(F)ccc(F)c1F)C2]

Compound was prepared analogous manner to Example 32 from (S)-1-(1H-imidazol-1-yl)-2-(2-methyl-3-thioxo-6-(2,3,6-trifluorophenyl)-2,5,6,7-tetrahydro-3H-pyrrolo[1,2-c]imidazol-1-yl)ethan-1-one and isolated as an off-white powder.

$^1$H NMR (DMSO$_{d6}$): 8.85 (1H, d, J=6.6 Hz), 7.47 (1H, qd, J=9.5, 5.0 Hz), 7.18 (1H, m), 4.79 (1H, m), 4.70 (2H, m), 4.41 (3H, m), 4.23 (1H, dd, J=11.4, 9.2 Hz), 3.81 (1H, dd, J=11.6, 7.9 Hz), 3.48 (2H, m), 3.39 (3H, s), 3.29 (1H, dd, J=15.8, 9.2 Hz), 2.91 (1H, dd, J=15.8, 8.3 Hz).

$^{13}$C NMR (DMSO$_{d6}$): 167.5, 157, 156.9, 156.3, 155.4, 155.3, 149.1, 149, 149, 149, 147.6, 147.5, 147.5, 147.5, 147.4, 147.4, 147.3, 145.9, 145.9, 145.9, 145.8, 128.6, 118.8, 118.7, 118.7, 118.6, 116.5, 116.5, 116.4, 116.3, 116, 112, 112, 112, 111.9, 111.8, 111.8, 111.8, 111.8, 77, 77, 49.5, 44.2, 34.7, 31.5, 31, 29.1.

Example 433: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-(oxetan-3-yl)acetamide

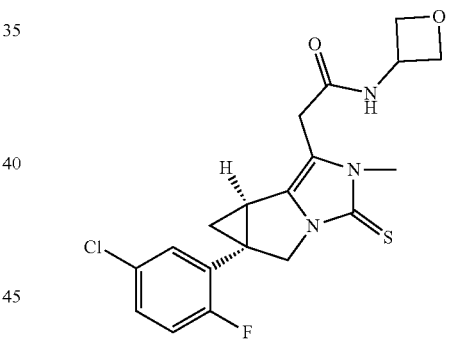

Compound was prepared analogous manner to Example 32 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

$^1$H NMR (DMSO$_{d6}$): 8.87 (1H, d, J=6.6 Hz), 7.47 (1H, dd, J=6.5, 2.7 Hz), 7.43 (1H, ddd, J=8.8, 4.4, 2.7 Hz), 7.30 (1H, dd, J=10.1, 8.8 Hz), 4.82 (1H, m), 4.72 (2H, dd, J=7.4, 6.1 Hz), 4.44 (2H, td, J=6.3, 2.6 Hz), 4.15 (1H, d, J=12.0 Hz), 3.86 (1H, d, J=12.0 Hz), 3.55 (2H, m), 3.34 (3H, s), 2.90 (1H, dd, J=8.4, 4.0 Hz), 1.69 (1H, dd, J=8.4, 5.3 Hz), 1.15 (1H, t, J=4.8 Hz).

$^{13}$C NMR (DMSO$_{d6}$): 167.5, 161.3, 159.6, 156.9, 131.2, 130.2, 130.2, 129.4, 129.3, 128.7, 128.6, 128.3, 128.3, 117.6, 117.4, 115.7, 77, 77, 52.4, 52.4, 44.2, 31.6, 31.5, 30.9, 22, 20.7.

Example 434: 2-((5aS,6aR)-5a-(5-chloro-2-fluorophenyl)-2-methyl-3-thioxo-2,3,5,5a,6,6a-hexahydro-cyclopropa[3,4]pyrrolo[1,2-c]imidazol-1-yl)-N-methyl-N-(tetrahydro-2H-pyran-4-yl)acetamide

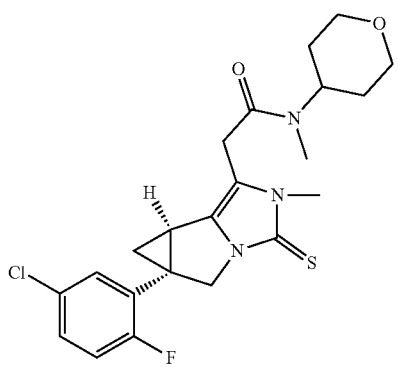

Compound was prepared analogous manner to Example 32 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

$^1$H NMR (DMSO$_{d6}$): 7.44 (2H, m), 7.30 (1H, m), 4.49 (0.6H, m), 4.15 (1H, br d, J=12.0 Hz), 4.01 (0.4H, m), 3.85 (3H, m), 3.80 (1H, m), 3.41 (3H, m), 3.31 (3H, m), 2.93 (2.2H, m), 2.87 (0.6H, dd, J=8.4, 4.3 Hz), 2.74 (1.2H, s), 1.87-1.59 (3.8H, m), 1.43 (1.2H, m), 1.13 (1H, m).

$^{13}$C NMR (DMSO$_{d6}$): 167.7, 167.6, 161.3, 159.6, 156.9, 156.8, 130.8, 130.7, 130.2, 130.2, 130.2, 129.4, 129.3, 128.8, 128.6, 128.3, 128.3, 117.6, 117.4, 116.4, 116.2, 66.5, 66.3, 53, 52.4, 49.8, 31.7, 31.6, 31.5, 31.5, 30.2, 30, 29.6, 29.3, 29.2, 29.1, 27.1, 22.2, 22.1, 20.7, 20.7.

Example 435: (S)—N-methyl-2-(2-methyl-3-thioxo-6-(2,3,6-trifluorophenyl)-2,5,6,7-tetrahydro-3H-pyrrolo[1,2-c]imidazol-1-yl)-N-(oxetan-3-yl)acetamide

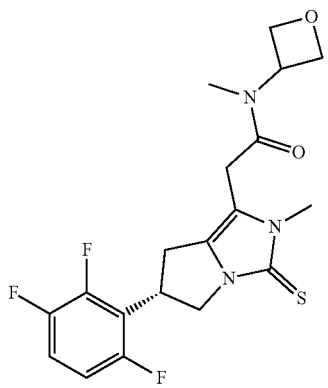

Compound was prepared analogous manner to Example 32 from (S)-1-(1H-imidazol-1-yl)-2-(2-methyl-6-(2,3,6-trifluorophenyl)-3-thioxo-2,5,6,7-tetrahydro-3H-pyrrolo[1,2-c]imidazol-1-yl)ethan-1-one and isolated as a yellowish powder.

$^1$H NMR (DMSO$_{d6}$): 7.47 (1H, m), 7.17 (1H, m), 5.24 (1H, m), 4.73, 4.64, 4.59 (4H, m), 4.42 (1H, m), 4.24 (1H, m), 3.81 (1H, m), 3.73 (2H, m), 3.33 (3H, 2 s), 3.25 (1H, m), 3.11 (1.8H, s), 3.03 (1.2H, s), 2.87 (1H, m).

$^{13}$C NMR (DMSO$_{d6}$): 168.6, 167.8, 157, 156.9, 156.9, 156.3, 155.3, 155.3, 149.2, 149.1, 149, 149, 149, 148.9, 147.5, 147.5, 147.5, 147.4, 147.4, 147.3, 145.9, 145.9, 145.8, 128.4, 128.1, 118.9, 118.8, 118.8, 118.7, 116.5, 116.4, 116.4, 116.3, 116.2, 112, 112, 112, 111.8, 111.8, 111.8, 111.8, 74.6, 74.6, 74.2, 74.2, 51, 49.4, 49.2, 34.7, 34.7, 31.5, 31.5, 31.4, 30.7, 29.9, 29.6, 29.3, 29.1, 29.1, 27.9.

Example 436: 2-((5aS,6aR)-5a-(5-bromo-2-fluorophenyl)-2-methyl-3-thioxo-2,3,5,5a,6,6a-hexahydro-cyclopropa[3,4]pyrrolo[1,2-c]imidazol-1-yl)-1-morpholinoethan-1-one

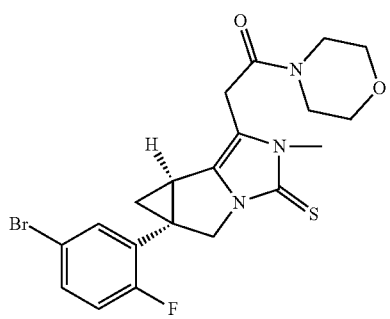

Compound was prepared analogous manner to Example 32 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a khaki solid.

$^1$H NMR (DMSO$_{d6}$): 7.57 (2H, m), 7.24 (1H, dd, J=10.1, 8.7 Hz), 4.15 (1H, d, J=12.0 Hz), 3.86 (1H, d, J=12.1 Hz), 3.82 (2H, m), 3.64 (2H, m), 3.58 (2H, m), 3.53 (2H, m), 3.47 (2H, m), 3.33 (3H, 2 s), 2.86 (1H, dd, J=8.4, 4.3 Hz), 1.71 (1H, dd, J=8.3, 5.4 Hz), 1.13 (1H, t, J=4.8 Hz).

$^{13}$C NMR (DMSO$_{d6}$): 166.9, 161.8, 160.2, 156.9, 133.1, 133.1, 132.4, 132.3, 130.7, 129.1, 129, 118, 117.9, 116.2, 116.2, 115.9, 66, 52.4, 45.7, 41.7, 31.6, 31.5, 28.9, 22.1, 20.7.

Example 437: 2-((5aS,6aR)-5a-(5-bromo-2-fluorophenyl)-2-methyl-3-thioxo-2,3,5,5a,6,6a-hexahydro-cyclopropa[3,4]pyrrolo[1,2-c]imidazol-1-yl)-N-(oxetan-3-yl)acetamide

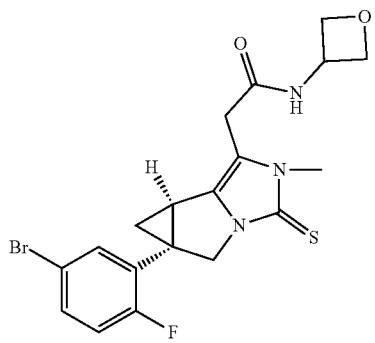 [SMILES: Cn1c(CC(=O)NC2COC2)c2n(c1=S)C[C@@]1(c3cc(Cl)ccc3F)C[C@@H]21]

Compound was prepared analogous manner to Example 32 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a grey solid.

¹H NMR (DMSO$_{d6}$): 8.87 (1H, d, J=6.7 Hz), 7.59 (1H, dd, J=6.7, 2.6 Hz), 7.56 (1H, ddd, J=8.7, 4.5, 2.6 Hz), 7.24 (1H, dd, J=10.1, 8.7 Hz), 4.82 (1H, m), 4.72 (2H, t, J=6.8 Hz), 4.44 (2H, td, J=6.4, 2.3 Hz), 4.14 (1H, d, J=12.0 Hz), 3.85 (1H, d, J=12.0 Hz), 3.55 (2H, m), 3.34 (3H, br s), 2.90 (1H, dd, J=8.4, 4.1 Hz), 1.69 (1H, dd, J=8.4, 5.4 Hz), 1.15 (1H, t, J=4.8 Hz).

¹³C NMR (DMSO$_{d6}$): 167.6, 161.8, 160.1, 156.9, 133.1, 133, 132.4, 132.3, 131.2, 129.2, 129.1, 118, 117.9, 116.2, 116.2, 115.7, 77, 77, 52.5, 52.4, 44.2, 31.5, 31.5, 30.9, 22, 20.7.

Example 438: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-methyl-N-(oxetan-3-yl)acetamide

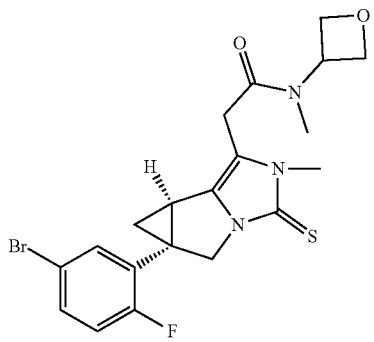

Compound was prepared analogous manner to Example 32 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

¹H NMR (DMSO$_{d6}$): 7.56 (2H, m), 7.24 (1H, dd, J=10.1, 8.7 Hz), 5.29 (1H, m), 4.75, 4.66, 4.62 (4H, 4 m), 4.14 (1H, m), 3.83 (3H, m), 3.29 (3H, 2 s), 3.15 (1.8H, s), 3.06 (1.2H, s), 2.87 (0.6H, dd, J=8.3, 4.2 Hz), 2.79 (0.4H, dd, J=8.3, 4.2 Hz), 1.69 (1H, m), 1.12 (0.6H, t, J=4.8 Hz), 1.08 (0.4H, m).

¹³C NMR (DMSO$_{d6}$): 168.6, 167.8, 161.8, 160.2, 156.9, 133.1, 133.1, 133, 132.4, 132.3, 130.9, 130.6, 129.2, 129.1, 129.1, 129, 118, 117.8, 116.2, 116.2, 116, 115.8, 74.7, 74.6, 74.3, 74.2, 52.4, 51.1, 49.1, 31.6, 31.5, 30.7, 29.7, 29.3, 27.9, 22.1, 22, 20.6, 20.6.

Example 439: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-methyl-N-(tetrahydro-2H-pyran-4-yl)acetamide

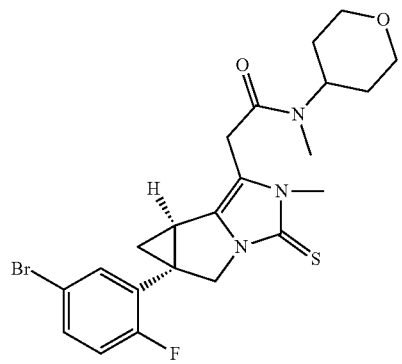 [SMILES: CN(C(=O)Cc1c2n(c(=S)n1C)C[C@@]1(c3cc(Cl)ccc3F)C[C@@H]21)C1CCOCC1]

Compound was prepared analogous manner to Example 32 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a light beige solid.

¹H NMR (DMSO$_{d6}$): 77.57 (2H, m), 7.24 (1H, m), 4.49 (0.6H, m), 4.15 (1H, br d, J=11.6 Hz), 4.01 (0.4H, m), 3.97-3.73 (5H, m), 3.51-3.24 (5H, m), 2.93 (2.2H, m), 2.87 (0.6H, dd, J=8.3, 4.2 Hz), 2.74 (1.2H, s), 1.88-1.58 (3.8H, m), 1.45 (1.2H, m), 1.12 (1H, m).

¹³C NMR (DMSO$_{d6}$): 167.7, 167.6, 161.8, 160.1, 156.9, 156.8, 133, 132.4, 132.3, 130.7, 130.7, 129.2, 129.1, 118, 117.8, 116.4, 116.2, 116.2, 66.5, 66.3, 52.9, 52.4, 49.7, 31.6, 31.5, 31.5, 30.2, 30.2, 30, 29.6, 29.3, 29.2, 29.1, 27.1, 22.2, 22.1, 20.7, 20.6.

Example 440: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-methyl-N-(tetrahydrofuran-3-yl)acetamide

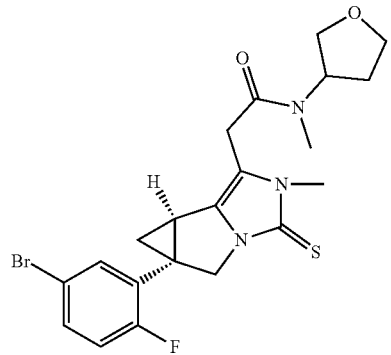 [SMILES: CN(C(=O)Cc1c2n(c(=S)n1C)C[C@@]1(c3cc(Br)ccc3F)C[C@@H]21)C1CCOC1]

Compound was prepared analogous manner to Example 34 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)acetic acid and isolated as a light yellow solid.

¹H NMR (DMSO$_{d6}$): 7.58 (2H, m), 7.25 (1H, dd, J=10.1, 8.9 Hz), 5.13 (0.6H, m), 4.73 (0.4H, m), 4.16 (1H, d, J=11.9

Hz), 4.0-3.51 (7H, m), 3.32 (3H, 2 s), 2.98 (1.8H, s), 2.87 (1H, m), 2.77 (1.2H, s), 2.26 (0.4H, m), 2.15 (0.6H, m), 1.91 (0.4H, m), 1.81 (0.6H, m), 1.70 (1H, m), 1.13 (1H, m).

$^{13}$C NMR (DMSO$_{d6}$): 168.3, 167.7, 167.6, 161.8, 161.8, 160.2, 160.1, 156.9, 156.8, 133.1, 133, 132.4, 132.3, 130.8, 130.7, 130.6, 129.2, 129.1, 129.1, 129, 118, 117.8, 116.2, 116.2, 116.1, 69.4, 69.3, 67.1, 67.1, 67, 53, 52.4, 31.6, 31.6, 31.5, 31.5, 31.3, 29.9, 29.9, 29.8, 29.4, 29.3, 27.7, 22.1, 21.6, 20.7.

Example 441: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-methyl-N-(tetrahydrofuran-3-yl)acetamide

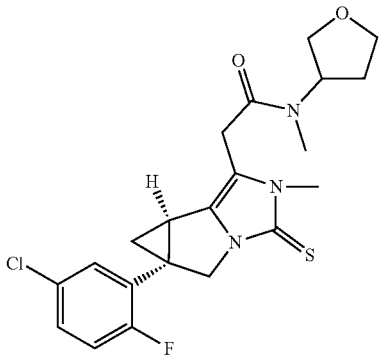 [SMILES: CN(C(=O)Cc1c2n(c(=S)n1C)C[C@@]1(c3cc(Cl)ccc3F)C[C@@H]21)C1CCOC1]

Compound was prepared analogous manner to Example 34 from 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)acetic acid and isolated as a beige solid.

$^1$H NMR (DMSO$_{d6}$): 7.45 (2H, m), 7.30 (1H, m), 5.13 (0.6H, m), 4.73 (0.4H, m), 4.15 (1H, br d, J=11.9 Hz), 4.0-3.52 (7H, m), 3.31 (3H, 2 s), 2.97 (1.8H, s), 2.86 (1H, m), 2.76 (1.2H, s), 2.26 (0.4H, m), 2.13 (0.6H, m), 1.91 (0.4H, m), 1.80 (0.6H, m), 1.69 (1H, m), 1.13 (1H, m).

$^{13}$C NMR (DMSO$_{d6}$): 168.3, 167.7, 161.3, 161.3, 159.7, 159.6, 156.9, 156.8, 130.8, 130.7, 130.6, 130.2, 129.4, 129.3, 128.8, 128.7, 128.7, 128.6, 128.3, 117.6, 117.4, 116.2, 116.1, 69.4, 69.4, 69.3, 67.1, 67.1, 56.6, 53, 52.4, 31.6, 31.5, 31.5, 29.9, 29.9, 29.8, 29.8, 29.4, 29.3, 27.7, 22.1, 20.7, 20.7.

Example 442: 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-N-methyl-N-(tetrahydrofuran-3-yl)acetamide

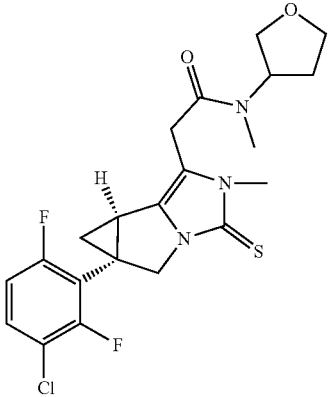 [SMILES: CN(C(=O)Cc1c2n(c(=S)n1C)C[C@@]1(c3c(F)ccc(Cl)c3F)C[C@@H]21)C1CCOC1]

Compound was prepared analogous manner to Example 34 from 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)acetic acid and isolated as a light beige solid.

$^1$H NMR (DMSO$_{d6}$): 7.63 (1H, m), 7.21 (1H, br t, J=9.0 Hz), 5.11 (0.6H, m), 4.72 (0.4H, m), 4.11 (1H, br d, J=12.2 Hz), 4.0-3.51 (7H, m), 3.32 (3H, 2 s), 2.96 (1.8H, s), 2.76 (2.2H, m), 2.25 (0.4H, m), 2.12 (0.6H, m), 1.89 (0.4H, m), 1.79 (0.6H, m), 1.68 (1H, m), 1.27 (1H, m).

$^{13}$C NMR (DMSO$_{d6}$): 168.3, 167.6, 161.3, 161.2, 159.6, 159.6, 157.8, 157.8, 156.9, 156.8, 156.2, 156.1, 130.4, 130.3, 130.2, 117, 117, 116.9, 116.8, 116.8, 116.6, 116.4, 115.8, 115.7, 115.6, 115.6, 112.9, 112.9, 112.8, 112.8, 69.3, 69.3, 67.1, 67.1, 67.1, 64.9, 56.6, 53, 52.2, 31.5, 31.5, 29.9, 29.9, 29.9, 29.8, 29.5, 29.5, 29.3, 29.2, 27.7, 27.6, 25.7, 21.8, 21.7, 21.2, 21.1.

Example 443: 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-N-methyl-N-(tetrahydro-2H-pyran-4-yl)acetamide

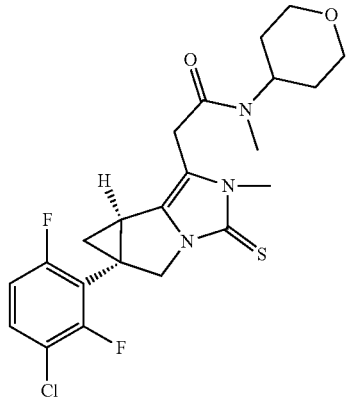 [SMILES: CN(C(=O)Cc1c2n(c(=S)n1C)C[C@@]1(c3c(F)ccc(Cl)c3F)C[C@@H]21)C1CCOCC1]

Compound was prepared analogous manner to Example 32 from 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a light beige solid.

$^1$H NMR (DMSO$_{d6}$): 7.64 (1H, m), 7.21 (1H, br t, J=9.1 Hz), 4.49 (0.6H, m), 4.11 (1H, dd, J=12.2, 2.2 Hz), 4.02 (0.4H, m), 3.98-3.74 (4.8H, m), 3.38 (2.2H, m), 3.32 (3H, 2 s), 2.92 (1.8H, s), 2.81 (0.4H, br dd, J=8.3, 4.3 Hz), 2.76 (0.6H, br d, J=4.3, 8.3 Hz), 2.74 (1.2H, s), 1.87-1.58 (4H, m), 1.44 (1H, m), 1.25 (1H, m).

$^{13}$C NMR (DMSO$_{d6}$): 167.7, 167.6, 161.3, 161.2, 159.6, 159.6, 157.8, 157.8, 156.8, 156.8, 156.2, 156.1, 130.4, 130.3, 130.3, 130.2, 117.1, 116.9, 116.8, 116.7, 116.5, 115.8, 115.7, 115.6, 115.6, 112.9, 112.9, 112.8, 112.8, 66.5, 66.5, 66.3, 53, 52.2, 31.5, 31.5, 30.2, 30.2, 30.1, 29.6, 29.3, 29.2, 29.1, 27.1, 25.7, 25.7, 21.9, 21.7, 21.2, 21.2, 21.2.

Example 444: (S)-2-(6-(3-chloro-2,6-difluorophenyl)-2-methyl-3-thioxo-2,5,6,7-tetrahydro-3H-pyrrolo[1,2-c]imidazol-1-yl)-1-(isoxazolidin-2-yl)ethan-1-one

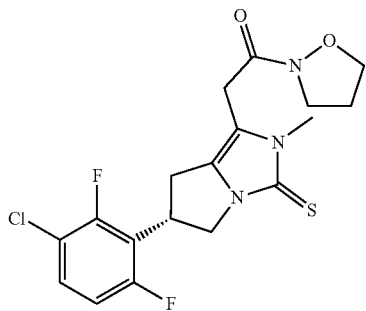 [SMILES: Cn1c(CC(=O)N2CCCO2)c2n(c1=S)C[C@H](c1c(F)ccc(Cl)c1F)C2]

Compound was prepared analogous manner to Example 168 from (S)-2-(6-(3-chloro-2,6-difluorophenyl)-3-thioxo-2,5,6,7-tetrahydro-3H-pyrrolo[1,2-c]imidazol-1-yl)acetic acid and isolated as an off-white solid.

$^1$H NMR (DMSO$_{d6}$): 7.62 (1H, td, J=8.8, 5.6 Hz), 7.22 (1H, m), 4.44 (1H, quin, J=8.6 Hz), 4.23 (1H, dd, J=11.5, 9.2 Hz), 3.97 (2H, t, J=6.8 Hz), 3.81 (1H, dd, J=11.6, 7.8 Hz), 3.75 (2H, br s), 3.59 (2H, m br), 3.39 (3H, s), 3.30 (1H, dd, J=9.3, 15.9 Hz), 2.90 (1H, dd, J=15.8, 8.1 Hz), 2.26 (2H, quin, J=7.1 Hz).

$^{13}$C NMR (DMSO$_{d6}$): 168.5, 160.2, 160.1, 158.5, 158.5, 156.6, 156.5, 156.3, 154.9, 154.9, 129.7, 129.7, 128.8, 118.8, 118.7, 118.6, 116.1, 116, 115.9, 115.9, 115.5, 113.3, 113.2, 113.1, 113.1, 69.3, 49.5, 43.3, 34.7, 31.5, 29.1, 28.5, 27.2.

Example 445: (R)-2-(6-(2,6-difluorophenyl)-2-methyl-3-thioxo-2,5,6,7-tetrahydro-3H-pyrrolo[1,2-c]imidazol-1-yl)-1-morpholinoethan-1-one

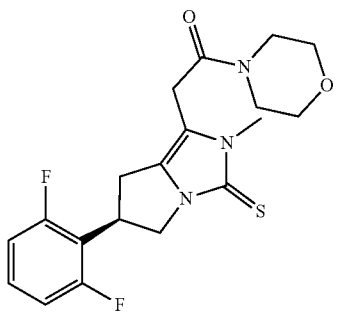 [SMILES: Cn1c(CC(=O)N2CCOCC2)c2n(c1=S)C[C@@H](c1c(F)cccc1F)C2]

Compound was prepared analogous manner to Example 32 from (R)-2-(6-(2,6-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as an off-white solid.

$^1$H NMR (DMSO$_{d6}$): 7.41 (1H, m), 7.14 (2H, t, J=8.1 Hz), 4.41 (1H, quin, J=8.7 Hz), 4.22 (1H, m), 3.78 (1H, dd, J=11.4, 8.1 Hz), 3.75 (2H, s), 3.60 (2H, m), 3.55 (2H, m), 3.49 (2H, m), 3.44 (2H, m), 3.36 (3H, m), 3.25 (1H, dd, J=9.3, 15.9 Hz), 2.86 (1H, dd, J=15.7, 8.5 Hz).

$^{13}$C NMR (DMSO$_{d6}$): 166.8, 161.6, 161.5, 160, 159.9, 156.3, 129.8, 129.7, 129.7, 128.3, 116.6, 116.5, 116.4, 116.2, 112.3, 112.2, 112.1, 112.1, 66, 66, 49.6, 45.6, 41.7, 34.4, 31.5, 29.3, 28.8.

Example 446: 2-((R)-6-(2,6-difluorophenyl)-2-methyl-3-thioxo-2,5,6,7-tetrahydro-3H-pyrrolo[1,2-c]imidazol-1-yl)-N—((R)-tetrahydrofuran-3-yl)acetamide

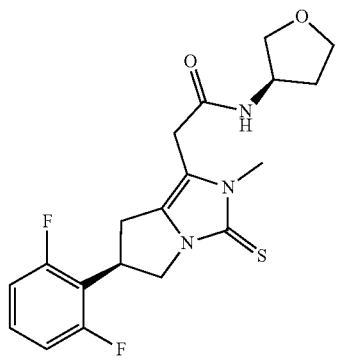 [SMILES: Cn1c(CC(=O)N[C@@H]2CCOC2)c2n(c1=S)C[C@@H](c1c(F)cccc1F)C2]

Compound was prepared analogous manner to Example 32 from (R)-1-(H-imidazol-1-yl)-2-(2-methyl-3-thioxo-6-(2,6-difluorophenyl)-2,5,6,7-tetrahydro-3H-pyrrolo[1,2-c]imidazol-1-yl)ethan-1-one and isolated as an off-white solid.

$^1$H NMR (DMSO$_{d6}$): 8.36 (1H, br d, J=6.6 Hz), 7.41 (1H, tt, J=8.4, 6.5 Hz), 7.14 (2H, m), 4.41 (1H, quin, J=8.8 Hz), 4.22 (2H, m), 3.77 (2H, m), 3.72 (1H, dd, J=8.9, 6.0 Hz), 3.66 (1H, td, J=8.3, 5.6 Hz), 3.46 (1H, dd, J=8.9, 3.7 Hz), 3.43 (2H, s), 3.40 (3H, s), 3.26 (1H, dd, J=15.7, 9.2 Hz), 2.88 (1H, dd, J=15.7, 8.5 Hz), 2.08 (1H, m), 1.71 (1H, m).

$^{13}$C NMR (DMSO$_{d6}$): 167.6, 161.6, 161.5, 160, 159.9, 156.2, 129.8, 129.8, 129.7, 128.5, 116.6, 116.4, 116.4, 116.3, 112.3, 112.2, 112.1, 112.1, 72.4, 66.3, 49.8, 49.6, 34.4, 32, 31.5, 31.1, 29.3.

Example 447 (R)-2-(6-(2,6-difluorophenyl)-2-methyl-3-thioxo-2,5,6,7-tetrahydro-3H-pyrrolo[1,2-c]imidazol-1-yl)-N-(tetrahydro-2H-pyran-4-yl)acetamide

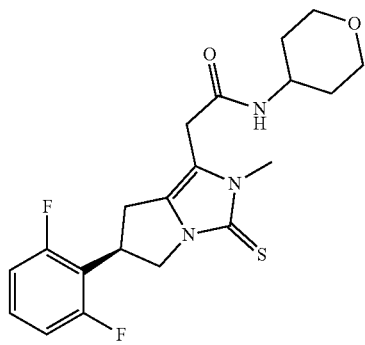 [SMILES: Cn1c(CC(=O)NC2CCOCC2)c2n(c1=S)C[C@@H](c1c(F)cccc1F)C2]

Compound was prepared analogous manner to Example 32 from (R)-2-(6-(2,6-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as an off-white solid.

¹H NMR (DMSO$_{d6}$): 8.11 (1H, br d, J=7.5 Hz), 7.41 (1H, m), 7.14 (2H, m), 4.41 (1H, quin, J=8.7 Hz), 4.21 (1H, dd, J=10.8, 9.8 Hz), 3.77 (4H, m), 3.42 (2H, m), 3.40 (3H, s), 3.33 (1H, m), 3.26 (1H, dd, J=15.7, 9.2 Hz), 2.88 (1H, dd, J=15.7, 8.5 Hz), 1.69 (2H, m), 1.38 (2H, m).

¹³C NMR (DMSO$_{d6}$): 166.9, 161.6, 161.5, 160, 159.9, 156.2, 129.8, 129.8, 129.7, 128.5, 116.6, 116.5, 116.3, 112.3, 112.2, 112.1, 112, 65.8, 49.6, 45.2, 34.4, 32.4, 31.5, 31.3, 29.3.

Example 448: (R)-2-(6-(2,6-difluorophenyl)-2-methyl-3-thioxo-2,5,6,7-tetrahydro-3H-pyrrolo[1,2-c]imidazol-1-yl)-N-methyl-N-(oxetan-3-yl)acetamide

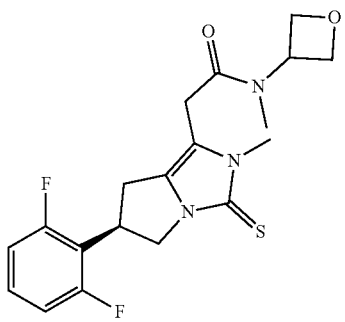 [SMILES: CN(C(=O)Cc1c2n(c(=S)n1C)C[C@@H](c1c(F)cccc1F)C2)C1COC1]

Compound was prepared analogous manner to Example 32 from (R)-1-(H-imidazol-1-yl)-2-(2-methyl-6-(2,6-difluorophenyl)-3-thioxo-2,5,6,7-tetrahydro-3H-pyrrolo[1,2-c]imidazol-1-yl)ethan-1-one and isolated as an off-white solid.

¹H NMR (DMSO$_{d6}$): 7.41 (1H, m), 7.13 (2H, m), 5.24 (1H, m), 4.72, 4.64, 4.59 (4H, m), 4.40 (1H, m), 4.22 (1H, m), 3.79 (1H, m), 3.75 (2H, m), 3.34 (3H, s), 3.22 (1H, m), 3.11 (1.8H, s), 3.03 (1.2H, s), 2.83 (1H, m).

¹³C NMR (DMSO$_{d6}$): 168.6, 167.8, 161.6, 161.5, 160, 159.9, 156.2, 129.8, 129.7, 129.7, 128.5, 128.3, 116.6, 116.5, 116.4, 116.3, 116.1, 112.3, 112.2, 112.1, 112.1, 74.6, 74.6, 74.2, 74.2, 51, 49.6, 49.2, 34.4, 31.5, 31.5, 30.7, 29.6, 29.3, 29.2, 29.2, 27.9.

Example 449: 2-((S)-6-(3-bromo-2,6-difluorophenyl)-2-methyl-3-thioxo-2,5,6,7-tetrahydro-3H-pyrrolo[1,2-c]imidazol-1-yl)-N—((S)-1-methyl-5-oxopyrrolidin-3-yl)acetamide

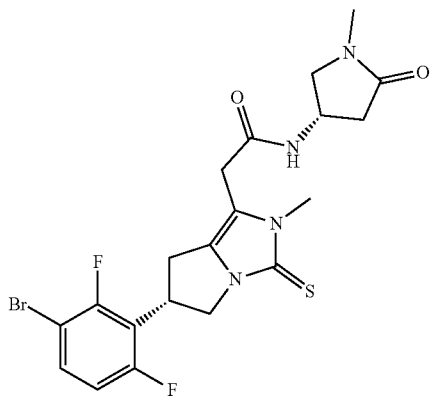 [SMILES: CN1C[C@@H](NC(=O)Cc2c3n(c(=S)n2C)C[C@H](c2c(F)ccc(Br)c2F)C3)CC1=O]

Compound was prepared analogous manner to Example 22 from (S)-2-(6-(3-bromo-2,6-difluorophenyl)-2-methyl-3-thioxo-2,5,6,7-tetrahydro-3H-pyrrolo[1,2-c]imidazol-1-yl)acetic acid and isolated as a cream powder.

¹H NMR (DMSO$_{d6}$): 8.54 (1H, br d, J=6.6 Hz), 7.73 (1H, td, J=8.4, 5.7 Hz), 7.18 (1H, m), 4.44 (1H, quin, J=8.6 Hz), 4.28 (1H, m), 4.22 (1H, dd, J=11.4, 9.2 Hz), 3.79 (1H, dd, J=11.6, 7.8 Hz), 3.60 (1H, dd, J=10.2, 7.0 Hz), 3.43 (2H, d, J=2.6 Hz), 3.39 (3H, s), 3.28 (1H, dd, J=9.6, 15.9 Hz), 3.11 (1H, dd, J=10.3, 3.5 Hz), 2.88 (1H, dd, J=15.8, 8.1 Hz), 2.70 (3H, s), 2.58 (1H, ddd, J=16.9, 8.5, 0.7 Hz), 2.11 (1H, dd, J=16.9, 4.3 Hz).

¹³C NMR (DMSO$_{d6}$): 171.7, 167.7, 160.8, 160.8, 159.2, 159.1, 157.6, 157.5, 156.2, 155.9, 155.9, 132.5, 132.4, 128.5, 118.8, 118.7, 118.5, 116.1, 113.8, 113.6, 104.1, 104.1, 103.9, 55.1, 49.6, 42.5, 36.8, 34.8, 31.5, 31.1, 29.2, 28.9.

Example 450: (S)-1-(2-((S)-6-(3-bromo-2,6-difluorophenyl)-2-methyl-3-thioxo-2,5,6,7-tetrahydro-3H-pyrrolo[1,2-c]imidazol-1-yl)acetyl)pyrrolidine-3-carbonitrile

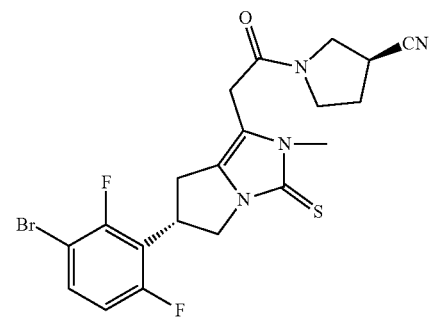 [SMILES: Cn1c(CC(=O)N2CC[C@H](C#N)C2)c2n(c1=S)C[C@H](c1c(F)ccc(Br)c1F)C2]

Compound was prepared analogous manner to Example 25 from (S)-1-(1H-imidazol-1-yl)-2-(2-methyl-3-thioxo-6-(3-bromo-2,6-difluorophenyl)-2,5,6,7-tetrahydro-3H-pyrrolo[1,2-c]imidazol-1-yl)ethan-1-one and isolated as a cream powder.

¹H NMR (DMSO$_{d6}$): 7.72 (1H, m), 7.16 (1H, t, J=9.4 Hz), 4.44 (1H, m), 4.23 (1H, dd, J=11.4, 9.2 Hz), 3.89-3.73 (2H, m), 3.73-3.58 (3.5H, m), 3.55 (1H, m), 3.49-3.37 (1.5H, m), 3.37 (3H, s), 3.29 (1H, m), 2.87 (1H, m), 2.31 (0.5H, m), 2.22 (1H, m), 2.09 (0.5H, m).

¹³C NMR (DMSO$_{d6}$): 166.6, 166.4, 160.8, 160.7, 159.2, 159.1, 157.5, 157.5, 156.2, 155.9, 155.9, 132.5, 132.4, 128.5, 128.4, 121.1, 120.9, 118.9, 118.8, 118.8, 118.7, 118.6, 118.6, 115.9, 113.8, 113.8, 113.6, 113.6, 104.1, 104, 103.9, 49.6, 48.7, 48.6, 44.8, 44.6, 34.8, 34.8, 31.5, 30.2, 30.1, 29.6, 29.2, 28.1, 28, 26.5.

Example 451: 2-((S)-6-(3-bromo-2,6-difluorophenyl)-2-methyl-3-thioxo-2,5,6,7-tetrahydro-3H-pyrrolo[1,2-c]imidazol-1-yl)-N-methyl-N—((R)-tetrahydrofuran-3-yl)acetamide

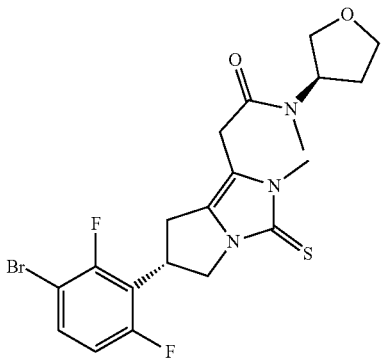 [SMILES: CN(C(=O)Cc1c2n(c(=S)n1C)C[C@H](c1c(F)ccc(Br)c1F)C2)[C@@H]1CCOC1]

Compound was prepared analogous manner to Example 34 from (S)-2-(2-methyl-6-(3-bromo-2,6-difluorophenyl)-3-thioxo-2,5,6,7-tetrahydro-3H-pyrrolo[1,2-c]imidazol-1-yl)acetic acid and isolated as a cream powder.

$^1$H NMR (DMSO$_{d6}$): 7.72 (1H, m), 7.16 (1H, s), 5.09 (0.6H, m), 4.65 (0.4H, m), 4.43 (1H, m), 4.22 (1H, dd, J=11.3, 9.4 Hz), 3.92 (1H, m), 3.81 (1.8H, m), 3.69 (2.2H, m), 3.63 (1H, m), 3.56 (1H, m), 3.36 (3H, m), 3.25 (1H, m), 2.93 (1.8H, s), 2.85 (1H, m), 2.74 (1.2H, s), 2.21 (0.4H, m), 2.09 (0.6H, m), 1.86 (0.4H, m), 1.76 (0.6H, m).

$^{13}$C NMR (DMSO$_{d6}$): 168.2, 167.6, 160.8, 160.7, 159.1, 159.1, 157.5, 157.5, 156.2, 156.1, 155.9, 155.9, 132.5, 132.4, 128.3, 128.1, 118.9, 118.8, 118.6, 116.5, 116.4, 113.8, 113.8, 113.6, 113.6, 104.1, 104, 103.9, 69.4, 69.2, 67.1, 67, 56.6, 53, 49.5, 34.8, 34.8, 31.5, 31.5, 29.9, 29.8, 29.7, 29.4, 29.3, 29.2, 29.2, 27.6.

Example 452: (S)-1-(2-(6-(3-bromo-2,6-difluorophenyl)-2-methyl-3-thioxo-2,5,6,7-tetrahydro-3H-pyrrolo[1,2-c]imidazol-1-yl)acetyl)-N,N-dimethylpiperidine-4-carboxamide

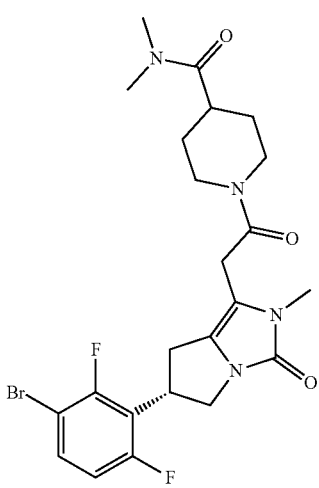 [SMILES: CN(C)C(=O)C1CCN(C(=O)Cc2c3n(c(=O)n2C)C[C@H](c2c(F)ccc(Br)c2F)C3)CC1]

Compound was prepared analogous manner to Example 25 from (S)-1-(1H-imidazol-1-yl)-2-(2-methyl-3-thioxo-6-(3-bromo-2,6-difluorophenyl)-2,5,6,7-tetrahydro-3H-pyrrolo[1,2-c]imidazol-1-yl)ethan-1-one using DIPEA as base and isolated as a cream powder.

$^1$H NMR (DMSO$_{d6}$): 7.72 (1H, td, J=8.3, 5.9 Hz), 7.16 (1H, t, J=9.1 Hz), 4.44 (1H, quin, J=8.5 Hz), 4.35 (1H, m), 4.22 (1H, dd, J=11.4, 9.3 Hz), 3.91 (1H, br d, J=12.6 Hz), 3.80 (1H, m), 3.75 (2H, s), 3.36 (3H, m), 3.26 (1H, m), 3.11 (1H, m), 3.03 (3H, s), 2.87 (2H, m), 2.80 (3H, s), 2.67 (1H, m), 1.65 (2H, m), 1.53 (1H, m), 1.33 (1H, m).

$^{13}$C NMR (DMSO$_{d6}$): 173.5, 166.2, 166.2, 160.8, 160.7, 159.2, 159.1, 157.5, 157.5, 156.2, 155.9, 155.9, 132.5, 132.4, 128.2, 118.8, 118.7, 118.6, 116.6, 113.8, 113.8, 113.6, 113.6, 104.1, 104, 103.9, 103.9, 49.5, 44.7, 40.8, 40.8, 37.1, 36.6, 35, 34.8, 31.5, 29.2, 29, 28.9, 28.6, 27.9.

Example 453: 1-(2-((S)-6-(3-bromo-2,6-difluorophenyl)-2-methyl-3-thioxo-2,5,6,7-tetrahydro-3H-pyrrolo[1,2-c]imidazol-1-yl)acetyl)-N,N-dimethylpyrrolidine-3-carboxamide

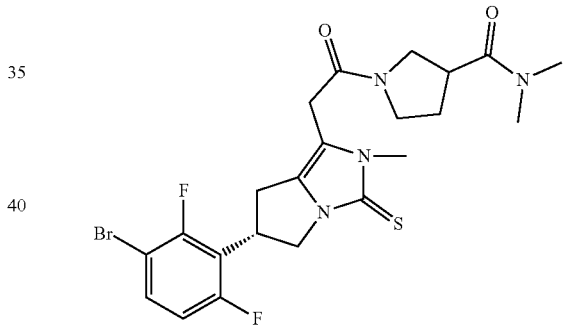

Compound was prepared analogous manner to Example 25 from (S)-1-(1H-imidazol-1-yl)-2-(2-methyl-3-thioxo-6-(3-bromo-2,6-difluorophenyl)-2,5,6,7-tetrahydro-3H-pyrrolo[1,2-c]imidazol-1-yl)ethan-1-one and isolated as a cream powder.

$^1$H NMR (DMSO$_{d6}$): 7.72 (1H, m), 7.16 (1H, t, J=9.4 Hz), 4.44 (1H, m), 4.22 (1H, dd, J=11.4, 9.3 Hz), 3.79 (1H, br dd, J=11.4, 7.8 Hz), 3.75-3.41 (5.5H, m), 3.38 (3H, s), 3.41-3.21 (2.5H, m), 3.03-3.01 (3H, 3 s), 2.88 (1H, m), 2.83-2.79 (3H, 4 s), 2.12 (0.5H, m), 2.04 (0.5H, m), 1.99 (0.5H, m), 1.85 (0.5H, m).

$^{13}$C NMR (DMSO$_{d6}$): 171.7, 171.3, 171.3, 166.1, 166, 166, 166, 160.8, 160.8, 159.2, 159.1, 157.6, 157.5, 156.2, 156.2, 155.9, 155.9, 132.5, 132.4, 128.3, 118.9, 118.8, 118.8, 118.8, 118.8, 118.7, 118.7, 118.6, 118.6, 118.6, 116.2, 116.2, 116.1, 116.1, 113.8, 113.8, 113.6, 113.6, 104.1, 104, 103.9, 103.9, 49.5, 49.5, 48.7, 48.4, 45.8, 45.3, 45.2, 40.2, 38.3, 38.3, 36.7, 35.1, 35.1, 35, 34.8, 34.8, 31.5, 30.3, 30.3, 30.3, 30.2, 29.2, 29.1, 29, 27.5.

Example 454: (S)-2-(6-(3-bromo-2,6-difluorophenyl)-2-methyl-3-thioxo-2,5,6,7-tetrahydro-3H-pyrrolo[1,2-c]imidazol-1-yl)-N-methyl-N-(oxetan-3-yl)acetamide

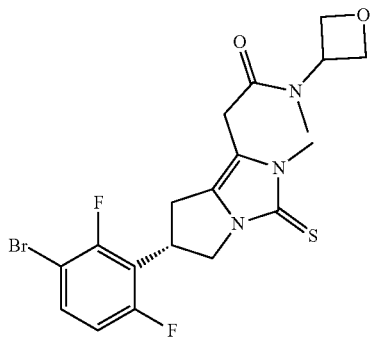 [SMILES: CN(C(=O)Cc1c2n(c(=S)n1C)C[C@H](c1c(F)ccc(Br)c1F)C2)C1COC1]

Compound was prepared analogous manner to Example 32 from (S)-1-(1H-imidazol-1-yl)-2-(2-methyl-6-(3-bromo-2,6-difluorophenyl)-3-thioxo-2,5,6,7-tetrahydro-3H-pyrrolo[1,2-c]imidazol-1-yl)ethan-1-one and isolated as a cream powder.

$^1$H NMR (DMSO$_{d6}$): 7.72 (1H, td, J=8.4, 5.9 Hz), 7.17 (1H, m), 5.24 (1H, m), 4.72 (1.33H, m), 4.64 (1.33H, m), 4.59 (1.33H, m), 4.43 (1H, m), 4.22 (1H, m), 3.75 (3H, m), 3.33 (3H, s), 3.23 (1H, m), 3.11 (1.8H, s), 3.03 (1.2H, s), 2.82 (1H, m).

$^{13}$C NMR (DMSO$_{d6}$): 168.6, 167.8, 160.8, 160.7, 159.1, 159.1, 157.5, 157.5, 156.2, 155.9, 155.9, 132.5, 132.4, 128.4, 128.2, 118.9, 118.8, 118.6, 116.2, 116.1, 113.8, 113.8, 113.6, 113.6, 104.1, 104, 103.9, 103.9, 74.6, 74.6, 74.2, 74.2, 51, 49.6, 49.2, 34.8, 31.5, 31.5, 30.7, 29.6, 29.3, 29.2, 29.1, 27.9.

Example 455: N-methyl-2-((R)-2-methyl-3-thioxo-6-(2,3,6-trifluorophenyl)-2,5,6,7-tetrahydro-3H-pyrrolo[1,2-c]imidazol-1-yl)-N—((R)-tetrahydrofuran-3-yl)acetamide

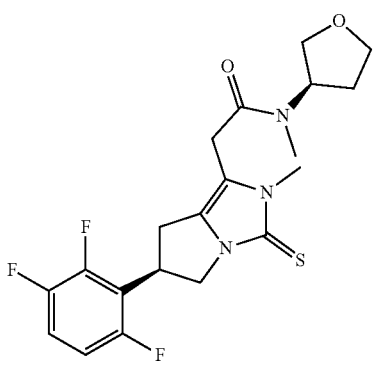 [SMILES: CN(C(=O)Cc1c2n(c(=S)n1C)C[C@@H](c1c(F)ccc(F)c1F)C2)[C@@H]1CCOC1]

Compound was prepared analogous manner to Example 34 from (R)-2-(2-methyl-6-(2,3,6-trifluorophenyl)-3-thioxo-2,5,6,7-tetrahydro-3H-pyrrolo[1,2-c]imidazol-1-yl)acetic acid and isolated as a cream powder.

$^1$H NMR (DMSO$_{d6}$): 7.47 (1H, m), 7.18 (1H, m), 5.09 (0.6H, m), 4.66 (0.4H, m), 4.43 (1H, m), 4.24 (1H, m), 3.92 (1H, m), 3.82 (1.8H, m), 3.71 (2.2H, m), 3.62 (1H, m), 3.56 (1H, m), 3.33 (3H, 2 s), 3.27 (1H, m), 2.93 (1.8H, s), 2.86 (1H, m), 2.74 (1.2H, s), 2.21 (0.4H, m), 2.10 (0.6H, m), 1.86 (0.4H, m), 1.79 (0.6H, m).

$^{13}$C NMR (DMSO$_{d6}$): 168.2, 167.6, 157, 156.9, 156.9, 156.2, 156.2, 155.3, 155.3, 149.1, 149, 149, 148.9, 147.5, 147.4, 147.4, 147.4, 145.9, 145.9, 145.8, 128.2, 128.1, 118.9, 118.8, 118.8, 118.8, 118.7, 116.6, 116.5, 116.5, 116.4, 116.4, 116.3, 112, 112, 112, 111.9, 111.8, 111.8, 111.8, 111.8, 69.4, 69.3, 67.1, 67.1, 56.5, 53, 49.4, 34.8, 31.5, 31.5, 30, 29.7, 29.7, 29.4, 29.3, 29.1, 29.1, 27.6.

Example 456: (S)-6-(3-bromo-2,6-difluorophenyl)-1-(2-hydroxyethyl)-2-methyl-2,5,6,7-tetrahydro-3H-pyrrolo[1,2-c]imidazole-3-thione

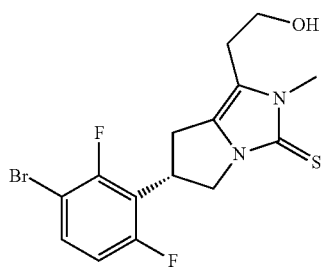 [SMILES: Cn1c(CCO)c2n(c1=S)C[C@H](c1c(F)ccc(Br)c1F)C2]

Compound was prepared analogous manner to Example 8 from (S)-2-(6-(3-bromo-2,6-difluorophenyl)-2-methyl-3-thioxo-2,5,6,7-tetrahydro-3H-pyrrolo[1,2-c]imidazol-1-yl)acetic acid (analogous to Example 229) and isolated as a cream powder.

$^1$H NMR (DMSO$_{d6}$): 7.72 (1H, m), 7.17 (1H, m), 4.78 (1H, t, J=5.3 Hz), 4.43 (1H, quin, J=8.7 Hz), 4.20 (1H, dd, J=11.5, 9.3 Hz), 3.78 (1H, dd, J=11.6, 7.9 Hz), 3.58 (2H, td, J=6.5, 5.3 Hz), 3.43 (3H, s), 3.31 (1H, m), 2.94 (1H, dd, J=15.7, 8.2 Hz), 2.65 (2H, t, J=6.4 Hz).

$^{13}$C NMR (DMSO$_{d6}$): 160.8, 160.8, 159.2, 159.1, 157.6, 157.5, 156, 155.9, 155.8, 132.5, 132.4, 127.5, 119.4, 118.8, 118.6, 118.5, 113.8, 113.8, 113.6, 113.6, 104.1, 104.1, 103.9, 103.9, 58.9, 49.3, 34.8, 31.3, 29.3, 27.7.

Example 457: 2-((S)-6-(3-bromo-2,6-difluorophenyl)-2-methyl-3-thioxo-2,5,6,7-tetrahydro-3H-pyrrolo[1,2-c]imidazol-1-yl)-N-(1-methyl-6-oxopiperidin-3-yl)acetamide

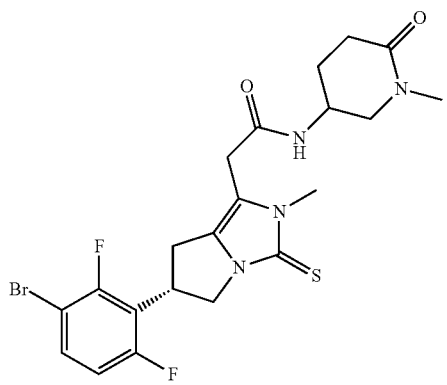 [SMILES: CN1CC(NC(=O)Cc2c3n(c(=S)n2C)C[C@H](c2c(F)ccc(Br)c2F)C3)CCC1=O]

Compound was prepared analogous manner to Example 22 from (S)-2-(6-(3-bromo-2,6-difluorophenyl)-2-methyl-3-thioxo-2,5,6,7-tetrahydro-3H-pyrrolo[1,2-c]imidazol-1-yl)acetic acid and isolated as a cream powder.

¹H NMR (DMSO_{d6}): 78.35 (1H, m), 7.74 (1H, m), 7.17 (1H, m), 4.44 (1H, quin, J=8.5 Hz), 4.22 (1H, dd, J=11.5, 9.2 Hz), 4.04 (1H, m), 3.79 (1H, dd, J=11.7, 7.7 Hz), 3.47 (2H, m), 3.42 (1H, m), 3.41 (3H, s), 3.28 (1H, m), 3.08 (1H, m), 2.88 (1H, dd, J=15.9, 8.0 Hz), 2.77 (3H, 2 s), 2.28 (2H, m), 1.86 (1H, m), 1.75 (1H, m).

¹³C NMR (DMSO_{d6}): 167.7, 167.6, 160.8, 160.8, 159.2, 159.1, 157.6, 157.5, 156.2, 155.9, 155.9, 132.5, 132.4, 128.5, 128.4, 118.8, 118.7, 118.6, 116.3, 113.8, 113.8, 113.6, 113.6, 104.1, 104.1, 103.9, 103.9, 52.9, 49.6, 43.4, 43.4, 34.8, 33.9, 31.5, 31.1, 31.1, 29.2, 29, 29, 26.1.

Example 458: 2-((S)-6-(3-bromo-2,6-difluorophenyl)-2-methyl-3-thioxo-2,5,6,7-tetrahydro-3H-pyrrolo[1,2-c]imidazol-1-yl)-1-(3-(fluoromethyl)pyrrolidin-1-yl)ethan-1-one

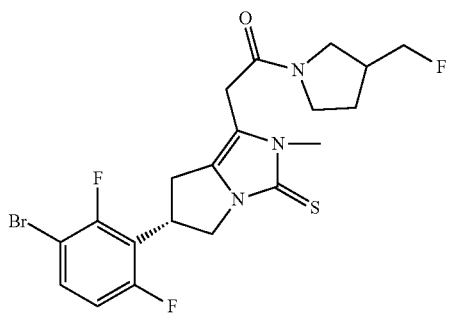 [SMILES: Cn1c(CC(=O)N2CCC(CF)C2)c2n(c1=S)C[C@H](c1c(F)ccc(Br)c1F)C2]

Compound was prepared analogous manner to Example 32 from (S)-2-(6-(3-bromo-2,6-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as a cream powder.

¹H NMR (DMSO_{d6}): 7.72 (1H, m), 7.16 (1H, t, J=9.4 Hz), 4.44 (3H, m), 4.22 (1H, dd, J=11.4, 9.2 Hz), 3.80 (1H, m), 3.70 (0.5H, m), 3.65 (2H, d, J=5.9 Hz), 3.61 (0.5H, m), 3.48 (1.5H, m), 3.37 (3H, 2 s), 3.28 (2H, m), 3.11 (0.5H, m), 2.85 (1H, m), 2.65 (0.5H, m), 2.56 (0.5H, m), 2.04 (0.5H, m), 1.92 (0.5H, m), 1.75 (0.5H, m), 1.62 (0.5H, m).

¹³C NMR (DMSO_{d6}): 166.3, 166.3, 160.8, 160.7, 159.2, 159.1, 157.6, 157.5, 156.2, 155.9, 155.9, 132.5, 132.4, 128.3, 128.3, 128.3, 118.9, 118.8, 118.7, 116.2, 113.8, 113.8, 113.6, 113.6, 104.1, 104.1, 103.9, 103.9, 84.8, 84.8, 83.7, 83.7, 49.6, 48, 47.9, 47.2, 47.2, 45.4, 45, 37.3, 37.2, 37.1, 37.1, 34.8, 31.5, 31.5, 30.3, 30.1, 30.1, 29.2, 27.2, 27.1, 25.4, 25.4, 25.4, 25.4.

Example 459: 2-((S)-6-(3-bromo-2,6-difluorophenyl)-2-methyl-3-thioxo-2,5,6,7-tetrahydro-3H-pyrrolo[1,2-c]imidazol-1-yl)-N—((S)-tetrahydrofuran-3-yl)acetamide

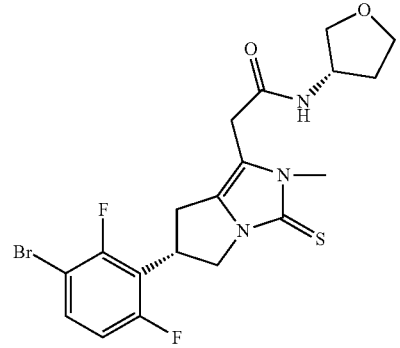 [SMILES: Cn1c(CC(=O)N[C@H]2CCOC2)c2n(c1=S)C[C@H](c1c(F)ccc(Br)c1F)C2]

Compound was prepared analogous manner to Example 32 from (S)-1-(1H-imidazol-1-yl)-2-(2-methyl-3-thioxo-6-(3-bromo-2,6-difluorophenyl)-2,5,6,7-tetrahydro-3H-pyrrolo[1,2-c]imidazol-1-yl)ethan-1-one and isolated as a cream powder.

¹H NMR (DMSO_{d6}): 8.36 (1H, d, J=6.6 Hz), 7.72 (1H, m), 7.16 (1H, t, J=9.3 Hz), 4.44 (1H, quin, J=8.6 Hz), 4.22 (2H, m), 3.78 (2H, m), 3.72 (1H, dd, J=8.9, 6.0 Hz), 3.66 (1H, td, J=8.3, 5.6 Hz), 3.46 (1H, dd, J=8.9, 3.5 Hz), 3.43 (2H, s), 3.40 (3H, s), 3.28 (1H, dd, J=15.8, 9.5 Hz), 2.88 (1H, dd, J=15.8, 7.9 Hz), 2.08 (1H, dq, J=12.8, 7.6 Hz), 1.71 (1H, m).

¹³C NMR (DMSO_{d6}): 167.6, 160.8, 160.8, 159.2, 159.1, 157.6, 157.5, 156.2, 155.9, 155.9, 132.5, 132.4, 128.4, 118.8, 118.7, 118.6, 116.4, 113.8, 113.8, 113.6, 113.6, 104.1, 104.1, 103.9, 103.9, 72.4, 66.3, 49.8, 49.6, 34.8, 32, 31.5, 31.1, 29.2.

Example 460: (S)-2-(6-(3-chloro-2,6-difluorophenyl)-2-(methyl-d)-3-thioxo-2,5,6,7-tetrahydro-3H-pyrrolo[1,2-c]imidazol-1-yl)-1-morpholinoethan-1-one

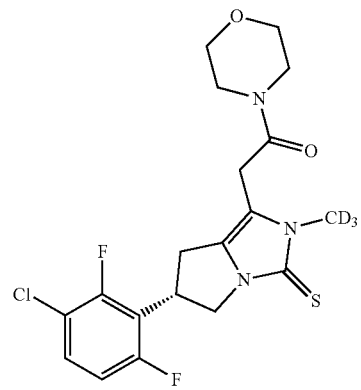 [SMILES: [2H]C([2H])([2H])n1c(CC(=O)N2CCOCC2)c2n(c1=S)C[C@H](c1c(F)ccc(Cl)c1F)C2]

Compound was prepared analogous manner to Example 32 from (S)-2-(6-(3-chloro-2,6-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as an off-white solid.

¹H NMR (DMSO$_{d6}$): 7.61 (1H, td, J=8.8, 5.6 Hz), 7.22 (1H, td, J=9.5, 1.6 Hz), 4.44 (1H, quin, J=8.5 Hz), 4.23 (1H, dd, J=11.5, 9.2 Hz), 3.80 (1H, dd, J=11.6, 7.8 Hz), 3.74 (2H, s), 3.60 (2H, m), 3.55 (2H, m), 3.49 (2H, m), 3.44 (2H, m), 3.27 (1H, dd, J=15.8, 9.4 Hz), 2.86 (1H, dd, J=15.8, 7.9 Hz).

¹³C NMR (DMSO$_{d6}$): 166.8, 160.1, 160.1, 158.5, 158.5, 156.6, 156.5, 156.2, 154.9, 154.9, 129.7, 129.6, 128.2, 118.9, 118.8, 118.6, 116.2, 116.1, 116, 115.9, 115.9, 113.3, 113.2, 113.1, 113.1, 66, 66, 49.5, 45.6, 41.7, 34.8, 29.2, 28.8.

Example 461: 2-((5aS,6aR)-5a-(5-bromo-2-fluorophenyl)-2-(methyl-d)-3-thioxo-2,3,5,5a,6,6a-hexahydrocyclopropa[3,4]pyrrolo[1,2-c]imidazol-1-yl)-N—((S)-tetrahydrofuran-3-yl)acetamide

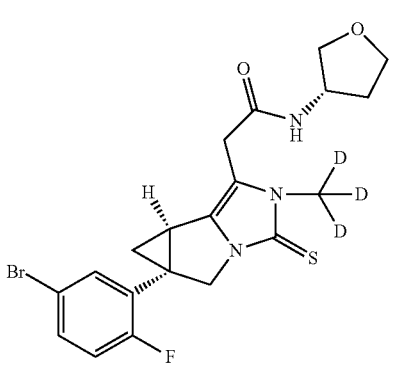 [SMILES: [2H]C([2H])([2H])n1c(CC(=O)N[C@H]2CCOC2)c2n(c1=S)C[C@@]1(c3cc(Br)ccc3F)C[C@@H]21]

Compound was prepared analogous manner to Example 32 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

¹H NMR (DMSO$_{d6}$): 8.39 (1H, d, J=6.7 Hz), 7.58 (1H, m), 7.56 (1H, m), 7.24 (1H, dd, J=10.1, 8.7 Hz), 4.26 (1H, m), 4.14 (1H, d, J=12.0 Hz), 3.85 (1H, d, J=12.0 Hz), 3.80 (2H, m), 3.74 (1H, dd, J=8.9, 5.9 Hz), 3.67 (1H, td, J=8.2, 5.6 Hz), 3.51 (2H, m), 3.49 (1H, dd, J=3.6, 8.9 Hz), 2.88 (1H, dd, J=8.4, 4.2 Hz), 2.10 (1H, m), 1.74 (1H, m), 1.70 (1H, dd, J=8.4, 5.4 Hz), 1.13 (1H, m).

¹³C NMR (DMSO$_{d6}$): 167.7, 161.8, 160.2, 156.8, 133.1, 133, 132.4, 132.3, 131, 129.2, 129.1, 118, 117.9, 116.2, 116.2, 116.1, 72.4, 66.3, 52.4, 49.8, 32, 31.5, 31, 22.1, 20.7.

Example 462: 2-((5aS,6aR)-5a-(5-bromo-2-fluorophenyl)-2-(methyl-d)-3-thioxo-2,3,5,5a,6,6a-hexahydrocyclopropa[3,4]pyrrolo[1,2-c]imidazol-1-yl)acetic Acid

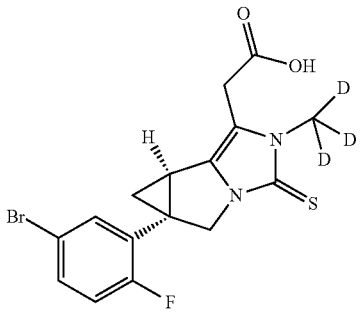 [SMILES: [2H]C([2H])([2H])n1c(CC(=O)O)c2n(c1=S)C[C@@]1(c3cc(Br)ccc3F)C[C@@H]21]

Compound was prepared analogous manner to Example 2 from (1R,5S)-3-(tert-butoxycarbonyl)-5-(5-bromo-2-fluorophenyl)-3-azabicyclo[3.1.0]hexane-2-carboxylic acid. The product was isolated as a beige solid.

¹H NMR (DMSO$_{d6}$): 12.78 (1H, br s), 7.57 (2H, m), 7.24 (1H, dd, J=10.1, 8.7 Hz), 4.16 (1H, d, J=11.9 Hz), 3.86 (1H, d, J=12.0 Hz), 3.75 (2H, m), 2.97 (1H, dd, J=8.5, 4.1 Hz), 1.70 (1H, dd, J=8.4, 5.4 Hz), 1.13 (1H, m).

¹³C NMR (DMSO$_{d6}$): 170.9, 161.8, 160.2, 157, 133, 133, 132.4, 132.3, 131.2, 129.1, 129, 118, 117.9, 116.2, 116.2, 115.2, 52.5, 52.4, 31.5, 29.7, 22.1, 20.6.

Example 463: 2-((5aS,6aR)-5a-(5-bromo-2-fluorophenyl)-2-(methyl-d)-3-thioxo-2,3,5,5a,6,6a-hexahydrocyclopropa[3,4]pyrrolo[1,2-c]imidazol-1-yl)-N-(tetrahydro-2H-pyran-4-yl)acetamide

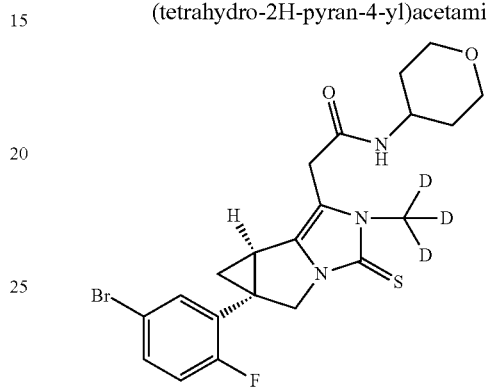

Compound was prepared analogous manner to Example 32 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

¹H NMR (DMSO$_{d6}$): 8.14 (1H, d, J=7.5 Hz), 7.58 (1H, m), 7.56 (1H, ddd, J=6.5, 4.4, 2.3 Hz), 7.24 (1H, dd, J=10.2, 8.7 Hz), 4.14 (1H, d, J=11.9 Hz), 3.85 (1H, d, J=12.2 Hz), 3.82 (2H, m), 3.77 (1H, m), 3.49 (2H, m), 3.33 (2H, m), 2.88 (1H, dd, J=8.4, 3.9 Hz), 1.71 (3H, m), 1.40 (2H, m), 1.13 (1H, t, J=4.8 Hz).

¹³C NMR (DMSO$_{d6}$): 167, 161.8, 160.2, 156.8, 133.1, 133.1, 132.4, 132.3, 131, 129.2, 129.1, 118, 117.9, 116.2, 116.2, 116.2, 65.9, 52.4, 45.2, 32.4, 32.4, 31.5, 31.2, 22.1, 20.7.

Example 464: 2-((5aS,6aR)-5a-(5-bromo-2-fluorophenyl)-2-(methyl-d)-3-thioxo-2,3,5,5a,6,6a-hexahydrocyclopropa[3,4]pyrrolo[1,2-c]imidazol-1-yl)-N—((R)-tetrahydro-2H-pyran-3-yl)acetamide

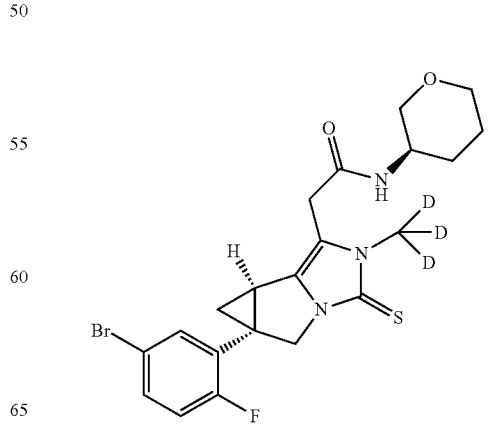

Compound was prepared analogous manner to Example 34 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)acetic acid and isolated as a beige solid.

$^1$H NMR (DMSO$_{d6}$): 8.14 (1H, br d, J=7.5 Hz), 7.58 (1H, dd, J=6.7, 2.6 Hz), 7.56 (1H, m), 7.24 (1H, dd, J=10.1, 8.7 Hz), 4.14 (1H, d, J=12.0 Hz), 3.85 (1H, d, J=12.2 Hz), 3.71 (2H, m), 3.65 (1H, dt, J=11.1, 4.3 Hz), 3.51 (2H, m), 3.39 (1H, m), 3.14 (1H, m), 2.88 (1H, dd, J=8.5, 4.1 Hz), 1.83 (1H, br d, J=12.0 Hz), 1.68 (2H, m), 1.50 (2H, m), 1.12 (1H, t, J=4.8 Hz).

$^{13}$C NMR (DMSO$_{d6}$): 167.4, 161.8, 160.2, 156.8, 133.1, 133, 132.4, 132.3, 131, 129.2, 129.1, 118, 117.9, 116.2, 116.2, 116.1, 70.1, 67, 52.4, 45.2, 31.5, 31.1, 28.6, 23.9, 22.1, 20.7.

Example 465: 2-((5aS,6aR)-5a-(5-bromo-2-fluorophenyl)-2-(methyl-d)-3-thioxo-2,3,5,5a,6,6a-hexahydrocyclopropa[3,4]pyrrolo[1,2-c]imidazol-1-yl)-N—((R)-tetrahydrofuran-3-yl)acetamide

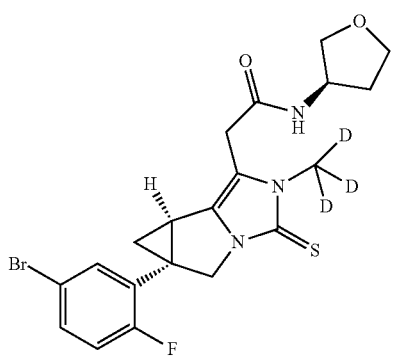 [SMILES: [2H]C([2H])([2H])n1c(CC(=O)N[C@@H]2CCOC2)c2n(c1=S)C[C@@]1(c3cc(Br)ccc3F)C[C@@H]21]

Compound was prepared analogous manner to Example 32 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-1-(1H-imidazol-1-yl)ethan-1-one and isolated as a beige solid.

$^1$H NMR (DMSO$_{d6}$): 8.40 (1H, d, J=6.7 Hz), 7.58 (1H, m), 7.56 (1H, m), 7.24 (1H, dd, J=10.1, 8.7 Hz), 4.26 (1H, m), 4.14 (1H, d, J=12.0 Hz), 3.85 (1H, d, J=12.0 Hz), 3.80 (2H, m), 3.74 (1H, dd, J=8.9, 5.9 Hz), 3.67 (1H, td, J=8.2, 5.6 Hz), 3.51 (2H, m), 3.49 (1H, dd, J=3.6, 8.9 Hz), 2.88 (1H, dd, J=8.4, 4.2 Hz), 2.10 (1H, m), 1.74 (1H, m), 1.70 (1H, dd, J=8.4, 5.4 Hz), 1.13 (1H, m).

$^{13}$C NMR (DMSO$_{d6}$): 167.7, 161.8, 160.2, 156.8, 133.1, 133, 132.4, 132.3, 131, 129.2, 129.1, 118, 117.9, 116.2, 116.2, 116.1, 72.3, 66.3, 52.4, 49.8, 32.1, 31.5, 31, 22.1, 20.7.

Example 466: 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)-N-methyl-N—((R)-tetrahydrofuran-3-yl)acetamide

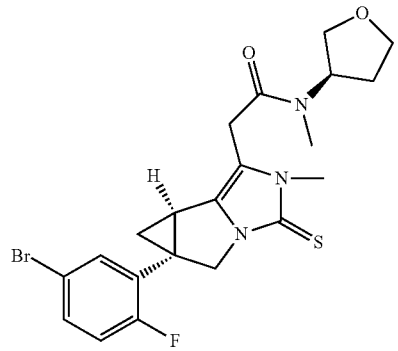

Compound was prepared analogous manner to Example 34 from 2-((5aS,6aR)-5a-(5-bromo-2-fluorophenyl)-2-methyl-3-thioxo-2,3,5,5a,6,6a-hexahydrocyclopropa[3,4]pyrrolo[1,2-c]imidazol-1-yl)acetic acid and isolated as a beige solid.

$^1$H NMR (DMSO$_{d6}$): 7.58 (2H, m), 7.24 (1H, m), 5.11 (0.6H, m), 4.72 (0.4H, m), 4.15 (1H, d, J=12.1 Hz), 4.0-3.51 (7H, m), 3.31 (3H, 2 s), 2.98 (1.8H, s), 2.86 (1H, m), 2.76 (1.2H, s), 2.24 (0.4H, m), 2.12 (0.6H, m), 1.89 (0.4H, m), 1.81 (0.6H, m), 1.70 (1H, m), 1.13 (1H, m).

$^{13}$C NMR (DMSO$_{d6}$): 168.3, 167.7, 161.8, 160.2, 160.2, 156.9, 156.8, 133.1, 133.1, 133, 132.4, 132.3, 130.8, 130.7, 129.2, 129.1, 129.1, 129, 118, 117.9, 116.2, 116.2, 116.2, 116.1, 69.4, 69.3, 67.2, 67.1, 56.6, 53, 52.4, 31.6, 31.6, 31.5, 31.5, 29.9, 29.8, 29.8, 29.4, 29.3, 22.1, 20.7.

Example 467: 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)-N-methyl-N—((R)-tetrahydrofuran-3-yl)acetamide

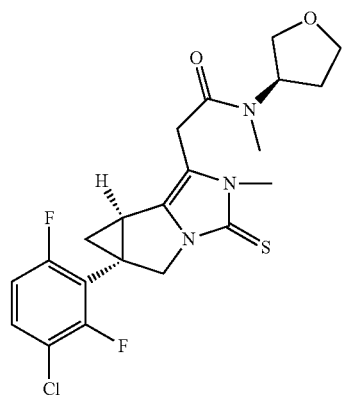 [SMILES: CN(C(=O)Cc1c2n(c(=S)n1C)C[C@@]1(c3c(F)ccc(Cl)c3F)C[C@@H]21)[C@@H]1CCOC1]

Compound was prepared analogous manner to Example 34 from 2-((5aS,6aR)-5a-(3-chloro-2,6-difluorophenyl)-2-methyl-3-thioxo-2,3,5,5a,6,6a-hexahydrocyclopropa[3,4]pyrrolo[1,2-c]imidazol-1-yl)acetic acid and isolated as a beige solid.

$^1$H NMR (DMSO$_{d6}$): 7.64 (1H, m), 7.21 (1H, br t, J=9.0 Hz), 5.11 (0.6H, m), 4.71 (0.4H, m), 4.11 (1H, br d, J=12.2

Hz), 4.0-3.51 (7H, m), 3.32 (3H, 2 s), 2.96 (1.8H, s), 2.76 (2.2H, m), 2.24 (0.4H, m), 2.12 (0.6H, m), 1.88 (0.4H, m), 1.80 (0.6H, m), 1.69 (1H, m), 1.26 (1H, m).

$^{13}$C NMR (DMSO$_{d6}$): 168.3, 167.6, 161.3, 161.2, 159.6, 159.6, 157.8, 157.8, 156.9, 156.8, 156.2, 156.1, 130.4, 130.3, 130.3, 117.1, 116.9, 116.8, 116.6, 116.5, 115.8, 115.7, 115.6, 115.6, 112.9, 112.9, 112.8, 112.8, 69.4, 69.3, 67.2, 67.1, 56.6, 53, 52.2, 31.5, 31.5, 29.9, 29.9, 29.8, 29.5, 29.3, 27.7, 25.7, 21.8, 21.7, 21.2, 21.2.

Example 468: 2-((5aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)-N-methyl-N—((R)-tetrahydrofuran-3-yl)acetamide

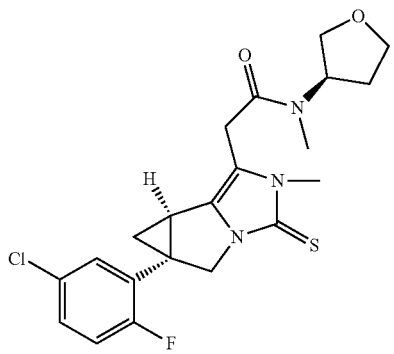 [SMILES: CN(C(=O)Cc1c2n(c(=S)n1C)C[C@@]1(c3cc(Cl)ccc3F)C[C@@H]21)[C@@H]1CCOC1]

Compound was prepared analogous manner to Example 34 from 2-((aS,6aR)-5a-(5-chloro-2-fluorophenyl)-2-methyl-3-thioxo-2,3,5,5a,6,6a-hexahydrocyclopropa[3,4]pyrrolo[1,2-c]imidazol-1-yl)acetic acid and isolated as a beige solid.

$^{1}$H NMR (DMSO$_{d6}$): 7.45 (2H, m), 7.30 (1H, m), 5.11 (0.6H, m), 4.72 (0.4H, m), 4.15 (1H, br d, J=11.9 Hz), 4.0-3.52 (7H, m), 3.31 (3H, 2s), 2.97 (1.8H, s), 2.86 (1H, m), 2.76 (1.2H, s), 2.24 (0.4H, m), 2.12 (0.6H, m), 1.89 (0.4H, m), 1.80 (0.6H, m), 1.70 (1H, m), 1.13 (1H, m).

$^{13}$C NMR (DMSO$_{d6}$): 168.3, 167.7, 161.3, 161.3, 159.7, 159.7, 156.9, 156.8, 130.8, 130.7, 130.2, 130.2, 129.4, 129.4, 128.8, 128.7, 128.7, 128.6, 128.6, 128.3, 117.6, 117.4, 116.3, 116.2, 69.4, 69.3, 67.2, 67.1, 56.6, 53.1, 52.4, 31.7, 31.6, 31.5, 31.5, 30, 29.8, 29.8, 29.5, 29.3, 27.7, 22.1, 20.7.

Example 469: (S)-2-(6-(3-chloro-2,6-difluorophenyl)-2-(methyl-d)-3-thioxo-2,5,6,7-tetrahydro-3H-pyrrolo[1,2-c]imidazol-1-yl)-N-(tetrahydro-2H-pyran-4-yl)acetamide

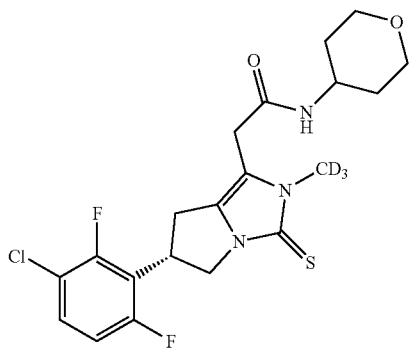 [SMILES: [2H]C([2H])([2H])n1c(CC(=O)NC2CCOCC2)c2n(c1=S)C[C@H](c1c(F)ccc(Cl)c1F)C2]

Compound was prepared analogous manner to Example 32 from (S)-2-(6-(3-chloro-2,6-difluorophenyl)-2-methyl-3-thioxo-2,5,6,7-tetrahydro-3H-pyrrolo[1,2-c]imidazol-1-yl)-1-(1H-imidazol-1-yl)ethan-1-one and isolated as an off-white solid.

$^{1}$H NMR (DMSO$_{d6}$): 8.11 (1H, d, J=7.5 Hz), 7.61 (1H, td, J=8.7, 5.6 Hz), 7.22 (1H, m), 4.44 (1H, quin, J=8.5 Hz), 4.22 (1H, dd, J=11.6, 9.2 Hz), 3.81 (3H, m), 3.74 (1H, m), 3.42 (2H, m), 3.33 (2H, m), 3.29 (1H, dd, J=9.0, 15.9 Hz), 2.89 (1H, dd, J=15.9, 8.0 Hz), 1.69 (2H, m), 1.38 (2H, m).

$^{13}$C NMR (DMSO$_{d6}$): 166.8, 160.1, 160.1, 158.5, 158.4, 156.6, 156.5, 156.2, 154.9, 154.9, 129.7, 129.6, 128.4, 118.8, 118.7, 118.6, 116.4, 116, 115.9, 113.2, 113.1, 65.8, 49.5, 45.2, 34.7, 32.4, 31.3, 29.2.

Example 470: R)-6-(2,3,6-trifluorophenyl)-1-(2-(((R)-tetrahydrofuran-3-yl)amino)ethyl)-2,5,6,7-tetrahydro-3H-pyrrolo[1,2-c]imidazole-3-thione

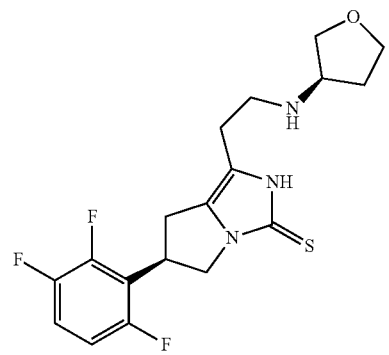 [SMILES: Fc1ccc(F)c([C@H]2Cc3c(CCN[C@@H]4CCOC4)[nH]c(=S)n3C2)c1F]

Compound was prepared analogous manner to Example 35 from 2-((R)-6-(2,3,6-trifluorophenyl)-3-thioxo-2,5,6,7-tetrahydro-3H-pyrrolo[1,2-c]imidazol-1-yl)-N—((R)-tetrahydrofuran-3-yl)acetamide and isolated as a cream powder.

$^{1}$H NMR (DMSO$_{d6}$): 1.90 (1H, br s), 9.24 (2H, m), 7.49 (1H, m), 7.19 (1H, m), 4.43 (1H, quin, J=8.8 Hz), 4.16 (1H, dd, J=11.2, 9.0 Hz), 3.92 (1H, m), 3.88 (1H, m), 3.82 (1H, m), 3.75 (2H, m), 3.65 (1H, m), 3.32 (1H, dd, J=9.1, 15.5 Hz), 3.15 (2H, m), 2.96 (1H, br dd, J=15.6, 8.7 Hz), 2.81 (2H, br t, J=7.6 Hz), 2.20 (1H, m), 2.01 (1H, m).

$^{13}$C NMR (DMSO$_{d6}$): 157, 156.9, 155.9, 155.4, 155.3, 150.9, 149.1, 149.1, 149, 149, 147.6, 147.5, 147.5, 147.5, 147.4, 147.4, 147.3, 145.9, 145.9, 145.8, 129.3, 118.5, 118.5, 118.4, 118.3, 116.6, 116.5, 116.4, 114.9, 112, 112, 112, 111.9, 111.8, 111.8, 111.8, 68.8, 66.4, 57.3, 48.3, 43.7, 35.7, 29, 28.8, 21.2.

Example 471: (R)-1-(3-(pyrrolidin-1-yl)propyl)-6-(2,3,5,6-tetrafluorophenyl)-2,5,6,7-tetrahydro-3H-pyrrolo[1,2-c]imidazole-3-thione

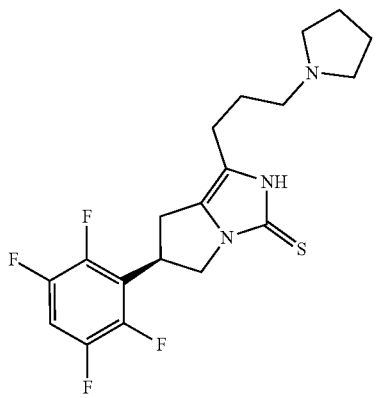 [SMILES: Fc1cc(F)c(F)c([C@H]2Cc3c(CCCN4CCCC4)[nH]c(=S)n3C2)c1F]

Compound was prepared analogous manner to Example 35 from (R)-1-(pyrrolidin-1-yl)-3-(6-(2,3,5,6-tetrafluorophenyl)-3-thioxo-2,5,6,7-tetrahydro-3H-pyrrolo[1,2-c]imidazol-1-yl)propan-1-one and isolated as an off-white powder.

$^1$H NMR (DMSO$_{d6}$): 1.81 (1H, br s), 7.84 (1H, m), 4.49 (1H, m), 4.15 (1H, dd, J=11.7, 9.1 Hz), 3.76 (1H, dd, J=11.7, 7.6 Hz), 3.29 (1H, dd, J=15.6, 9.3 Hz), 2.90 (1H, dd, J=15.7, 7.8 Hz), 2.38 (6H, m), 2.33 (2H, t, J=7.1 Hz), 1.66 (6H, m).

$^{13}$C NMR (DMSO$_{d6}$): 155, 146.4, 146.4, 146.3, 146.3, 146.3, 146.3, 146.2, 145.3, 145.3, 145.3, 145.3, 145.2, 145.2, 145.2, 145.2, 144.8, 144.8, 144.7, 144.7, 144.7, 144.6, 144.6, 143.7, 143.7, 143.7, 143.6, 143.6, 143.6, 143.6, 143.5, 127.4, 120.6, 120.5, 120.4, 119.6, 105.8, 105.7, 105.5, 54.6, 53.5, 48.3, 35.8, 29, 26.9, 23.1, 22.

Example 472: (R)-1-(3-(isopropylamino)propyl)-6-(2,3,6-trifluorophenyl)-2,5,6,7-tetrahydro-3H-pyrrolo[1,2-c]imidazole-3-thione hydrofluoride

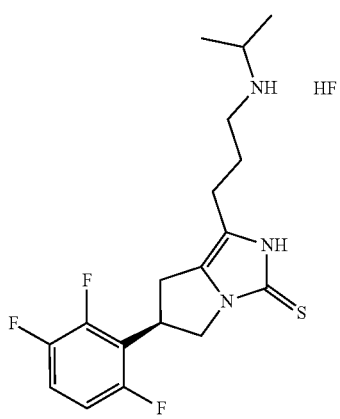

Compound was prepared analogous manner to Example 35 from (R)—N-isopropyl-3-(3-thioxo-6-(2,3,6-trifluorophenyl)-2,5,6,7-tetrahydro-3H-pyrrolo[1,2-c]imidazol-1-yl)propanamide and isolated as a light beige solid.

$^1$H NMR (DMSO$_{d6}$): 11.85 (1H, br s), 8.44 (2H, br), 7.48 (1H, qd, J=9.4, 5.0 Hz), 7.18 (1H, m), 4.47 (1H, quin, J=8.5 Hz), 4.16 (1H, dd, J=11.5, 9.2 Hz), 3.74 (1H, dd, J=11.7, 7.8 Hz), 3.31 (1H, dd, J=9.5, 15.8 Hz), 3.25 (1H, m), 2.91 (1H, dd, J=15.6, 7.8 Hz), 2.84 (2H, m), 2.45 (2H, t, J=7.4 Hz), 1.83 (2H, quin, J=7.6 Hz), 1.19 (6H, d, J=6.6 Hz).

$^{13}$C NMR (DMSO$_{d6}$): 156.9, 156.9, 155.4, 155.3, 155.3, 149.1, 149.1, 149, 149, 148.9, 147.6, 147.6, 147.5, 147.5, 147.5, 147.4, 147.4, 147.4, 147.3, 147.3, 147.3, 146, 145.9, 145.9, 145.9, 128.1, 119.1, 119, 119, 118.9, 118.2, 116.5, 116.5, 116.4, 116.4, 112, 112, 112, 112, 112, 111.9, 111.8, 111.8, 111.8, 49.5, 48.5, 43.2, 35.6, 29.1, 24.7, 21.2, 18.7, 18.6.

Example 473: (R)-1-(2-(((tetrahydro-2H-pyran-4-yl)methyl)amino)ethyl)-6-(2,3,6-trifluorophenyl)-2,5,6,7-tetrahydro-3H-pyrrolo[1,2-c]imidazole-3-thione hydrochloride

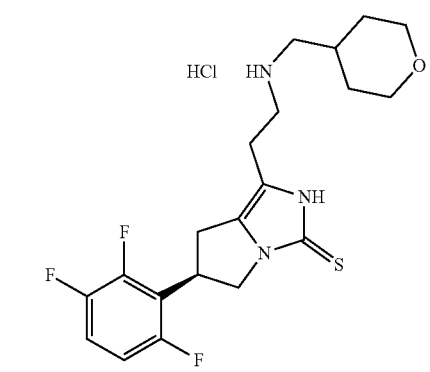 [SMILES: Fc1ccc(F)c([C@H]2Cc3c(CCNCC4CCOCC4)[nH]c(=S)n3C2)c1F ; Cl]

Compound was prepared analogous manner to Example 35 from (R)—N-((tetrahydro-2H-pyran-4-yl)methyl)-2-(3-thioxo-6-(2,3,6-trifluorophenyl)-2,5,6,7-tetrahydro-3H-pyrrolo[1,2-c]imidazol-1-yl)acetamide and isolated as a yellow solid.

$^1$H NMR (DMSO$_{d6}$): 1.91 (1H, s), 8.93 (2H, m), 7.50 (1H, m), 7.19 (1H, m), 4.44 (1H, quin, J=8.7 Hz), 4.16 (1H, dd, J=11.5, 9.2 Hz), 3.86 (2H, m), 3.75 (1H, dd, J=11.5, 8.3 Hz), 3.32 (1H, dd, J=15.5, 9.2 Hz), 3.27 (2H, td, J=11.7, 2.1 Hz), 3.12 (2H, m), 2.95 (1H, dd, J=15.6, 8.7 Hz), 2.82 (4H, m), 1.94 (1H, m), 1.67 (2H, m), 1.21 (2H, qd, J=12.2, 4.5 Hz).

$^{13}$C NMR (DMSO$_{d6}$): 156.9, 156.9, 155.8, 155.3, 155.3, 129.2, 118.6, 118.5, 118.5, 118.4, 116.6, 116.5, 116.5, 116.4, 115, 112, 112, 112, 111.9, 111.8, 111.8, 111.8, 66.3, 51.9, 48.3, 45.4, 35.7, 31.7, 30, 29, 20.8.

Example 474: (R)-2-methyl-1-(2-(pyrrolidin-1-yl)ethyl)-6-(2,3,6-trifluorophenyl)-2,5,6,7-tetrahydro-3H-pyrrolo[1,2-c]imidazole-3-thione hydrofluoride

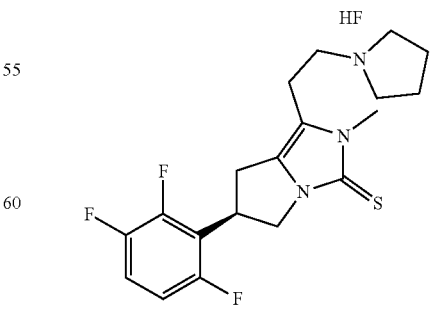

Compound was prepared analogous manner to Example 35 from (R)-2-(2-methyl-3-thioxo-6-(2,3,6-trifluorophenyl)-2, 5,6,7-tetrahydro-3H-pyrrolo[1,2-c]imidazol-1-yl)-1-(pyrrolidin-1-yl)ethan-1-one and isolated as a light beige solid.

¹H NMR (DMSO$_{d6}$): 9.65 (1H, m), 7.49 (1H, m), 7.19 (1H, m), 4.44 (1H, quin, J=8.6 Hz), 4.23 (1H, dd, J=9.3, 11.3 Hz), 3.82 (1H, dd, J=11.6, 7.9 Hz), 3.47 (3H, s), 3.38 (1H, dd, J=9.4, 15.7 Hz), 3.25-2.95 (6H, m), 3.00 (1H, dd, J=15.7, 8.2 Hz), 2.87 (2H, m), 1.89 (4H, m).

¹³C NMR (DMSO$_{d6}$): 156.9, 156.9, 156.5, 155.3, 155.3, 149.1, 149, 149, 148.9, 147.5, 147.5, 147.4, 147.4, 147.3, 145.9, 145.9, 145.9, 145.8, 145.8, 127.9, 118.8, 118.7, 118.7, 118.6, 117.4, 117.3, 116.5, 116.5, 116.4, 116.4, 112, 112, 112, 111.9, 111.8, 111.8, 111.8, 111.8, 53.3, 51.8, 49.3, 34.8, 31.3, 29.3, 22.7, 21.6.

Example 475: (R)-1-(2-((((S)-tetrahydrofuran-2-yl)methyl)amino)ethyl)-6-(2,3,6-trifluorophenyl)-2,5,6,7-tetrahydro-3H-pyrrolo[1,2-c]imidazole-3-thione hydrochloride

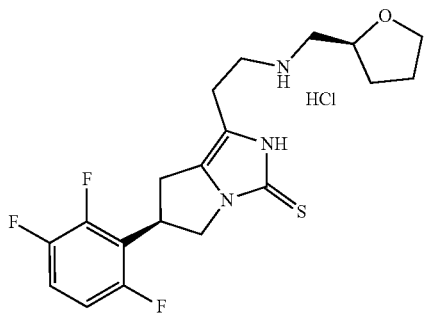 [SMILES: Fc1ccc(F)c([C@H]2Cc3c(CCNC[C@@H]4CCCO4)[nH]c(=S)n3C2)c1F ; Cl]

Compound was prepared analogous manner to Example 35 from N—(((S)-tetrahydrofuran-2-yl)methyl)-2-((R)-3-thioxo-6-(2,3,6-trifluorophenyl)-2,5,6,7-tetrahydro-3H-pyrrolo[1,2-c]imidazol-1-yl)acetamide and isolated as a cream powder.

¹H NMR (DMSO$_{d6}$): 11.90 (1H, s), 8.92 (2H, m), 7.49 (1H, m), 7.19 (1H, m), 4.44 (1H, quin, J=8.7 Hz), 4.15 (2H, m), 3.80 (1H, dt, J=8.1, 6.9 Hz), 3.75 (1H, dd, J=11.6, 8.4 Hz), 3.71 (1H, td, J=7.8, 6.1 Hz), 3.30 (1H, dd, J=15.6, 9.1 Hz), 3.15 (2H, m), 3.06 (1H, m), 2.94 (1H, dd, J=8.6, 15.6 Hz), 2.89 (1H, m), 2.79 (2H, t, J=7.6 Hz), 2.00 (1H, m), 1.85 (2H, m), 1.55 (1H, m).

¹³C NMR (DMSO$_{d6}$): 157, 156.9, 155.8, 155.4, 155.3, 149.1, 149.1, 149.1, 149, 149, 149, 147.6, 147.6, 147.5, 147.5, 147.5, 147.5, 147.4, 147.4, 147.3, 146, 145.9, 145.9, 145.9, 129.2, 118.6, 118.5, 118.5, 118.4, 116.6, 116.5, 116.5, 116.4, 115, 112, 112, 112, 112, 111.9, 111.9, 111.8, 111.8, 73.7, 67.6, 50.3, 48.3, 45.3, 35.8, 29, 28.8, 25, 20.9.

Example 476: (R)-1-(2-(tert-butylamino)ethyl)-2-methyl-6-(2,3,6-trifluorophenyl)-2,5,6,7-tetrahydro-3H-pyrrolo[1,2-c]imidazole-3-thione Hydrofluoride

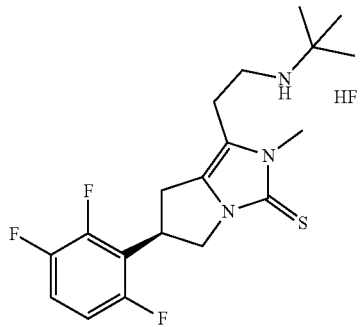

Compound was prepared analogous manner to Example 35 from (R)—N-(tert-butyl)-2-(2-methyl-3-thioxo-6-(2,3,6-trifluorophenyl)-2,5,6,7-tetrahydro-3H-pyrrolo[1,2-c]imidazol-1-yl)acetamide and isolated as an off-white solid.

¹H NMR (DMSO$_{d6}$): 8.61 (2H, m), 7.50 (1H, m), 7.21 (1H, m), 4.44 (1H, quin, J=8.8 Hz), 4.24 (1H, dd, J=9.5, 11.2 Hz), 3.83 (1H, dd, J=11.6, 8.2 Hz), 3.48 (3H, s), 3.42 (1H, dd, J=9.3, 15.5 Hz), 3.04 (1H, dd, J=8.5, 15.8 Hz), 3.02 (2H, m), 2.83 (2H, m), 1.25 (9H, br s).

¹³C NMR (DMSO$_{d6}$): 157, 156.5, 155.4, 149.2, 149.1, 147.6, 147.5, 147.5, 146.1, 146, 145.9, 128.1, 118.7, 118.6, 118.5, 117.2, 116.6, 116.5, 116.5, 116.4, 112, 111.8, 55.7, 49.3, 39.8, 34.8, 31.4, 29.1, 25.7, 22.2.

Example 477: (R)-2-methyl-1-(2-(((tetrahydro-2H-pyran-4-yl)methyl)amino)ethyl)-6-(2,3,6-trifluorophenyl)-2,5,6,7-tetrahydro-3H-pyrrolo[1,2-c]imidazole-3-thione hydrochloride

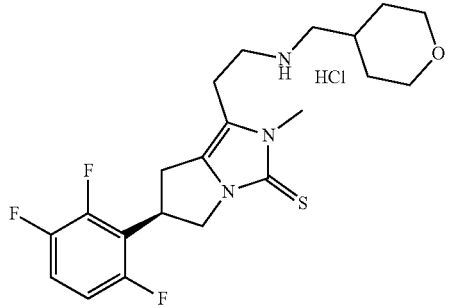 [SMILES: Cn1c(CCNCC2CCOCC2)c2n(c1=S)C[C@@H](c1c(F)ccc(F)c1F)C2 ; Cl]

Compound was prepared analogous manner to Example 35 from (R)-2-(2-methyl-3-thioxo-6-(2,3,6-trifluorophenyl)-2,5,6,7-tetrahydro-3H-pyrrolo[1,2-c]imidazol-1-yl)-N-((tetrahydro-2H-pyran-4-yl)methyl)acetamide and isolated as a beige solid.

¹H NMR (DMSO$_{d6}$): 8.87 (2H, m), 7.49 (1H, m), 7.19 (1H, m), 4.44 (1H, quin, J=8.7 Hz), 4.23 (1H, dd, J=11.4, 9.3 Hz), 3.85 (2H, m), 3.82 (1H, dd, J=11.7, 8.1 Hz), 3.47 (3H, s), 3.39 (1H, dd, J=9.3, 15.7 Hz), 3.28 (2H, td, J=11.7, 2.1 Hz), 3.12 (2H, m), 3.0 (1H, dd, J=8.3, 15.7 Hz), 2.97 (2H, m), 2.84 (2H, q, J=6.5 Hz), 1.94 (1H, m), 1.67 (2H, m), 1.22 (2H, qd, J=12.3, 4.8 Hz).

$^{13}$C NMR (DMSO$_{d6}$): 157, 156.9, 156.6, 155.4, 155.3, 149.1, 149.1, 149.1, 149, 149, 147.6, 147.5, 147.4, 147.4, 146, 145.9, 145.9, 145.9, 128.4, 118.7, 118.7, 118.6, 118.5, 116.7, 116.6, 116.6, 116.5, 116.4, 112.1, 112, 112, 112, 111.9, 111.9, 111.8, 111.8, 66.3, 52.1, 49.4, 45.2, 34.8, 31.9, 31.4, 30, 29.2, 20.8.

Example 478: (R)-1-(3-(pyrrolidin-1-yl)propyl)-6-(2,3,6-trifluorophenyl)-2,5,6,7-tetrahydro-3H-pyrrolo[1,2-c]imidazole-3-thione hydrofluoride

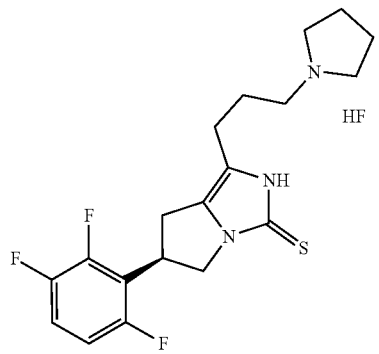

Compound was prepared analogous manner to Example 35 from (R)-1-(pyrrolidin-1-yl)-3-(3-thioxo-6-(2,3,6-trifluorophenyl)-2,5,6,7-tetrahydro-3H-pyrrolo[1,2-c]imidazol-1-yl)propan-1-one and isolated as a light beige solid.

$^1$H NMR (DMSO$_{d6}$): 11.84 (1H, s), 9.83 (1H, m), 7.48 (1H, m), 7.19 (1H, m), 4.45 (1H, quin, J=8.6 Hz), 4.16 (1H, dd, J=11.4, 9.1 Hz), 3.74 (1H, dd, J=11.7, 8.1 Hz), 3.29 (1H, dd, J=9.0, 15.6 Hz), 3.19-2.86 (4H, br), 3.05 (2H, m), 2.93 (1H, dd, J=15.6, 8.4 Hz), 2.43 (2H, br t, J=7.5 Hz), 1.94 (6H, m).

$^{13}$C NMR (DMSO$_{d6}$): 156.9, 156.9, 155.4, 155.3, 155.3, 149.1, 149.1, 149, 149, 147.6, 147.5, 147.5, 147.4, 147.4, 147.3, 146, 145.9, 145.9, 128.1, 118.9, 118.8, 118.7, 118.7, 118.2, 116.6, 116.5, 116.4, 116.4, 112, 112, 112, 112, 111.9, 111.8, 111.8, 111.8, 53.2, 48.4, 35.7, 29, 24.2, 22.6, 21.2.

G. Dopamine-β-Hydroxylase Inhibition Assay

The ability of a compound to inhibit DβH activity may be assessed using the following cell assay. For the purposes of the present invention, a compound is considered to be a "DβH inhibitor" if it exhibits activity in "% of control" of ≤20% at 10 μM in this cell assay. Preferred compounds of the present invention (including almost all of the specific Examples above) exhibit activity in "% of control" of ≤50% at 1.0 μM in this cell assay. More preferred compounds of the present invention exhibit activity in "% of control" of ≤20% at 1.0 μM in this cell assay. Especially preferred compounds of the present invention exhibit activity in "% of control" of ≤50% at 100 nM in this assay.

SK-N-SH cells (ATCC HTB-11), obtained from LGC Standards (Teddington, UK) were cultured in Eagle's minimum essential medium supplemented with 25 mM Hepes, 100 U/mL penicillin G, 0.25 μg/mL amphotericin B, 100 μg/mL streptomycin and 10% Gibco© fetal bovine serum. Cells were grown in T162 cm flasks (Corning, N.Y.) in a humidified atmosphere of 5% CO$_2$-95% air at 37° C. Fetal bovine serum was removed from cells for 4 h prior to collection.

For the preparation of cellular homogenates, media was removed and cell monolayers were washed with 50 mM Tris-HCl pH 7.4. Cells were subsequently scraped off the flasks and were resuspended in 50 mM Tris pH 7.4. Cell suspensions were homogenized with SilentCrusher M (Heidolph) for a short stroke and resultant homogenates were aliquoted and stored frozen at −80° C.

Total protein was quantified in cellular homogenates with BioRad Protein Assay (BioRad) using a standard curve of BSA (50-250 μg/mL).

DβH activity was measured by a modification of the method of Nagatsu and Udenfriend (Nagatsu, T. and S. Udenfriend: "Photometric assay of dopamine-hydroxylase activity in human blood." *Clin. Chem.* 18(9): 980-983, 1972) which is based on the enzymatic hydroxylation of tyramine into octopamine. The octopamine formed is subsequently oxidized to p-hydroxybenzaldehyde and measured by spectrophotometry. In brief, reaction mixture (total volume 500 μl) contained: cellular homogenate (75 μg total protein), sodium acetate pH 5.0 (200 mM), N-ethylmaleimide (30 mM), CuSO$_4$ (5 μM), catalase aqueous solution (0.5 mg/mL), pargyline-HCl (1 mM), sodium fumarate (10 mM), ascorbic acid (10 mM), inhibitor or vehicle and tyramine (25 mM). After a 10 min pre-incubation period at 37° C., the reaction was initiated by the addition of tyramine. Reaction was carried out for 45 min at 37° C. before termination with 50 μl perchloric acid (2 M). Samples were centrifuged for 3 min at 16100 g and supernatants were subjected to solid phase extraction. Solid phase extraction was performed using either SPE cartridges ISOLUTE SCX-3 (100 mg, 1 mL) or SPE 2 mL fixed 96 well plates ISOLUTE SCX-3 (100 mg) previously equilibrated with MilliQ water. Columns/plates were centrifuged at 150 g for 2 min. Eluate was discarded and matrix was washed with 1 mL of MilliQ water after which octopamine was eluted with 2×0.25 mL ammonium hydroxide (4 M). The oxidation of octopamine to p-hydroxybenzaldehyde was carried out for 6 min with 100 μl sodium periodate (2%) and was stopped with 100 μl sodium metabisulfite (10%). Absorbance was measured at 330 nm on a Spectramax microplate reader (Molecular Devices, Sunnyvale, Calif.). All enzymatic reactions were performed in duplicate.

Results are reported in the table below as activity in % of control at the inhibitor concentration tested.

Furthermore, the ability of a compound to inhibit DβH activity may be assessed in human plasma using the following assay. For the purposes of the present invention, a compound is considered to be a "DβH inhibitor" if it exhibits activity in "% of control" of ≤20% at 10 μM in this assay. Preferred compounds of the present invention (including most of the specific Examples above) exhibit activity in "% of control" of ≤50% at 1.0 μM in this cell assay. More preferred compounds of the present invention exhibit activity in "% of control" of ≤20% at 1.0 μM in this cell assay. Especially preferred compounds of the present invention exhibit activity in "% of control" of ≤50% at 100 nM in this assay.

Dopamine beta hydroxylase activity in human plasma was measured by the method of Nagatsu and Udenfriend (Nagatsu, T. and Udenfriend, S. "Photometric assay of dopamine-μ-hydroxylase activity in human blood." *Clin. Chem.* 18(9) 980-983, 1972) with minor modifications. Catalase, N-ethylmaleimide, tyramine, disodium fumarate, pargyline, sodium acetate, ascorbic acid, copper sulfate and octopamine were obtained from Sigma Chemical Co., St. Louis, Mo. 63178. Human plasma samples were obtained from healthy donors (Instituto Português do Sangue Transplantação, Centro Sangue Transplantação, Porto, Portugal). From date of collection, plasma was stored at −80° C. until use. Test compounds were initially prepared in dimethyl sulfoxide at a concentration of 10 mM and diluted in dimethyl sulfoxide to the required concentrations. Test compounds were further diluted in ultrapure water to a concentration 20-fold to that of the final concentration to be tested. Final concentrations of test compounds were 10, 100 and 1000 nM. The various reagents used to make up the incubation buffer were premixed and consisted of the following components: sodium acetate buffer (1 M, pH 5.0, 18 ml), sodium fumarate (0.2 M, 4.5 ml), ascorbic acid (0.2 M, 4.5 ml, freshly prepared), pargyline (20 mM, freshly prepared, 4.5 ml), N-ethylmaleimide (0.2 M, 4.5 ml), catalase (10 000 U/ml, 9 ml), copper sulfate (20 µM, 4.5 ml) and 4.5 ultrapure water. The standard incubation mixture (total volume, 950 µl) contained: 50 µL of compound or vehicle (dimethyl sulfoxide 2%); 700 µL of incubation buffer; 125 µl of plasma (or saline for blank reaction or standard curve); 75 µl of saline. The reaction mixture was placed in water bath, shaking at 37° C. and pre-incubated for 10 minutes. Tyramine (0.5 M) was added and incubation proceeded for 45 minutes. The reaction contents were exposed to air. A sample of enzyme preparation (with 125 µl of plasma) that had been added perchloric acid 2 M at the end of the pre-incubation period was used as blank. A blank for each of the tested compounds was used. For octopamine standard curve, perchloric acid 2 M was replaced by increasing concentrations of octopamine prepared in perchloric acid 2 M (0.5, 1, 2.5, 5, 7.5, 10, 15, 20 µg/ml, final concentration). The incubation was stopped by adding 200 µl of 2 M molar perchloric acid, and the mixture was centrifuged at 9000 g for 5 min. The supernatant fluid (800 µL) was transferred to a column (SPE cartridge ISOLUTE SCX-3, 100 mg) and centrifuged at 150 g for 2 min. The column was washed two more times with 0.5 ml of ultrapure water by centrifuging at 150 g for 2 min. The adsorbed octopamine was eluted twice with 0.3 ml of 4 M ammonium hydroxide by centrifuging at 150 g for 2 min. Octopamine in the eluate was then converted to p-hydroxybenzaldehyde by adding 200 µl of sodium periodate (2%) and incubating for 6 min. Excess periodate was than reduced by adding 200 µl of sodium metabisulfite (10%). Absorbance was measured at 330 mm in a 96-well plate by use of a SpectraMAX plus 384 (Molecular Devices) with software SOFTmax® PRO Software 5.3 spectrophotometer. Absorbance was linear with octopamine concentration from 0.5 to 20 µg/ml. Dopamine beta hydroxylase activity is determined as nmol of octopamine formed/ml of plasma/hour and effect of compounds is presented as % control.

Results are reported in the table below as activity in % of control at the inhibitor concentration tested.

H. Evaluation of Pharmacokinetic Profile

Adult male Wistar rats were kept under controlled environmental conditions (12 h light/dark cycle, room temperature 22±1° C. and humidity 50±5%, food and tap water ad libitum). On the day before the experiment, the animals were fasted. In experiments designed to evaluate the pharmacokinetic profile of Examples 56, 66, 199 and 232, rats (n=4) were administered orally (p.o.) with examples 56, 66, 199 and 232 (10 mg/kg/4 mL; vehicle: 40% kleptose) and plasma and brain samples were collected from anaesthetized animals at 1 and 2 h post-dosing. Animals were anaesthetized by intraperitoneal administration of sodium pentobarbital (60 mg/kg). Blood was collected from cardiac punction into heparinised tubes and kept on ice until centrifugation at 1,500 g for 15 min at 4° C. Plasma and brain samples were stored at less than −20° C. until analysis.

After thawing, 200 µL of acetonitrile 0.1% formic acid was added to 100 µL of plasma. The samples were vortexed and centrifuged for 10 min at 10 000 g. Supernatant was filtered and injected into a mass spectrometer.

After thawing and weighing, water was added to the brain to give a tissue concentration of 0.1 mg/ml. The samples were then homogenized using a Heidolph DIAX 900 mixer and transferred to plastic tubes. Following centrifugation at 10 000 g for 20 min, supernatant was taken and treated as described for plasma.

I. DβH Activity in Rat Adrenal Gland Homogenates

Dopamine beta hydroxylase activity in rat adrenal gland homogenates was measured by the method of Nagatsu and Udenfriend (Nagatsu, T. and Udenfriend, S. "Photometric assay of dopamine-µ-hydroxylase activity in human blood." *Clin. Chem.* 18(9) 980-983, 1972) with minor modifications. Catalase, N-ethylmaleimide, tyramine, disodium fumarate, pargyline, sodium acetate, ascorbic acid, copper sulfate and octopamine were obtained from Sigma Chemical Co., St. Louis, Mo. 63178. Test compounds were prepared in kleptose 40% at a concentration of 0.75, 2.5 or 7.5 mg/mL to be administered at a dose of 10 mg/kg. Compounds and vehicle (kleptose 40%) were administered to wistar rats and adrenals were collected 0.5 h, 1 h, 2 h, 4 h, 6 h, 8 h, 15 h and 24 h after administration. Samples were constituted by the right and left adrenals of each animal. Adrenals were stored in 200 µL of 50 mM Tris pH 7.4 at −30° C., from date of collection. The samples were homogenized and homogenates were then quantified for protein. Protein concentration was adjusted to 1.6 mg/ml. The various reagents used to make up the incubation buffer were premixed and consisted of the following components: sodium acetate buffer (1 M, pH 5.0, 6.0 mL), sodium fumarate (0.2 M, 1.5 mL), ascorbic acid (0.2 M, 1.5 mL, freshly prepared), pargyline (20 mM, freshly prepared, 1.5 mL), N-ethylmaleimide (0.2 M, 1.5 mL), catalase (55 000 U/ml, 3 mL), copper sulfate (90 µM, 1.67 mL) and ultrapure water (1.33 mL). The standard incubation mixture (total volume, 500 µL) contained: 350 µL of incubation buffer; 125 µL of protein sample (or buffer for blank reaction or standard curve). The reaction mixture was placed in water bath with shaking at 37° C. and pre-incubated for 10 minutes. Tyramine (0.4 M, 25 µL) was added and incubation proceeded for 45 minutes. The reaction contents were exposed to air. A sample of enzyme preparation (with 125 µL of protein sample) that had been added perchloric acid 2 M at the end of the pre-incubation period was used as blank. A blank for each of the tested compounds was used. For octopamine standard curve, perchloric acid 2 M was replaced by increasing concentrations of octopamine prepared in perchloric acid 2 M (0.5, 1, 2.5, 5, 7.5, 10 µg/mL, final concentration). The incubation was stopped by adding 50 µL of 2 M molar perchloric acid, and the mixture was centrifuged at 16000 g for 3 min. The supernatant fluid (500 µL) was transferred to a column (SPE cartridge ISOLUTE SCX-3, 100 mg) and centrifuged at 150 g for 2 min. The column was washed two more times with 0.5 ml of ultrapure water by centrifuging at 150 g for 2 min. The adsorbed octopamine was eluted twice with 250 µL of 4 M ammonium hydroxide by centrifuging at 150 g for 2 min. Octopamine in the eluate was then converted to p-hydroxybenzaldehyde by adding 100 µL of sodium periodate (2%) and incubating for 6 min. Excess periodate was than reduced by adding 100 µl of sodium metabisulfite (10%). Absorbance was measured at 330 mm in a 96 well plate by use of a SpectraMAX plus 384 (Molecular Devices) with software SOFTmax® PRO Software 5.3 spectrophotometer. Absorbance was linear with octopamine concentration from 0.5 to 10 µg/mL. Dopamine beta hydroxylase activity is determined as nmol of octopamine formed/mg of protein/hour and effect of compounds is presented as % of control.

J. Catecholamine Determination

Catecholamines quantification in brain stem was performed as previously described (Bonifacio, M. J.; Sousa, F.; Neves, M.; Palma, N.; Igreja, B.; Pires, N. M.; Wright, L. C.; Soares-da-Silva, P. "Characterization of the interaction of the novel anthyhypertensive etamicastat with human dopamine-beta-hydroxylase: comparison with nepicastat." *Eur. J. Pharmacol.* 751, 50-58, 2015) with minor modifications. Test compounds were prepared in 40% of kleptose at a concentration of 2.5 mg/ml to be administered at a dose of 10 mg/kg. Compounds and vehicle (kleptose 40%) were administered to Wistar rats and tissues (brain stem or heart left ventricle) collected in perchloric acid (0.2M) at defined time points after administration. Tissues were stored overnight at 4° C. and the solution was then filtered by centrifugation (1500 g, 4 min, 4° C.) through 0.22 µm pore size filters (Costar Spin-x from Corning Inc., USA). Catecholamines were quantified in filtrates by directly injecting 50 µl of sample volume on a HPLC system with electrochemical detection, using a Spheri-5RP-185 mm column (Perkin-Elmer). Mobile phase consisted of a solution containing 0.1M citric acid, 0.1M sodium acetate, 0.15 mM EDTA, 1 mM dibutylamine, 1 mM octylsulfate, and 5% methanol adjusted to pH 3.5 with perchloric acid.

K. Biological Data

TABLE 1

| Example | SKNSH (1 µM) | SKNSH (0.1 µM) | Plasma (1 µM) | Plasma (0.1 µM) | Plasma (0.01 µM) |
|---|---|---|---|---|---|
| 1 | 37.9 | | | | |
| 2 | 49.3 | | | | |
| 3 | 35.8 | | | | |
| 4 | 20.3 | | | | |
| 5 | 19.9 | | | | |
| 6 | 3.7 | 36.9 | | | |
| 7 | 3.6 | 45.6 | | | |
| 8 | 15.3 | | | | |
| 9 | 54.9 | | | | |
| 10 | 2.1 | 46.4 | | | |
| 11 | 28.5 | | | | |
| 12 | | | 3.3 | 30.8 | |
| 13 | | | 13.9 | 68.0 | |
| 14 | | | 45.6 | 92.8 | |
| 15 | | | 11.4 | 66.0 | |
| 16 | | | 12.7 | 72.9 | |
| 17 | | | 32.2 | 79.0 | |
| 18 | | | 19.8 | 81.0 | |
| 19 | 16.4 | | | | |
| 20 | | | 2.6 | 31.0 | |
| 21 | | | 16.7 | 69.2 | |
| 22 | | | 4.4 | 45.1 | |
| 23 | | | 8.8 | 56.6 | |
| 24 | | | 45.6 | 100.2 | |
| 25 | | | 17.6 | 71.3 | |
| 26 | | | 18.2 | 64.0 | |
| 27 | | | 7.6 | 51.6 | |
| 28 | | | | 33.8 | 78.1 |
| 29 | | | | 29.1 | 72.5 |
| 30 | | | | 73.2 | 92.0 |
| 31 | | | 16.7 | 67.7 | |
| 32 | | | 9.7 | 46.2 | |
| 33 | 33.4 | | | | |
| 34 | | | 0 | 10.4 | |
| 35 | 45.9 | | | | |
| 36 | 50.1 | | | | |
| 37 | 15.7 | | | | |
| 38 | 20.9 | | | | |
| 39 | 29.8 | | | | |
| 40 | 29.3 | | | | |
| 41 | 60.7 | | | | |
| 42 | 8.0 | 51.5 | | | |
| 43 | 45.6 | | | | |
| 44 | 45.9 | | | | |
| 45 | 46.8 | | | | |
| 46 | 4.3 | 41.5 | | | |
| 47 | 62.9 | | | | |
| 48 | 48.4 | | | | |
| 49 | 33.7 | | | | |
| 50 | 1.8 | 57.5 | | | |
| 51 | 0 | 0.4 | 0 | 5.7 | |
| 52 | 0.2 | 9.2 | 1.6 | 10.3 | |
| 53 | 0 | 13.4 | 2.7 | 26.2 | |
| 54 | 4.2 | 33.8 | 3.4 | 32.2 | |
| 55 | 3.9 | 48.9 | 11.1 | 62.1 | |
| 56 | 5.2 | 45.6 | 5.5 | 38.5 | |
| 57 | 0.2 | 11.6 | 0.1 | 18.1 | |
| 58 | 9.3 | 56.8 | 14.0 | 59.2 | |
| 59 | | | 4.1 | 20.8 | |
| 60 | | | 14.0 | 68.9 | |
| 61 | | | 47.9 | 99.1 | |
| 62 | | | 10.9 | 66.4 | |
| 63 | | | 11.9 | 58.3 | |
| 64 | | | 47.2 | 88.4 | |
| 65 | | | 12.6 | 64.5 | |
| 66 | | | 6.4 | 52.3 | |
| 67 | | | 13.2 | 76.1 | |
| 68 | | | 13.5 | 55.6 | |
| 69 | | | 24.1 | 82.1 | |
| 70 | | | 2.9 | 36.6 | |
| 71 | | | 11.9 | 57.0 | |
| 72 | | | 28.9 | 90.8 | |
| 73 | | | 19.1 | 75.9 | |
| 74 | | | 8.1 | 70.3 | |
| 75 | | | 56.3 | 91.0 | |
| 76 | | | 13.1 | 65.8 | |
| 77 | | | 38.9 | 87.2 | |
| 78 | | | 24.4 | 77.3 | |
| 79 | | | 10.3 | 54.3 | |
| 80 | | | 9.8 | 60.7 | |
| 81 | | | 15.9 | 63.1 | |
| 82 | | | 16.6 | 69.2 | |
| 83 | | | 15.9 | 78.8 | |
| 84 | | | 1.0 | 24.5 | |
| 85 | | | 12.2 | 59.1 | |
| 86 | | | 14.7 | 70.9 | |
| 87 | | | 13.8 | 62.8 | |
| 88 | | | 6.1 | 44.1 | |
| 89 | | | 0 | 4.3 | |
| 90 | | | 0.4 | 9.9 | |
| 91 | | | 0 | 19.0 | |
| 92 | | | 0.1 | 37.5 | |
| 93 | | | 1.0 | 32.1 | |
| 94 | | | 0.8 | 47.5 | |
| 95 | | | 0 | 24.0 | |
| 96 | | | 0.8 | 22.4 | |
| 97 | | | 0.5 | 22.7 | |
| 98 | | | 11.7 | 53.1 | |
| 99 | | | 10.3 | 55.7 | |
| 100 | | | 2.1 | 26.2 | |
| 101 | | | 3.3 | 37.2 | |
| 102 | | | 1.7 | 20.3 | |
| 103 | | | 1.8 | 21.6 | |
| 104 | | | 19.5 | 67.9 | |
| 105 | | | 22.0 | 74.9 | |

TABLE 1-continued

| Example | SKNSH (1 μM) | SKNSH (0.1 μM) | Plasma (1 μM) | Plasma (0.1 μM) | Plasma (0.01 μM) |
|---|---|---|---|---|---|
| 106 | | | 4.1 | 33.9 | |
| 107 | | | 6.3 | 40.1 | |
| 108 | | | 5.3 | 46.9 | |
| 109 | | | 1.5 | 5.4 | |
| 110 | | | 9.7 | 52.4 | |
| 111 | | | | 36.7 | 89.6 |
| 112 | | | | 0 | 9.9 |
| 113 | | | | 25.6 | 85.1 |
| 114 | | | | 7.5 | 58.4 |
| 115 | | | | 0 | 48.0 |
| 116 | | | | 68.8 | 93.8 |
| 117 | | | | 43.0 | 74.5 |
| 118 | | | | 49.0 | 89.2 |
| 119 | | | | 87.7 | 118.2 |
| 120 | | | | 86.2 | 132.5 |
| 121 | | | | 62.6 | 79.3 |
| 122 | | | | 13.0 | 70.8 |
| 123 | | | | 6.3 | 51.9 |
| 124 | | | | 3.3 | 42.8 |
| 125 | | | | 43.7 | 106.5 |
| 126 | | | | 40.2 | 100.2 |
| 127 | | | | 83.8 | 81.3 |
| 128 | | | | 29.7 | 98.1 |
| 129 | | | | 10.3 | 50.1 |
| 130 | | | | 8.4 | 55.7 |
| 131 | | | | 50.5 | 89.8 |
| 132 | | | | 62.3 | 91.9 |
| 133 | | | | 82.4 | 95.9 |
| 134 | | | | 3.2 | 24.9 |
| 135 | | | | 58.1 | 88.3 |
| 136 | | | | 6.8 | 44.3 |
| 137 | | | | 21.5 | 72.9 |
| 138 | | | | 5.0 | 46.6 |
| 139 | | | | 20.8 | 77.8 |
| 140 | | | | 26.8 | 73.1 |
| 141 | | | | 76.1 | 93.2 |
| 142 | | | | 16.2 | 60.0 |
| 143 | | | 0.2 | 20.1 | |
| 144 | | | 0.1 | 14.7 | |
| 145 | | | 2.0 | 18.2 | |
| 146 | | | 0.9 | 13.8 | |
| 147 | | | 2.4 | 29.0 | |
| 148 | | | 0.9 | 17.1 | |
| 149 | | | | 3.0 | 52.5 |
| 150 | | | | 17.1 | 64.8 |
| 151 | | | | 20.2 | 73.7 |
| 152 | | | | 17.8 | 72.1 |
| 153 | | | | 28.4 | 85.5 |
| 154 | | | | 38.6 | 89.5 |
| 155 | | | | 19.7 | 91.5 |
| 156 | | | | 40.3 | 88.6 |
| 157 | | | | 24.2 | 84.2 |
| 158 | | | | 52.1 | 90.9 |
| 159 | | | | 50.9 | 84.3 |
| 160 | | | | 50.8 | 84.7 |
| 161 | | | | 46.0 | 85.0 |
| 162 | | | | 31.3 | 87.2 |
| 163 | | | | 2.4 | 14.8 |
| 164 | | | | 17.1 | 65.8 |
| 165 | | | | 14.8 | 74.3 |
| 166 | | | | 14.1 | 66.9 |
| 167 | | | | 3.2  28.0* | 50.8  78.0* |
| 168 | | | | 10.5 | 51.9 |
| 169 | | | | 17.1 | 59.3 |
| 170 | | | | 2.0 | 64.9 |
| 171 | | | | 3.7 | 40.4 |
| 172 | | | 8.1 | 46.3 | |
| 173 | | | | 33.1 | 94.2 |
| 174 | | | 8.5 | 52.7 | |
| 175 | | | 13.8 | 61.7 | |
| 176 | | | | 74.9 | 95.3 |
| 177 | | | | 77.1 | 99.9 |
| 178 | | | | 29.5 | 88.2 |
| 179 | | | | 48.8 | 93.5 |
| 180 | | | | 22.3 | 99.2 |
| 181 | | | | 18.3 | 68.9 |
| 182 | | | | 71.0 | 94.6 |
| 183 | | | | 79.8 | 92.2 |
| 184 | | | | 43.7 | 89.2 |
| 185 | | | | 30.9 | 72.9 |
| 186 | | | | 18.0 | 62.7 |
| 187 | | | | 21.6 | 72.6 |
| 188 | | | | 15.4 | 60.9 |
| 189 | | | | 23.2 | 87.4 |
| 190 | | | | 19.9 | 68.6 |
| 191 | | | | 26.0 | 82.3 |
| 192 | | | | 12.1 | 73.4 |
| 193 | | | | 46.3 | 86.0 |
| 194 | | | | 62.4 | 82.9 |
| 195 | | | | 41.7 | 77.3 |
| 196 | | | | 68.6 | 102.2 |
| 197 | | | | 29.4 | 75.9 |
| 198 | | | | 11.1  99.1* | 52.2  84.5* |
| 199 | | | | 0.6  84.9* | 27.4  119.3* |
| 200 | | | | 66.4 | 85.2 |
| 201 | | | | 13.3 | 62.4 |
| 202 | | | | 22.7 | 67.7 |
| 203 | | | | 75.8 | 95.8 |
| 204 | | | | 1.1 | 26.5 |
| 205 | | | | 18.2 | 76.9 |
| 206 | | | | 8.7 | 22.4 |
| 207 | | | | 30.2 | 76.6 |
| 208 | | | | 13.3 | 62.0 |
| 209 | | | | 60.3 | 87.6 |
| 210 | | | | 73.5 | 94.6 |
| 211 | | | | 94.8 | 104.9 |
| 212 | | | | 46 | 86.5 |
| 213 | | | | 66.6 | 105.9 |
| 214 | | | | 72.1 | 109.1 |
| 215 | | | | 34.2 | 74.3 |
| 216 | | | | 47.1 | 84.5 |
| 217 | | | | 92.3 | 99.8 |
| 218 | | | | 69.1 | 89.2 |
| 219 | | | | 19.7 | 69.9 |
| 220 | | | | 17.7 | 76.5 |
| 221 | | | | 30.0 | 79.3 |
| 222 | | | | 12.9 | 73.6 |
| 223 | | | | 7.2 | 42.7 |
| 224 | | | | 0.6 | 22.6 |
| 225 | | | | 12.5 | 65.3 |
| 226 | | | | 47.4 | 100.8 |
| 227 | | | | 54.9 | 86.8 |
| 228 | | | | 56.0 | 90.2 |
| 229 | | | | 38.3 | 84.3 |
| 230 | | | | 41.6 | 82.0 |
| 231 | | | | 5.6 | 35.9 |
| 232 | | | | 6.4 | 48.8 |
| 233 | | | | 66.8  9.7* | 83.8  59.3* |
| 234 | | | | 12.2 | 43.4 |
| 235 | | | | 1.2 | 11.4 |
| 236 | | | | 51.0 | 104.2 |
| 237 | | | | 61.6 | 92.9 |
| 238 | | | | 88.5 | 93.4 |
| 239 | | | | 3.9 | 60.1 |
| 240 | | | | 39.2 | 76.1 |
| 241 | | | | 8.9 | 51.7 |
| 242 | | | | 53.6 | 91.5 |
| 243 | | | | 4.4  37.6* | 38.0  87.3* |
| 244 | | | | 32.9 | 83.6 |
| 245 | | | | 93 | 107.8 |
| 246 | | | | 80.3 | 115.2 |
| 247 | | | | 35.9 | 81.7 |
| 248 | | | | 51.8 | 98.2 |
| 249 | | | | 40.9 | 96.0 |
| 250 | | | | 7.3 | 46.1 |
| 251 | | | | 36.0 | 80.0 |
| 252 | | | | 54.8  6.7* | 82.2  46.0* |
| 253 | | | | 24.5 | 63.4 |
| 254 | | | | 62.2 | 81.4 |
| 255 | | | | 24.6 | 71.8 |
| 256 | | | | 29.2 | 61.7 |
| 257 | | | | 92.4 | 105.9 |
| 258 | | | | 21.3 | 84.2 |
| 259 | | | | 76.1 | 90.8 |

TABLE 1-continued

| Example | SKNSH (1 μM) | SKNSH (0.1 μM) | Plasma (1 μM) | Plasma (0.1 μM) | Plasma (0.01 μM) |
|---|---|---|---|---|---|
| 260 | | | | 26.5 | 84.1 |
| 261 | | | | 31.8 | 86.2 |
| 262 | | | | 70.1 | 82.6 |
| 263 | | | | 87.1 | 103.3 |
| 264 | | | | 54.2 | 98.4 |
| 265 | | | | 70.6 | 94.9 |
| 266 | | | | 56.0 | 85.3 |
| 267 | | | | 55.8 | 90.8 |
| 268 | | | | 57.7 | 99.8 |
| 269 | | | | 83.7 | 105.6 |
| 270 | | | | 53.8 | 88.1 |
| 271 | | | | 13.2 | 62.1 |
| 272 | | | | 22.7 | 73.5 |
| 273 | | | | 28.9 | 86.6 |
| 274 | | | | 11.2 | 55.9 |
| 275 | | | | 24.4 | 79.0 |
| 276 | | | | 33.3 | 83.3 |
| 277 | | | | 3.4 | 35.4 |
| 278 | | | | 62.0 | 84.2 |
| 279 | | | | 15.7 | 61.7 |
| 280 | | | | 51.4 | 92.8 |
| 281 | | | | 29.8 | 107.9 |
| 282 | | | | 75.4 | 99.6 |
| 283 | | | | 72.9 | 96.0 |
| 284 | | | | 41.9 | 84.8 |
| 285 | | | | 22.2 | 55.8 |
| 286 | | | | 3.4 | 73.8 |
| 287 | | | | 15.5 | 66.8 |
| 288 | | | | 81.1 | 82.0 |
| 289 | | | | 58.3 | 87.1 |
| 290 | | | | 3.8 | 37.6 |
| 291 | | | | 1.7 | 30.2 |
| 292 | | | | 68.3 | 101.9 |
| 293 | | | | 86.0 | 104.8 |
| 294 | | | | 1.7 | 39.7 |
| 295 | | | | 71.5 | 95.6 |
| 296 | | | | 74.5 | 89.2 |
| 297 | | | | 35.4 | 78.7 |
| 298 | | | | 28.2 | 83.5 |
| 299 | | | | 48.4 | 84.3 |
| 300 | | | | 10.9 | 57.0 |
| 301 | | | | 6.4 | 49.1 |
| 302 | | | | 7.7 | 62.7 |
| 303 | | | | 34.7 | 79.3 |
| 304 | | | | 21.1 | 51.9 |
| 305 | | | | 12.2 | 61.2 |
| 306 | | | | 18.0 | 70.6 |
| 307 | | | | 33.0 | 73.9 |
| 308 | | | | 12.8 | 64.2 |
| 309 | | | | 38.8 | 86.2 |
| 310 | | | | 22.3 | 65.9 |
| 311 | | | | 21.6 | 87.2 |
| 312 | | | 51.7 | 15.0* | 84.8  67.6* |
| 313 | | | | 9.6 | 37.6 |
| 314 | | | 34.8 | 1.4* | 80.2  41.9* |
| 315 | | | 17.0 | 53.3* | 67.0  94.0* |
| 316 | | | 4.5 | 16.6* | 43.4  73.1* |
| 317 | | | | 5.3 | 45.6 |
| 318 | | | | 61.4 | 88.4 |
| 319 | | | | 16.5 | 67.9 |
| 320 | | | | 31.1 | 90.3 |
| 321 | | | | 13.3 | 89.7 |
| 322 | | | | 43.4 | 62.3 |
| 323 | | | | 43.3 | 86.3 |
| 324 | | | | 53.1 | 88.6 |
| 325 | | | | 3.8 | 34.2 |
| 326 | | | | 59.5 | 96.6 |
| 327 | | | | 7.0 | 49.9 |
| 328 | | | | 9.4 | 63.1 |
| 329 | | | | 16.1 | 41.7 |
| 330 | | | | 32.5 | 71.7 |
| 331 | | | | 50.2 | 77.4 |
| 332 | | | | 2.7 | 32.8 |
| 333 | | | | 11.7 | 47.5 |
| 334 | | | | 41.9 | 80.3 |
| 335 | | | | 8.7 | 44.9 |
| 336 | | | | 9.4 | 50.0 |
| 337 | | | | 9.4 | 48.2 |
| 338 | | | | 6.2 | 36.4 |
| 339 | | | | 4.3 | 42.3 |
| 340 | | | | 27.0 | 87.6 |
| 341 | | | | 33.6 | 91.1 |
| 342 | | | | 16.5 | 66.6 |
| 343 | | | | 59.5 | 94.9 |
| 344 | | | | 73.7 | 88.2 |
| 345 | | | | 40.3 | 77.2 |
| 346 | | | | 74.9 | 109.6 |
| 347 | | | | 17.7 | 79.0 |
| 348 | | | | 44.8 | 92.4 |
| 349 | | | | 12.5 | 72.3 |
| 350 | | | | 28.2 | 85.7 |
| 351 | | | | 16.5 | 46.2 |
| 352 | | | | 10.9 | 40.8 |
| 353 | | | | 38.4 | 90.6 |
| 354 | | | | 53.4 | 106.2 |
| 355 | | | | 14.0 | 56.4 |
| 356 | | | | 6.6 | 35.4 |
| 357 | | | | 15.1 | 62.1 |
| 358 | | | | 24.9 | 90.1 |
| 359 | | | | 53.3 | 101.2 |
| 360 | | | 1.4 | 22.5* | 31.8  90.1* |
| 361 | | | | 10.4 | 60.0 |
| 362 | | | | 11.8 | 43.2 |
| 363 | | | | 20.8 | 89.5 |
| 364 | | | | 54.7 | 97.0 |
| 365 | | | | 56.9 | 101.3 |
| 366 | | | | 81.4 | 124.8 |
| 367 | | | | 4.3 | 45.4 |
| 368 | | | | 63.1 | 104.4 |
| 369 | | | | 60.1 | 86.0 |
| 370 | | | | 64.7 | 88.5 |
| 371 | | | | 17.7 | 79.0 |
| 372 | | | | 32.0 | 93.4 |
| 373 | | | | 12.8 | 66.1 |
| 374 | | | | 50.0 | 97.4 |
| 375 | | | | 40.7 | 90.0 |
| 376 | | | | 59.3 | 116.3 |
| 377 | | | | 56.8 | 102.0 |
| 378 | | | | 52.6 | 110.2 |
| 379 | | | | 50.1 | 108.7 |
| 380 | | | | 27.4 | 74.9 |
| 381 | | | | 3.2 | 30.0 |
| 382 | | | | 6.0 | 37.6 |
| 383 | | | | 14.8 | 65.6 |
| 384 | | | | 43.4 | 104.5 |
| 385 | | | | 19.3 | 68.1 |
| 386 | | | | 79.4 | 101.8 |
| 387 | | | | 43.7 | 92.9 |
| 388 | | | | 71.1 | 80.8 |
| 389 | | | | 33.1 | 75.2 |
| 390 | | | | 52.0 | 75.0 |
| 391 | | | | 40.7 | 83.8 |
| 392 | | | | 13.2 | 62.3 |
| 393 | | | | 65.7 | 90.6 |
| 394 | | | | 47.6 | 92.1 |
| 395 | | | | 47.8 | 96.9 |
| 396 | | | | 10.8 | 66.9 |
| 397 | | | | 24.1 | 79.9 |
| 398 | | | | 23.0 | 94.3 |
| 399 | | | | 4.0 | 40.6 |
| 400 | | | | 7.3 | 31.9 |
| 401 | | | | 35.2 | 66.5 |
| 402 | | | | 20.9 | 59.6 |
| 403 | | | | 4.8 | 29.9 |
| 404 | | | | 26.2 | 78.7 |
| 405 | | | | 4.5 | 50.7 |
| 406 | | | | 2.8 | 28.9 |
| 407 | | | | 42.3 | 102.6 |
| 408 | | | | 14.7 | 77.0 |
| 409 | | | | 64.4 | 112.6 |
| 410 | | | | 11.1 | 62.3 |
| 411 | | | | 78.6 | 104.2 |
| 412 | | | | 63.2 | 106.2 |
| 413 | | | | 3.1 | 42.4 |

TABLE 1-continued

| Example | SKNSH (1 μM) | SKNSH (0.1 μM) | Plasma (1 μM) | Plasma (0.1 μM) | Plasma (0.01 μM) |
|---|---|---|---|---|---|
| 414 | | | | 49.0 | 95.4 |
| 415 | | | | 2.1 | 14.9 |
| 416 | | | | 25.4 | 75.3 |
| 417 | | | | 60.5 | 87.7 |
| 418 | | | | 3.0 | 27.7 |
| 419 | | | | 61.0 | 92.5 |
| 420 | | | | 48.5 | 87.8 |
| 421 | | | | 5.8 | 26.1 |
| 422 | | | | 23.2 | 68.1 |
| 423 | | | | 1.7 | 18.5 |
| 424 | | | | 20.6 | 59.5 |
| 425 | | | | 52.0 | 78.6 |
| 426 | | | | 66.3 | 83.5 |
| 427 | | | | 34.2 | 78.1 |
| 428 | | | | 32.3 | 68.2 |
| 429 | | | | 5.8 | 37.8 |
| 430 | | | | 2.2 | 25.3 |
| 431 | | | | 10.1 | 54.3 |
| 432 | | | | 43.7 | 79.7 |
| 433 | | | | 9.2 | 56.9 |
| 434 | | | | 8.5 | 52.5 |
| 435 | | | | 36.6 | 66.5 |
| 436 | | | | 23.9 | 73.6 |
| 437 | | | | 6.1 | 62.7 |
| 438 | | | | 7.5 | 64.0 |
| 439 | | | | 11.8 | 67.2 |
| 440 | | | | 8.4 | 57.2 |
| 441 | | | | 37.4 | 72.8 |
| 442 | | | | 10.0 | 43.6 |
| 443 | | | | 11.5 | 59.2 |
| 444 | | | | 57.7 | 73.5 |
| 445 | | | | 73.7 | 95.1 |
| 446 | | | | 62.9 | 83.0 |
| 447 | | | | 33.2 | 94.4 |
| 448 | | | | 65.3 | 93.3 |
| 449 | | | | 2.3 | 27.8 |
| 450 | | | | 2.3 | 32.6 |
| 451 | | | | 5.5 | 39.8 |
| 452 | | | | 12.8 | 49.6 |
| 453 | | | | 10.4 | 56.6 |
| 454 | | | | 8.1 | 56.8 |
| 455 | | | | 50.2 | 131.0 |
| 456 | | | | 20.2 | 86.8 |
| 457 | | | | 7.3 | 42.1 |
| 458 | | | | 12.2 | 58.5 |
| 459 | | | | 13.5 | 65.6 |
| 460 | | | | 18.2 | 43.9 |
| 461 | | | | 6.9 | 45.6 |
| 462 | | | | 10.3 | 50.2 |
| 463 | | | | 3.7 | 29.1 |
| 464 | | | | 4.5 | 33.4 |
| 465 | | | | 9.0 | 62.3 |
| 466 | | | | 6.5 | 49.6 |
| 467 | | | | 4.0 | 27.9 |
| 468 | | | | 13.1 | 65.8 |
| 469 | | | | 1.5 | 33.7 |
| 470 | | | | 79.4 | 112.0 |
| 472 | | | | 14.2 | 63.3 |
| 473 | | | | 46.2 | 98.9 |
| 474 | | | | 79.3 | 92.5 |
| 475 | | | | 67.0 | 85.0 |
| 476 | | | | 64.8 | 94.3 |
| 477 | | | | 59.4 | 84.6 |
| 478 | | | | 5.1 | 46.7 |

*Compound was re-tested under the same experimental conditions. It is believed that the difference between the previously generated data and the retest data is due to human error. Asterisked data are believed to be correct.

The following table shows DβH inhibition in human SKNSH cell line and human plasma for the compounds:

TABLE 2

| Example | $C_{pl}$ (ng/mL) at 1 h | $C_{pl}$ (ng/mL) at 2 h | $C_{br}$ (ng/g) at 1 h | $C_{br}$ (ng/g) at 2 h |
|---|---|---|---|---|
| 56 | 1498 | 1128 | 20 | 21 |
| 66 | 779 | 429 | 0 | 0 |
| 199 | 1642 | 777 | 45 | 0 |
| 232 | 1712 | 1311 | 24 | 46 |

The following table shows plasma ($C_{pl}$) and brain ($C_{br}$) concentrations (10 mg/kg, rat, po) for the examples 56, 66, 199 and 232:

As can be seen from the table above, the examples 56, 66, 199 and 232 are peripherally selective, i.e. they exhibit significantly greater exposure in plasma compared to brain.

TABLE 3

| Example | DβH activity in ADR (% Control) | NA in Br.s (% Control) |
|---|---|---|
| 174 | 39 ± 18 | 84 ± 8 |
| 191 | 45 ± 8 | 83 ± 10 |
| 195 | 21 ± 9 | 123 ± 55 |
| 219 | 43 ± 16 | 92 ± 23 |
| 231 | 43 ± 9 | 99 ± 14 |
| 256 | 44 ± 22 | 128 ± 64 |
| 403 | 0 ± 0 | 87 ± 16 |

The following table shows the maximal DβH activity in rat adrenal gland homogenates (ADR) (within a period of 6 h post-dose) and levels of noradrenaline (NA) in brain stem (Br.s) (15 h post-dose) after oral administration of 10 mg/kg of compounds of Examples 174, 191, 195, 219, 231, 256 and 403. Each experiment represents mean±SD of 4 rats.

The above table shows that examples 174, 191, 195, 219, 231, 256 and 403 inhibit DβH at a dose of 10 mg/kg in peripheral tissues such as ADR. Furthermore, they failed to reduce levels of NA in CNS tissues such as in brain stem, suggesting that the compounds are peripherally selective.

The invention claimed is:

1. A compound of formula Ia, or a pharmaceutically acceptable salt or solvate thereof:

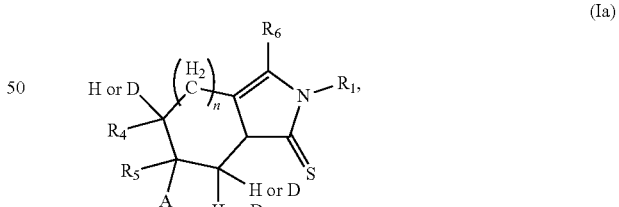

wherein:
$R_1$ is hydrogen, $C_1$-$C_6$ alkyl, partially or fully deuterated $C_1$-$C_6$ alkyl or $C_3$-$C_6$ cycloalkyl;
$R_4$ is hydrogen or $C_1$-$C_3$ alkyl;
$R_5$ is hydrogen;
or $R_4$ and $R_5$ combine, together with the carbon atoms to which they are attached, to form a cyclopropyl ring;
$R_6$ is —COOH, —CHO, or —(CH$_2$)$_m$—X,
wherein:
m is 1, 2 or 3 and one —CH$_2$— moiety within —(CH$_2$)$_m$— may optionally be replaced by

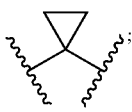 [SMILES: *C1(*)CC1]

X is hydroxy, $C_1$-$C_3$ alkoxy, cyano, —N=CH(NHCN) ($NH_2$), —NH—C(pyrrolidin-1-yl)=NCN, 5- or 6-membered heteroaryl optionally substituted with one methyl group, phenyl, —$SO_2$—$R_7$, —$NR_8R_9$, —$CO_2R_{10}$, —CH($CO_2R_{10}$)$_2$, —$CONR_{11}R_{12}$ or —$NR_{13}COR_{14}$;

wherein:

$R_7$ is $C_1$-$C_3$ alkyl;

$R_8$ is hydrogen or $C_1$-$C_3$ alkyl;

$R_9$ is hydrogen,
- $C_1$-$C_4$ alkyl optionally substituted with up to three fluoro substituents or with one substituent selected from the group consisting of hydroxy, methylsulfonyl,
- $C_3$-$C_6$ cycloalkyl, phenyl, 5- or 6-membered heterocyclyl and 5- or 6-membered heteroaryl optionally substituted with one methyl substituent,
- $C_3$-$C_6$ cycloalkyl,
- 5- or 6-membered heteroaryl, or
- 5- or 6-membered heterocyclyl optionally substituted with one or two oxo substituents;

or $R_8$ and $R_9$ combine together with the N atom to which they are attached to form a 5- or 6-membered N-heterocyclyl group optionally substituted with one substituent selected from methyl, trifluoromethyl, hydroxy, hydroxymethyl, methoxymethyl, methylsulfonyl, amido, (N,N-dimethyl)acetamide and pyridyl or with one or two substituents selected from fluoro and oxo, or a 9- or 10-membered heterospirocyclyl group;

$R_{10}$ is hydrogen or $C_1$-$C_3$ alkyl;

$R_{11}$ is hydrogen or $C_1$-$C_3$ alkyl;

$R_{12}$ is hydrogen,
- $C_1$-$C_4$ alkyl optionally substituted with up to three fluoro substituents or with one substituent selected from the group consisting of cyano, hydroxy, methylsulfonyl,
- $C_1$-$C_2$ alkoxy, dimethylamino, $C_3$-$C_6$ cycloalkyl, phenyl, 5- or 6-membered heteroaryl optionally substituted with one methyl substituent and 5- or 6-membered heterocyclyl optionally substituted with one t-Boc group or with one or two fluoro substituents,
- $C_3$-$C_6$ cycloalkyl optionally substituted with one substituent selected from the group consisting of cyano, hydroxy, hydroxymethyl and oxo,
- cyano,
- methylsulfonyl,
- $CH_2COO(C_1$-$C_3$ alkyl),
- 5- or 6-membered heteroaryl optionally substituted with one methyl substituent,
- 4-, 5- or 6-membered heterocyclyl optionally substituted with one or two substituents selected from oxo and methyl,
- $CH_2CH(NH_2)(COOH)$, or
- $CH(CH_3)CONH_2$;

or $R_{11}$ and $R_{12}$ combine together with the N atom to which they are attached to form a 5- or 6-membered N-heterocyclyl group optionally substituted with one substituent selected from monofluoromethyl, trifluoromethyl, hydroxy, hydroxymethyl, methoxymethyl, methyl sulfonyl, cyano, amido, (N,N-dimethyl)acetamide and pyridyl, or with one or two substituents selected from fluoro, methyl and oxo, or optionally fused to a cyclopropyl ring which may be substituted with one or two methyl substituents, or a 9- or 10-membered heterospirocyclyl group;

$R_{13}$ is hydrogen or $C_1$-$C_3$ alkyl;

$R_{14}$ is $C_1$-$C_4$ alkyl optionally substituted with up to three fluoro substituents or with one substituent selected from the group consisting of hydroxy, methylsulfonyl, $C_3$-$C_6$ cycloalkyl and phenyl, $C_3$-$C_6$ cycloalkyl, 5- or 6-membered heteroaryl, or 5- or 6-membered heterocyclyl optionally substituted with one or two oxo substituents;

A is $C_5$-$C_7$ cycloalkyl, furanyl, thiophenyl, methylthiophenyl or

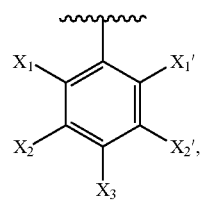

wherein:

$X_1$ is hydrogen, halo or methyl;

$X_1'$ is hydrogen or halo;

$X_2$ is hydrogen, halo or methyl;

$X_2'$ is hydrogen or halo;

$X_3$ is hydrogen or fluoro;

n is 0 or 1, and when n is 0 a single bond joins the carbon atoms to which the $CH_2$ moiety would be attached when n is 1.

2. A compound according to claim 1, wherein n is 0.

3. A compound according to claim 1, wherein $R_4$ and $R_5$ combine, together with the carbon atom to which they are attached, to form a cyclopropyl ring.

4. A compound according to claim 1, wherein more than 50% of substituents $R_5$ and A have the stereochemical configuration of formula Id

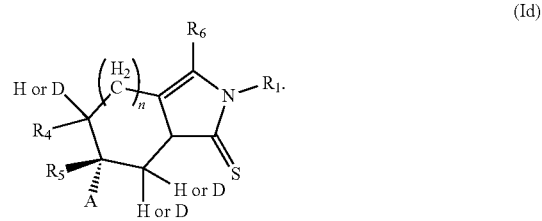

(Id)

5. A compound according to claim 1, wherein more than 50% of substituents $R_5$ and A have the stereochemical configuration of formula Ie

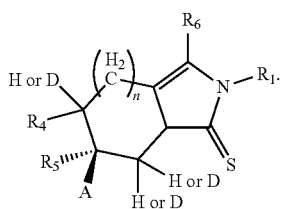

(Ie)

6. A compound according to claim 1, wherein A is

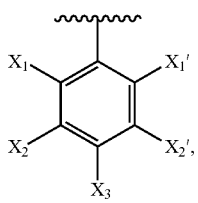

wherein $X_1$, $X_1'$, $X_2$, $X_2'$ and $X_3$ are as defined in claim 1.

7. A compound according to claim 1, wherein $R_1$ is hydrogen, methyl or $d_3$-methyl.

8. A compound according to claim 1, wherein $R_4$ is hydrogen or methyl.

9. A compound according to claim 1, wherein $R_5$ is hydrogen.

10. A compound according to claim 1, wherein $R_6$ is —COOH, —CHO, or —(CH$_2$)$_m$—X,
wherein:
m is 1, 2 or 3 and one —CH$_2$— moiety within —(CH$_2$)$_m$— may optionally be replaced by

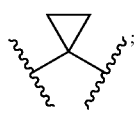 [SMILES: *C1(*)CC1]

X is hydroxy, ethoxy, cyano, —N=C(NHCN)(NH$_2$), —NH—C(pyrrolidin-1-yl)=NCN, 1-methylimidazol-2-yl, 3-methyl-1,2,4-oxadiazol-5-yl, tetrazol-5-yl, pyridin-2-yl, pyridin-3-yl, pyridin-4-yl, phenyl, —SO$_2$—R$_7$, —NR$_8$R$_9$, —COOR$_{10}$, —CH(COOR$_{10}$)$_2$, —CONR$_{11}$R$_{12}$ or —NR$_{13}$COR$_{14}$;
wherein:
$R_7$ is methyl;
$R_8$ is hydrogen or methyl;
$R_9$ is hydrogen, methyl, cyclopropylmethyl, benzyl, 2-hydroxyethyl, 2,2,2-trifluoroethyl, 2-methylsulfonylethyl, 1-cyclohexylethyl, isopropyl, butyl, cyclopropyl, cyclobutyl, cyclopentyl, tetrahydrofuran-3-yl, (tetrahydrofuran-2-yl)methyl, (1,1-dioxido)tetrahydrothiopyran-4-yl, (tetrahydro-2H-pyran-4-yl)methyl, pyridin-2-yl, pyridin-3-yl, tetrahydropyran-3-yl, cyclohexyl, (pyridin-2-yl)methyl or (1-methylpyrazol-4-yl)methyl;
or $R_8$ and $R_9$ combine together with the N atom to which they are attached to form a pyrrolidinyl, piperidinyl, 4-methyl sulfonyl-piperidinyl, 4,4-difluoro-piperidinyl or morpholinyl group;
$R_{10}$ is methyl, ethyl or ethyl;
$R_{11}$ is hydrogen or methyl;

$R_{12}$ is hydrogen, methyl, cyanomethyl, cyclopropylmethyl, benzyl, (pyridin-2-yl)methyl, (pyridin-3-yl)methyl, (N-t-Boc-pyrrolidin-2-yl)methyl, 2-hydroxyethyl, 2-methoxyethyl, 2,2,2-trifluoroethyl, 2-methylsulfonylethyl, 1-cyclohexylethyl, 2-(pyridin-2-yl)ethyl, 2-(1H-pyrazol-1-yl)ethyl, 2-(4,4-difluoropiperidin-1-yl)ethyl, propyl, isopropyl, 3-(N,N-dimethylamino)propyl, 3-(morpholin-1-yl)propyl, butyl, cyclopropyl, 1-cyanocyclopropyl, cyclobutyl, cyclopentyl, 2-hydroxycyclopentyl, 2-hydroxymethylcyclopentyl, 2-oxocyclopentyl, cyclohexyl, 2-hydroxycyclohexyl, 4-hydroxycyclohexyl, cyano, methylsulfonyl, CH$_2$COOEt, tetrahydrofuran-3-yl, 2-oxotetrahydrofuran-3-yl, tetrahydropyran-3-yl, tetrahydropyran-4-yl, (1,1-di oxido)tetrahydrothiopyran-4-yl, 1,3,4-thiadiazol-2-yl, pyridin-2-yl, pyridin-3-yl, CH$_2$CH(NH$_2$)(COOH), CH(CH$_3$)CONH$_2$, oxazol-2-yl, (pyrazine-2-yl)methyl, oxetan-3-yl, (tetrahydrofuran-2-yl)methyl, (1-methylpyrazol-4-yl)methyl, thiazol-2-yl, 2-oxopyrrolidin-3-yl, 2-cyanocyclopentyl, isoxazol-4-yl, 3-methyl-1,2,4-oxadiazol-5-yl, (tetrahydropyran-4-yl)methyl, 2-oxopiperidin-3-yl, 1-methylpyrazol-4-yl, isothiazol-4-yl, 1-methyl-2-oxopiperidin-5-yl, 1-methyl-2-oxopyrrolidin-3-yl, 1-methyl-5-oxopyrrolidin-3-yl or 1-methyl-2-oxopyrrolidin-4-yl;

or $R_{11}$ and $R_{12}$ combine together with the N atom to which they are attached to form a pyrrolidinyl, 2-hydroxymethyl-pyrrolidinyl, 2-methoxymethyl-pyrrolidinyl, 2-trifluoromethyl-pyrrolidinyl, 3-(fluoromethyl)pyrrolidinyl, 3-methylsulfonyl-pyrrolidinyl, N,N-dimethylpyrrolidinyl-3-carboxamide, piperidinyl, 3-hydroxy-piperidinyl, 4-hydroxy-piperidinyl, 4-methyl-piperidinyl, 4-hydroxymethyl-piperidinyl, 4-amido-piperidinyl, 4-methyl sulfonyl-piperidinyl, 4,4-difluoro-piperidinyl, N,N-dimethylpiperidinyl-4-carboxamide, N4-methylpiperazinyl, N4-(N,N-dimethyl)acetamide-piperazinyl, N4-(pyridine-2-yl)piperazinyl, morpholinyl, thiomorpholinyl, 1-oxidothiomorpholinyl, 1,1-dioxidothiomorpholinyl, 2-oxa-7-azaspiro[4.4]nonanyl, 2-oxa-8-azaspiro[4.5]decanyl, 1,4-dioxa-8-azaspiro[4.5]decanyl, 6,6-dimethyl-3-azabicyclo[3.1.0]hexanyl, piperazinyl, 3-oxopiperazinyl, 4-methyl-3-oxopiperazinyl, 2-cyanopyrrolidinyl, 3-cyanopyrrolidinyl, 3-fluoromethylpyrrolidinyl or 3-(N,N-dimethylacetamide)pyrrolidinyl;

$R_{13}$ is hydrogen or methyl;
$R_{14}$ is cyclopropyl, cyclopentyl, pyrrolidin-1-yl, tetrahydropyran-4-yl or pyridin-3-yl.

11. A compound according to claim 1, wherein A is

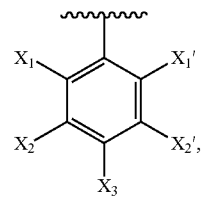

wherein:
$X_1$ is hydrogen, fluoro, chloro or methyl;
$X_1'$ is hydrogen, fluoro or chloro;
$X_2$ is hydrogen, fluoro, chloro, bromo or methyl;

$X_2'$ is hydrogen, fluoro, chloro or bromo;

$X_3$ is hydrogen or fluoro.

12. A pharmaceutical composition comprising (i) a compound of formula Ia, as defined in claim 1, or a pharmaceutically acceptable salt or solvate thereof; and (ii) a pharmaceutically acceptable excipient.

13. A compound of formula Ia, as defined in claim 1, or a pharmaceutically acceptable salt or solvate thereof, with the proviso that the compound (5)-1-benzyl-6-(3,5-difluorophenyl)-6,7-dihydro-2H-pyrrolo[1,2-c]imidazole-3(5H)-thione is excluded.

14. A compound according to claim 1, wherein the compound is selected from the group consisting of:

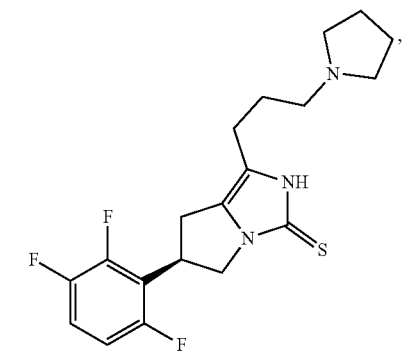

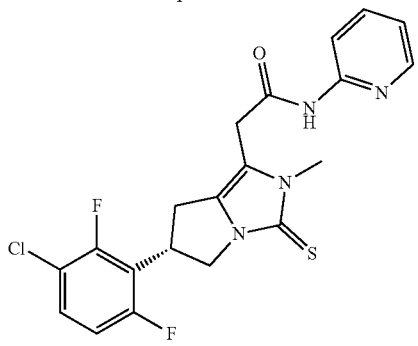

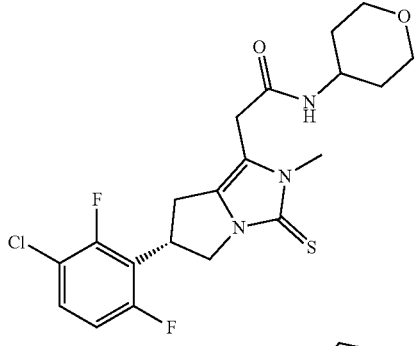

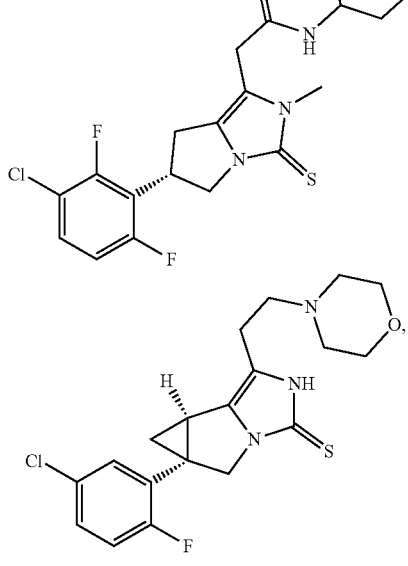

-continued

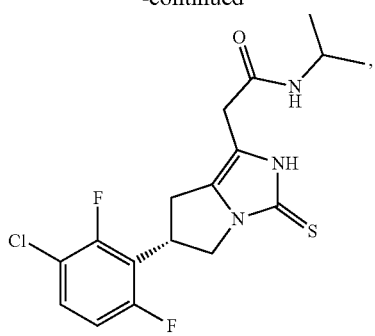

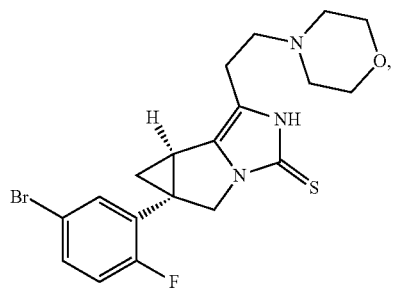

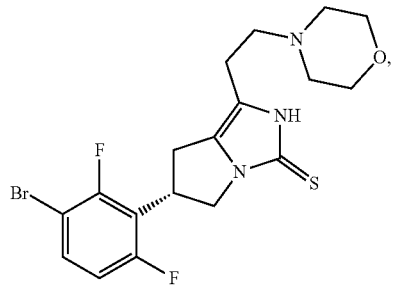

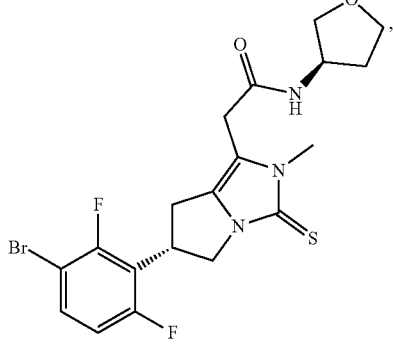

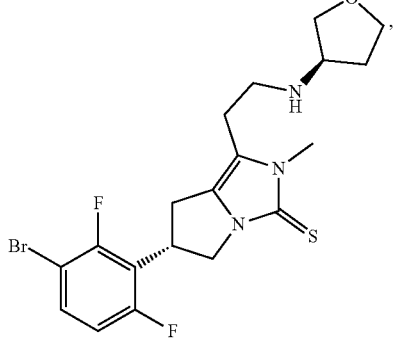

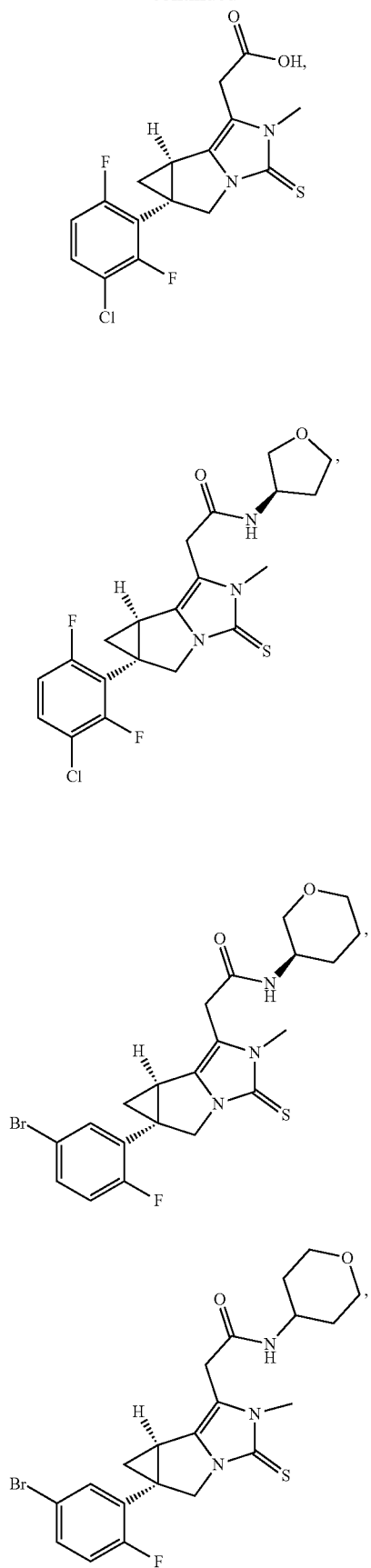
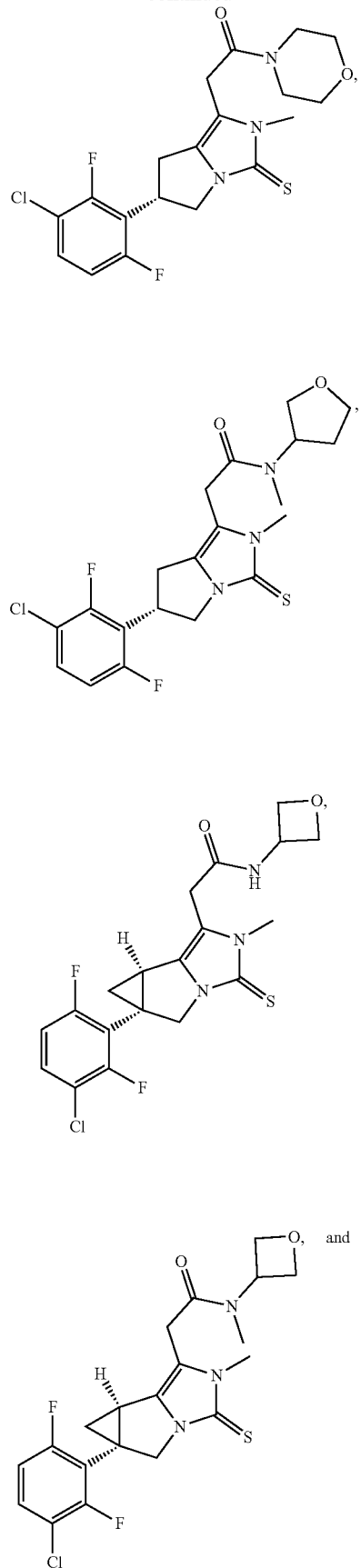

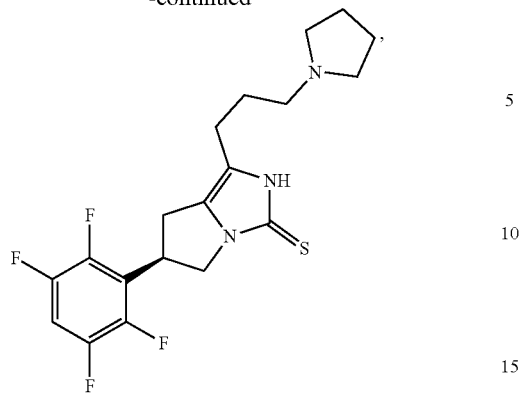
or a pharmaceutically acceptable salt or solvate thereof.
* * * * *